United States Patent
Bamdad et al.

(10) Patent No.: US 11,931,347 B2
(45) Date of Patent: Mar. 19, 2024

(54) METHOD OF SCREENING FOR AGENTS FOR DIFFERENTIATING STEM CELLS

(71) Applicant: MINERVA BIOTECHNOLOGIES CORPORATION, Waltham, MA (US)

(72) Inventors: Cynthia Bamdad, Waltham, MA (US); Scott Moe, Waltham, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

(21) Appl. No.: 15/762,897

(22) PCT Filed: Sep. 23, 2016

(86) PCT No.: PCT/US2016/053571
§ 371 (c)(1),
(2) Date: Mar. 23, 2018

(87) PCT Pub. No.: WO2017/053886
PCT Pub. Date: Mar. 30, 2017

(65) Prior Publication Data
US 2018/0263964 A1    Sep. 20, 2018

Related U.S. Application Data

(60) Provisional application No. 62/222,713, filed on Sep. 23, 2015.

(51) Int. Cl.
| | |
|---|---|
| *A61P 29/00* | (2006.01) |
| *A61K 31/4045* | (2006.01) |
| *A61K 31/437* | (2006.01) |
| *A61K 31/444* | (2006.01) |
| *A61P 35/04* | (2006.01) |
| *C12Q 1/686* | (2018.01) |
| *C12Q 1/6886* | (2018.01) |
| *G01N 33/50* | (2006.01) |
| *G01N 33/574* | (2006.01) |

(52) U.S. Cl.
CPC ........ *A61K 31/437* (2013.01); *A61K 31/4045* (2013.01); *A61K 31/444* (2013.01); *A61P 29/00* (2018.01); *A61P 35/04* (2018.01); *C12Q 1/686* (2013.01); *C12Q 1/6886* (2013.01); *G01N 33/5073* (2013.01); *G01N 33/574* (2013.01); *C12Q 2600/136* (2013.01); *C12Q 2600/158* (2013.01); *G01N 2800/7028* (2013.01)

(58) Field of Classification Search
CPC .............. A61K 31/437; A61K 31/4045; A61K 31/444; A61P 35/04; A61P 29/00; C12Q 1/686; G01N 33/5073; G01N 33/574
See application file for complete search history.

(56) References Cited

U.S. PATENT DOCUMENTS

| | | | | |
|---|---|---|---|---|
| 5,276,051 | A * | 1/1994 | Lesieur | C07D 209/16 514/235.2 |
| 2001/0051344 | A1 | 12/2001 | Shalon et al. | |
| 2005/0215580 | A1* | 9/2005 | Wang | A61P 35/00 514/291 |
| 2005/0282849 | A1* | 12/2005 | Moon | A61K 31/337 514/291 |
| 2008/0064680 | A1* | 3/2008 | Bamdad | A61K 31/517 514/212.03 |
| 2010/0179132 | A1* | 7/2010 | Moon | A61K 31/337 514/218 |
| 2014/0302026 | A1 | 10/2014 | Lee et al. | |
| 2015/0218288 | A1 | 8/2015 | Bamdad | |

FOREIGN PATENT DOCUMENTS

| | | |
|---|---|---|
| CN | 103880841 A | 6/2014 |
| EP | 1637521 A1 | 3/2006 |
| JP | 2007529534 A | 10/2007 |
| JP | 2008536876 A | 9/2008 |
| WO | WO-9743287 A1 | 11/1997 |
| WO | 2005/070930 A2 | 8/2005 |
| WO | WO-2005089764 A1 | 9/2005 |
| WO | WO-2007076055 A2 * | 7/2007 ............ A61K 31/44 |
| WO | 2009/022104 A1 | 2/2009 |
| WO | 2009/042815 A2 | 4/2009 |
| WO | WO-2009140260 A2 | 11/2009 |
| WO | WO-2011159960 A2 | 12/2011 |
| WO | WO-2012026222 A1 | 3/2012 |
| WO | WO-2014036654 A1 | 3/2014 |
| WO | 2014/130741 A2 | 8/2014 |
| WO | WO2015/023694 A2 | 2/2015 |
| WO | WO-2017053886 A2 | 3/2017 |

OTHER PUBLICATIONS

Horm et al., "MUC1 and metastatic cancer, Expression, function and therapeutic targeting," Cell Adhesion and Migration 7:2, 187-198; Mar./Apr. 2013.*
Nath, S. et al., "MUC1: a multifaceted oncoprotein with a key role in cancer progression", Trends in Molecular Medicine, Jun. 2014, vol. 20, No. 6, p. 332-342, Abstract only.
Cahn et al. IUPAC 1974 Recommendations For Section E, Fundamental Stereochemistry, Pure Appl. Chem. 45:13-30 (1976).
Groth et al. Synthesis of aldehyde building blocks protected as acid labile N-Boc N,O-acetals: toward combinatorial solid phase synthesis of novel peptide isosteres. J Comb Chem 3(1):34-44 (2001).
Liu et al. Discovery of tetrahydro-beta-carbolines as inhibitors of the mitotic kinesin KSP. Bioorg Med Chem 18(12):4167-4177 (2010).

(Continued)

*Primary Examiner* — Jared Barsky
(74) *Attorney, Agent, or Firm* — Wilson Sonsini Goodrich & Rosati

(57) ABSTRACT

The present application discloses a method for identifying an agent for the treatment or prevention of cancer or metastatic cancer comprising the steps of contacting stem cell with a potential agent, and identifying an agent that induces differentiation, or inhibits stem cell pluripotency or growth of the stem cell, wherein such agent is determined to be an anti-cancer agent.

21 Claims, 185 Drawing Sheets
Specification includes a Sequence Listing.

(56) References Cited

OTHER PUBLICATIONS

PCT/US2016/053571 International Search Report and Written Opinion dated Apr. 4, 2017.
Zhao et al. Easy generation of an enantiopure general indolalkaloid building block by kinetic resolution. Tetrahedron: Asymmetry 10(20):3899-3905 (1999).
Nichols J, Smith A. "Naive and primed pluripotent states." Cell Stem Cell. 2009;4:487-492.
Silva J, Barrandon O, Nichols J, Kawaguchi J, Theunissen TW, A Smith. "Promotion of reprogramming to ground state pluripotency by signal inhibition." PLoS Biol. 2008;6:e253.
Gafni O, Weinberger L, Mansour AA, Manor YS, Chomsky E, Ben-Yosef D, Kalma Y, Viukov S, Maza I, Zviran A, Rais Y, Shipony Z, Mukamel Z, Krupalnik V, Zerbib M, Geula S, Caspi I, Schneir D, Shwartz T, Gilad S, Amann-Zalcenstein D, Benjamin S, Amit I, Tanay A, Massarwa R, Novershtern N, Hanna JH. "Derivation of novel human ground state naive pluripotent stem cells." Nature. 2013;504:282-286.
Theunissen TW, Powell BE, Wang H, Mitalipova M, Faddah DA, Reddy J, Fan ZP, Maetzel D, Ganz K, Shi L, Lungjangwa T, Imsoonthornruksa S, Stelzer Y, Rangarajan S, D'Alessio A, Zhang J, Gao Q, Dawlaty MM, Young RA, Gray NS, Jaenisch R. "Systematic identification of culture conditions for induction and maintenance of naive human pluripotency." Cell Stem Cell. 2014;15:471-487.
Smagghe BJ, Stewart AK, Carter MG et al. "MUC1* ligand, NM23-H1, is a novel growth factor that maintains human stem cells in a more naive state." PLoS One. 2013;8:e58601.
Hikita ST, Kosik KS, Clegg DO et al. "MUC1* mediates the growth of human pluripotent stem cells." PLoS One. 2008;3:e3312.
Hanna J, Cheng AW, Saha K, Kim J, Lengner CJ, Soldner F, Cassady JP, Muffat J, Carey BW, Jaenisch R. "Human embryonic stem cells with biological and epigenetic characteristics similar to those of mouse ESCs." Proc Natl Acad Sci USA. 2010;107:9222-9227.
Ware CB, Nelson AM, Mecham B, Hesson J, Zhou W, Jonlin EC, Jimenez-Caliani AJ, Deng X, Cavanaugh C, Cook S, Tesar PJ, Okada J, Margaretha L, Sperber H, Choi M, Blau CA, Treuting PM, Hawkins RD, Cirulli V, Ruohola-Baker H. "Derivation of naive human embryonic stem cells." Proc Natl Acad Sci USA. 2014;111:4484-4489.
Belkina AC, Nikolajczyk BS, Denis GV. "BET protein function is required for inflammation: Brd2 genetic disruption and BET inhibitor JQ1 impair mouse macrophage inflammatory responses." J Immunol. 2013; 190(7):3670-8.
Tang X, Peng R, Phillips JE, Deguzman J, Ren Y, Apparsundaram S, Luo Q, Bauer CM, Fuentes ME, DeMartino JA, Tyagi G, Garrido R, Hogaboam CM, Denton CP, Holmes AM, Kitson C, Stevenson CS, Budd DC. "Assessment of Brd4 inhibition in idiopathic pulmonary fibrosis lung fibroblasts and in vivo models of lung fibrosis." Am J Pathol. 2013 183(2):470-9.
Filippakopoulos P, Qi J, Picaud S, Shen Y, Smith WB, Fedorov O, Morse EM, Keates T, Hickman TT, Felletar I, Philpott M, Munro S, McKeown MR, Wang Y, Christie AL, West N, Cameron MJ, Schwartz B, Heightman TD, La Thangue N, French CA, Wiest O, Kung AL, Knapp S, Bradner JE. "Selective inhibition of BET bromodomains." Nature. 2010;468(7327):1067-73.
Horm TM, Bitler BG, Broka DM, Louderbough JM, Schroeder JA. "MUC1 drives c-Met-dependent migration and scattering." Mol Cancer Res. 2012 10(12):1544-54.
Meng XG, Yue SW. "Dexamethasone disrupts cytoskeleton organization and migration of T47D Human breast cancer cells by modulating the AKT/mTOR/RhoA pathway." Asian Pac J Cancer Prev. 2014;15(23):10245-50.
Zheng C1, Fang Y, Tong W, Li G, Wu H, Zhou W, Lin Q, Yang F, Yang Z, Wang P, Peng Y, Pang X, Yi Z, Luo J, Liu M, Chen Y. "Synthesis and biological evaluation of novel tetrahydro-β-carboline derivatives as antitumor growth and metastasis agents through inhibiting the transforming growth factor-β signaling pathway." J Med Chem. 2014;57(3).
Carter MG, Smagghe BJ, Stewart AK, Rapley JA, Lynch E, Bernier KJ, Keating KW, Hatziioannou VM, Hartman EJ, Bamdad CC. "A Primitive Growth Factor, NME7AB, Is Sufficient to Induce Stable Naïve Differentiation." Stem Cells. 2016;34(4):847-59.
Mani SA, Guo W, Liao MJ, Eaton EN, Ayyanan A, Zhou AY, Brooks M, Reinhard F, Zhang CC, Shipitsin M, Campbell LL, Polyak K, Brisken C, Yang J, Weinberg RA. "The epithelial-mesenchymal transition generates cells with properties of stem cells." Cell. 2008;133(4).
S. Meng, L. Zhang, Y. Tang, Q. Tu, L. Zheng, L. Yu, D. Murray, J. Cheng, S.H. Kim, X. Zhou and J. Chen. "BET Inhibitor JQ1 Blocks Inflammation and Bone Destruction." J Dent Res. 2014; 93(7): 657-62.
McInroy et al. "Down-regulation of vimentin expression inhibits carcinoma cell migration and adhesion." Biochem Biophys Res Commun, Jun. 15, 2007, vol. 360, No. 1, pp. 109-114. Entire document.
Sangha et al. "Neurofibromin 1 (NF1) Defects Are Common in Human Ovaries Serous Carcinomas and Co-occur with TP53 Mutations." Neoplasia, Dec. 31, 2008, vol. 10, No. 12, pp. 1362-1372. Entire document.
Lucentini, Jack. "Gene Association Studies Typically Wrong: Reproducible gene-disease associations are few and far between." The Scientist, vol. 18, No. 24, Dec. 20, 2004, pp. 1-6.
Kroese, Mark et al. "Genetic tests and their evaluation: Can we answer the key questions?" Genetics in Medicine, vol. 6, No. 6, Nov./Dec. 2004, pp. 475-480.
Hnisz, Denes et al. "Transcriptional super-enhancers connected to cell identity and disease." Cell, vol. 155, No. 4, Nov. 7, 2013, pp. 1-24.
Ware CB, Nelson AM, Mecham B, Hesson J, Zhou W, Jonlin EC, Jimenez-Caliani AJ, Deng X, Cavanaugh C, Cook S, Tesar PJ, Okada J, Margaretha L, Sperber H, Choi M, Blau CA, Treating PM, Hawkins RD, Cirulli V, Ruohola-Baker H. "Derivation of naive human embryonic stem cells." Proc Natl Acad Sci USA. 2014;111:4484-4489.
Carter MG, Smagghe BJ, Stewart AK, Rapley JA, Lynch E, Bernier KJ, Keating KW, Hatziioannou VM, Hartman EJ, Bamdad CC. "A Primitive Growth Factor, NME7AB, Is Sufficient to Induce Stable Naïve State Human Pluripotency; Reprogramming in This Novel Growth Factor Confers Superior Differentiation." Stem Cells. 2016;34(4):847-59.
CAS Registry No. 1252169-54-2; Entry Date 2010-11-09; 2,2-Dimethyl-N-[4-oxo-4-(1,3,4,9-tetrahydro-1-methyl-2H-pyrido[3,4-b]indol-2-yl)butyl]propenamide [2].
CAS Registry No. 1326621-70-8; Entry Date 2011-09-01; N-[3-(1-Cyclohexyl-1,3,4,9- tetrahydro-2H-pyrido[3,4-b]indol-2-yl)-3-oxopropyl]acetamide [2].
CAS Registry No. 1947367-43-2; Entry Date 2016-07-07; N-[2-Oxo-2-(1,3,4,9-tetrahydro- 2H-pyrido[3,4-b]indol-2-yl)ethyl]cyclopentaneacetamide [2].
CAS Registry No. 337333-14-9; Entry Date 2001-05-22; N-[2-Oxo-2-[1,3,4,9-tetrahydro-1- (1-methylethyl)-2H-pyrido[3,4-b]indol-2-yl]ethyl]tetradecanamide [2].
CAS Registry No. 337338-04-2; Entry Date 2001-05-22; 2,2-Dimethyl-N-[3-oxo-3-[1,3,4,9- tetrahydro-1-(1-methylethyl)-2H-pyrido[3,4-b]indol-2-yl]propyl]-N-(2-phenylethyl)propenamide [2].
CAS Registry No. 337339-22-7; Entry Date 2001-05-22; 3-Methyl-N-[3-oxo-3-[1,3,4,9- tetrahydro-1-(1-methylethyl)-2H-pyrido[3,4-b]indol-2-yl]propyl]-N-(2-phenylethyl)butanamide [2].
CAS Registry No. 337339-62-5; Entry Date 2001-05-22; N'-(1,1-Dimethylethyl)-N-[3-oxo-3- [1,3,4, 9-tetrahydro-1-(1-methylethyl)-2H-pyrido[3,4-b]indol-2-yl]propyl]-N-(2-phenylethyl)urea [2].
CAS Registry No. 337340-09-7; Entry Date 2001-05-22; N'-[3,5-Bis(trifluoromethyl)phenyl]- N-[3-oxo-3-[1,3,4,9-tetrahydro-1-(1-methylethyl)-2H-pyrido[3,4-b]indol-2-yl]propyl]-N-(2- phenylethyl) urea [2].
MN 0716. Registry, Chemical Abstracts Service, Columbus, Ohio, U.S., (May 10, 2001).

(56) References Cited

OTHER PUBLICATIONS

MN 0733. Registry, Chemical Abstracts Service, Columbus, Ohio, U.S., (Oct. 10, 2000).
MN 1058. Registry, Chemical Abstracts Service, Columbus, Ohio, U.S., (May 10, 2001).
U.S. Appl. No. 15/762,897 Office Action dated Jan. 31, 2023.

* cited by examiner

Summary of results in stem cell drug screen: drug candidates added to naïve stem cells versus primed stem cells photographed at 96h; small molecules dosed once at 6µM; "-" indicates no inhibition of pluripotency or proliferation at 6uM, "+" indicates inhibition of pluripotency or proliferation; ND = no data

| Compound | Primed Stem Cells FGFR1 MEFs | Primed Stem Cells no growth factor during experiment | Naïve Stem Cells NME7 on MNC antibody surface | Naïve Stem Cells no growth factor during experiment |
|---|---|---|---|---|
| E6 Fab 40 ug/mL | - | - | + | ++ |
| MUC1* ecd peptide 10 µM | - | - | + | ++ |
| PBS control | ND | ND | - | ND |
| DMSO 0.2% control | ND | ND | - | ND |
| Anti-NME7 Ab #56 | - | - | ND | - |
| Anti-NME7 Ab #61 | - | - | ND | ++ |
| MN0642 | + | + | ++ | ++ |
| MN1130 | + | + | ++++ | ++++ |
| MN0572 | - | + | - | + |
| MN0947 | - | - | - | - |
| MN0129 | - | - | - | - |
| MN0676 | - | - | - | - |
| MN0402 | - | - | - | - |
| MN0992 | - | - | - | - |

Figure 2

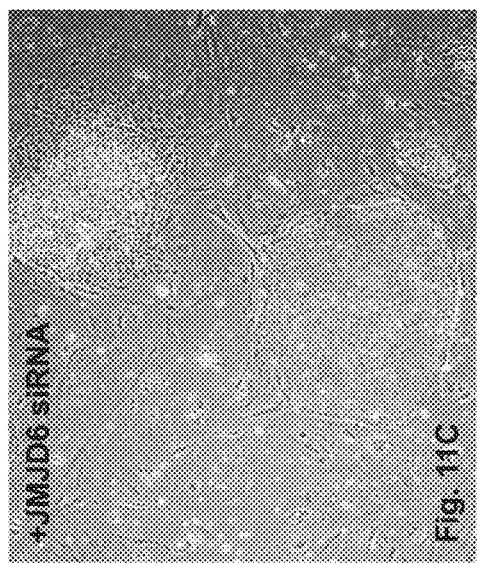
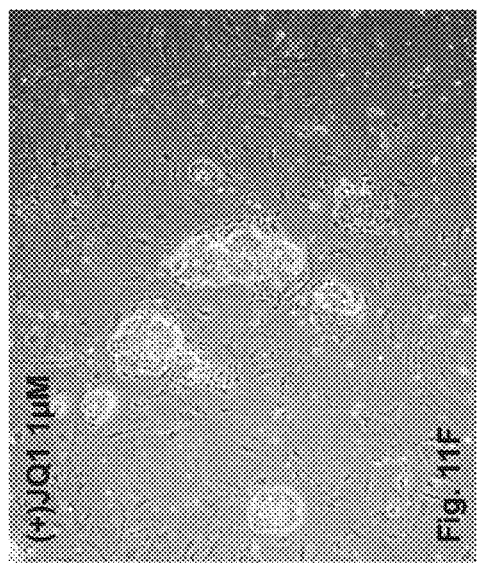
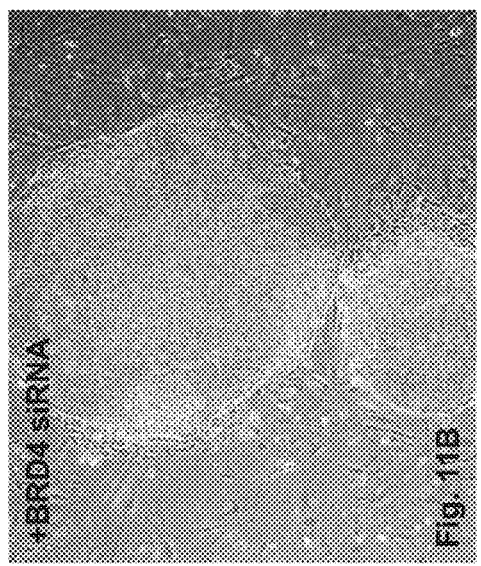
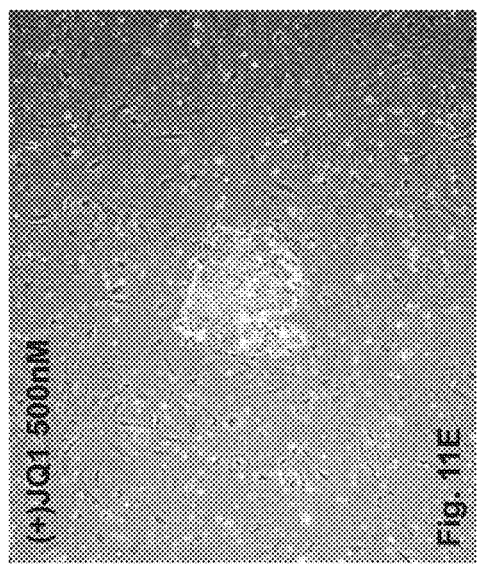
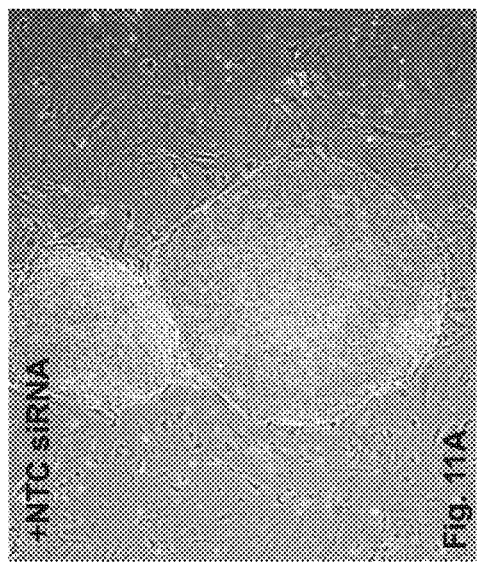
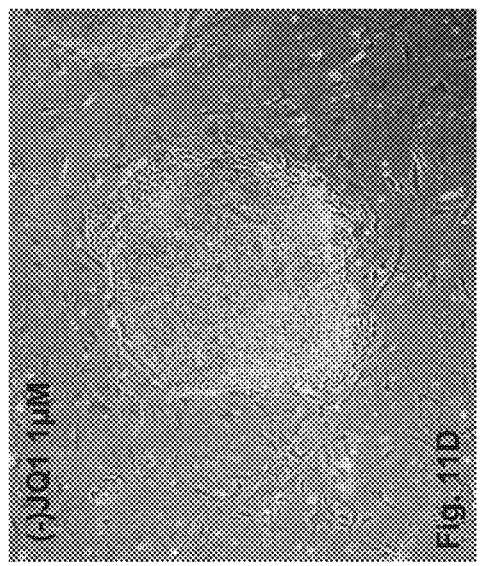
Figure 11

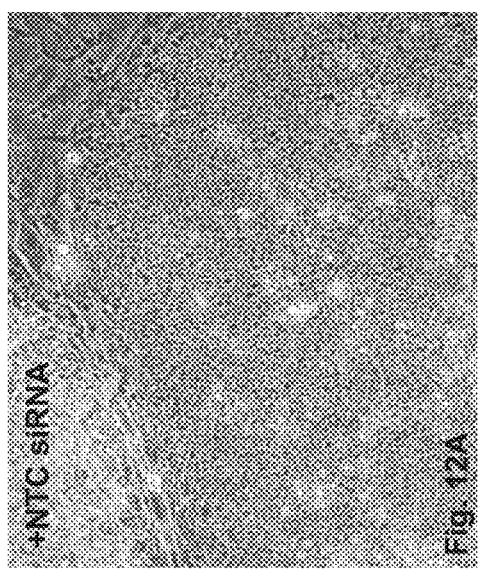
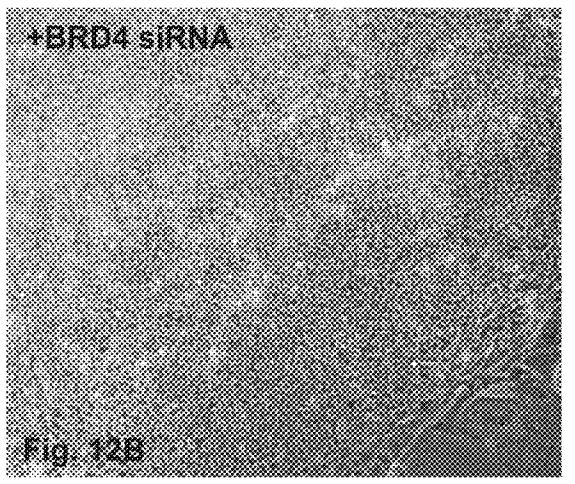
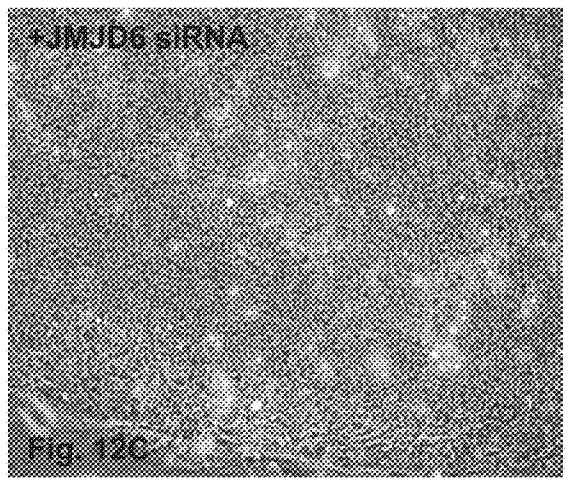
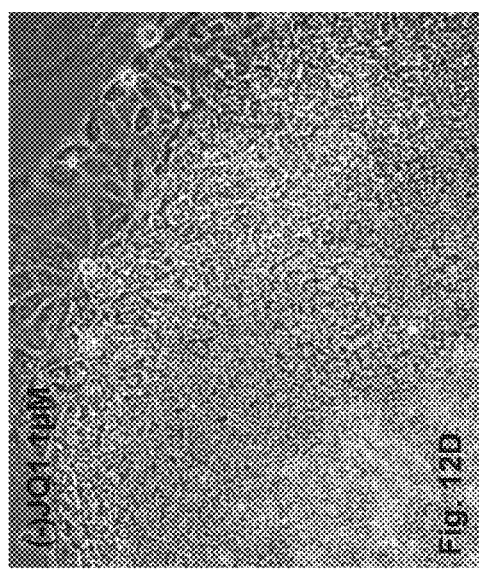
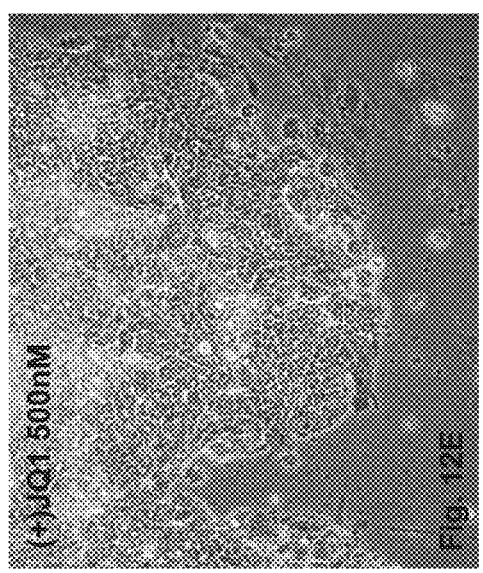
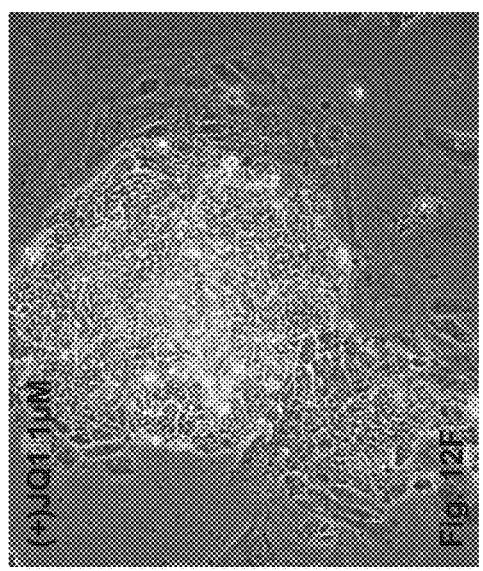
Figure 12

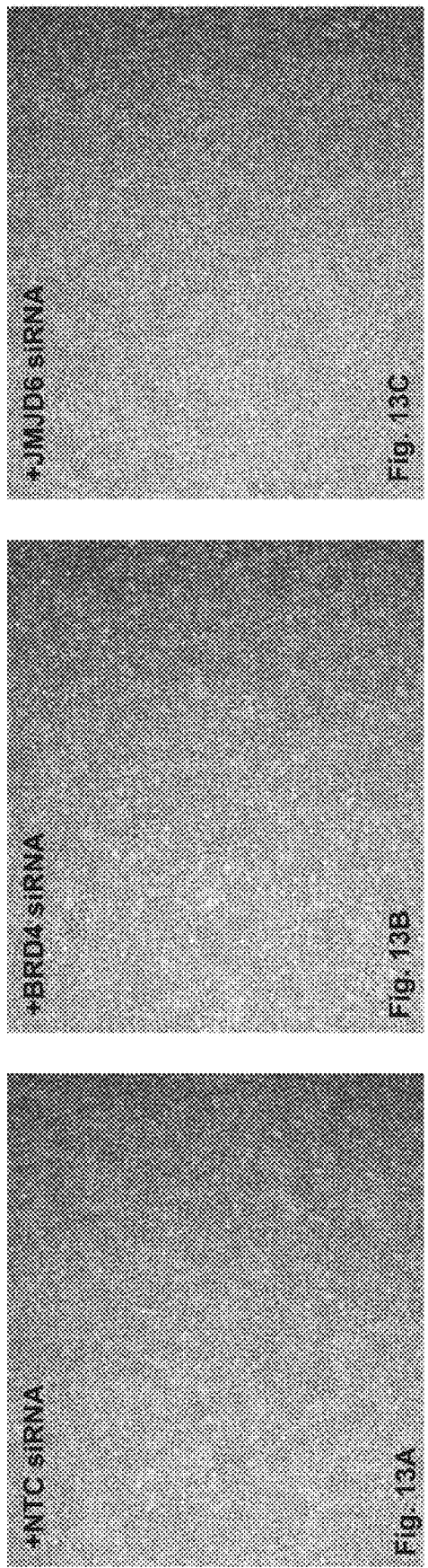
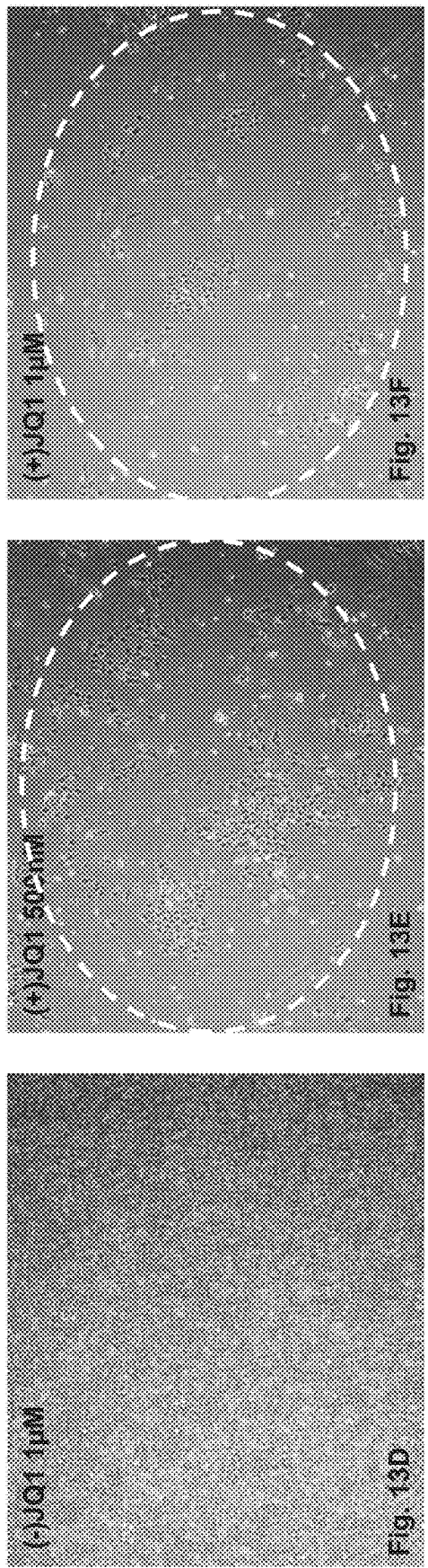
Figure 13

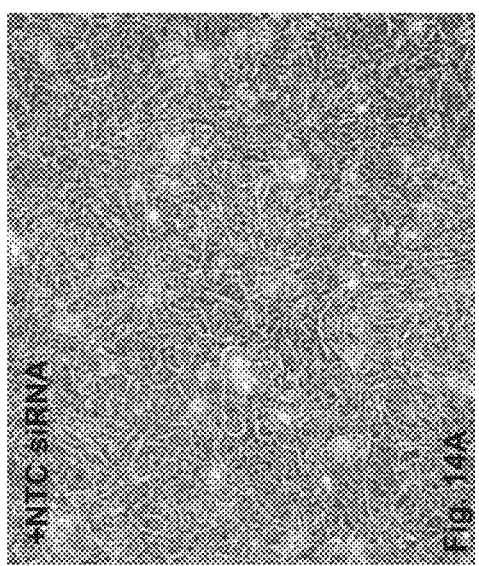
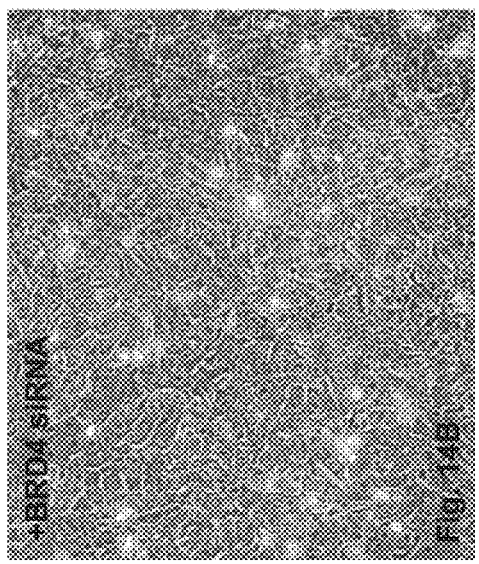
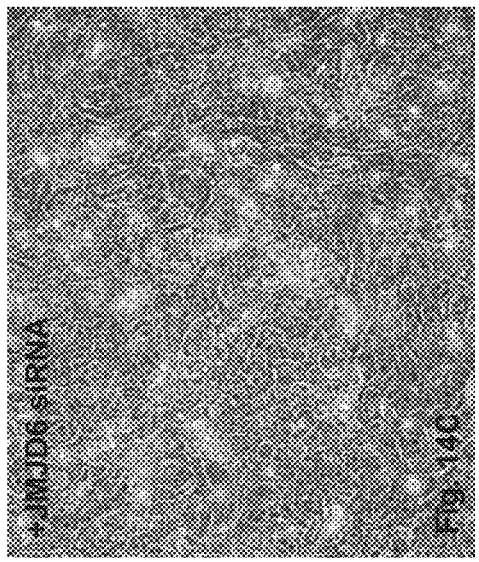
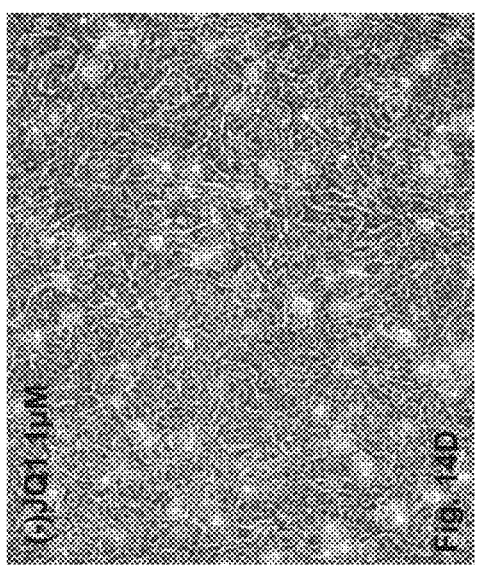
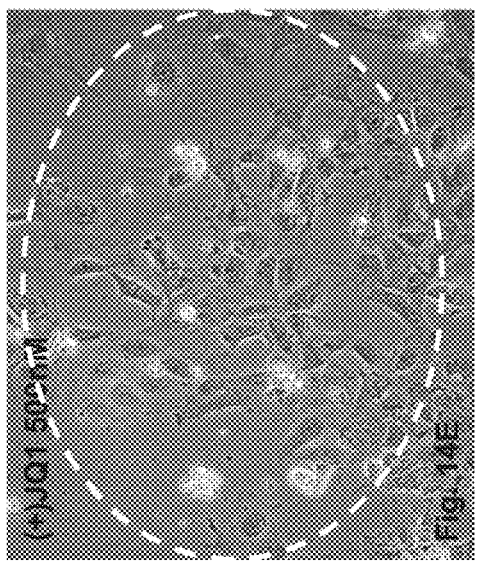
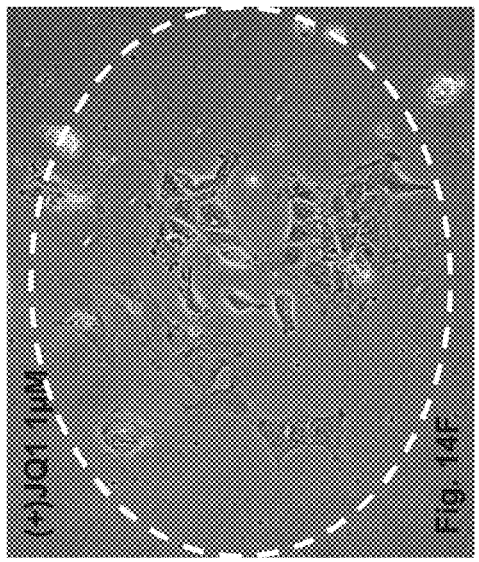
Figure 14

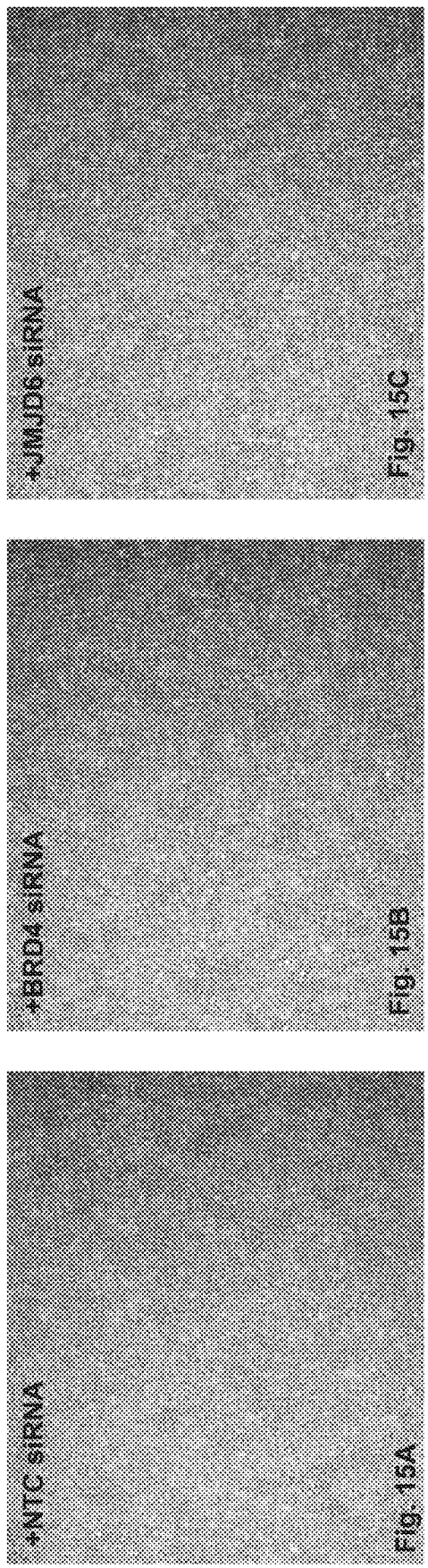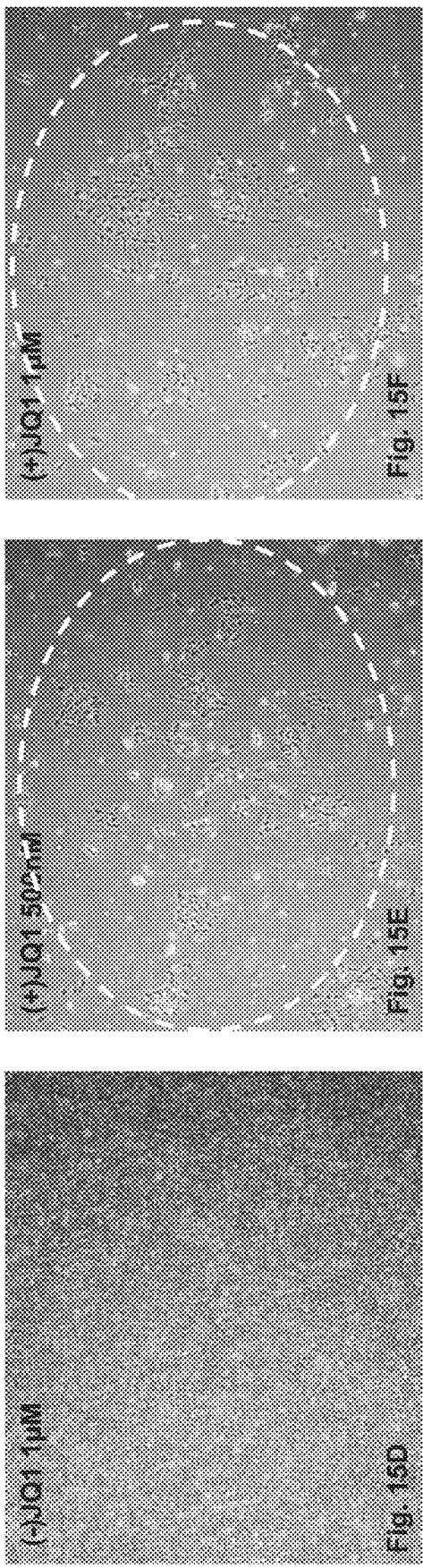
Figure 15

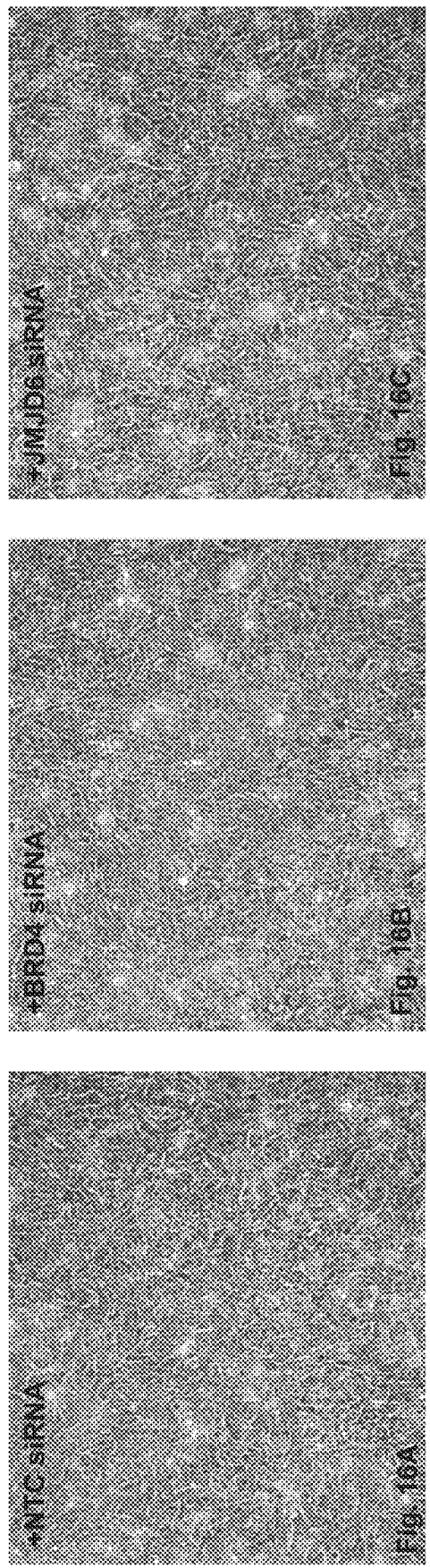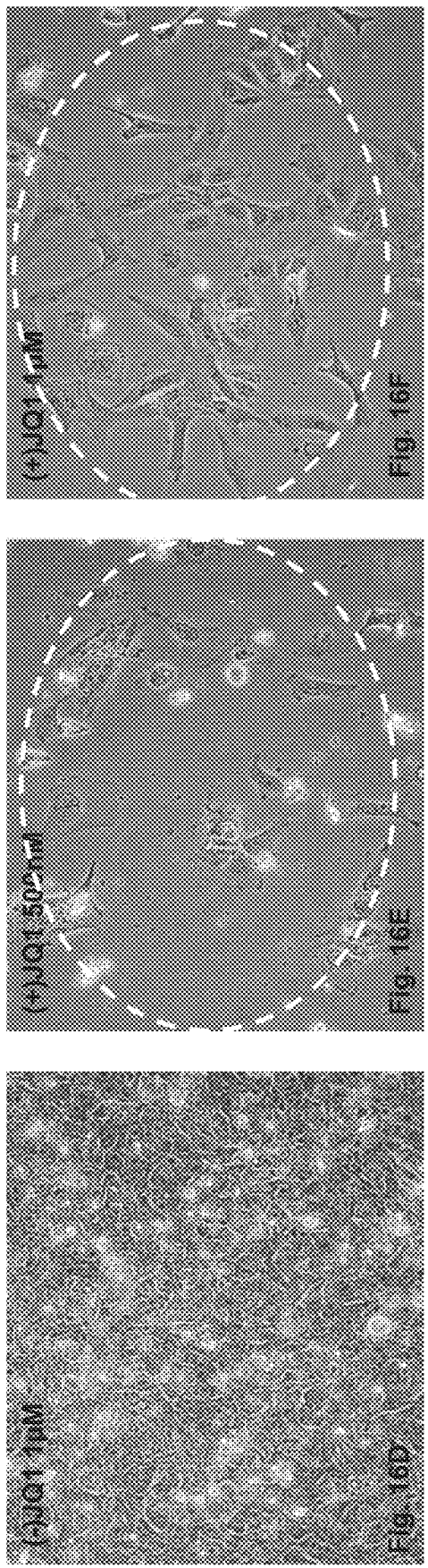
Figure 16

Figure 17
Reference Compounds:
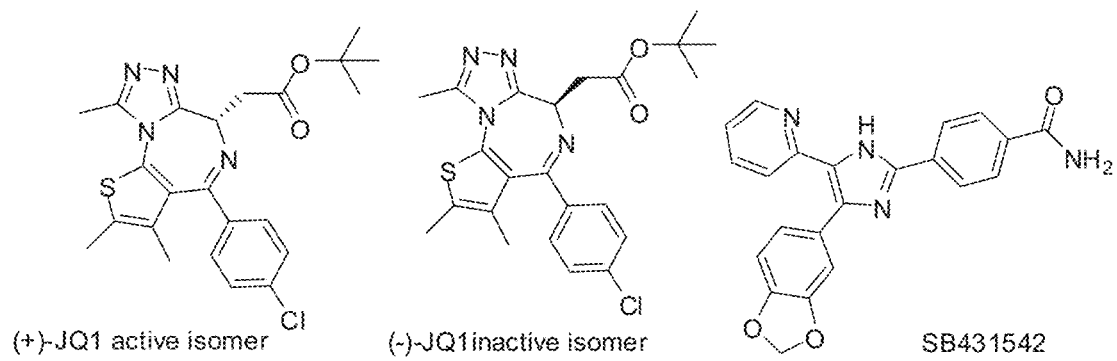
(+)-JQ1 active isomer    (-)-JQ1 inactive isomer    SB431542
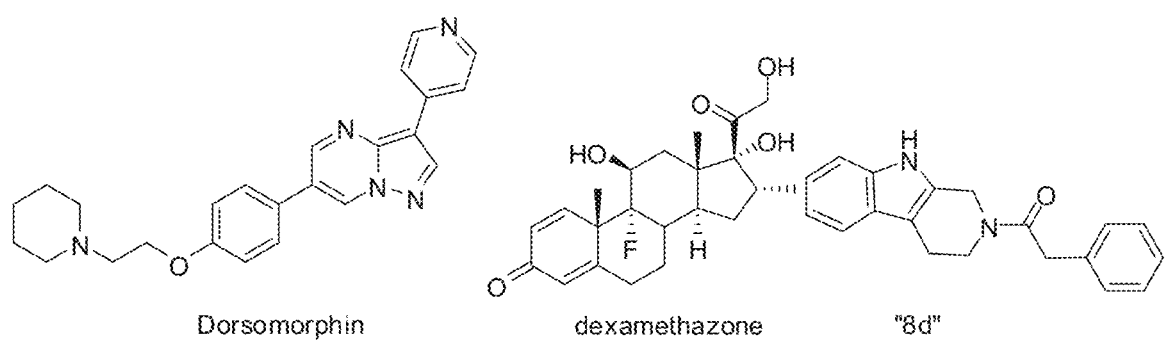
Dorsomorphin    dexamethazone    "8d"
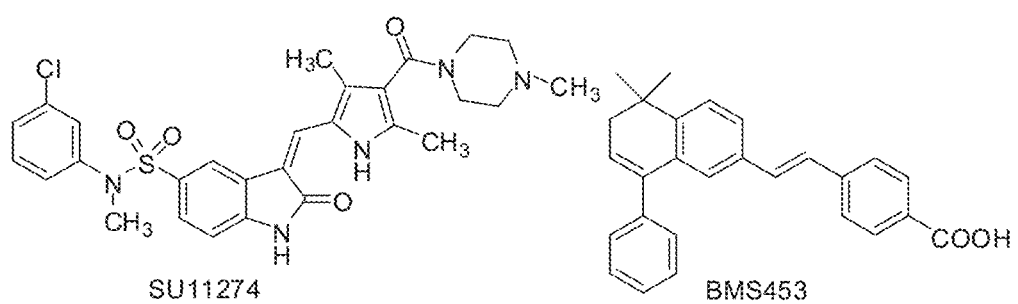
SU11274    BMS453

Compounds of the Patent:

Figure 28

| Compound Number | Other Name | % Inhibition of Cancer Cell Migration @ 6uM | Cancer Cell Migration IC50 (uM) | Primed State Stem Cells Cmpd @ 6uM | Naïve State Stem Cells Cmpd @ 6uM | Inhibit Cancer Cell Proliferation @ 6uM |
|---|---|---|---|---|---|---|
| MN0477 | | 16% | | 0 | 1 | 3 |
| MN0580 | | 3% | | 0 | 2 | 1 |
| MN0618 | | 0% | | 0 | 2 | 2 |
| MN0642 | | 11% | | 0 | 3 | 3 |
| MN0716 | | 33% | | 0 | 1 | 2 |
| MN0733 | | 8% | | 0 | 1 | 1 |
| MN0908 | | 26% | | 1 | 3 | |
| MN1058 | | 16% | | 0 | 1 | 1 |
| MN1130 | | 30% | 13.42 | 1 | 4 | 2** |
| MN1131 | | 36% | | 0 | 1 | 2 |
| MN1132 | | 14% | | 1 | 4 | 1 |
| MN1133 | | 12% | | 1 | 4 | 4 |
| MN1137 | | 32% | 13.42 | 2 | 4 | 3 |
| MN1138 | | 7% | | 1 | 4 | 1 |
| MN1151 | | 60% | | 0 | 2 | 2 |
| MN1152 | | 70% | | 0 | 1 | 3 |
| MN1156 | | 82% | | 0 | 3 | 4 |
| MN1157 | | 36% | | 1 | 3 | 2 |
| MN1158 | | 20% | | 0 | 2 | 1 |
| MN1160 | | 24% | | 0 | 2 | 1 |
| MN1169 | | 0% | | 4 | 4 | 4 |
| MN1171 | | 21% | | 1 | 1 | 1 |
| MN1172 | | 18% | | 0 | 3 | 2 |
| - | (+)-JQ1 | 0% | | 2 | 4 | 3*** |
| - | (-)-JQ1 | 10% | | 1 | 1 | 0*** |
| - | SB431542 | 3% | | 1 | 2 | 0 |
| - | SU5402 | 0% | | 2 | 4 | 1 |
| - | dorsomorphin | 31% | | 0 | 1 | 1 |
| MN1184 | | 12% | | 0 | 0 | 0 |
| MN1186 | | 34% | 6.31 | 2 | 4 | 3* |
| MN1188 | | 8% | | 2 | 3 | 1 |
| MN1189 | | 23% | | 1 | 4 | 1 |
| MN1190 | | 48% | 4.32 | 1 | 3 | 1* |
| MN1193 | | 10% | | 0 | 0 | 0* |
| MN1194 | | 64% | 5.20-5.46 | 1 | 4 | 3* |
| MN1195 | | 53% | 2.86 | 0 | 2 | 3* |
| MN1197 | | 12% | | 0 | 4 | 4 |
| MN1203 | | 27% | 12.33 | 1 | 1 | 1 |
| - | "8d" | 50% | 14.86 | 0 | 0 | ND |
| - | dexamethazone | 34% | | 1 | 1 | ND |
| MN1206 | | 40% | | 0 | 2 | 1 |
| MN1207 | | 21% | | 0 | 2 | 0 |
| MN1208 | | 8% | | 2 | 3 | ND |
| MN1209 | | 8% | | 1 | 1 | 0 |
| MN1210 | | 8% | | 3 | 3 | ND |
| MN1211 | | 11% | | 0 | 1 | 1 |
| MN1212 | | 29% | | 0 | 4 | 1 |
| MN1213 | | 29% | | 0 | 4 | 2 |
| MN1214 | | 26% | | 2 | 3 | 2 |
| - | BMS453 | 7% | | 0 | 0 | ND |
| MN1216 | | 27% | | 0 | 0 | 3 |
| MN1217 | | 26% | | 1 | 1 | 3 |
| MN1218 | | 12% | | 2 | 0 | 0 |
| MN1219 | | 0% | | 1 | 1 | 2 |
| MN1220 | | 30% | 6.37 | 2 | 2 | 2* |
| MN1221 | | 7% | | 1 | 1 | 2* |

Figure 28 (continued)

| | | | | | | |
|---|---|---|---|---|---|---|
| MN1222 | | 24% | 10.46-15.65 | 0 | 0 | 1* |
| MN1223 | | 18% @ 10uM | 10.04 | 0 | 0 | 0* |
| MN1224 | | 16% @ 10uM | 10.48 | 0 | 0 | 1* |
| MN1225 | | 13% | 10.36 | 0 | 0 | 1* |
| MN1226 | | 53% | 4.08-12.5 | 1 | 1 | 1* |
| MN1227 | | 58% | 2.91-6.24 | 2 | 4 | 3* |
| MN1228 | | 55% | 5.71 | 2 | 4 | 3* |
| MN1229 | | 44% | 3.31 | 2 | 4 | 3* |
| MN1230 | | 26% | 6.53 | 2 | 4 | 3* |
| MN1231 | | 32% @ 10uM | 18.28 | 2 | 2 | 1 |
| MN1232 | | 37% @ 10uM | | 2 | 3 | 1 |
| MN1233 | | 51% | 5.19-5.87 | 1 | 1 | 4 |
| MN1234 | | 27% | 6.12-10.25 | 0 | 0 | 4 |
| MN1235 | | 70% | 3.62-4.41 | 0 | 2 @ 12uM | 4** |
| MN1236 | | 66% | 3.78-5.62 | 0 | 0 | 0 |
| MN1237 | | 54% | 5.22-5.73 | 0 | 0 | 0 |
| MN1238 | | 42% | 4.62-5.19 | 1 | 0 | 0 |
| MN1239 | | 16% | 10.54-11.99 | 1 | 0 | 4 |
| MN1240 | | 35% | 6.37-8.15 | 1 | 0 | 4 |
| MN1241 | | 20% | 10.54-11.72 | 0 | 0 | 0 |
| MN1242 | | 31% | 10.25-10.61 | 0 | 0 | 4 |
| MN1243 | | 43% | 6.83-12.84 | 0 | 1 | 4 |
| MN1244 | | 41% | 7.21-13.2 | 4 | 4 | 3 |
| MN1245 | | 18% | 9.18-11.65 | 0 | 2 | 1 |
| MN1246 | | 61% | 2.1-2.9 | 0 | 3 | 3 |
| MN1247 | | 47% | 5.34 | 3 | 4 | 3 |
| MN1248 | | 29% | 8.82 | 3 | 2 | 1 |
| MN1249 | | 28% | 7.84 | 2 | 1 | 4 |
| MN1250 | | 17% | 9.86 | 3 | 4 | 3 |
| MN1251 | | 15% | 14.81 | 2 | 3 | 2 |
| MN1252 | | 42% | | 2 | 4 | 2 |
| MN1253 | | 21% | | 3 | 4 | 1 |
| MN1254 | | 35% | | 2 | 2 | 4 |
| MN1255 | | 31% | | 1 | 2 | 4 |
| MN1256 | | 16% | | 2 | 2 | 3 |
| MN1257 | | 27% | | 1 | 2 | 2 |
| MN1258 | | 10% | | 0 | 1 | 1 |
| MN1259 | | 71% | | 0 | 2 @ 12uM | 1 |
| MN1260 | | 33% | | 0 | 1 | 1 |
| MN1261 | | 35% | | 0 | 1 | 2 |
| MN1262 | | 18% | | 2 | 3 | 2 |
| MN1263 | | 13% | | 1 | 1 | 2 |
| MN1264 | | 53% | | 0 | 0 | 0 |
| - | SU11274 | 69% @ 6uM | 2.62 | 0 | 1 | 2** |
| MN1265 | | 41% | 2.4 | ND | 4 | 4 |
| MN1266 | | 52% | 1.9 | ND | 3 | 3 |
| MN1270 | | 81% | 2.5 | ND | 0 | 4 |
| MN1271 | | 74% | 2.6 | ND | 0 | 4 |
| MN1272 | | 70% | 2.5 | ND | 0 | 4 |
| MN1279 | | 21% | 19.2 | ND | 0 | 1 |
| MN1280 | | 39% | 11.6 | ND | 2 | 0 |
| MN1285 | | 30% | 6.9 | ND | 2 | 2 |
| MN1286 | | 61% | 3.5 | ND | 1 | 3 |
| MN1289 | | 28% | 7.4 | ND | 4 | 4 |
| MN1290 | | 22% | | ND | 2 | 3 |
| MN1291 | | 25% | | ND | 1 | 1 |

* = 10 uM
** = 20 uM
*** = 1 uM

Naive Stem Cells
MN0477
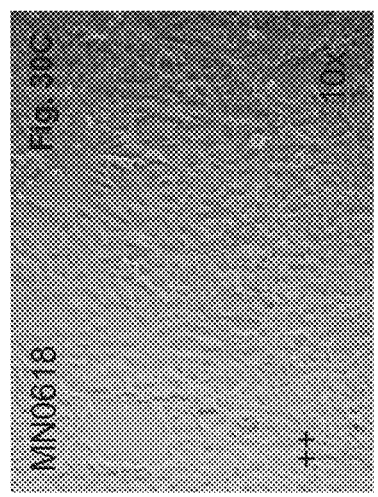
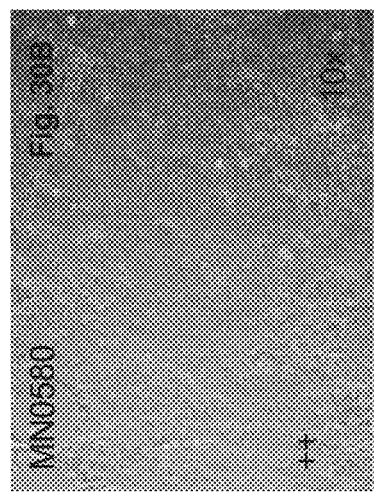
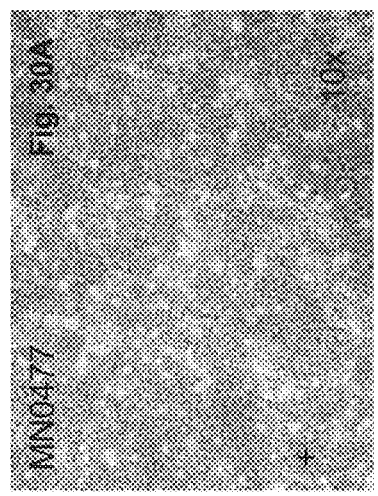
MN0580
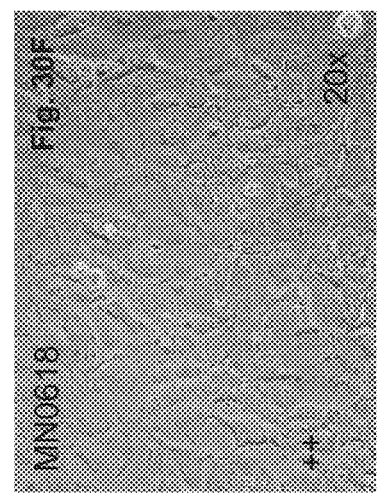
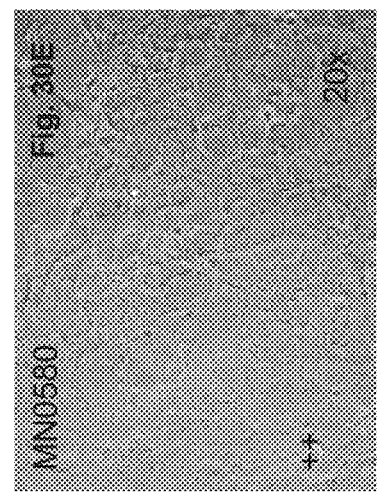
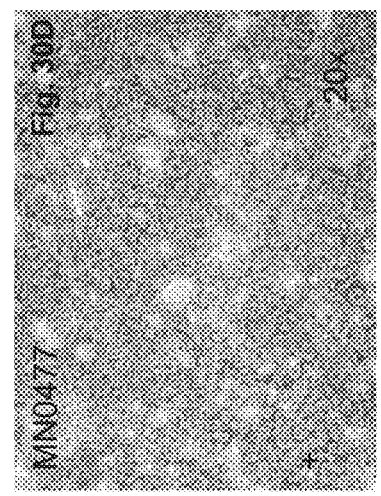
MN0618
Figure 30

Primed Stem Cells
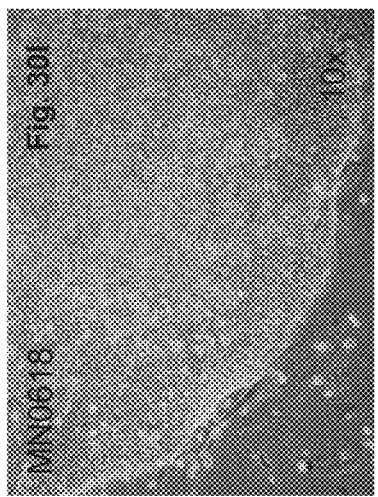
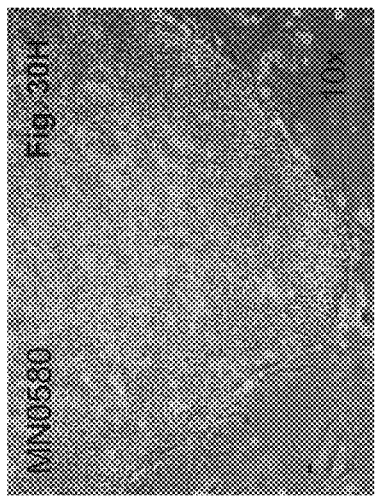
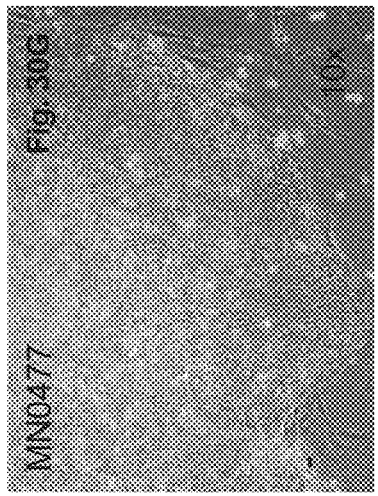
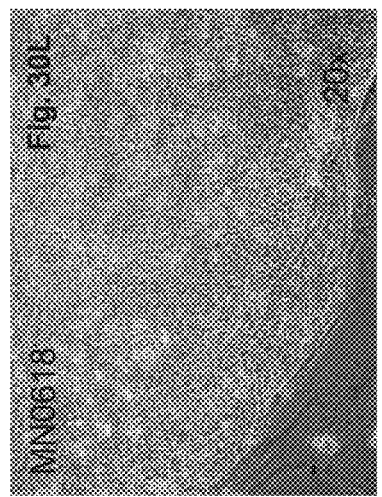
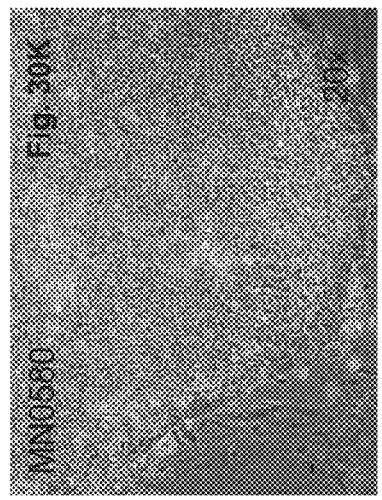
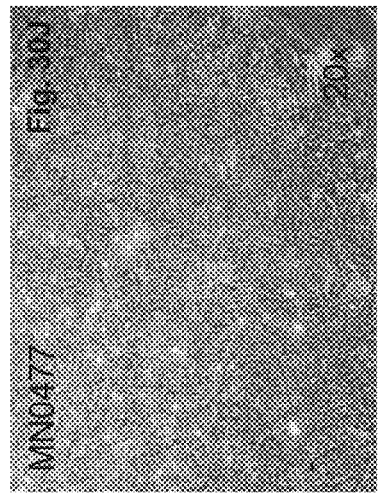
Figure 30

Naive Stem Cells
MN0642
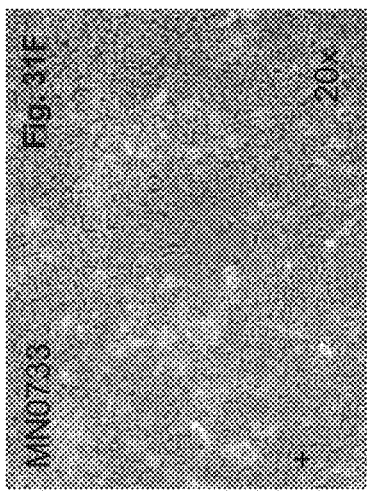
MN0716
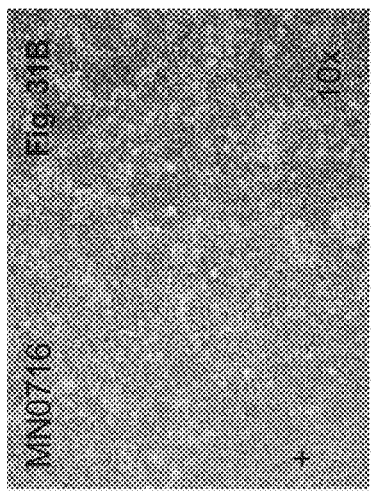
MN0733
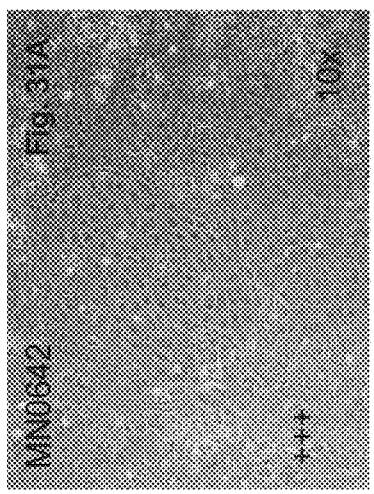
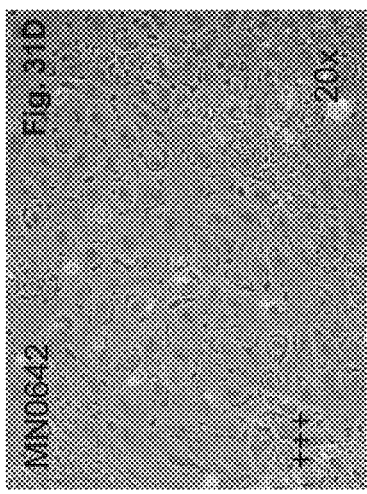
Figure 31

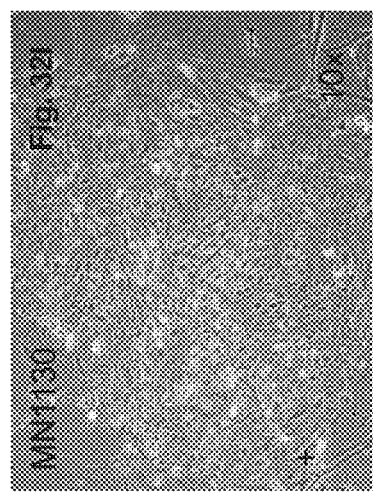
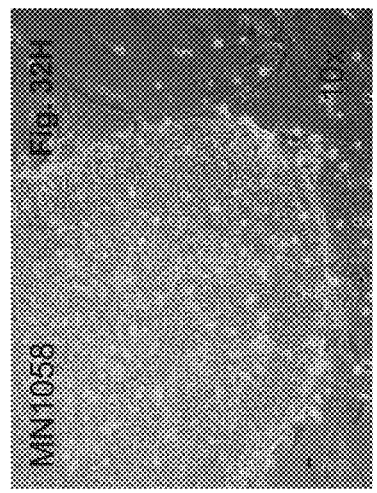
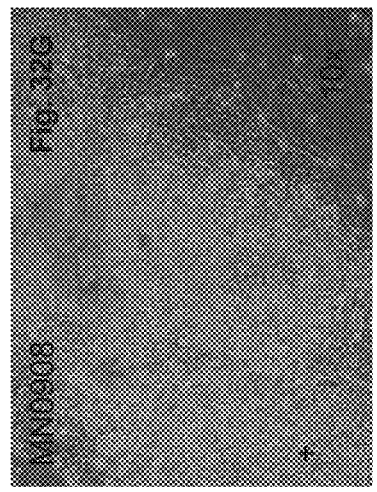
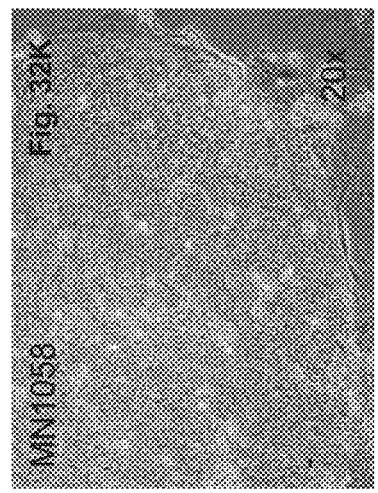
Figure 32

Naïve Stem Cells
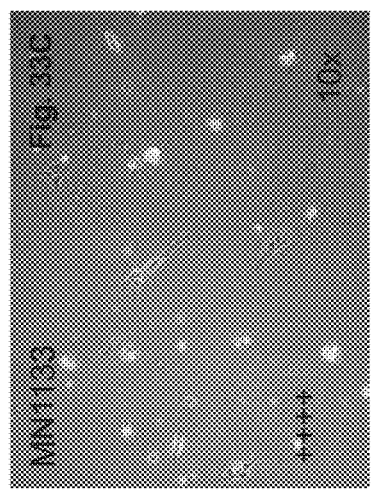
MN1131
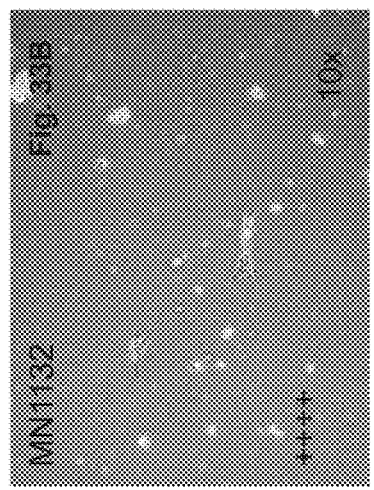
MN1132
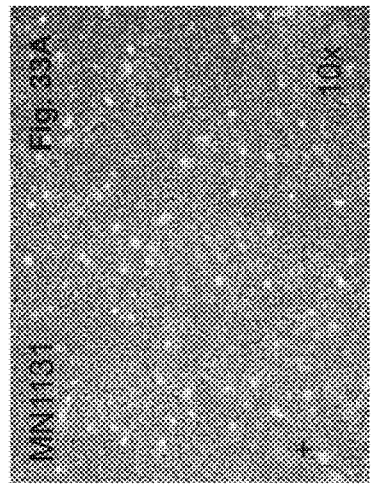
MN1133
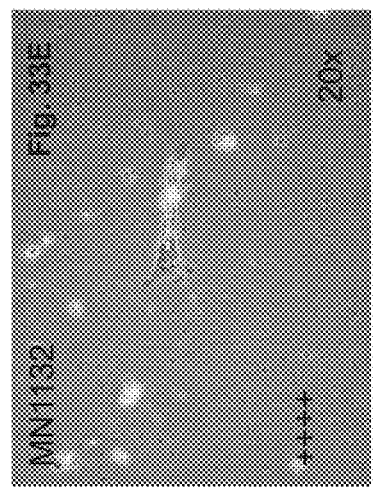
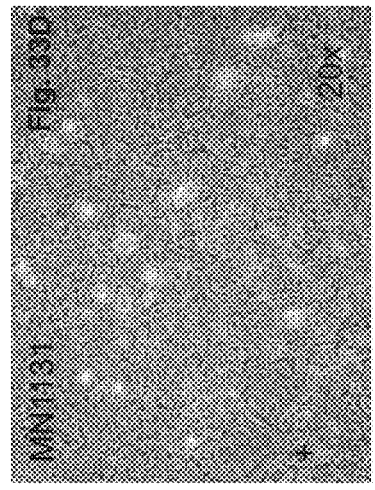
Figure 33

Primed Stem Cells
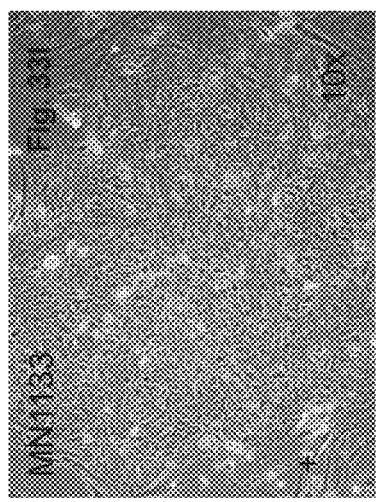
MN1131
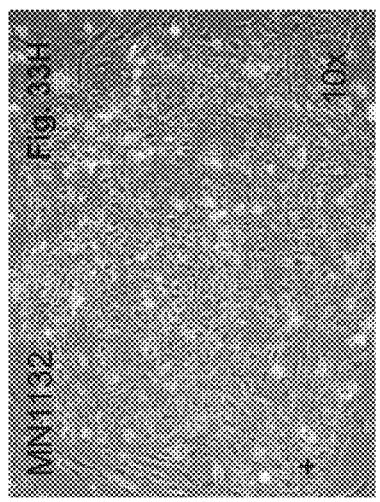
MN1132
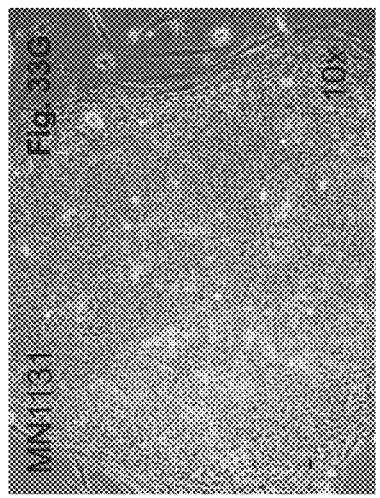
MN1133
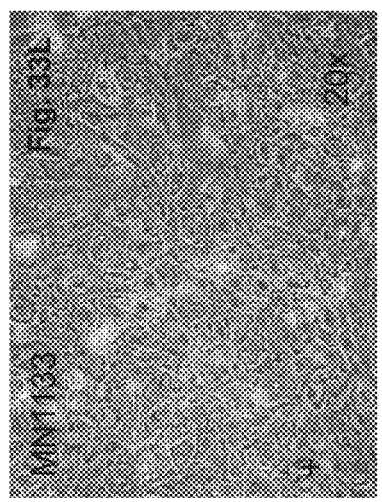
MN1131
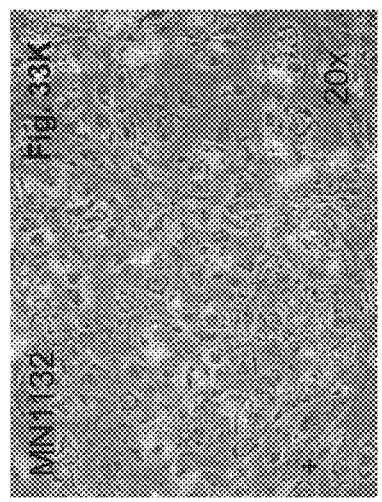
MN1132
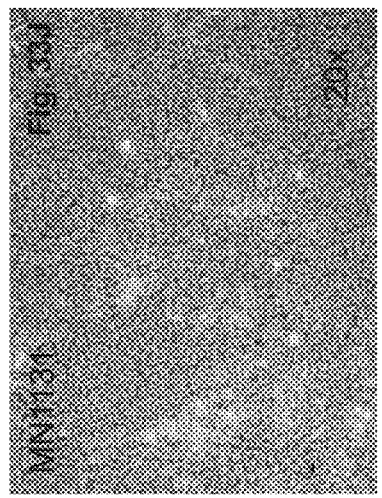
MN1133
Figure 33

Naïve Stem Cells
MN1137
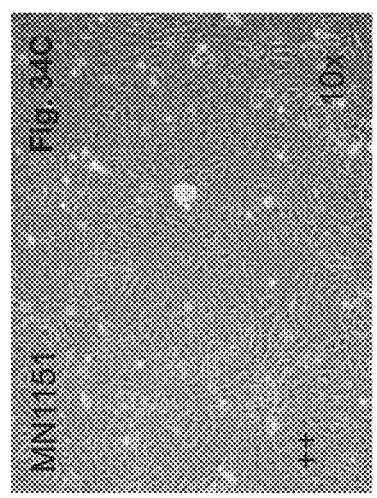
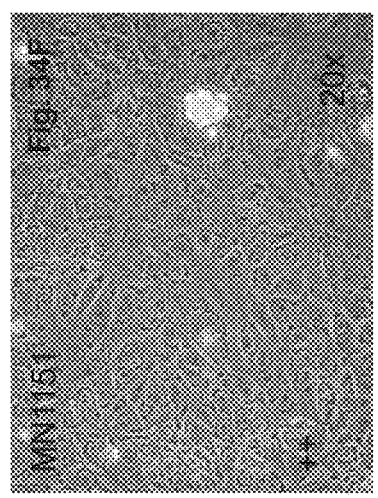
MN1138
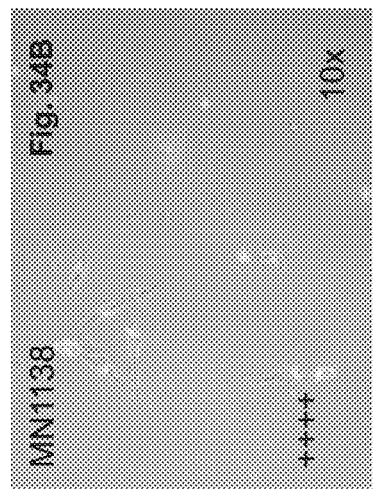
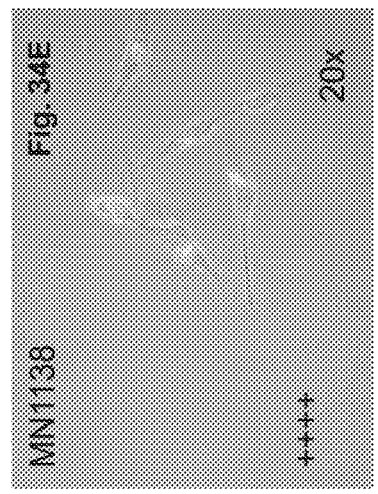
MN1151
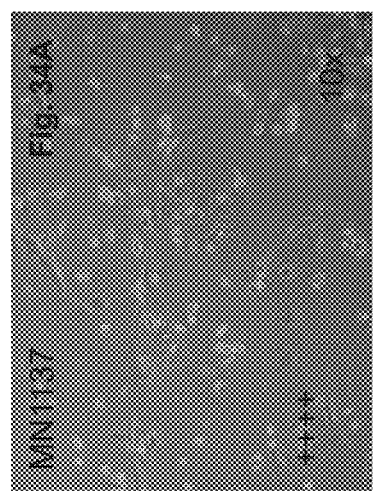
Figure 34

Primed Stem Cells
MN1137 | MN1138 | MN1151
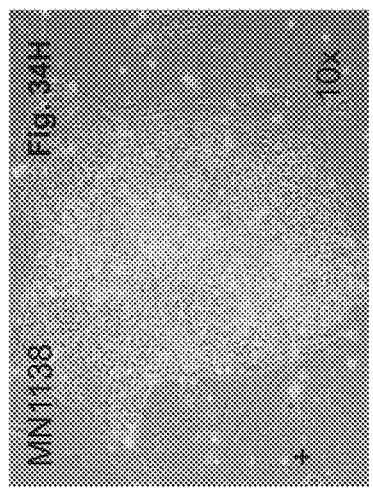 
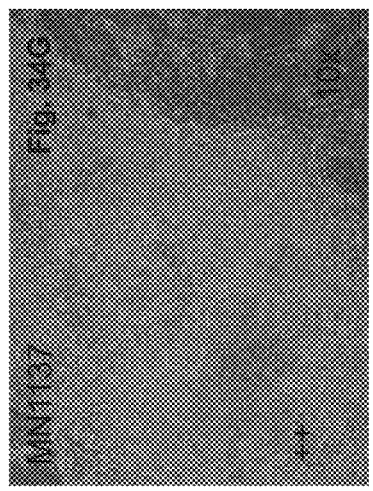 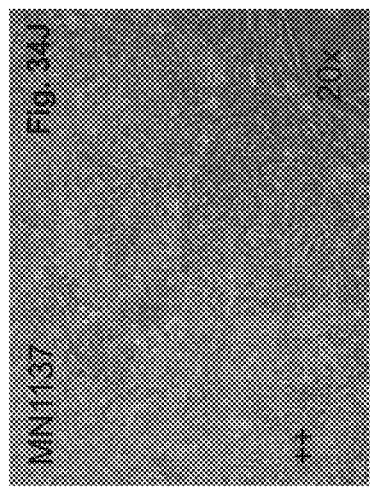
Figure 34

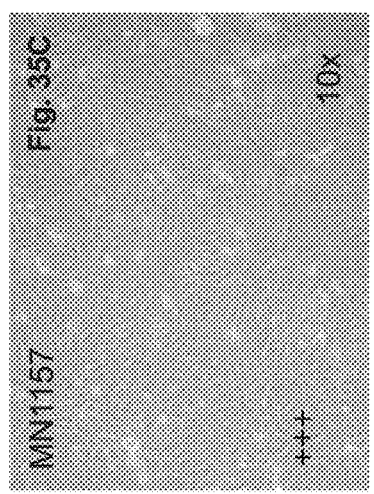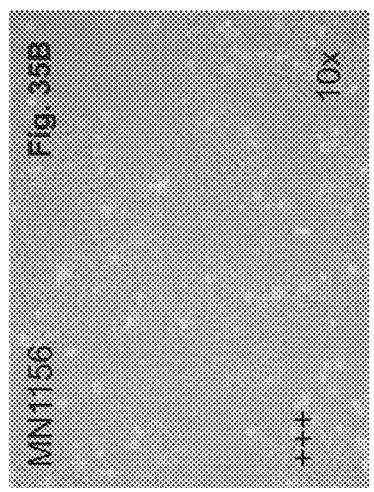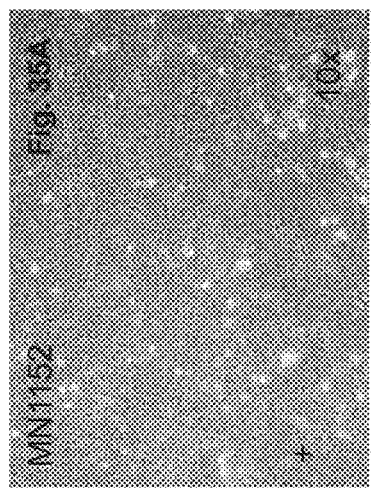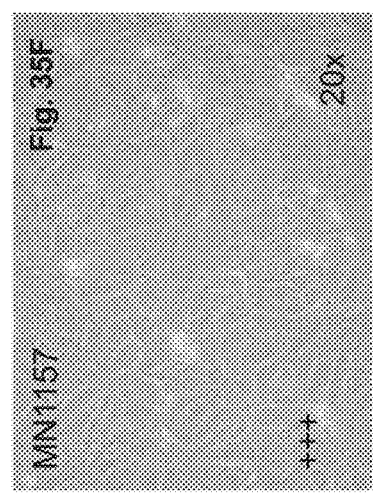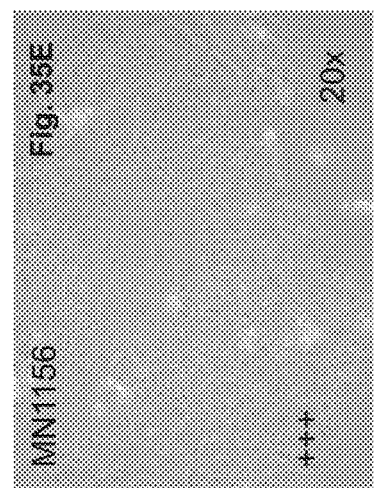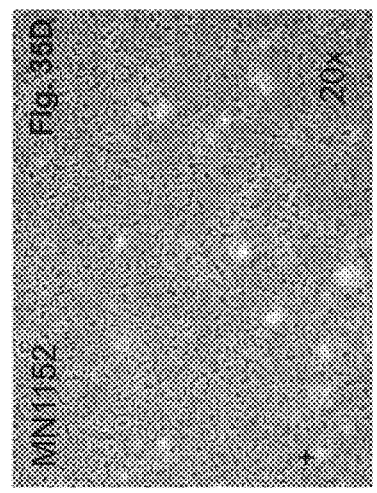
Figure 35

Primed Stem Cells
MN1152
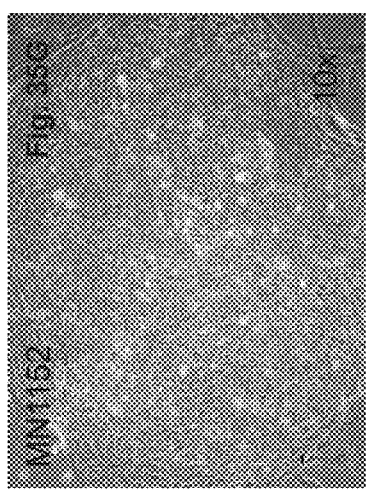
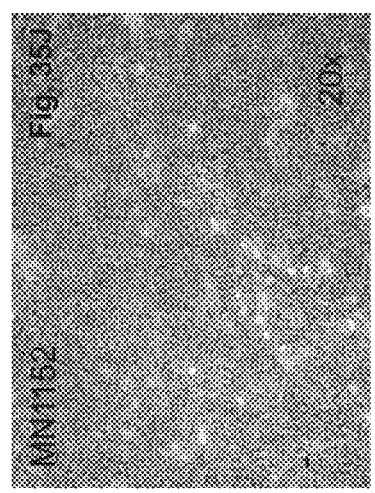
MN1156
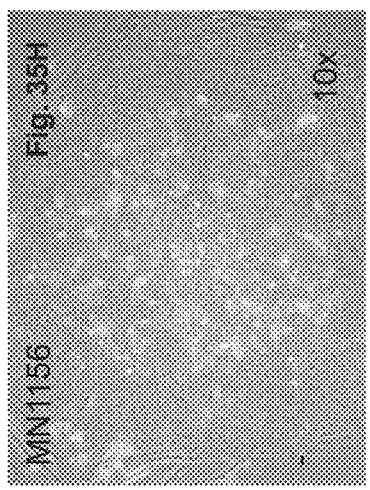
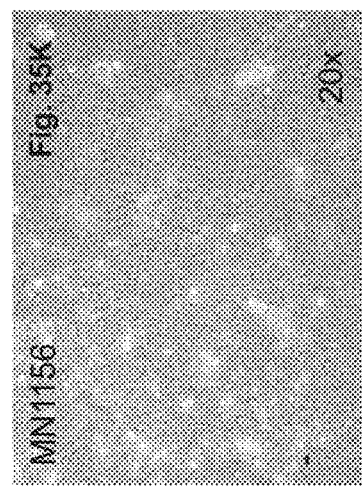
MN1157
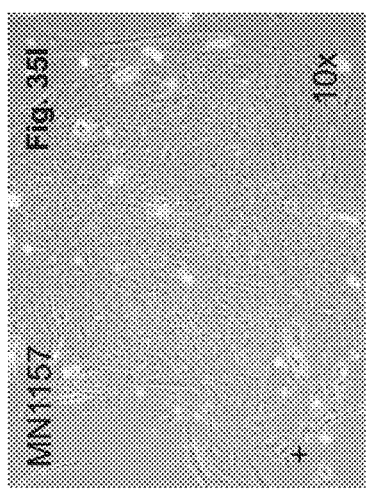
Figure 35

Naïve Stem Cells
MN1158
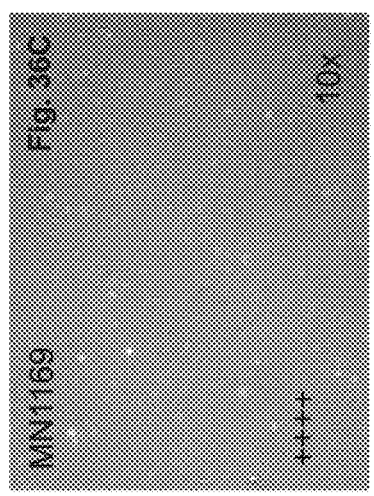
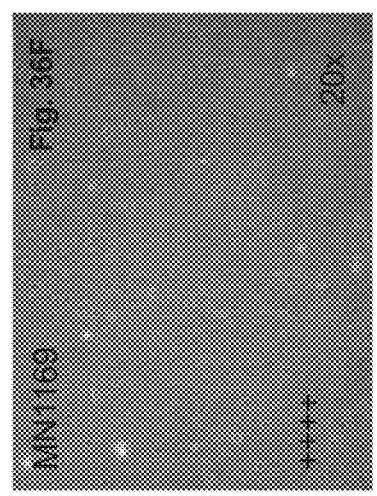
MN1160
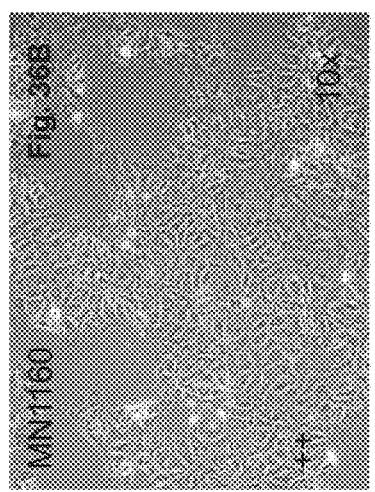
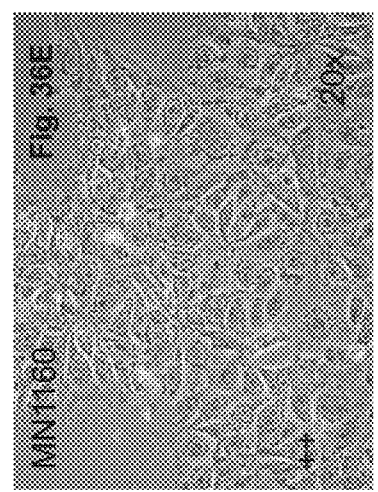
MN1169
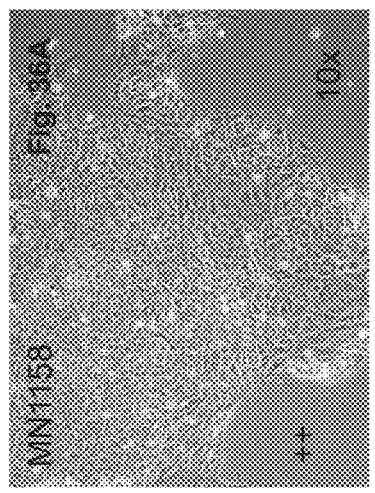
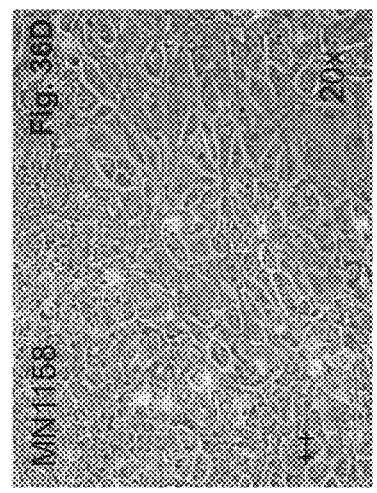
Figure 36

Primed Stem Cells
MN1158
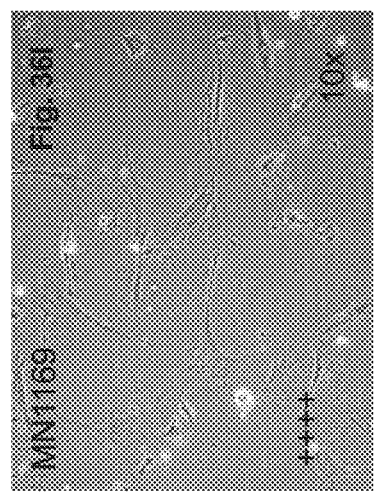
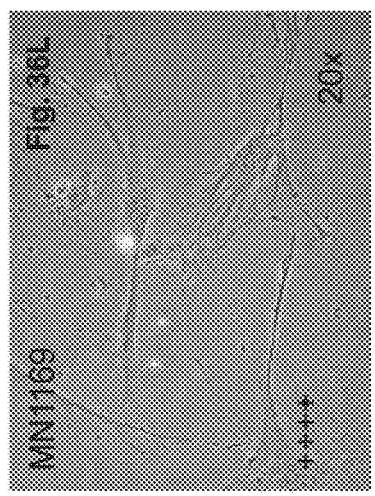
MN1160
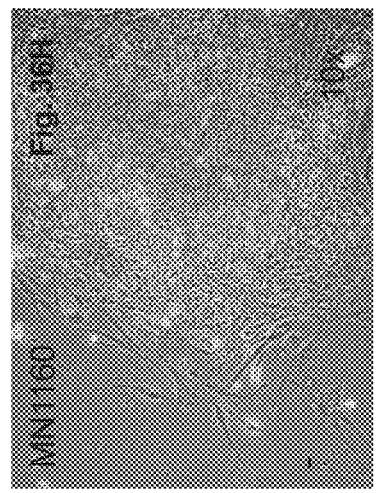
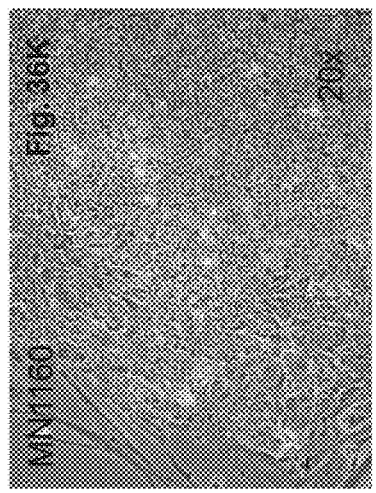
MN1169
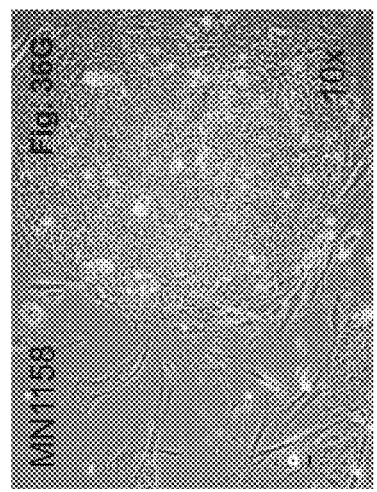
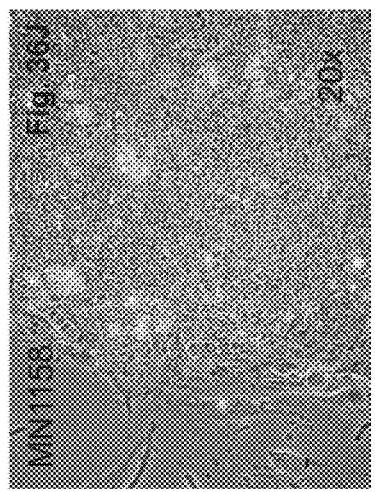
Figure 36

Naïve Stem Cells
MN1171
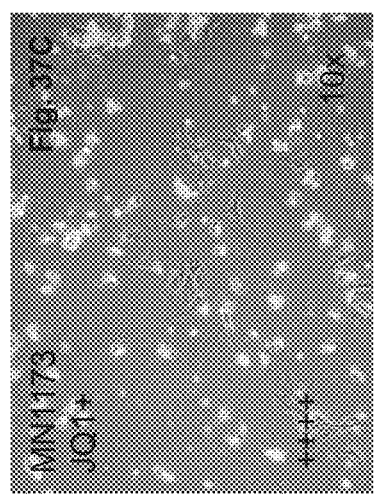
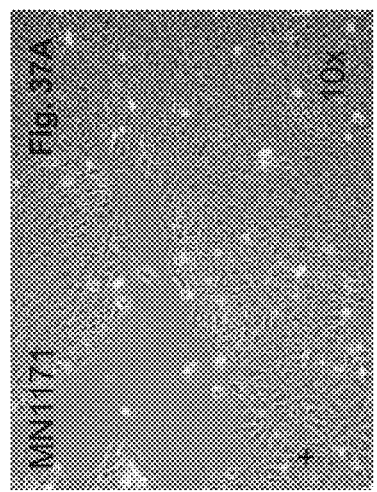
MN1172
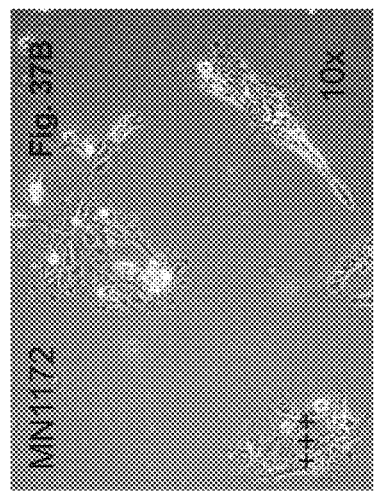
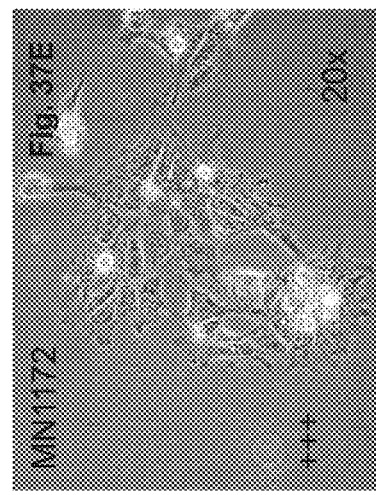
MN1173
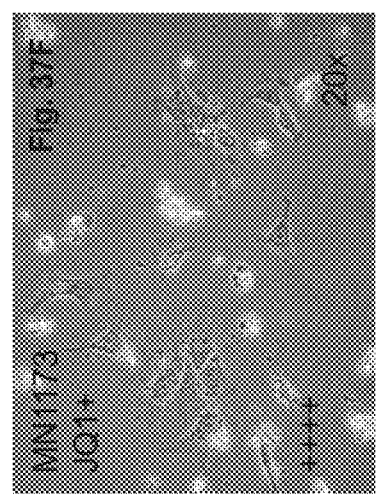
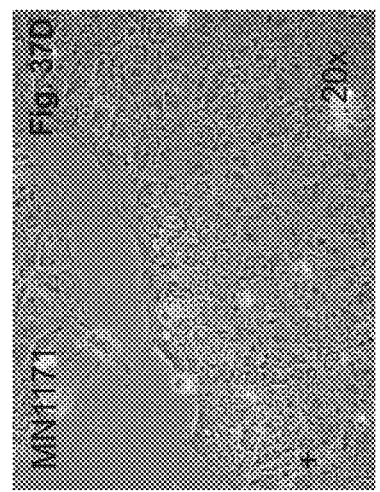
Figure 37

Primed Stem Cells
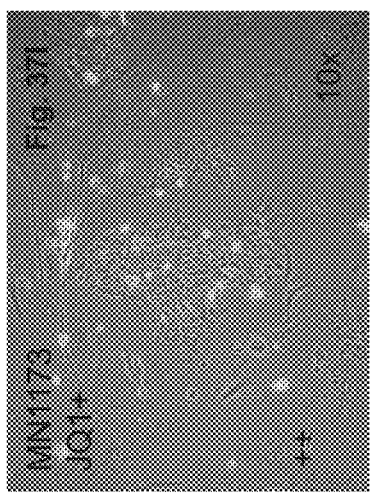
MN1171
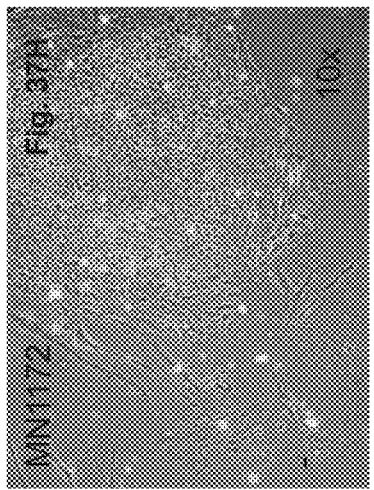
MN1172
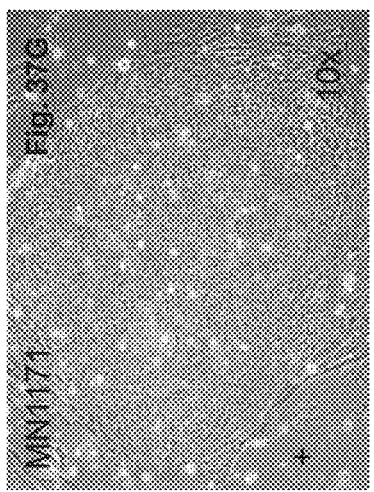
MN1173
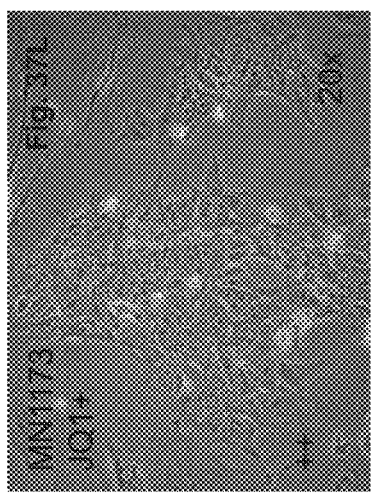
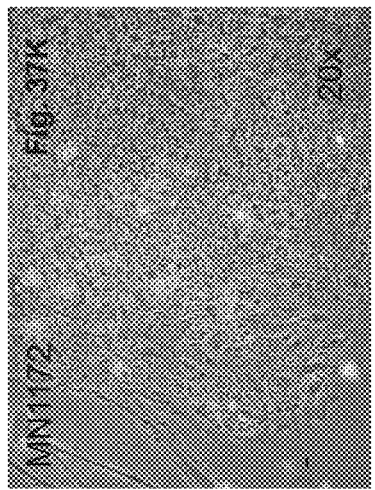
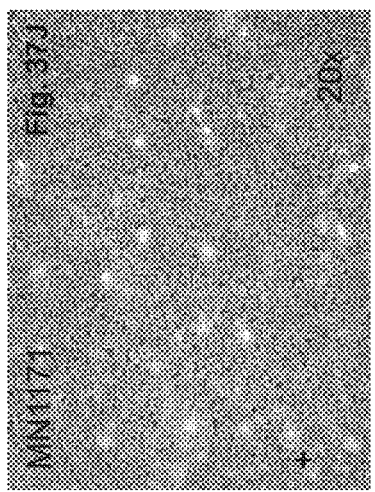
Figure 37

Naïve Stem Cells
MN1174
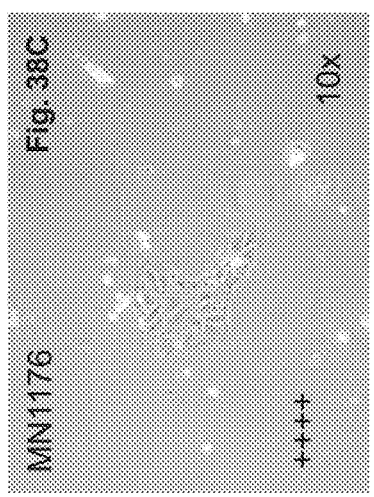
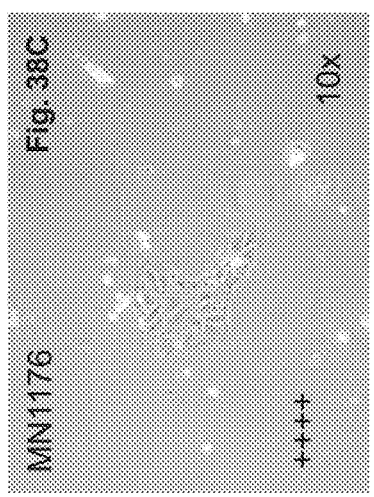
MN1175
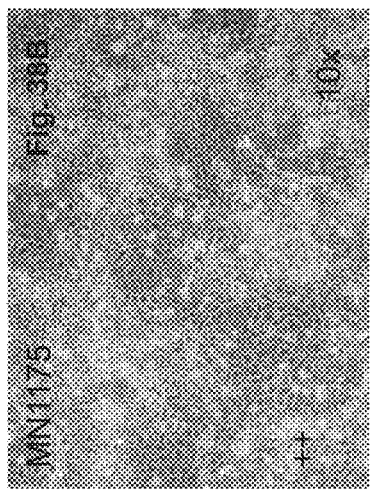
MN1176
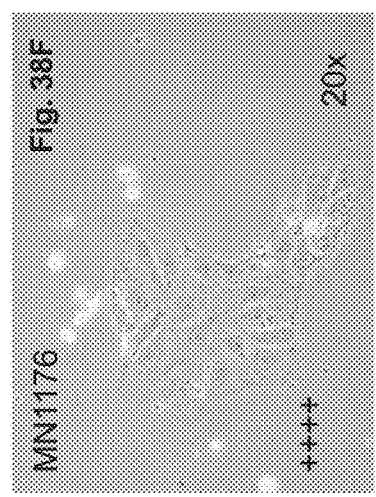
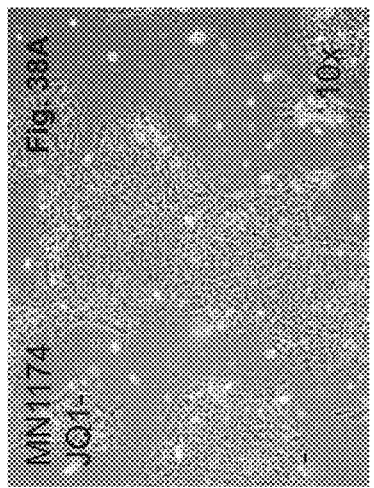
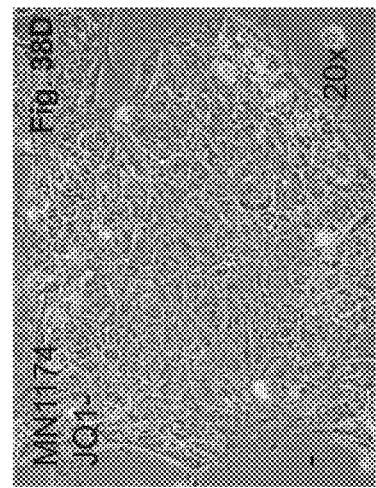
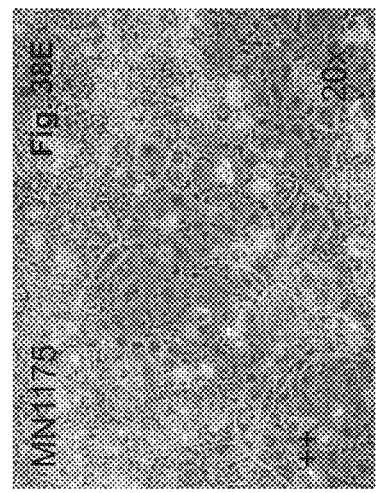
Figure 38

Primed Stem Cells
MN1174
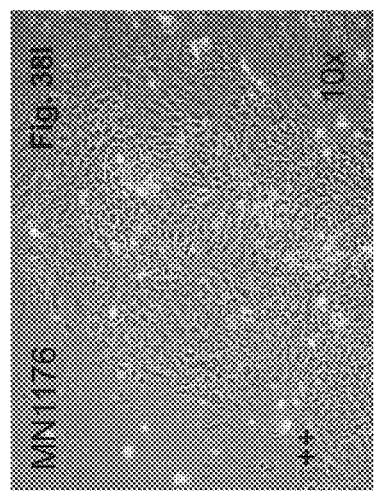 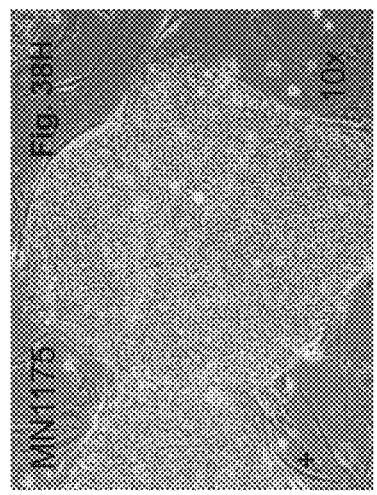 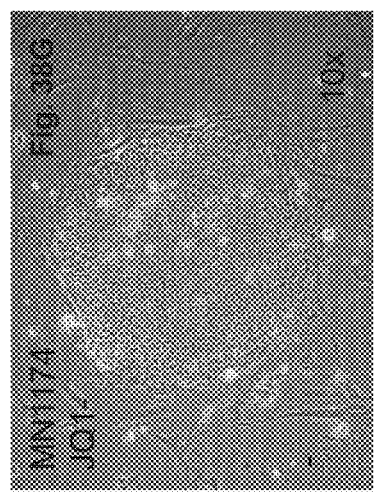
MN1175
MN1176
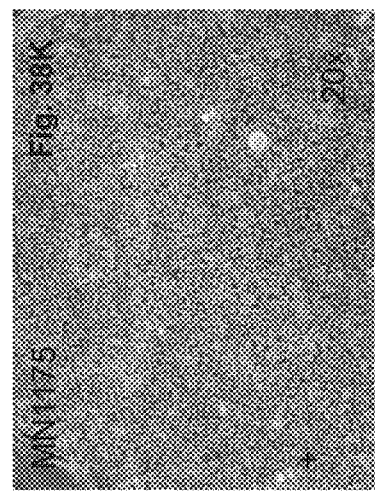 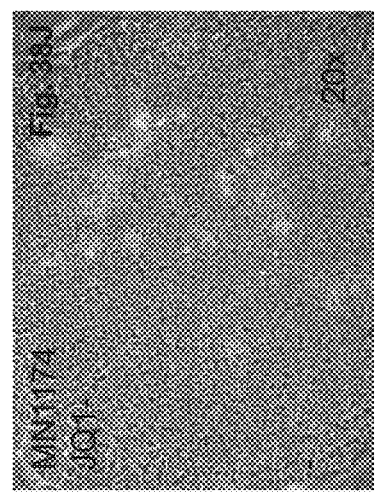
Figure 38

Naïve Stem Cells
MN1177
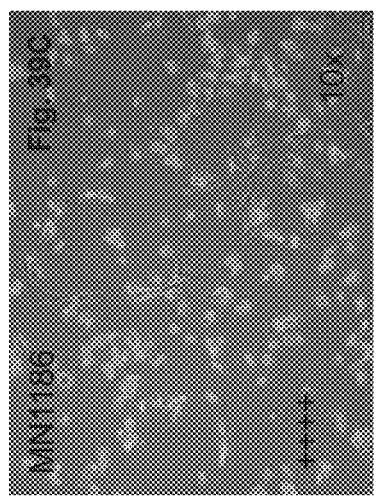
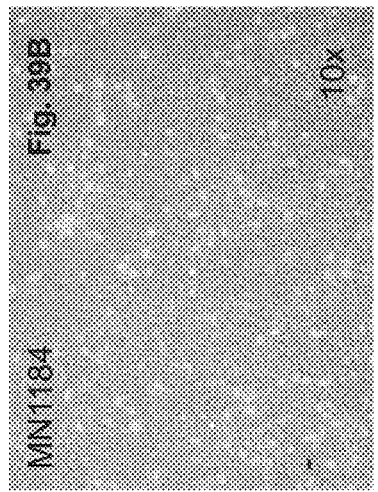
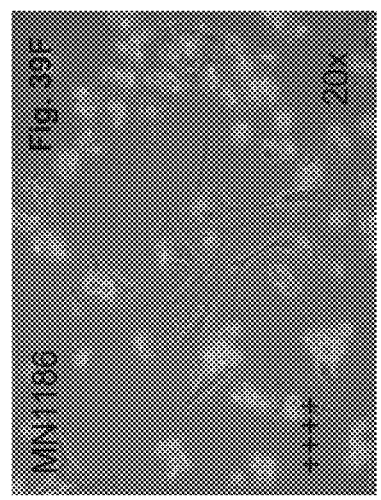
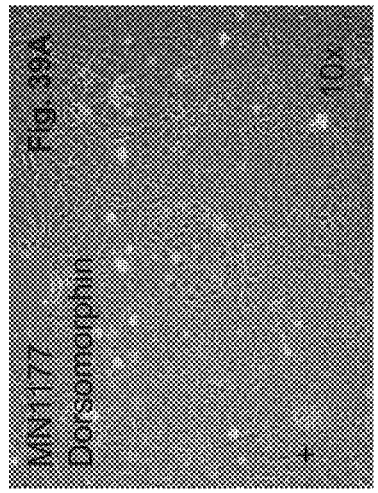
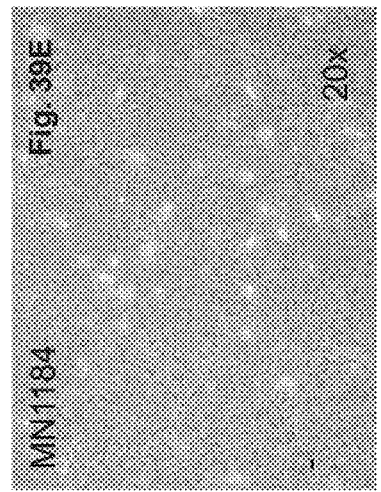
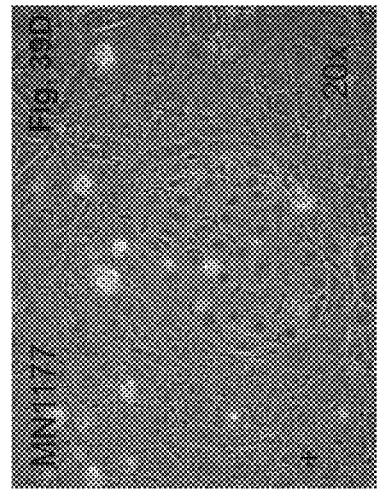
Figure 39

Primed Stem Cells
MN1177 / MN1184 / MN1186
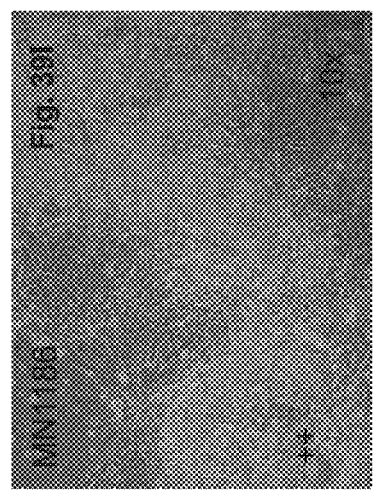
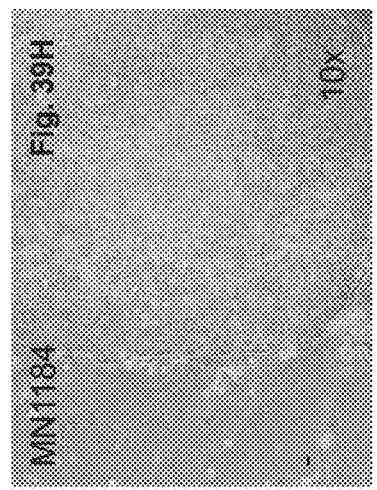
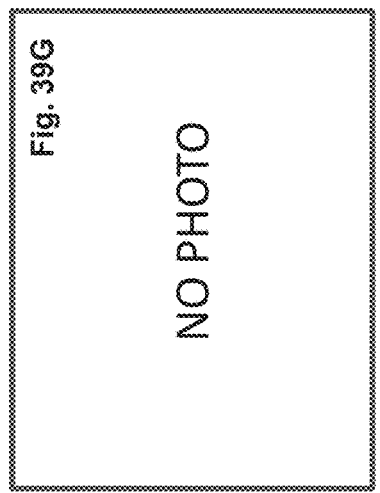
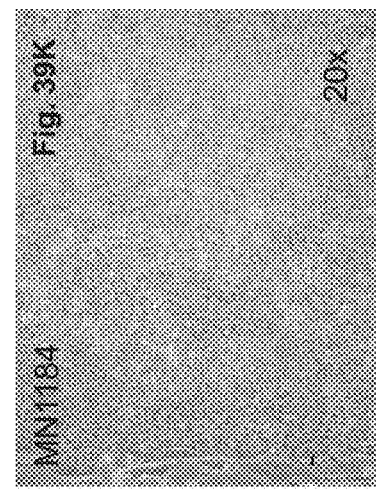
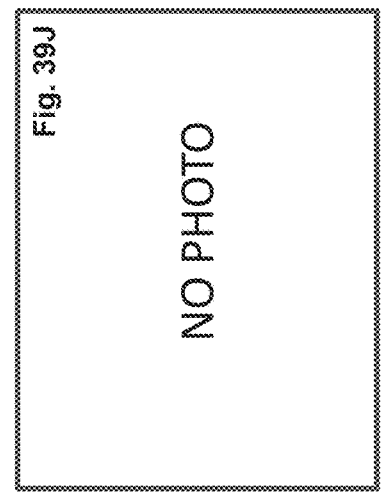
Figure 39

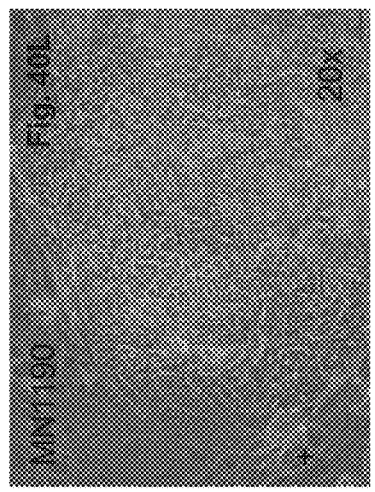
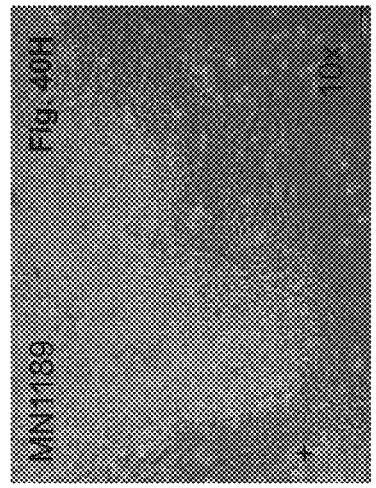
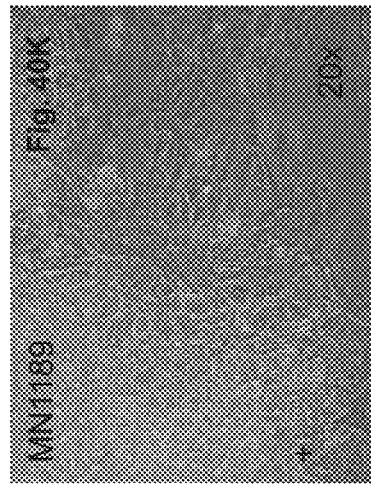
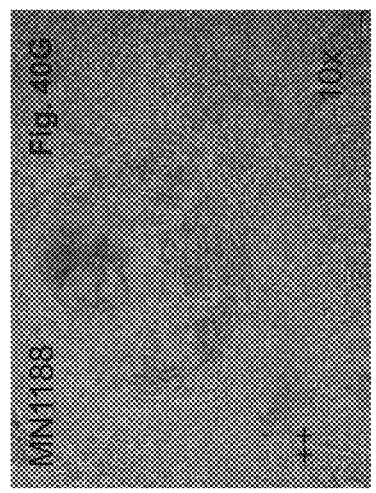
Figure 40

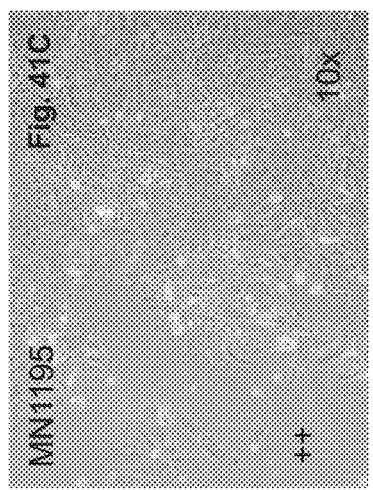
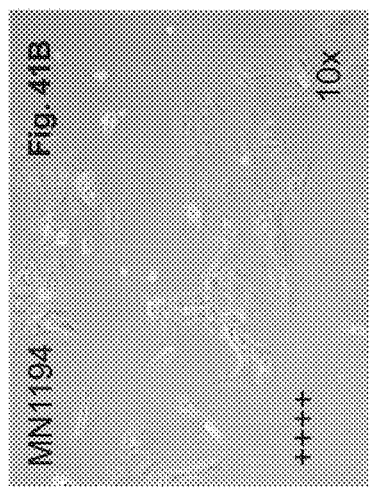
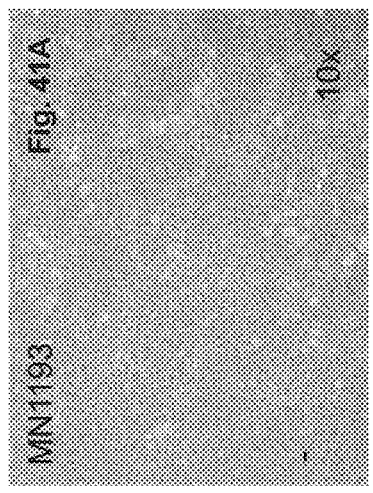
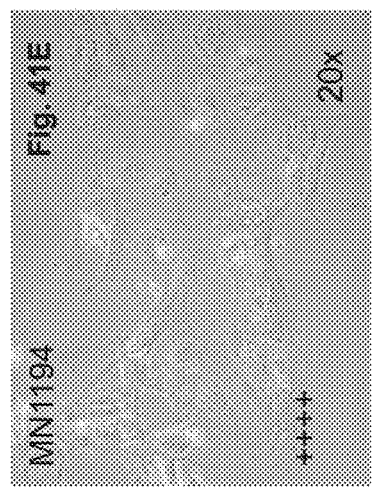
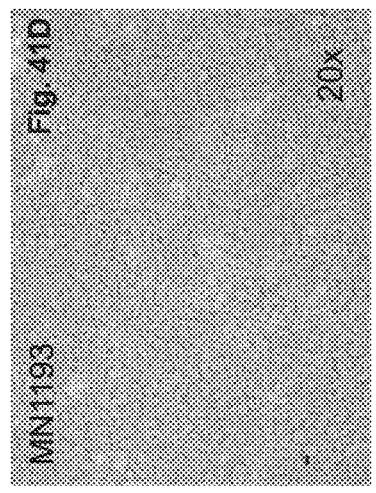
Figure 41

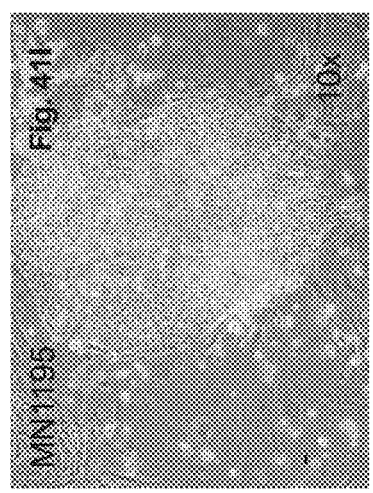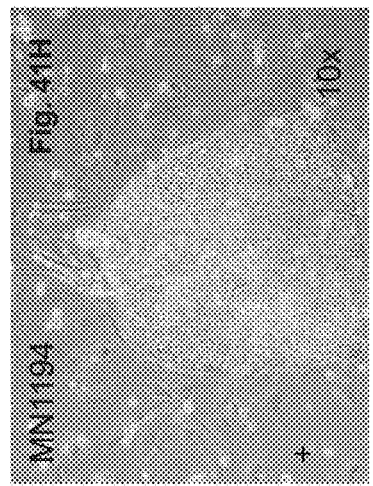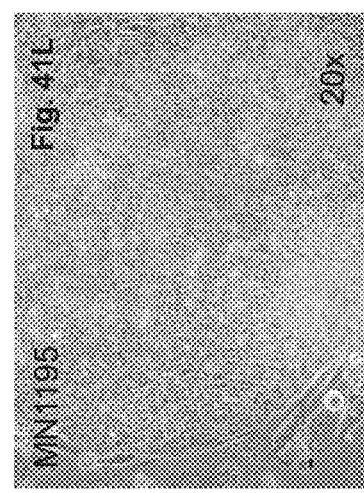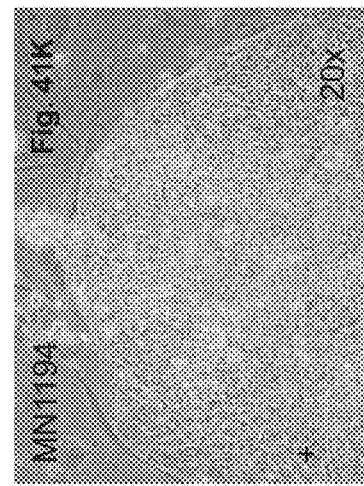
Figure 41

Naïve Stem Cells
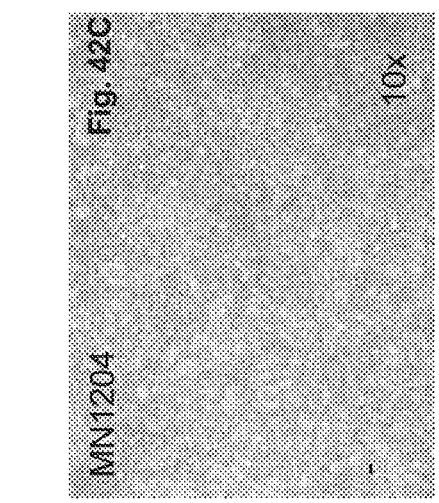
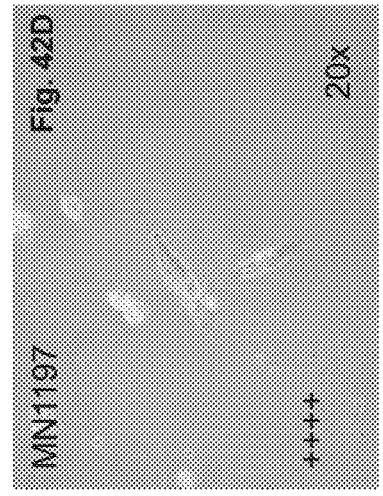
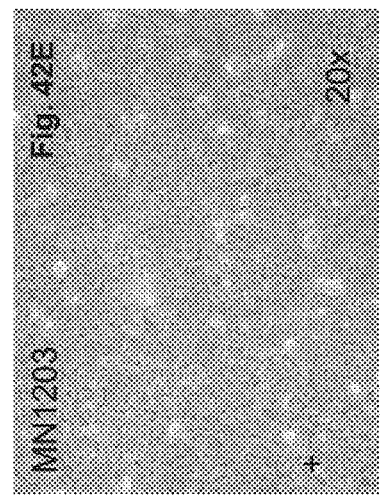
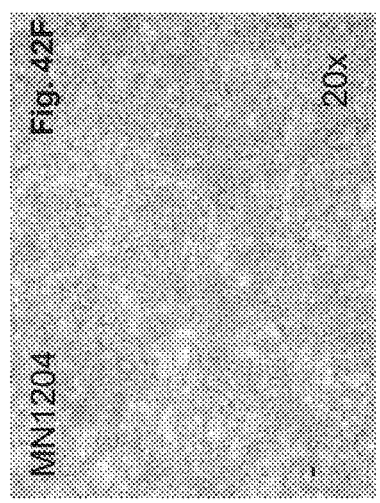
Figure 42

Primed Stem Cells
MN1197
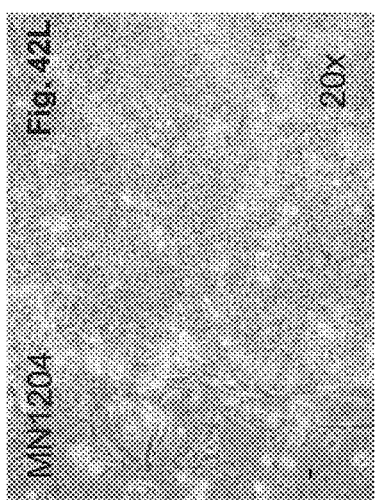
MN1203
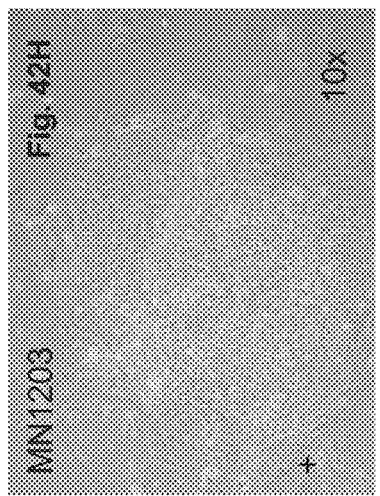
MN1204
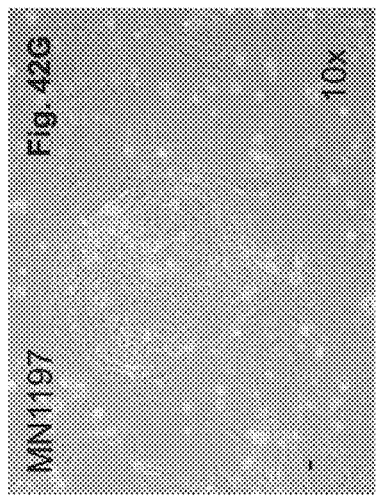
Figure 42

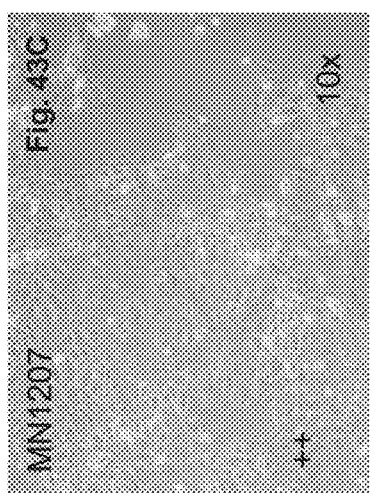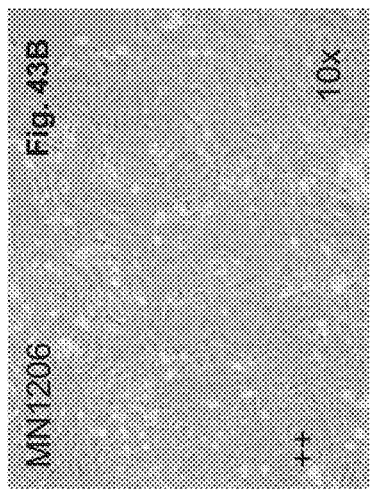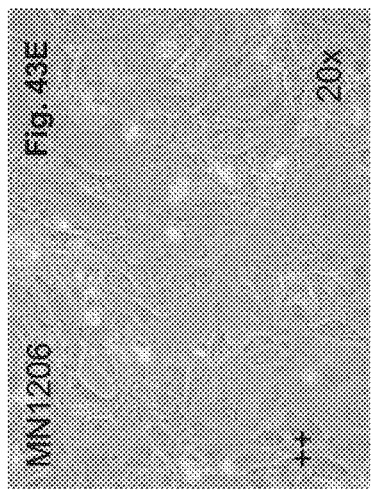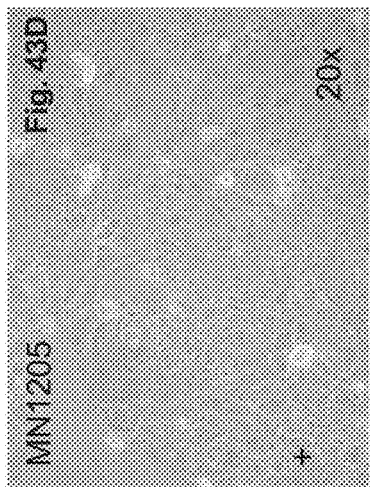
Figure 43

Primed Stem Cells
MN1205
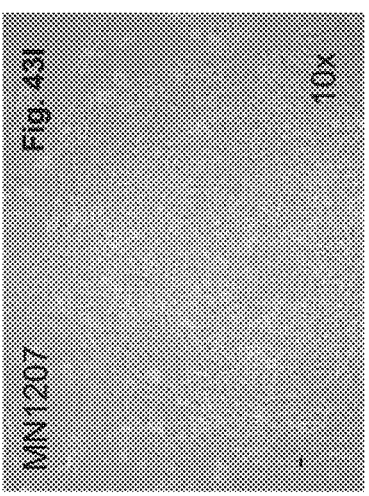
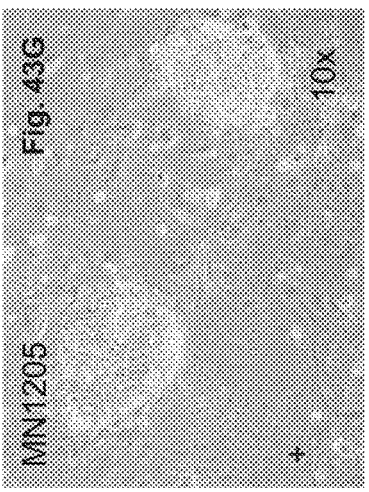
MN1206
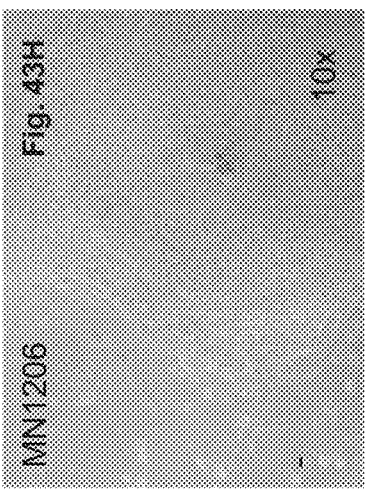
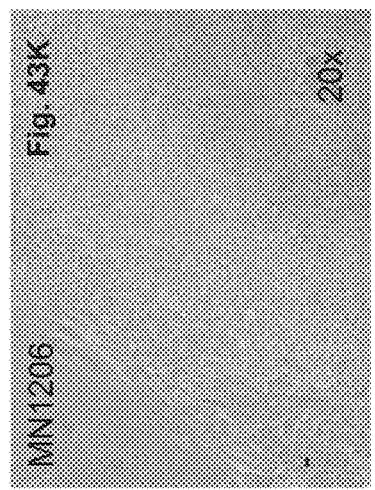
MN1207
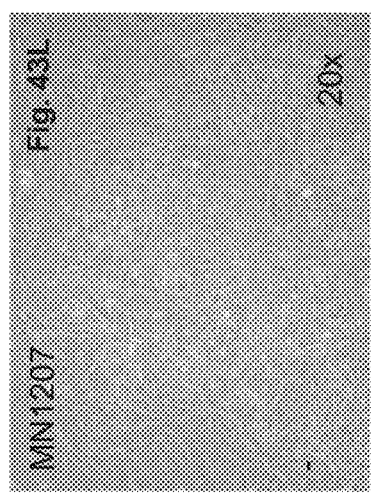
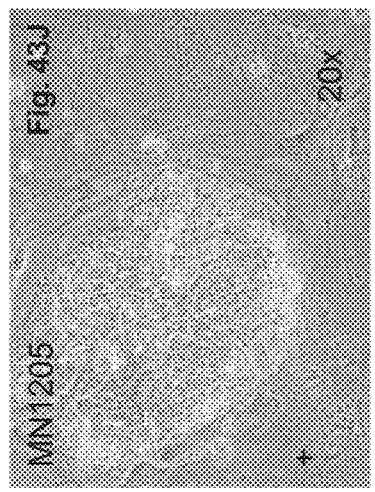
Figure 43

Naïve Stem Cells
MN1208
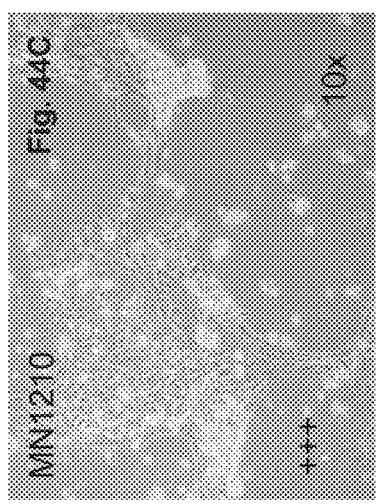
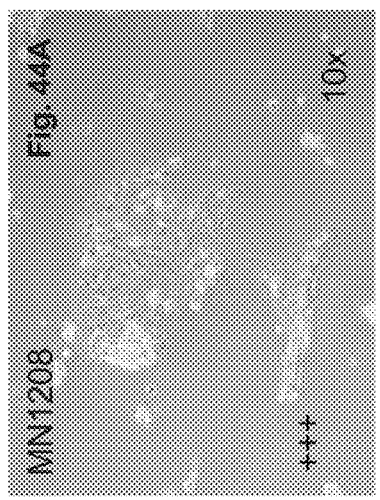
MN1209
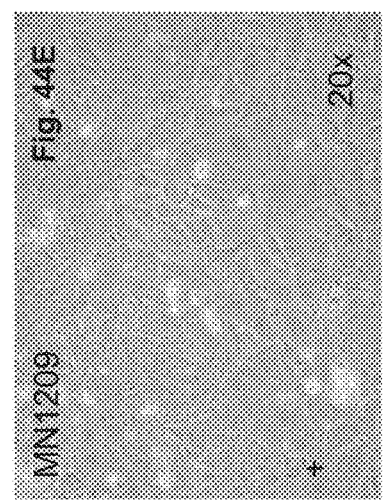
MN1210
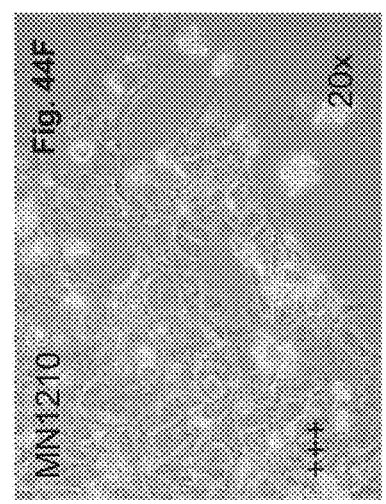
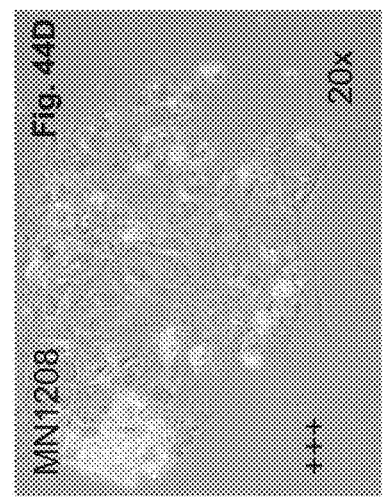
Figure 44

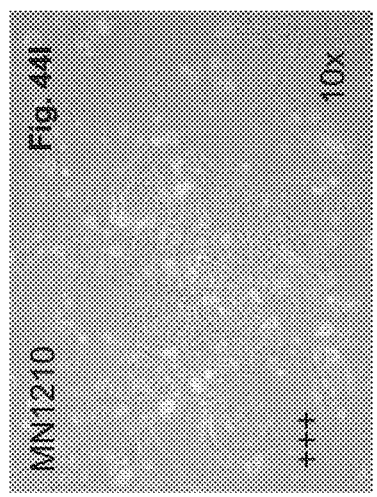
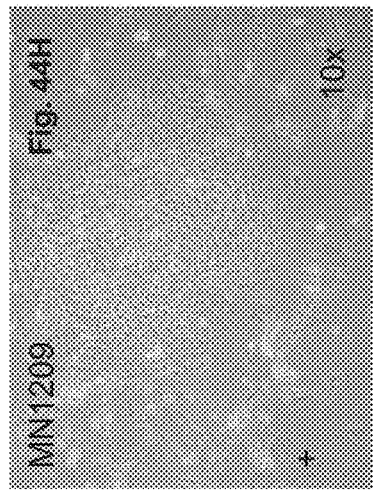
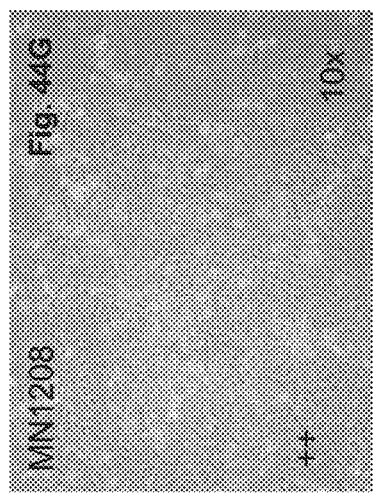
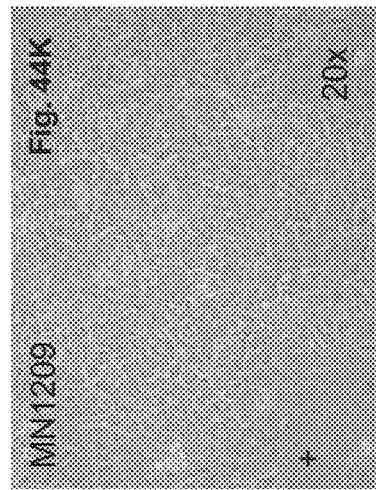
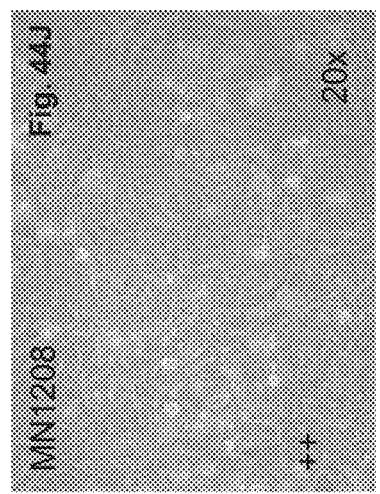
Figure 44

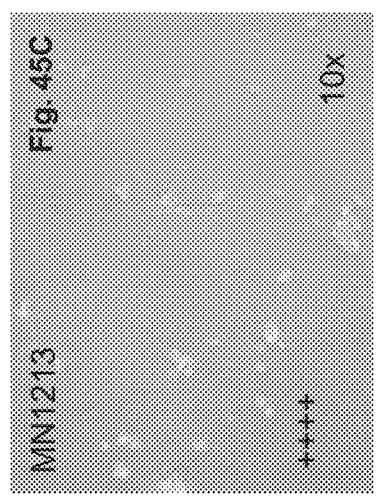
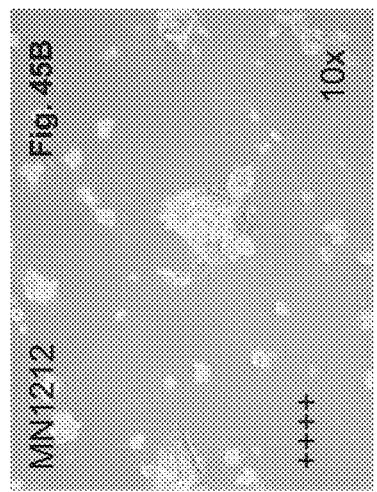
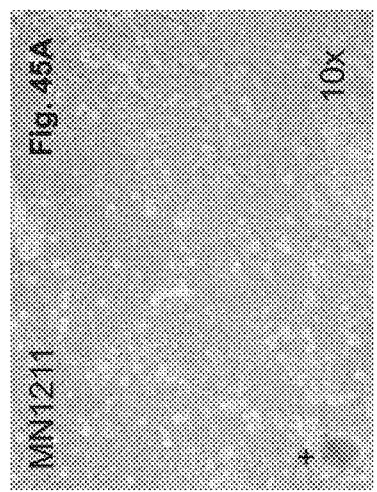
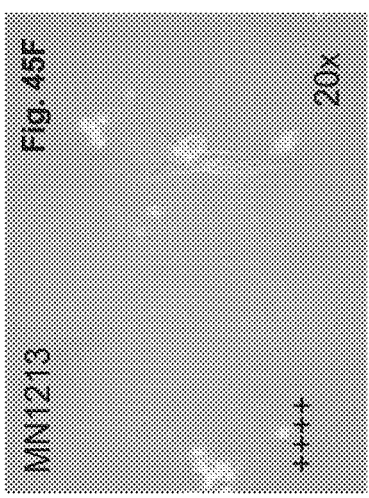
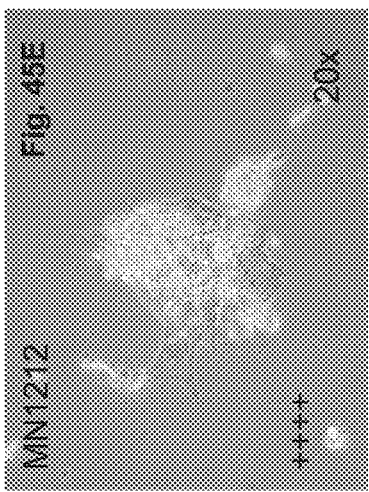
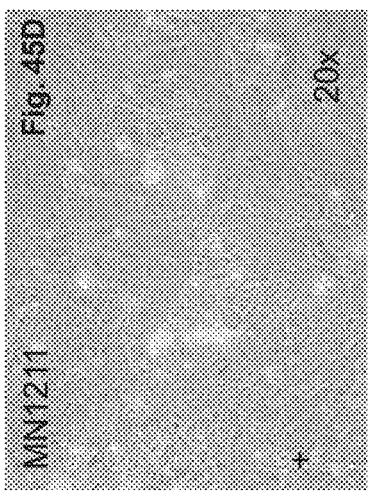
Figure 45

Primed Stem Cells
MN1211
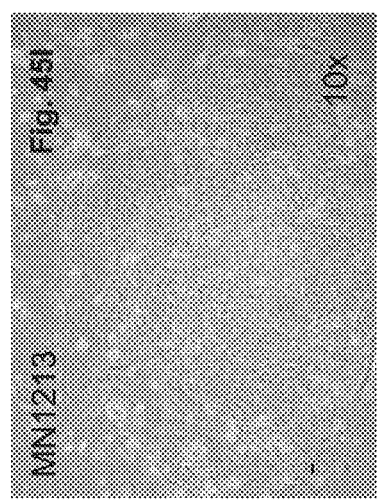
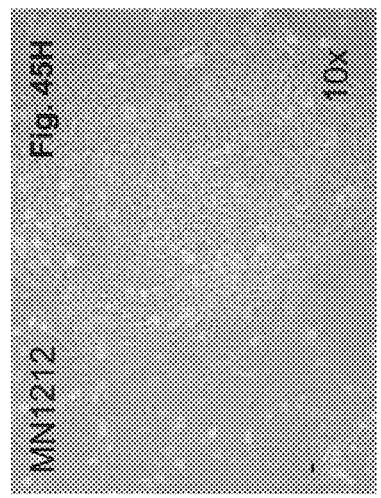
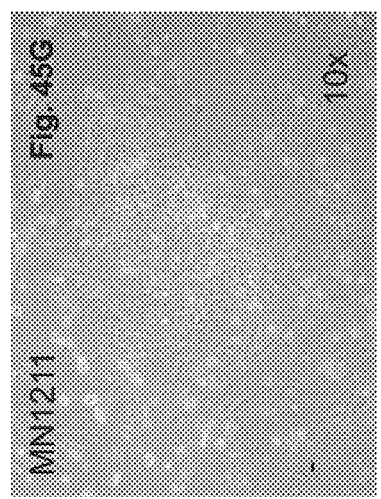
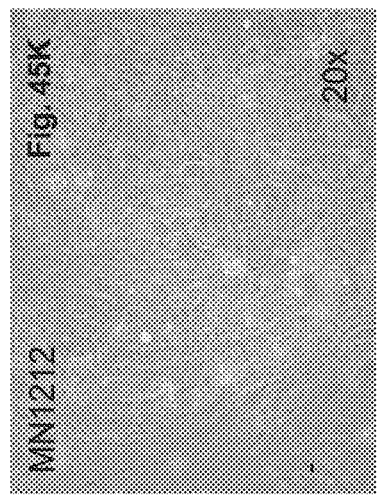
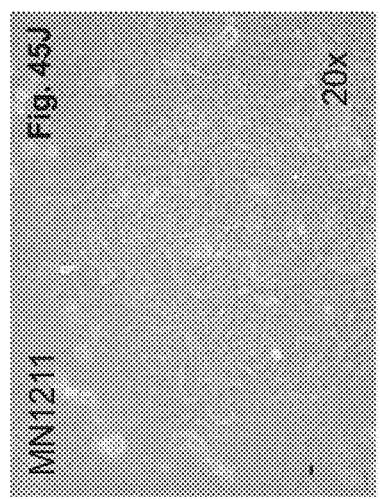
Figure 45

Naïve Stem Cells
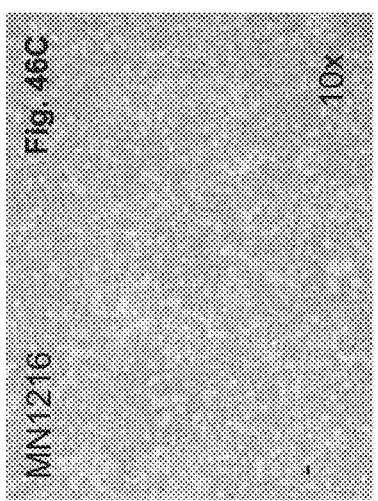
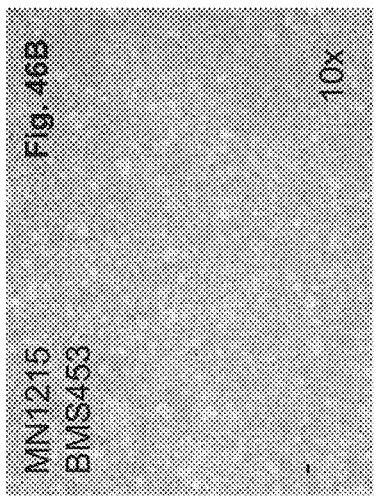
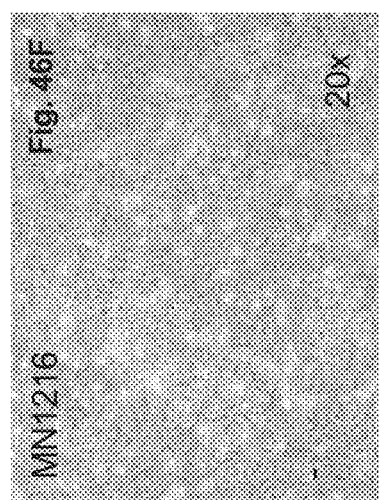
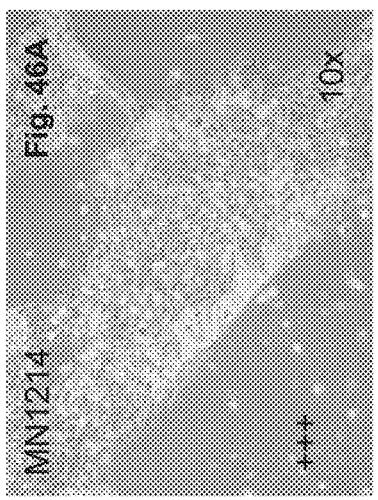
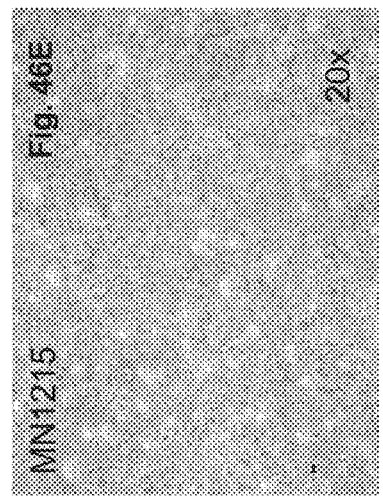
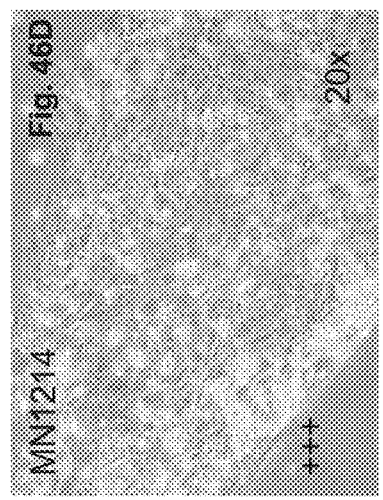
Figure 46

Primed Stem Cells
MN1214
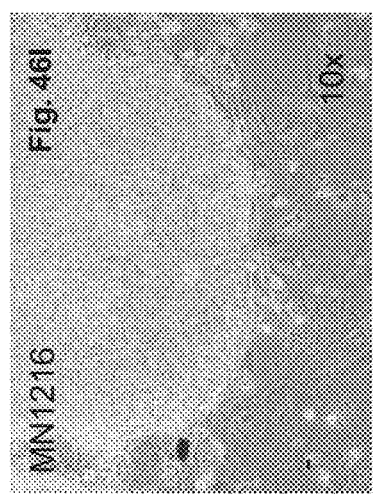
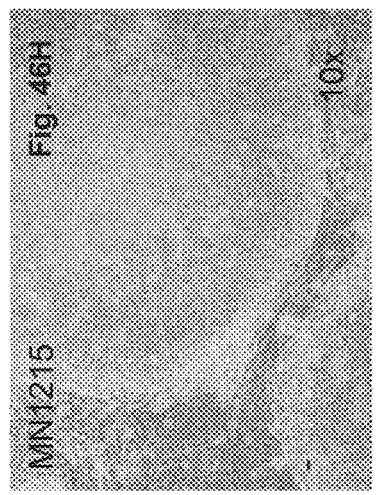
MN1215
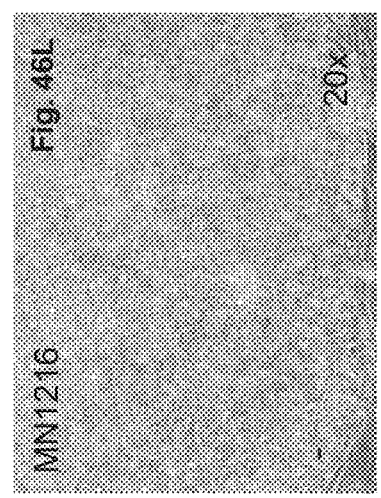
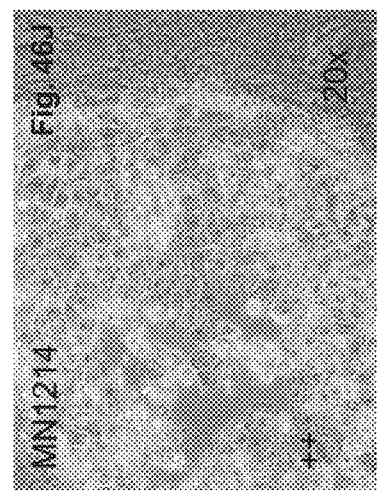
MN1216
Figure 46

Naïve Stem Cells
MN1217
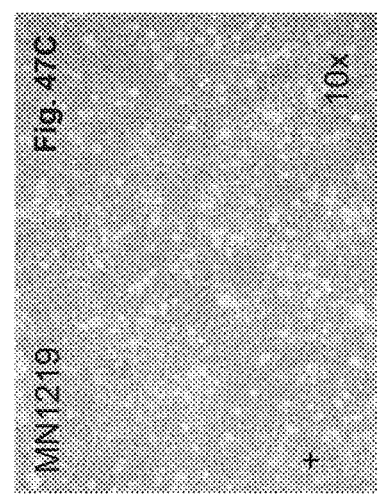
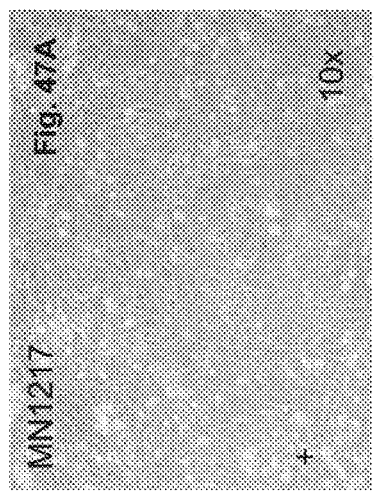
MN1218
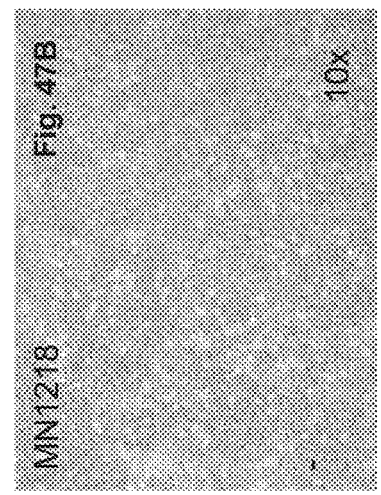
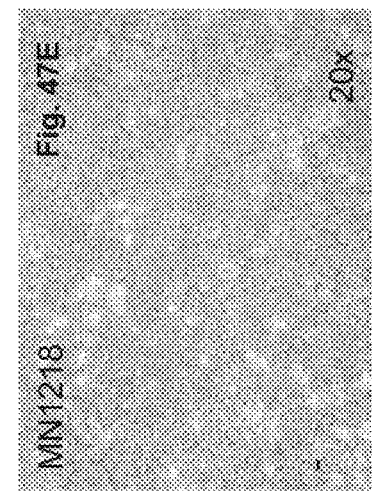
MN1219
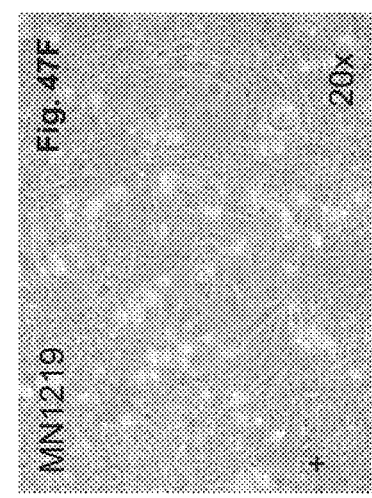
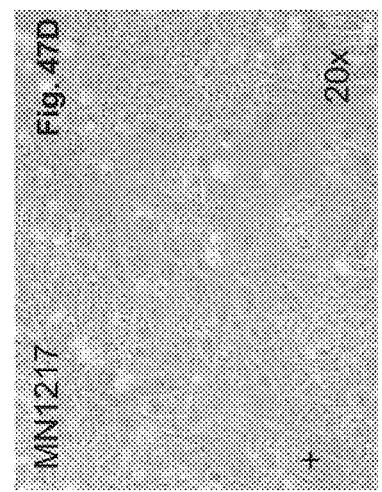
Figure 47

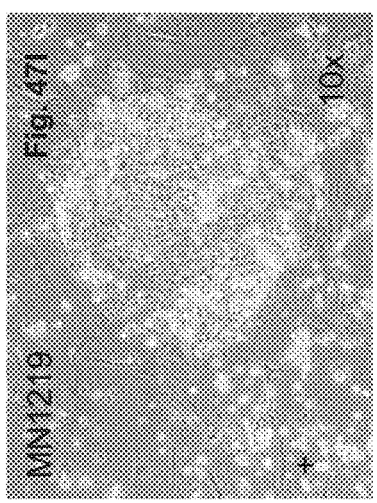
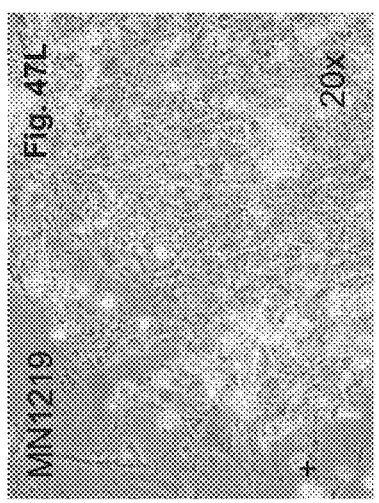
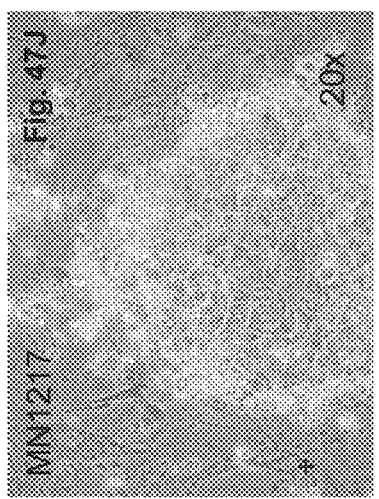
Figure 47

Naïve Stem Cells

| MN1220 | MN1221 | MN1222 |

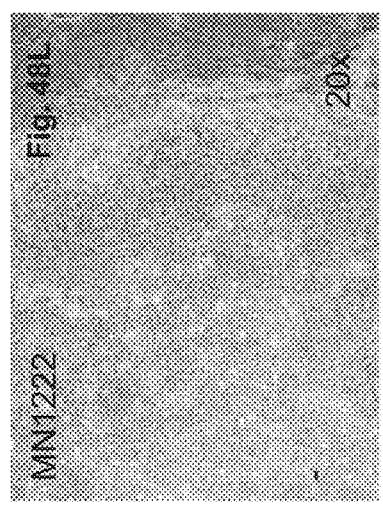
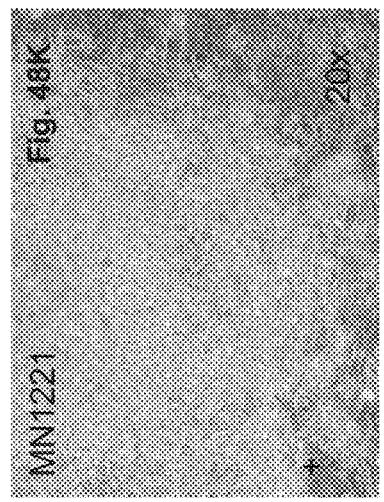
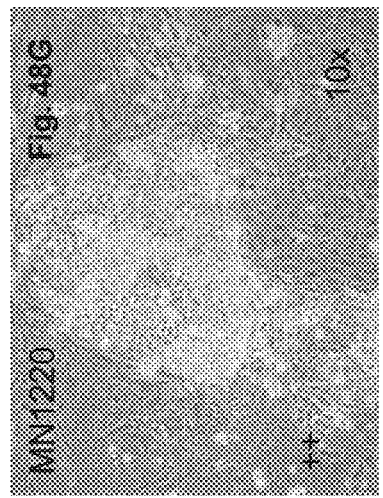
Figure 48

Naïve Stem Cells
MN1223
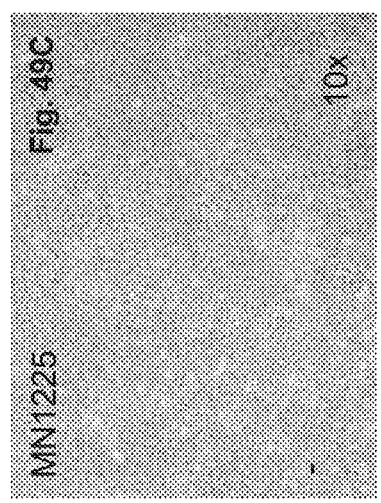
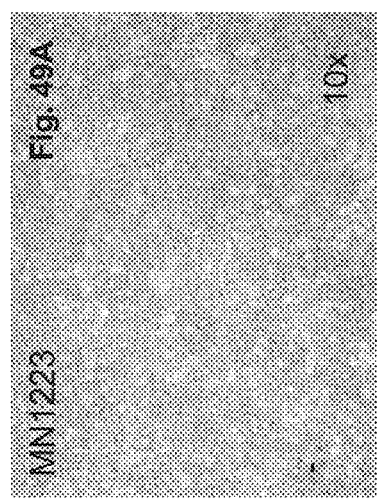
MN1224
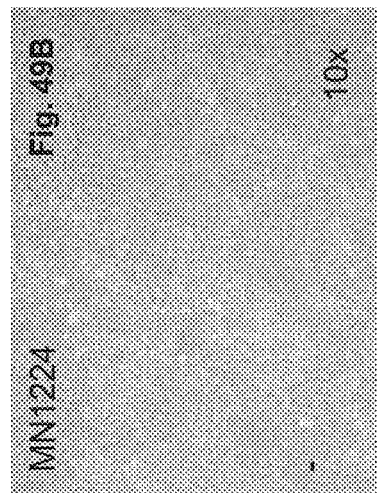
MN1225
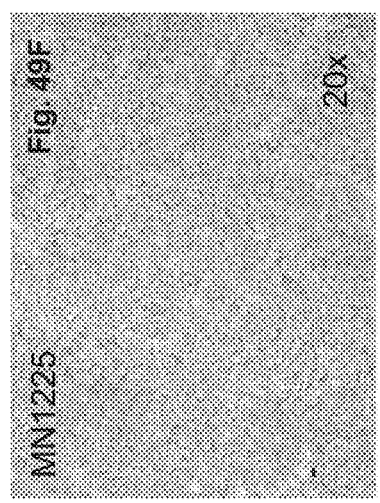
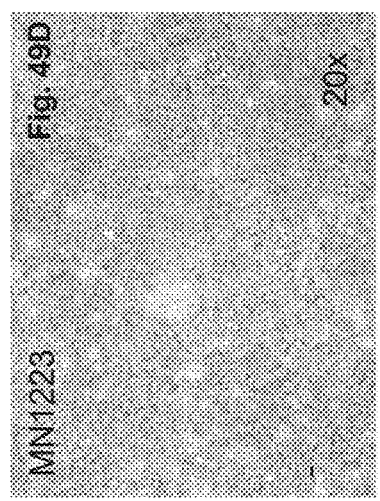
Figure 49

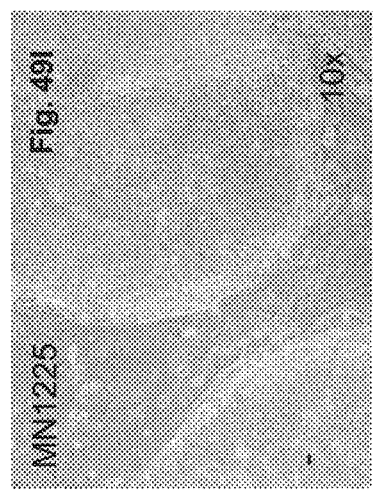
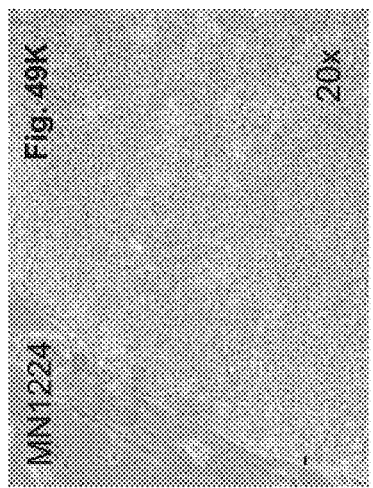
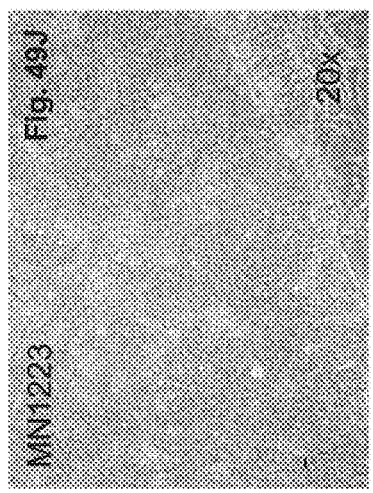
Figure 49

Naïve Stem Cells
MN1226
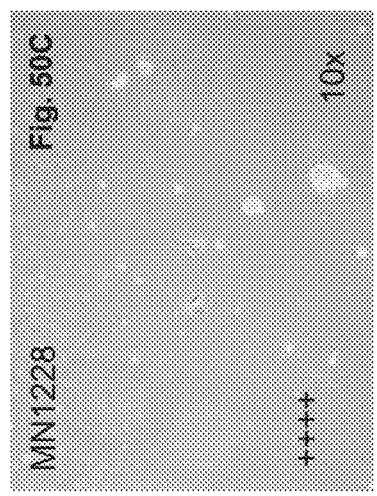
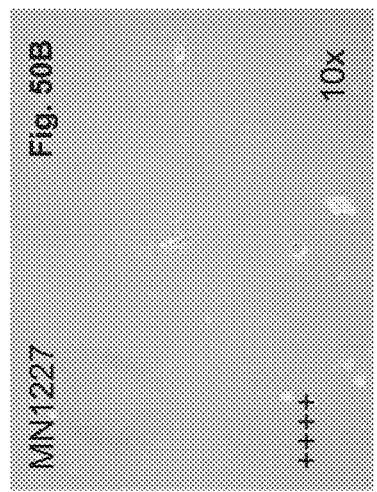
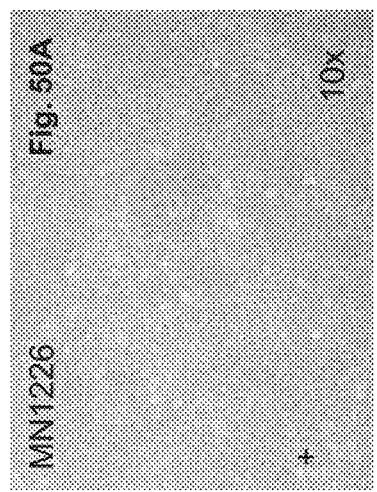
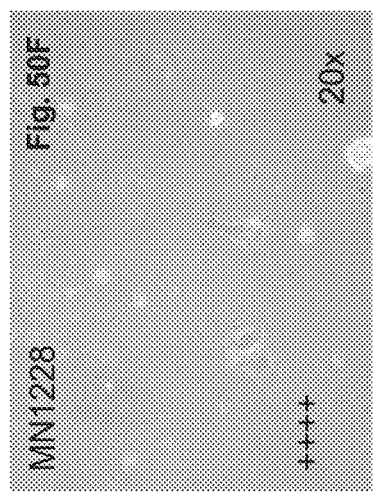
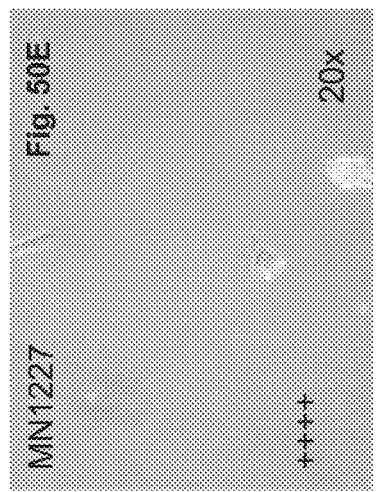
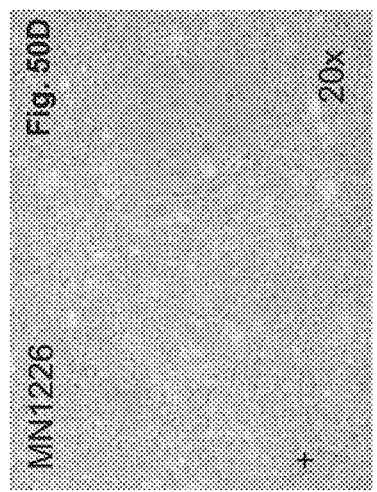
Figure 50

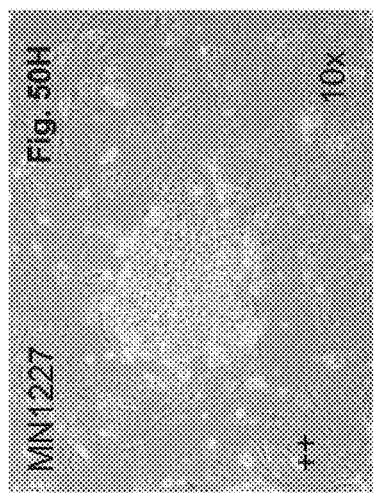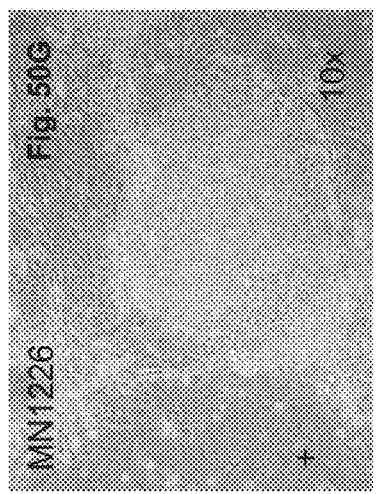
Figure 50

Naïve Stem Cells
MN1229
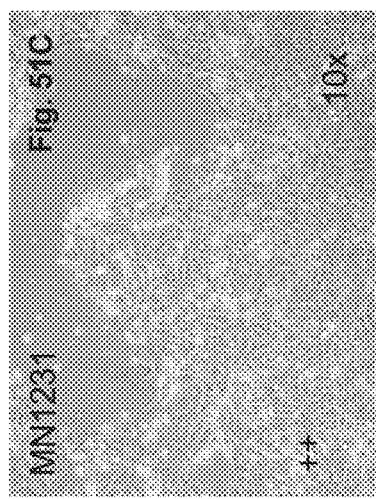
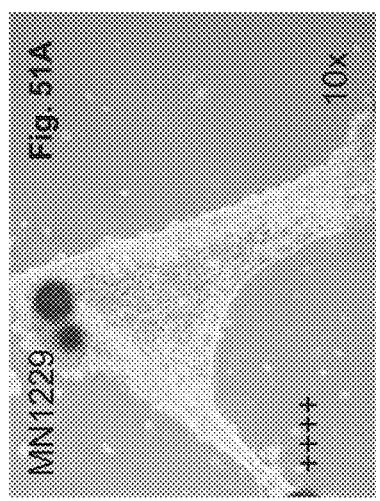
MN1230
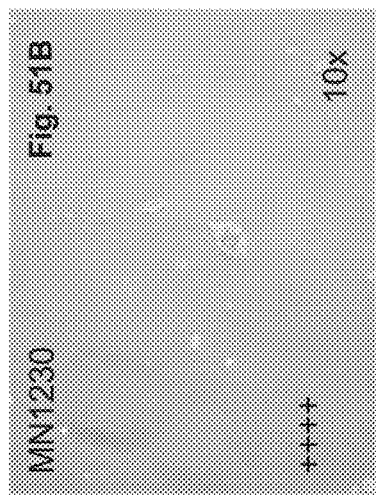
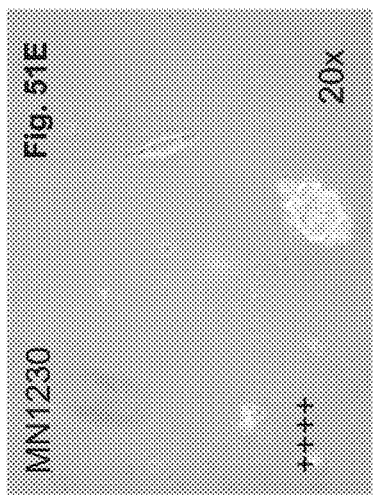
MN1231
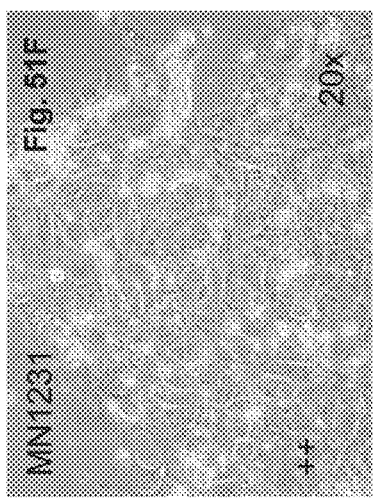
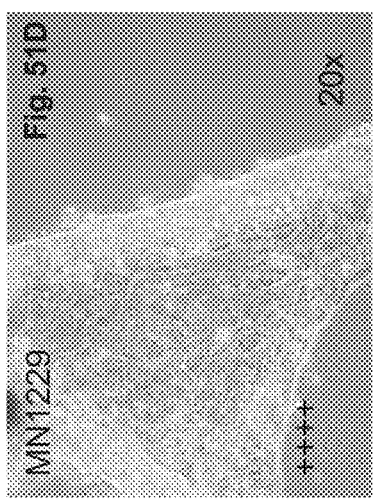
Figure 51

Primed Stem Cells
 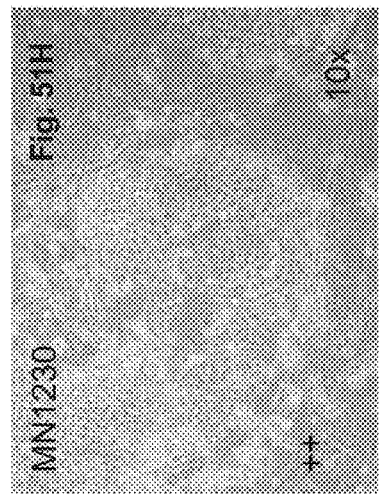 
 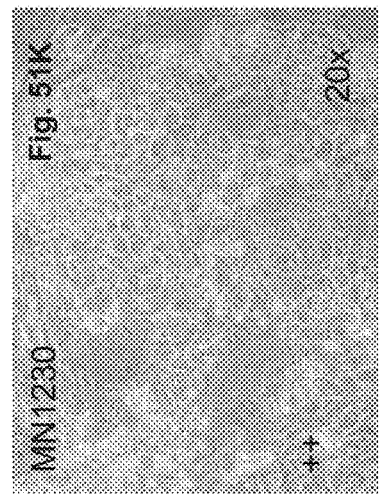 
Figure 51

Naïve Stem Cells
MN1232
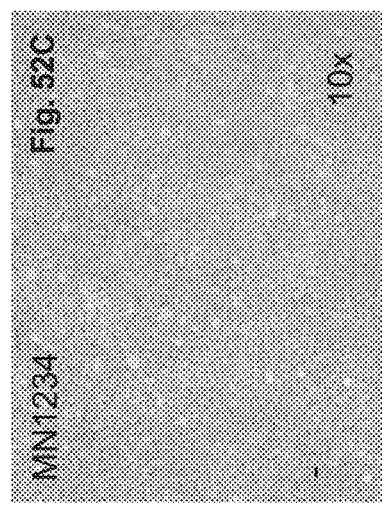
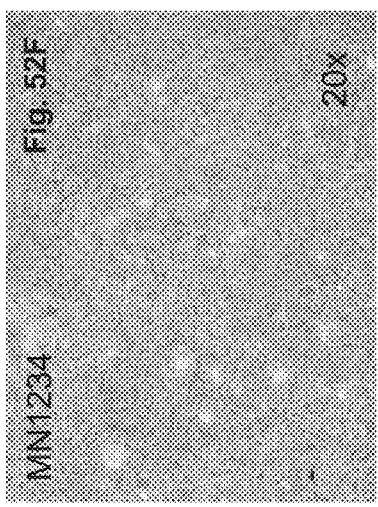
MN1233
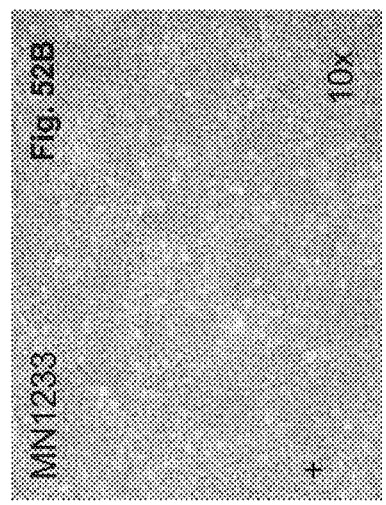
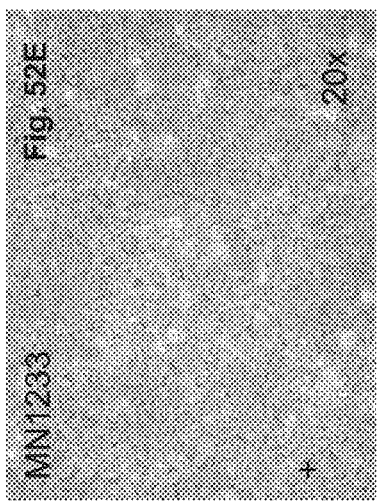
MN1234
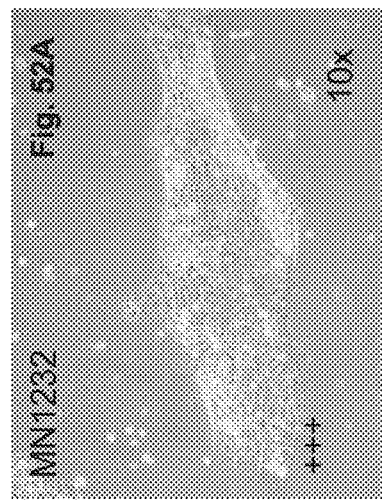
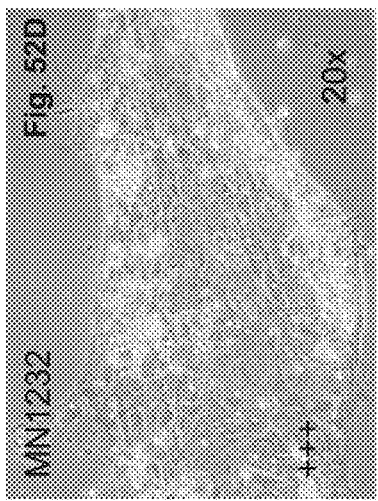
Figure 52

Primed Stem Cells
MN1232
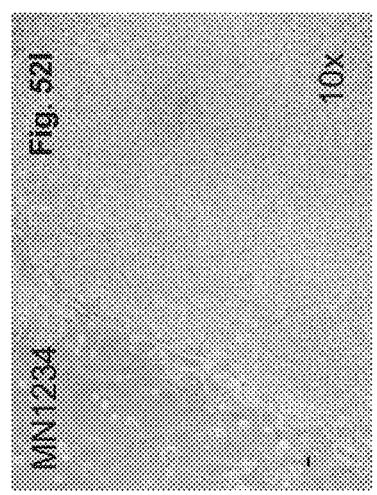
MN1233
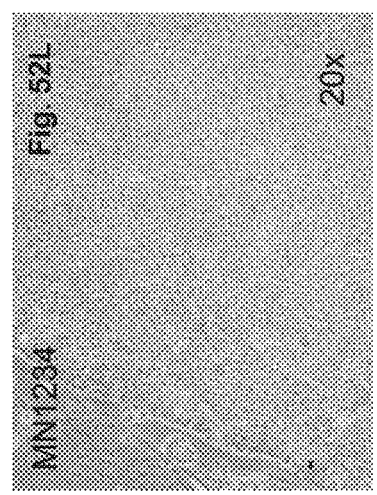
MN1234
Figure 52

Naïve Stem Cells
MN1235
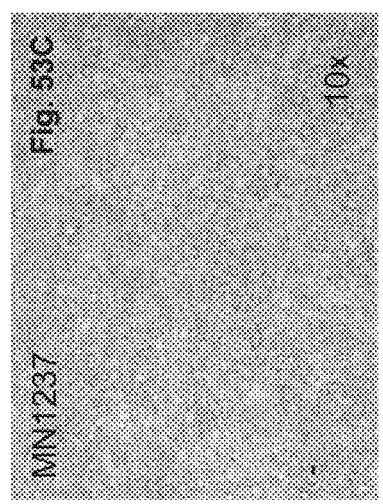
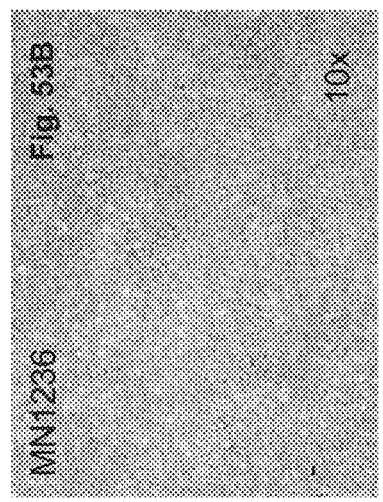
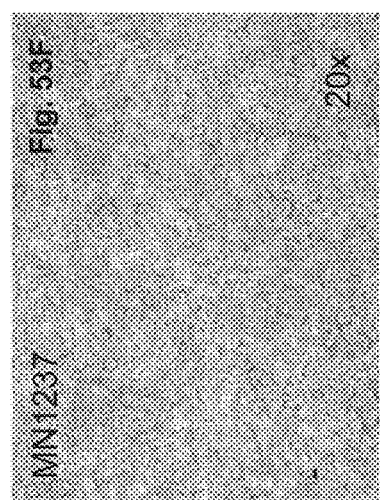
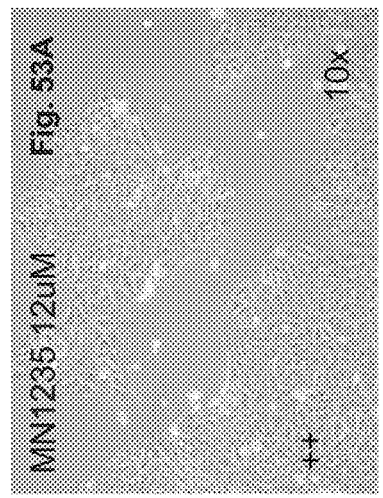
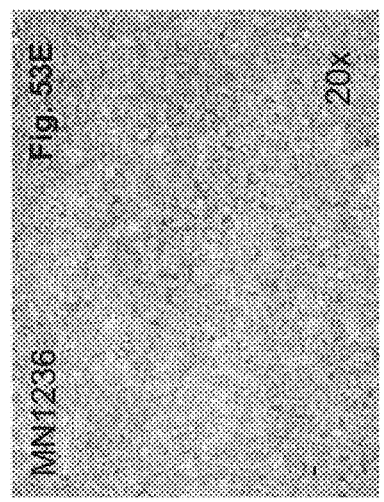
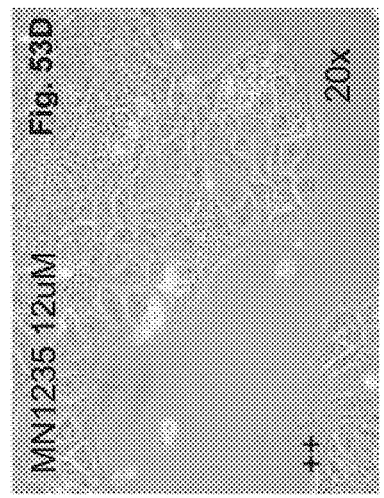
Figure 53

Primed Stem Cells
MN1235
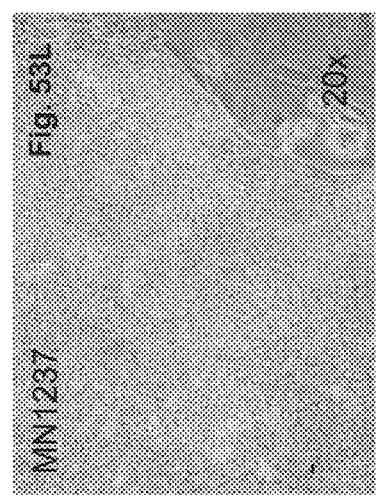
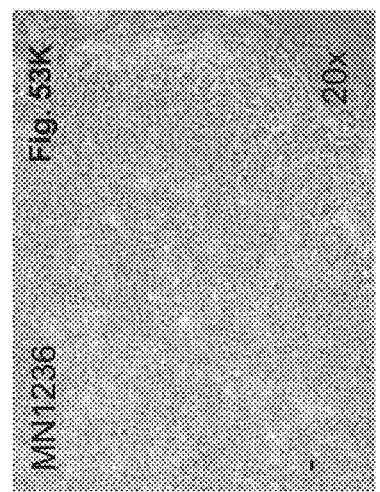
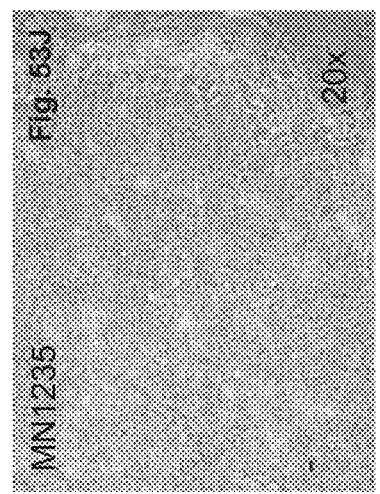
Figure 53

Naïve Stem Cells
MN1238
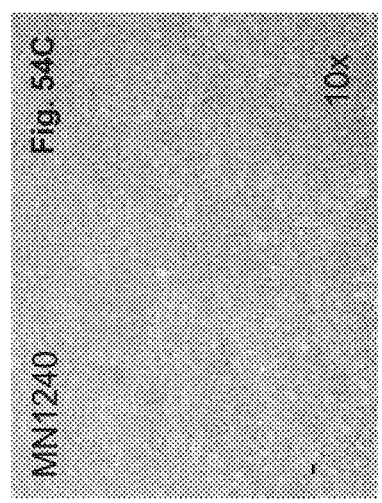
MN1239
MN1240
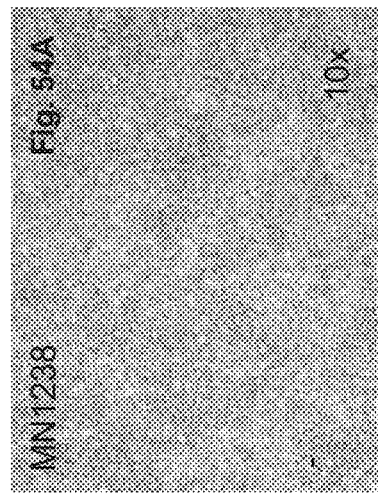
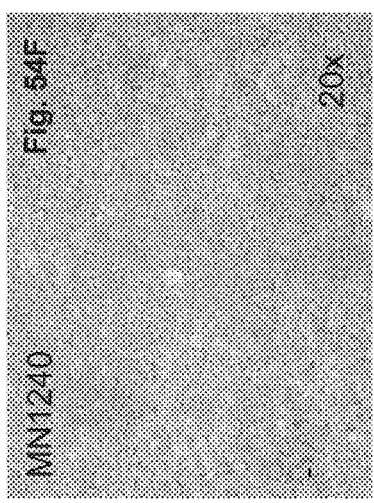
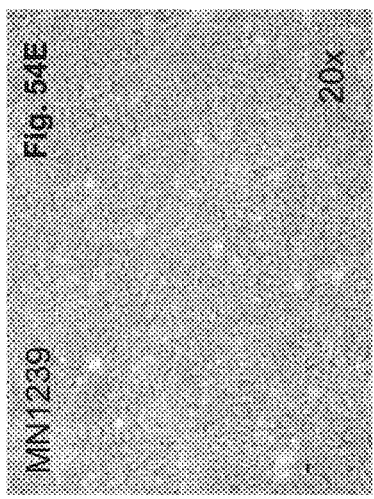
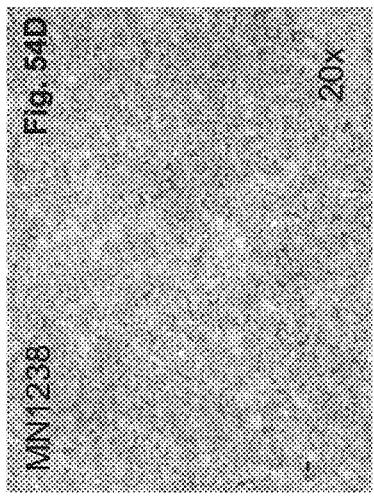
Figure 54

Primed Stem Cells
MN1238
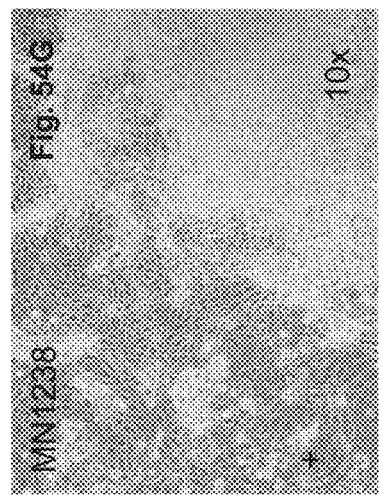
MN1239
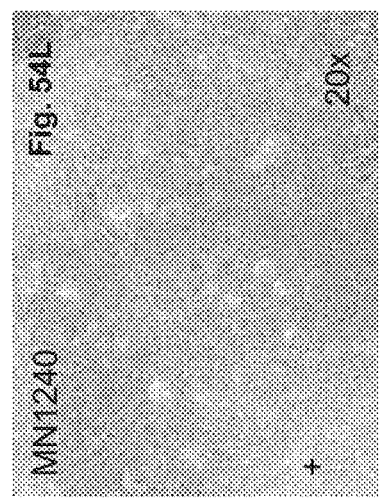
MN1240
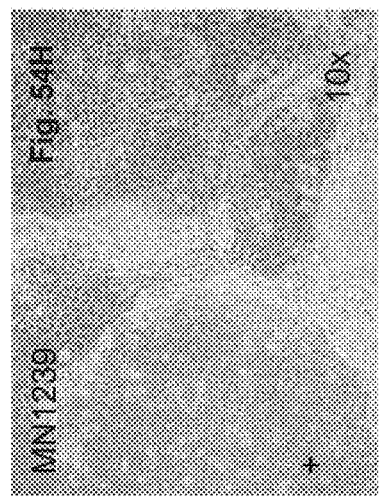
Figure 54

Naïve Stem Cells
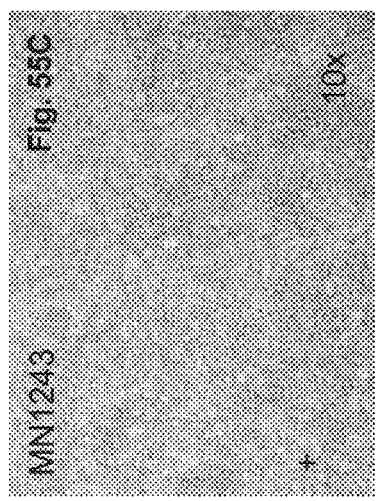 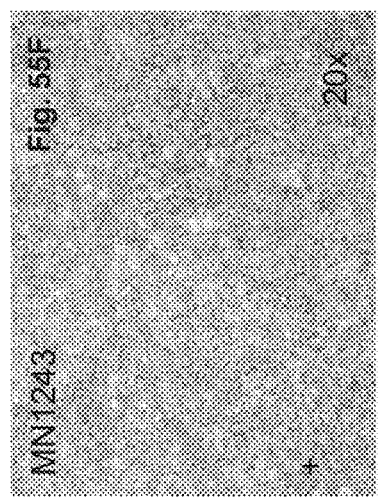
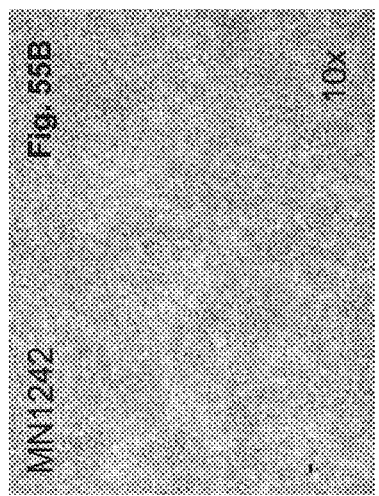 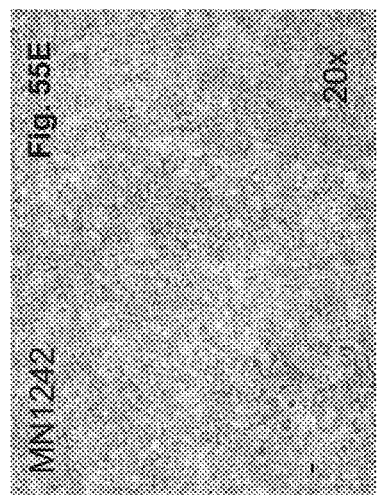
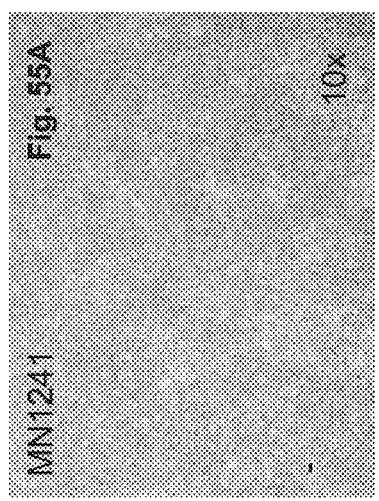 
Figure 55

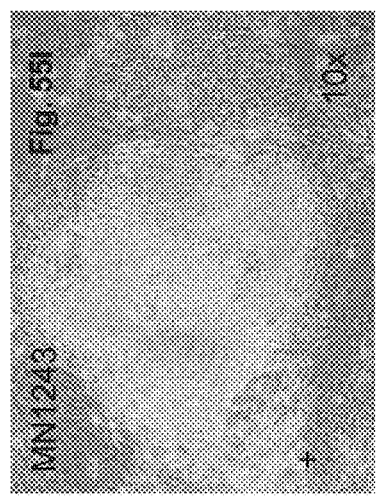
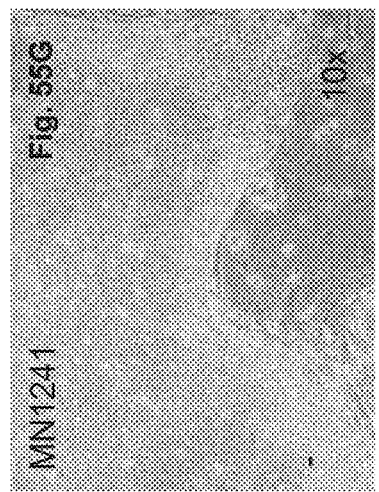
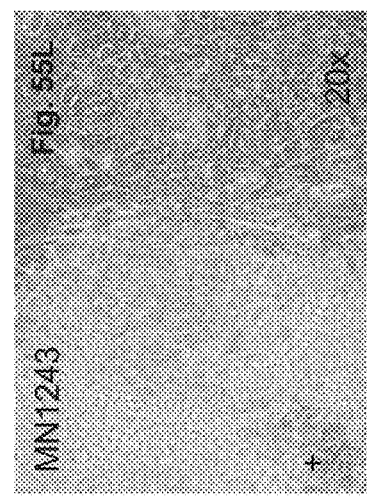
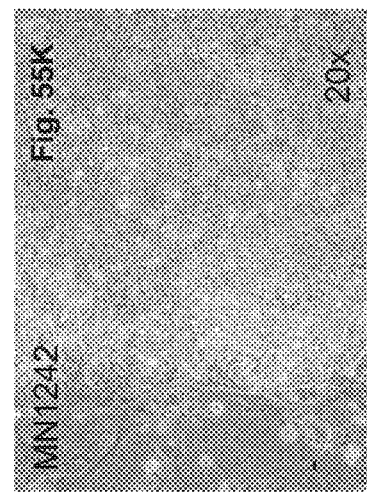
Figure 55

Naïve Stem Cells
MN1244
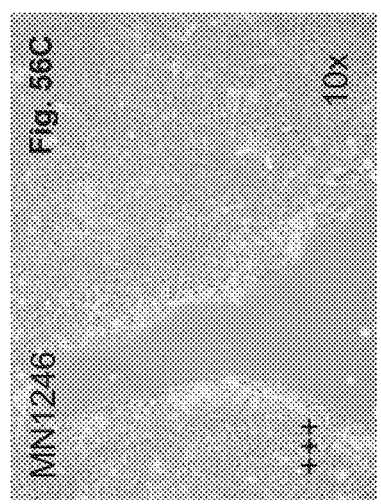
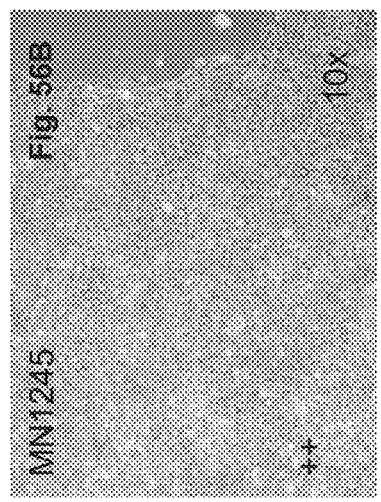
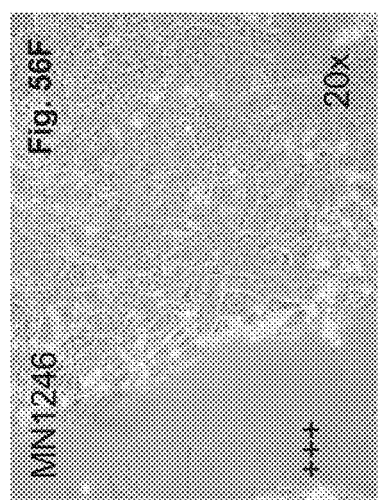
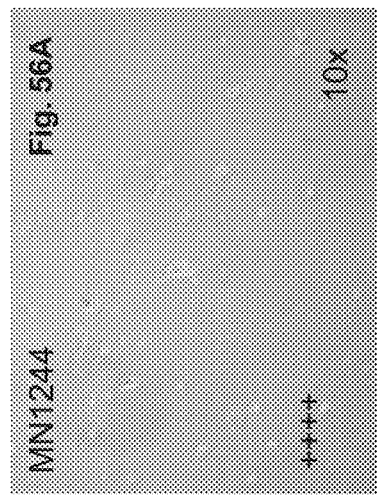
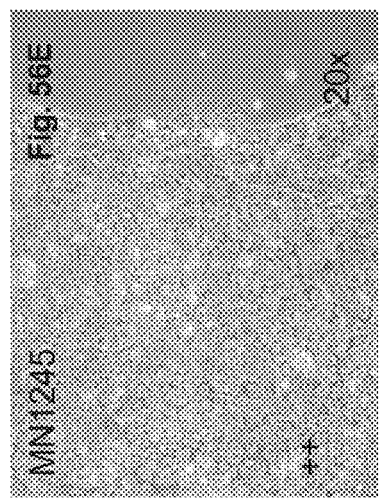
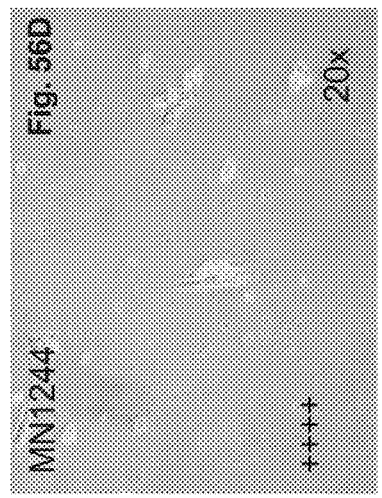
Figure 56

Primed Stem Cells
MN1244
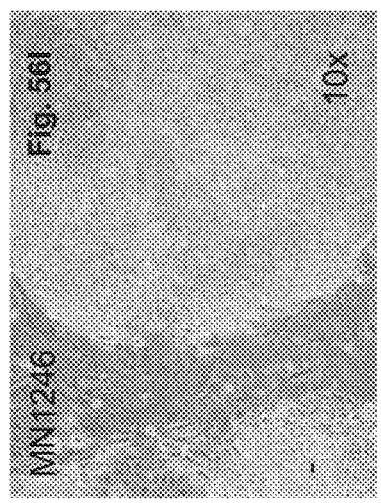
MN1245
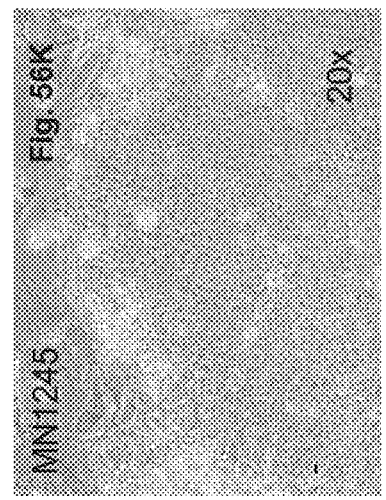
MN1246
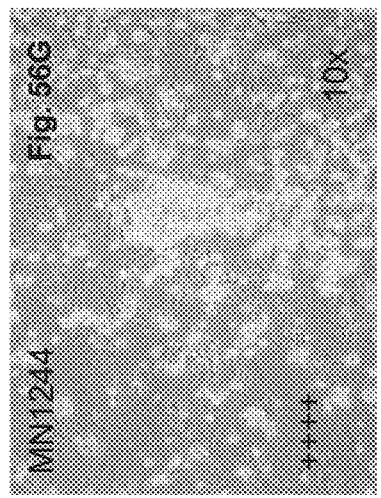
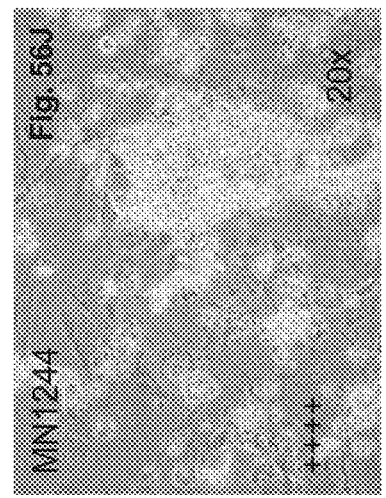
Figure 56

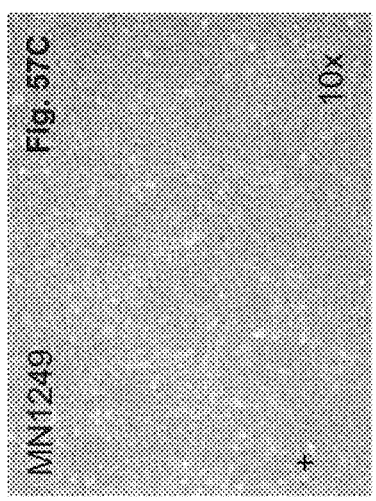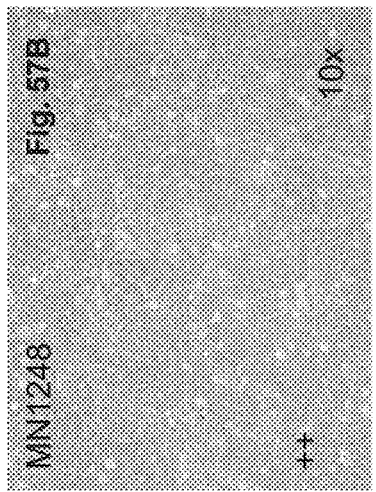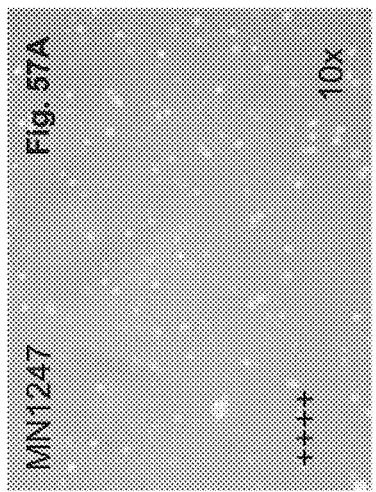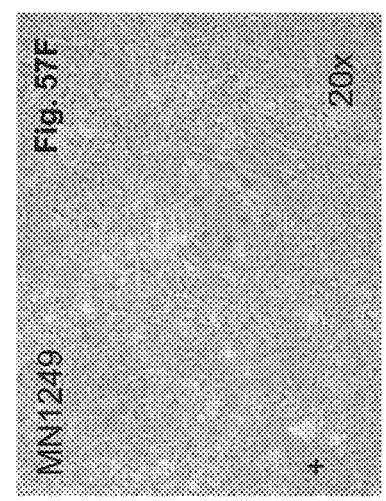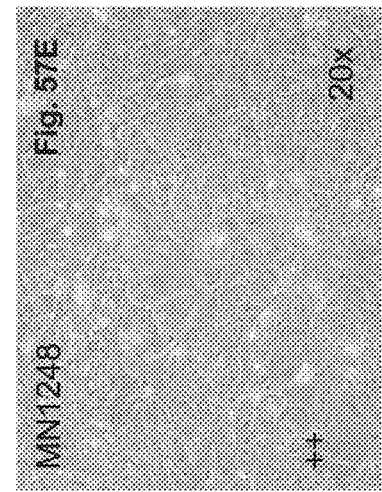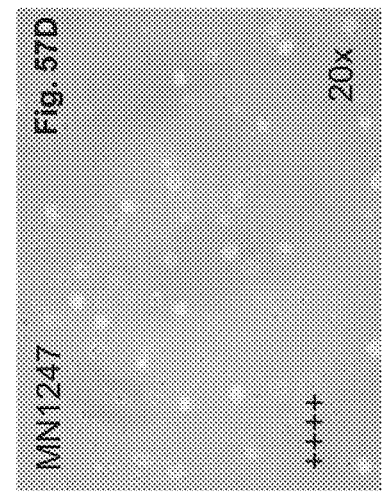
Figure 57

Primed Stem Cells
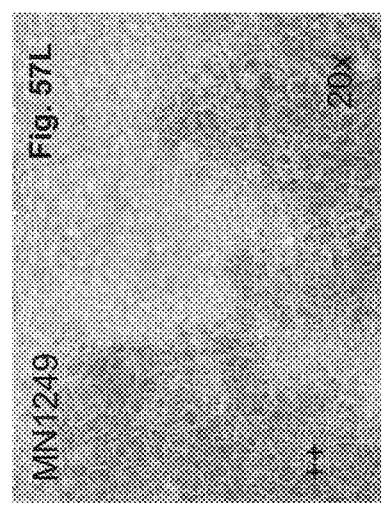
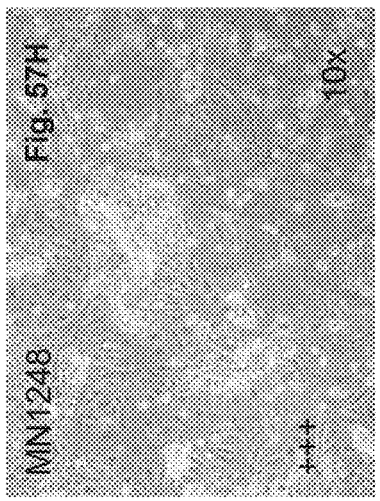
Figure 57

Naïve Stem Cells
MN1250
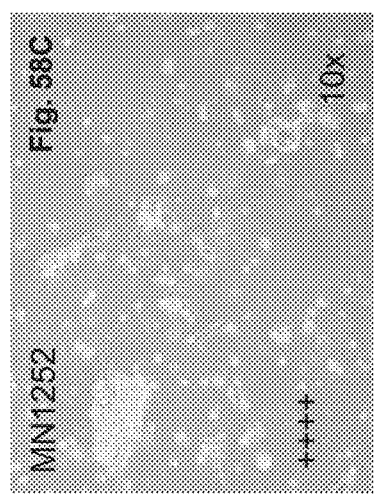
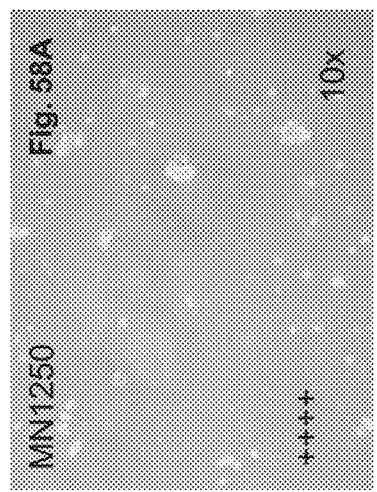
MN1251
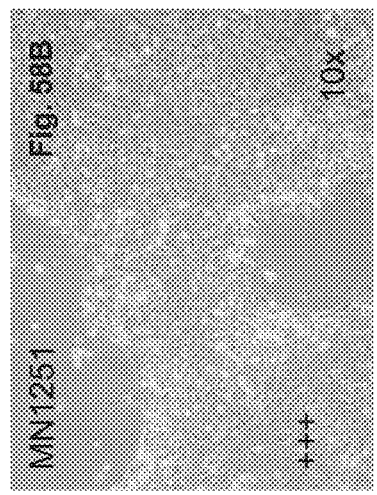
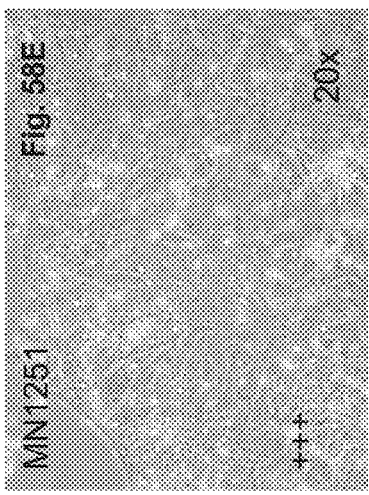
MN1252
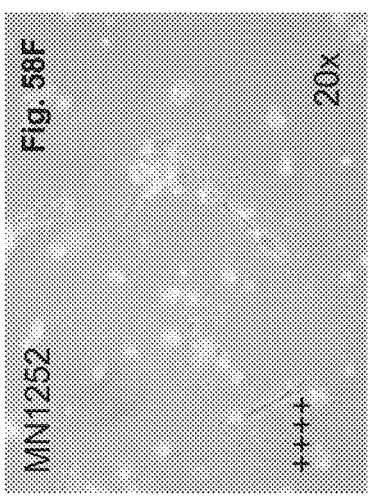
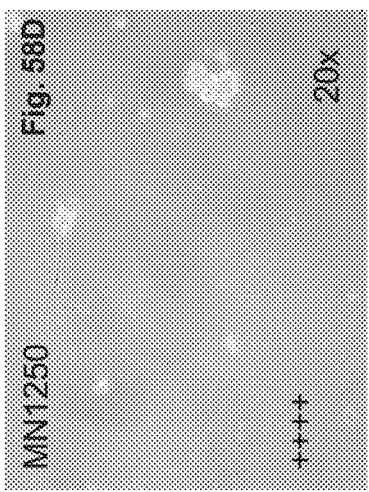
Figure 58

Primed Stem Cells
MN1250
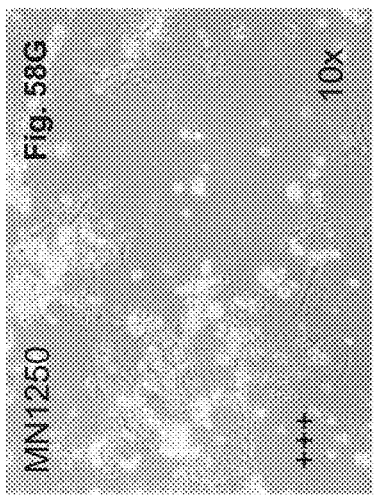
MN1251
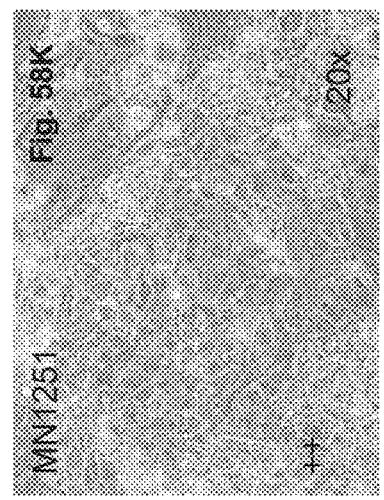
MN1252
Figure 58

Figure 59

Primed Stem Cells
MN1253
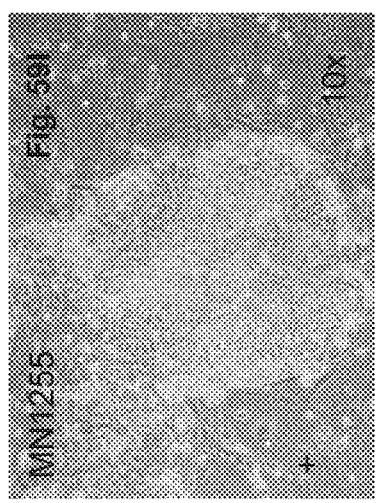
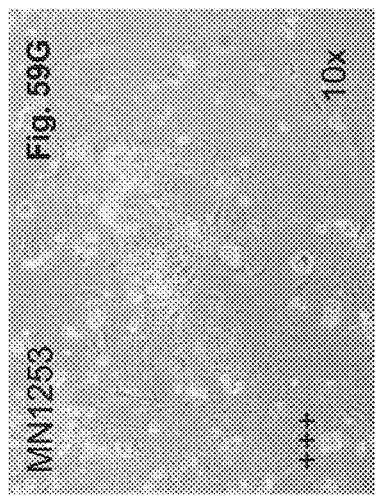
MN1254
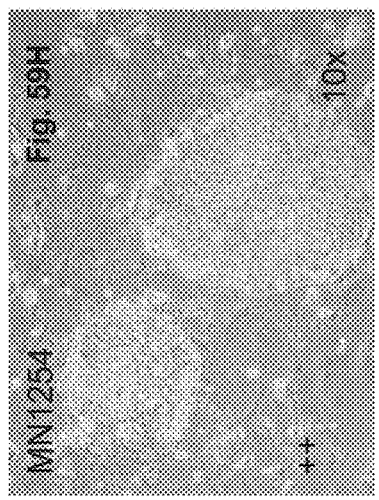
MN1255
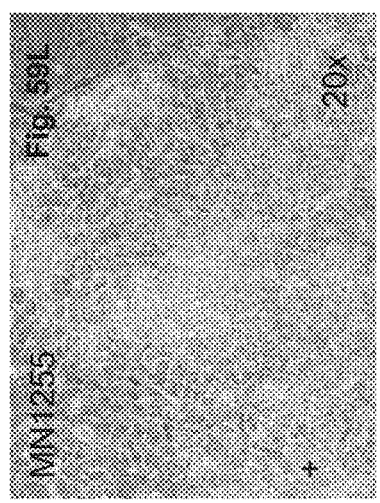
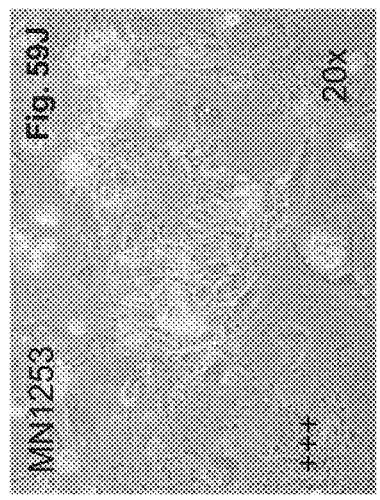
Figure 59

Naïve Stem Cells
MN1256
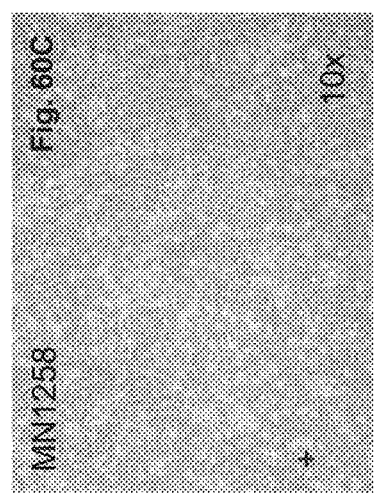
MN1257
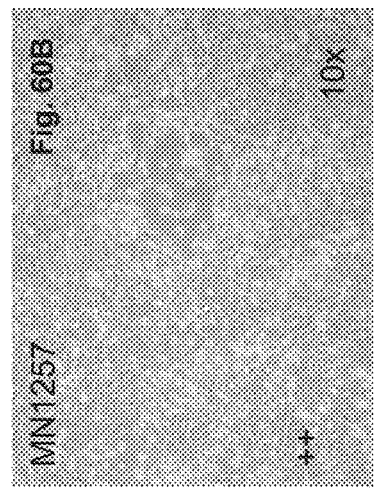
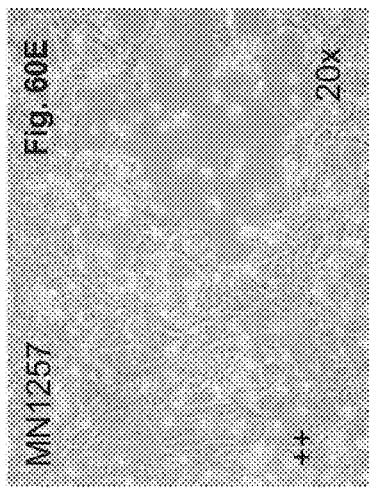
MN1258
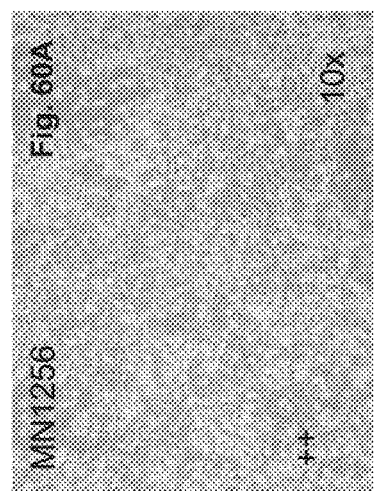
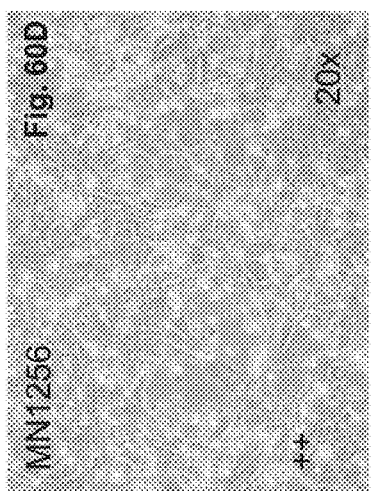
Figure 60

Primed Stem Cells
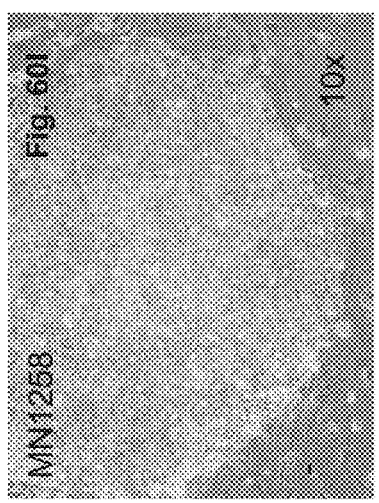
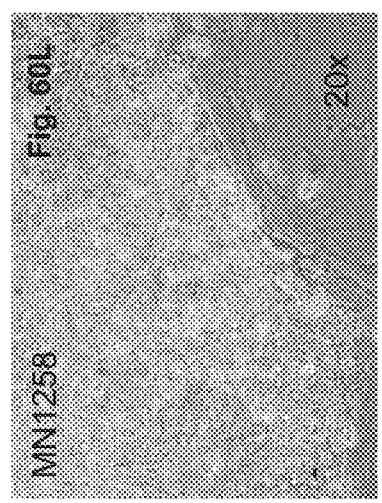
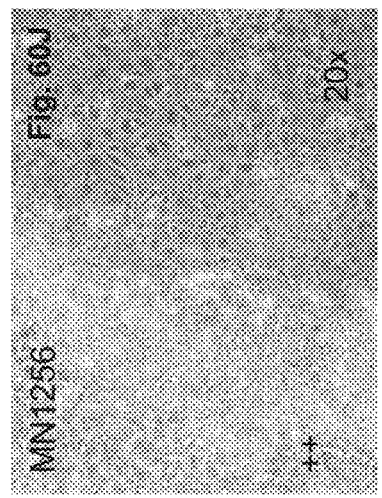
Figure 60

Naïve Stem Cells

Primed Stem Cells
MN1259
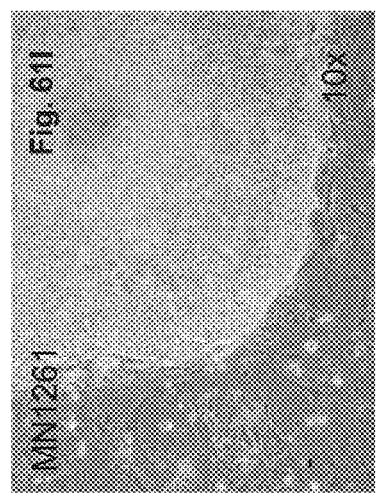
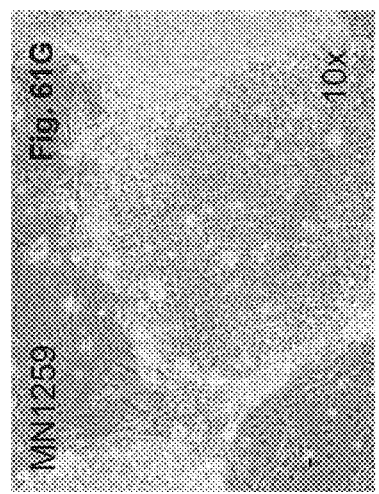
MN1260
MN1261
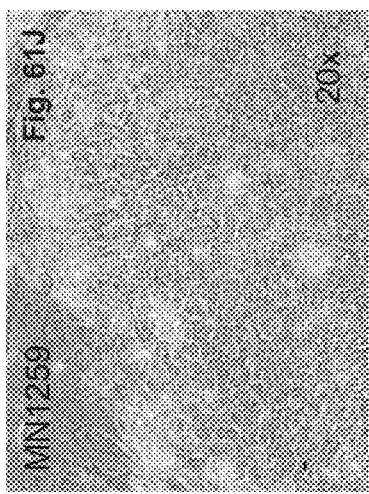
Figure 61

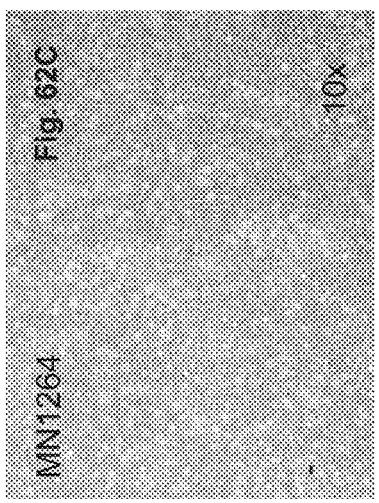
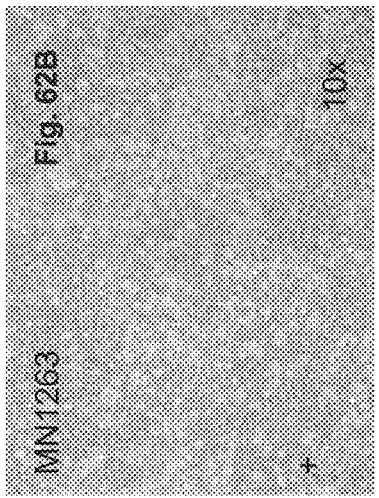
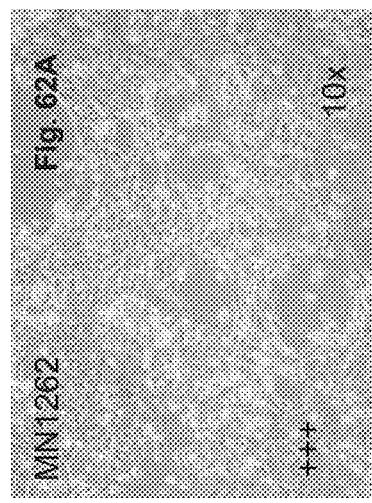
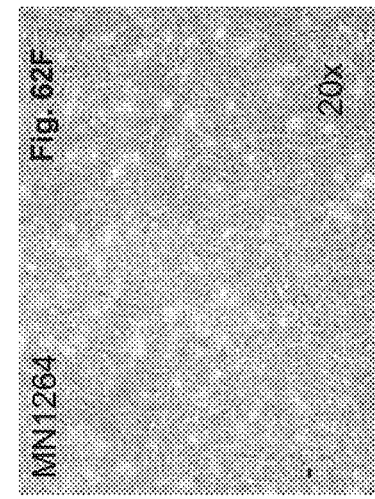
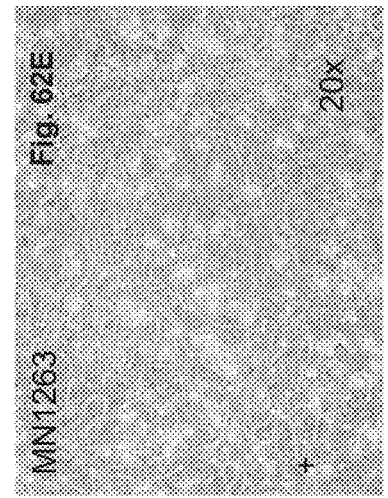
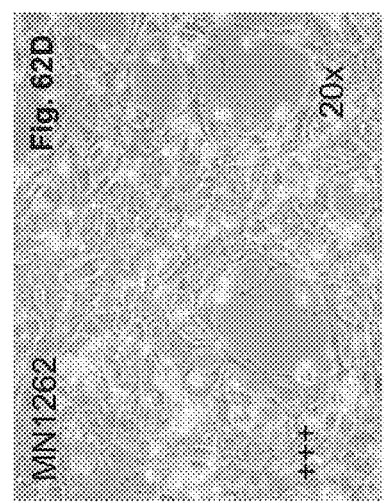
Figure 62

Primed Stem Cells
MN1262
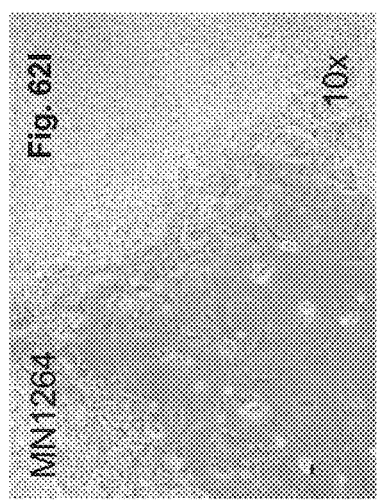
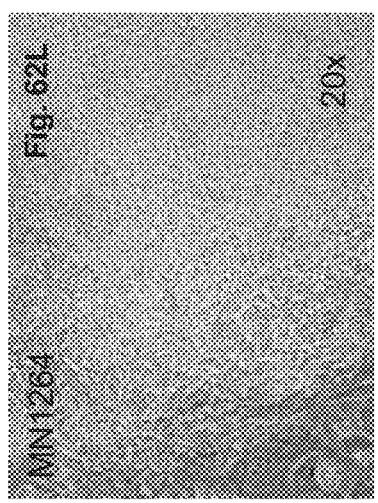
MN1263
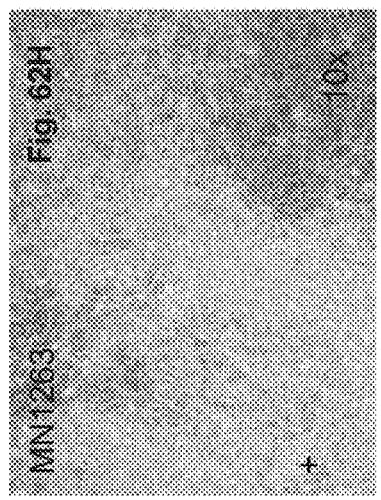
MN1264
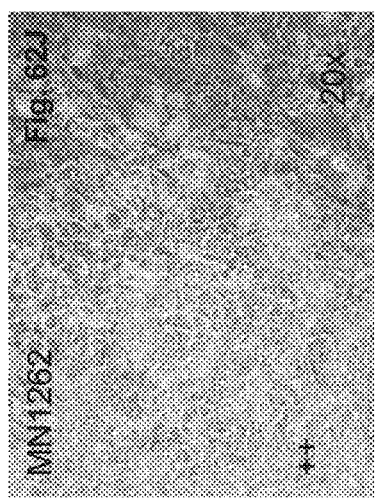
Figure 62

Primed Stem Cells
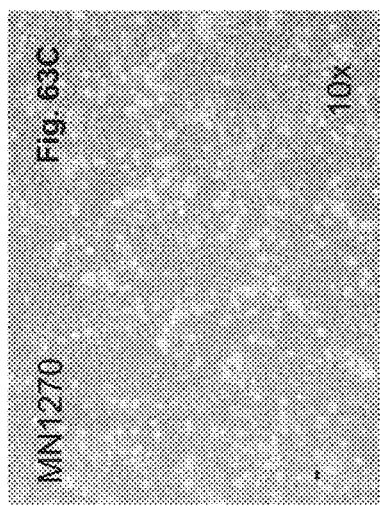
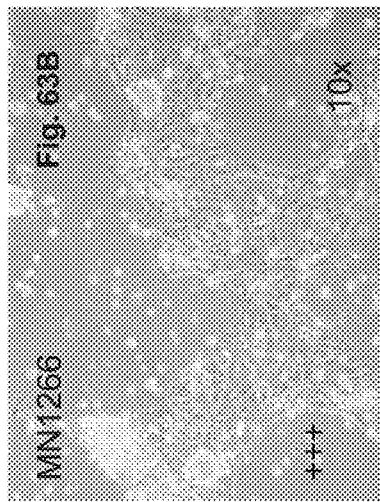
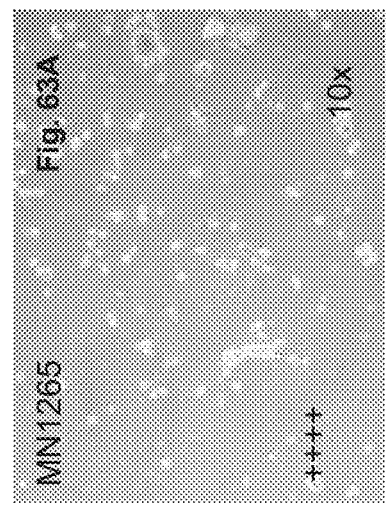
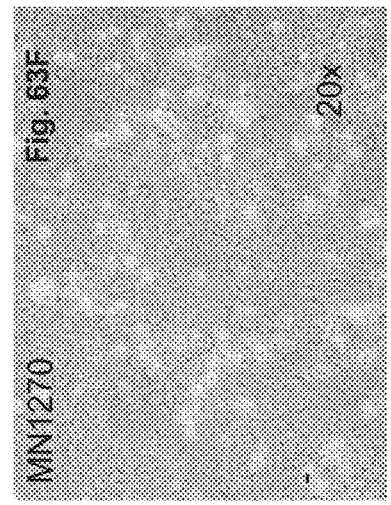
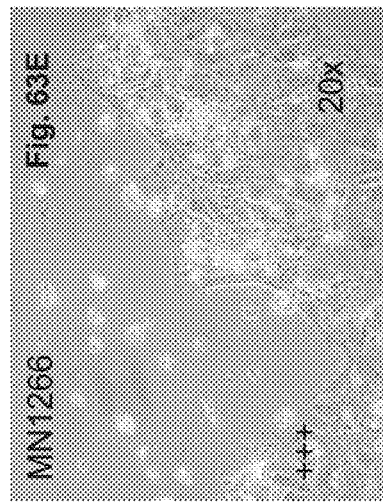
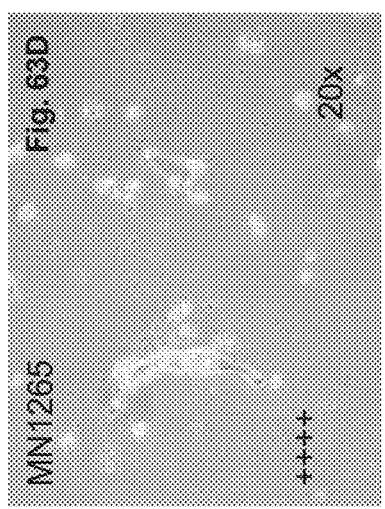
Figure 63

Naïve Stem Cells
MN1271
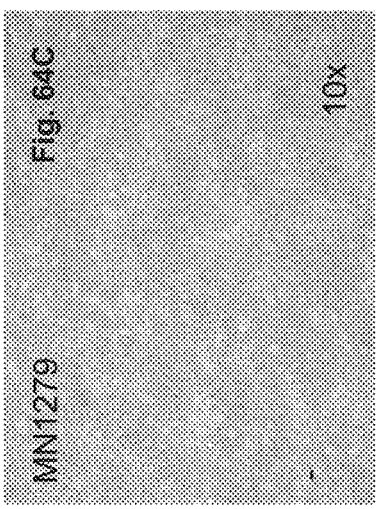
MN1272
MN1279
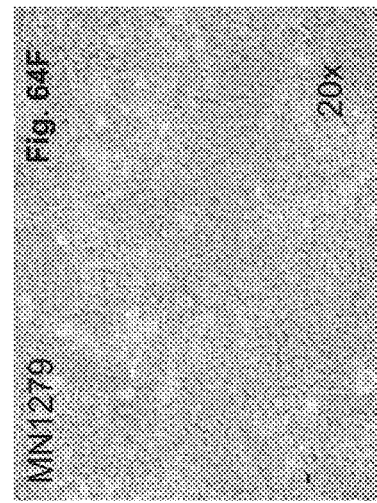
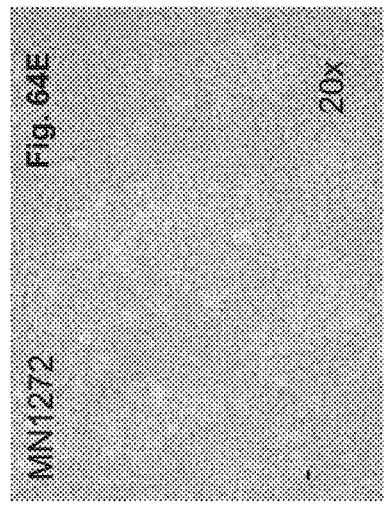
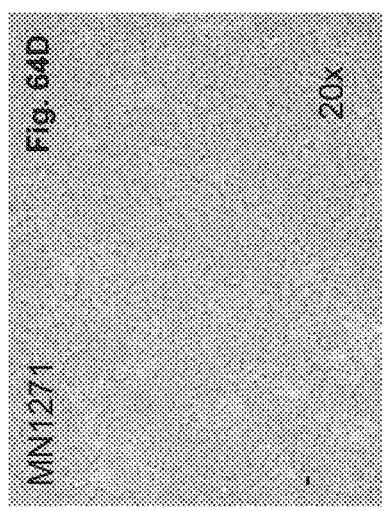
Figure 64

Naïve Stem Cells
MN1280
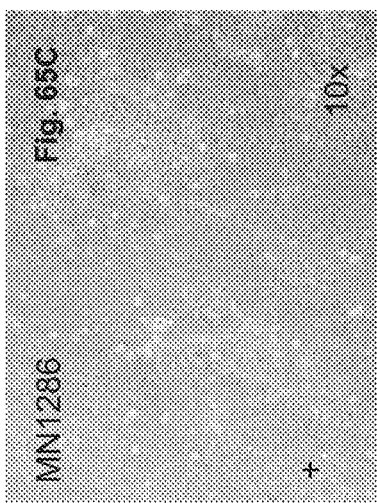
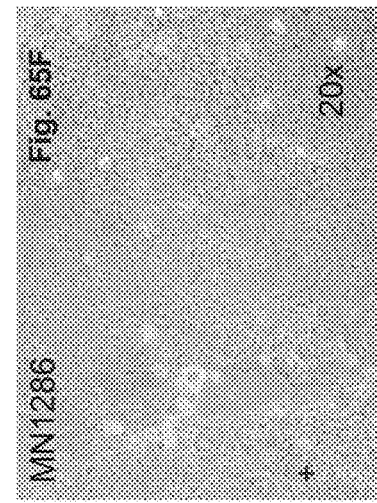
MN1285
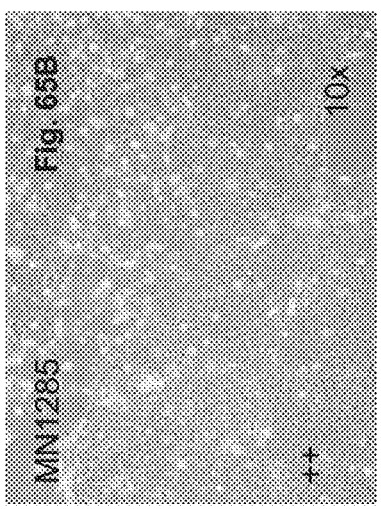
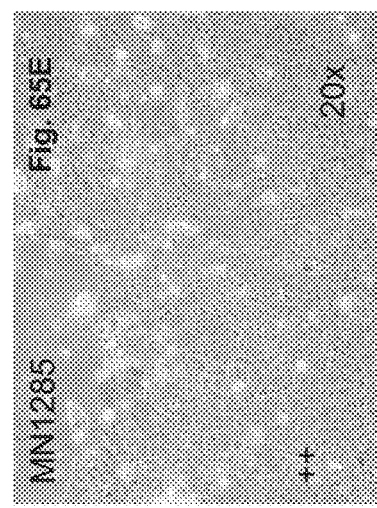
MN1286
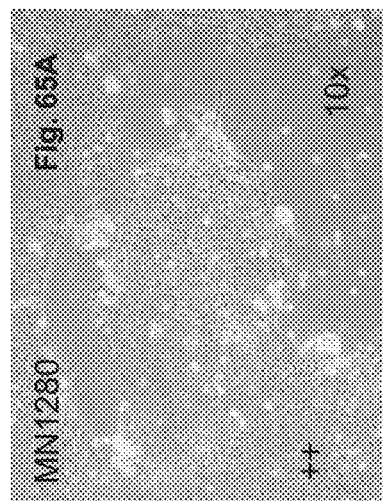
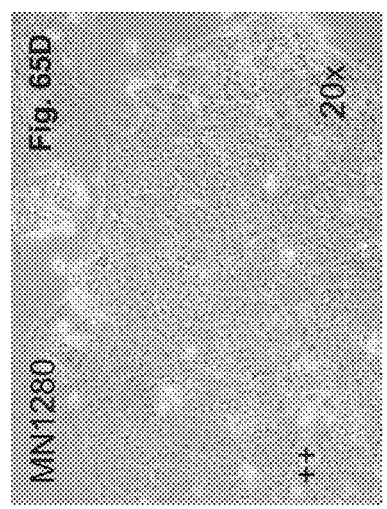
Figure 65

Naïve Stem Cells
MN1289
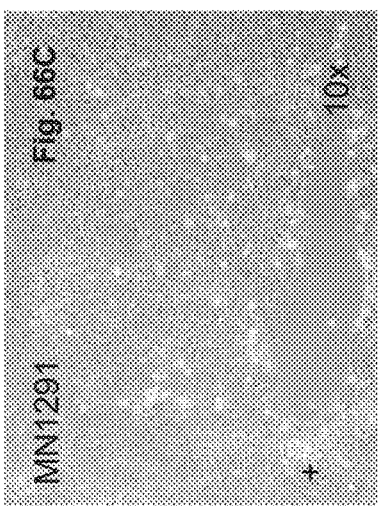
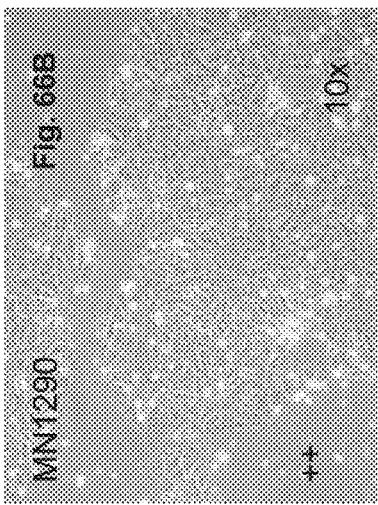
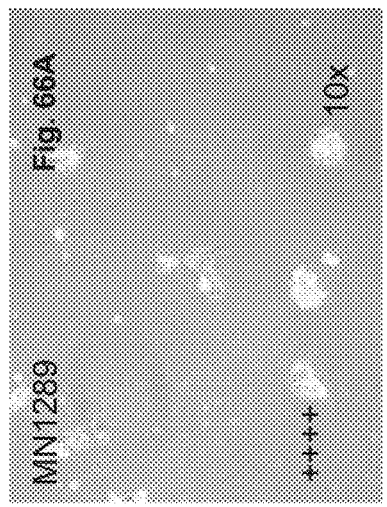
MN1290
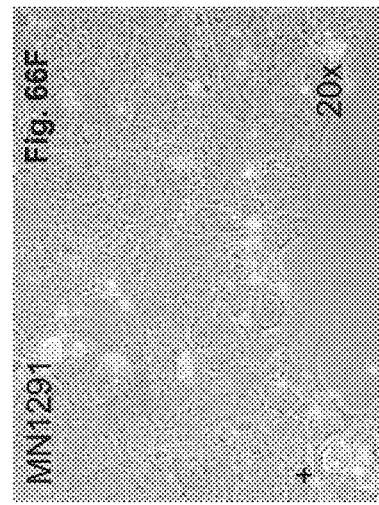
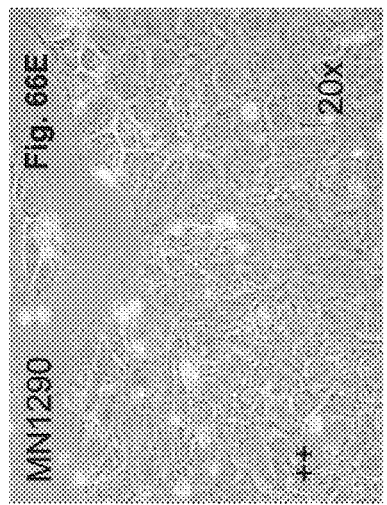
MN1291
Figure 66

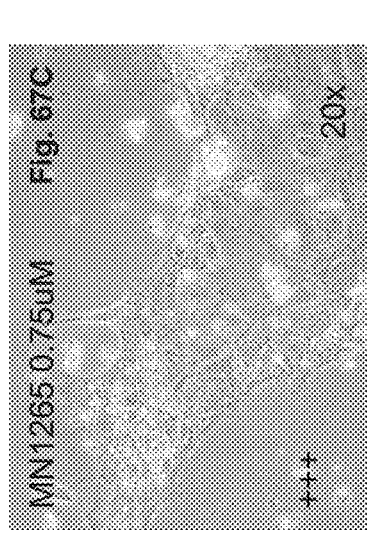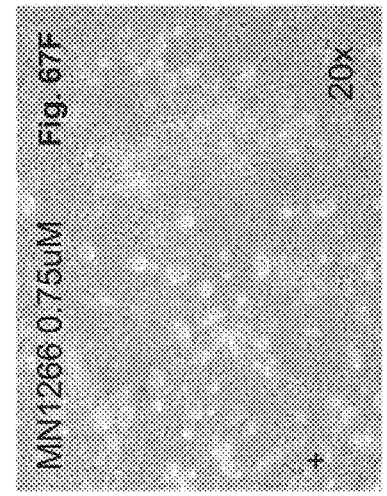
Figure 67

Naïve Stem Cells
MN1270 12uM
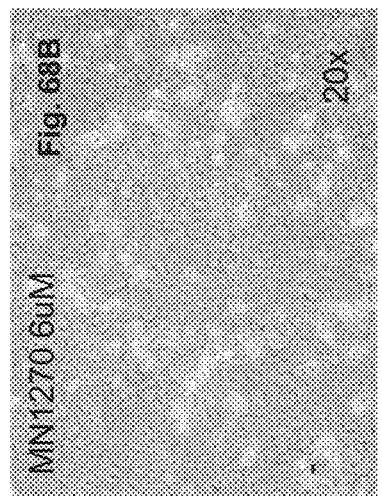
MN1270 6uM
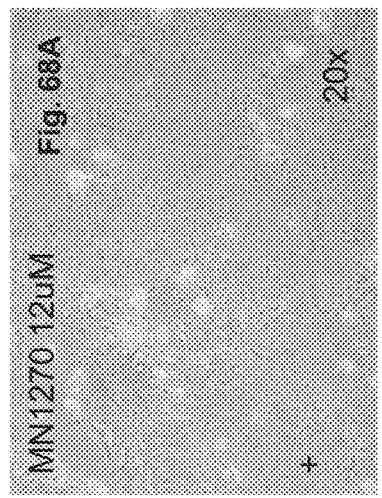
MN1270 0.75uM
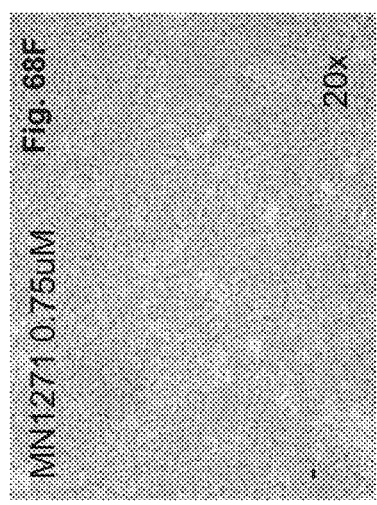
MN1271 12uM
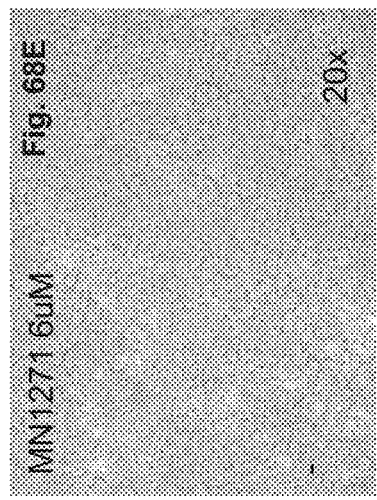
MN1271 6uM
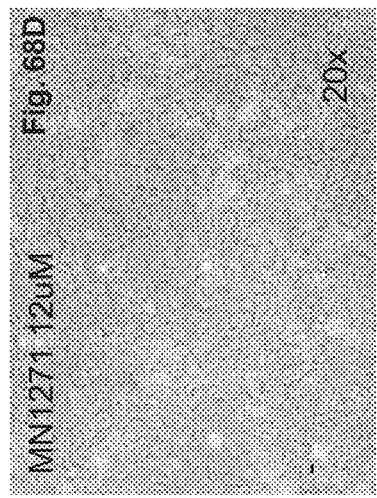
MN1271 0.75uM
Figure 68

Naïve Stem Cells
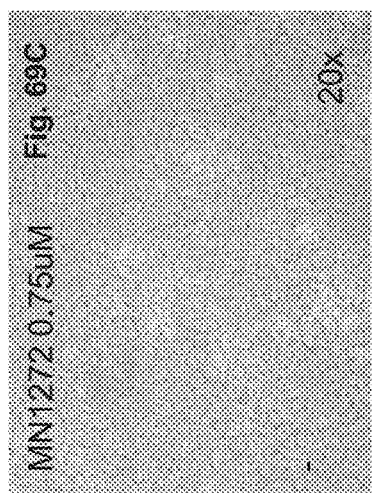
MN1272 12uM
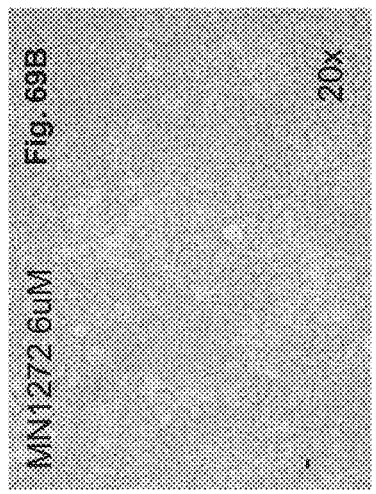
MN1272 6uM
MN1272 0.75uM
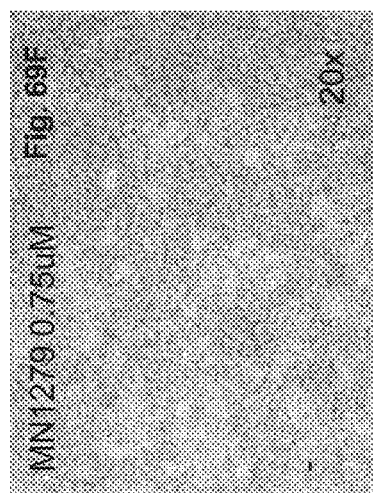
MN1279 12uM
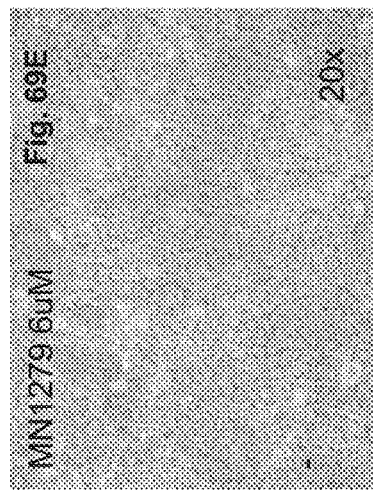
MN1279 6uM
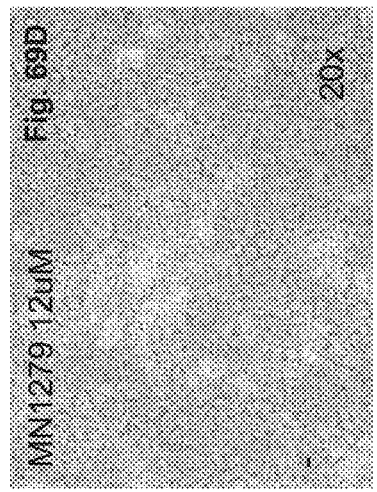
MN1279 0.75uM
Figure 69

Naïve Stem Cells
| MN1290 12uM | MN1290 6uM | MN1290 0.75uM |
|---|---|---|
| 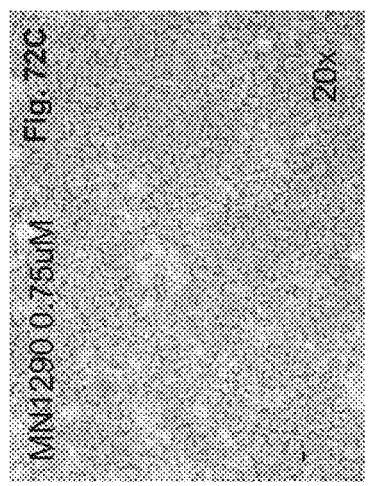 Fig. 72A | 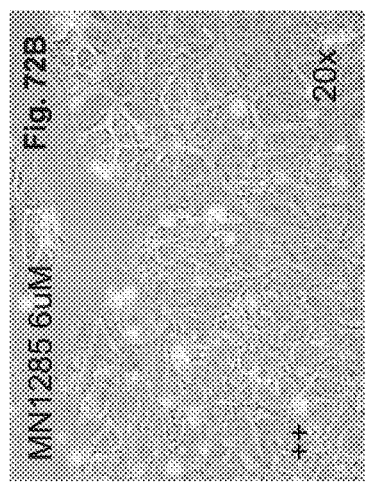 Fig. 72B |  Fig. 72C |
| MN1291 12uM | MN1291 6uM | MN1291 0.75uM |
|---|---|---|
| 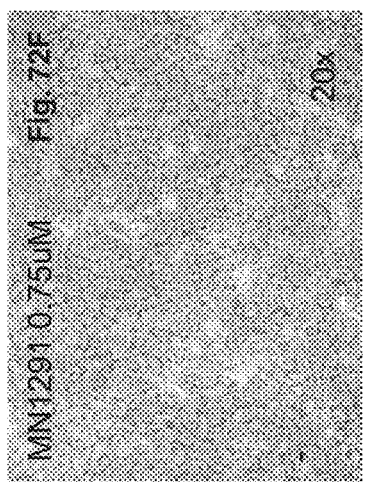 Fig. 72D | 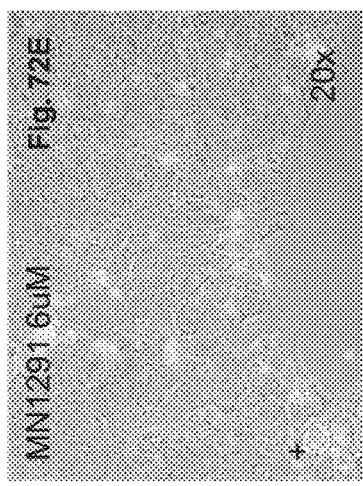 Fig. 72E | 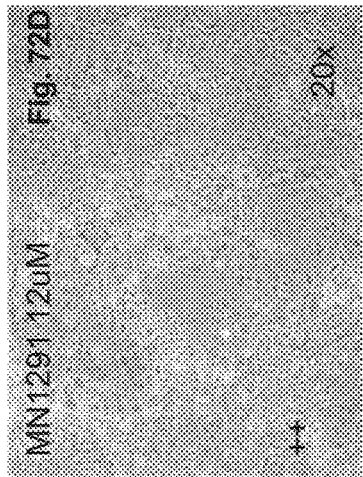 Fig. 72F |
Figure 72

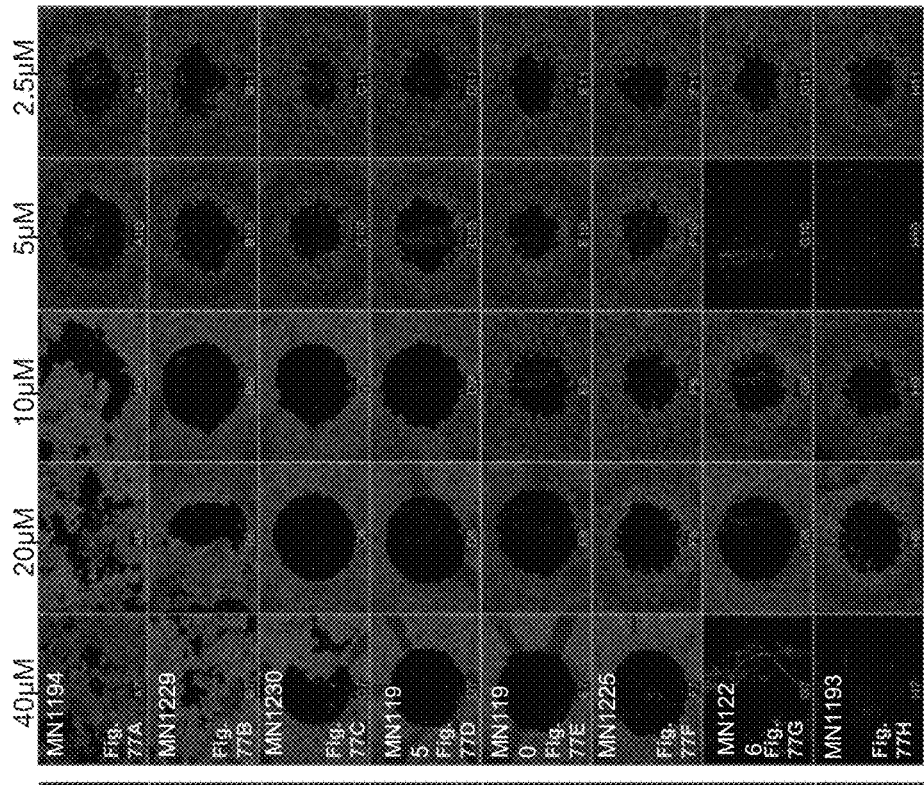
Figure 77 Cell Proliferation (MN1194 analogs)
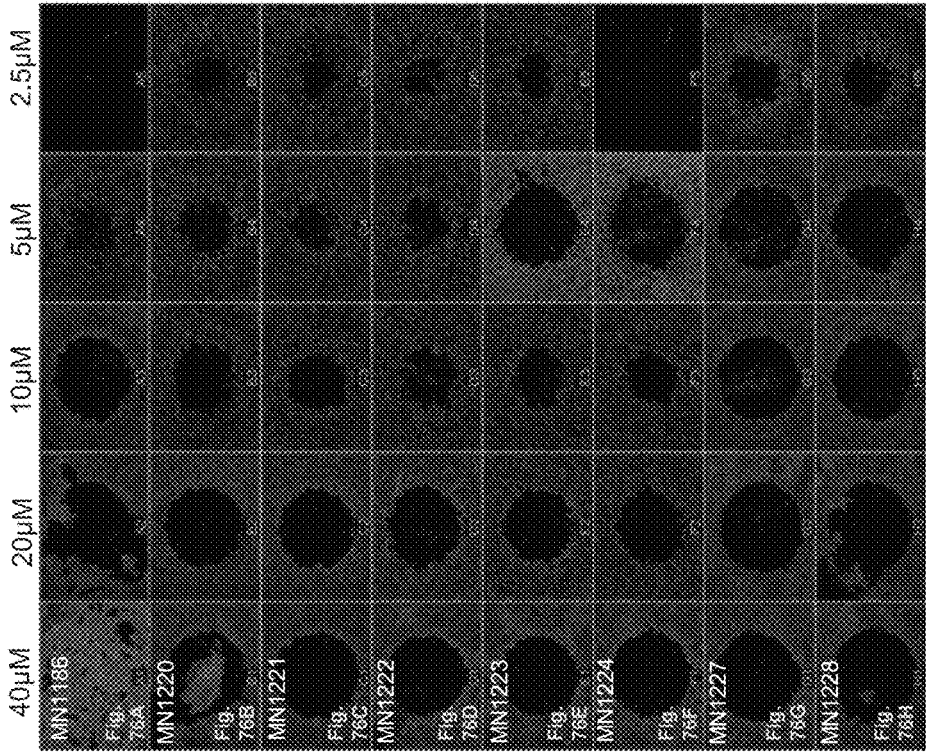
Figure 76 Cell Migration Assay (MN1186 analogs)
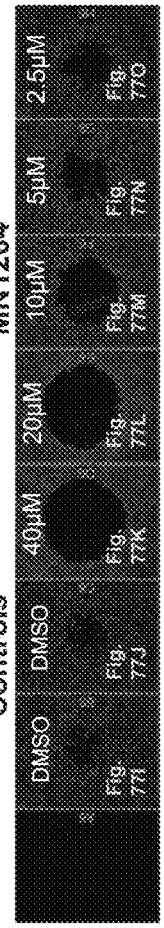

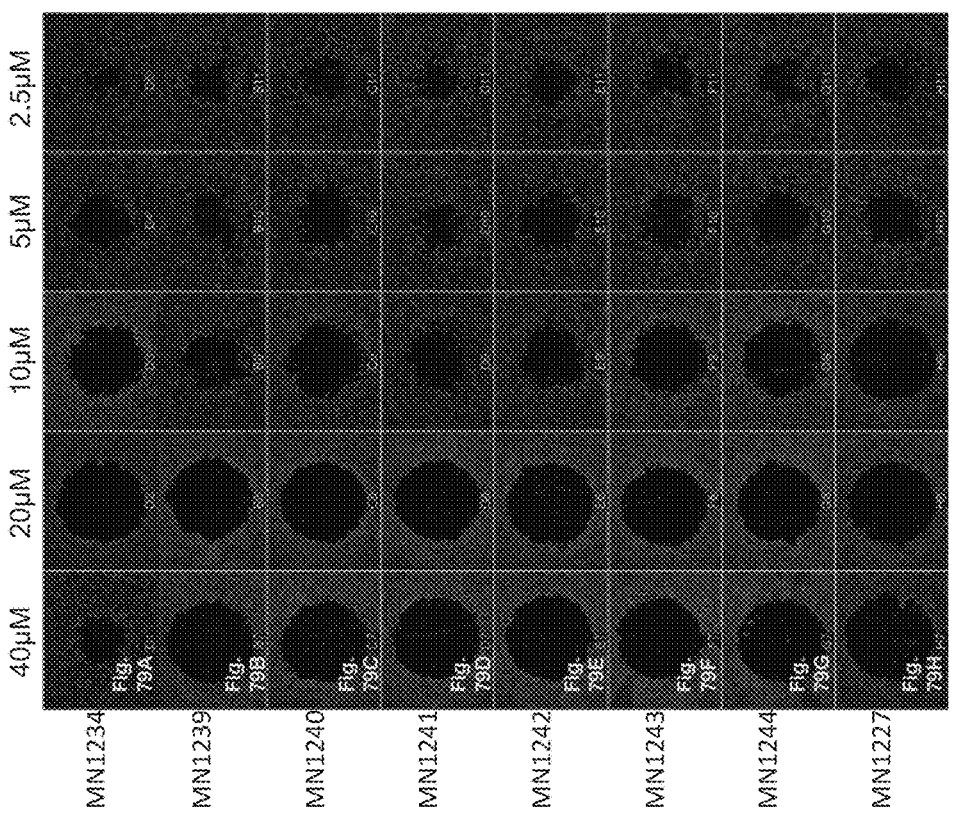
Figure 78  Cancer Migration (@120h)
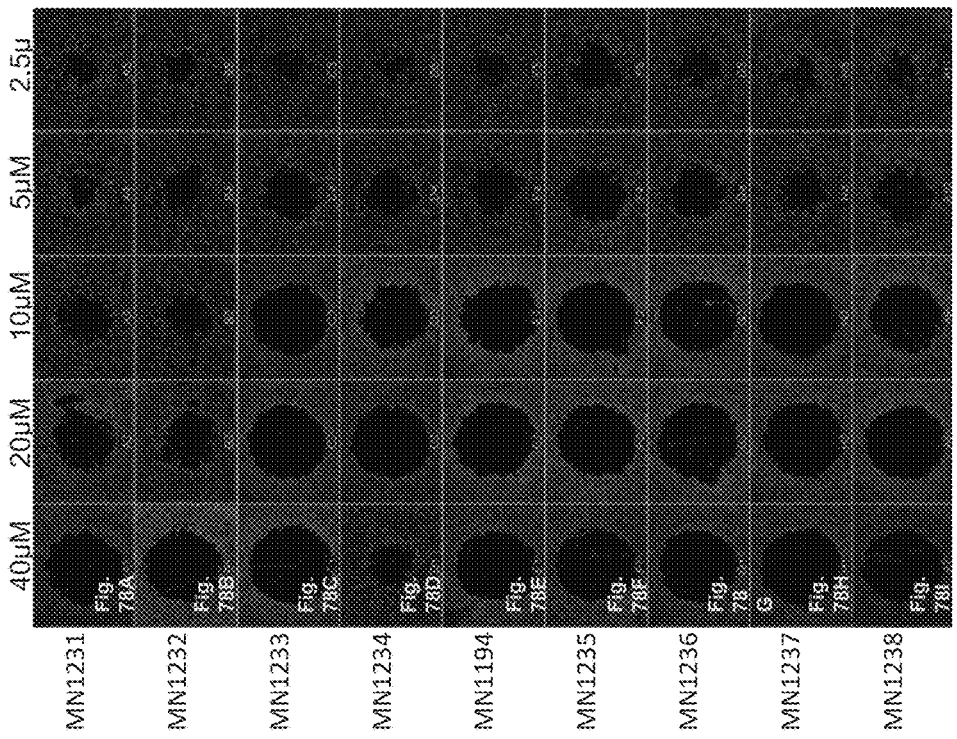
Figure 79  Cancer Migration (@120h)

Figure 80

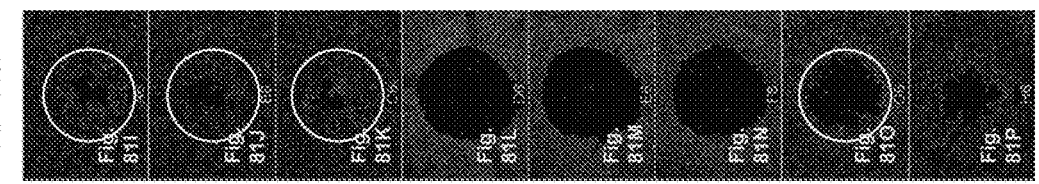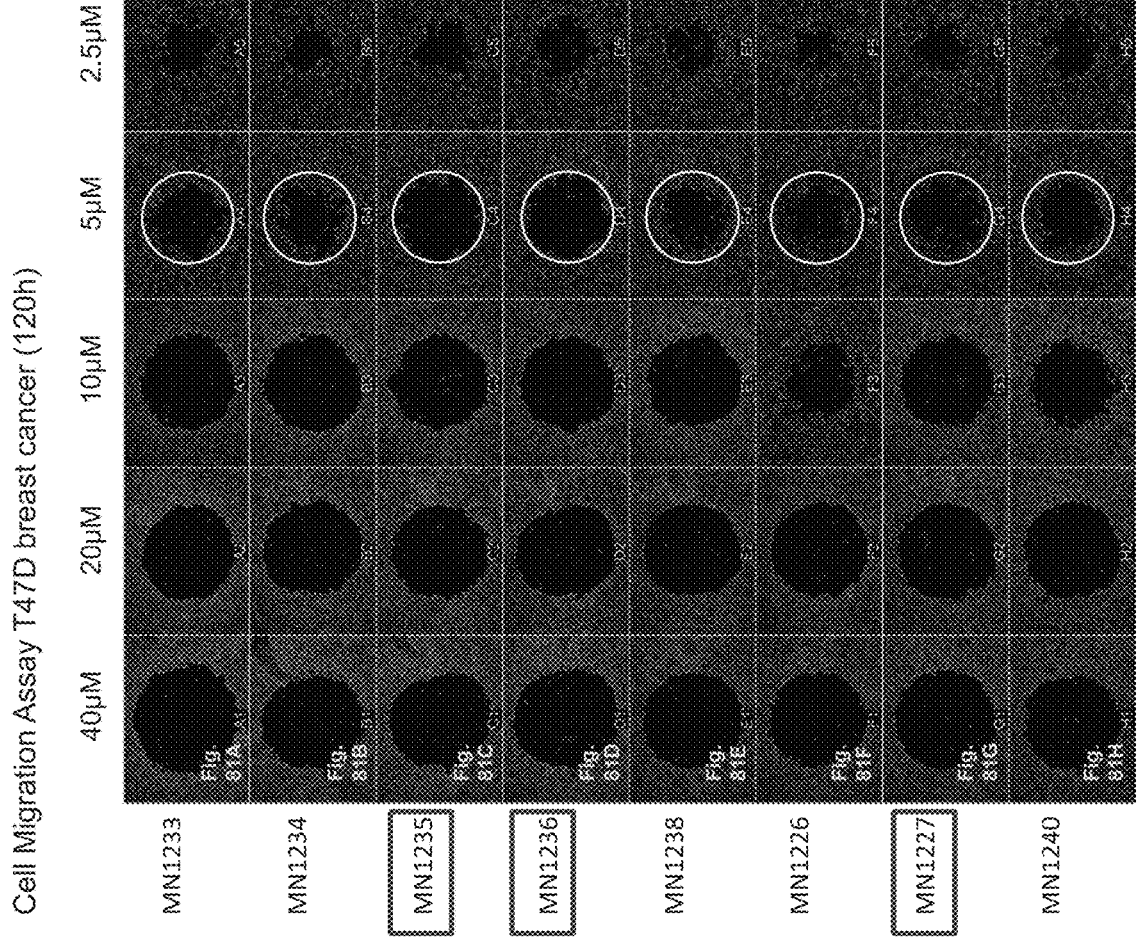
Figure 81

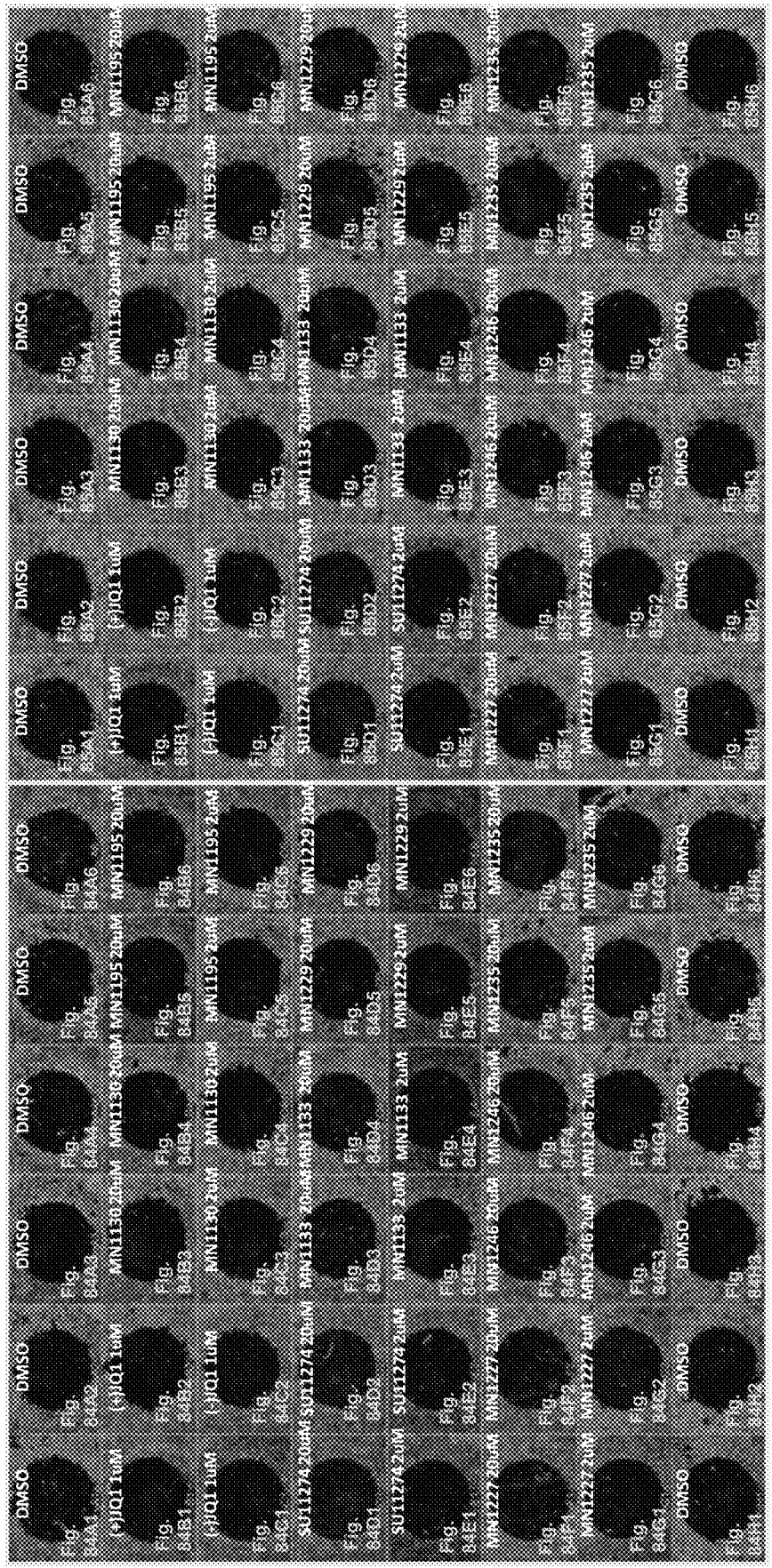
Inhibition of cancer cell migration: t = 0
Figure 84 DU145
Figure 85 SK-OV-3

Inhibition of cancer cell migration: t = 24 hrs

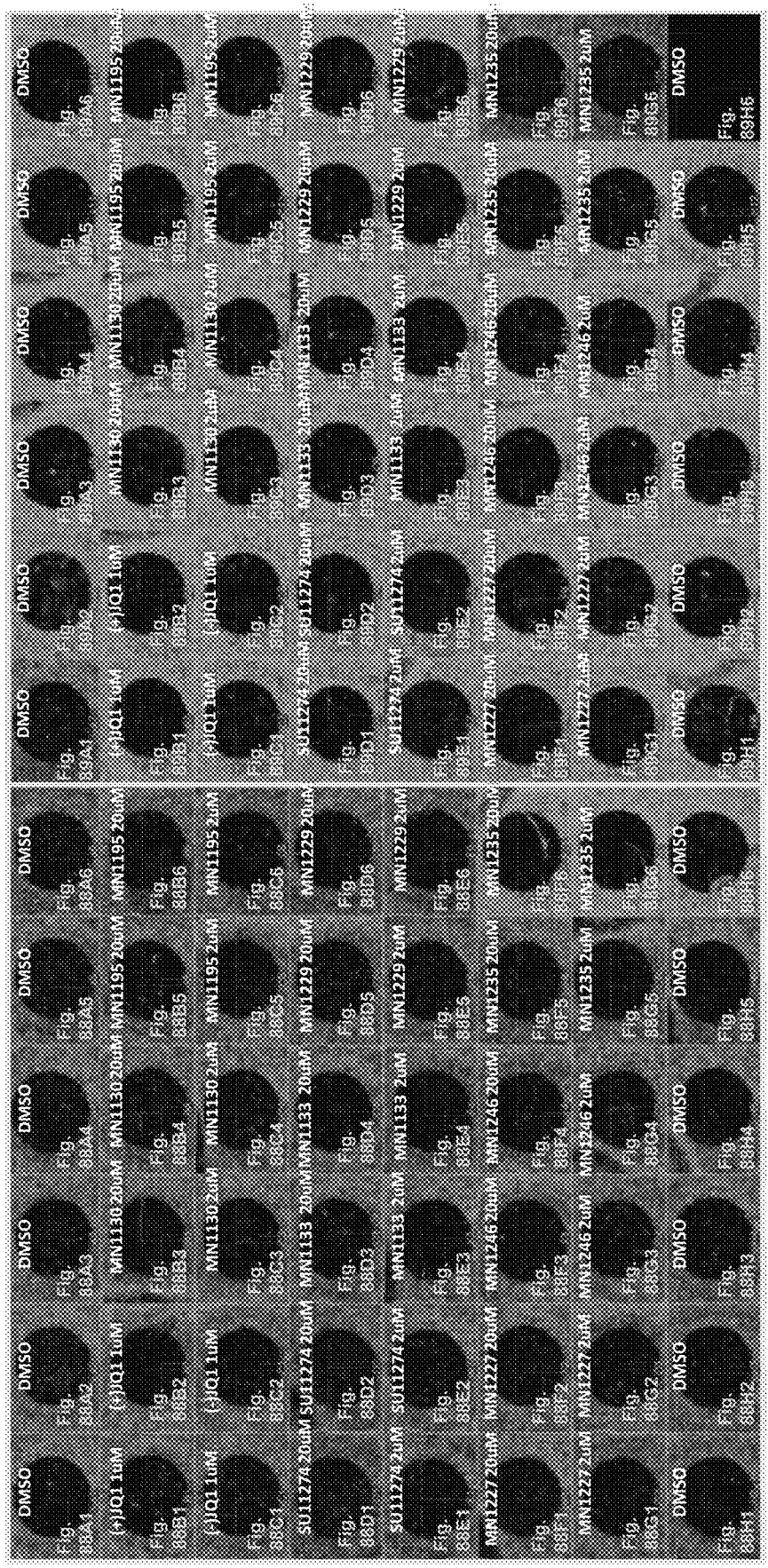

Inhibition of cancer cell migration: t = 20hrs

Inhibition of cancer cell migration: t = 26hrs

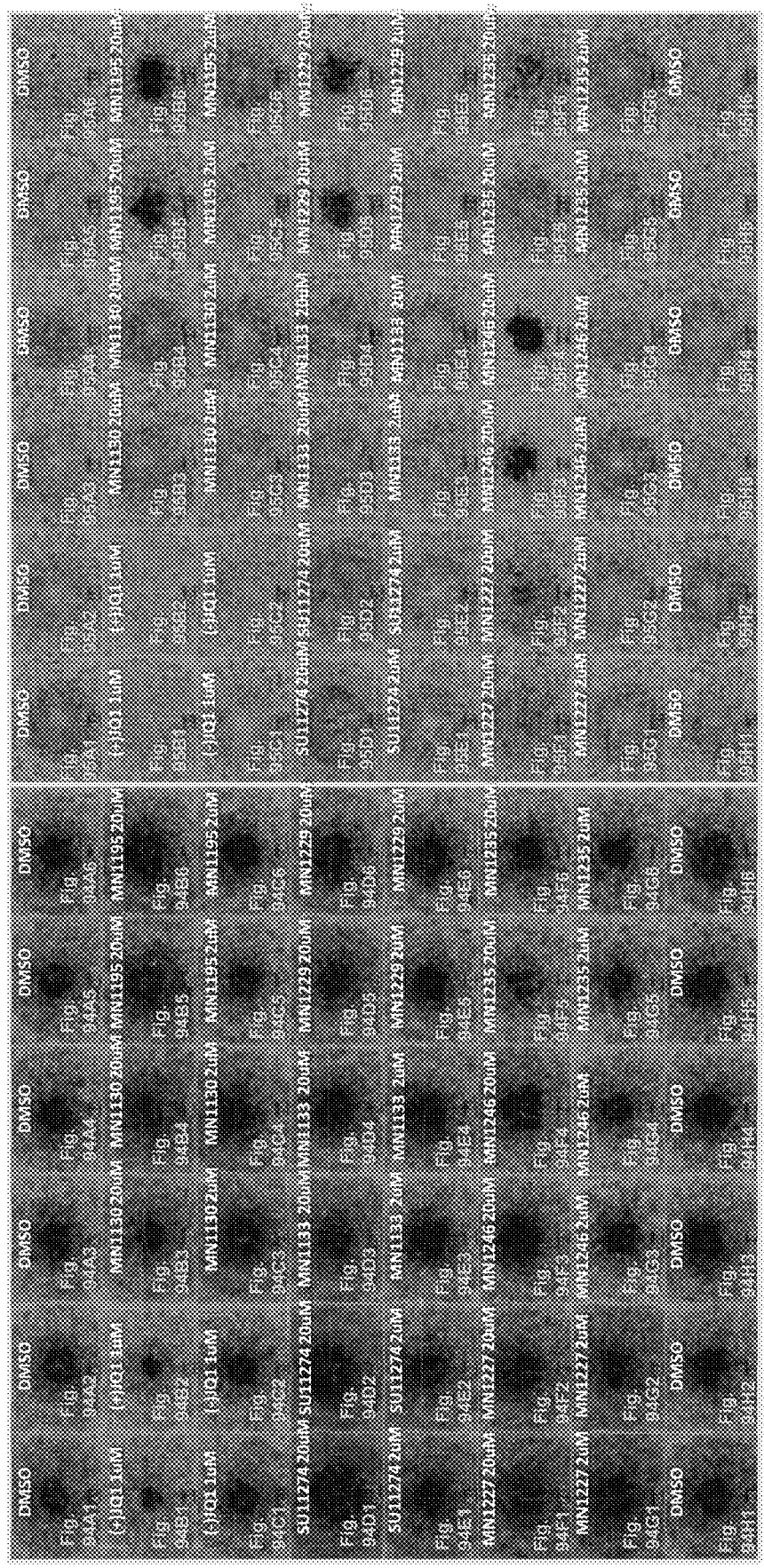

Inhibition of cancer cell migration: t = 0hrs

Figure 96  CHL-1

Figure 97  OV-90

Inhibition of cancer cell migration: t = 40hrs

Figure 98  CHL-1

Figure 99  OV-90

Inhibition of cancer cell migration: t = 72hrs

Figure 100 CHL-1

Figure 101 OV-90

Figure 102 CAPAN-2

Figure 103 CRL-1500 aka ZR-75-1

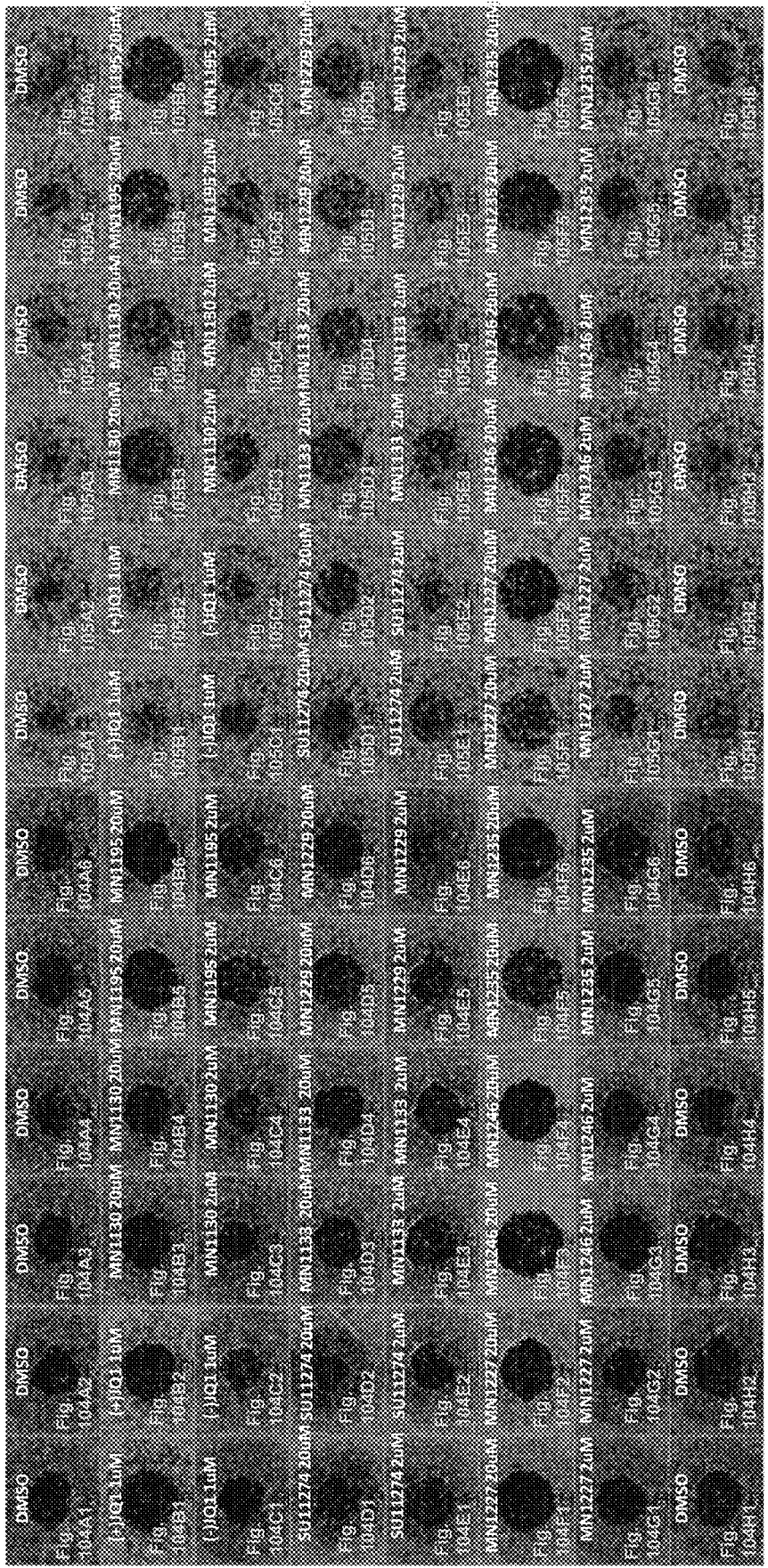
Inhibition of cancer cell migration: t = 72hrs
Figure 104  CAPAN-1  Figure 105  CRL-1500 aka ZR-75-1
Figure 104  CAPAN-2

Figure 106

Inhibition of cancer cell migration: t = 120hrs

CAPAN-2  CRL-1500 aka ZR-75-1

Inhibition of cancer cell proliferation T47D @ 120 hrs, measured by calcein staining Figure 107  MN1194 analogs Figure 108  MN1186 analogs Inhibition of cancer cell proliferation @ 96 hrs, measured by calcein staining Figure 109 prostate cancer (MUC1+/NME7_AB +++/NME7-X1+++)

Figure 110 breast cancer (MUC1^LO)

Figure 111 prostate cancer (MUC1+/NME7_AB +++/NME7-X1+++)

Figures 112, 113, 114:
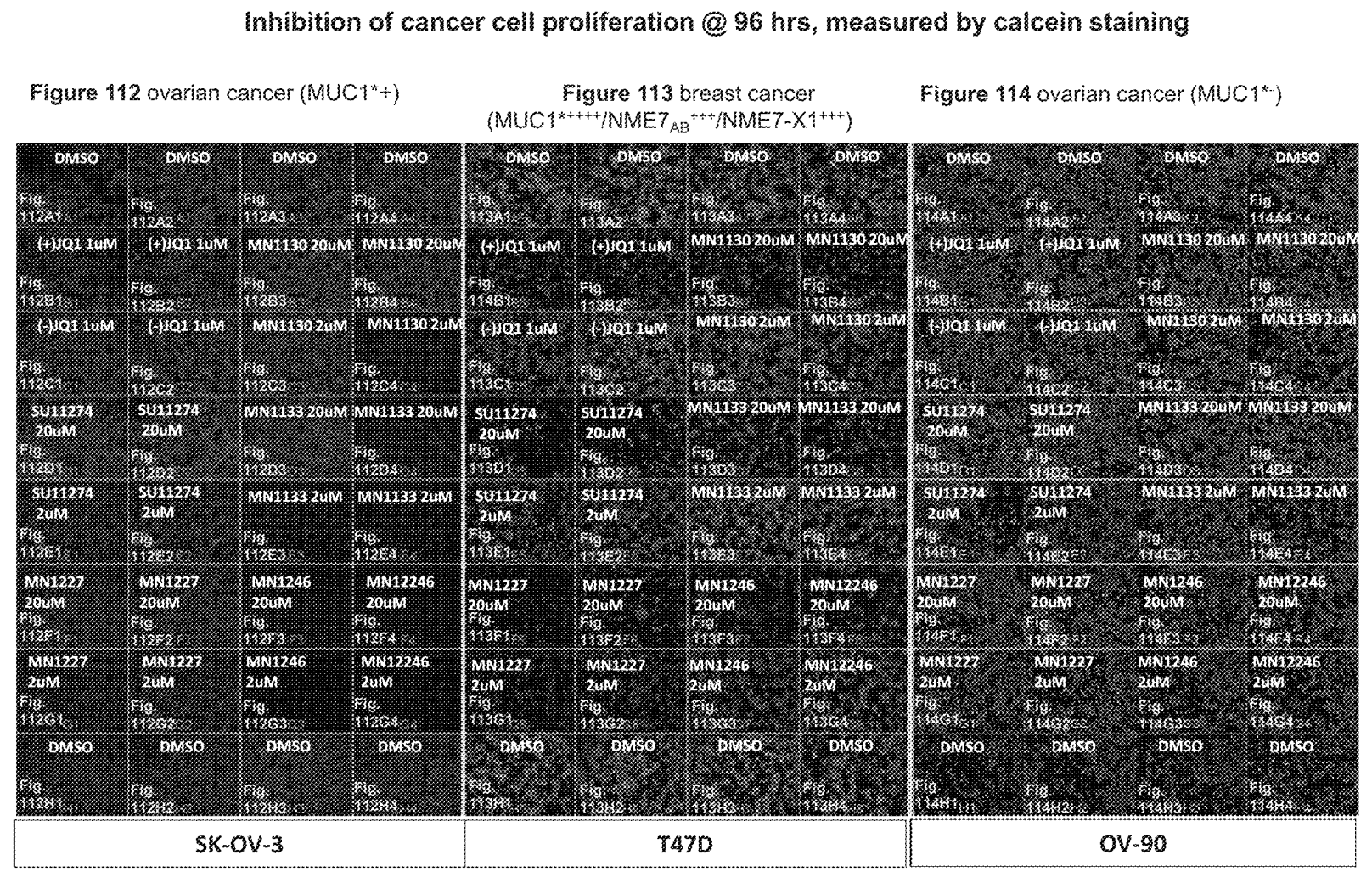

Inhibition of cancer cell proliferation @ 96 hrs, measured by calcein staining

Figure 112 ovarian cancer (MUC1*+)

Figure 113 breast cancer (MUC1*++++/NME7$_{AB}$+++/NME7-X1+++)

Figure 114 ovarian cancer (MUC1*)

Figure 115

Inhibition of cancer cell proliferation T47D @ 120 hrs, measured by calcein staining, compounds @ 6uM Inhibition of cancer cell proliferation @ 50 hrs, measured by calcein staining Figure 116 DU145 prostate cancer (MUC1++/NME7_AB+++/NME7-X1+++)

Figure 117 SK-OV-3 ovarian cancer (MUC1++)

Figure 118
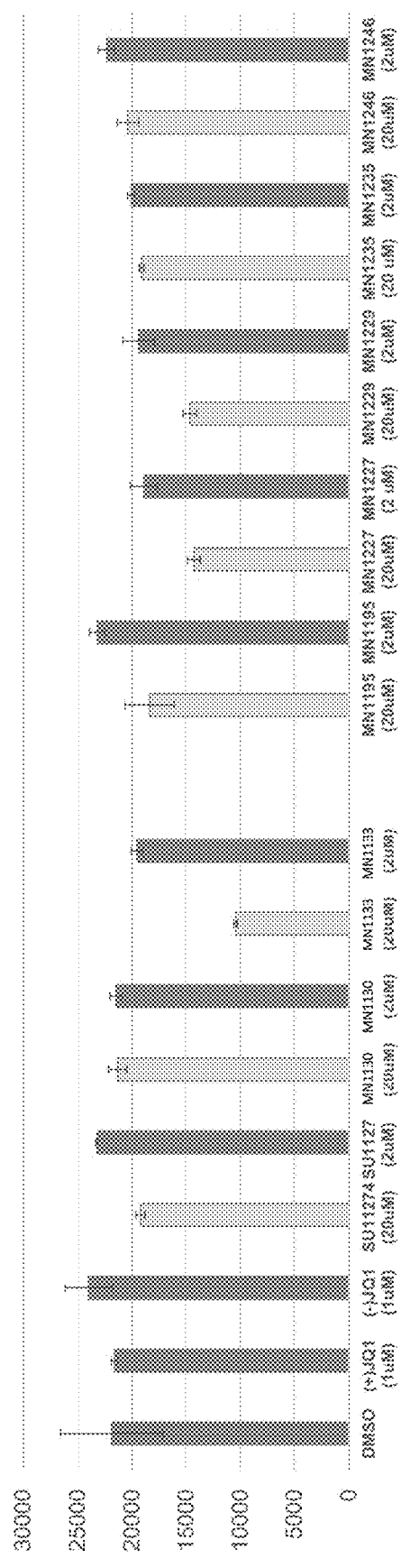
Fig. 118A DU145 MUC1*(+) prostate cancer cells proliferation data t = 50 h
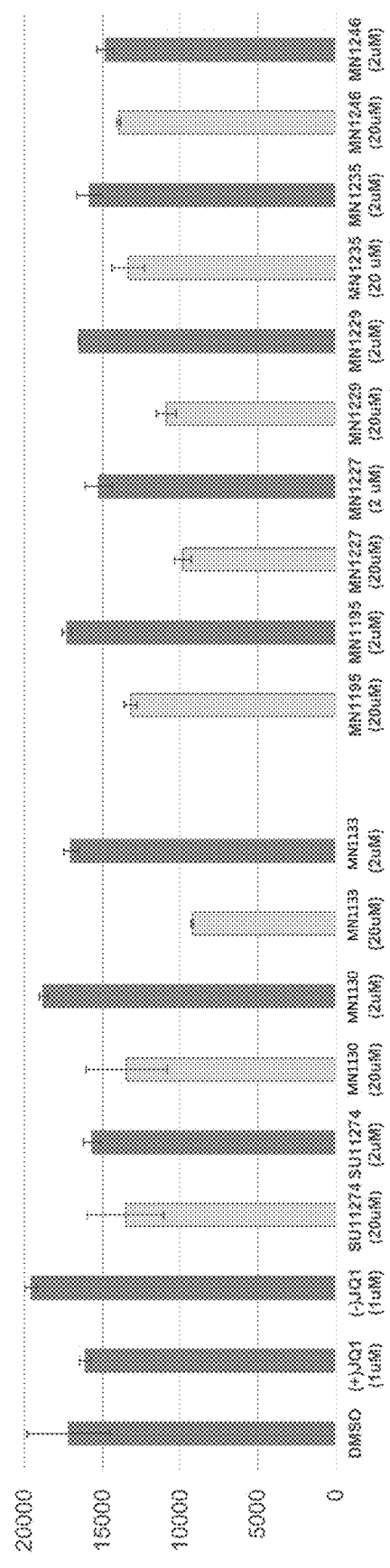
Fig. 118B SK-OV-3 MUC1*(+) ovarian cancer cells proliferation data t = 50 h Inhibition of cancer cell proliferation @ 40 hrs, measured by calcein staining Figure 119 A549 lung cancer (MUC1* positive)

Figure 120 PC-3 prostate cancer (MUC1* negative but highly NME7 AB & K1 positive)

Figure 121
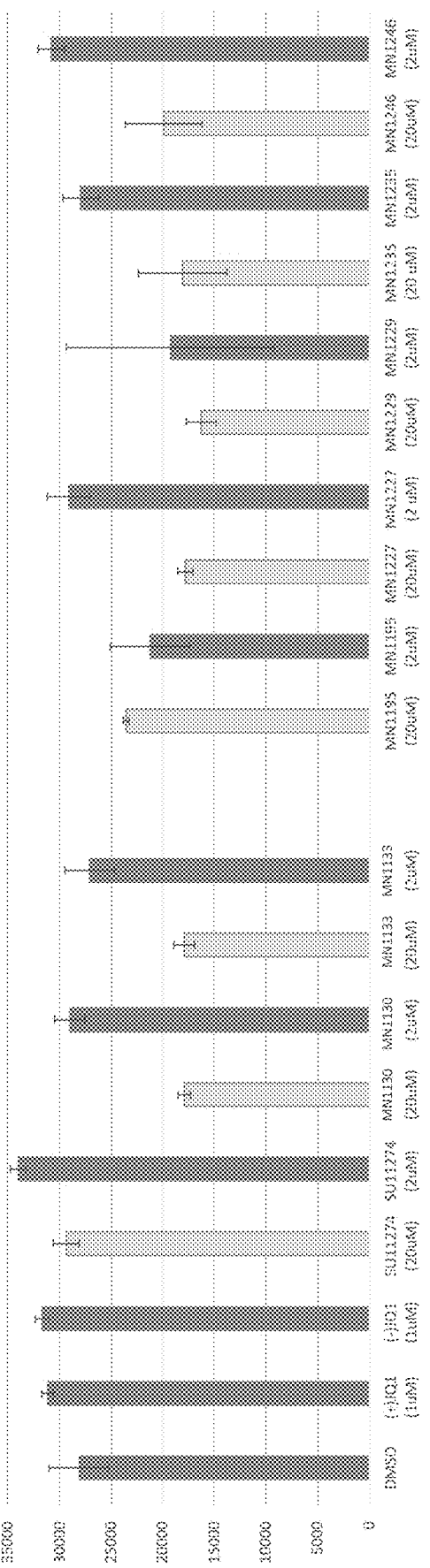
Fig. 121A A549 MUC1*(+) lung cancer cells proliferation data t = 40 h
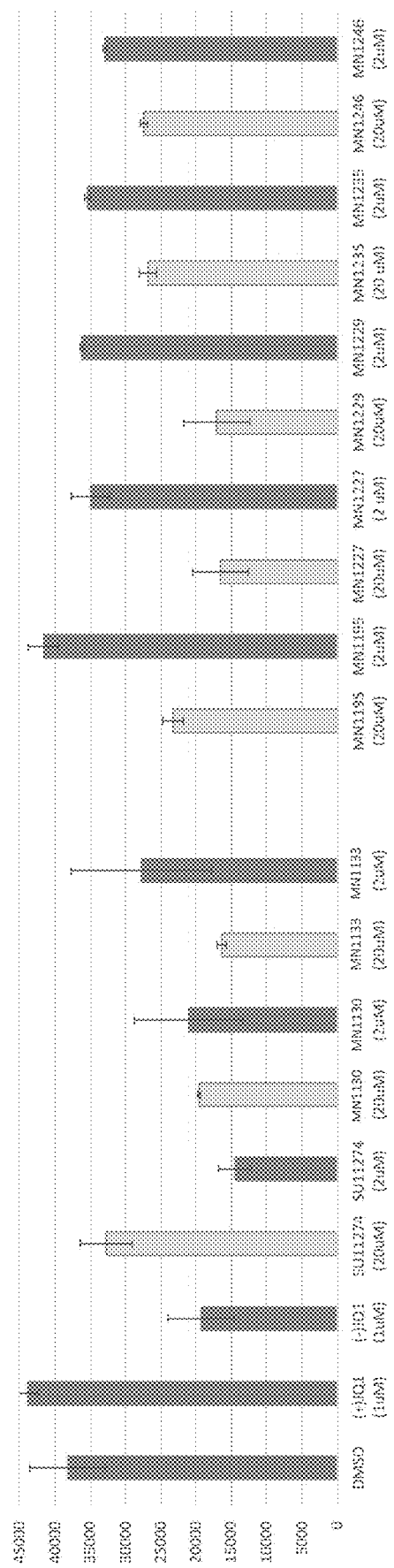
Fig. 121B PC-3 MUC1*(-)/NME7_AB+++ & NME7-X1+++ prostate cancer cells proliferation t = 40 h Figure 122 CHL-1 melanoma (MUC1*+/NME7$_{AB}$ & -X1$^{++}$)

Figure 123 OV-90 ovarian cancer (MUC1*-)

Inhibition of cancer cell proliferation @ 120 hrs, measured by calcein staining

Figure 124
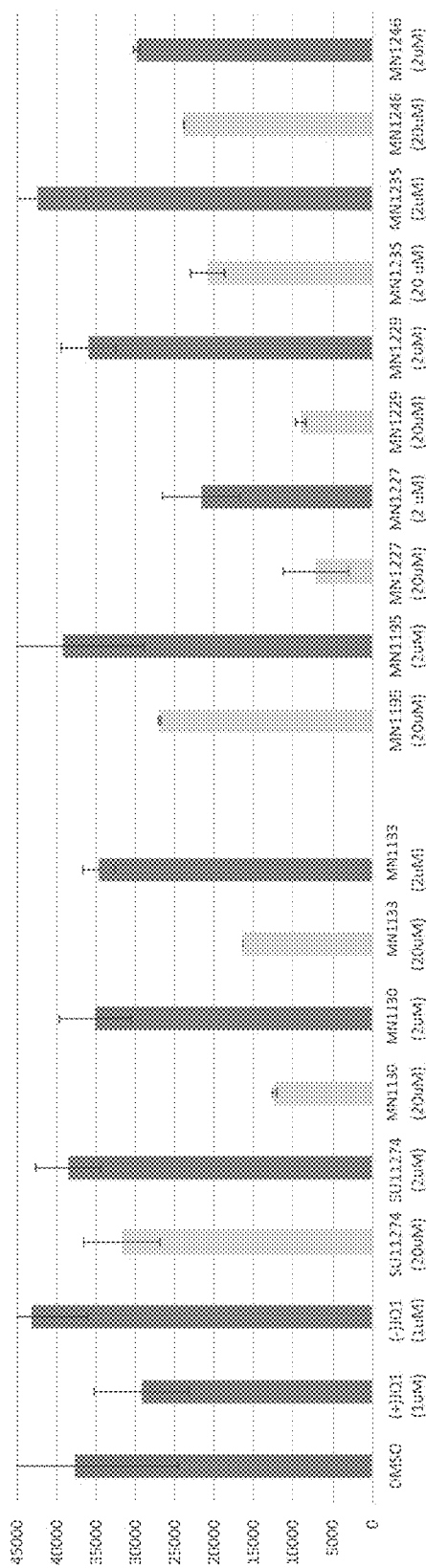
Fig. 124A CHL-1 MUC1*(+)/NME7_AB++ & NME7-X1++ melanoma cancer cells proliferation data t = 120 h
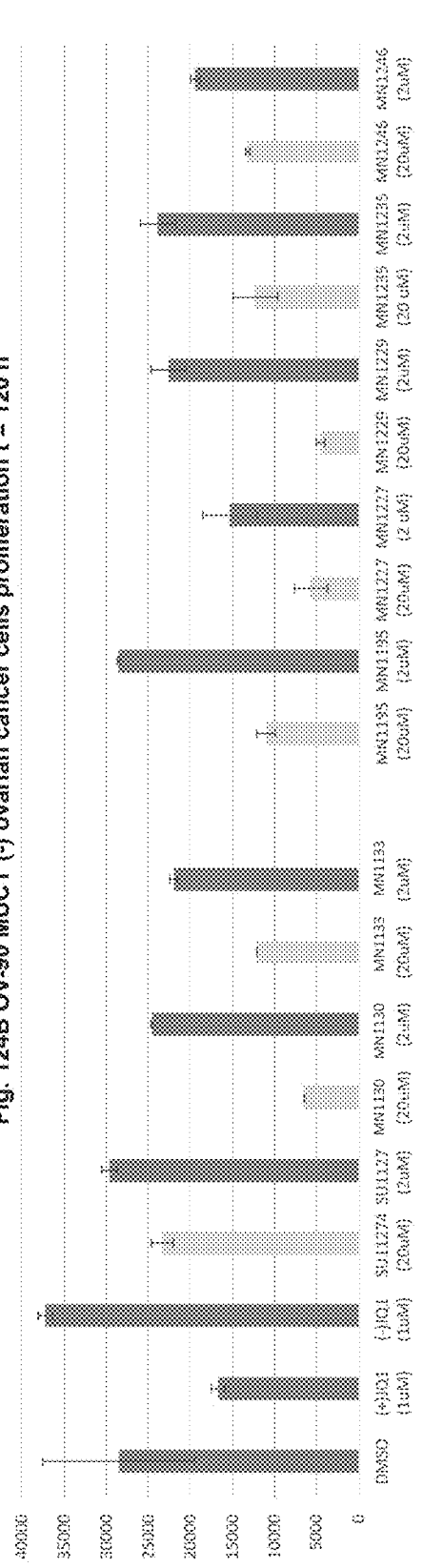
Fig. 124B OV-90 MUC1*(-) ovarian cancer cells proliferation t = 120 h Inhibition of cancer cell proliferation @ 120 hrs, measured by calcein staining Figure 125 CAPAN-2 pancreatic cancer (MUC1*+)

Figures 125, 126:
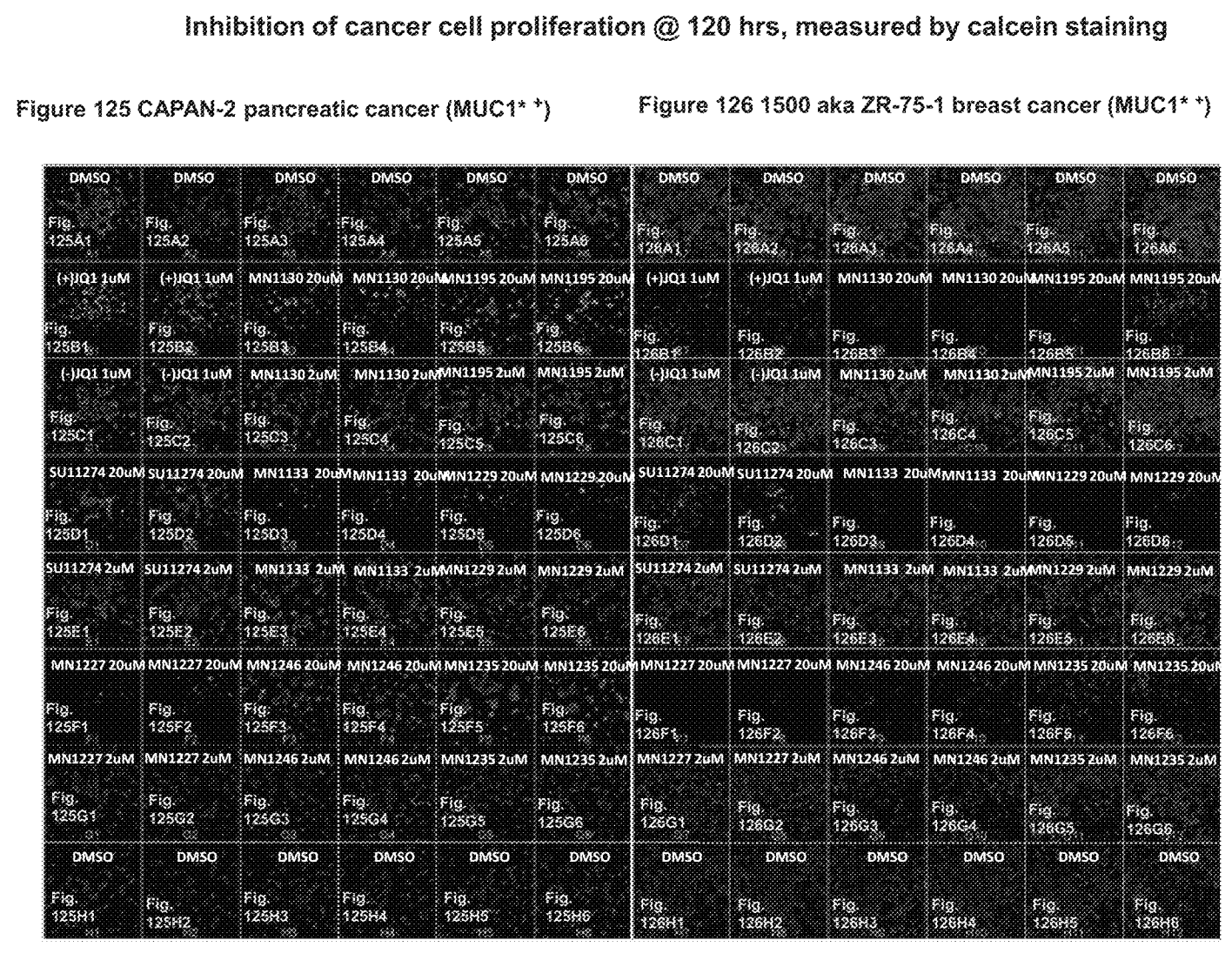

Figure 126 1500 aka ZR-75-1 breast cancer (MUC1*+)

Figure 127
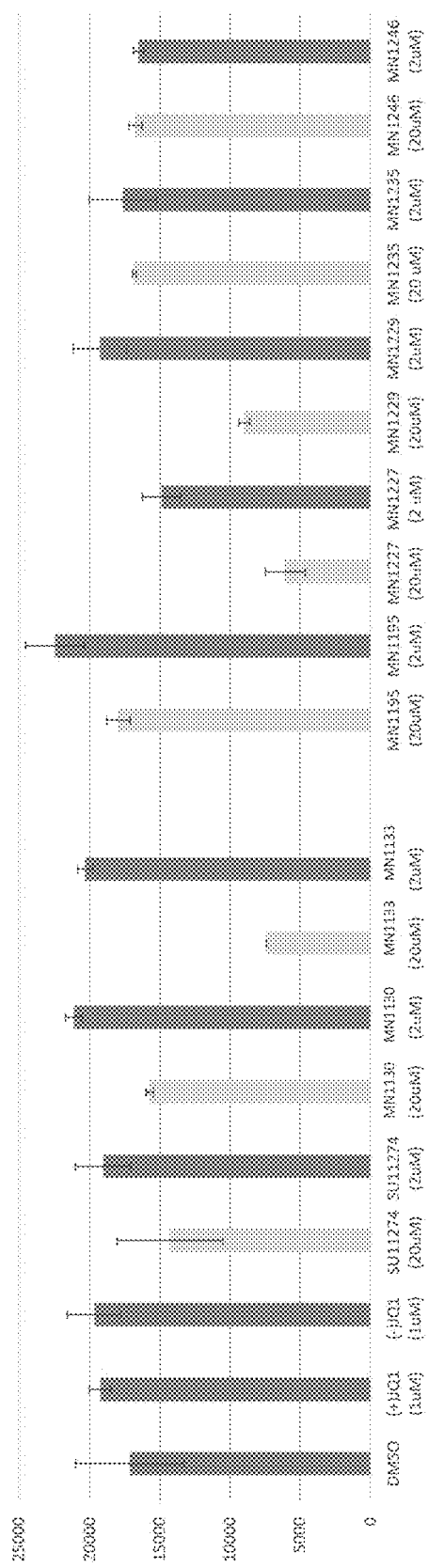
Fig. 127A CAPAN-2 (MUC1*+) pancreatic cancer cells proliferation data t = 120 h
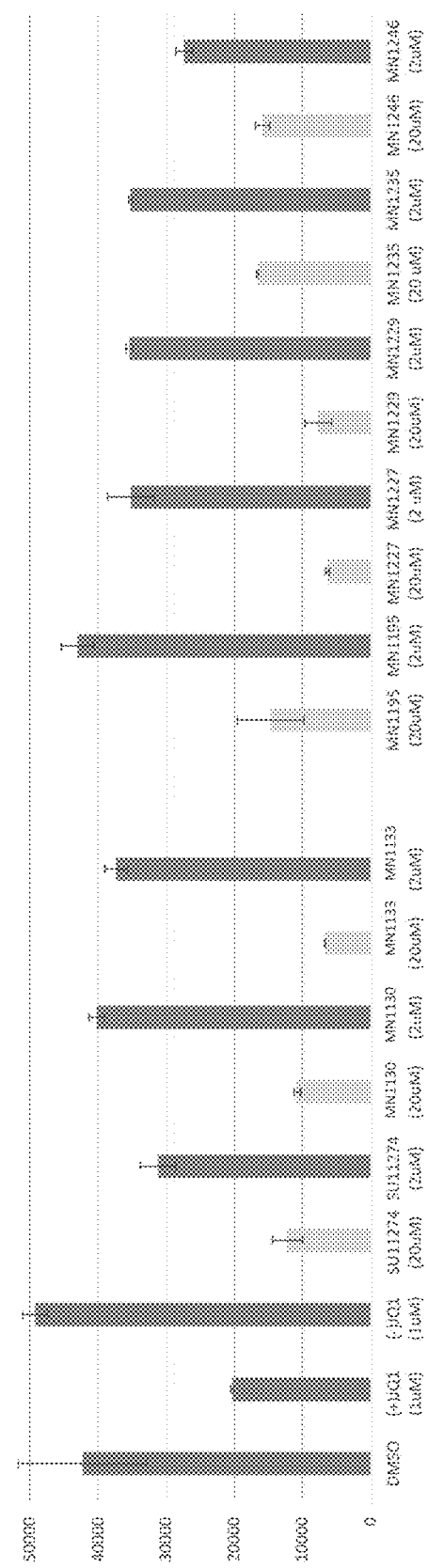
Fig. 127B 1500 aka ZR-75-1 (MUC1*+) breast cancer cells proliferation t = 120 h Figure 136  Calcein measurement of live cells Figure 137  bright field images of cells Proliferation Assay: effect of compounds @ 6uM on T47D breast cancer cells T=96h

NME7$_{AB}$ is only expressed in the earliest naïve state stem cells; Day 3 human blastocyst, all cells are naïve and express NME7$_{AB}$; by Day 5, NME7$_{AB}$ is only expressed in the naïve cells of inner cell mass. NME7$_{AB}$ is then turned off in adult life except in testis.
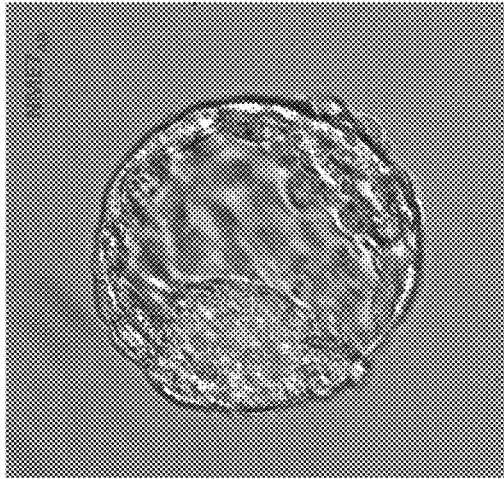
Fig. 164A
Day 3 human blastocyst
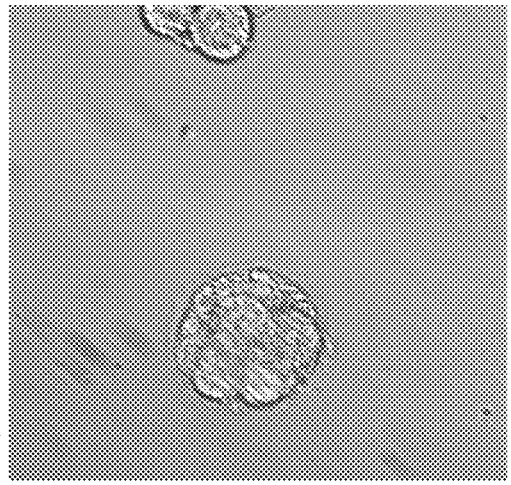
Fig. 164B
Day 5 human blastocyst
Figure 164

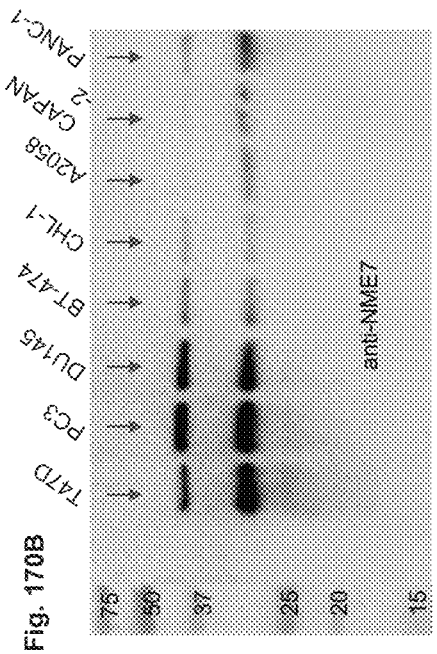
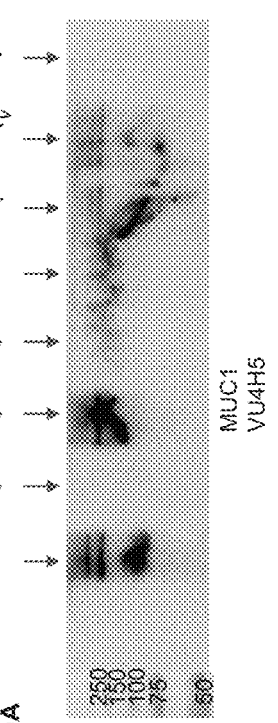
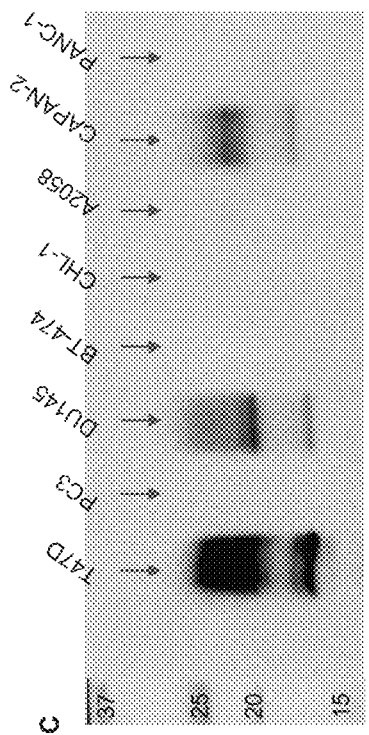
Figure 170

METHOD OF SCREENING FOR AGENTS FOR DIFFERENTIATING STEM CELLS

BACKGROUND

Field of the Invention

This invention generally relates to methods and compositions for the treatment of cancers that are characterized by the function of the compounds to differentiate stem cells.

Description of the Related Art

It was recently discovered that human stem cells, cultured under standard conditions, are not in a truly pluripotent state. Rather they have undergone some differentiation and have made certain cell fate decisions as evidenced by the accumulation of various methylation marks. When comparing human cultured stem cells to cells of mouse embryos it was determined that the human cultured stem cells look and behave more like mouse stem cells from the epiblast portion of the embryo, which has begun to differentiate, rather than the truly pluripotent stem cells of the inner cell mass. Researchers dubbed the true pluripotent stem cells of the inner cell mass 'naïve' and the more differentiated cells 'primed'. Further studies showed that both mouse and human primed state stem cells self-replicate by culture in bFGF, whereas mouse naïve stem cells self-replicate by culture in LIF. The growth factor that makes human stem cells grow in the naïve state was not known. Primed state stem cells are prone to spontaneous differentiation and must be manually dissected to remove the differentiating parts whereas naïve stem cells naturally resist spontaneous differentiation. In addition, primed stem cells cannot be passed as single cells and have a very low cloning efficiency, whereas naïve stem cells can be passed as single cells and have a high cloning efficiency. Female naïve stem cells have two active X chromosomes whereas primed state stem cells have already inactivated one X chromosome by methylation. Additionally, it is now known that naïve state stem cells have far less methylation marks, which essentially are early differentiation decisions, also known as cell fate decisions, which limit the types of mature cells that the stem cells can become.

SUMMARY OF THE INVENTION

In one aspect of the invention, a drug screen is disclosed in which agents are screened for their ability to preferentially inhibit pluripotency of naïve stem cells more than primed stem cells. Agents that are screened may be antibodies or antibody like molecules, polyclonal, monoclonal, antibody fragment fusion proteins, antibody mimics, peptides or peptide mimics, small molecules or natural products.

In another aspect of the invention agents are disclosed that inhibit cancer growth, inhibit the growth of metastatic cancer cells, or inhibit the metastatic potential of cancer cells wherein the agents were identified by their ability to induce differentiation or inhibit pluripotency of naïve stem cells and their relative inability to induce differentiation or inhibit pluripotency of primed stem cells.

In yet another aspect of the invention, the agents that are disclosed are disclosed for use as an anti-cancer or anti-metastasis therapeutic for the treatment or prevention of cancers.

In another aspect of the invention, novel anti-cancer or anti-metastasis drug targets are identified by identifying genes that are upregulated in naïve stem cells but not in primed stem cells.

In yet another aspect of the invention, novel anti-cancer or anti-metastasis drug targets are identified by identifying microRNAs that are upregulated in naïve stem cells but not in primed stem cells.

In one aspect, the invention is directed to a method for identifying an agent for the treatment or prevention of cancer or metastatic cancer comprising the steps of (i) contacting stem cell with a potential agent, and (ii) identifying an agent that induces differentiation, or inhibits stem cell pluripotency or growth of the stem cell, wherein such agent is determined to be an anti-cancer agent. The stem cell may be naïve state stem cell. Or, in step (i), the stem cell may be naïve state or primed state stem cell, wherein the effect of the agent on naïve state stem cell is compared to the effect on primed state stem cell, wherein if the agent has a greater effect on the naïve state stem cell compared with primed state stem cell, then the agent is determined to be an anti-cancer agent. The agent may be a polyclonal antibody, monoclonal antibody, antibody like molecule, antibody fragment fusion protein, antibody mimic, peptide, peptide mimic, small molecule or natural product. The stem cell may be human. The stem cell may be maintained in a naïve state by culturing in a medium comprising $NME7_{AB}$ or NME7-X1. The cancer may be breast, ovarian, melanoma, prostate, lung or pancreatic. The cancer may be MUC1 positive or MUC1* positive cancer. The cancer may be $NME7_{AB}$ or NME7-X1 positive cancer. The agent may not be generally cytotoxic. The agent may not be cytotoxic to fibroblasts or fibroblast progenitor cells.

In another aspect, the invention is directed to a method for preventing or treating cancer comprising administering to the subject the agent obtained by the method according to above. The cancer may be breast, ovarian, melanoma, prostate, lung or pancreatic. The cancer may be a MUC1 positive or MUC1* positive cancer. The cancer may be an $NME7_{AB}$ or NME7-X1 positive cancer.

In another aspect, the invention is directed to a method for preventing metastasis of cancer comprising administering to the subject the agent obtained by the method according to above.

In another aspect, the invention is directed to a method of inhibiting cancer growth comprising administering to the subject the agent obtained by the method according to above.

In another aspect, the invention is directed to a method of inhibiting the growth of metastatic cancer cells comprising administering to the subject the agent obtained by the method according to above.

In another aspect, the invention is directed to a method of identifying anti-cancer or anti-metastasis target for drug discovery comprising identifying a gene or gene product that is upregulated in naïve state stem cells compared to primed state stem cells.

In another aspect, the invention is directed to a method of identifying anti-cancer or anti-metastasis target for drug discovery comprising identifying a gene or gene product that is downregulated in naïve state stem cells compared to primed state stem cells.

In another aspect, the invention is directed to a method of identifying anti-cancer or anti-metastasis agent comprising (i) identifying gene or gene product that is downregulated in naïve state stem cells compared to primed state stem cells; (ii) contacting the naïve stem cells with an agent; and (iii)

identifying an agent that increases expression or activity of the downregulated gene or gene product in naïve state stem cells. The down-regulated gene may be a gene that is upregulated when stem cells initiate differentiation. The down-regulated gene may be fibronectin, vimentin, or NF1.

In another aspect, the invention is directed to a method of identifying anti-cancer or anti-metastasis agent comprising (i) identifying gene or gene product that is upregulated in naïve state stem cells compared to primed state stem cells; (ii) contacting the naïve stem cells with an agent; and (iii) identifying an agent that inhibits expression or activity of the upregulated gene or gene product in naïve state stem cells. The upregulated gene may be E-cadherin or CXCR4.

In another aspect, the invention is directed to a method of identifying anti-cancer or anti-metastasis agent comprising (i) identifying gene or gene product that is upregulated in naïve state stem cells compared to fibroblast cells; (ii) contacting the naïve stem cells with an agent; and (iii) identifying an agent that inhibits expression or activity of the upregulated gene or gene product in naïve state stem cells. The upregulated gene may be E-cadherin or CXCR4.

In another aspect, the invention is directed to a method of identifying anti-cancer or anti-metastasis agent comprising (i) identifying gene or gene product that is downregulated in naïve state stem cells compared to fibroblast cells; (ii) contacting the naïve stem cells with an agent; and (iii) identifying an agent that increases expression or activity of the downregulated gene or gene product in naïve state stem cells. The down-regulated gene may be a gene that is upregulated when stem cells initiate differentiation. The down-regulated gene may be fibronectin, vimentin, or NF1.

In another aspect, the invention is directed to a method of identifying anti-cancer or anti-metastasis agent comprising (i) identifying microRNA that is upregulated in naïve state stem cells compared to primed stem cells or fibroblast cells; (ii) contacting the naïve stem cells with an agent; and (iii) identifying an agent that inhibits expression or activity of the upregulated microRNA in naïve state stem cells.

In another aspect, the invention is directed to the compounds of Formulae 1 to 10.

In another aspect, the invention is directed to a method of treating cancer in a subject, comprising administering to the subject a compound of Formula 1 to 10 or as set forth in FIGS. 18-27. The cancer may be a MUC1 positive or MUC1* positive cancer. The cancer may be an NME7$_{AB}$ or NME7-X1 positive cancer.

In another aspect, the invention is directed to a method for preventing or treating cancer comprising the steps of: (i) analyzing a cancerous sample from the patient and determining that it is MUC1* positive, NME7$_{AB}$ positive or NME7-X1 positive; and
(ii) administering to the patient an effective amount of a compound of Formula 1 to 10. The analyzing step may be carried out by PCR. In one aspect, when the cancerous sample may express mRNA level of MUC1 gene, NME7 gene or NME7-X1 gene that is at least 0.5% of the mRNA expression level of EEF1A1 gene, it is determined to be MUC1* positive, NME7$_{AB}$ positive or NME7-X1 positive. The analyzing step may be carried out by immunohistochemistry. In one aspect, when the cancerous sample may be contacted with an antibody that binds to the PSMGFR peptide or the N-10 peptide and stains the tissue with a pathologist's standard score 1-4 ("+-++++"), it is determined to be MUC1* positive. When the cancerous sample may be contacted with an antibody that binds to the B3 peptide of NME7 and stains the tissue with a pathologist's standard score 1-4 ("+-++++"), it is determined to be NME7$_{AB}$ positive or NME7-X1 positive.

In another aspect, the invention is directed to a method of identifying an agent for the prevention or treatment of an inflammatory disease or condition, comprising the steps of (i) exposing stem cells to an agent, and (ii) identifying an agent that inhibits stem cell pluripotency or growth, or induces stem cell differentiation, wherein the agent or its analog is an agent for treating inflammatory disease or condition. The inflammatory disease or condition may be rheumatoid arthritis, inflammatory bowel syndrome, Crohn's disease, osteoarthritis, asthma, dermatitis, psoriasis, cystic fibrosis, post transplantation late and chronic solid organ rejection, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, autoimmune diabetes, diabetic retinopathy, rhinitis, ischemia-reperfusion injury, post-angioplasty restenosis, chronic obstructive pulmonary diseases (COPD), Graves' disease, gastrointestinal allergy, conjunctivitis, atherosclerosis, coronary artery disease, angina, cancer metastasis, small artery disease, or mitochondrial disease.

In another aspect, the invention is directed to a method of treating an inflammatory disease or condition comprising administering to a person in need thereof, an agent that when contacted with stem cells, inhibits stem pluripotency or growth or induces stem cell differentiation. The inflammatory disease or condition may be rheumatoid arthritis, inflammatory bowel syndrome, Crohn's disease, osteoarthritis, asthma, dermatitis, psoriasis, cystic fibrosis, post transplantation late and chronic solid organ rejection, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, autoimmune diabetes, diabetic retinopathy, rhinitis, ischemia-reperfusion injury, post-angioplasty restenosis, chronic obstructive pulmonary diseases (COPD), Graves' disease, gastrointestinal allergy, conjunctivitis, atherosclerosis, coronary artery disease, angina, cancer metastasis, small artery disease, or mitochondrial disease. The agent may be a compound of Formula 1 to 10 or as set forth in FIGS. 18-27.

These and other objects of the invention will be more fully understood from the following description of the invention, the referenced drawings attached hereto and the claims appended hereto.

DESCRIPTION OF THE DRAWINGS

The present invention will become more fully understood from the detailed description given herein below, and the accompanying drawings which are given by way of illustration only, and thus are not limitative of the present invention, and wherein;

FIG. 2 is a Table that summarizes the results of testing small molecules, an anti-MUC1*Fab "E6", a MUC1*extracellular domain peptide "FLR" and anti-NME7 antibodies #56 and #61.

FIG. 3A shows photograph of primed stem cells cultured in presence of an anti-MUC1*Fab, named E6, FIG. 3B shows photograph of primed stem cells cultured in presence of a MUC1*extracellular domain peptide, FLR, FIG. 3C shows photograph of control primed stem cells, FIG. 3D shows photograph of primed stem cells cultured in 0.2% DMSO as control for small molecules in 0.2% DMSO, FIG. 3E shows photograph of primed stem cells cultured in the presence of MN0642, FIG. 3F shows photograph of primed stem cells cultured in the presence of MN1130, FIG. 3G shows photograph of primed stem cells cultured in the presence of MN0572, FIG. 3H shows photograph of primed stem cells cultured in the presence of MN0947, FIG. 3I shows photograph of primed stem cells cultured in the presence of MN0129, FIG. 3J shows photograph of primed stem cells cultured in the presence of MN0676, FIG. 3K shows photograph of primed stem cells cultured in the presence of MN0992, and FIG. 3L shows photograph of primed stem cells cultured in the presence of MN0402.

FIG. 4A-4L shows photographs at 20× magnification of human primed state stem cells, grown in stem cell media with growth factor FGF, over a layer of MEFs and treated for 3 days with in the presence of a test agent. Dotted lines indicate areas where stem cell pluripotency or growth is inhibited or differentiation is induced. FIG. 4A shows photograph of primed stem cells cultured in presence of an anti-MUC1*Fab, named E6, FIG. 4B shows photograph of primed stem cells cultured in presence of a MUC1*$_{ecd\ peptide}$ extracellular domain peptide, also known as FLR, FIG. 4C shows photograph of control primed stem cells, FIG. 4D shows photograph of primed stem cells cultured in 0.2% DMSO as control for small molecules in 0.2% DMSO, FIG. 4E shows photograph of primed stem cells cultured in the presence of MN0642, FIG. 4F shows photograph of primed stem cells cultured in the presence of MN1130, FIG. 4G shows photograph of primed stem cells cultured in the presence of MN0572, FIG. 4H shows photograph of primed stem cells cultured in the presence of MN0947, FIG. 4I shows photograph of primed stem cells cultured in the presence of MN0129, FIG. 4J shows photograph of primed stem cells cultured in the presence of MN0676, FIG. 4K shows photograph of primed stem cells cultured in the presence of MN0992, and FIG. 3L shows photograph of primed stem cells cultured in the presence of MN0402.

FIG. 5A shows photograph of primed stem cells cultured in presence of an anti-MUC1*Fab, named E6, FIG. 5B shows photograph of primed stem cells cultured in presence of a MUC1*extracellular domain peptide, FLR, FIG. 5C shows photograph of primed stem cells cultured in presence of an anti-NME7 polyclonal antibody #56, FIG. 5D shows photograph of primed stem cells cultured in presence of an anti-NME7 polyclonal antibody #61, FIG. 5E shows photograph of primed stem cells cultured in the presence of MN0642, FIG. 5F shows photograph of primed stem cells cultured in the presence of MN1130, FIG. 5G shows photograph of primed stem cells cultured in the presence of MN0572, FIG. 5H shows photograph of primed stem cells cultured in the presence of MN0947, FIG. 5I shows photograph of primed stem cells cultured in the presence of MN0129, FIG. 5J shows photograph of primed stem cells cultured in the presence of MN0676, FIG. 5K shows photograph of primed stem cells cultured in the presence of MN0992, and FIG. 5L shows photograph of primed stem cells cultured in the presence of MN0402.

FIG. 6A-6L shows photographs at 20× magnification of human primed state stem cells, grown in stem cell media without growth factor FGF, over a layer of MEFs and treated for 3 days with in the presence of a test agent. Dotted lines indicate areas where stem cell pluripotency or growth is inhibited or differentiation is induced. FIG. 6A shows photograph of primed stem cells cultured in presence of an anti-MUC1* Fab, named E6, FIG. 6B shows photograph of primed stem cells cultured in presence of a MUC1* extracellular domain peptide, FLR, FIG. 6C shows photograph of primed stem cells cultured in presence of an anti-NME7 polyclonal antibody #56, FIG. 6D shows photograph of primed stem cells cultured in presence of an anti-NME7 polyclonal antibody #61, FIG. 6E shows photograph of primed stem cells cultured in the presence of MN0642, FIG. 6F shows photograph of primed stem cells cultured in the presence of MN1130, FIG. 6G shows photograph of primed stem cells cultured in the presence of MN0572, FIG. 6H shows photograph of primed stem cells cultured in the presence of MN0947, FIG. 6I shows photograph of primed stem cells cultured in the presence of MN0129, FIG. 6J shows photograph of primed stem cells cultured in the presence of MN0676, FIG. 6K shows photograph of primed stem cells cultured in the presence of MN0992, and FIG. 6L shows photograph of primed stem cells cultured in the presence of MN0402.

FIG. 7A-7L shows photographs at 10× magnification of human naïve state stem cells, grown in stem cell media with growth factor NME7$_{AB}$, over a MUC1* antibody, C3, surface and treated for 3 days with in the presence of a test agent. Dotted lines indicate areas where stem cell pluripotency or growth is inhibited or differentiation is induced. FIG. 7A shows photograph of naïve stem cells cultured in presence of an anti-MUC1* Fab, named E6, FIG. 7B shows photograph of naïve stem cells cultured in presence of a MUC1* extracellular domain peptide, FLR, FIG. 7C shows photograph of control naïve stem cells, FIG. 7D shows photograph of naïve stem cells cultured in 0.2% DMSO as control for small molecules in 0.2% DMSO, FIG. 7E shows photograph of naïve stem cells cultured in the presence of MN0642, FIG. 7F shows photograph of naïve stem cells cultured in the presence of MN1130, FIG. 7G shows photograph of naïve stem cells cultured in the presence of MN0572, FIG. 7H shows photograph of naïve stem cells cultured in the presence of MN0947, FIG. 7I shows photograph of naïve stem cells cultured in the presence of MN0129, FIG. 7J shows photograph of naïve stem cells cultured in the presence of MN0676, FIG. 7K shows photograph of naïve stem cells cultured in the presence of MN0992, and FIG. 7L shows photograph of naïve stem cells cultured in the presence of MN0402.

FIG. 8A shows photograph of naïve stem cells cultured in presence of an anti-MUC1* Fab, named E6, FIG. 8B shows photograph of naïve stem cells cultured in presence of a MUC1* extracellular domain peptide, FLR, FIG. 8C shows photograph of control naïve stem cells, FIG. 8D shows photograph of naïve stem cells cultured in 0.2% DMSO as control for small molecules in 0.2% DMSO, FIG. 8E shows photograph of naïve stem cells cultured in the presence of MN0642, FIG. 8F shows photograph of naïve stem cells cultured in the presence of MN1130, FIG. 8G shows photograph of naïve stem cells cultured in the presence of MN0572, FIG. 8H shows photograph of naïve stem cells cultured in the presence of MN0947, FIG. 8I shows photograph of naïve stem cells cultured in the presence of MN0129, FIG. 8J shows photograph of naïve stem cells cultured in the presence of MN0676, FIG. 8K shows photograph of naïve stem cells cultured in the presence of MN0992, and FIG. 8L shows photograph of naïve stem cells cultured in the presence of MN0402.

FIG. 9A shows photograph of naïve stem cells cultured in presence of an anti-MUC1* Fab, named E6, FIG. 9B shows photograph of naïve stem cells cultured in presence of a MUC1* extracellular domain peptide, FLR, FIG. 9C shows photograph of naïve stem cells cultured in presence of an anti-NME7 polyclonal antibody #56, FIG. 9D shows photograph of naïve stem cells cultured in presence of an anti-NME7 polyclonal antibody #61, FIG. 9E shows photograph of naïve stem cells cultured in the presence of MN0642, FIG. 9F shows photograph of naïve stem cells cultured in the presence of MN1130, FIG. 9G shows photograph of naïve stem cells cultured in the presence of MN0572, FIG. 9H shows photograph of naïve stem cells cultured in the presence of MN0947, FIG. 9I shows photograph of naïve stem cells cultured in the presence of MN0129, FIG. 9J shows photograph of naïve stem cells cultured in the presence of MN0676, FIG. 9K shows photograph of naïve stem cells cultured in the presence of MN0992, and FIG. 9L shows photograph of naïve stem cells cultured in the presence of MN0402.

FIG. 10A shows photograph of naïve stem cells cultured in presence of an anti-MUC1* Fab, named E6, FIG. 10B shows photograph of naïve stem cells cultured in presence of a MUC1* extracellular domain peptide, FLR, FIG. 10C shows photograph of naïve stem cells cultured in presence of an anti-NME7 polyclonal antibody #56, FIG. 10D shows photograph of naïve stem cells cultured in presence of an anti-NME7 polyclonal antibody #61, FIG. 10E shows photograph of naïve stem cells cultured in the presence of MN0642, FIG. 10F shows photograph of naïve stem cells cultured in the presence of MN1130, FIG. 10G shows photograph of naïve stem cells cultured in the presence of MN0572, FIG. 10H shows photograph of naïve stem cells cultured in the presence of MN0947, FIG. 10I shows photograph of naïve stem cells cultured in the presence of MN0129, FIG. 10J shows photograph of naïve stem cells cultured in the presence of MN0676, FIG. 10K shows photograph of naïve stem cells cultured in the presence of MN0992, and FIG. 10L shows photograph of naïve stem cells cultured in the presence of MN0402.

FIG. 11A-11F shows photographs at 4× magnification of human primed state stem cells, previously grown in bFGF over MEFs, but cultured in the absence of bFGF during the experiment, and treated for 3 days with a test agent. Dotted lines indicate areas where stem cell pluripotency or growth is inhibited or differentiation is induced. FIG. 11A shows photograph of primed stem cells cultured in presence of a control scrambled sequence siRNA, FIG. 11B shows photograph of primed stem cells cultured in presence of a BRD4 specific siRNA, FIG. 11C shows photograph of primed stem cells cultured in presence of a JMJD6 specific siRNA, FIG. 11D shows photograph of primed stem cells cultured in presence of an inactive stereoisomer of purported BRD4 inhibitor JQ1 aka JQ1-, FIG. 11E shows photograph of primed stem cells cultured in presence of the active stereoisomer of purported BRD4 inhibitor JQ1 aka JQ1+ at 500 nM, and FIG. 11F shows photograph of primed stem cells cultured in presence of the active stereoisomer of purported BRD4 inhibitor JQ1+ at 1 uM.

FIG. 12A-12F shows photographs at 20× magnification of human primed state stem cells, previously grown in bFGF over MEFs, but cultured in the absence of bFGF during the experiment, and treated for 3 days with a test agent. Dotted lines indicate areas where stem cell pluripotency or growth is inhibited or differentiation is induced. FIG. 12A shows photograph of primed stem cells cultured in presence of a control scrambled sequence siRNA, FIG. 12B shows photograph of primed stem cells cultured in presence of a BRD4 specific siRNA, FIG. 12C shows photograph of primed stem cells cultured in presence of a JMJD6 specific siRNA, FIG. 12D shows photograph of primed stem cells cultured in presence of an inactive stereoisomer of purported BRD4 inhibitor JQ1 aka JQ1-, FIG. 12E shows photograph of primed stem cells cultured in presence of the active stereoisomer of purported BRD4 inhibitor JQ1 aka JQ1+ at 500 nM, and FIG. 12F shows photograph of primed stem cells cultured in presence of the active stereoisomer of purported BRD4 inhibitor JQ1+ at 1 uM.

FIG. 13A-13F shows photographs at 4× magnification of human naïve state stem cells, previously grown in NME7$_{AB}$ over a MUC1* antibody surface, C3, but cultured in the absence of NME7$_{AB}$ during the experiment, and treated for 3 days with a test agent. Dotted lines indicate areas where stem cell pluripotency or growth is inhibited or differentiation is induced. FIG. 13A shows photograph of naïve stem cells cultured in presence of a control scrambled sequence siRNA, FIG. 13B shows photograph of naïve stem cells cultured in presence of a BRD4 specific siRNA, FIG. 13C shows photograph of naïve stem cells cultured in presence of a JMJD6 specific siRNA, FIG. 13D shows photograph of naïve stem cells cultured in presence of an inactive stereoisomer of purported BRD4 inhibitor JQ1 aka JQ1-, FIG. 13E shows photograph of naïve stem cells cultured in presence of the active stereoisomer of purported BRD4 inhibitor JQ1 aka JQ1+ at 500 nM, and FIG. 13F shows photograph of naïve stem cells cultured in presence of the active stereoisomer of purported BRD4 inhibitor JQ1+ at 1 uM.

FIG. 14A-14F shows photographs at 20× magnification of human naïve state stem cells, previously grown in NME7AB over a MUC1* antibody surface, C3, but cultured in the absence of NME7AB during the experiment, and treated for 3 days with a test agent. Dotted lines indicate areas where stem cell pluripotency or growth is inhibited or differentiation is induced. FIG. 14A shows photograph of naïve stem cells cultured in presence of a control scrambled sequence siRNA, FIG. 14B shows photograph of naïve stem cells cultured in presence of a BRD4 specific siRNA, FIG. 14C shows photograph of naïve stem cells cultured in presence of a JMJD6 specific siRNA, FIG. 14D shows photograph of naïve stem cells cultured in presence of an inactive stereoisomer of purported BRD4 inhibitor JQ1 aka JQ1-, FIG. 14E shows photograph of naïve stem cells cultured in presence of the active stereoisomer of purported BRD4 inhibitor JQ1 aka JQ1+ at 500 nM, and FIG. 14F shows photograph of naïve stem cells cultured in presence of the active stereoisomer of purported BRD4 inhibitor JQ1+ at 1 uM.

FIG. 15A-15F shows photographs at 4× magnification of human naïve state stem cells, previously grown in NME1 dimers over a MUC1* antibody surface, C3, but cultured in the absence of $NME7_{AB}$ during the experiment, and treated for 3 days with a test agent. Dotted lines indicate areas where stem cell pluripotency or growth is inhibited or differentiation is induced. FIG. 15A shows photograph of naïve stem cells cultured in presence of a control scrambled sequence siRNA, FIG. 15B shows photograph of naïve stem cells cultured in presence of a BRD4 specific siRNA, FIG. 15C shows photograph of naïve stem cells cultured in presence of a JMJD6 specific siRNA, FIG. 15D shows photograph of naïve stem cells cultured in presence of an inactive stereoisomer of purported BRD4 inhibitor JQ1 aka JQ1−, FIG. 15E shows photograph of naïve stem cells cultured in presence of the active stereoisomer of purported BRD4 inhibitor JQ1 aka JQ1+ at 500 nM, and FIG. 15F shows photograph of naïve stem cells cultured in presence of the active stereoisomer of purported BRD4 inhibitor JQ1+ at 1 uM.

FIG. 16A-16F shows photographs at 20× magnification of human naïve state stem cells, previously grown in NME1 dimers over a MUC1* antibody surface, C3, but cultured in the absence of NME1 dimers during the experiment, and treated for 3 days with a test agent. Dotted lines indicate areas where stem cell pluripotency or growth is inhibited or differentiation is induced. FIG. 16A shows photograph of naïve stem cells cultured in presence of a control scrambled sequence siRNA, FIG. 16B shows photograph of naïve stem cells cultured in presence of a BRD4 specific siRNA, FIG. 16C shows photograph of naïve stem cells cultured in presence of a JMJD6 specific siRNA, FIG. 16D shows photograph of naïve stem cells cultured in presence of an inactive stereoisomer of purported BRD4 inhibitor JQ1 aka JQ1−, FIG. 16E shows photograph of naïve stem cells cultured in presence of the active stereoisomer of purported BRD4 inhibitor JQ1 aka JQ1+ at 500 nM, and FIG. 16F shows photograph of naïve stem cells cultured in presence of the active stereoisomer of purported BRD4 inhibitor JQ1+ at 1 uM.

FIG. 17 shows chemical structures of compounds that were previously known to inhibit inflammation or inhibit cancer cell growth, migration or invasion.

FIG. 28 shows summary of biological data for compounds of the invention and various other previously known chemical compounds.

FIG. 29A-29P shows photographs of human stem cells cultured for 3 days with either control media or a small molecule that had been previously reported to inhibit cancer cell migration, which is a characteristic of cancer metastasis. In FIG. 29A-29H, the cells were naïve state stem cells, previously grown in the growth factor $NME7_{AB}$ over a MUC1* antibody surface, C3, but cultured in the absence of $NME7_{AB}$ during the experiment. In FIG. 29I-29P, the cells were primed state stem cells, previously grown in the growth factor FGF over a layer of inactivated MEFs, but cultured in the absence of FGF during the experiment.

FIGS. 30-66 A-F show photographs of human naïve state stem cells, previously grown in $NME7_{AB}$ over a MUC1* antibody surface, C3, but cultured in the absence of $NME7_{AB}$ during the experiment, and treated for 3 days with a small molecule drug candidate at a final concentration of 6 uM. In each panel, a score of −, or +, ++, +++, or ++++ is given, wherein "−" indicates that at 6 uM the drug candidate did not have an obvious effect on the pluripotency or proliferation of the stem cells. A "+" indicates a mild effect and "++++" indicates a profound effect on pluripotency or proliferation. Inhibition of proliferation can be seen as holes, or blank areas, in the layer of stem cells. Inhibition of pluripotency, which is also induction of differentiation, is seen as increase in cell size with a decrease in the size of the nucleus, elongation and flattening of cells or rounding up of cells and floating off the plate.

FIGS. 30-66 G-L show photographs of human primed state stem cells, previously grown in FGF over a layer of MEFs, but cultured in the absence of FGF during the experiment, and treated for 3 days with a small molecule drug candidate at a final concentration of 6 uM. In each panel, a score of −, or +, ++, +++, or ++++ is given, wherein "−" indicates that at 6 uM the drug candidate did not have an obvious effect on the pluripotency or proliferation of the stem cells. A "+" indicates a mild effect and "++++" indicates a profound effect on pluripotency or proliferation. Primed state stem cells grow in defined colonies rather than a uniform layer like naïve stem cells. Inhibition of proliferation can be seen as a reduction in the colony size. Inhibition of pluripotency, which is also induction of differentiation, is seen as increase in cell size with a decrease in the size of the nucleus, elongation and flattening of cells or rounding up of cells and floating off the plate.

FIG. 67-72 show photographs of human naïve state stem cells, previously grown in $NME7_{AB}$ over a MUC1* antibody surface, C3, but cultured in the absence of $NME7_{AB}$ during the experiment, and treated for 3 days with a small molecule drug candidate at a 3 different final concentrations. In FIG. 67-72 A,D compound concentration is 12 uM. In FIG. 67-72 B,E compound concentration is 6 uM. In FIG. 67-72 C,F compound concentration is 0.75 uM.

FIG. 74A-74P shows representative photographs of the cancer cell migration assay at 126 hours, wherein the cancer cells were treated with a panel of agents. Small molecules were dosed at 6 uM final concentration unless otherwise indicated. The "+" or "−" indicates the score each agents received in the naïve/primed stem cell assay. For example +++/− indicates the compound profoundly inhibited the pluripotency and proliferation of naïve stem cells but had no effect on primed stem cells. FIG. 74A cells were treated with control PBS. FIG. 74B-74D cells were treated with anti-MUC1* Fab E6. FIG. 74E-74I shows cells treated with control amount of DMSO at time zero. FIG. 74F-74G cells were treated with JQ1. FIG. 74H-74M shows cells treated with control amount of DMSO at 126 hours. FIG. 74J shows cells treated with novel molecule MN1194. FIG. 74K shows cells treated with novel molecule MN1186. FIG. 74L shows cells treated with novel molecule MN1137. FIG. 74N shows cells treated with novel molecule MN1193. FIG. 74O shows cells treated with novel molecule MN1203. FIG. 74P shows cells treated with novel molecule MN1184.

FIG. 75A-75X shows the results of cancer cell migration assays in which novel compounds of the invention that inhibited naïve stem cell pluripotency or proliferation were tested for their ability to inhibit cancer cell invasion or migration. FIG. 75A-75U shows photographs of a migration, invasion assay performed on T47D breast cancer cells in the presence of novel compounds of the invention or the control, DMSO alone, at 120 hours. FIG. 75V is a graph showing the measured inhibition of cancer cell migration at time 0, 24 hours or 48 hours for a number of compounds. FIG. 75W is a graph showing the inhibitory effect of the small molecules as a function of concentration. FIG. 75X is a graph showing how IC50's of the small molecules of the invention were measured and calculated.

FIG. 76A-76H shows photographs of a cancer cell migration, invasion assay performed on T47D breast cancer cells in the presence of compounds of the invention, over a range of concentrations, or the control, DMSO alone, at 120 hours.

FIG. 77A-77O shows photographs of a cancer cell migration, invasion assay performed on T47D breast cancer cells in the presence of compounds of the invention, over a range of concentrations, or the control, DMSO alone, at 120 hours.

FIG. 78A-78Q shows photographs of a cancer cell migration, invasion assay performed on T47D breast cancer cells in the presence of compounds of the invention, over a range of concentrations, or the control, DMSO alone, at 120 hours.

FIG. 79A-79P shows photographs of a cancer cell migration, invasion assay performed on T47D breast cancer cells in the presence of compounds of the invention, over a range of concentrations, or the control, DMSO alone, at 120 hours.

Figure 80:
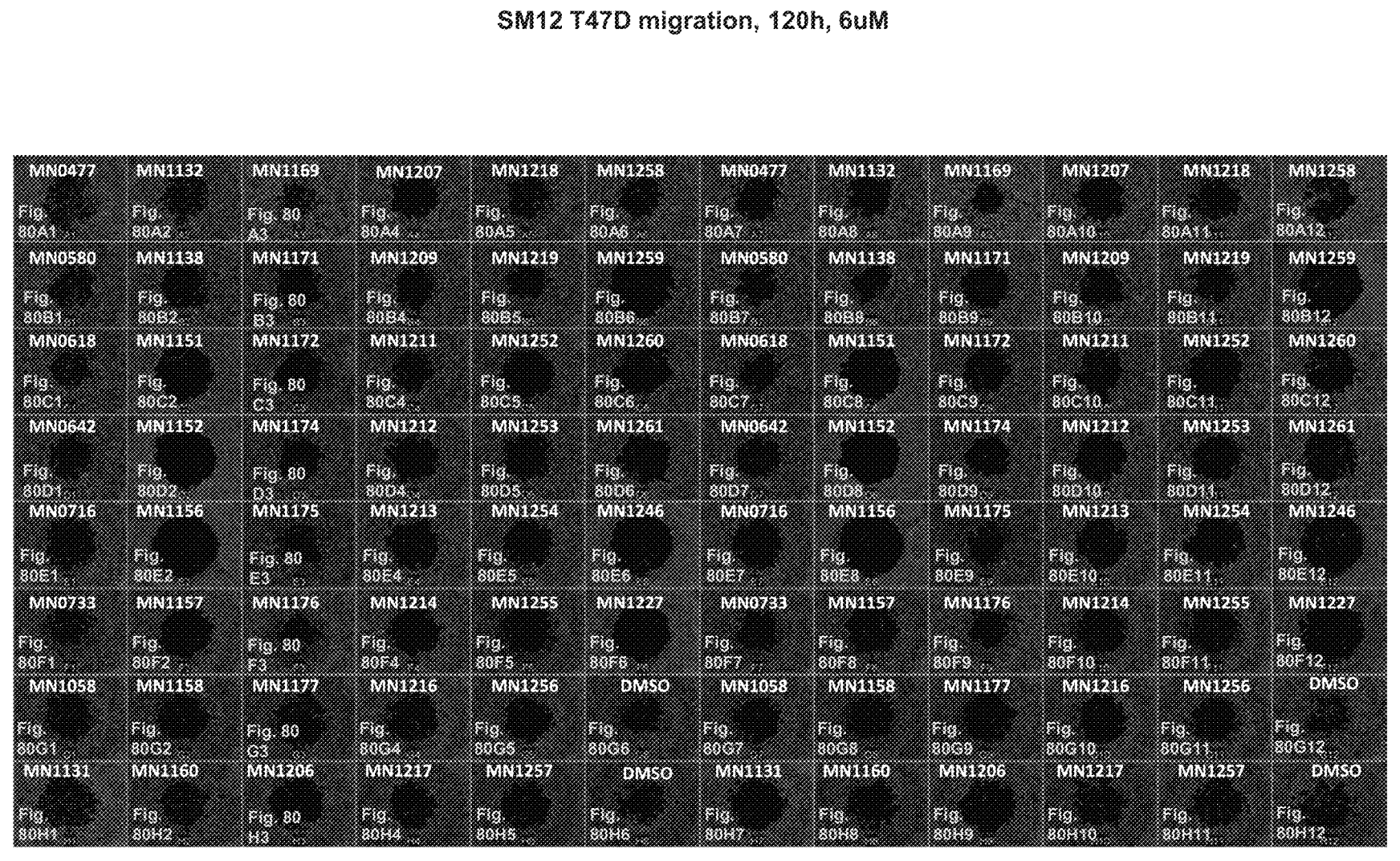

FIG. 80A1-H12 shows photographs of a cancer cell migration, invasion assay performed on T47D breast cancer cells in the presence of compounds of the invention, at a final concentration of 6 uM, or the control, DMSO alone, at 120 hours.

FIG. 81A-81P shows photographs of a cancer cell migration, invasion assay, in which analogs of MN1194, which was a hit in the stem cell drug screen, are tested for their ability to inhibit the migration of breast cancer cells as a function of final compound concentration. These experiments were performed on T47D breast cancer cells and photographed at 120 hours.

FIG. 84A1-84H6 shows photographs of the effect of compounds of the invention, on the migration, invasion of DU145 MUC1* positive prostate cancer cells. Photographs taken at time=0.

FIG. 85A1-85H6 shows photographs of the effect of compounds of the invention, on the migration, invasion of SK-OV-3 MUC1* positive ovarian cancer cells. Photographs taken at time=0.

FIG. 86A1-86H6 shows photographs of the effect of compounds of the invention, on the migration, invasion of DU145 MUC1* positive prostate cancer cells. Photographs taken at time=24 hours.

FIG. 87A1-87H6 shows photographs of the effect of compounds of the invention, on the migration, invasion of SK-OV-3 MUC1* positive ovarian cancer cells. Photographs taken at time=24 hours.

FIG. 88A1-88H6 shows photographs of the effect of compounds of the invention, on the migration, invasion of A549 MUC1* positive lung cancer cells. Photographs taken at time=0.

FIG. 89A1-89H6 shows photographs of the effect of compounds of the invention, on the migration, invasion of PC-3 MUC1* negative, but highly NME7 and NME7-X1 positive prostate cancer cells. Photographs taken at time=0.

FIG. 90A1-90H6 shows photographs of the effect of compounds of the invention, on the migration, invasion of A549 MUC1* positive lung cancer cells. Photographs taken at time=20 hours.

FIG. 91A1-91H6 shows photographs of the effect of compounds of the invention, on the migration, invasion of PC-3 MUC1* negative, but highly NME7 and NME7-X1 positive prostate cancer cells. Photographs taken at time=20 hours.

FIG. 92A1-92H6 shows photographs of the effect of compounds of the invention, on the migration, invasion of A549 MUC1* positive lung cancer cells. Photographs taken at time=26 hours.

FIG. 93A1-93H6 shows photographs of the effect of compounds of the invention, on the migration, invasion of PC-3 MUC1* negative, but highly NME7 and NME7-X1 positive prostate cancer cells. Photographs taken at time=26 hours.

FIG. 94A1-94H6 shows photographs of the effect of compounds of the invention, on the migration, invasion of A549 MUC1* positive lung cancer cells. Photographs taken at time=40 hours.

FIG. 95A1-95H6 shows photographs of the effect of compounds of the invention, on the migration, invasion of PC-3 MUC1* negative, but highly $NME7_{AB}$ and NME7-X1 positive prostate cancer cells. Photographs taken at time=40 hours.

Figures 96, 97:
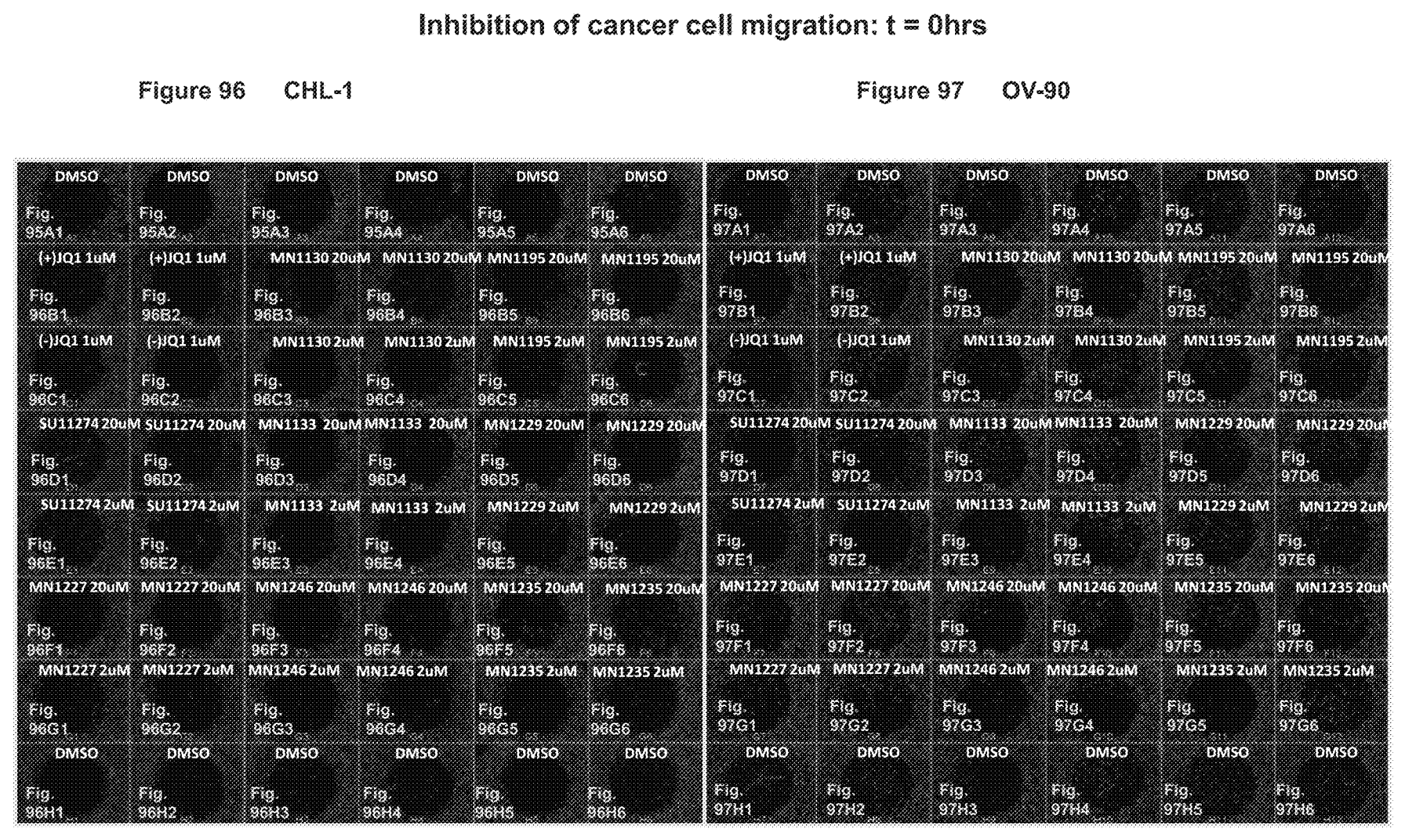

FIG. 96A1-96H6 shows photographs of the effect of compounds of the invention, on the migration, invasion of CHL-1 MUC1* positive melanoma cancer cells. Photographs taken at time=0.

FIG. 97A1-97H6 shows photographs of the effect of compounds of the invention, on the migration, invasion of OV-90 MUC1* negative ovarian cancer cells. Photographs taken at time=0.

Figures 98, 99:
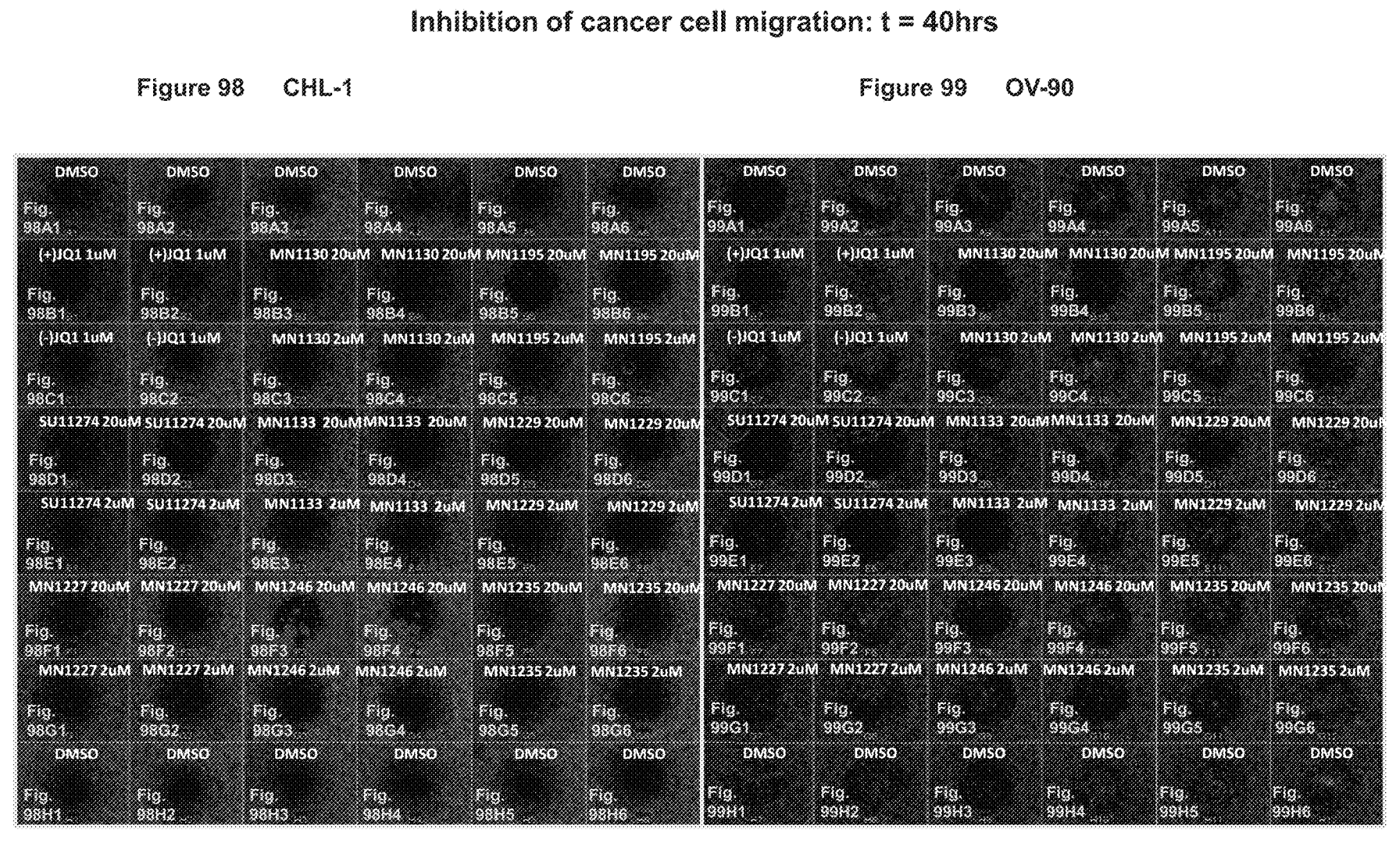

FIG. 98A1-98H6 shows photographs of the effect of compounds of the invention, on the migration, invasion of CHL-1 MUC1* positive melanoma cancer cells. Photographs taken at time=40 hours.

FIG. 99A1-99H6 shows photographs of the effect of compounds of the invention, on the migration, invasion of OV-90 MUC1* negative ovarian cancer cells. Photographs taken at time=40 hours.

Figures 100, 101:
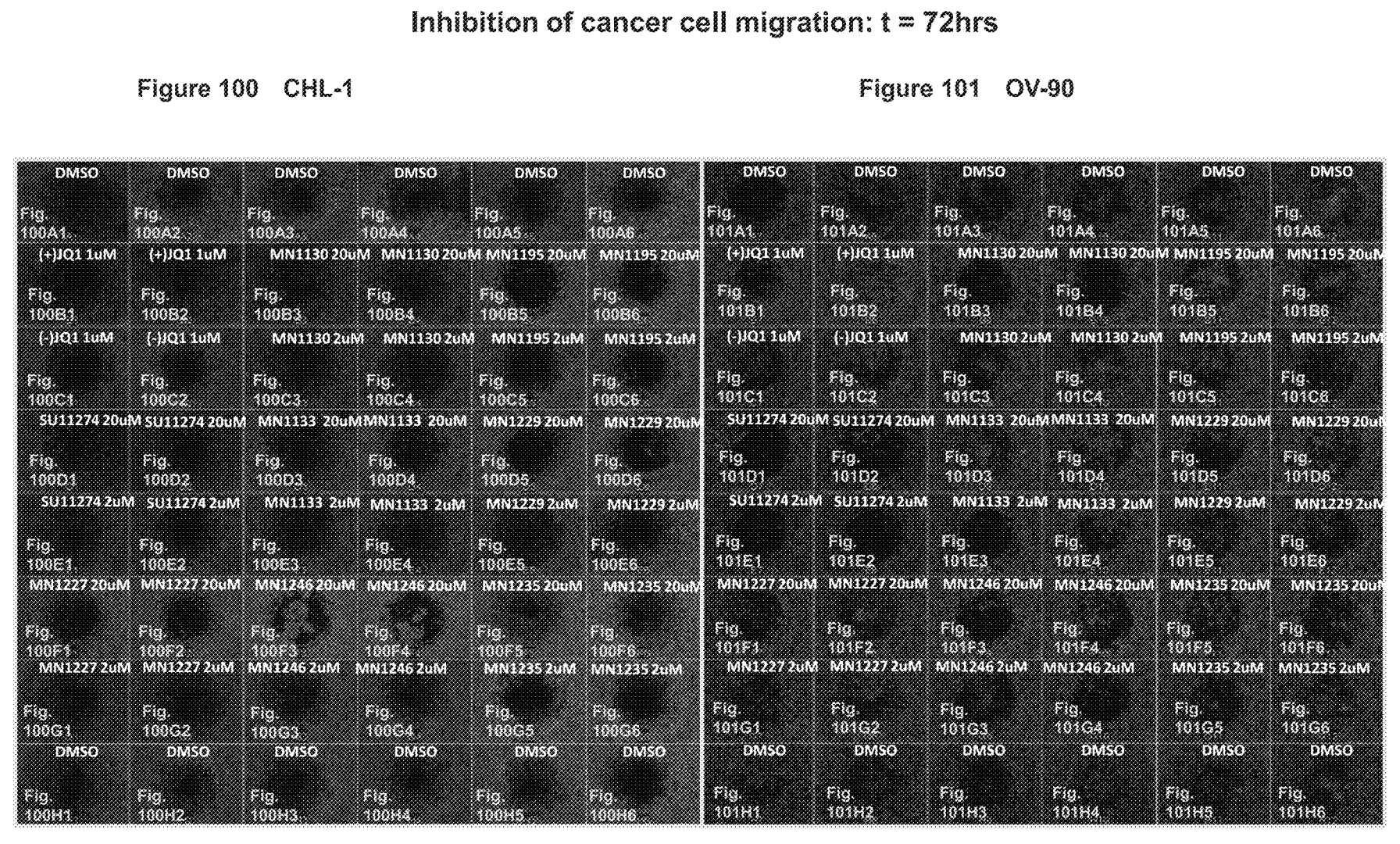

FIG. 100A1-100H6 shows photographs of the effect of compounds of the invention, on the migration, invasion of CHL-1 MUC1* positive melanoma cancer cells. Photographs taken at time=72 hours.

FIG. 101A1-101H6 shows photographs of the effect of compounds of the invention, on the migration, invasion of OV-90 MUC1* negative ovarian cancer cells. Photographs taken at time=72 hours.

Figures 102, 103:
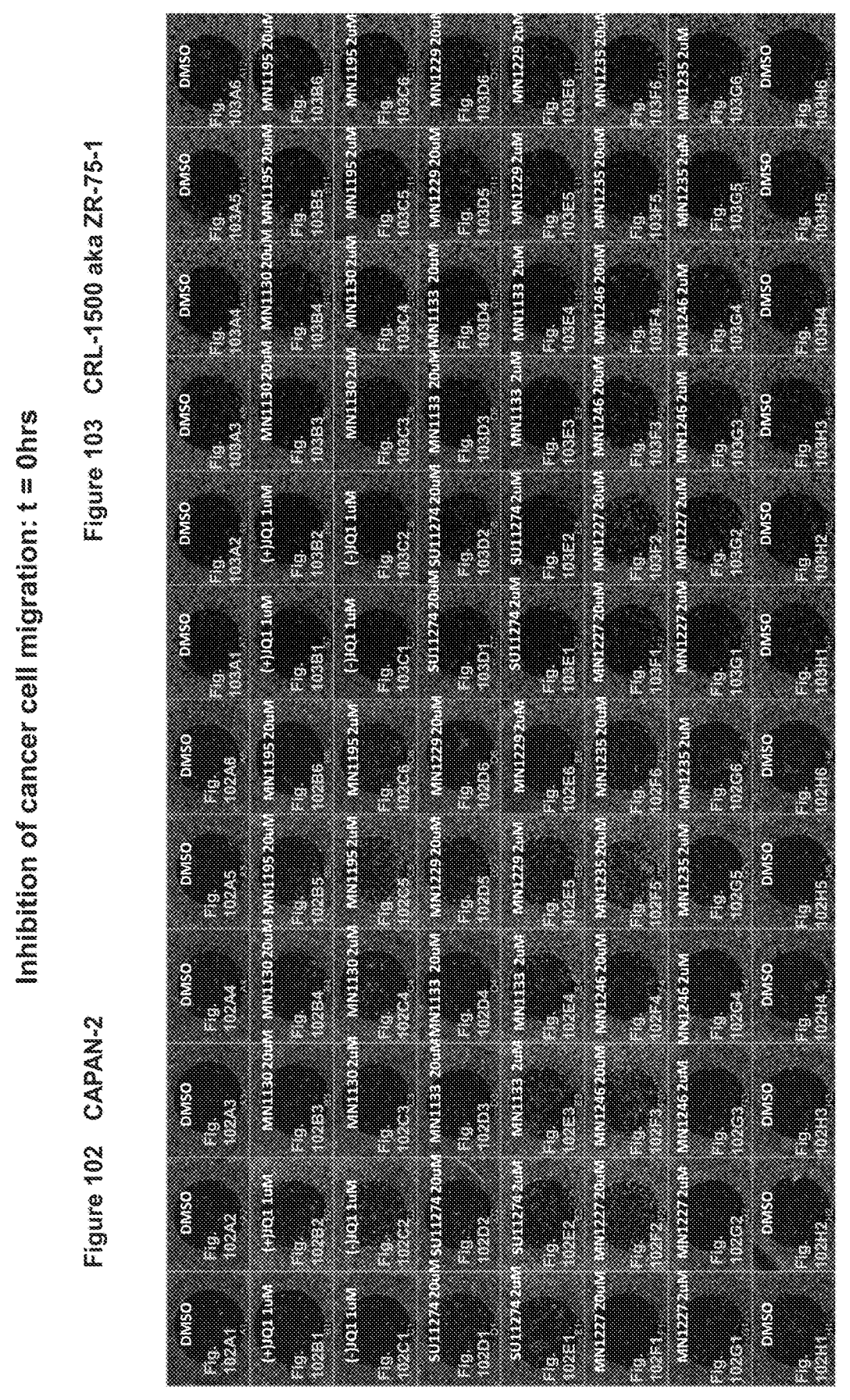

FIG. 102A1-102H6 shows photographs of the effect of compounds of the invention, on the migration, invasion of CAPAN-2 MUC1* positive pancreatic cancer cells. Photographs taken at time=0.

FIG. 103A1-103H6 shows photographs of the effect of compounds of the invention, on the migration, invasion of 1500, aka ZR-75-1, MUC1* positive breast cancer cells. Photographs taken at time=0.

FIG. 104A1-104H6 shows photographs of the effect of compounds of the invention, on the migration, invasion of CAPAN-2 MUC1* positive pancreatic cancer cells. Photographs taken at time=72 hours.

FIG. 105A1-105H6 shows photographs of the effect of compounds of the invention, on the migration, invasion of 1500, aka ZR-75-1, MUC1* positive breast cancer cells. Photographs taken at time=72 hours.

FIG. 106A1-106H6 shows photographs of the effect of compounds of the invention, on the migration, invasion of cancer cells. FIG. 106A1-105H6 shows the effect of the compounds on migration of CAPAN-2 MUC1* positive pancreatic cancer cells. Photographs taken at time=120 hours. FIG. 106A7-106H12 shows photographs of the effect of compounds of the invention, on the migration, invasion of 1500, aka ZR-75-1, MUC1* positive breast cancer cells. Photographs taken at time=120 hours.

Figures 107, 108:
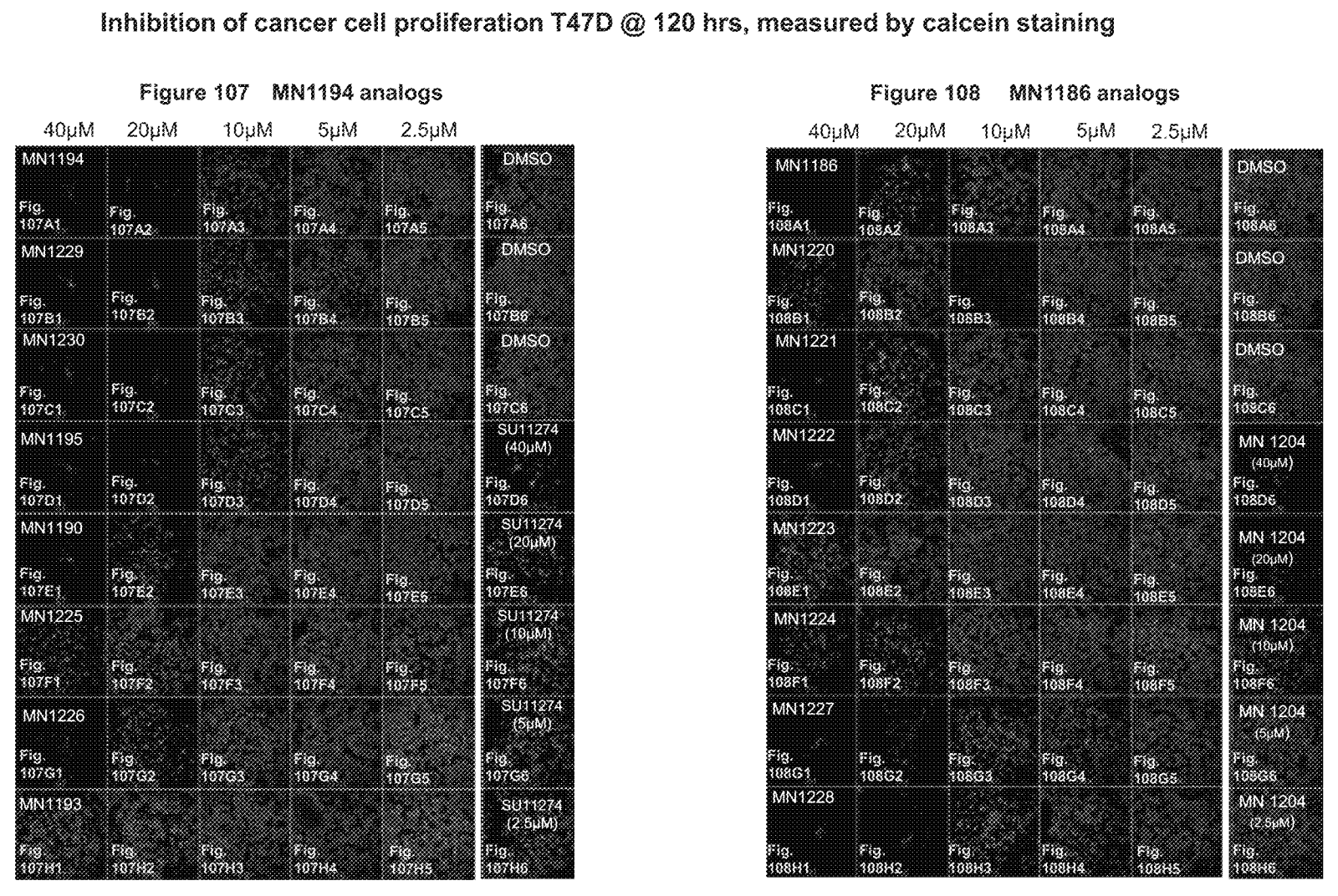

FIG. 107A1-107H6 shows photographs of the ability of MN1194, and analogs thereof, to inhibit the proliferation of MUC1* positive T47D breast cancer cells as a function of compound concentration. Photographs taken at 120 hours. Proliferation measured by Calcein staining.

FIG. 108A1-108H6 shows photographs of the ability of MN1186, and analogs thereof, to inhibit the proliferation of MUC1* positive T47D breast cancer cells as a function of compound concentration. Photographs taken at 120 hours. Proliferation measured by Calcein staining.

FIG. 109A1-109H4 shows photographs of the ability of compounds of the invention to inhibit the proliferation of MUC1* positive DU145 prostate cancer cells. Photographs taken at 96 hours. Proliferation measured by Calcein staining.

FIG. 110A1-110H4 shows photographs of the ability of compounds of the invention to inhibit the proliferation of MDA-MB-453, very low MUC1* positive, breast cancer cells. Photographs taken at 96 hours. Proliferation measured by Calcein staining.

FIG. 111A1-111H4 shows photographs of the ability of compounds of the invention to inhibit the proliferation of PC-3 MUC1* negative, but highly NME7$_{AB}$ and NME7-X1 positive prostate cancer cells. Photographs taken at 96 hours. Proliferation measured by Calcein staining.

FIG. 112A1-112H4 shows photographs of the ability of compounds of the invention to inhibit the proliferation of MUC1* positive SK-OV-3 ovarian cancer cells. Photographs taken at 96 hours. Proliferation measured by Calcein staining.

FIG. 113A1-113H4 shows photographs of the ability of compounds of the invention to inhibit the proliferation of MUC1* positive T47D breast cancer cells. Photographs taken at 96 hours. Proliferation measured by Calcein staining.

FIG. 114A1-114H4 shows photographs of the ability of compounds of the invention to inhibit the proliferation of MUC1* negative OV-90 ovarian cancer cells. Photographs taken at 96 hours. Proliferation measured by Calcein staining.

Figure 115:
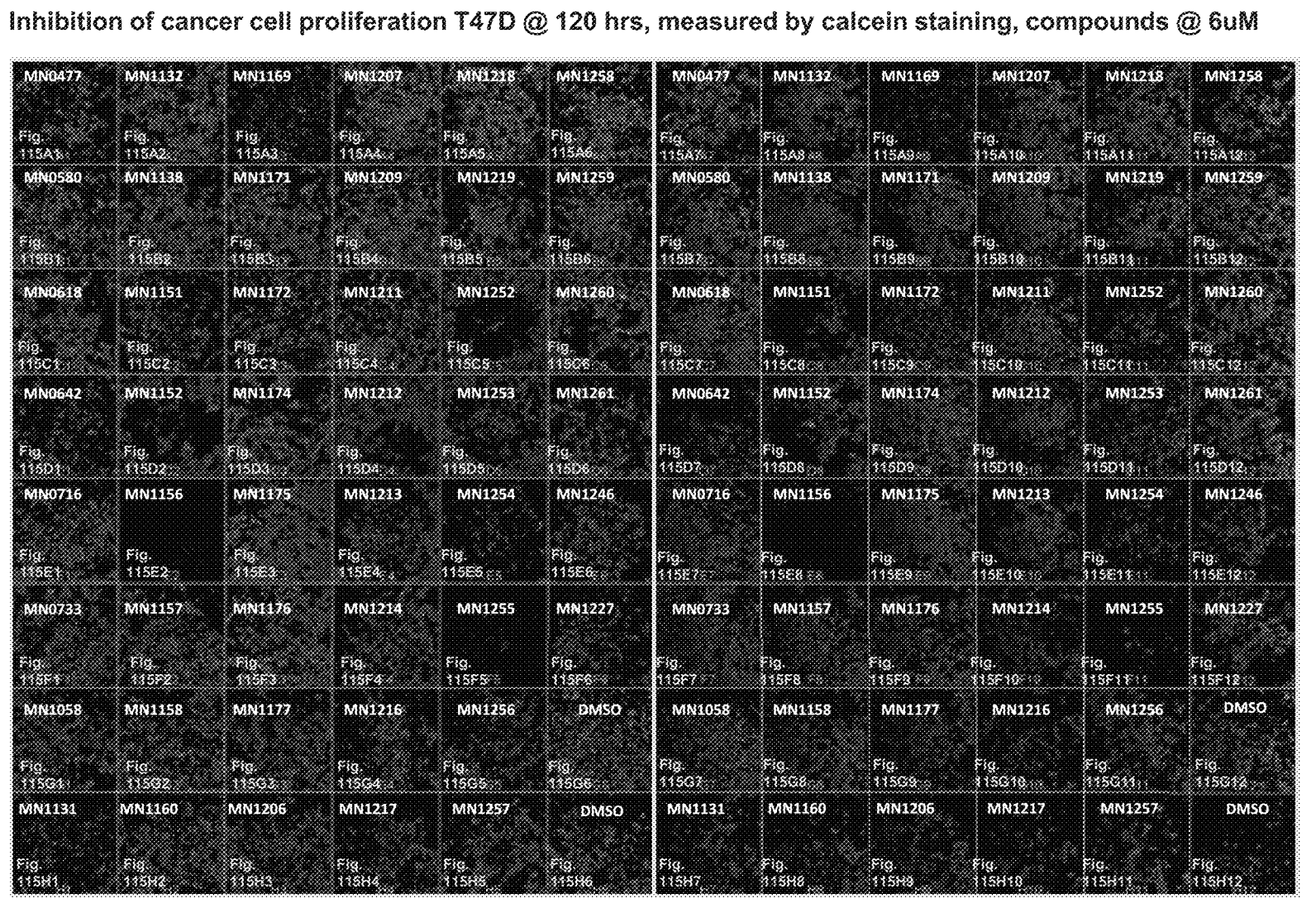

FIG. 115A1-115H12 shows photographs of the ability of compounds of the invention, at a final concentration of 6 uM, to inhibit the proliferation of MUC1* positive T47D breast cancer cells. Photographs taken at 120 hours. Proliferation measured by Calcein staining.

FIG. 116A1-116H6 shows photographs of the effect of compounds of the invention, compared to known anti-cancer agents, on the proliferation of MUC1* positive DU145 prostate cancer cells. Known anti-cancer compounds shown are the BRD4 inhibitor JQ1+ and its inactive enantiomer JQ1-, and anti-migration compound SU11274. Photographs taken at 50 hours. Proliferation measured by Calcein staining.

FIG. 117A1-117H6 shows photographs of the effect of compounds of the invention, compared to known anti-cancer agents, on the proliferation of MUC1* positive SK-OV-3 ovarian cancer cells. Known anti-cancer compounds shown are the BRD4 inhibitor JQ1+ and its inactive enantiomer JQ1-, and anti-migration compound SU11274. Photographs taken at 50 hours. Proliferation measured by Calcein staining.

FIG. 118A-118B shows graphs of the automated Calcein measurement of the inhibitory effects of compounds of the invention, or known anti-cancer drugs, on the proliferation of cancer cells. FIG. 118A shows the effect of the compounds on DU145 MUC1* positive prostate cancer cells. FIG. 118B shows the effect of the compounds on SK-OV-3 MUC1* positive ovarian cancer cells.

FIG. 119A1-119H6 shows photographs of the effect of compounds of the invention, compared to known anti-cancer agents, on the proliferation of MUC1* positive A549 lung cancer cells. Known anti-cancer compounds shown are the BRD4 inhibitor JQ1+ and its inactive enantiomer JQ1-, and anti-migration compound SU11274. Photographs taken at 40 hours. Proliferation measured by Calcein staining.

FIG. 120A1-120H6 shows photographs of the effect of compounds of the invention, compared to known anti-cancer agents, on the proliferation of PC-3 MUC1* negative, but highly NME7$_{AB}$ and NME7-X1 positive prostate cancer cells. Known anti-cancer compounds shown are the BRD4 inhibitor JQ1+ and its inactive enantiomer JQ1-, and anti-migration compound SU11274. Photographs taken at 40 hours. Proliferation measured by Calcein staining.

FIG. 121A-121B shows graphs of the automated Calcein measurement of the inhibitory effects of compounds of the invention, or known anti-cancer drugs, on the proliferation of cancer cells. FIG. 121A shows the effect of the compounds on A549 MUC1* positive lung cancer cells. FIG. 121B shows the effect of the compounds on PC-3 MUC1* negative, but highly NME7$_{AB}$ and NME7-X1 positive prostate cancer cells.

FIG. 122A1-122H6 shows photographs of the effect of compounds of the invention, compared to known anti-cancer agents, on the proliferation of CHL-1 MUC1* positive melanoma cancer cells. Known anti-cancer compounds shown are the BRD4 inhibitor JQ1+ and its inactive enantiomer JQ1-, and anti-migration compound SU11274. Photographs taken at 120 hours. Proliferation measured by Calcein staining.

FIG. 123A1-123H6 shows photographs of the effect of compounds of the invention, compared to known anti-cancer agents, on the proliferation of OV-90 MUC1* negative, but NME7AB and NME7-X1 positive ovarian cancer cells. Known anti-cancer compounds shown are the BRD4 inhibitor JQ1+ and its inactive enantiomer JQ1−, and anti-migration compound SU11274. Photographs taken at 120 hours. Proliferation measured by Calcein staining.

FIG. 124A-124B shows graphs of the automated Calcein measurement of the inhibitory effects of compounds of the invention, or known anti-cancer drugs, on the proliferation of cancer cells. FIG. 124A shows the effect of the compounds on CHL-1 MUC1* positive melanoma cancer cells. FIG. 124B shows the effect of the compounds on OV-90 MUC1* negative, but NME7$_{AB}$ and NME7-X1 positive ovarian cancer cells.

FIG. 125A1-125H6 shows photographs of the effect of compounds of the invention, compared to known anti-cancer agents, on the proliferation of CAPAN-2 MUC1* positive pancreatic cancer cells. Known anti-cancer compounds shown are the BRD4 inhibitor JQ1+ and its inactive enantiomer JQ1−, and anti-migration compound SU11274. Photographs taken at 120 hours. Proliferation measured by Calcein staining.

FIG. 126A1-126H6 shows photographs of the effect of compounds of the invention, compared to known anti-cancer agents, on the proliferation of MUC1* positive breast cancer cells 1500s aka ZR-75-1. Known anti-cancer compounds shown are the BRD4 inhibitor JQ1+ and its inactive enantiomer JQ1−, and anti-migration compound SU11274. Photographs taken at 120 hours. Proliferation measured by Calcein staining.

FIG. 127A-127B shows graphs of the automated Calcein measurement of the inhibitory effects of compounds of the invention, or known anti-cancer drugs, on the proliferation of cancer cells. FIG. 127A shows the effect of the compounds on CAPAN-2 MUC1* positive pancreatic cancer cells. FIG. 127B shows the effect of the compounds on 1500 aka ZR-75-1 MUC1* positive breast cancer cells.

FIG. 128A1-128 H12 shows photographs of the effect of compounds of the invention, on the migration, invasion of cancer cells as a function of compound concentration. Compounds were tested on MUC1* positive breast cancer cell line T47D and photographs were taken at 72 hours post treatment. In FIG. 128A1-128A12 the compounds were dosed at a final concentration of 24 uM. In FIG. 128B1-128B12 the compounds were dosed at a final concentration of 12 uM. In FIG. 128C1-128C12 the compounds were dosed at a final concentration of 6 uM. In FIG. 128D1-128D12 the compounds were dosed at a final concentration of 3 uM. In FIG. 128E1-128AE12 the compounds were dosed at a final concentration of 1.5 uM. In FIG. 128F1-128F12 the compounds were dosed at a final concentration of 0.75 uM. In FIG. 128G1-128G12 the compounds were dosed at a final concentration of 0.375 uM. In FIG. 128H1-128H12 the compounds were dosed at a final concentration of 6 uM. Control wells contained 0.2% DMSO, which is the same concentration DMSO as in the compound wells.

FIG. 130A1-130 H12 shows photographs of the effect of compounds of the invention, on the migration, invasion of cancer cells as a function of compound concentration. Compounds were tested on MUC1* positive breast cancer cell line T47D and photographs were taken at 93 hours post treatment. In FIG. 130A1-130A12 the compounds were dosed at a final concentration of 24 uM. In FIG. 130B1-130B12 the compounds were dosed at a final concentration of 12 uM. In FIG. 130C1-130C12 the compounds were dosed at a final concentration of 6 uM. In FIG. 130D1-130D12 the compounds were dosed at a final concentration of 3 uM. In FIG. 130E1-130AE12 the compounds were dosed at a final concentration of 1.5 uM. In FIG. 130F1-130F12 the compounds were dosed at a final concentration of 0.75 uM. In FIG. 130G1-130G12 the compounds were dosed at a final concentration of 0.375 uM. In FIG. 130H1-130H12 the compounds were dosed at a final concentration of 6 uM. Control wells contained 0.2% DMSO, which is the same concentration DMSO as in the compound wells.

FIG. 132A1-132 H12 shows photographs of the effect of compounds of the invention, on the proliferation of cancer cells as a function of compound concentration. Compounds were tested on MUC1* positive breast cancer cell line T47D and photographs were taken at 96 hours post treatment. In FIG. 132A1-132A12 the compounds were dosed at a final concentration of 24 uM. In FIG. 132B1-132B12 the compounds were dosed at a final concentration of 12 uM. In FIG. 132C1-132C12 the compounds were dosed at a final concentration of 6 uM. In FIG. 132D1-132D12 the compounds were dosed at a final concentration of 3 uM. In FIG. 132E1-132AE12 the compounds were dosed at a final concentration of 1.5 uM. In FIG. 132F1-132F12 the compounds were dosed at a final concentration of 0.75 uM. In FIG. 132G1-132G12 the compounds were dosed at a final concentration of 0.375 uM. In FIG. 132H1-132H12 the compounds were dosed at a final concentration of 6 uM. Control wells contained 0.2% DMSO, which is the same concentration DMSO as in the compound wells.

Figures 136, 137:
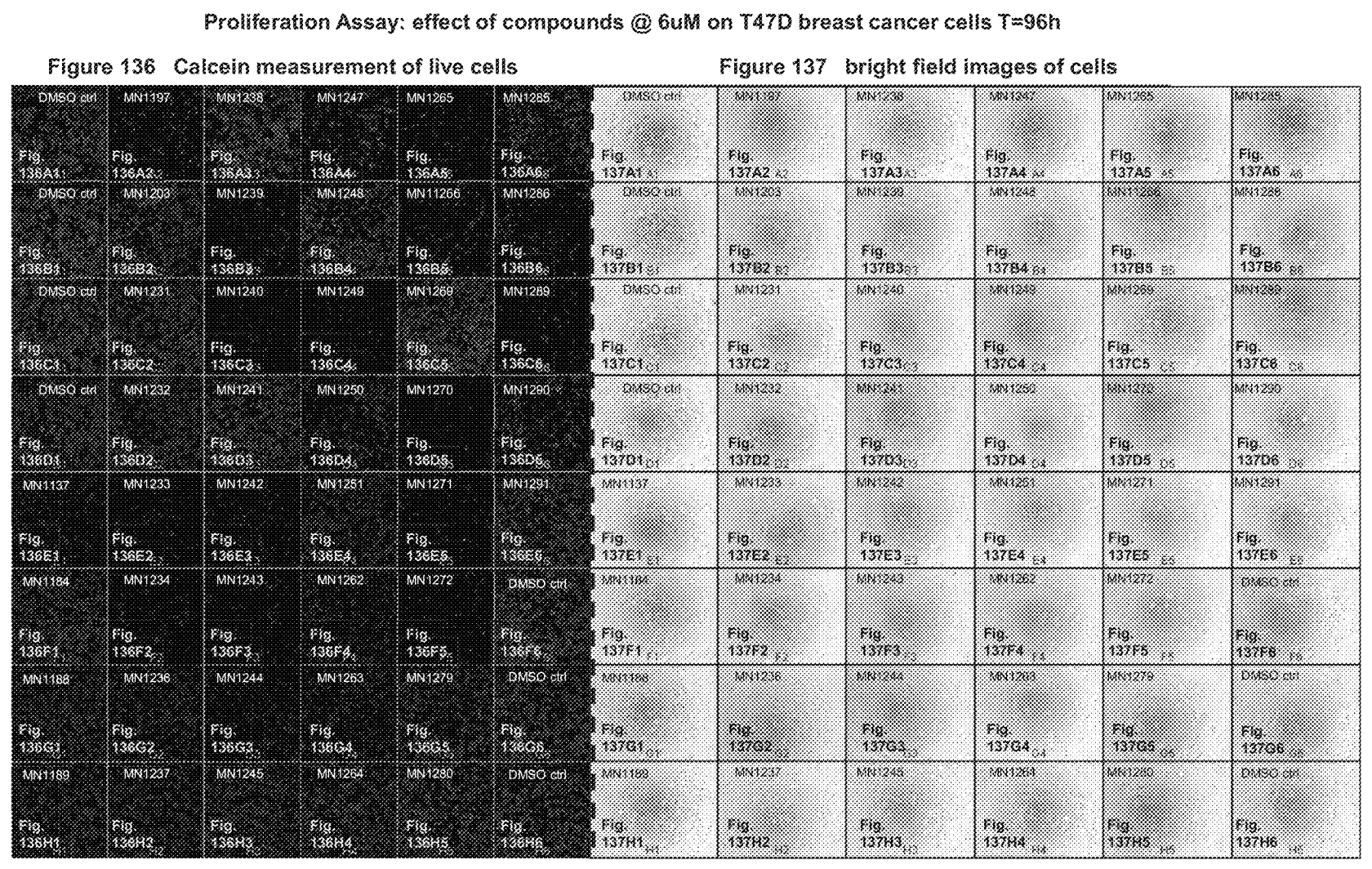

FIG. 136A1-136H6 shows photographs of the inhibitory effects of compounds MN1197, MN1238, MN1247, MN1265, MN1285, MN1203, MN1239, MN1248, MN1266, MN1286, MN1231, MN1240, MN1249, MN1269, MN1269, MN1289, MN1232, MN1241, MN1250, MN1270, MN1290, MN1237, MN1233, MN1242, MN1251, MN1271, MN1291, MN1284, MN1234, MN1243, MN1262, MN1272, MN1288, MN1236, MN1244, MN1263 and MN1279 on cancer cell proliferation at 6 uM at 96 hours post treatment. Cells are stained by Calcein live cell assay.

FIG. 137A1-137H6 shows bright field photographs of the cells described in FIG. 136A1-136H6 just prior to Calcein assay.

FIG. 140A1-140E12 shows photographs of a cancer cell migration assay in which anti-MUC1* antibody Fabs and a truncated MUC1* extracellular domain peptide, N-10, are tested for their ability to inhibit migration or invasion of cancer cells. The cancer sub-types that were tested were CHL-1 melanoma (MUC1*+/NME7+/NME7-X1+), A2058 melanoma (MUC1*+/NME7$_{AB}$+/NME7-X1++), SK-OV-3 ovarian cancer (MUC1*+/NME7+/NME7-X1+), A549 lung cancer (MUC1*$^{LO}$), T47D breast cancer (MUC1*+++/NME7$_{AB}$+++/NME7-X1+++), DU145 (MUC1*++/NME7$_{AB}$+++/NME7-X1+++) prostate cancer and PC-3 (MUC1*−/NME7$_{AB}$+++/NME7-X1+++) prostate cancer cells. The antibodies tested for ability to inhibit migration were the Fab of monoclonal anti-MUC1* extracellular domain antibody E6 that binds to the N-10 peptide, the Fab of another monoclonal antibody that also binds to the N-10 peptide and the N-10 peptide. Both the E6 Fab and C2 Fab competitively inhibit the binding of NME1 dimers, NME7$_{AB}$ and NME7-X1 to the extracellular domain of the MUC1* growth factor receptor. NME1 dimers, NME7$_{AB}$ and NME7-X1 bind to the N-10 sequence of the MUC1* extracellular domain, so the N-10 peptide also competitively inhibits binding of NME1 dimers, NME7$_{AB}$ and NME7-X1 to their cognate receptors.

Figure 141:
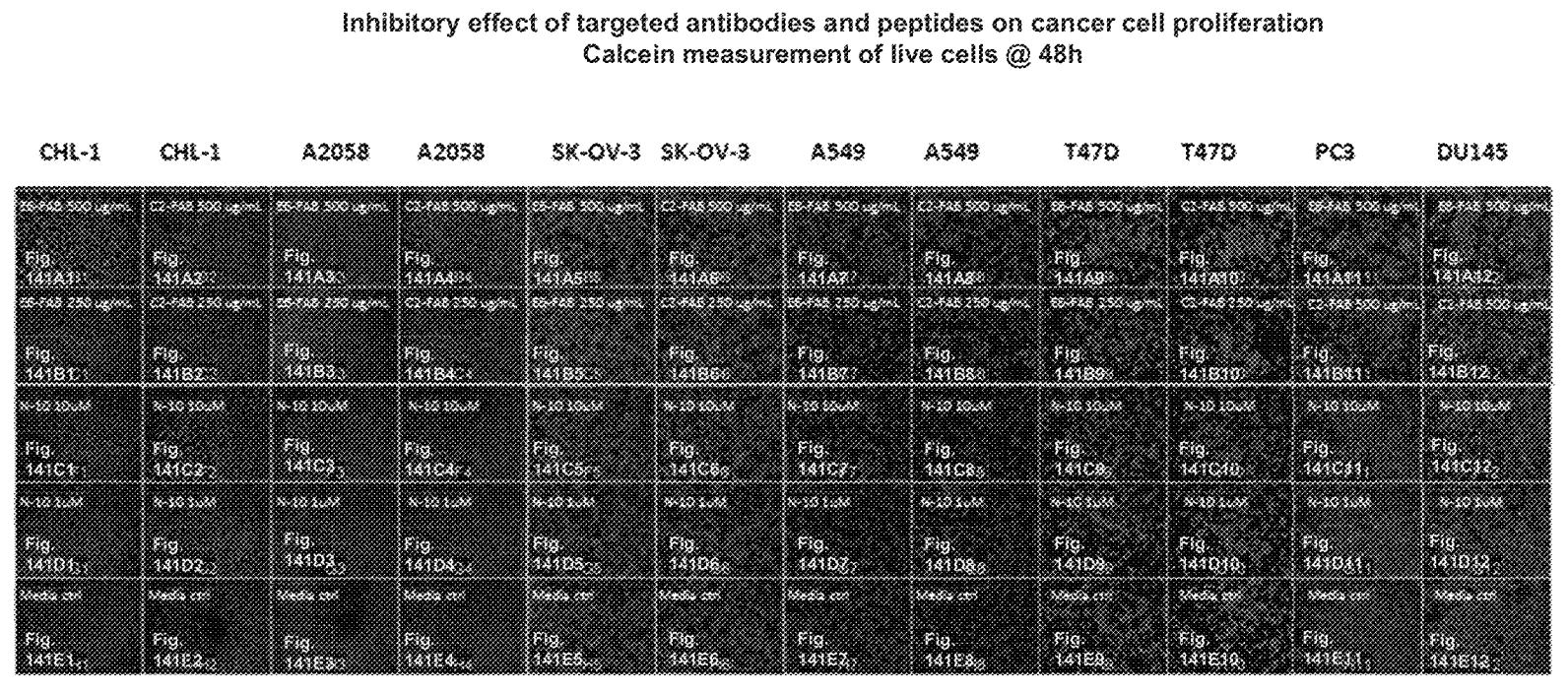

FIG. 141A1-141H12 shows photographs of a cancer cell proliferation assay showing the effect of the biologicals described above in FIG. 140 on cancer sub-types.

FIGS. 144A-153F—show photographs of the effect of compounds of the invention on naïve stem cells (FIG. 144A,D-153A,D), primed state stem cells (FIG. 144B,E-153B,E) or fibroblast progenitor cells (FIG. 144C,F-153C,F).

Figure 158:
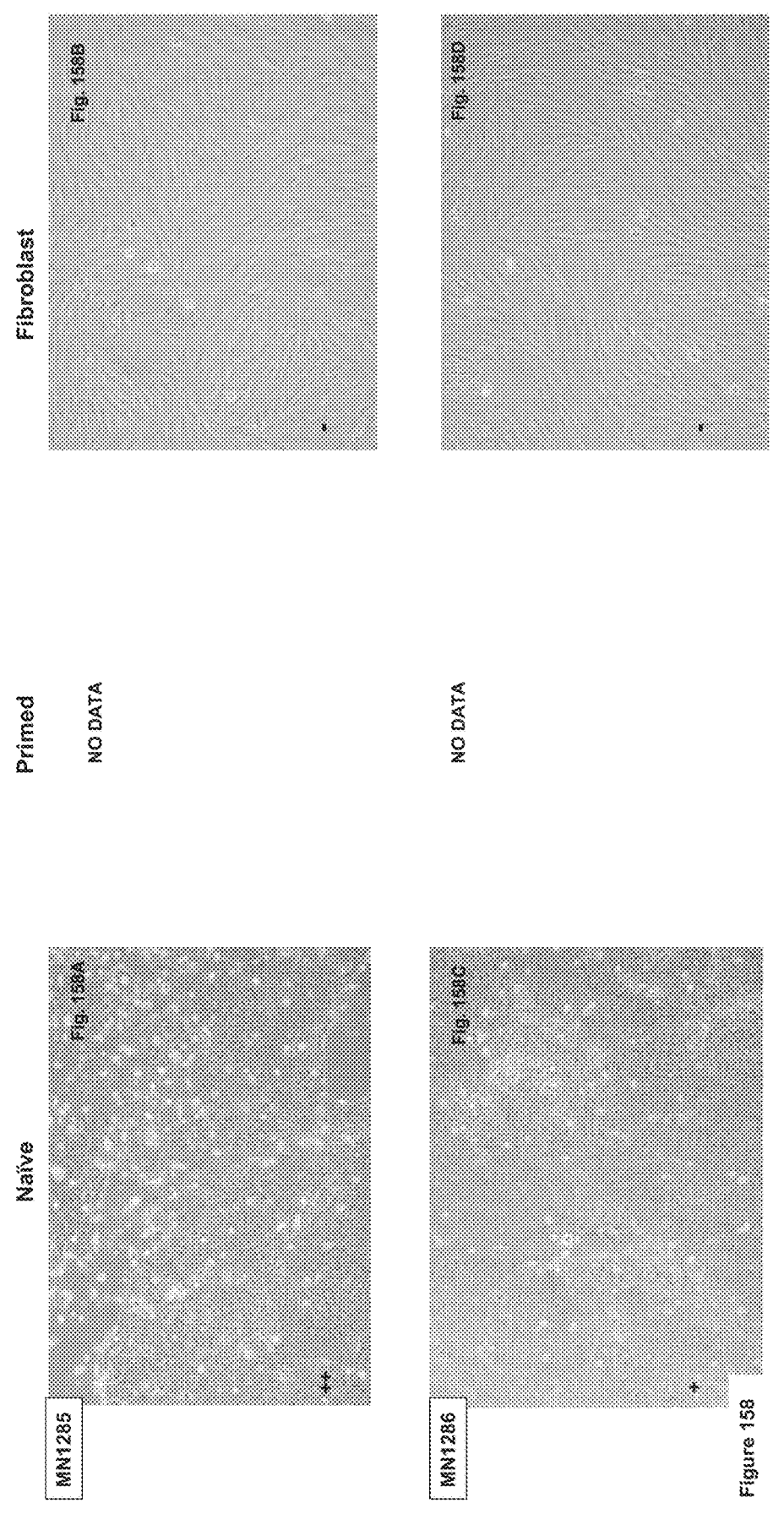

FIGS. 155A-159D—show photographs of the effect of compounds of the invention on naïve stem cells (FIG. 155A,C-159A,C), or fibroblast progenitor cells (FIG. 155B,D-159B,D).

FIG. 164A-164B shows photographs of human embryos at Day 3 (FIG. 164A) or Day 5 (FIG. 164B) that were stained with anti-NME7$_{AB}$ antibody #61 that binds to the B3 peptide of the B domain of NME7$_{AB}$ or NME7-X1. As can be seen, all the cells at Day 3 are positive for NME7$_{AB}$ but by Day 5, when the morula begins to differentiate, the NME7$_{AB}$ positive cells are restricted to the naïve cells of the inner cell mass.

FIG. 165B shows a Western blot of recombinant NME7$_{AB}$ and NME7-X1. To show that NME7$_{AB}$ and NME7-X1 bind to MUC1* and not to full-length MUC1, the gel of FIG. 165A was stripped and re-robed with an anti-MUC1* antibody that binds to the PSMGFR sequence.

FIG. 170A-170C shows Western blots of various cancer cell lines. FIG. 170A shows a Western blot of cancer cell lines probed for expression of full-length MUC1, where the probing antibody was anti-tandem repeat antibody VU4H5. FIG. 170B shows a Western blot of cancer cell lines probed for expression of cleaved MUC1, MUC1*, where the probing antibody was an antibody that binds to the PSMGFR sequence of the MUC1* extracellular domain. FIG. 170C shows a Western blot of cancer cell lines probed for expression of NME7, where the probing antibody was a polyclonal antibody that binds to the sequence of NME7$_{AB}$ or NME7-X1.

FIG. 171A shows a Western blot of cancer cell lines probed with our anti-NME7 antibody that binds to the B3 peptide. FIG. 171B-171C shows Western blots of cancer cell lines probed with commercially available anti-NME7 antibodies B9 and H278 respectively. As can be seen, antibody 61 binds to NME7AB and NME7-X1 (33 kDa and 30 kDa) but does not bind to related proteins NME1 and NME2 at 17 kDa and 21 kDa. NME1 and NME2 are expressed in all cells. In contrast, B9 only recognizes full-length NME7 42 kDa and H278 recognizes lower molecular weight NME1 and NME2.

DETAILED DESCRIPTION OF THE INVENTION

Definitions

Figure 1:
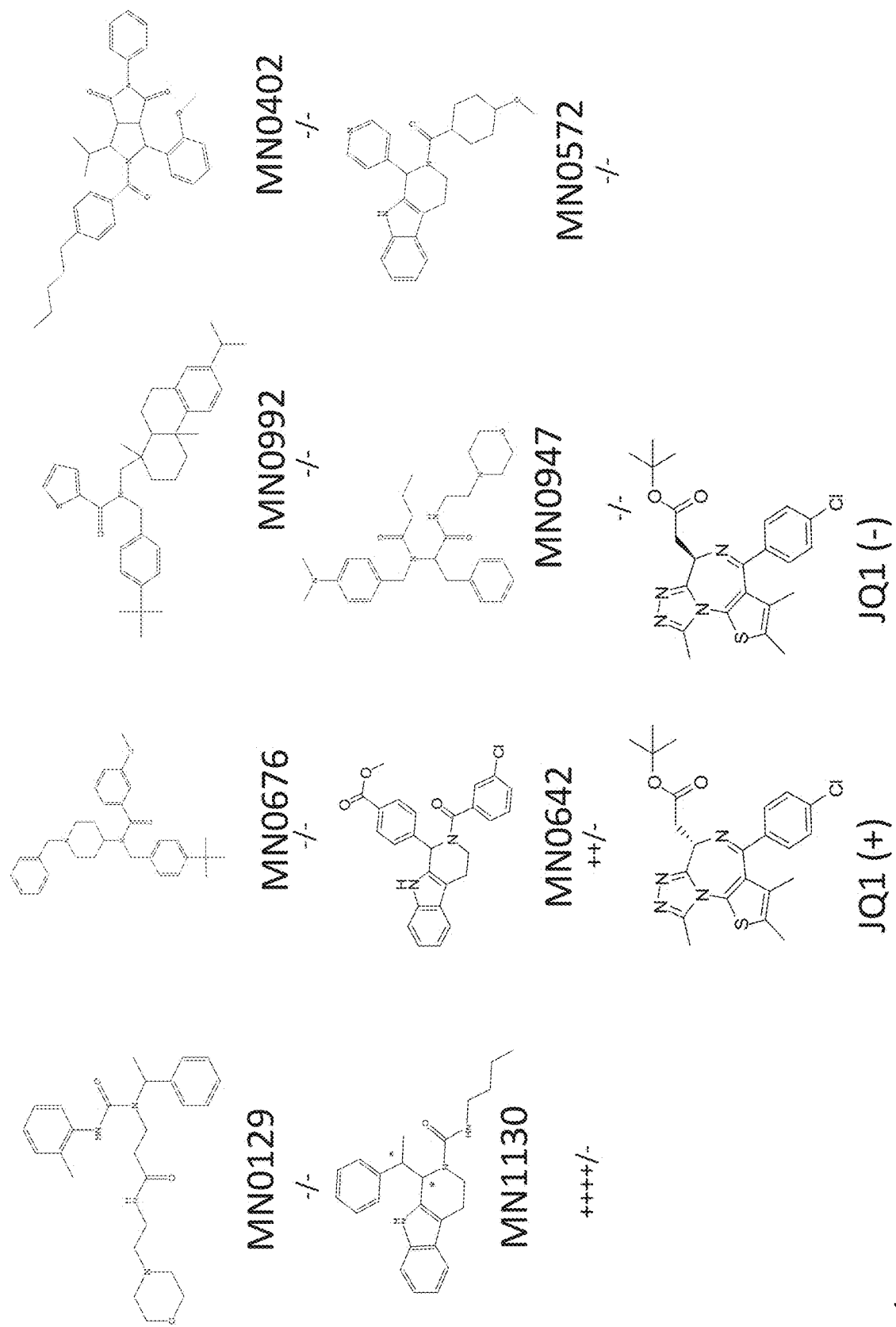
FIG. 1 shows the chemical structures of a set of small molecules that were tested for their ability to inhibit pluripotency, growth or induce differentiation of naïve state or primed state stem cells.
Figure 3:
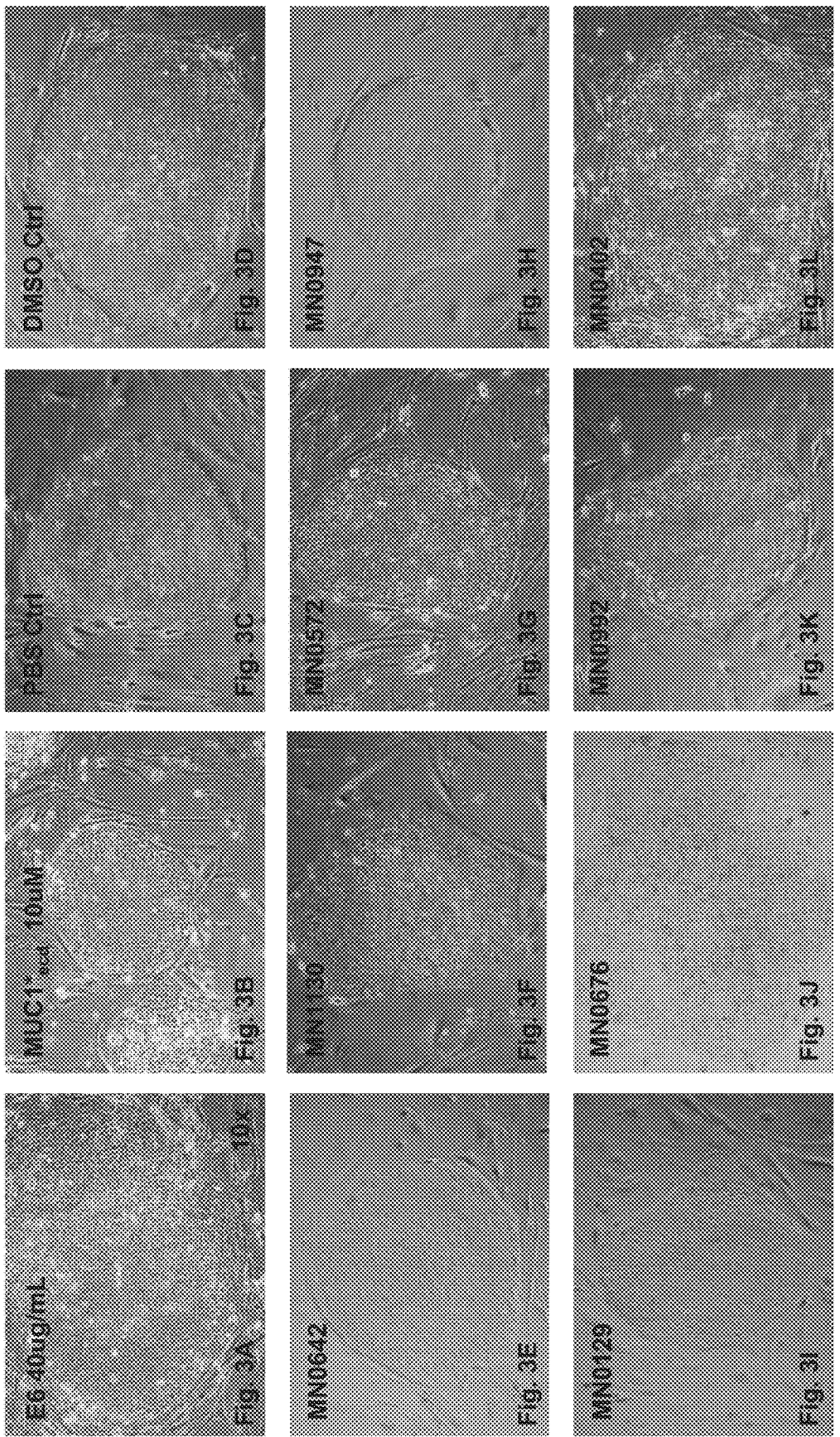
FIG. 3A-3L shows photographs at 10× magnification of human primed state stem cells, grown in stem cell media with growth factor FGF, over a layer of MEFs and treated for 3 days with in the presence of a test agent.
Figure 4:
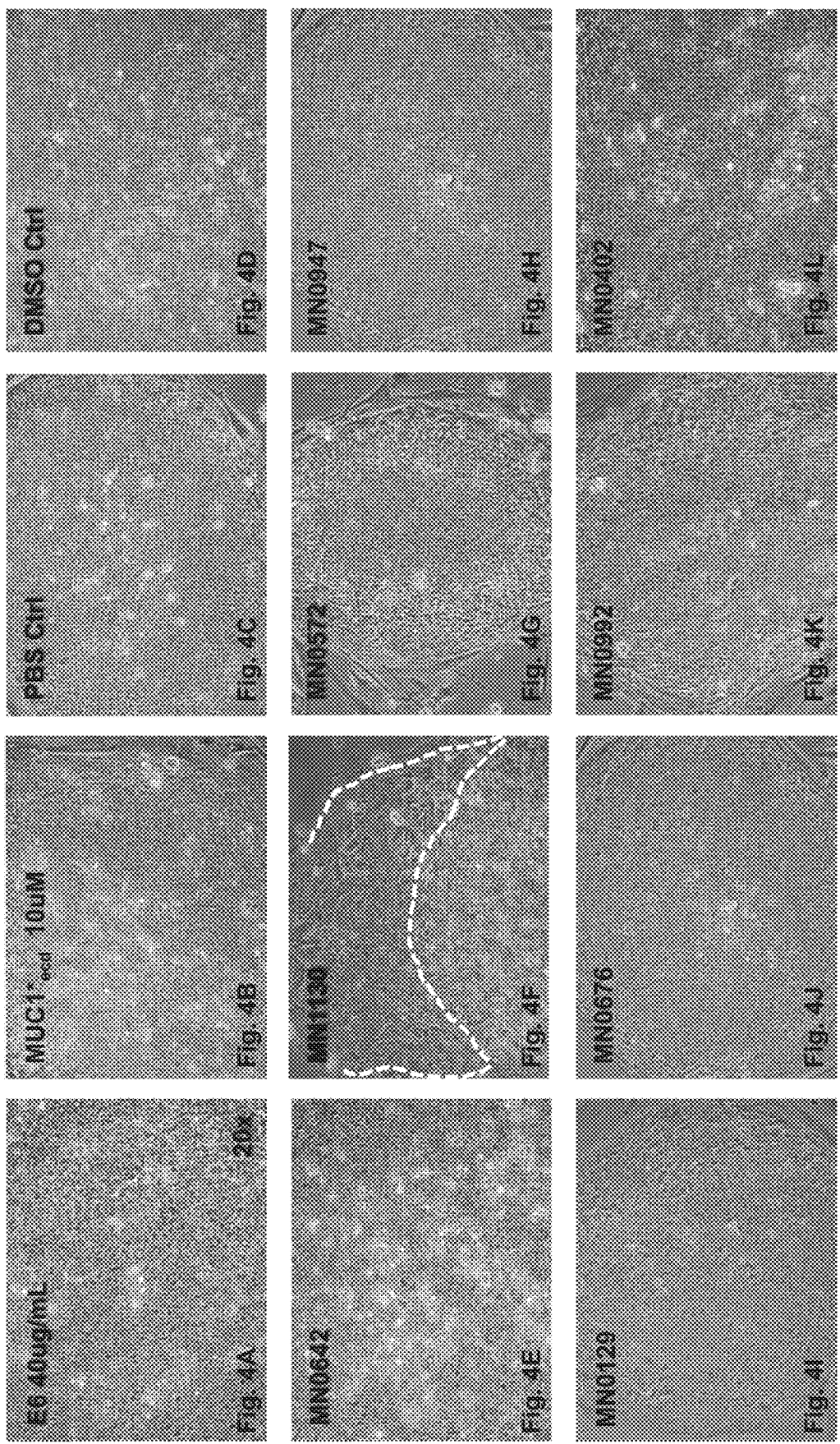
Figure 5:
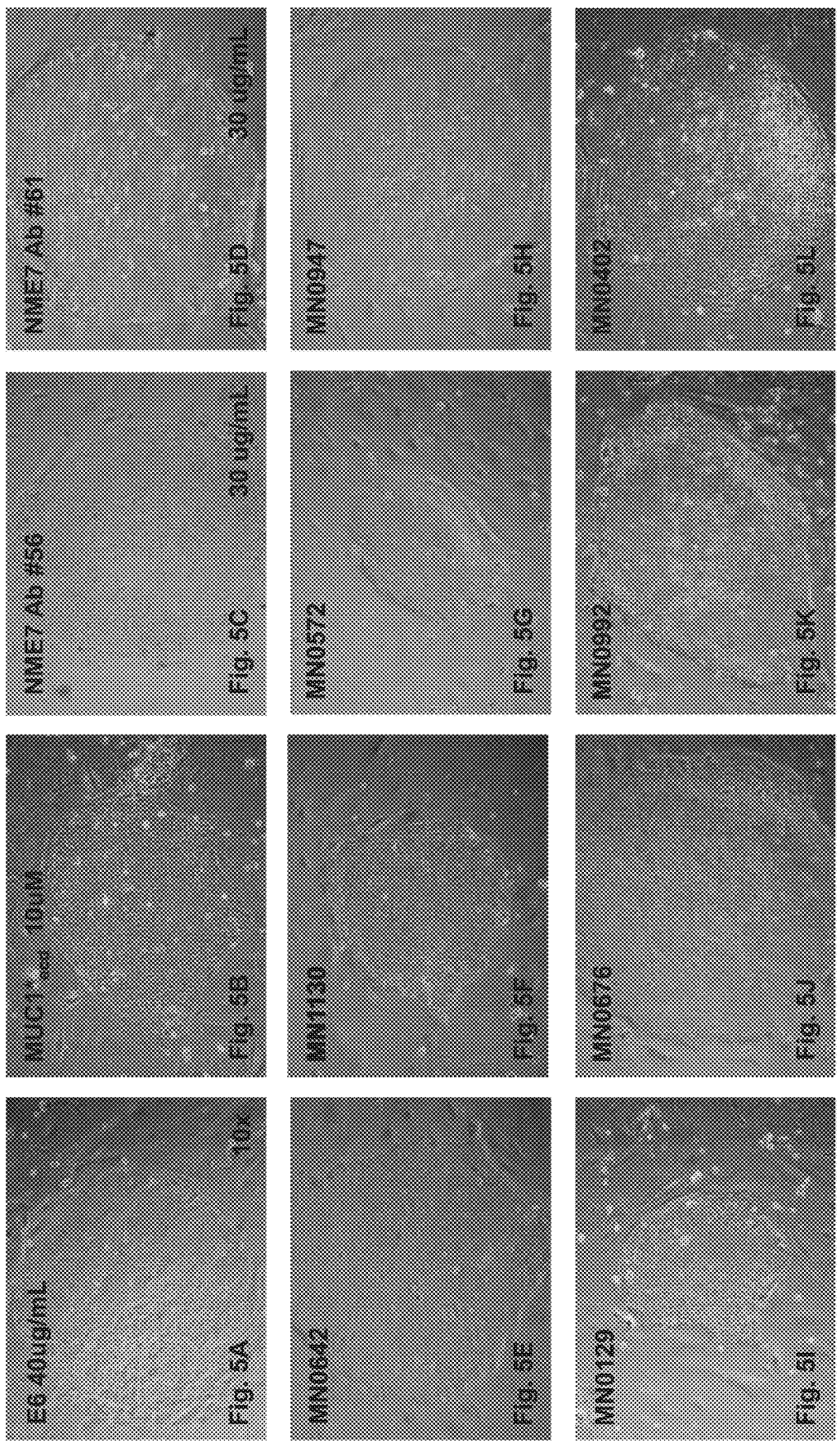
FIG. 5A-5L shows photographs at 10× magnification of human primed state stem cells, grown in stem cell media without growth factor FGF, over a layer of MEFs and treated for 3 days with in the presence of a test agent.
Figure 6:
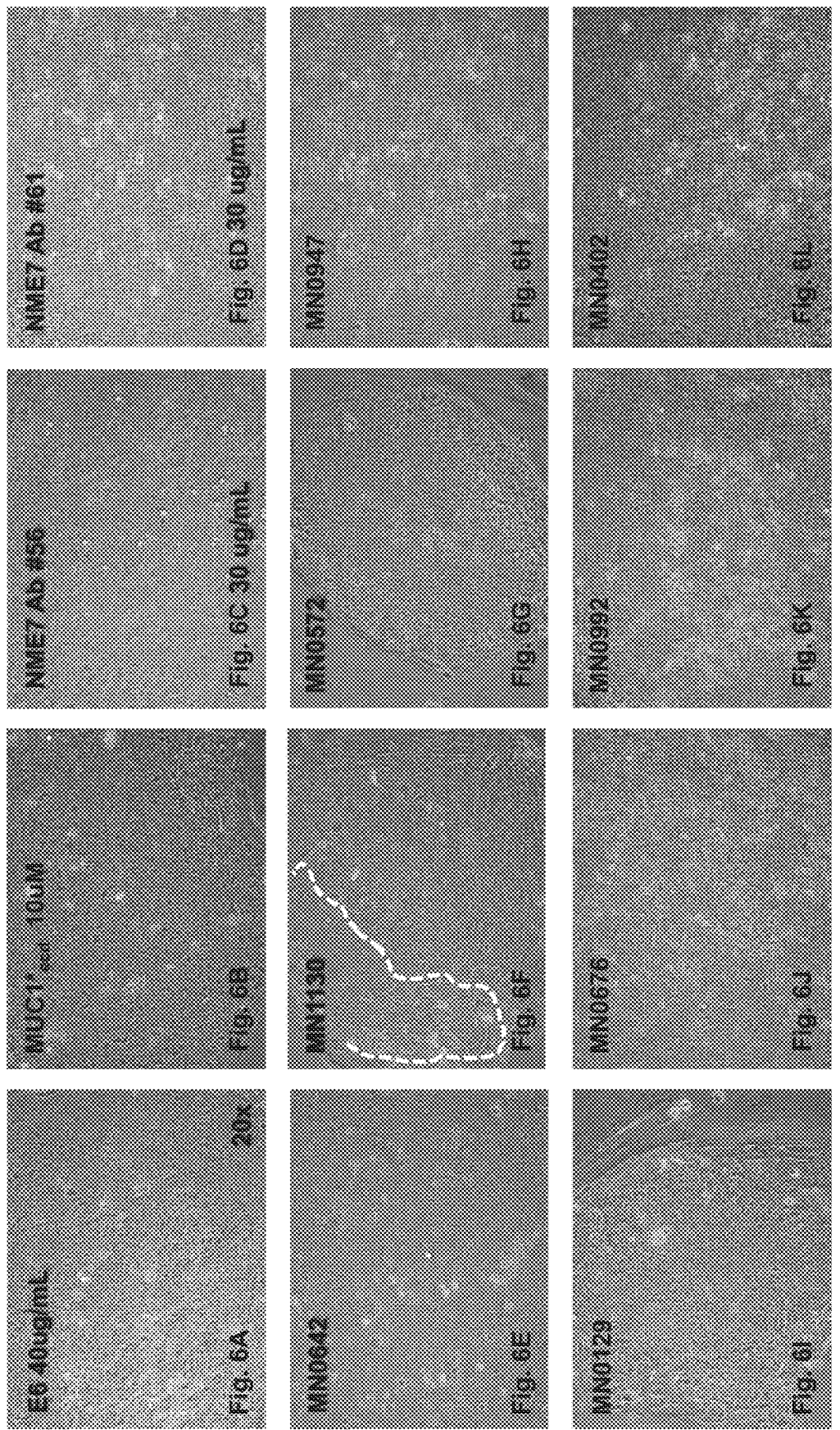
Figure 7:
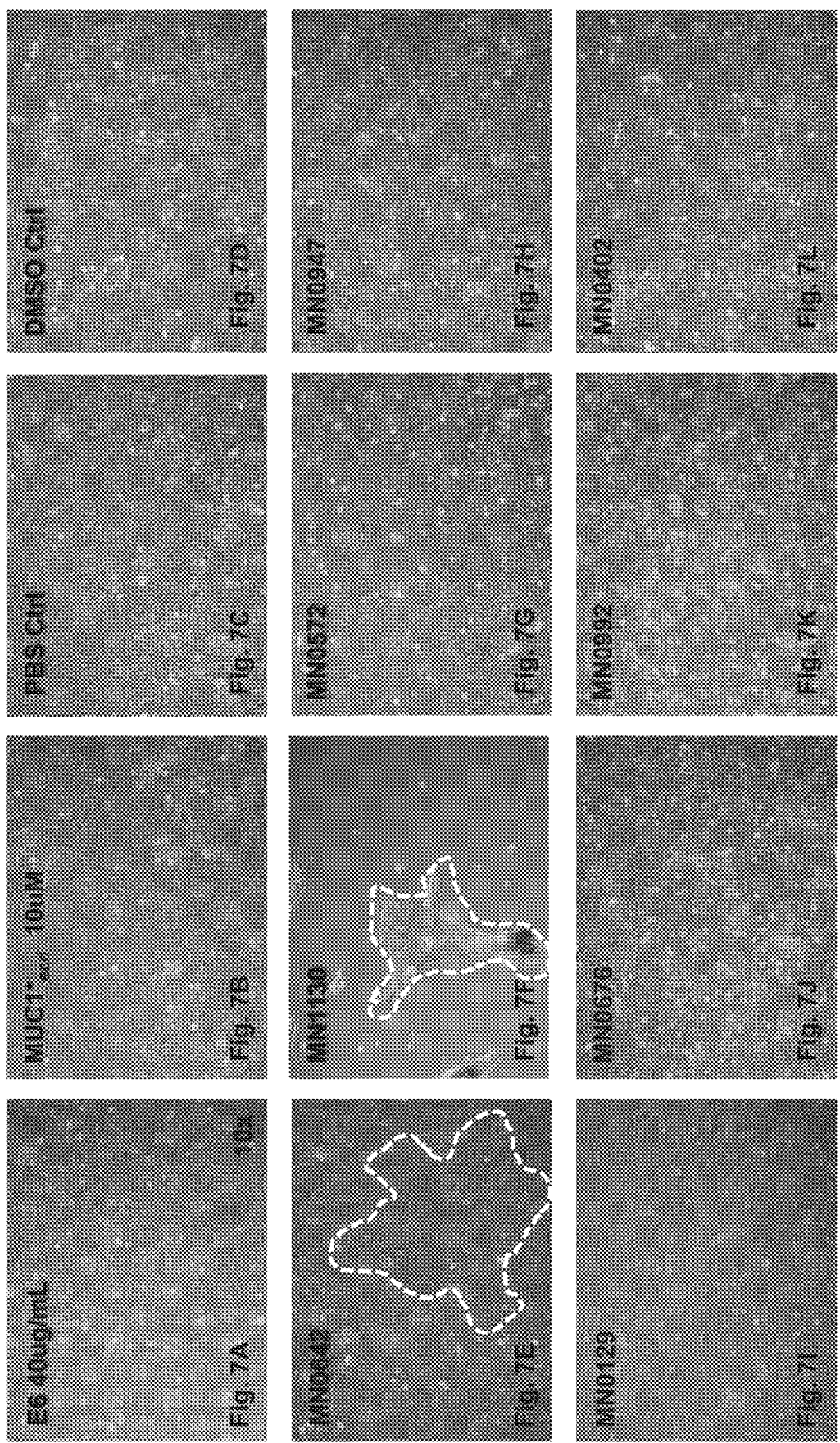
Figure 8:
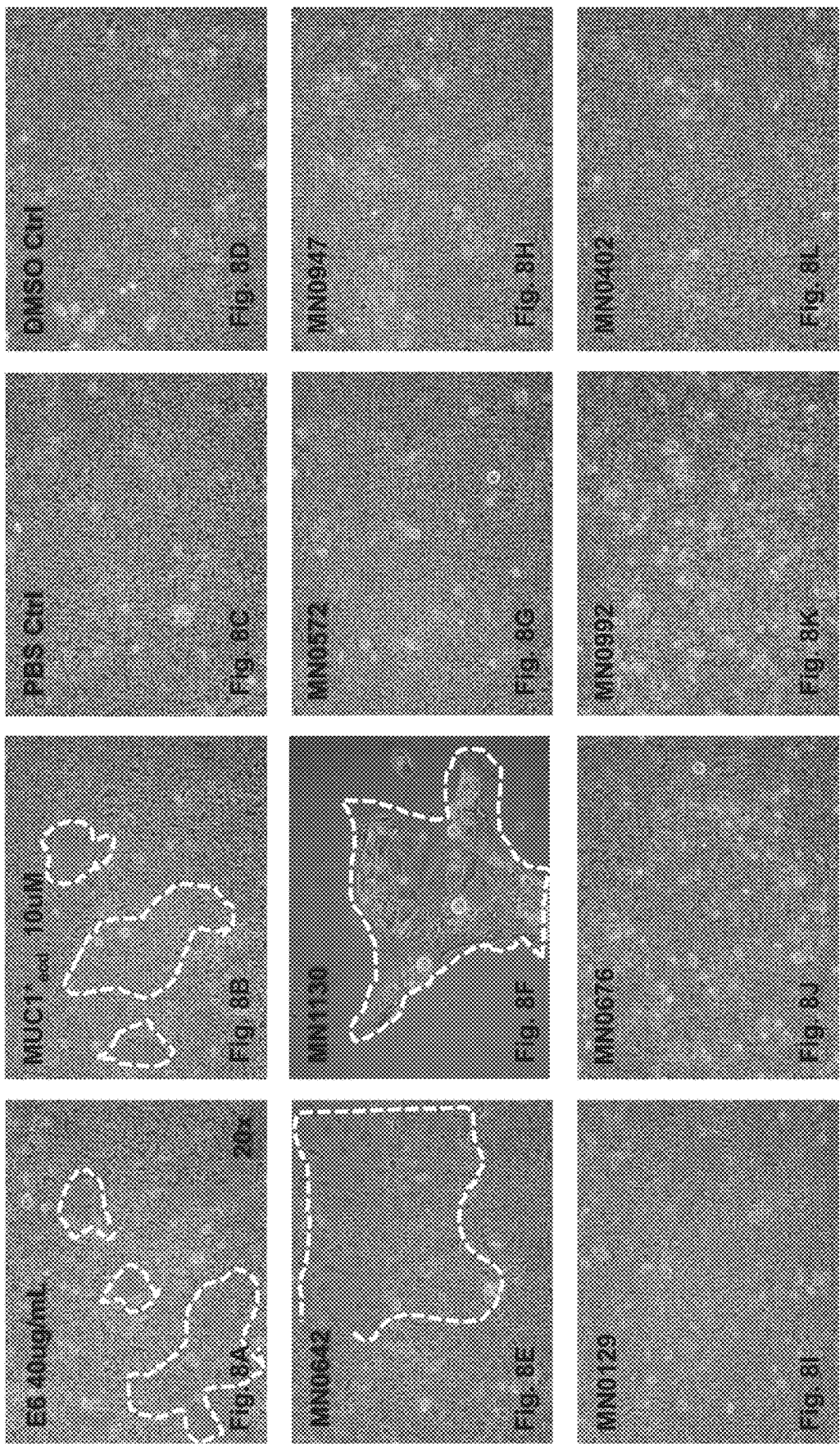
FIG. 8A-8L shows photographs at 20× magnification of human naïve state stem cells, grown in stem cell media with growth factor NME7$_{AB}$, over a MUC1* antibody, C3, surface and treated for 3 days with in the presence of a test agent. Dotted lines indicate areas where stem cell pluripotency or growth is inhibited or differentiation is induced.
Figure 9:
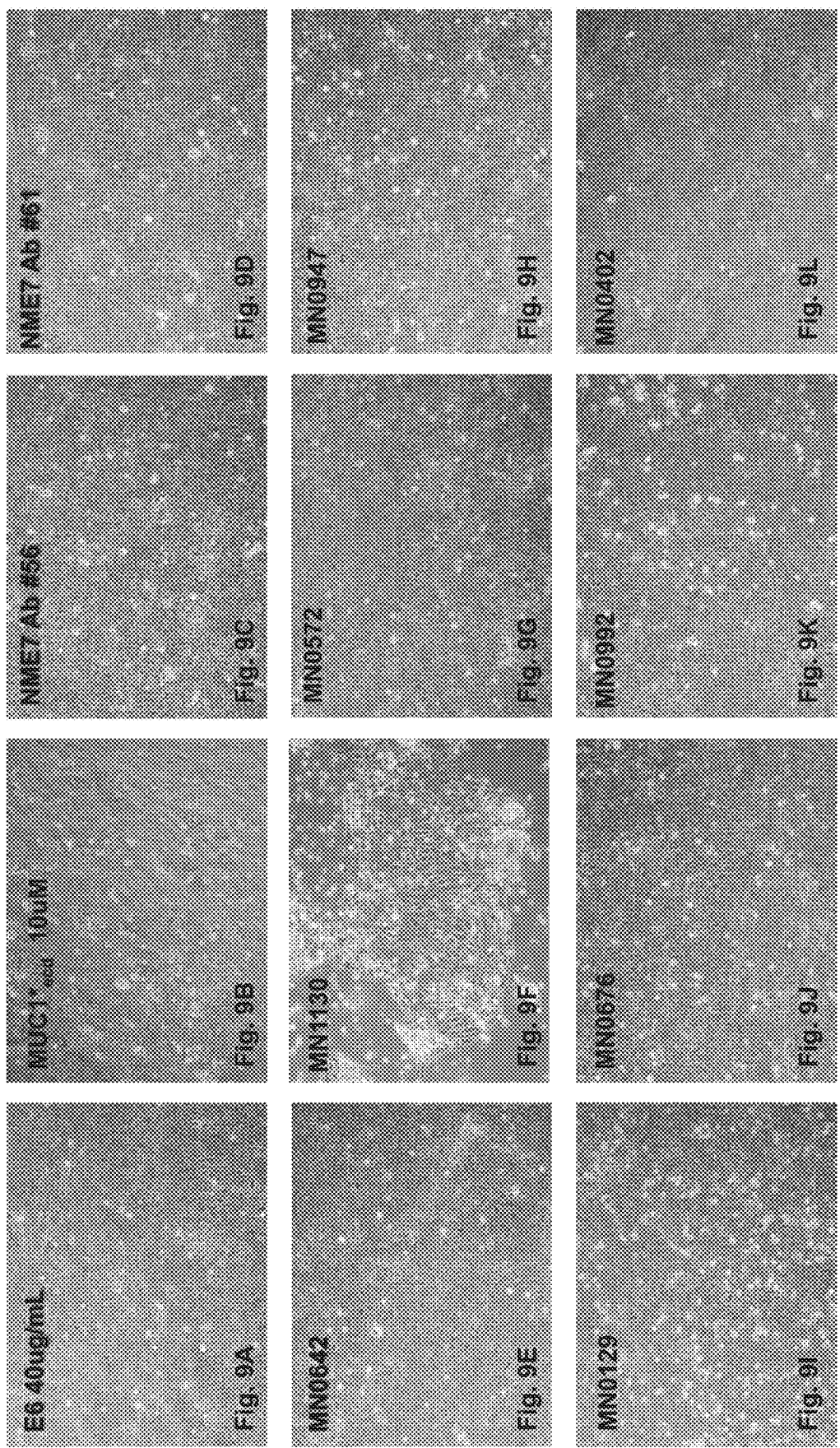
FIG. 9A-9L shows photographs at 10× magnification of human naïve state stem cells, grown in stem cell media without growth factor NME7$_{AB}$, over a MUC1* antibody, C3, surface and treated for 3 days with in the presence of a test agent. Dotted lines indicate areas where stem cell pluripotency or growth is inhibited or differentiation is induced.
Figure 10:
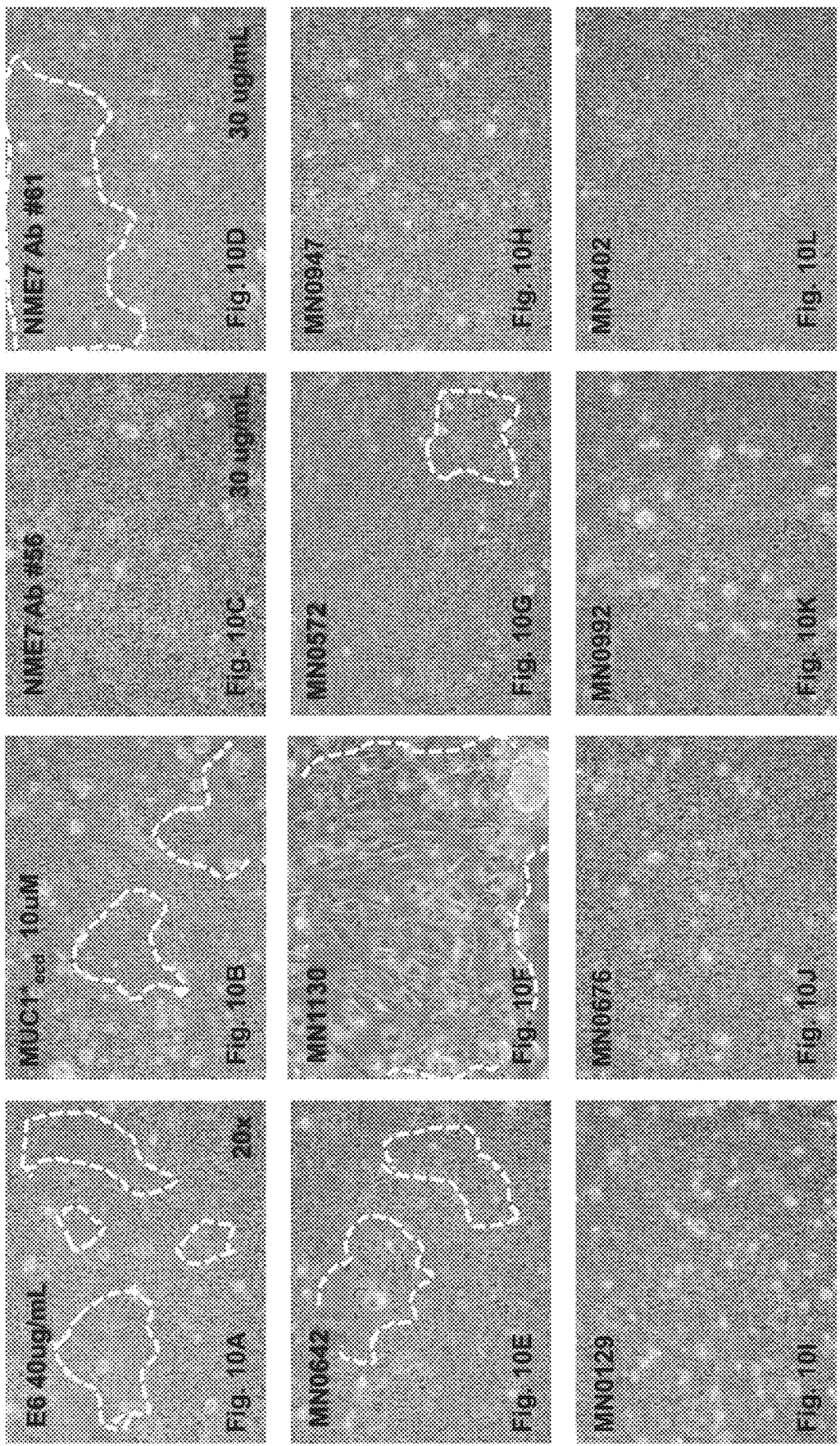
FIG. 10A-10L shows photographs at 20× magnification of human naïve state stem cells, grown in stem cell media without NME7AB, over a MUC1* antibody, C3, surface and treated for 3 days with in the presence of a test agent. Dotted lines indicate areas where stem cell pluripotency or growth is inhibited or differentiation is induced.
Figure 18:
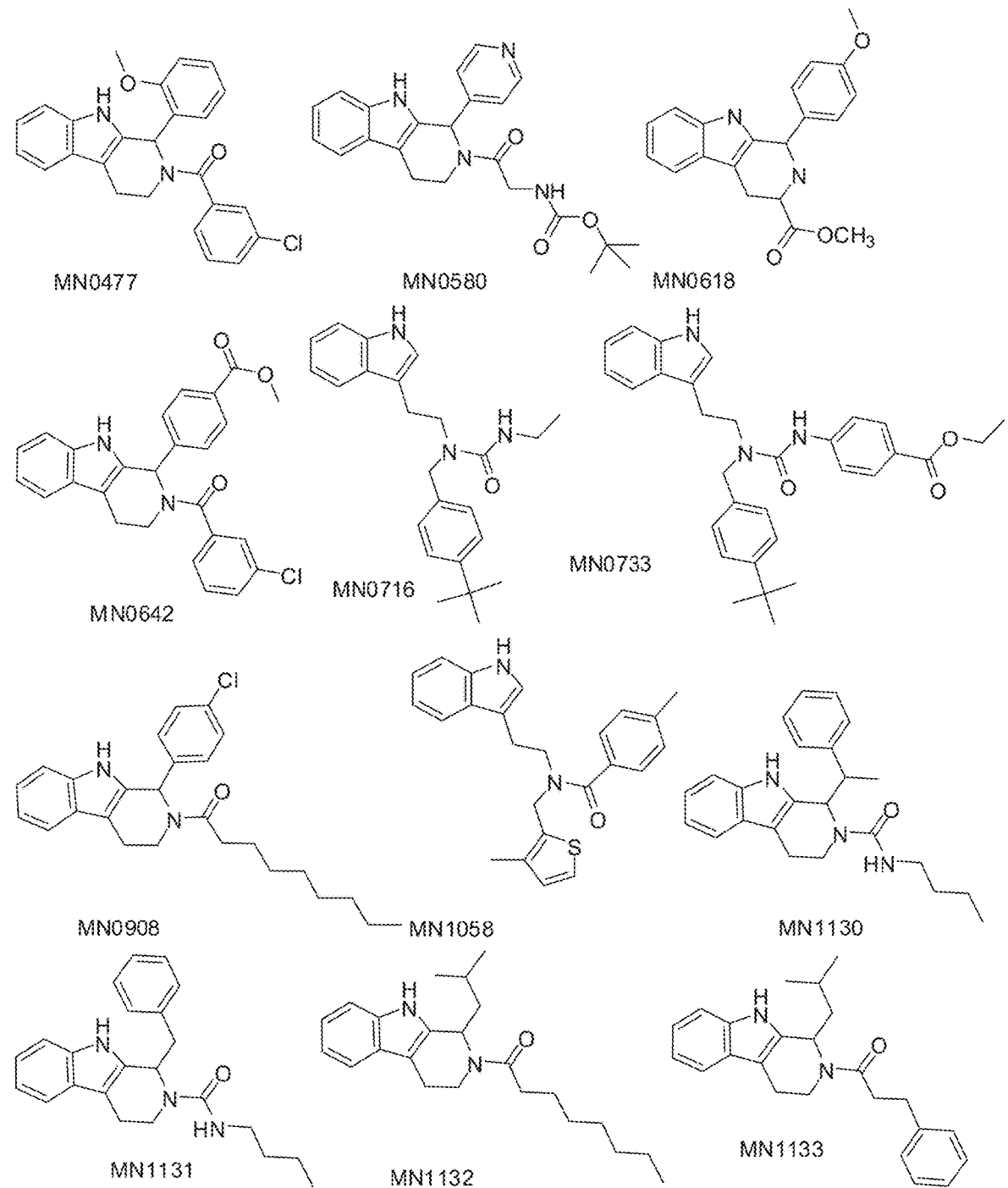
FIGS. 18-27 show chemical structures of compounds identified using methods of the invention that inhibit cancer cell growth, migration or invasion. They also had an inhibitory effect on naïve stem cells but not on primed state stem cells or had a much lesser effect on primed state stem cells.
Figure 19:
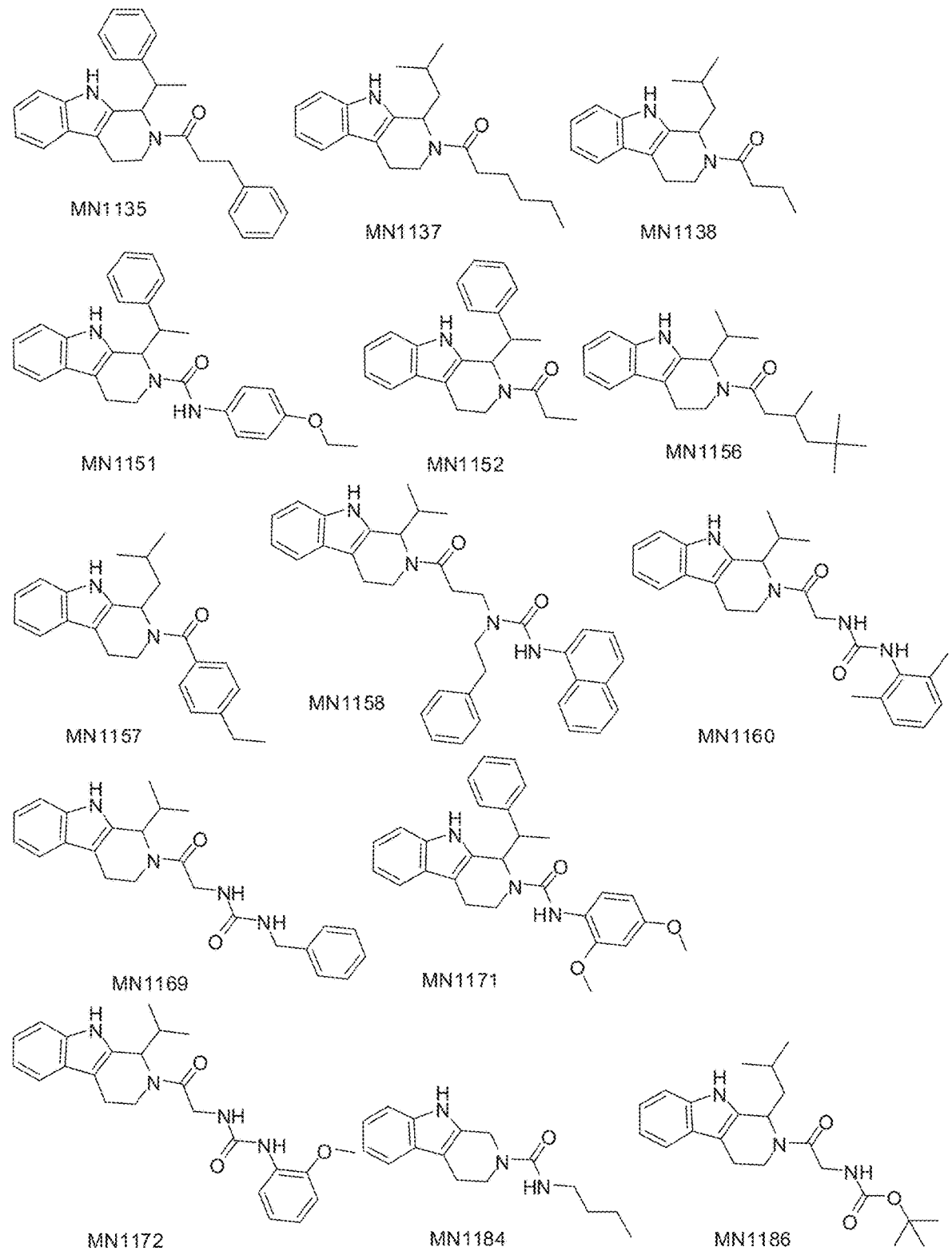
Figure 20:
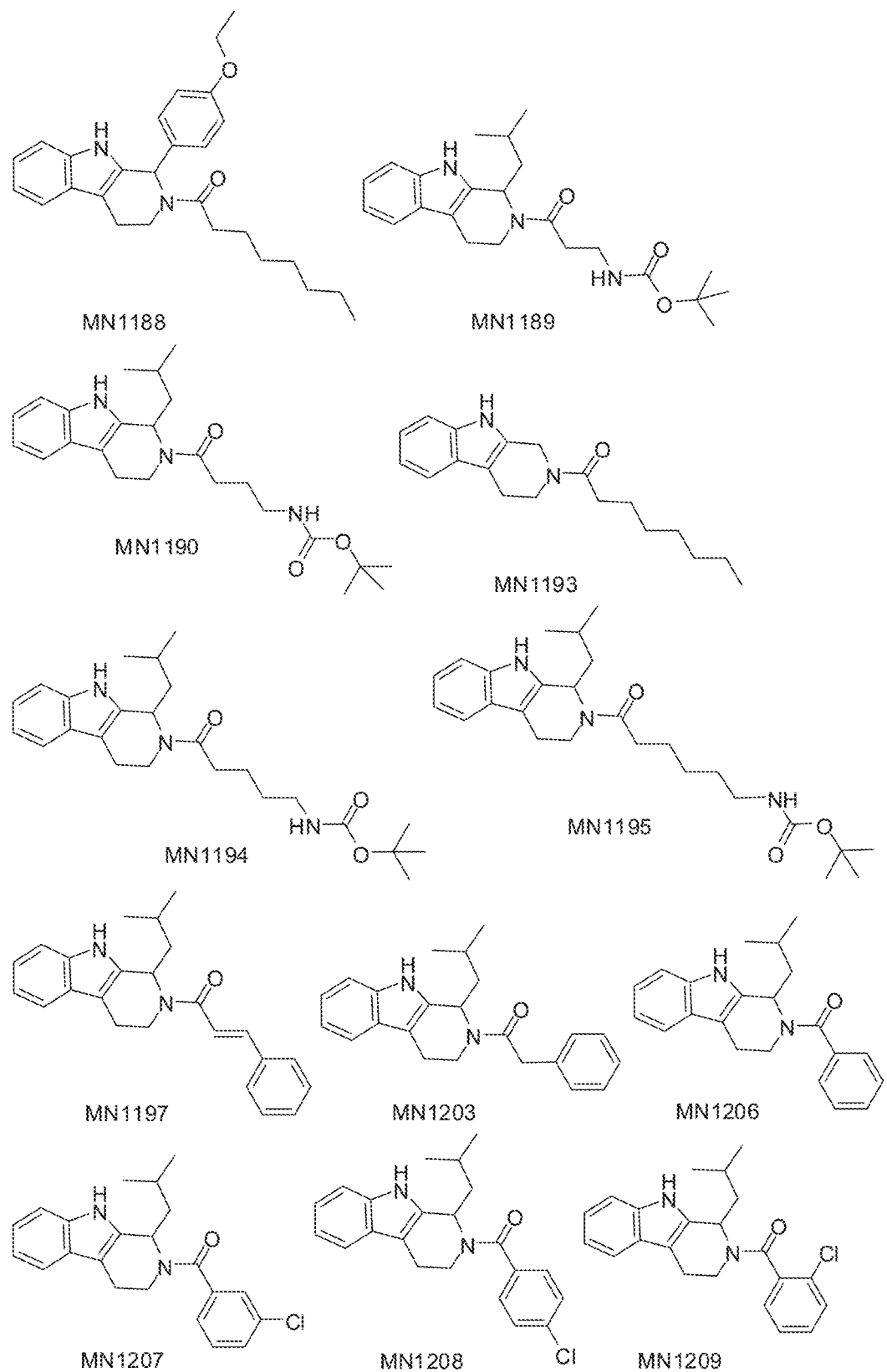
Figure 21:
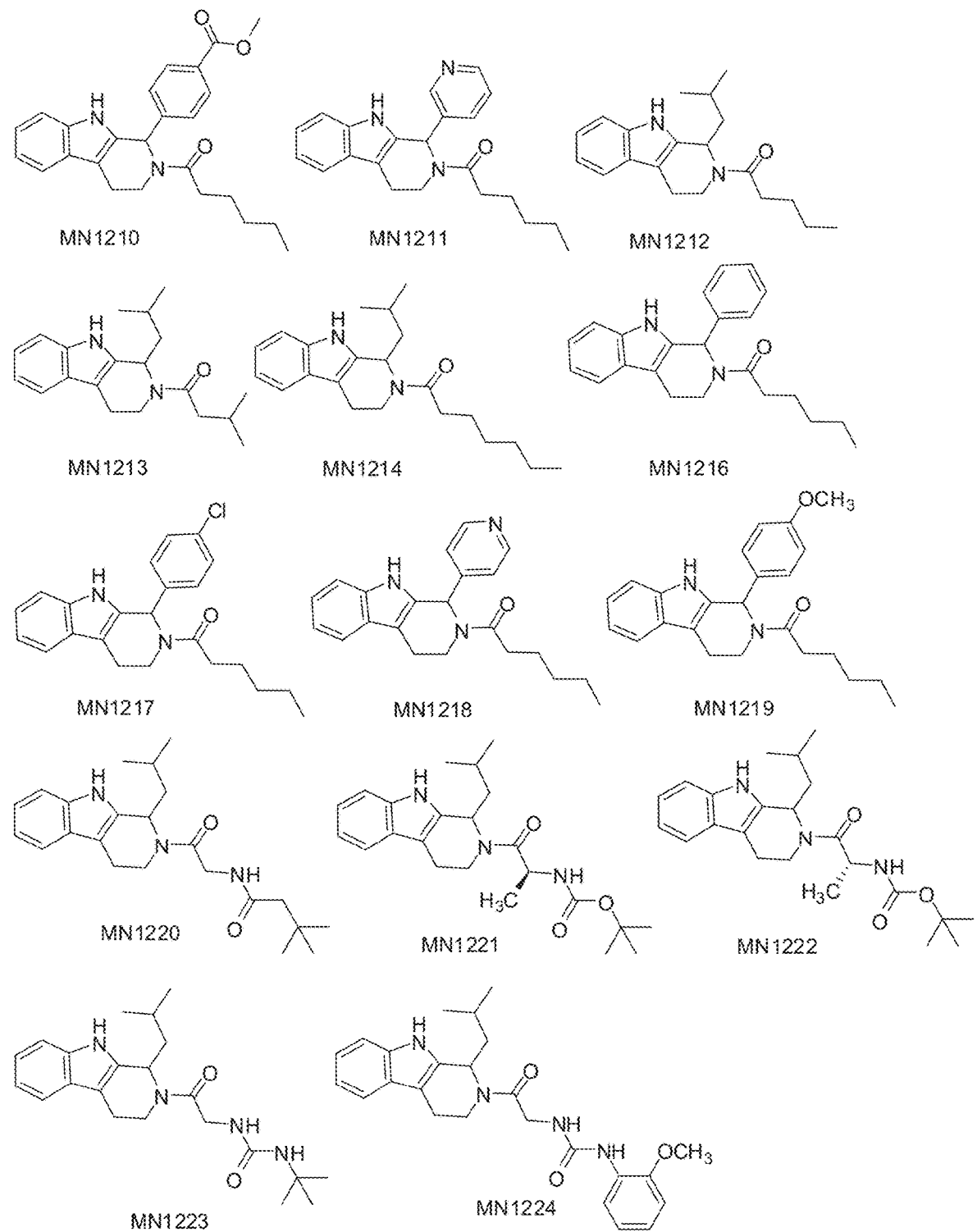
Figure 22:
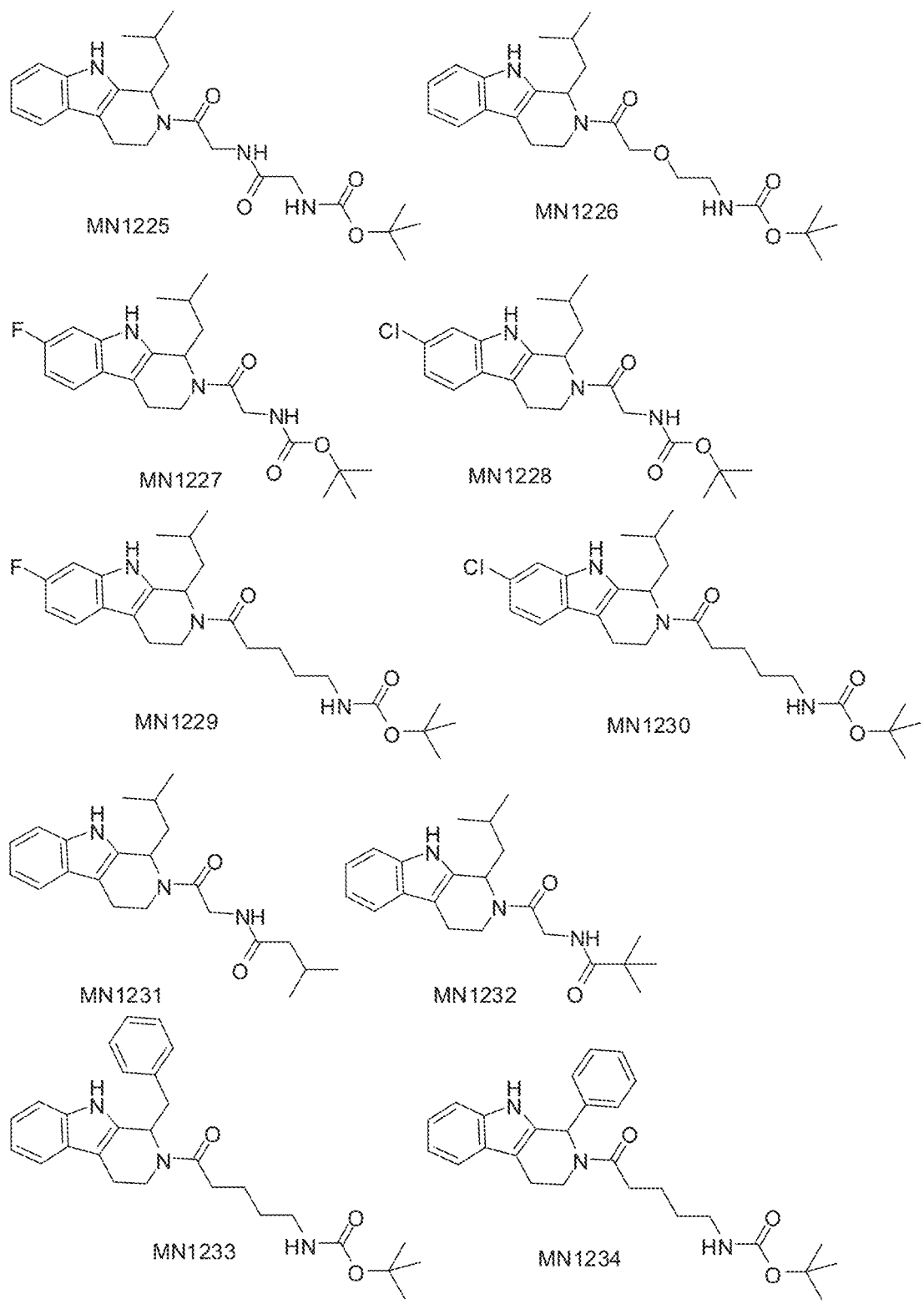
Figure 23:
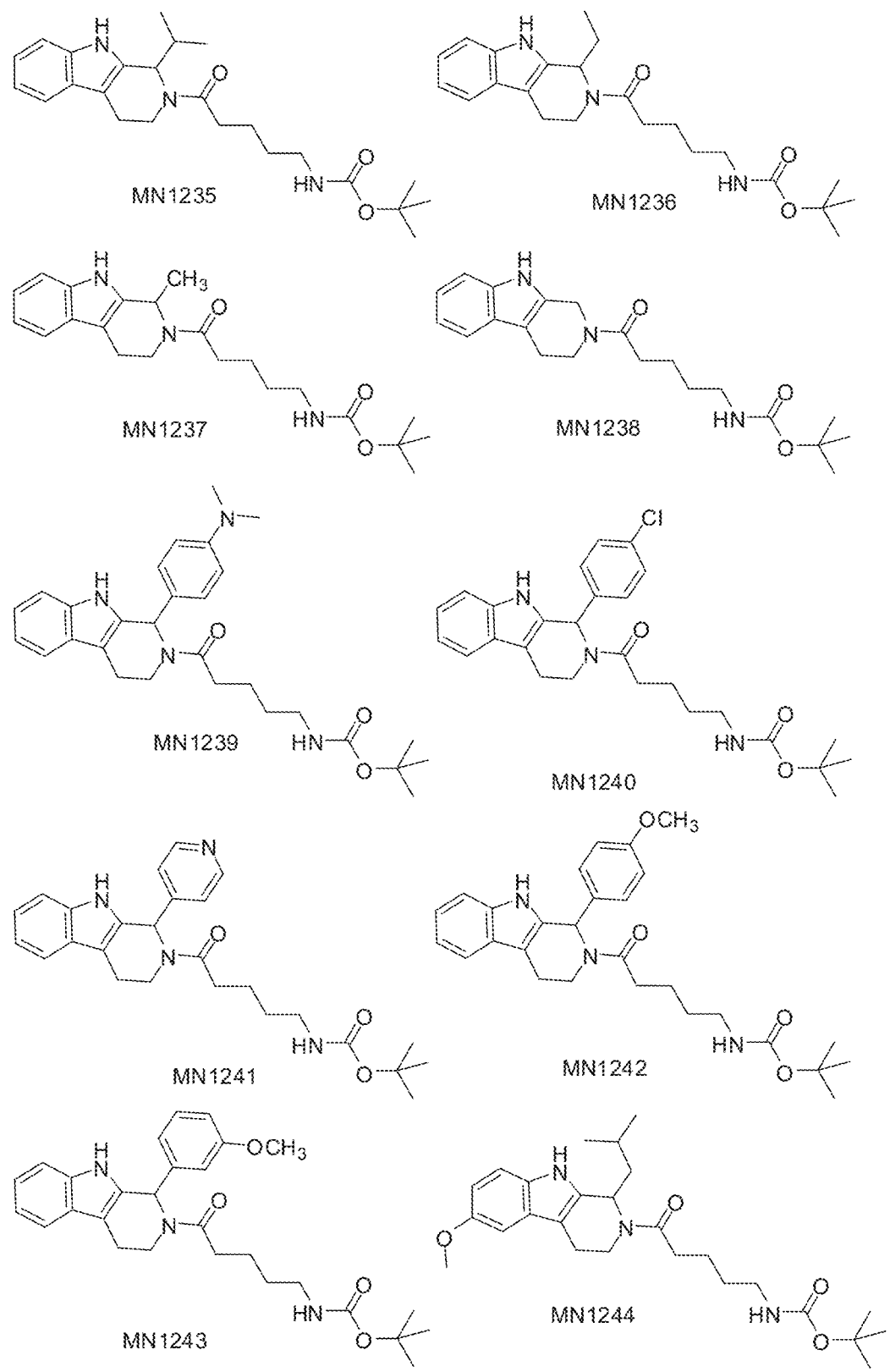
Figure 24:
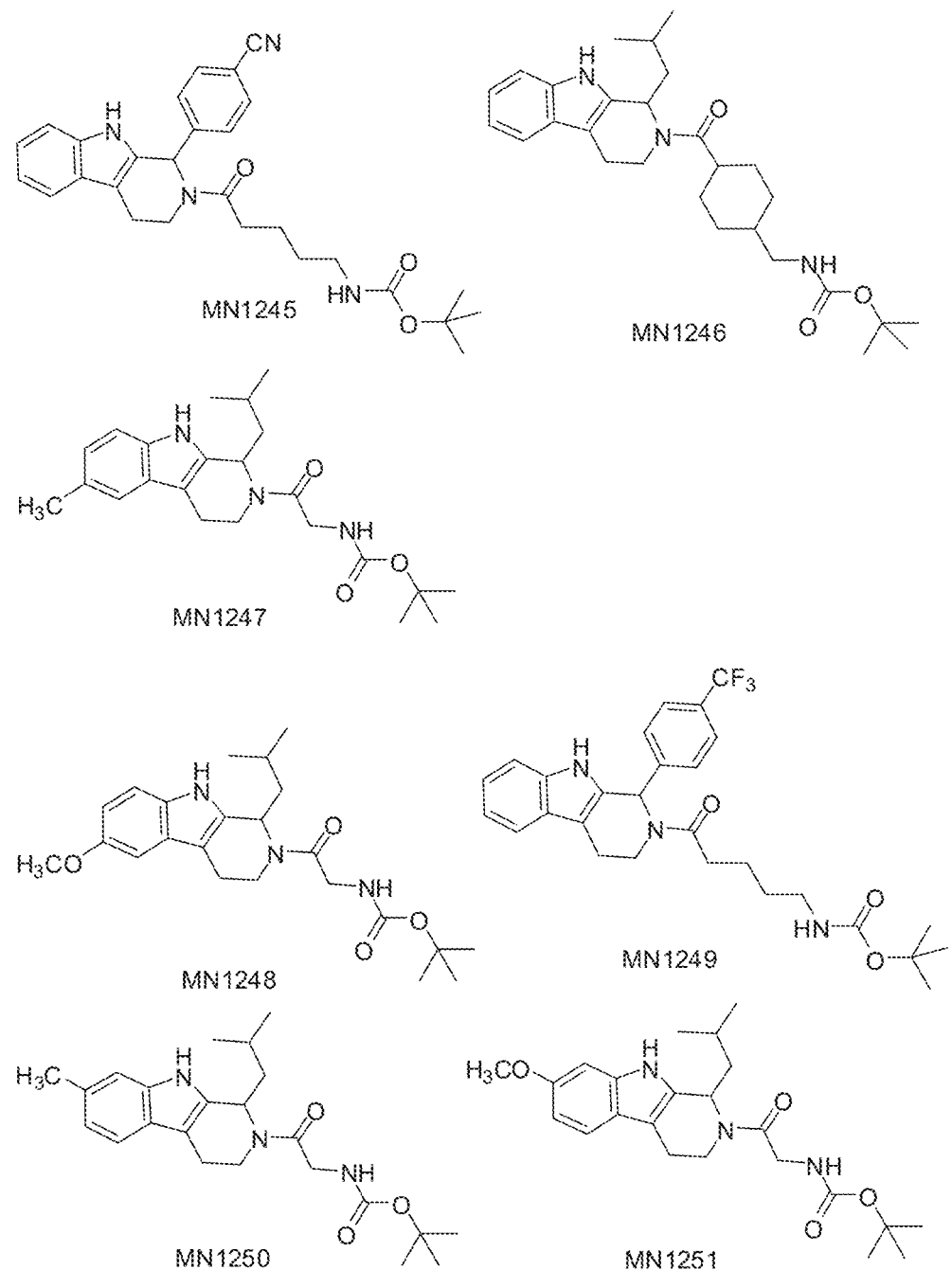
Figure 25:
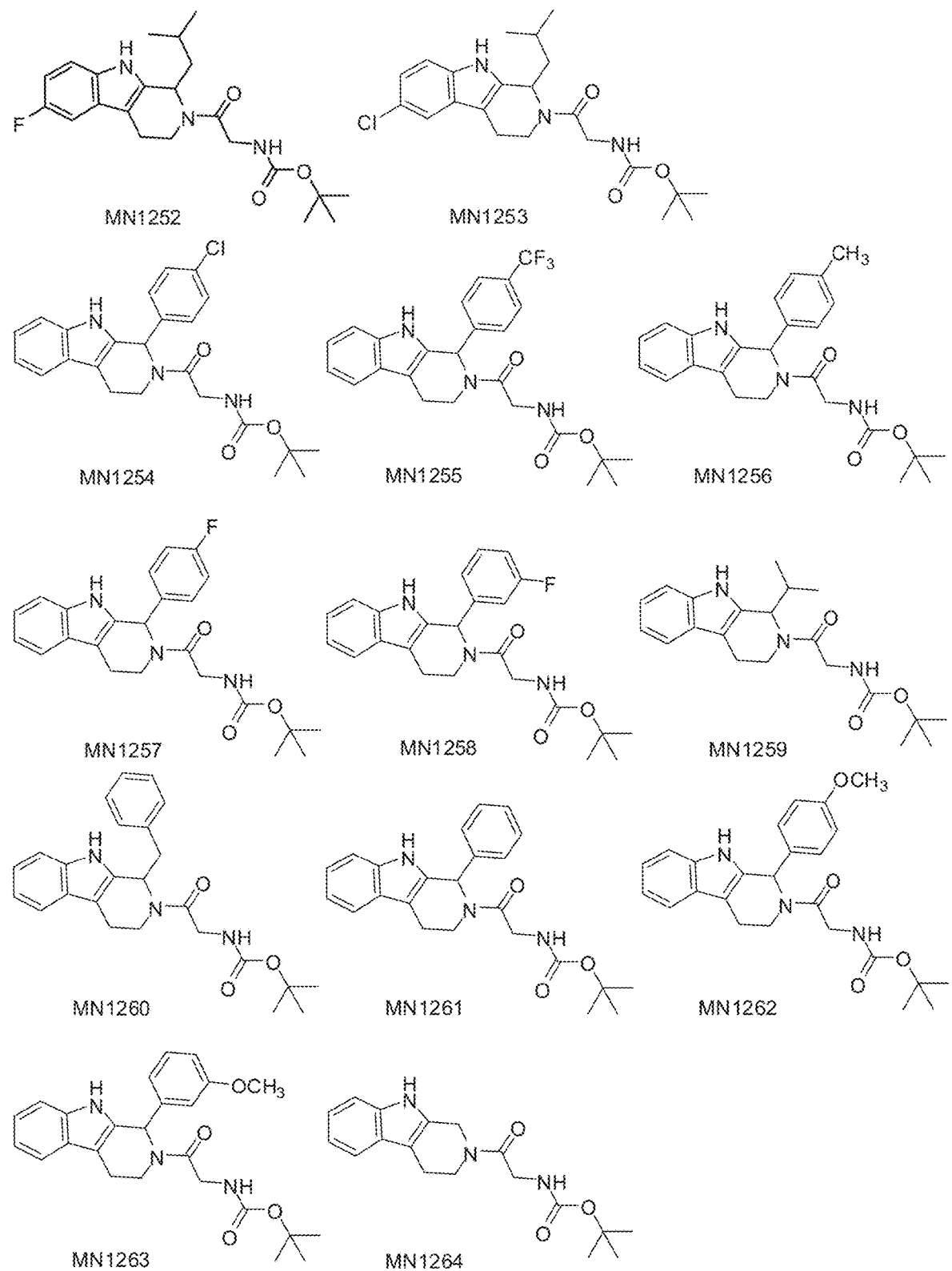
Figure 26:
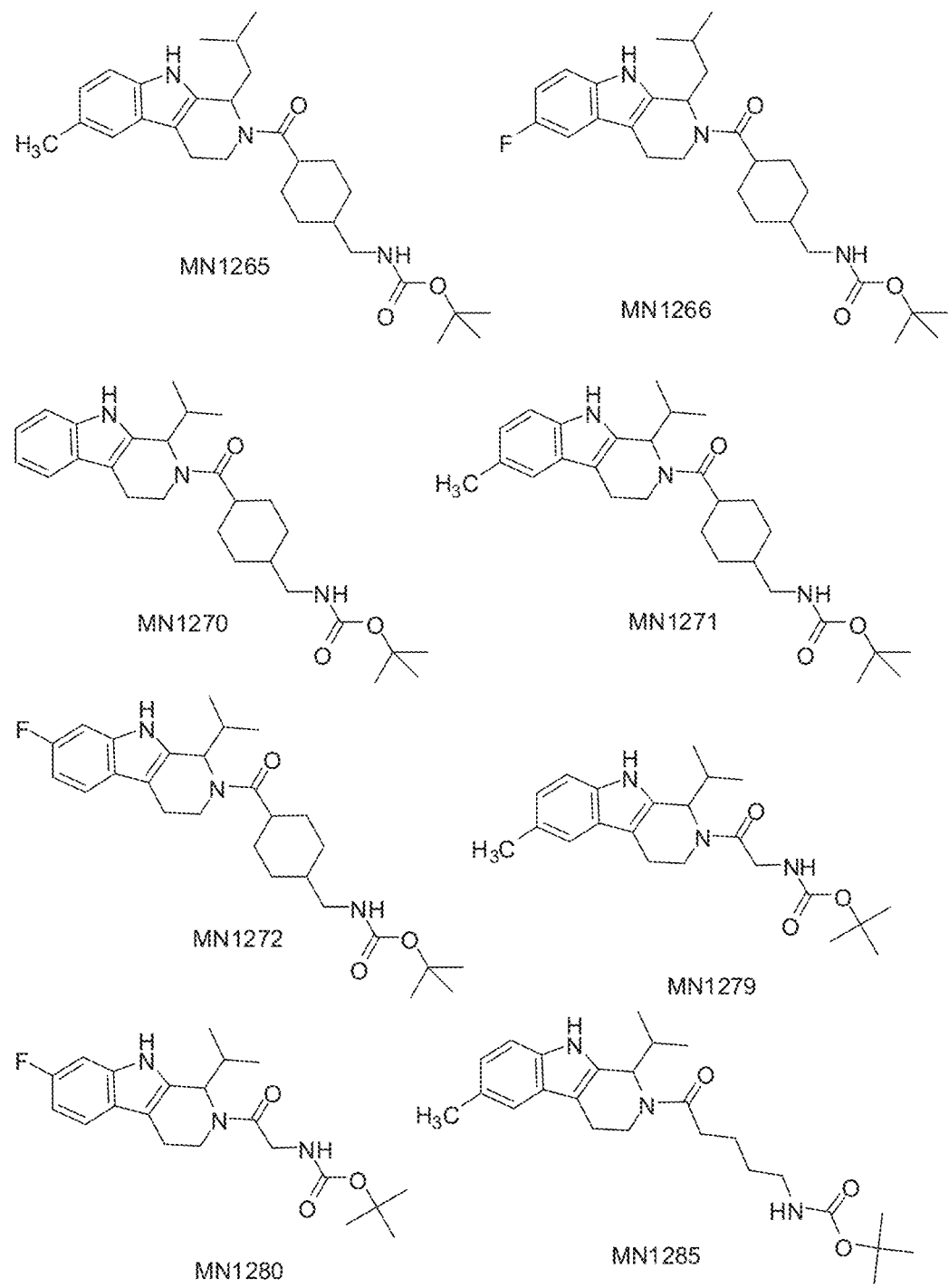
Figure 27:
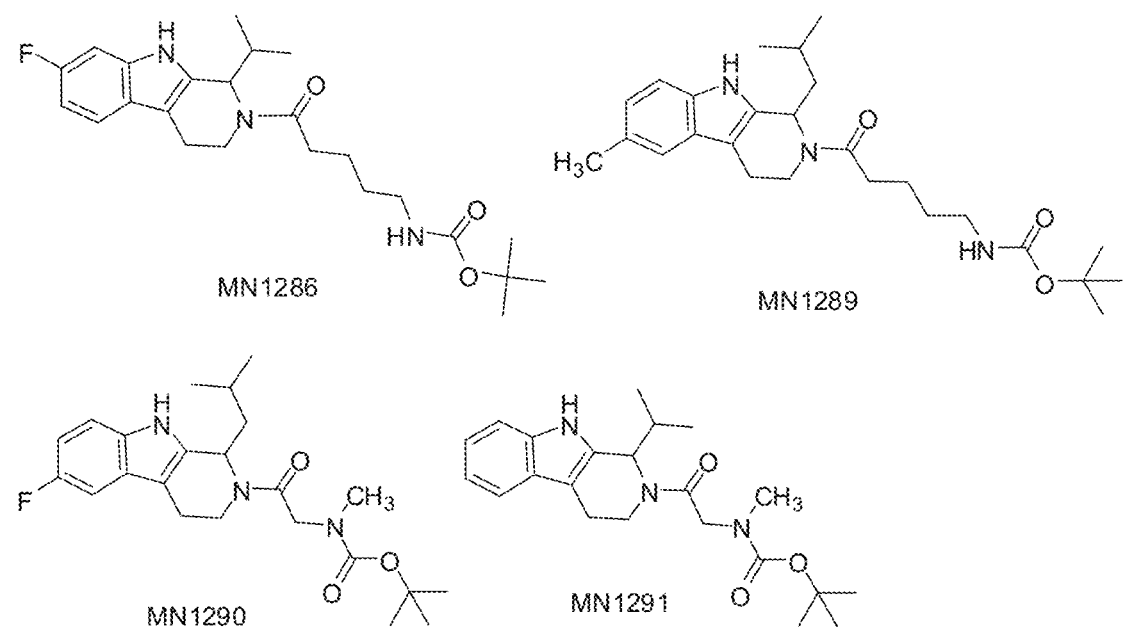
Figure 29:
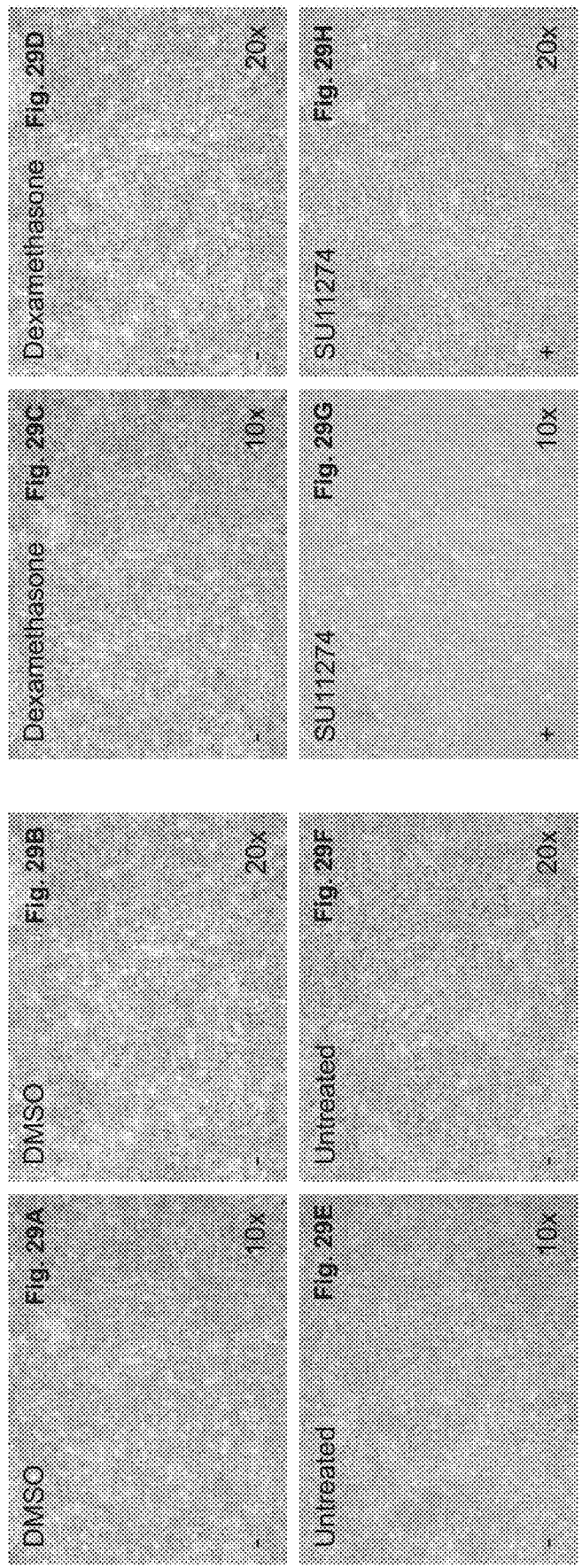
Figure 29:
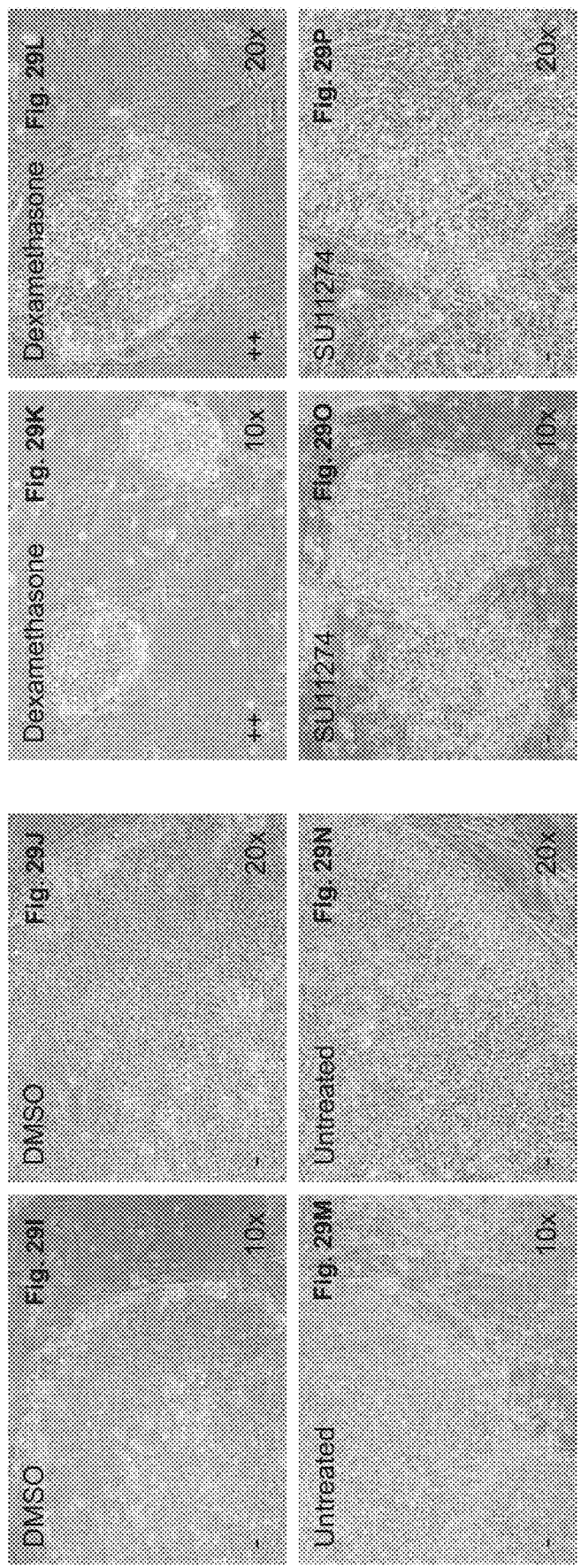
Figure 31:
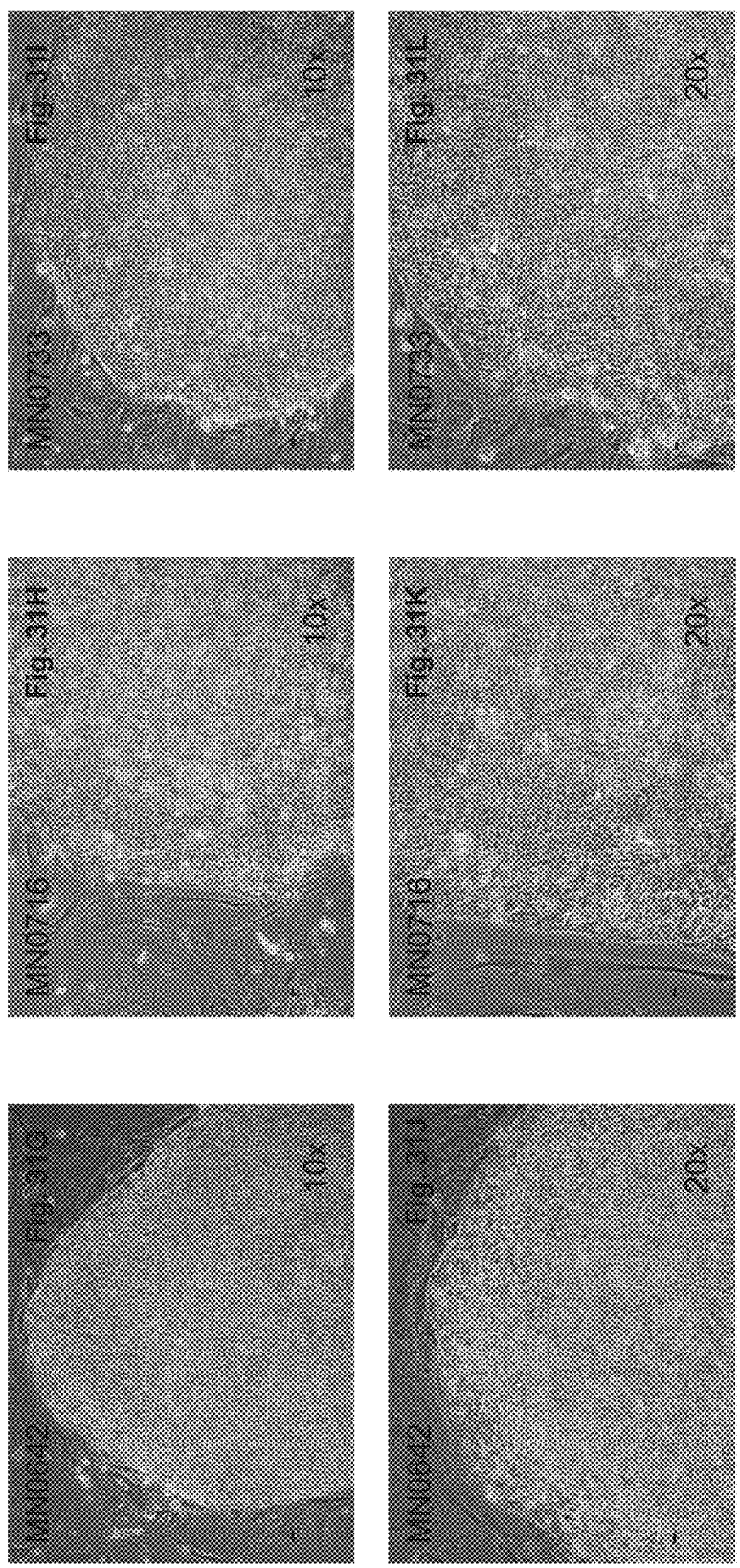
Figure 32:
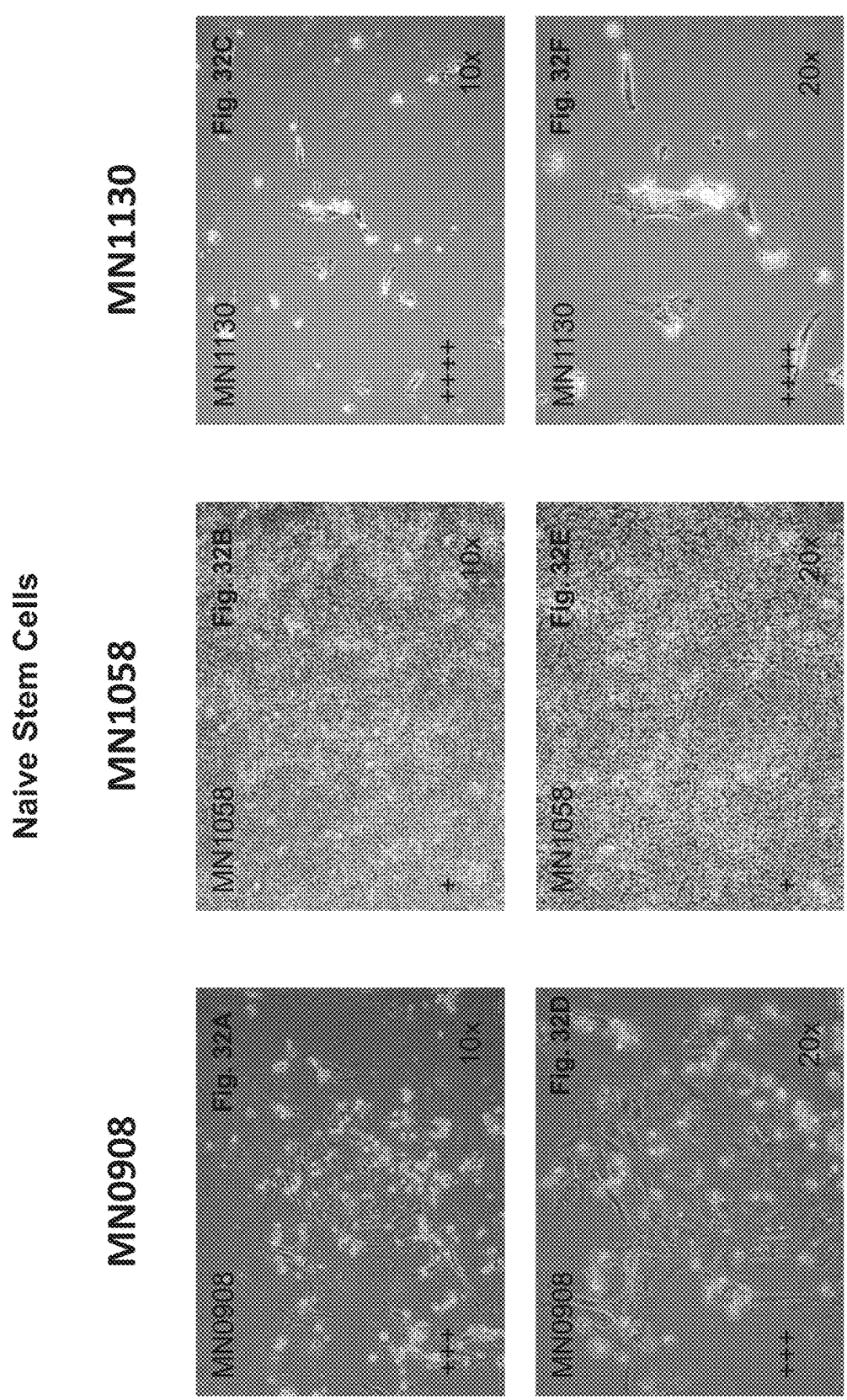
Figure 40:
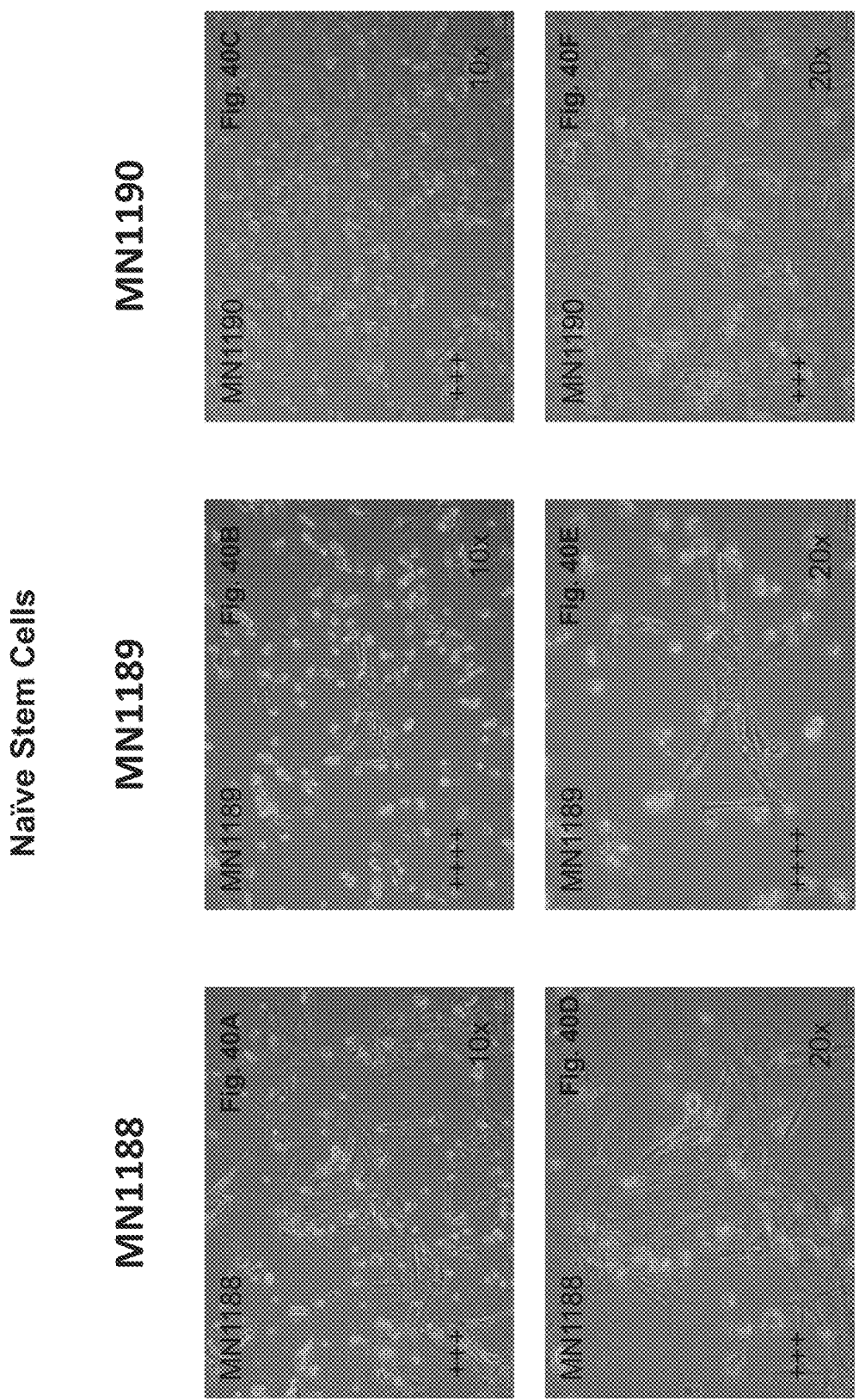
Figure 70:
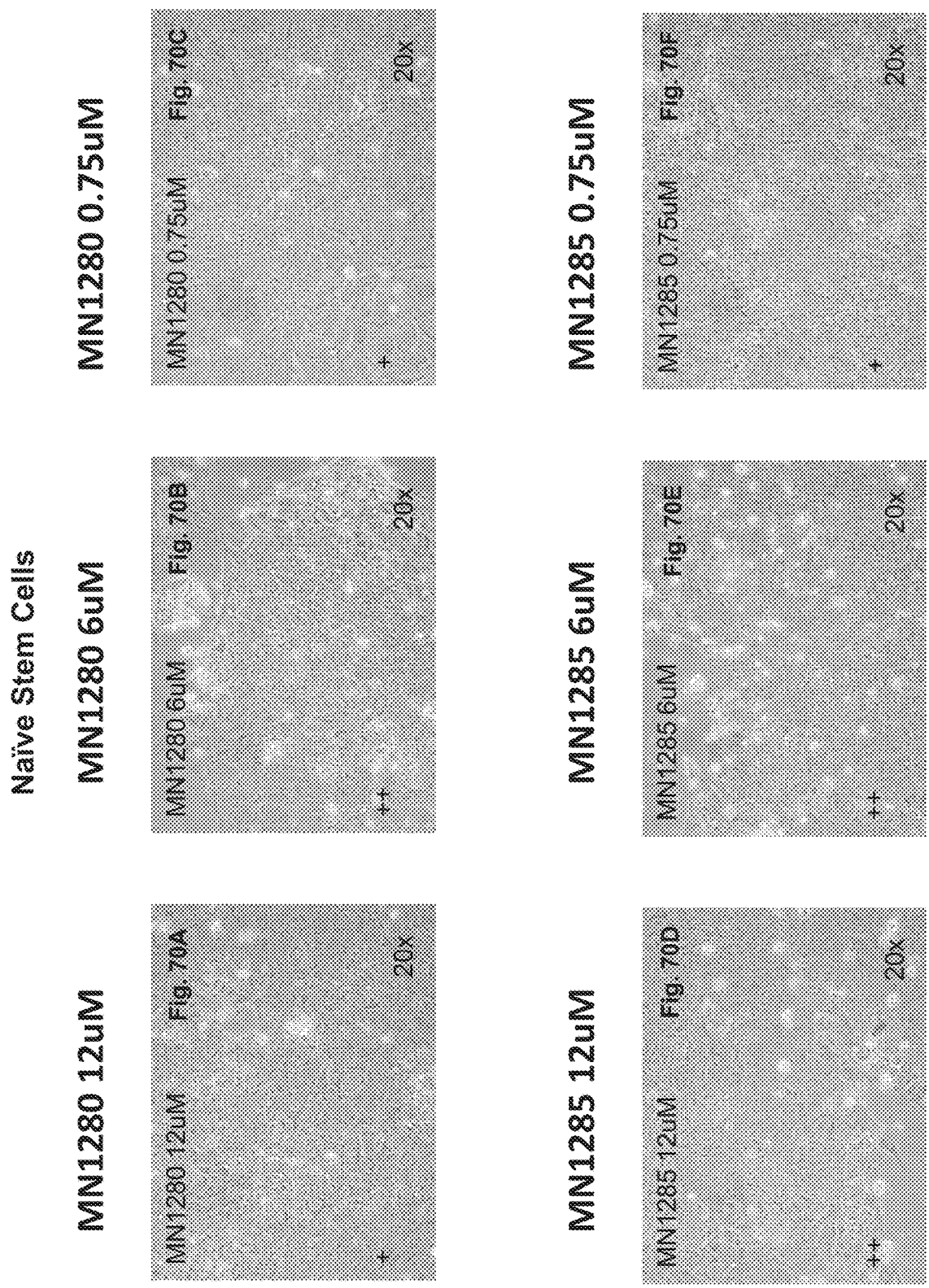
Figure 71:
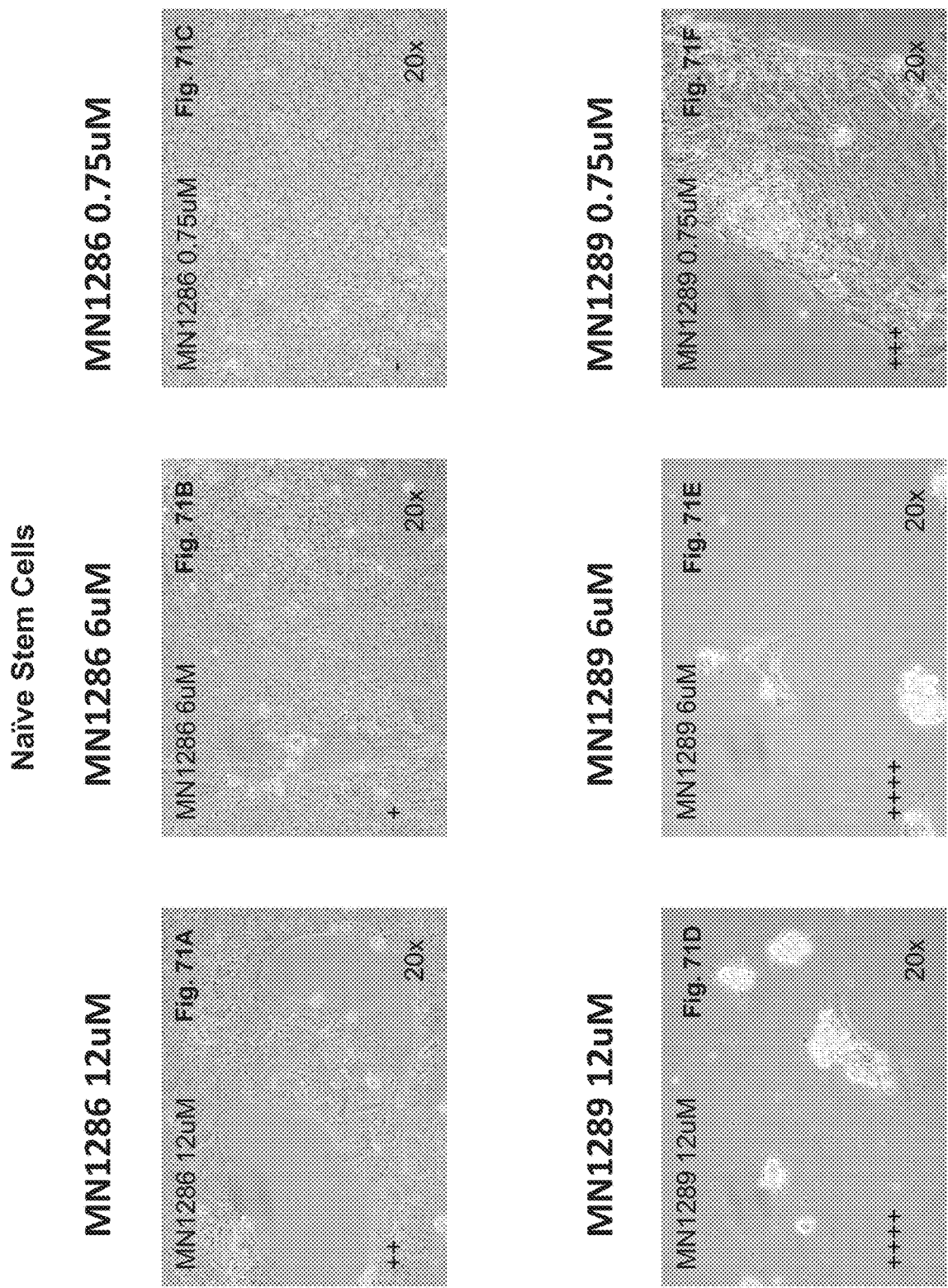

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents includes simultaneous (concurrent) and consecutive administration in any order.

As used herein, "carriers" include pharmaceutically acceptable carriers, excipients, or stabilizers which are nontoxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 μg to about 2000 mg. Expressed in proportions, the active compound is generally present in from about 0.5 μg/ml of carrier. In the case of compositions containing supplementary active ingredients, the dosages are determined by reference to the usual dose and manner of administration of the said ingredients.

The term "MUC1 Growth Factor Receptor" (MGFR) is a functional definition meaning that portion of the MUC1 receptor that interacts with an activating ligand, such as a growth factor or a modifying enzyme such as a cleavage enzyme, to promote cell proliferation. The MGFR region of MUC1 is that extracellular portion that is closest to the cell surface and is defined by most or all by the primary sequence of MGFR (PSMGFR). The MGFR is inclusive of both unmodified peptides and peptides that have undergone enzyme modifications, such as, for example, phosphorylation, glycosylation, etc. Results of the invention are consistent with a mechanism in which this portion is made accessible to the ligand upon MUC1 cleavage at a site associated with tumorigenesis that causes release of the some or all of the IBR from the cell. MGFR is also known as MUC1*.

The term "Primary Sequence of the MUC1 Growth Factor Receptor" (PSMGFR) or "FLR" is a peptide sequence that defines most or all of the MGFR in some cases, and functional variants and fragments of the peptide sequence, as defined below. The PSMGFR is defined as SEQ ID NO:3 listed below in Table 1, and all functional variants and fragments thereof having any integer value of amino acid substitutions up to 20 (i.e. 1, 2, 3, 4, 5, 6, 7, 8, 9, 10, 11, 12, 13, 14, 15, 16, 17, 18, 19, or 20) and/or any integer value of amino acid additions or deletions up to 20 at its N-terminus and/or C-terminus. A "functional variant or fragment" in the above context refers to such variant or fragment having the ability to specifically bind to, or otherwise specifically interact with, ligands that specifically bind to, or otherwise specifically interact with, the peptide of SEQ ID NO:3. One example of a PSMGFR that is a functional variant of the PSMGFR peptide of SEQ NO:3 (referred to as nat-PSMGFR—for "native") is SEQ ID NO:11 (referred to as var-PSMGFR), which differs from nat-PSMGFR by including an -SPY- sequence instead of the native -SRY- (see bold text in sequence listings). Var-PSMGFR may have enhanced conformational stability, when compared to the native form, which may be important for certain applications such as for antibody production. The PSMGFR is inclusive of both unmodified peptides and peptides that have undergone enzyme modifications, such as, for example, phosphorylation, glycosylation, etc.

As used herein, the term "PSMGFR" is an acronym for Primary Sequence of MUC1 Growth Factor Receptor as set forth as GTINVHDVETQFNQYKTEAAS-RYNLTISDVSVSDVPFPFSAQSGA (SEQ ID NO:3). In this regard, the "N-number" as in "N-10 PSMGFR", "N-15 PSMGFR", or "N-20 PSMGFR" refers to the number of amino acid residues that have been deleted at the N-terminal end of PSMGFR. Likewise "C-number" as in "C-10 PSMGFR", "C-15 PSMGFR", or "C-20 PSMGFR" refers to the number of amino acid residues that have been deleted at the C-terminal end of PSMGFR.

As used herein, the "extracellular domain of MUC1*" refers to the extracellular portion of a MUC1 protein that is devoid of the tandem repeat domain. In most cases, MUC1* is a cleavage product wherein the MUC1* portion consists of a short extracellular domain devoid of tandem repeats, a transmembrane domain and a cytoplasmic tail. The precise location of cleavage of MUC1 is not known perhaps because it appears that it can be cleaved by more than one enzyme. The extracellular domain of MUC1* will include most of the PSMGFR sequence but may have an additional 10-20 N-terminal amino acids.

As used herein, "NME family proteins" or "NME family member proteins", numbered 1-10, are proteins grouped together because they all have at least one NDPK (nucleotide diphosphate kinase) domain. In some cases, the NDPK domain is not functional in terms of being able to catalyze the conversion of ATP to ADP. NME proteins were formerly known as NM23 proteins, numbered H1 and H2. Recently, as many as ten (10) NME family members have been identified. Herein, the terms NM23 and NME are interchangeable. Herein, terms NME1, NME2, NME5, NME6, NME7, NME8 and NME9 are used to refer to the native protein as well as NME variants. In some cases these variants are more soluble, express better in *E. coli* or are more soluble than the native sequence protein. For example, NME7 as used in the specification can mean the native protein or a variant, such as NME7-AB that has superior commercial applicability because variations allow high yield expression of the soluble, properly folded protein in *E. coli*. NME7-AB consists primarily of the NME7 A and B domains but is devoid of most of the DM10 domain (SEQ ID NO:12), which is at the N-terminus of the native protein. "NME1" as referred to herein is interchangeable with "NM23-H1". It is also intended that the invention not be limited by the exact sequence of the NME proteins. The mutant NME1-S120G, also called NM23-S120G, are used interchangeably throughout the application. The S120G mutants and the P96S mutant are preferred because of their preference for dimer formation, but may be referred to herein as NM23 dimers, NME1 dimers, or dimeric NME1, or dimeric NM23.

NME7 as referred to herein is intended to mean native NME7 having a molecular weight of about 42 kDa.

A "family of NME7" refers to full length NME7 as well as naturally occurring or artificially created cleaved form having a molecular weight about 30 kDa, 33 kDa, or a cleaved form having a molecular weight of about 25 kDa, a variant devoid or partially devoid of the DM10 leader sequence (SEQ ID NO: 12), which is NME7 about amino acids 1-95 of NME7 represented by SEQ ID NO:5, such as NME7b, NME7-X1, NME7-AB or a recombinant NME7 protein, or variants thereof whose sequence may be altered to allow for efficient expression or that increase yield, solubility or other characteristics that make the NME7 more effective or commercially more viable. The "family of NME7" may also include "NME7-AB-like" protein, which is a protein in the range of 30 to 33 kDa that is expressed in cancer cells.

As used herein, an agent that "induces differentiation, or inhibits stem cell pluripotency or growth of the stem cell" refers to a protein, small molecule or nucleic acid that alone or in combination causes the stem cells either in the prime state or in the naïve state, to differentiate or inhibit stem cell pluripotency or growth of the stem cell. Examples of such agents include SMAD inhibitors and dorsomorphin.

As used herein, an agent that "inhibits expression or activity of an up regulated gene in the naïve state" with reference to primed stem cell refers to a protein, small molecule or nucleic acid that alone or in combination causes the inhibition of the normally upregulated gene in naïve stem cells. Examples of such agents include siRNA, anti-sense nucleic acids and small molecules.

As used herein, an agent that "increases expression or activity of down regulated gene in the naïve state" with reference to primed cell refers to a protein, small molecule or nucleic acid that alone or in combination causes the upregulation of the normally down regulated gene in naïve stem cells. Examples of such agents include genes coding for proteins that are indicative of differentiation such as vimentin, fibronectin and NF1 ans also microRNAs such as miR-145.

As used herein, an agent that "inhibits expression or activity of an up regulated gene in the naïve state" with reference to fibroblasts refers to a protein, small molecule or nucleic acid that alone or in combination causes the inhibition of the normally upregulated gene in naïve stem cells. Examples of such agents include anti-sense nucleic acids or siRNA specific for pluripotency genes OCT4, SOX2, KLF4 or c-Myc, and genes that encode vimentin, fibronectin, NF1 or the gene products themselves.

As used herein, an agent that "increases expression or activity of down regulated gene in the naïve state" with reference to fibroblasts refers to a protein, small molecule or nucleic acid that alone or in combination causes the upregulation of the normally down regulated gene in naïve stem cells. Examples of such agents include nucleic acids that encode the downregulated genes or the proteins themselves, and agents that induce differentiation such as SMAD inhibitors, dorsomorphin and the like.

As used herein, an "an agent that promotes pluripotency" or "reverts somatic cells to a stem-like or cancer-like state" refers to a protein, small molecule or nucleic acid that alone or in combination induces expression of or suppresses expression of certain genes such that the genetic signature shifts to one that more closely resembles stem cells or cancer cells. Examples include but are not limited to NME1 dimers, NME7, NME7-X1, NME7-AB, 2i, 5i, nucleic acids such as siRNA that suppress expression of MBD3, CHD4, BRD4, or JMJD6, microbial NME proteins that have high sequence homology to human NME1, NME2, NME5, NME6, NME7, NME8, or NME9, preferably with the regions that house NDPK domains.

As used herein, in reference to an agent being referred to as a "small molecule", it may be a synthetic chemical or chemically based molecule having a molecular weight between 50 Da and 2000 Da, more preferably between 150 Da and 1000 Da, still more preferably between 200 Da and 750 Da.

As used herein, in reference to an agent being referred to as a "natural product", it may be chemical molecule or a biological molecule, so long as the molecule exists in nature.

The term "cancer", as used herein, may include but is not limited to: biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Preferred cancers are; breast, prostate, lung, ovarian, colorectal, and brain cancer. Neoplasms in benign or malignant form are also considered within the purview of cancerous state.

The term "cancer treatment" as described herein, may include but is not limited to: chemotherapy, radiotherapy, adjuvant therapy, or any combination of the aforementioned methods. Aspects of treatment that may vary include, but are not limited to: dosages, timing of administration, or duration or therapy; and may or may not be combined with other treatments, which may also vary in dosage, timing, or duration. Another treatment for cancer is surgery, which can be utilized either alone or in combination with any of the aforementioned treatment methods. One of ordinary skill in the medical arts may determine an appropriate treatment.

As used herein, "inflammatory disease" or condition refers to disease or conditions characterized by an immune response that involves non-specific immune responses in particular areas. Such disease or condition may include without limitation, rheumatoid arthritis, inflammatory bowel syndrome, Crohn's disease, osteoarthritis, asthma, dermatitis, psoriasis, cystic fibrosis, post transplantation late and chronic solid organ rejection, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, autoimmune diabetes, diabetic retinopathy, rhinitis, ischemia-reperfusion injury, post-angioplasty restenosis, chronic obstructive pulmonary diseases (COPD), Graves' disease, gastrointestinal allergy, conjunctivitis, atherosclerosis, coronary artery disease, angina, cancer metastasis, small artery disease, or mitochondrial disease.

As used herein, "bodily sample" refers to any body tissue or body fluid sample obtained from a subject. Preferred are body fluids, for example lymph, saliva, blood, urine, milk and breast secretions, and the like. Blood is preferred in certain embodiments. Samples of tissue and/or cells for use in the various methods described herein can be obtained through standard methods including, but not limited to: tissue biopsy, including punch biopsy and cell scraping, needle biopsy, and collection of blood or other bodily fluids by aspiration or other methods.

A "subject", as used herein, refers to any mammal (preferably, a human), and preferably a mammal that has a disease that may be treated by administering the inventive composition to a site within the subject. Examples include a human, non-human primate, cow, horse, pig, sheep, goat, dog, or cat. Generally, the invention is directed toward use with humans.

As used herein, a "MUC1-positive cancer" or a "MUC1*-positive cancer" refers to a cancer that is characterized by the aberrant expression of MUC1, wherein aberrant may refer to the overexpression of the MUC1 gene or gene product, or the loss of the normal expression pattern of MUC1 or MUC1* which, in the healthy state, is restricted to the apical border of the cell or the luminal edge of a duct or an increase in the amount of MUC1 that is cleaved and shed from the cell surface.

Sequence Listing Free Text

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

```
                                                  (SEQ ID NO: 1)
MTPGTQSPFF  LLLLLTVLTV  VTGSGHASST  PGGEKETSAT

QRSSVPSSTE  KNAVSMTSSV  LSSHSPGSGS  STTQGQDVTL

APATEPASGS  AATWGQDVTS  VPVTRPALGS  TTPPAHDVTS

APDNKPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS
```

```
APDTRPAPGS TAPPAHGVTS APDNRPALGS TAPPVHGVTS

ASGSASGSAS TLVHNGTSAR ATTTPASKST PFSIPSHHSD

TPTTLASHST KTDASSTHHS SVPPLTSSNH STSPQLSTGV

SFFFLSFHIS NLQFNSSLED PSTDYYQELQ RDISEMFLQI

YKQGGFLGLS NIKFRPGSVV VQLTLAFREG TINVHDVETQ

FNQYKTEAAS RYNLTISDVS VSDVPFPFSA QSGAGVPGWG

IALLVLVCVL VALAIVYLIA LAVCQCRRKN YGQLDIFPAR

DTYHPMSEYP TYHTHGRYVP PSSTDRSPYE KVSAGNGGSS

LSYTNPAVAA ASANL
``` describes full-length MUC1 Receptor (Mucin 1 precursor, Genbank Accession number: P15941).

```
                                        (SEQ ID NO: 2)
GTINVHDVETQFNQYKTEAASRYNLTISDVSVSDVPFPFSAQSGAGVPGW

GIALLVLVCVLVALAIVYLIALAVCQCRRKNYGQLDIFPARDTYHPMSEY

PTYHTHGRYVPPSSTDRSPYEKVSAGNGGSSLSYTNPAVAAASANL
``` describes a truncated MUC1 receptor isoform having nat-PSMGFR at its N-terminus and including the transmembrane and cytoplasmic sequences of a full-length MUC1 receptor.

```
                                        (SEQ ID NO: 3)
     GTINVHDVETQFNQYKTEAASRYNLTISDVSVSDVPFPFSAQSGA
``` describes the extracellular domain of Native Primary Sequence of the MUC1 Growth Factor Receptor (nat-PSMGFR—an example of "PSMGFR").

QFNQYKTEAASRYNLTISDVSVSDVPFPFSAQSGA (SEQ ID NO:4) describes N-10 peptide of PSMGFR in which ten amino acids at the N-terminus has been removed.

```
                                        (SEQ ID NO: 5)
DPETMNHSERFVFIAEWYDPNASLLRRYELLFYPGDGSVEMHDVKNHRT

FLKRTKYDNLHLEDLFIGNKVNVFSRQLVLIDYGDQYTARQLGSRKEKTL

ALIKPDAISKAGEIIEIINKAGFTITKLKMMMLSRKEALDFHVDHQSRPF

FNELIQFITTGPIIAMEILRDDAICEWKRLLGPANSGVARTDASESIRAL

FGTDGIRNAAHGPDSFASAAREMELFFPSSGGCGPANTAKFTNCTCCIVK

PHAVSEGMLNTLYSVHFVNRRAMFIFLMYFMYRK
``` describes NME7 amino acid sequence (NME7: GENBANK ACCESSION AB209049).

```
                                        (SEQ ID NO: 6)
MEKTLALIKPDAISKAGEIIEIINKAGFTITKLKMMMLSRKEALDFHVDH

QSRPFFNELIQFITTGPIIAMEILRDDAICEWKRLLGPANSGVARTDASE

SIRALFGTDGIRNAAHGPDSFASAAREMELFFPSSGGCGPANTAKFTNCT

CCIVKPHAVSEGLLGKILMAIRDAGFEISAMQMFNMDRVNVEEFYEVYKG

VVTEYHDMVTEMYSGPCVAMEIQQNNATKTFREFCGPADPEIARHLRPGT

LRAIFGKTKIQNAVHCTDLPEDGLLEVQYFFKILDN
``` describes human NME7-AB.

```
                                        (SEQ ID NO: 7)
MMMLSRKEALDFHVDHQSRPFFNELIQFITTGPIIAMEILRDDAICEWKR

LLGPANSGVARTDASESIRALFGTDGIRNAAHGPDSFASAAREMELFFPS

SGGCGPANTAKFTNCTCCIVKPHAVSEGLLGKILMAIRDAGFEISAMQMF

NMDRVNVEEFYEVYKGVVTEYHDMVTEMYSGPCVAMEIQQNNATKTFREF

CGPADPEIARHLRPGTLRAIFGKTKIQNAVHCTDLPEDGLLEVQYFFKIL

DN*
``` describes human NME7-X1.

```
                                        (SEQ ID NO: 8)
MEKTLALIKPDAISKAGEIIEIINKAGFTITKLKMMMLSRKEALDFHVDH

QSRPFFNELIQFITTGPIIAMEILRDDAICEWKRLLGPANSGVARTDASE

SIRALFGTDGIRNAAHGPDSFASAAREMELFF-
``` describes Human NME7-A1

```
                                        (SEQ ID NO: 9)
MPSSGGCGPANTAKFTNCTCCIVKPHAVSEGLLGKILMAIRDAGFEISAM

QMFNMDRVNVEEFYEVYKGVVTEYHDMVTEMYSGPCVAMEIQQNNATKTF

REFCGPADPEIARHLRPGTLRAIFGKTKIQNAVHCTDLPEDGLLEVQYFF

KILDN
``` describes Human NME7-B3.

```
AIFGKTKIQNAVHCTDLPEDGLLEVQYFF           (SEQ ID NO: 10)
``` describes B3, which is NME7B peptide 3 (B domain).

```
                                        (SEQ ID NO: 11)
     GTINVHDVETQFNQYKTEAASPYNLTISDVSVSDVPFPFSAQSGA
``` describes the extracellular domain of "SPY" functional variant of the native Primary Sequence of the MUC1 Growth Factor Receptor having enhanced stability (var-PSMGFR—An example of "PSMGFR").

```
                                        (SEQ ID NO: 12)
MNHSERFVFIAEWYDPNASLLRRYELLFYPGDGSVEMHDVKNHRTFLKR

TKYDNLHLEDLFIGNKVNVFSRQLVLIDYGDQYTARQLGSRK
``` describes DM10 domain of NME7.

Cancer Cells and Stems Cells

Stem cells and cancer cells have a lot in common. Researchers are now discovering that many of the markers of undifferentiated stem cells are in fact also markers of cancer cells. Conversely, many of the molecular markers that were once considered markers of cancer are now being redefined as stem cell markers. For example, we have found that CXCR4 which was previously identified as a marker of metastatic cancer, is a marker of naïve stem cells. Cancer cells have also been characterized as undergoing epithelial to mesenchymal transition (EMT), where epithelial cells are terminally differentiated and mesenchymal cells are less differentiated and stem-like cell (Mani et al., 2008). Oncologists have long observed that as cancer stage progresses, the cells of the affected tissue look less and less mature or differentiated and look more like stem cells. Pathologists use the appearance of the degree of differentiation to classify cancer stage, with early cancers classified as moderately differentiated and aggressive or metastatic cancers being classified as poorly differentiated.

Further, we previously reported our discovery that the growth factor receptor MUC1* that mediates the growth of over 75% of all cancers is present on 100% of pluripotent human stem cells (Hikita et al., 2008; Smagghe et al., 2013). More recently, we discovered a growth factor, $NME7_{AB}$, that binds to and activates growth, survival and self-renewal functions of MUC1* (Carter et al., 2016). Human stem cells can be maintained in a pluripotent state by culturing in a minimal media containing $NME7_{AB}$ as the only growth factor. Stem cells cultured in NME7AB are maintained in the earliest state called naïve. $NME7_{AB}$ is in every cell of Day 3 human morula, where all the cells are in the earliest naïve state. By Day 5 of the human blastocyst, NME7AB is confined to the inner cell mass, where the cells are naïve by definition. $NME7_{AB}$ should be turned off after Day 5 of a human blastocyst except that it is found in testis. However, we found that NME7, in truncated forms corresponding to NME7AB and NME7-X1, are expressed in aggressive and metastatic cancers (WO2015/023694). We demonstrated that adding $NME7_{AB}$ to regular cancer cells made them transition to more metastatic cancer cells that formed tumors in animals from as few as 50 implanted cancer cells, whereas non-metastatic cancer cells require 4-6M implanted cells to form a tumor. Additionally, injecting the animals with $NME7_{AB}$ caused the engrafted cancer cells to metastasize. These data further establish a functional link, at the molecular level, between stem cells and cancer cells and more particularly between aggressive or metastatic cancers and naïve stem cells.

These results imply that the pathways that promote pluripotency in stem cells are the same pathways that promote cancer. Agents that inhibit stem pluripotency or growth, or induce stem cell differentiation are agents that, when administered to a patient, are effective anti-cancer agents for the prevention or treatment of cancers.

The inventors have shown that agents that convert or maintain stem cells in a naïve state are able to transition cancer cells to a more metastatic state. Thus, naïve stem cells are similar in many ways to aggressive or metastatic cancer cells. These results imply that the pathways that promote pluripotency in naïve stem cells are the same pathways that promote metastasis in cancer cells. The prediction is that agents that inhibit naïve stem pluripotency or growth, or induce stem cell differentiation are agents that, when administered to a patient, are effective anti-cancer agents for the prevention or treatment of metastatic cancers.

The vast differences between naïve stem cells and primed stem cells suggest that these two distinct types of stem cells grow pluripotently and resist differentiation by different pathways. Therefore, drug candidates that inhibit the pluripotency or proliferation of naïve stem cells, but not of primed state stem cells, or have a milder effect on primed state stem cells, are drug candidates that would be most effective in the treatment or prevention of aggressive or metastatic cancers.

In one aspect of the invention, stem cells are cultured in the presence of an agent that may be a drug candidate, it is observed that the agent inhibits stem cell pluripotency, or growth, or induces stem cell differentiation and said agent is administered to a patient for the prevention or treatment of cancers. In one aspect of the invention, the stem cells are human. In another aspect the stem cells are in the naïve state.

In some cases the stem cells are maintained in the naïve state by culturing in NME1 dimers, NME7, $NME7_{AB}$, NME7-X1 or by other methods reported to maintain stem cells in a more naïve state (Silva et al., 2008; Hanna et al., 2010; Gafni et al., 2013; Theunissen et al., 2014; Ware et al., 2014). In yet another aspect, the agent is observed to inhibit pluripotency, or growth, or induce differentiation of naïve stem cells, but not primed state stem cells, or the agent has a lesser effect on primed state stem cells and the agent is administered to a patient at risk of developing or has been diagnosed with metastatic cancer. Because we have found that all pluripotent stem cells are MUC1* positive, and naïve stem cells express $NME7_{AB}$, agents identified as described above will be most effective for the treatment of MUC1* positive, or $NME7_{AB}$ positive, or NME7-X1 positive cancers.

Drug Screen

Here we describe therapeutics and methods for identifying therapeutics for the prevention or treatment of cancers, metastatic cancers or for the prevention of cancer recurrence. In one embodiment, these therapeutics are for the prevention or treatment of cancers that are MUC1-positive, MUC1*-positive, NME7-positive, $NME7_{AB}$ positive or NME7-X1-positive. We have determined that the signaling pathways that control the growth and pluripotency of naïve stem cells are different from those that control the growth and pluripotency of primed stem cells. Further, we discovered that the same pathways that mediate growth or pluripotency of naïve stem cells also mediate the growth and metastatic potential of cancer cells. We found that agents that inhibit stem cell pluripotency or growth, or induce stem cell differentiation are agents that inhibit cancer cell proliferation and when administered to a patient, are effective agents for the prevention or treatment of cancers. Agents that inhibit naïve stem cell pluripotency or growth, or induce naïve stem cell differentiation are agents that inhibit cancer cell migration, which is a characteristic of metastatic cancers, and when administered to a patient, would be effective anti-cancer agents for the prevention or treatment of aggressive or metastatic cancers. Agents that inhibit pluripotency or growth, or induce stem cell differentiation of naïve stem cells but not primed stem cells, or have a far lesser effect on primed stem cells are effective agents for the prevention or treatment of aggressive or metastatic cancers.

Thus, to identify therapeutic agents to treat patients at risk of developing or diagnosed with cancer: 1) grow stem cells in pluripotent state; 2) contact populations of pluripotent stem cells with drug candidates; 3) identify drug candidates that inhibit pluripotency or growth, or induce differentiation of pluripotent stem cells; and 4) conclude that drug candidates that inhibit pluripotency or growth, or induce differentiation of pluripotent stem cells are anti-cancer agents.

To identify therapeutic agents to treat patients at risk of developing or diagnosed with metastatic cancer: 1) grow stem cells in naïve state; 2) contact stem cells with drug candidates; 3) identify drug candidates that inhibit pluripotency or growth, or induce differentiation of naïve stem cells; and 4) conclude that drug candidates that inhibit pluripotency or growth, or induce differentiation of naïve stem cells are anti-cancer agents for the treatment or prevention of aggressive cancers or cancer metastasis.

Alternatively, to identify therapeutic agents to treat patients at risk of developing or diagnosed with metastatic cancer: 1) grow stem cells in naïve state and, optionally, in parallel grow stem cells in primed state; 2) contact both populations of stem cells with drug candidates; 3) identify drug candidates that inhibit pluripotency or growth, or induce differentiation of naïve stem cells, but, optionally, not primed stem cells or have a far lesser effect on primed stem cells; and 4) conclude that drug candidates that inhibit pluripotency or growth, or induce differentiation of naïve stem cells, but, optionally not primed stem cells, or have a far lesser effect on primed stem cells, are anti-cancer agents for the treatment or prevention of cancer metastasis.

Agents screened in these ways to assess their potential as anti-cancer or anti-metastasis agents may be of any form including but not limited to small molecules, natural products, antibodies, antibody fragments, libraries or antibodies or antibody fragments, peptides, peptide mimics, nucleic acids, anti-sense nucleic acids, DNA, RNA, coding or non-coding, inhibitory RNAs, bacteria and microbes. In one aspect of the invention, the stem cells are of human origin. In yet another aspect of the invention, the stem cells are of primate origin. In yet another aspect of the invention, the stem cells are of mammal origin. In yet another aspect of the invention, the stem cells are of rodent origin.

In another aspect of the invention, novel anti-cancer or anti-metastasis drug targets are identified by identifying genes that are upregulated in naïve stem cells but not in primed stem cells. In yet another aspect of the invention, novel anti-cancer or anti-metastasis drug targets are identified by identifying microRNAs that are upregulated in naïve stem cells but not in primed stem cells.

Drug Screen Results

WO2009/042815 discloses that in a direct binding assay a series of carboline molecules inhibited the interaction between the extracellular domain of MUC1* and NME proteins, especially NME1 dimers and NME7AB. We also previously showed that the same series of carbolines that inhibited MUC1*-NME interaction also inhibited cancer cell growth. We tested a panel of ten small molecules, including three carbolines (FIG. 1), and biologicals for their ability to inhibit naïve stem cell pluripotency or growth compared to primed state stem cells. We previously demonstrated that the Fab of anti-MUC1* monoclonal antibody, E6, or a synthetic peptide corresponding to the extracellular domain of MUC1*, FLR also known as PSMGFR, inhibit both cancer and stem cell pluripotency and growth by inhibiting the MUC1*-NME7$_{AB}$ or MUC1*-NME1 interaction. We also tested novel anti-NME7 antibodies #56 and #61; we had previously shown that they inhibit NME7$_{AB}$'s ability to transform regular cancer cells into metastatic cancer cells, although #61 is much more potent than #56. We also previously showed that some carboline small molecules inhibit the growth of cancers by inhibiting the MUC1*-NME7$_{AB}$ or MUC1*-NME1 interaction.

JQ1 is a small molecule that reportedly inhibits BRD4 and has been shown to inhibit cancer cell migration and cancer cell proliferation, but has not been reported to have any effect on stem cells. The stem cell screening assay, was performed in both the presence and absence of the stem cell growth factors: NME7$_{AB}$ for growing naïve stem cells or FGF for growing primed stem cells. If the cognate growth factor was present, then the biological or small molecule would have to compete away the growth factor to get an effect. Therefore, we expected to see more of an effect when the growth factor, FGF for primed stem cells or NME7$_{AB}$ or NME1 dimers for naïve stem cells, was absent. The results are summarized in the table of FIG. 2. The effect of the compounds on stem cells was visually determined and compounds were ranked 0-4, with 4 being the greatest effect and 0 being no observable effect. The major effect that was observed was a change from pluripotent stem cell morphology, which is a cobblestone pattern of small round cells with a large nucleus to cytoplasm ratio, to that of differentiating stem cells, which are elongated, large and flattened cells with a smaller nucleus to cytoplasm ratio. Some compounds also severely inhibited growth of the stem cells. The compounds were added to a final concentration of 6 uM to either naïve state stem cells or primed state stem cells. In this particular case, the naïve state stem cells were maintained in a naïve state by culturing in a media containing NME7$_{AB}$ or NME1 dimers. However, other methods such as 2i and 5i (Silva et al., 2008, Nichols and Smith, 2009, Theunissen et al., 2014)] can be used to maintain stem cells in a more naïve state. In this case primed state stem cells were cultured in bFGF over a layer of MEFs, although it is known that any bFGF containing media will maintain stem cells in the primed state.

We have shown that JQI has an inhibitory effect on naïve stem cell growth but not primed stem cell growth. In addition, previous studies have shown JQ1 has anti-inflammatory effects (Belkina et al, 2013; Meng et al, 2014). Therefore the compounds identified in this study should also have anti-inflammatory effects and be useful in the treatment of inflammation in obesity, asthma, chronic peptic ulcer, tuberculosis, rheumatoid arthritis, chronic periodontitis, ulcerative colitis and Crohn's disease, chronic sinusitis, Chronic active hepatitis etc.

Of the ten small molecules and four biologicals tested, none had an effect on primed stem cells except MN1130, which had a modest effect on primed stem cell colonies. However, when the same agents were tested on naïve stem cells, three of the four biologicals and two of the three carbolines profoundly inhibited stem cells pluripotency and growth and induced differentiation. Note that the agents induced changes in the morphology of the naïve stem cells that are consistent with the morphological changes that take place when stem cells initiate differentiation (indicated by dotted line). The cells flatten, take on a more spindle shape and the ratio of nucleus to cytoplasm decreases.

In addition to the small molecules pictured in FIG. 1, an anti-MUC1* Fab, the FLR peptide, aka PSMGFR peptide, and anti-NME7 antibodies #56 and #61 were tested. FIG. 2 is a summary of how those drug candidates performed in the naïve versus primed stem cell drug in which a confirmed drug hit is one in which the compound induced differentiation of the naïve stem cells but had no effect or a lesser effect on the FGF-grown primed stem cells. FIGS. 3-10 show photographs of stem cells that were treated with the small molecules, the Fab, the MUC1* extracellular domain peptide "FLR" or the small molecules. FIGS. 3-6 shows that none of the agents or compounds significantly induced differentiation of primed state stem cells. However, FIGS. 7-10 show that several agents induced differentiation of naïve state stem cells. Differentiating portions are indicated by dashed lines. Specifically at these concentrations, the anti-MUC1* E6 Fab, the FLR peptide, anti-NME7 #61, MN572, MN0642 and MN1130 all induced differentiation of naïve state stem cells and are predicted to be potent inhibitors of cancer and inhibitors of metastatic cancers. They could be administered to patients for the prevention or treatment of cancers or metastatic cancers. The E6 Fab has been shown to inhibit the growth of all MUC1* positive cancer cells. In addition, the anti-MUC1* E6 Fab was shown to robustly inhibit MUC1* positive tumor growth in animals. Compound MN0642 similarly has been shown to inhibit the growth of cancer cells in vitro. The FLR (PSMGFR) peptide and anti-NME7 #61 have been shown to inhibit the transition of regular cancer cells to metastatic cancer cells.

Several other small molecules that bear no resemblance to carbolines but that were reported to inhibit cancer growth or migration were tested and found to inhibit pluripotency, or growth or induce differentiation of stem cells, particularly naïve stem cells. For example, a small molecule that bears no resemblance to carbolines, JQ1(+) (FIG. 1), reportedly inhibits inflammation (Belkina et al., 2013), cancer pluripotency (Fillippakopoulos et al., 2010) and cancer cell migration (Tang et al., 2013). JQ1(+) reportedly inhibits BRD4 and its inactive enantiomer, JQ1(−), has no effect (Fillippakopoulos et al., 2010). BRD4 has been reported to be a regulator of NME7, a regulator of oncogene c-Myc and a component of super-enhancers that overexpress a selected few genes in cancer cells and in stem cells. At this time it is not entirely clear which of these purported functions of BRD4 are correct. Primed state stem cells were treated for 3 days with JQ1(+), inactive stereoisomer JQ1(−), BRD4 specific siRNA, or JMJD6 specific siRNA. None of these agents appeared to induce differentiation of primed state stem cells, but JQ1(+) may have a modest effect on the size of primed stem cell colonies (FIG. 11) and also appeared to cause some abnormal morphology (FIG. 12). However, JQ1(+) dramatically induced differentiation of naïve state stem cells and inhibited their growth (FIGS. 14 E-F, 15 E-F and 16 E-F). Whether the naïve stem cells were cultured in NME7$_{AB}$ (FIG. 13-14) or NME1 dimers (FIG. 15-16), JQ1 (+) inhibited naïve stem cell pluripotency and growth and induced differentiation. Since JQ1 (+) is a known inhibitor of inflammation, cancer cell migration and cancer cell proliferation, these results show that agents that are effective treatments for inflammation or the prevention or treatment of cancers, also inhibit naïve stem cell pluripotency or growth or induce stem cell differentiation. Therefore, the agents that inhibit naïve stem cell pluripotency or growth or induce stem cell differentiation are also effective treatments for inflammation or the prevention or treatment of cancers.

Figure 73:
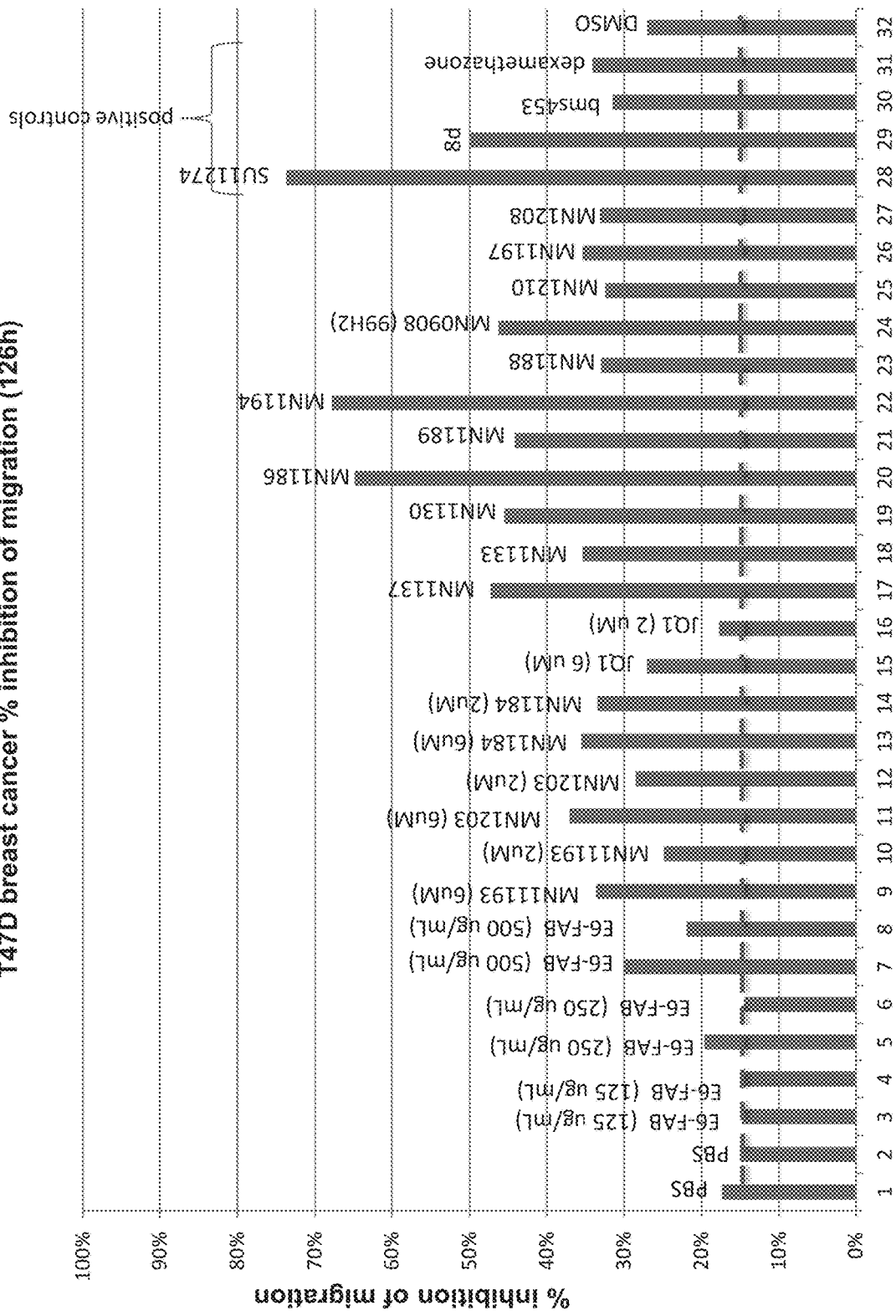
FIG. 73 is a bar graph showing the measured percent inhibition of cancer cell migration. The cancer cell line used was T47D breast cancer cell line. Multi-well plate was coated with collagen and cells were plated using Platypus system that restricts cells from entering center of wells until cells have attached. The percent area that remains free of cells at 126 hrs was measured using Image J and graphed. The agents that were tested were: an anti-MUC1* Fab "E6", which has been shown to inhibit proliferation of virtually all MUC1* positive cells tested, in vitro and in vivo; JQ1, a BRD4 inhibitor reported to inhibit cancer cell migration and proliferation in vitro and in vivo; small molecules reported by others to inhibit migration of a range of cancer cells; and novel small molecules of the invention.
Figure 74:
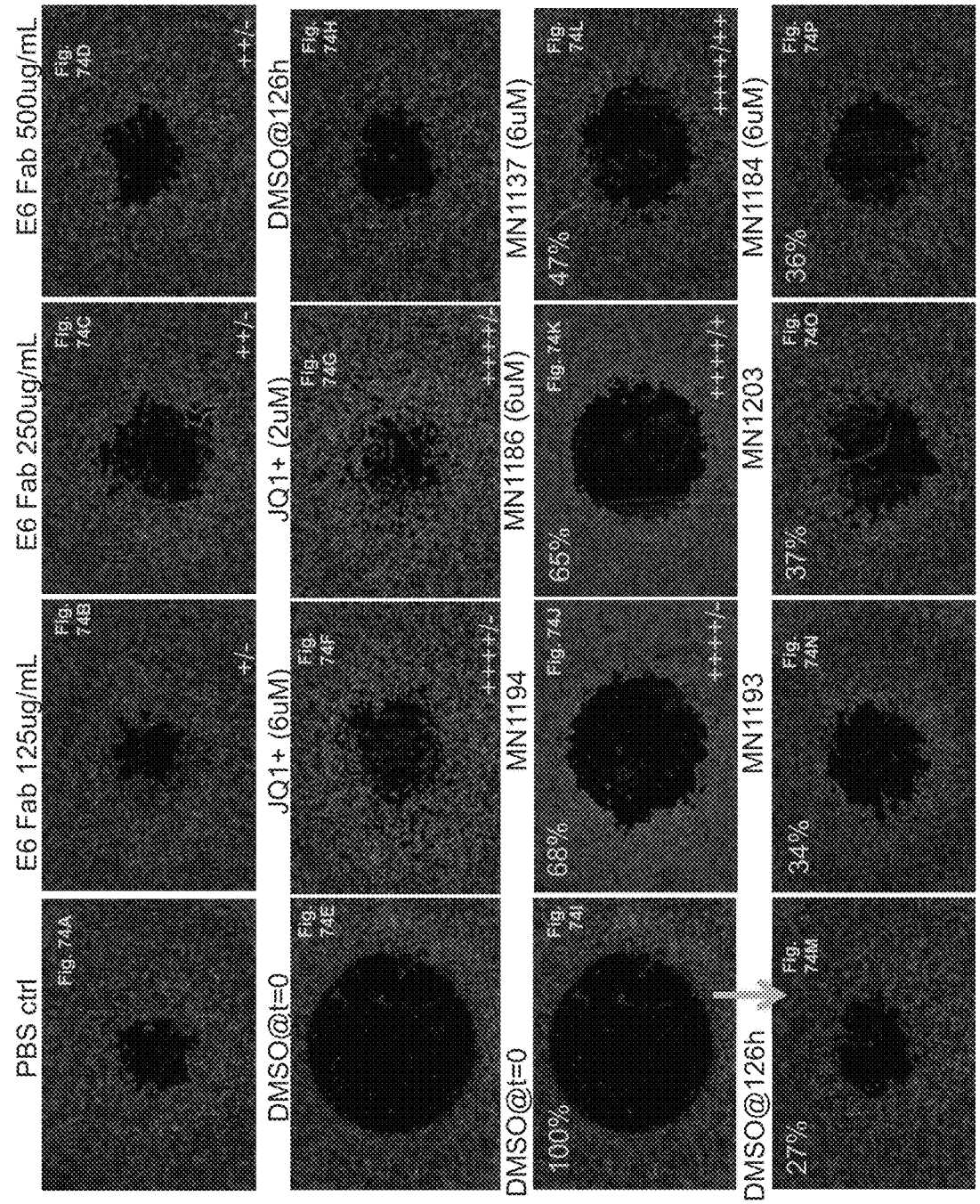
Figure 75:
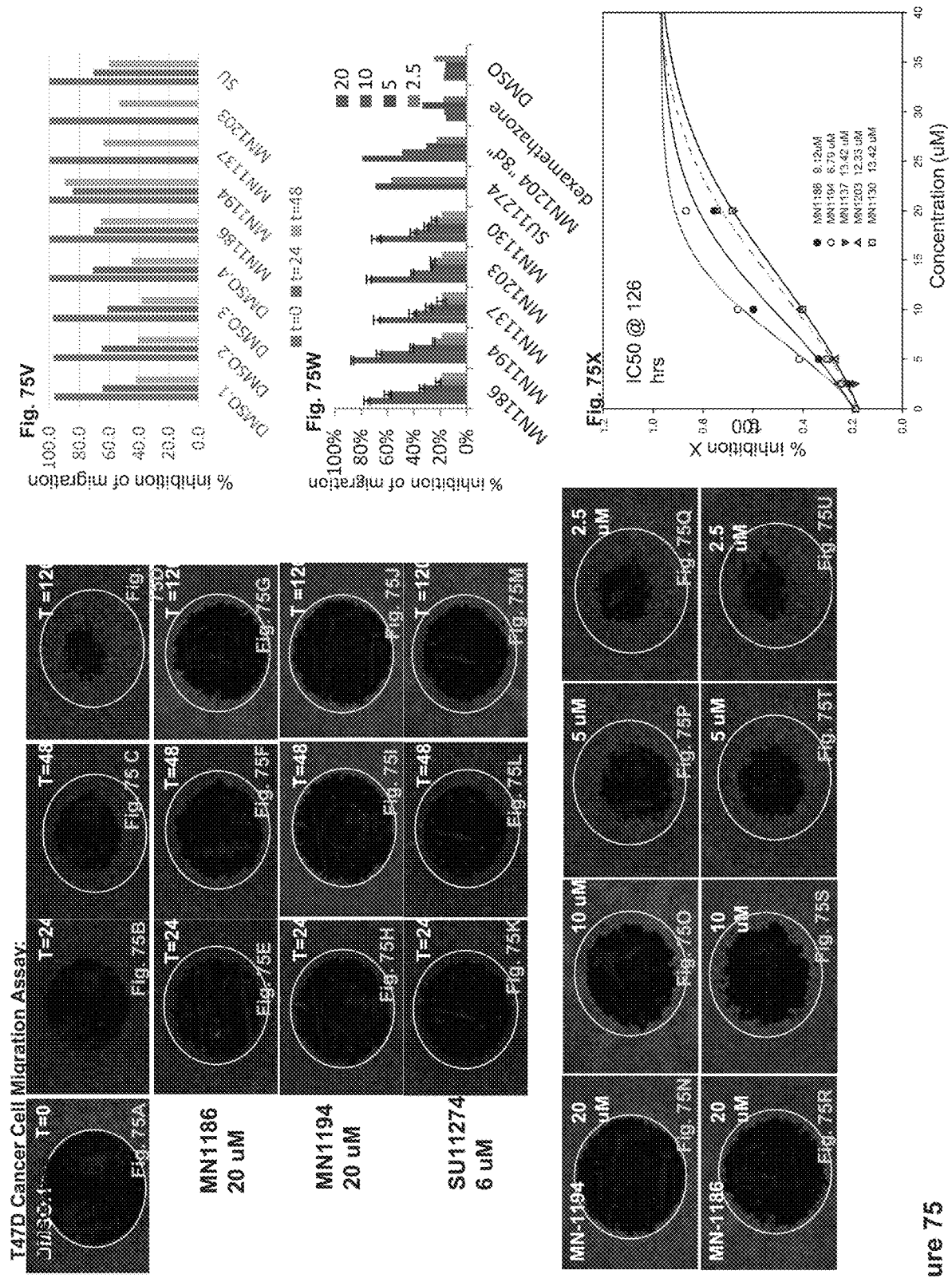
Figure 82:
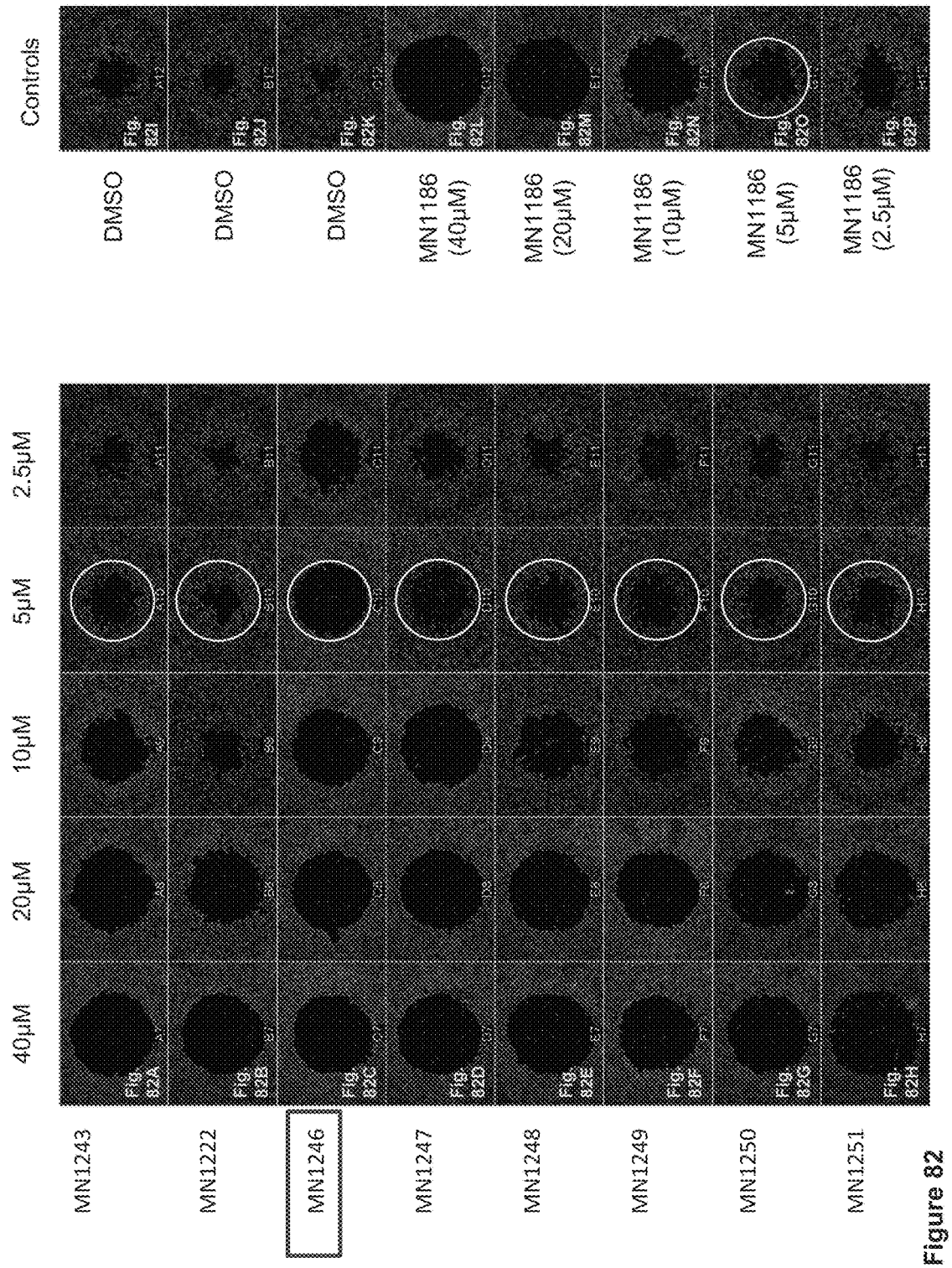
FIG. 82A-82P shows photographs of a cancer cell migration, invasion assay, in which analogs of MN1186, which was a hit in the stem cell drug screen, are tested for their ability to inhibit the migration of breast cancer cells as a function of final compound concentration. These experiments were performed on T47D breast cancer cells and photographed at 120 hours.
Figure 83:
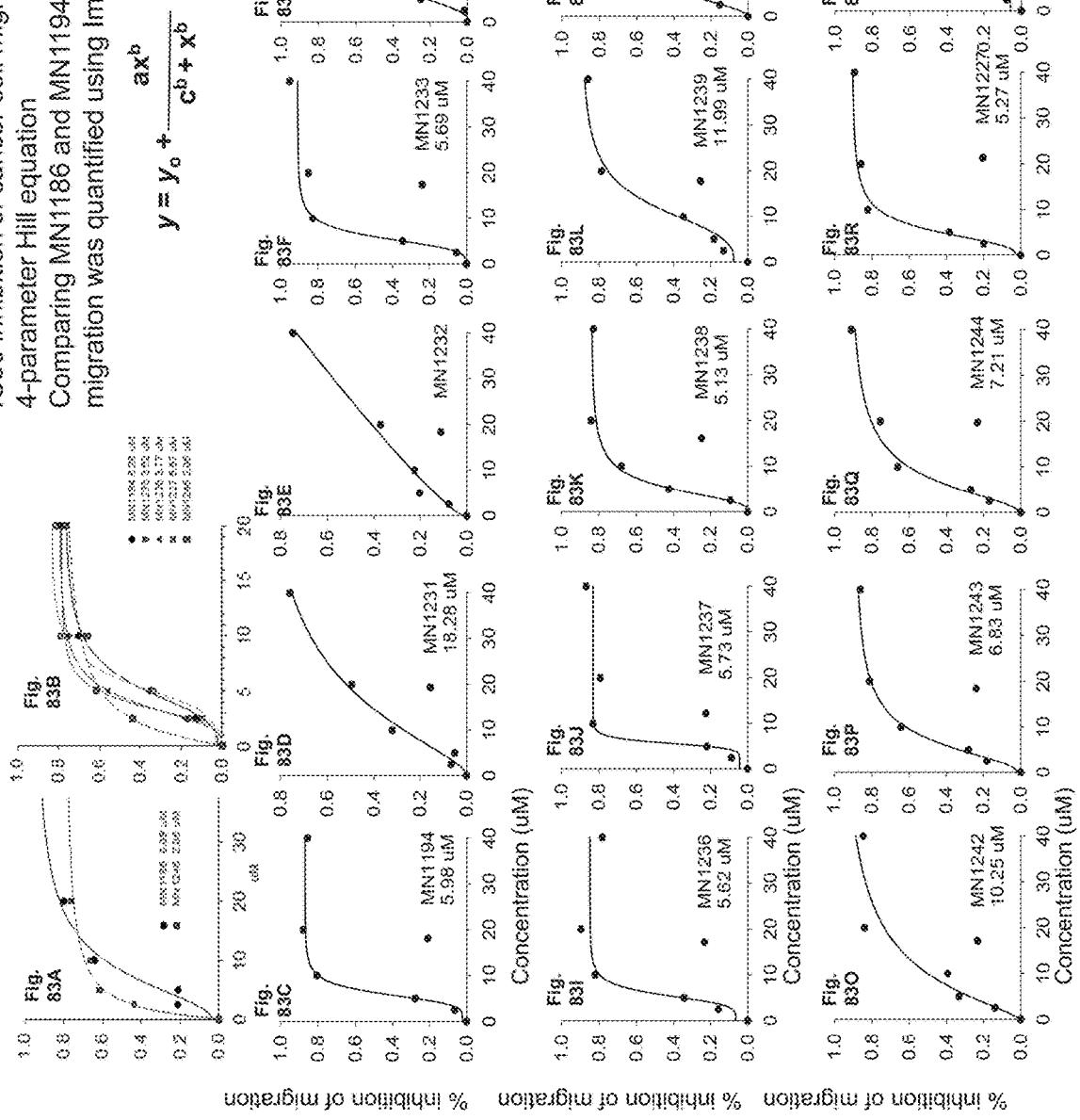
FIG. 83A-83T shows graphs of the effect of MN1186 and MN1194 and analogs thereof on the migration of MUC1* positive T47D breast cancer cells and calculated IC50s. Percent inhibition relative to the control was measured using Image J.
Figure 128:
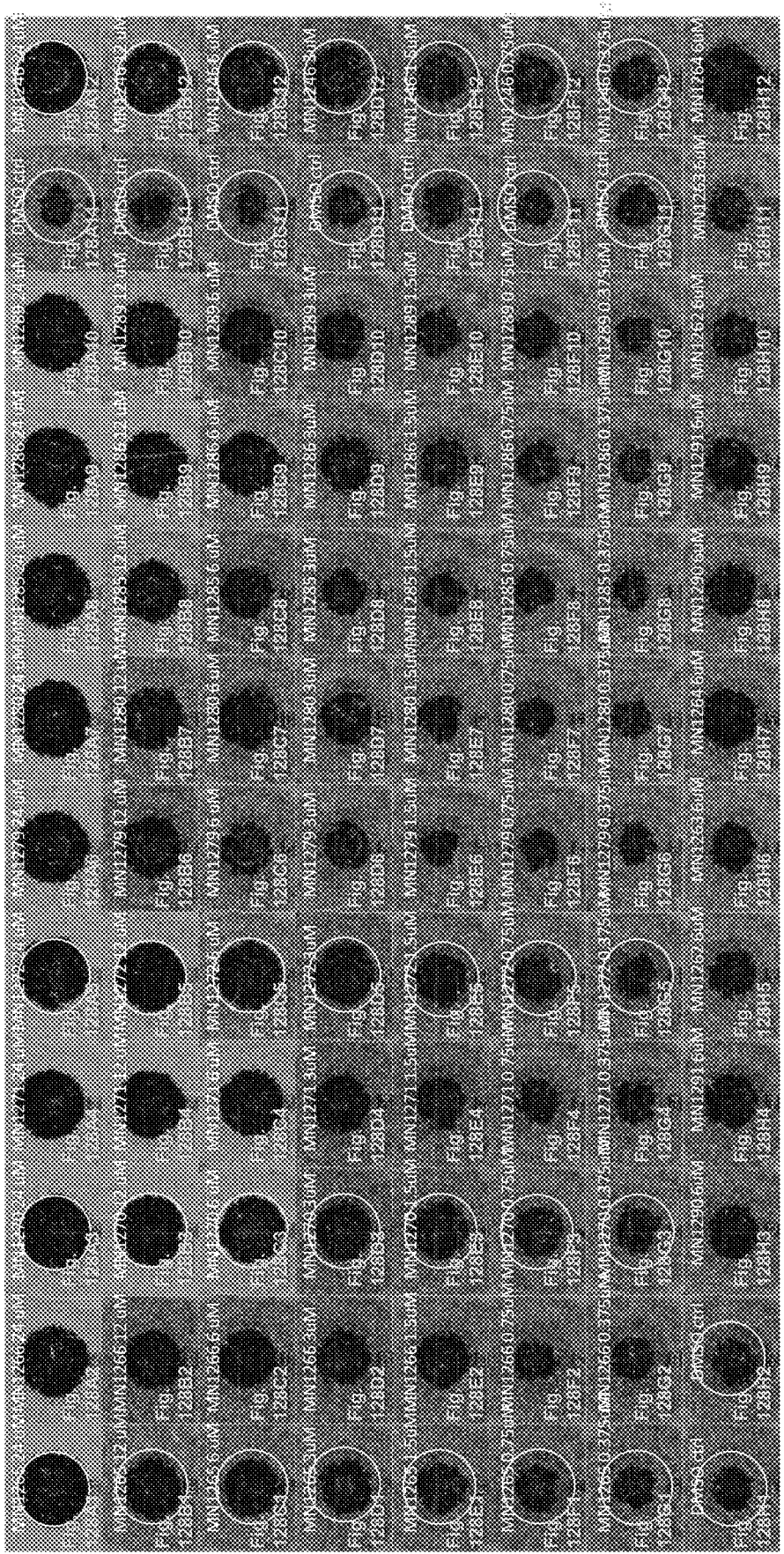
Figure 129:
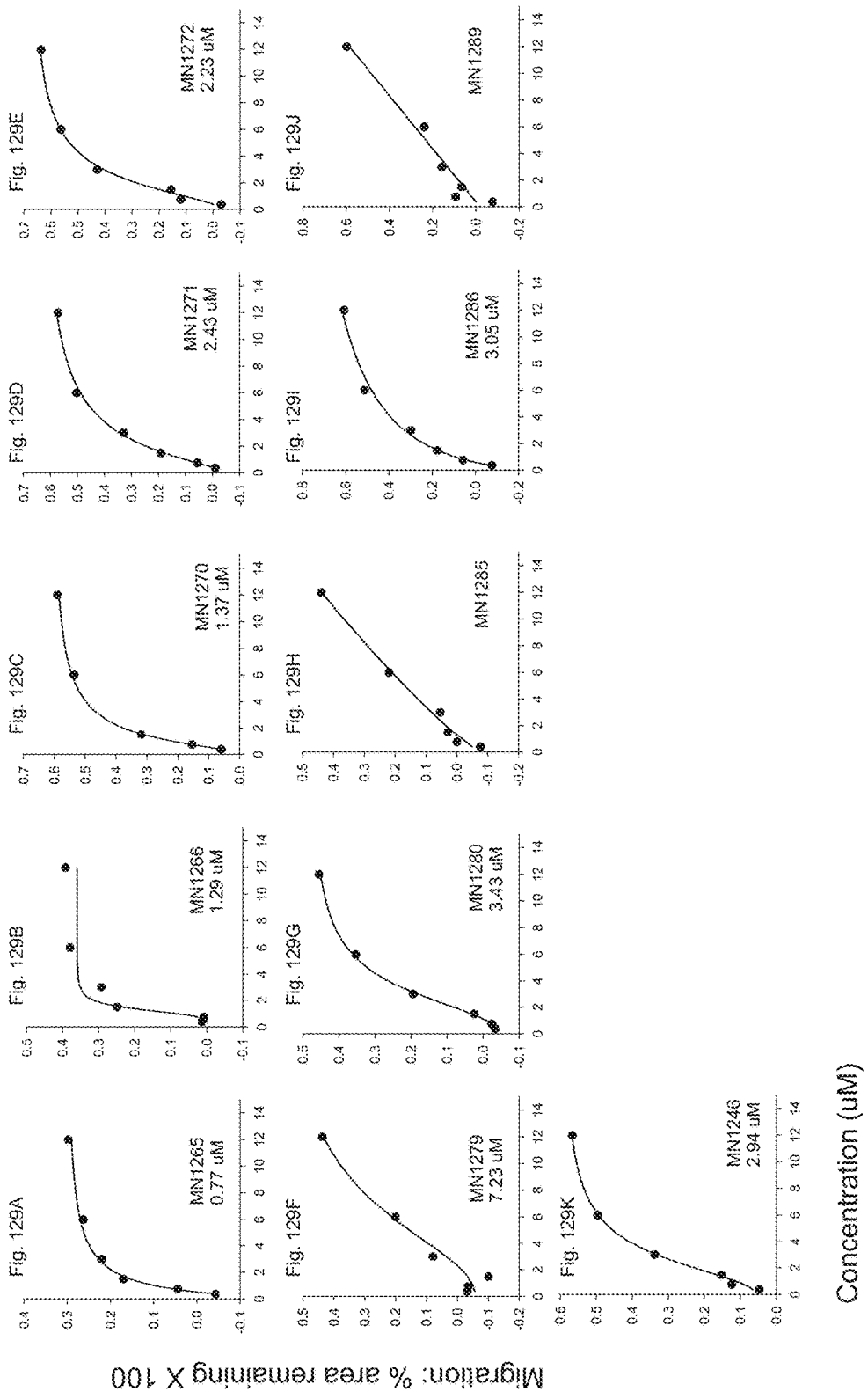
FIG. 129A-129K shows graphs of the inhibitory effects of compounds MN1265, MN1266, MN1270, MN1271, MN1272, MN1279, MN1280, MN1285, MN1286, MN1289 and MN1246 on cancer cell migration at 72 hours post treatment. IC50's for each compound were derived from these graphs. The percent inhibition of migration, relative to the control, was measured using Image J.
Figure 130:
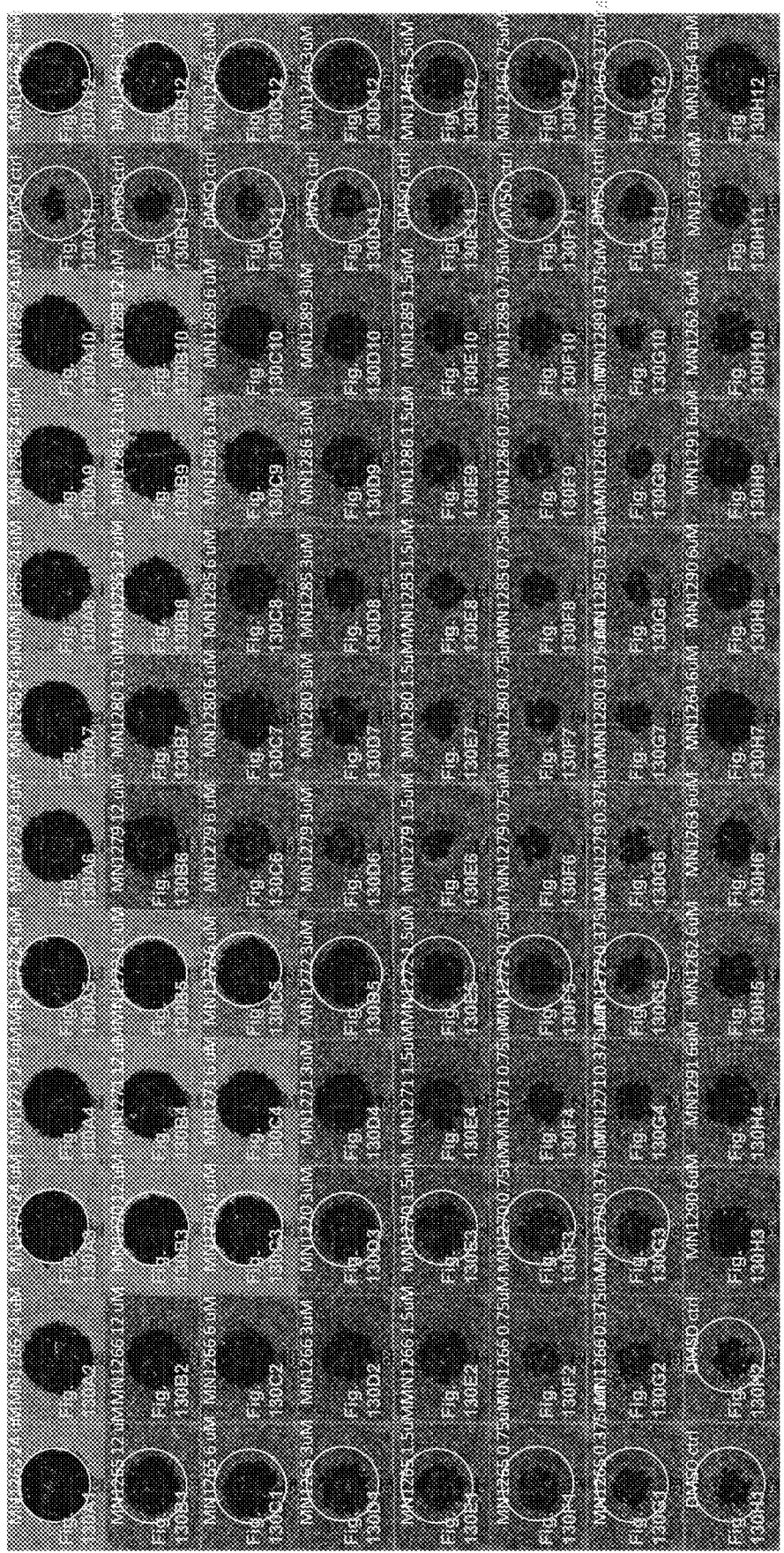
Figure 131:
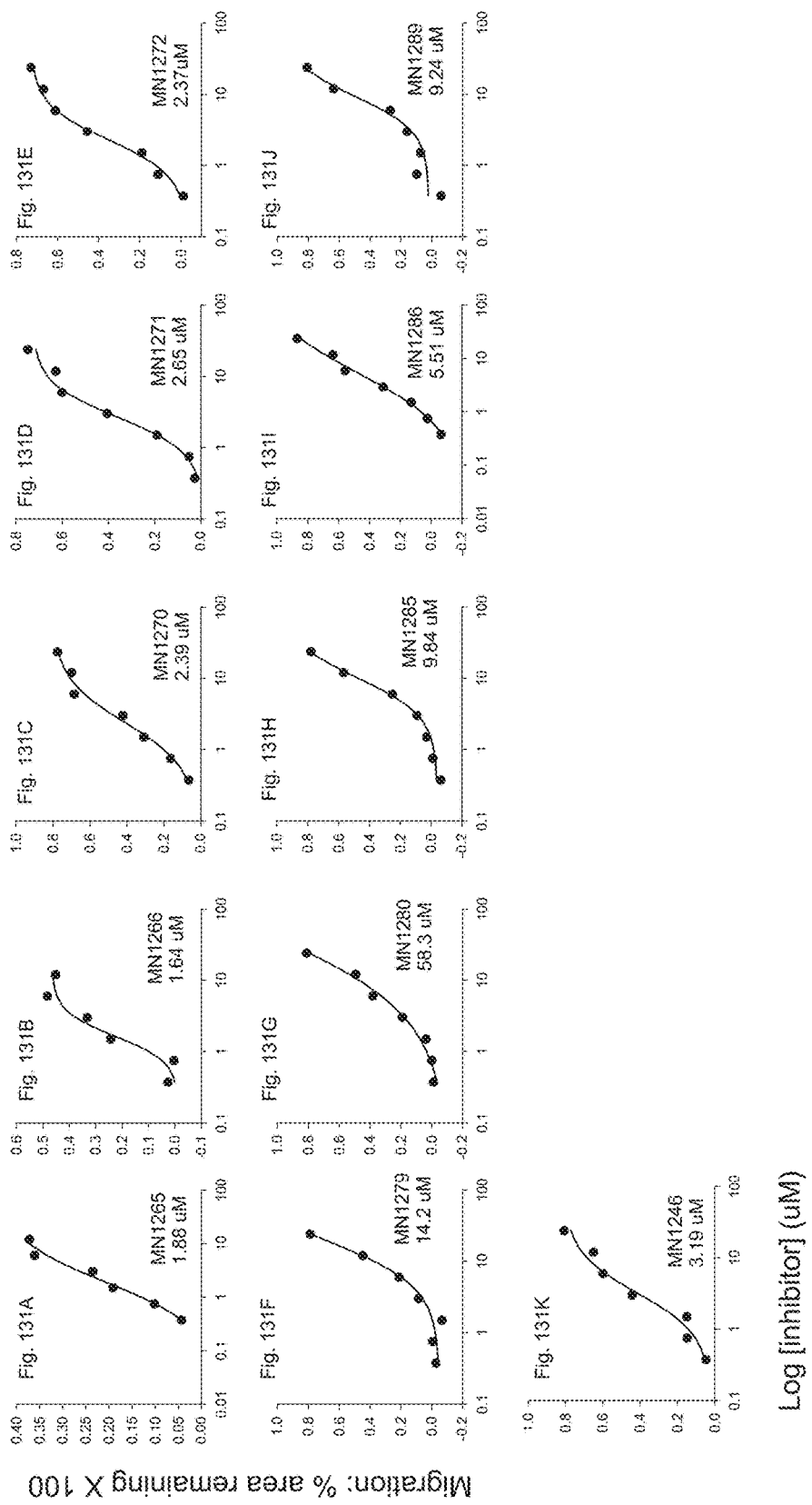
FIG. 131A-131K shows graphs of the inhibitory effects of compounds MN1265, MN1266, MN1270, MN1271, MN1272, MN1279, MN1280, MN1285, MN1286, MN1289 and MN1246 on cancer cell migration at 93 hours post treatment. IC50's for each compound were derived from these graphs. The percent inhibition of migration, relative to the control, was measured using Image J.
Figure 132:
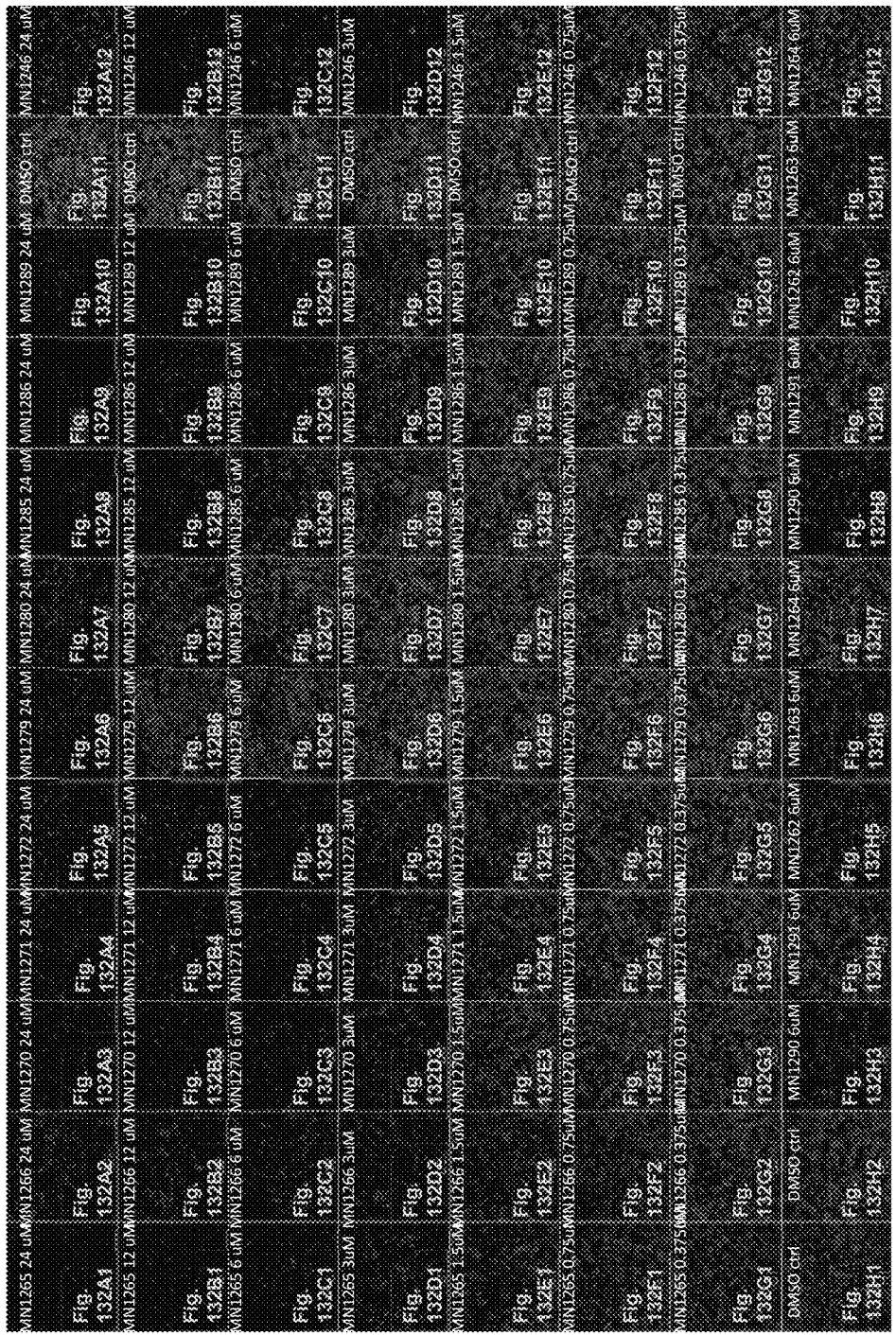

We then tested an expanded panel of agents, including agents known to inhibit cancer growth or migration (FIG. 17) (Horm et al., 2012; Meng & Yue, 2014; Zhen et al., 2014), which is characteristic of aggressive or metastatic cancers. We also synthesized a series of novel small molecules, tested them in the stem cell drug screening assay, and then synthesized analogs of the best hits. These small molecules are pictured in FIGS. 18-27. Both the known compounds and the novel compounds were tested in the stem cell drug screening assay. The effects of the small molecules on naïve versus primed state stem cells are shown in the photographs of FIGS. 29-72. The small molecules pictured in FIGS. 17-27 and the biologicals were also tested in a cancer cell migration assay. A structure activity relationship table is seen in FIG. 28. Potent cancer cell migration is characteristic of cancer cell invasion of other tissues and of metastasis. Typical migration assays involve coating a cell culture plate with fibronectin, collagen or the like, plating cancer cells and making a scar across through the cells and measuring the time it takes for the cancer cells to invade the void space. An alternative approach that gives more reliable data is the Platypus System which is a special multi-well cell culture plate with a juxtaposed set of plugs that block off a circle in the center of each well. Cancer cells are plated while the plugs are in place, then they are removed after the cells attach to the plate surface. Drug candidates are added to each well and photographs are then taken as a function of time to track the inhibitory effect of the drug candidates on cancer cell migration or invasion. The results of the cancer cell migration assay are shown in FIGS. 73-106. A bar graph summarizing the results of the known anti-migration compounds compared to the anti-MUC1* Fab E6 and the first few small molecules synthesized is shown in FIG. 73. Photographs of the cancer cell migration assay and bar graphs summarizing their activities are shown in FIG. 74. The effect of two novel small molecules MN1186 and MN1194, compared to the known anti-migration molecule SU11274, is shown in FIG. 75A-75U. FIG. 75V is a graph showing the measured inhibition of cancer cell migration at time 0, 24 hours or 48 hours for a number of compounds. FIG. 75W is a graph showing the inhibitory effect of the small molecules as a function of concentration. FIG. 75X is a graph showing how IC50's of the small molecules of the invention were measured and calculated.

As can be seen in FIGS. 73-75, two of the most potent inhibitors of cancer cell migration are MN1186 and MN1194, which also inhibited stem cell pluripotency and growth. The effect of MN1186 on naïve stem cells was ++++(4), meaning it inhibited stem cell pluripotency and proliferation at the highest level (FIG. 39C, 39F), but had only a moderate effect of ++(2) primed state stem cells (FIG. 39I, 39L). The effect of MN1194 on naïve stem cells was ++++(4), meaning it inhibited stem cell pluripotency and proliferation at the highest level (FIG. 41B, 41E), but barely affected primed state stem cells (FIG. 41H, 41K). We then made analogs on MN1186 and MN1194. MN1186 analogs include MN1220, MN1221, MN1222, MN1223, MN1224, MN1227 and MN1228; MN1194 analogs include MN1190, MN1193, MN1195, MN1225, MN1226, MN1229 and MN1230. We tested parent compound MN1186 and its analogs (FIGS. 76A-76H) and MN1194 and its analogs (FIG. 77A-77H) for their ability to inhibit cancer cell migration. These studies show that compounds MN1227 (FIGS. 50B, 50E, 50H, 50K and FIG. 76G), MN1228 (FIGS. 50C, 50F, 50I, 50L and FIG. 76H), MN1229 (FIGS. 51A, 51D, 51G, 51J and FIG. 77B), MN1190 (FIGS. 40C, 40F, 40I, 40L and FIG. 77E) and MN1195 (FIGS. 41C, 41F, 41I, 41L and FIG. 77D) are improvements over MN1186 (FIGS. 39C, 39F, 39I, 39L and FIG. 76A) and MN1194 (FIGS. 41B, 41E, 41H, 41K and FIG. 77A), and all are considerably better than the previously known migration inhibitors SU11274 and MN1204 (Zhen et al., 2014).

These analogs of MN1194 and 1186 were also tested in a cell growth assay (FIGS. 107A1-107H6 and FIG. 108A1-108H6, respectively). In this experiment, both parent compound and analogs thereof were added to normal cell culture media to final concentrations of 40 uM, 20 uM, 10 uM, 5 uM or 2.5 uM. For comparison, previously known cancer cell migration inhibitors SU11274 and MN1204 were included in the same experiment. After 120 hours of culture in the presence of the test compounds, T47D cancer cells were subjected to a Calcein assay, which stains live cells. Relative cell proliferation is quantified on a standard plate reader that reads the fluorescence of the Calcein that is taken up by live cells. As in the cell migration assay, analogs MN1190, MN1195, MN1227, MN1228, MN1229 inhibit cancer cell proliferation better than parent compounds MN1186 and 1194, with inhibition apparent at 5 uM-2 uM, and all inhibit cancer cell growth better than the known compounds SU11274 and MN1204.

Other variations on the chemical structures of MN1186 and MN1194 were also tested in the cancer migration assay (FIGS. 78A-78Q and FIGS. 79A-79P).

Medicinal chemistry techniques and our observed structure-activity relationships were brought to bear in the design and synthesis of additional small molecules. They were tested in the stem cell assay and also in a cancer cell migration assay (FIG. 80A1-80H12), wherein the molecules were dosed at 6 uM final concentration and the cell line used was the highly positive MUC1* breast cancer cell line T47D. Photographs of another cancer cell migration, invasion assay, in which analogs of MN1194, which was a hit in the stem cell drug screen, were tested for their ability to inhibit the migration of breast cancer cells as a function of final compound concentration (FIG. 81A-81P). These experiments were performed on T47D breast cancer cells and photographed at 120 hours. FIG. 82A-82P shows photographs of a cancer cell migration, invasion assay, in which analogs of MN1186, which was a hit in the stem cell drug screen, were tested for their ability to inhibit the migration of breast cancer cells as a function of final compound concentration. These experiments were performed on T47D breast cancer cells and photographed at 120 hours. Testing the effects of the small molecules as a function of compound concentration allowed us to calculate an IC50 for each compound (FIGS. 83A-83T and FIG. 28).

All human pluripotent stem cells are MUC1* positive. Naïve state stem cells also express the primitive growth factor $NME7_{AB}$ which is an activating ligand of MUC1*. The breast cancer cell line T47D was derived from a metastatic breast cancer patient. T47D cells express the highest levels of MUC1* of any commercially available cell line. We discovered that T47D cells also express NME7AB and an alternative splice isoform NME7-X1, which are both growth factors that activate the MUC1* growth factor receptor.

Most of the novel compounds of the invention are carbolines or carboline-like molecules. We previously showed in a nanoparticle direct binding assay that some of these carbolines inhibited the binding of NME1 dimers or $NME7_{AB}$ to the MUC1* extracellular domain. However, in our nanoparticle assay, we can only determine that a compound disrupts the interaction between MUC1* extracellular domain peptide and NME1 dimers or $NME7_{AB}$. We cannot tell if the compound does so by binding to MUC1* or its ligand. Recall that our compound hits are first identified in the stem cell drug screening assay for their ability to inhibit stem cell pluripotency or proliferation. We then test the hits for their ability to inhibit cancer cell migration, invasion, which is a characteristic of metastatic cancers, and then finally we test the hits for their ability to inhibit cancer cell proliferation. Therefore, we first tested the compounds of the invention on MUC1* positive, $NME7_{AB}$ positive and NME7-X1 positive T47D cells. The general result was that compounds and biologicals that inhibited stem cell pluripotency or proliferation also inhibited T47D cancer cell migration and proliferation. We then expanded these studies to other cancer sub-types that were MUC1* positive, $NME7_{AB}$ positive, both MUC1* and $NME7_{AB}$ positive or MUC1* negative cells lines. Small molecule inhibition of cancer cell migration studies were performed on DU145 (MUC1*+/NME7AB+++/NME7-X1+++) prostate cancer cells and SK-OV-3 (MUC1*+) ovarian cancer cells (FIG. 84A1-87H6); A549 (MUC1*$^{LO}$) lung cancer cells and PC-3 (MUC1*−/$NME7_{AB}$+++/NME7-X1+++) prostate cancer cells (FIG. 88A1-95H6); CHL-1 (MUC1*+/NME7+) melanoma cells and OV-90 (MUC1*−) ovarian cancer cells (FIG. 96A1-101H6); CAPAN-2 (MUC1*+) pancreatic cancer cells and ZR-75-1 (MUC1*++) breast cancer cells (FIG. 102A1-106H6).

Small molecule inhibition of cancer cell proliferation studies were also performed on several cancer sub-types. Small molecules of the invention, along with BRD4 inhibitor JQ1+ and its inactive enantiomer JQ1− and c-Met inhibitor SU11274, were tested for their ability to inhibit the growth of: DU145 (MUC1*+/$NME7_{AB}$+++/NME7-X1+++) prostate cancer cells (FIG. 109A1-109H4); MDA-MB-453 (MUC1*$^{LO}$) breast cancer cells (FIG. 110A1-110H4); PC-3 (MUC1*−/$NME7_{AB}$+++/NME7-X1+++) prostate cancer cells (FIG. 111A1-111H4); SK-OV-3 (MUC1*+) ovarian cancer cells (FIG. 112A1-112H4); T47D (MUC1*++++/$NME7_{AB}$++/NME7-X1+++) breast cancer cells (FIG. 113A1-113H4); and OV-90 (MUC1*−) ovarian cancer cells (FIG. 114A1-114H4). The small molecules of the invention had the most robust effect on T47D breast cancer cells, which are highly positive for MUC1* growth factor receptor, and its activating ligands $NME7_{AB}$ and NME7-X1. As can be seen in the live cell Calcein stain experiment of FIG. 113, MN1130, MN1133, MN1246 and MN1227 severely inhibited growth of these cells. JQ1+ and SU11274, previously reported to inhibit cancer cell proliferation also inhibited growth of these cells. However, neither the compounds of the invention nor JQ1 or SU11274 had any apparent effect on MUC1*-negative ovarian cancer cells OV-90 (FIG. 114). Compounds of the invention inhibited the growth of MUC1*-positive ovarian cancer cells SK-OV-3, while c-Met inhibitor SU11274 had no effect and JQ1+ had a slight effect (FIG. 112). The compounds of the invention, MN1130, MN1133, MN1246 and MN1227 also inhibited the growth of MUC1*-positive DU145 prostate cancer cells (FIG. 109) as well as MUC1*-negative but $NME7_{AB}$ positive PC-3 prostate cancer cells (FIG. 111) and MUC1*$^{LO}$ MDA-MB-453 breast cancer cells (FIG. 110).

A more extensive cancer cell proliferation assay was performed on T47D cancer cells so that the relative inhibitory strength of each of the compounds could be compared. Forty-six compounds were dosed at a final concentration of 6 uM. After 120 hours, live cells were stained with Calcein. Photographs of the assay are shown in FIG. 115. Compounds were also assayed for their ability to inhibit proliferation of DU145 prostate cancer cells (FIGS. 116A1-116H6) and SK-OV-3 ovarian cancer cells (FIG. 117A1-117H6). An automated measure of live cells relative to controls is graphed and shown in FIGS. 118A and 118B, respectively. These same compounds were also assayed for their ability to inhibit proliferation of A549 lung cancer cells (FIGS. 119A1-119H6) and PC-3 prostate cancer cells (FIG. 120A1-120H6). An automated measure of live cells relative to controls for these cells is graphed and shown in FIGS. 121A and 121B, respectively. These same compounds were also assayed for their ability to inhibit proliferation of CHL-1 melanoma cells (FIG. 122A1-122H6) and OV-90 ovarian cancer cells (FIG. 123A1-123H6). An automated measure of live cells relative to controls for these cells is graphed and shown in FIGS. 124A and 124B, respectively. These same compounds were also assayed for their ability to inhibit proliferation of CAPAN-2 pancreatic cancer cells (FIGS. 125A1-125H6) and ZR-75-1 breast cancer cells (FIG. 126A1-126H6). An automated measure of live cells relative to controls for these cells is graphed and shown in FIGS. 127A and 127B, respectively.

Figure 133:
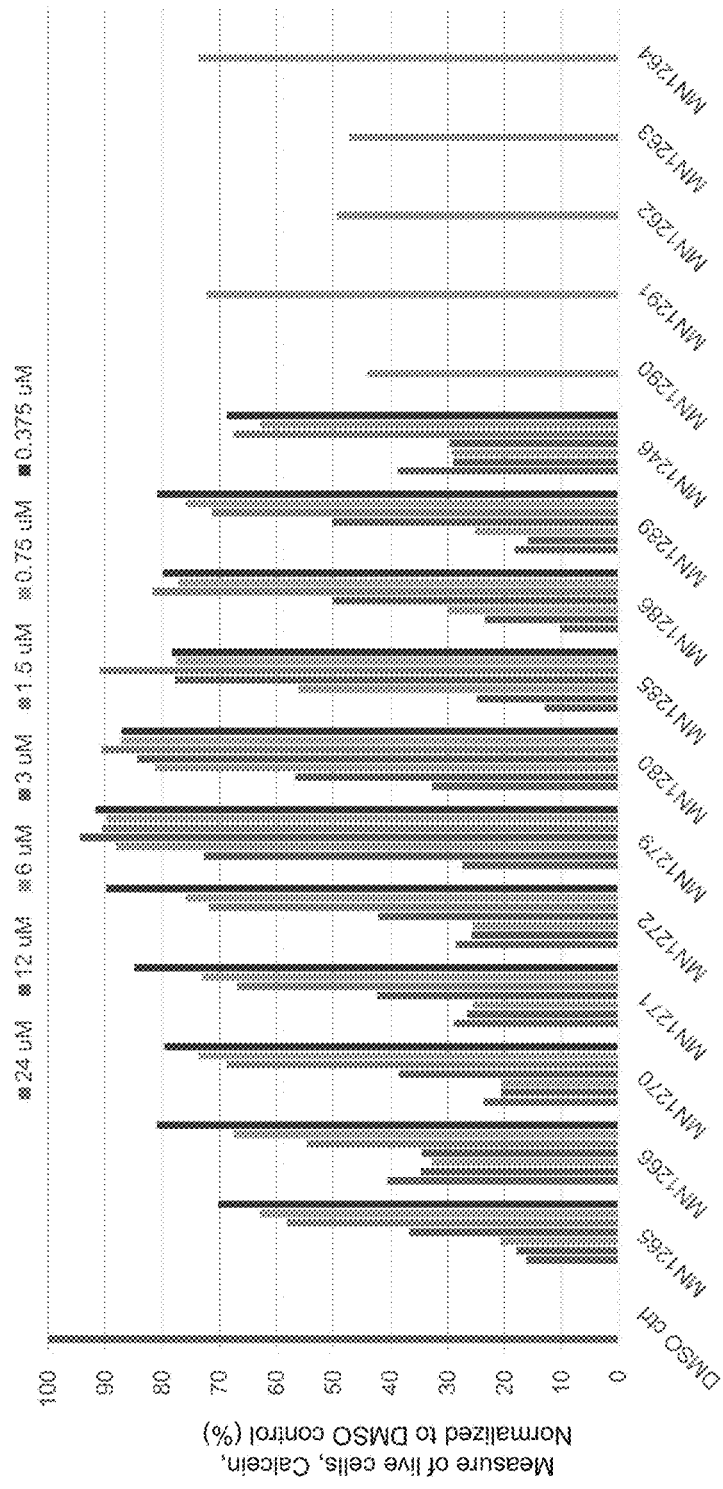
FIG. 133 is a graph of the inhibitory effects of compounds pictured in FIG. 132A1-132H12 on cancer cell proliferation. Relative cell number was measured in a Calcein live cell assay.
Figure 134:
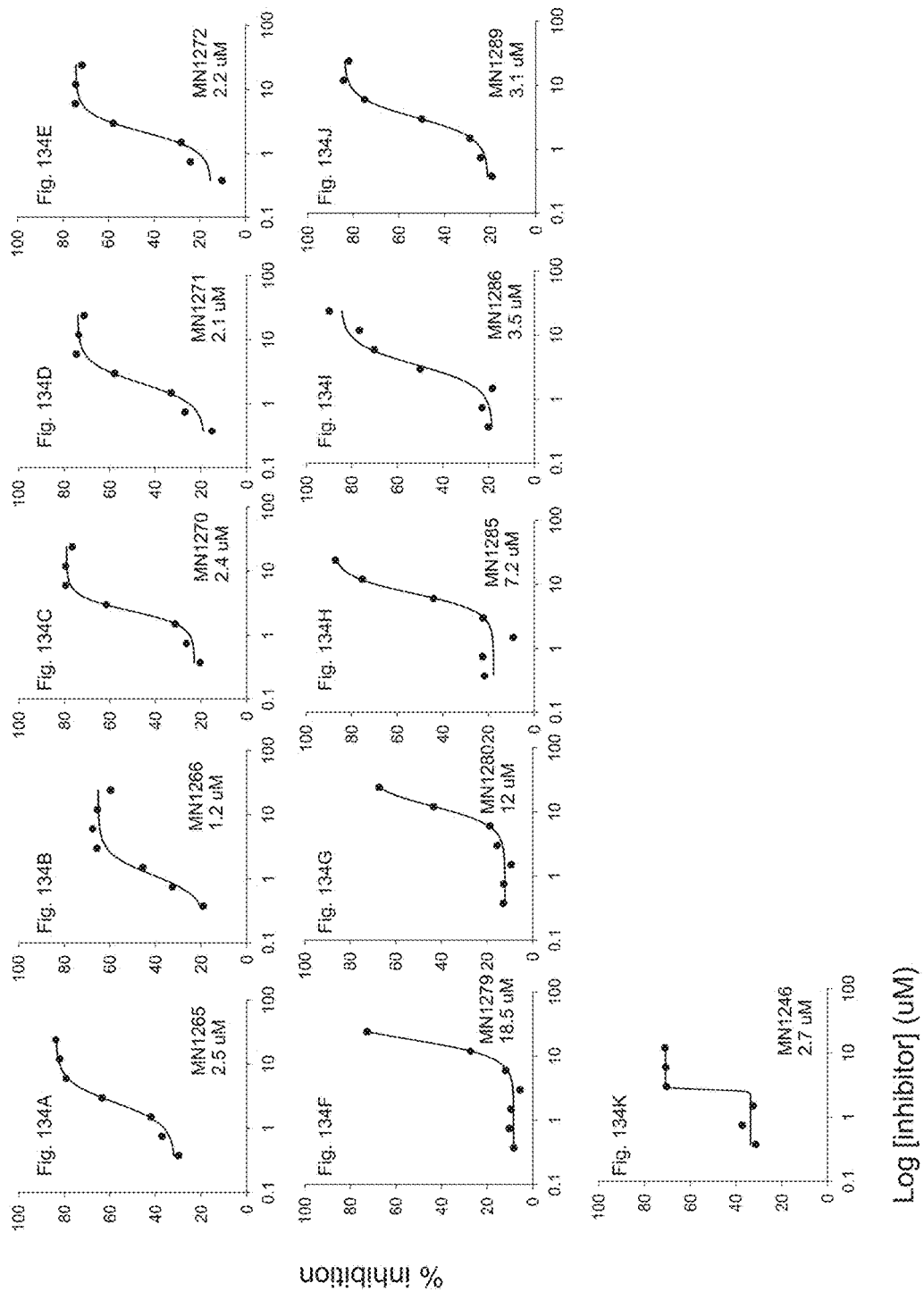
FIG. 134A-134K shows graphs of the inhibitory effects of compounds MN1265, MN1266, MN1270, MN1271, MN1272, MN1279, MN1280, MN1285, MN1286, MN1289 and MN1246 on cancer cell proliferation at 96 hours post treatment. IC50's for each compound were derived from these graphs. Inhibition of proliferation relative to the control was measured using a Calcein live cell assay.
Figure 135:
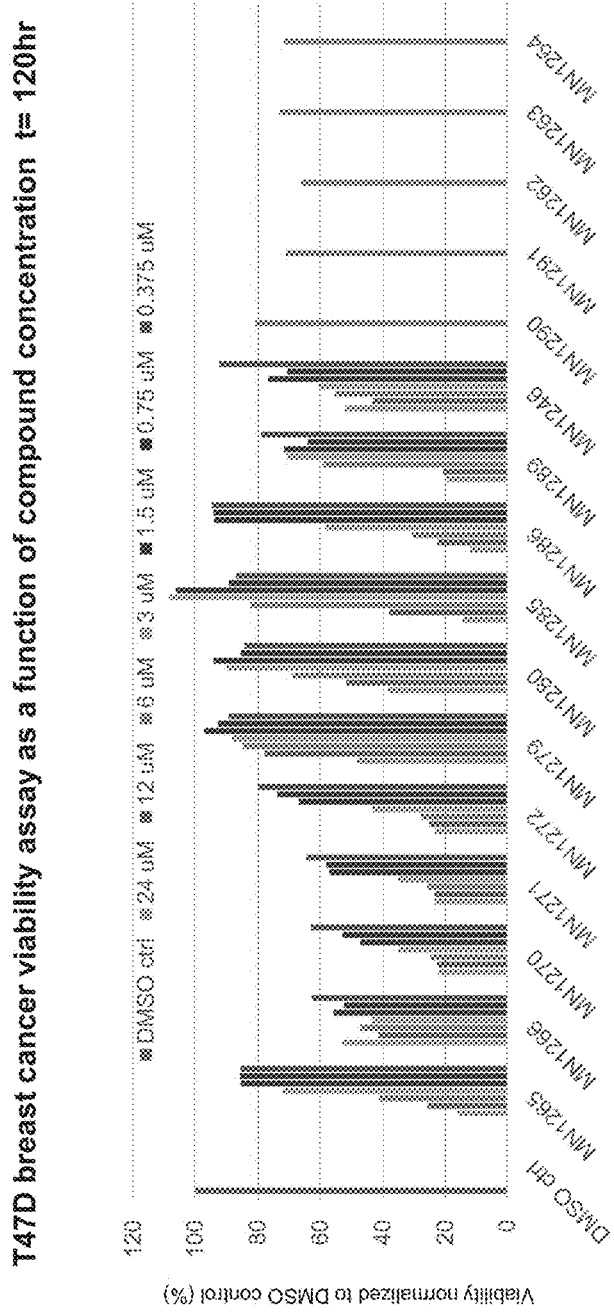
FIG. 135 is a graph showing the number of viable cells, relative to the DMSO control, as a function of compound concentration. Cell count was measured at 120 hours post treatment using a Calcein assay.
Figure 138:
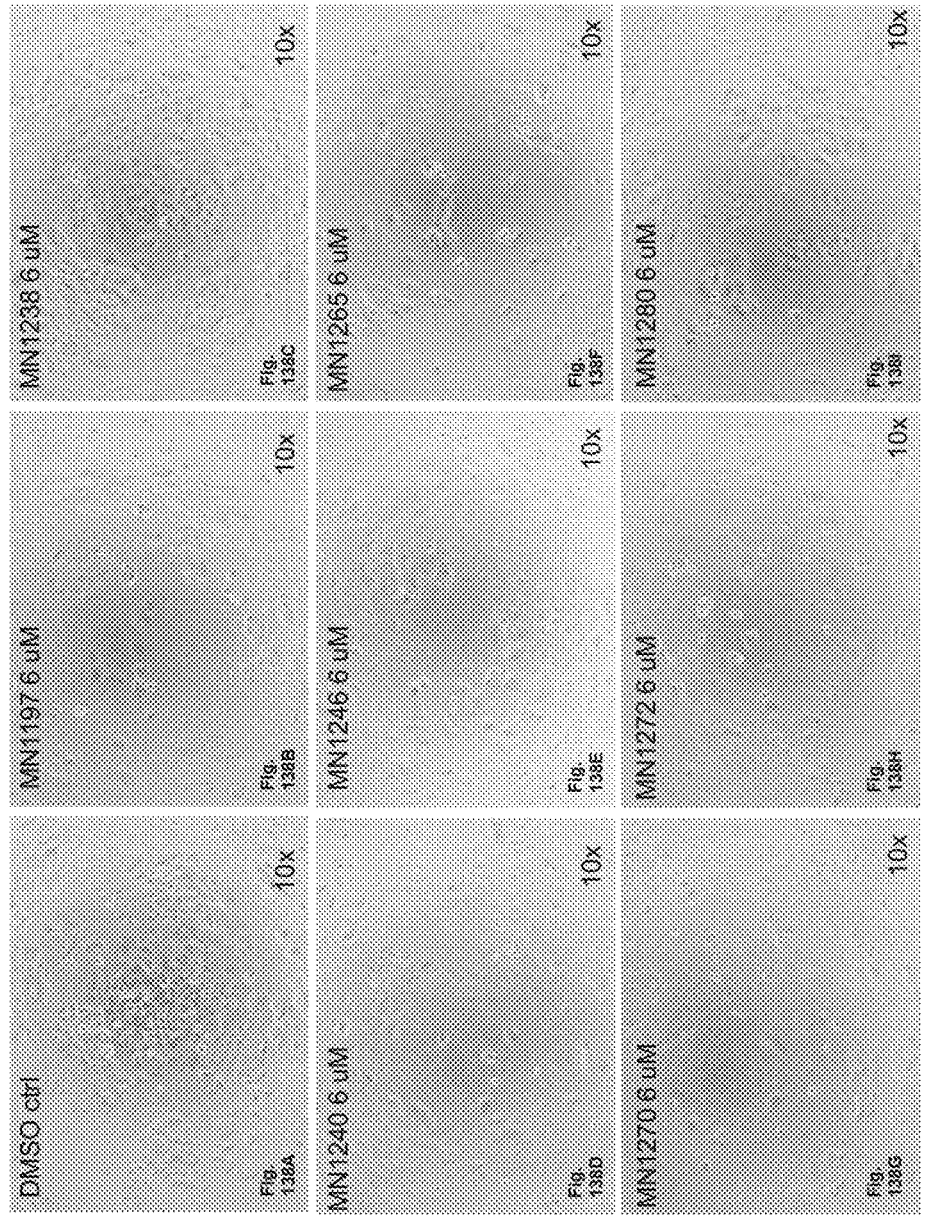
FIG. 138A-138I shows large bright field photographs of the inhibitory effect of compounds MN1197, MN1238, MN1240, MN1246, MN1265, MN1270, MN1272, and MN1280 on cancer cell proliferation.

Further medicinal chemistry and structure-activity relationship observations were made which led to yet another round of synthesis of additional compounds. The inhibitory effect of compounds MN1265, MN1265, MN1266, MN1270, MN1271, MN1272, MN1279, MN1280, MN1285, MN1286, MN1289, MN1290 and MN1291 on cancer cell migration was tested. Photographs of the cells were taken at 72 hours (FIGS. 128A1-128H12) and at 93 hours (FIG. 130A1-130H12). Because the compounds were dosed over a range of concentrations, IC50 curves could be generated and are shown in FIG. 129A-129K, then also shown on a log scale in FIG. 131A-131K. In the cancer cell migration assays, the number of cells that have migrated into the empty space is quantified using Image J software. The data shows that the medicinal chemistry techniques and knowledge gained from structure-activity relationships, led to a great reduction in the IC50 concentrations of this group of compounds, with the IC50 of MN1265 at 0.77 uM and that of MN1266 at 1.29 uM for curves calculated from 72 hour post dosing time point. These compounds were also tested for their ability to inhibit cancer cell proliferation. Photographs of Calcein stained live cells are shown in FIG. 132A1-132H12. Calcein fluorescence was then quantified on a plate reader (TECAN SAFIRE, Tecan Group Ltd., Switzerland) and the inhibitory effect on cancer cell proliferation as a function of compound concentration is graphed (FIG. 133). Graphs of the inhibition of cancer cell proliferation as a function of concentration and calculated IC50s are shown in FIG. 134A-134K. A cell viability assay was also performed and the results were graphed (FIG. 135).

Figure 139:
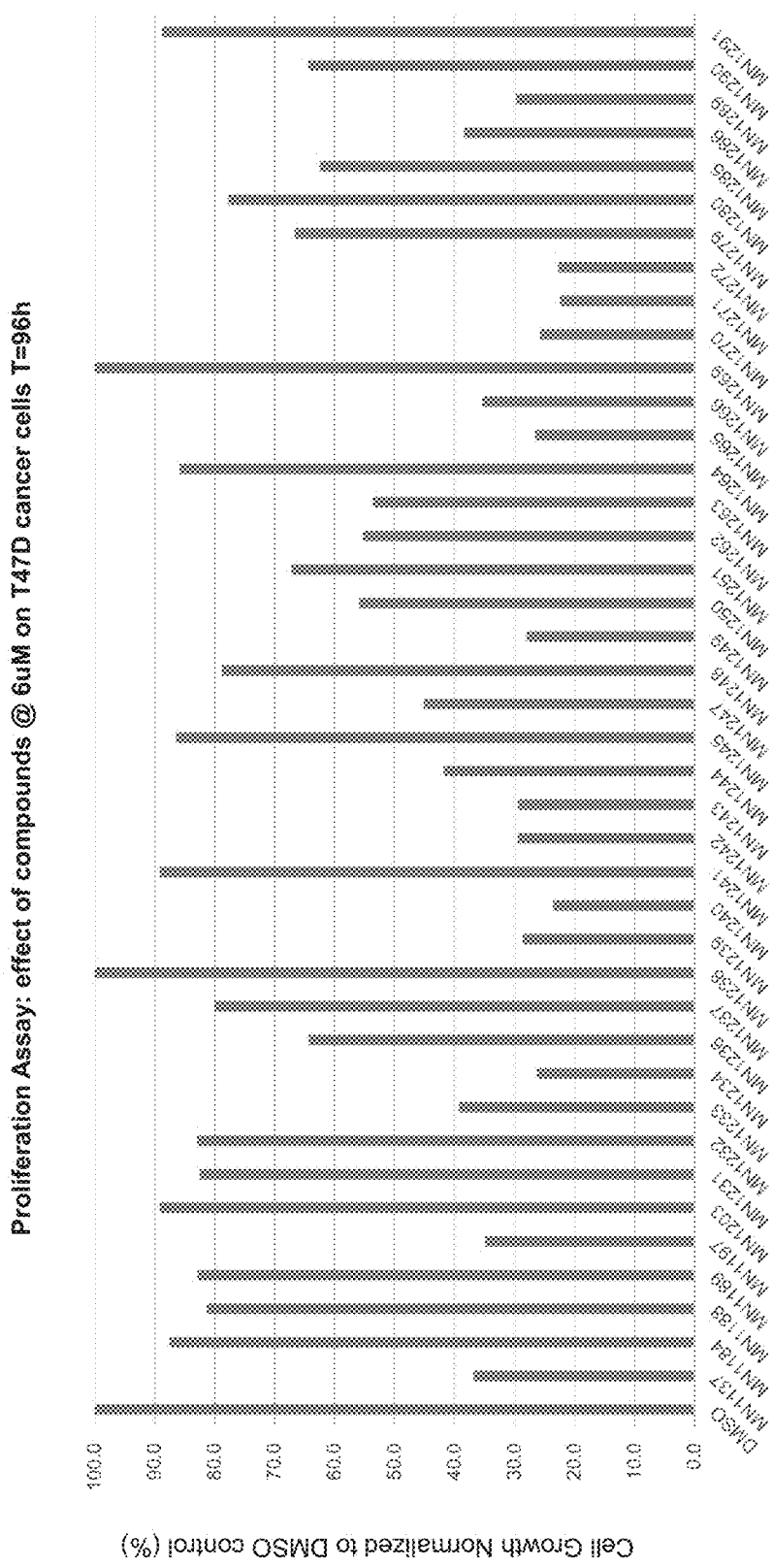
FIG. 139 shows a graph of the automated Calcein measurement of live cells, showing the inhibitory effects of the compounds at 6 uM on MUC1* positive breast cancer cells at 96 hours post treatment.
Figure 140:
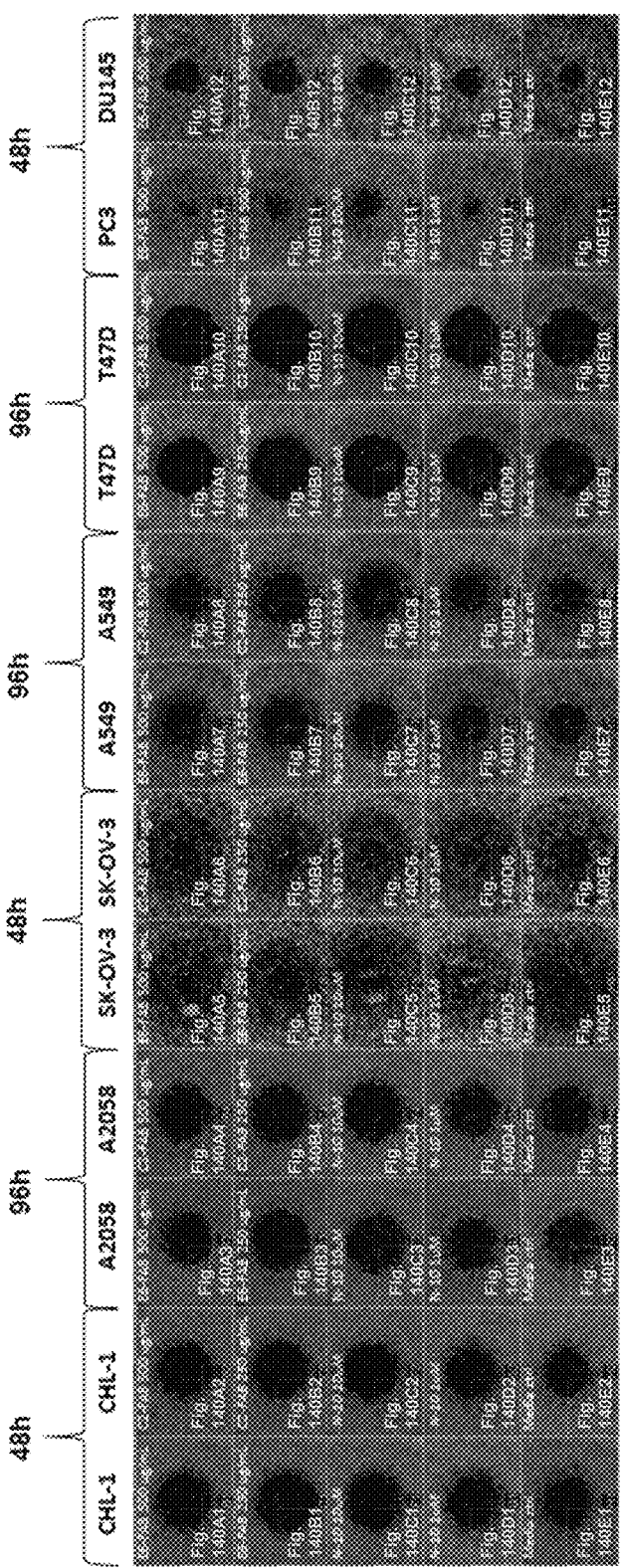
Figure 142:
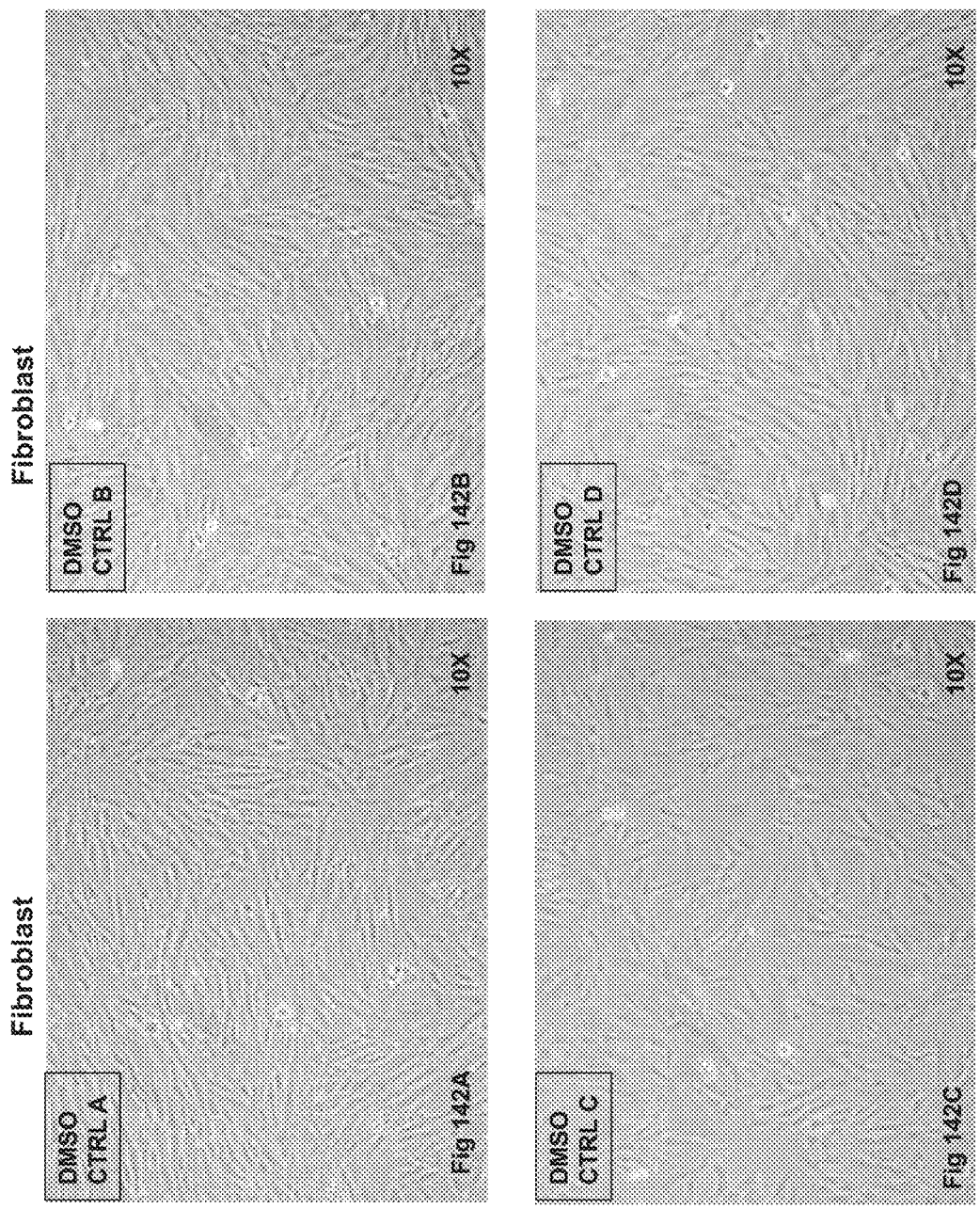
FIG. 142A-142D shows photographs of human fibroblasts in culture, treated only with 0.2% DMSO as a control.

A diverse group of small molecules of the invention were together tested for their ability to inhibit proliferation of T47D cells, when dosed at a final concentration of 6 uM. Tested were MN1197, MN1238, MN1247, MN1265, MN1285, MN1203, MN1239, MN1248, MN1266, MN1286, MN1231, MN1240, MN1249, MN1269, MN1269, MN1289, MN1232, MN1241, MN1250, MN1270, MN1290, MN1237, MN1233, MN1242, MN1251, MN1271, MN1291, MN1284, MN1234, MN1243, MN1262, MN1272, MN1288, MN1236, MN1244, MN1263 and MN1279. Cells were stained by Calcein live cell assay after 96 hours post treatment (FIG. 136A1-136H6). The brightfield photographs were taken prior to Calcein staining (FIG. 137A1-137H6). Enlarged bright field photographs of the inhibitory effect of compounds MN1197, MN1238, MN1240, MN1246, MN1265, MN1270, MN1272, and MN1280 on cancer cell proliferation are shown in FIG. 138A-138I. The automated Calcein measurement of live cells, showing the inhibitory effects of the compounds at 6 uM on MUC1* positive breast cancer cells at 96 hours post treatment was graphed (FIG. 139).

Recall that we had previously shown that some carbolines inhibited the binding of ligands NME1 or NME7$_{AB}$ to the extracellular domain of the MUC1* growth factor receptor. The assay we used was a gold nanoparticle assay that only gives a readout when the targeted interaction is disrupted, so it could not determine whether the carbolines disrupted binding of MUC1* to its ligands by binding to the ligand, NME7$_{AB}$, or to MUC1*. In this next set of experiments, we tested antibodies and peptides on various cancer sub-types in an effort to predict which cancers would be most affected by compounds of the invention. E6 and C2 are anti-MUC1* monoclonal antibodies that have been shown to competitively inhibit the binding of NME1 and NME7AB to the extracellular domain of MUC1*. The Fabs of both E6 and C2 have been shown to inhibit the growth of all MUC1* positive cancer cells in vitro and inhibit MUC1* breast and prostate cancers in vivo. In addition, the E6 and C2 monoclonal antibodies have been shown to only bind to cancerous tissues, but not normal tissues, for breast, prostate, ovarian, lung, pancreas, colorectal, stomach and liver cancers (thousands of human tissue specimens tested). Importantly, antibodies E6 and C2, along with NME1 dimers and NME7$_{AB}$ all bind to the N-10 peptide, which consists of the sequence of the membrane proximal 35 amino acids of the MUC1* extracellular domain. The N-10 peptide, also binds to NME7$_{AB}$ and NME7-X1 and inhibits their binding to their cognate receptors including the MUC1* extracellular domain.—

FIG. 140A1-140E12 shows photographs of a cancer cell migration assay in which anti-MUC1* antibody Fabs E6 and C2 and a truncated MUC1* extracellular domain peptide, N-10, are tested for their ability to inhibit migration or invasion of cancer cells. The cancer sub-types that were tested were CHL-1 melanoma (MUC1*$^+$/NME7$^+$/NME7-X1$^+$), A2058 melanoma (MUC1*$^+$/NME7$_{AB}$$^+$/NME7-X1$^{++}$), SK-OV-3 ovarian cancer (MUC1*$^+$/NME7$^+$/NME7-X1$^+$), A549 lung cancer (MUC1*$^{LO}$), T47D breast cancer (MUC1*$^{+++}$/NME7$_{AB}$$^{+++}$/NME7-X1$^{+++}$), DU145 (MUC1*$^{++}$/NME7$_{AB}$$^{+++}$/NME7-X1$^{+++}$) prostate cancer and PC-3 (MUC1*$^-$/NME7$_{AB}$$^{+++}$/NME7-X1$^{+++}$) prostate cancer cells. As can be seen, only the N-10 peptide inhibited migration of PC-3 prostate cancer cells, because they are MUC1* negative but highly positive for NME7$_{AB}$ and NME7-X1, so the peptide would inhibit their interactions. Fabs of E6 and C2 as well as the N-10 peptide all inhibited migration of T47D breast cancer cells and DU146 prostate cancer cells, which are both highly positive for MUC1*, NME7$_{AB}$ and NME7-X1. The Fabs and the N-10 peptide inhibited migration and proliferation (FIG. 141A1-141E12) of other cancer cell lines that are MUC1* positive or NME7 positive and the degree of inhibition was proportional to the amount of MUC1* or NME7$_{AB}$ or NME7-X1 that the cancer cell line expresses.

Figure 143:
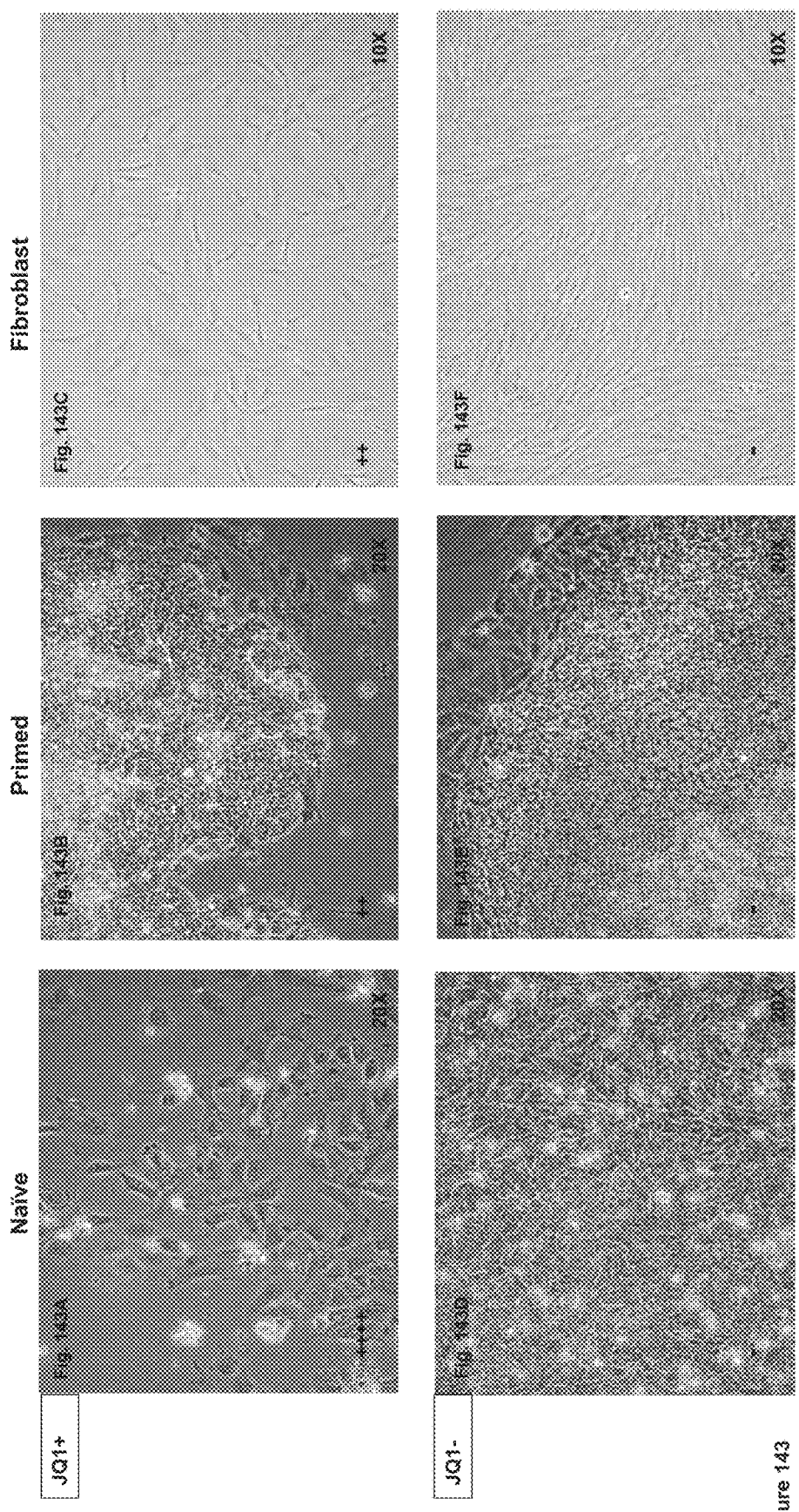
FIG. 143A-143F shows photographs of the effect of JQ1+(FIG. 143A-143C) versus the effect of the inactive enantiomer JQ1− (FIG. 143D-143F) on human naïve state stem cells (FIG. 143A, 143D), human primed state stem cells (FIG. 143B, 143E), or human fibroblasts (FIG. 143C, 143F).
Figure 144:
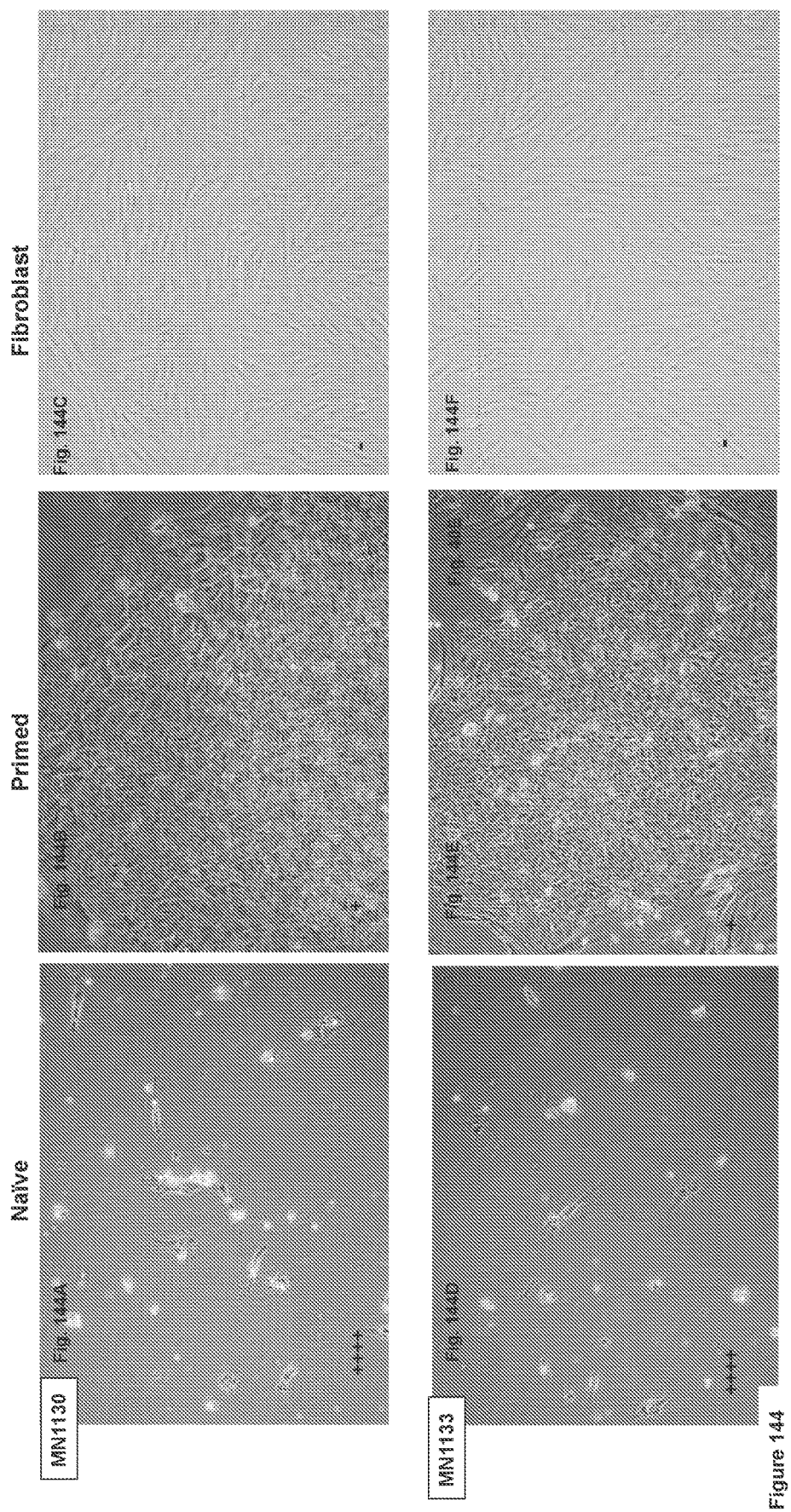
Figure 145:
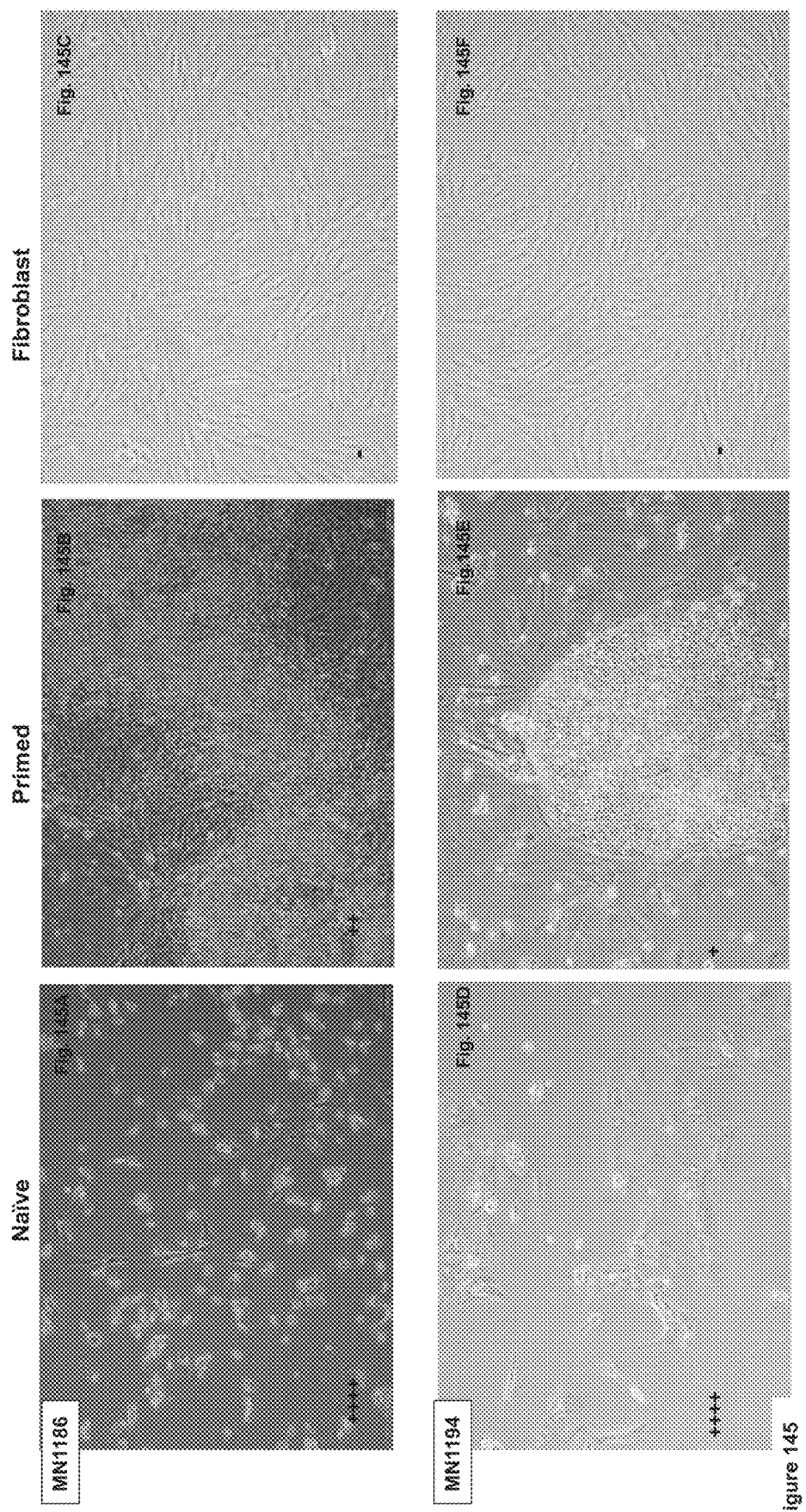
Figure 146:
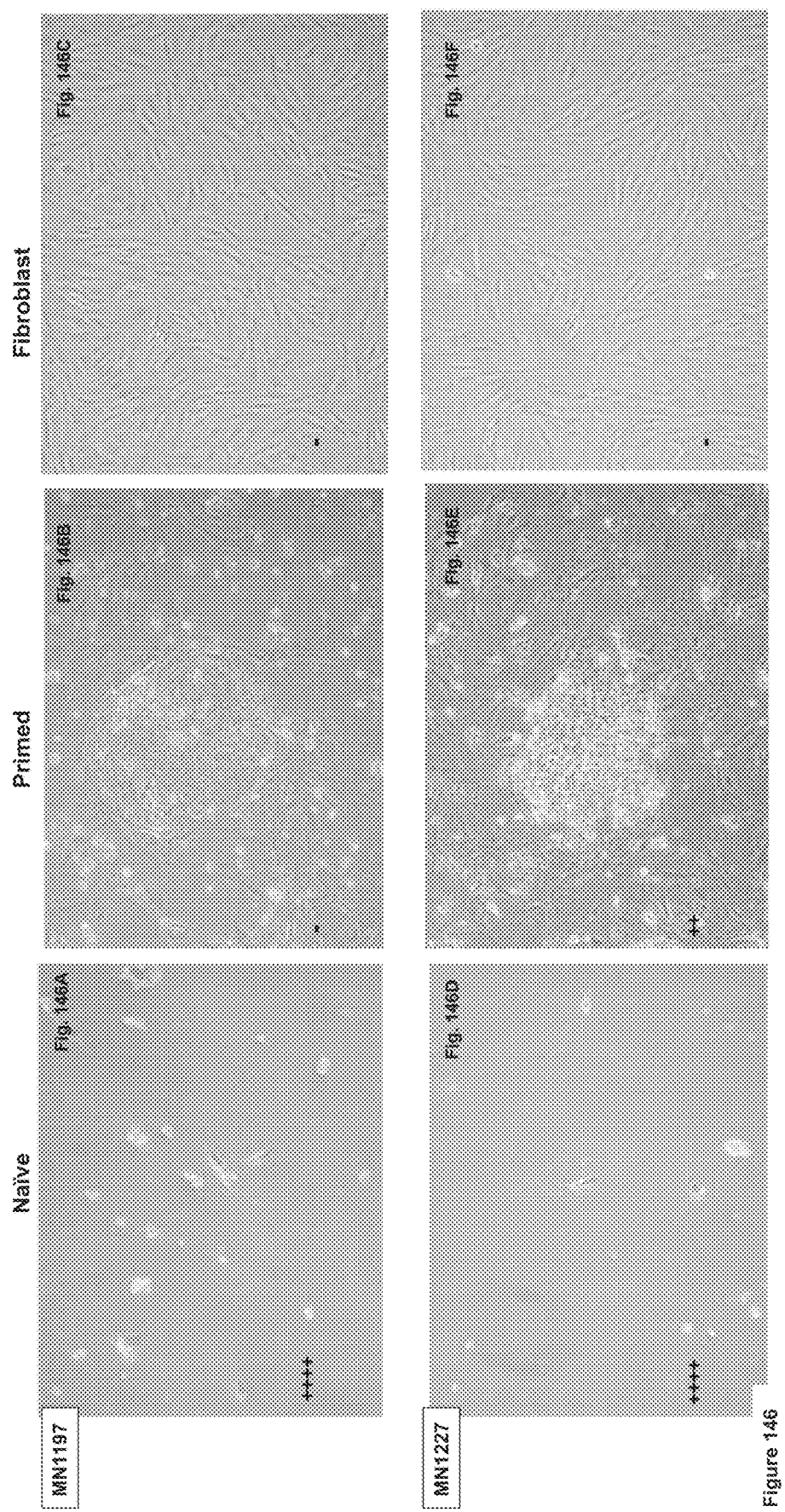
Figure 147:
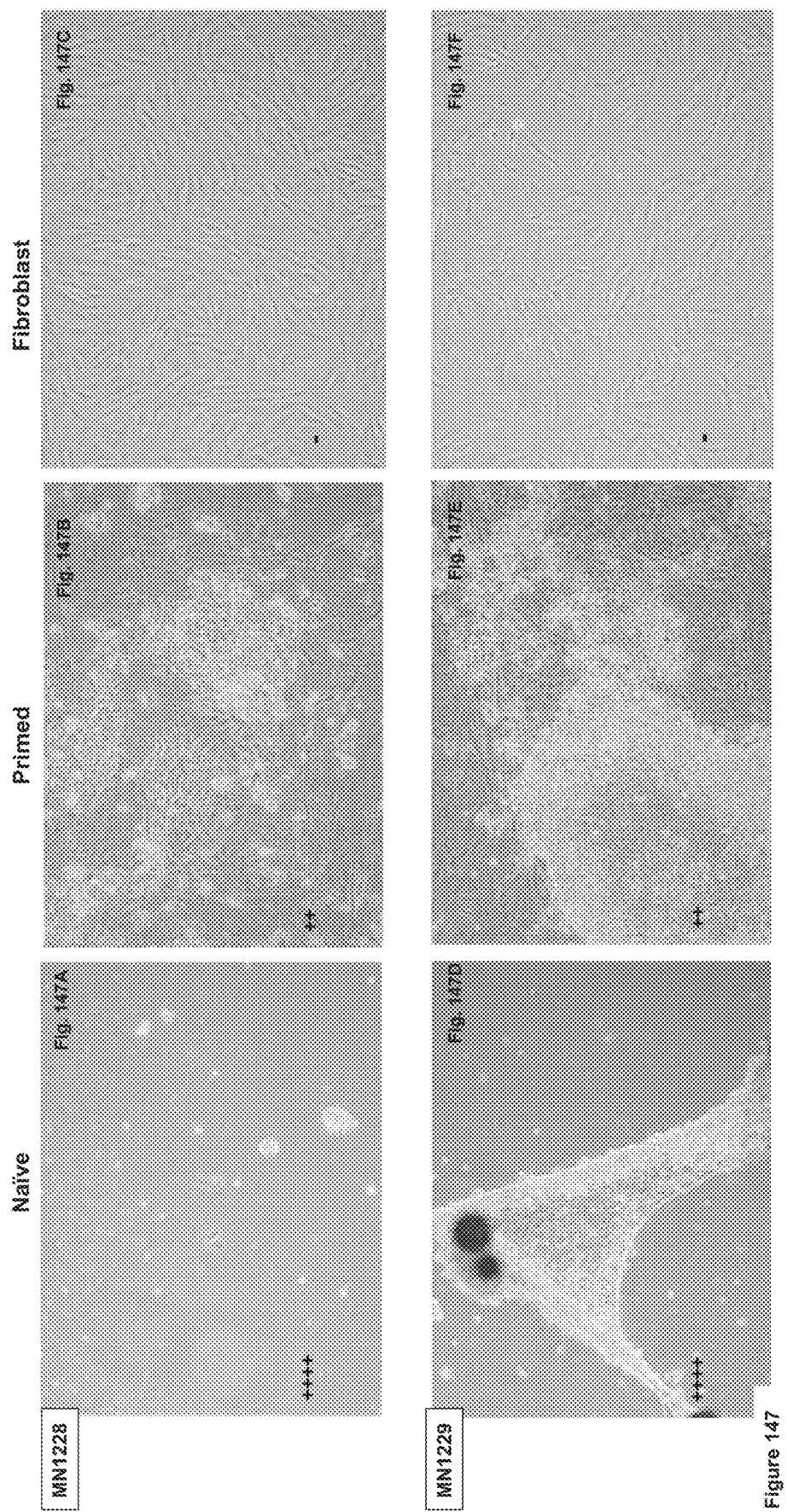
Figure 148:
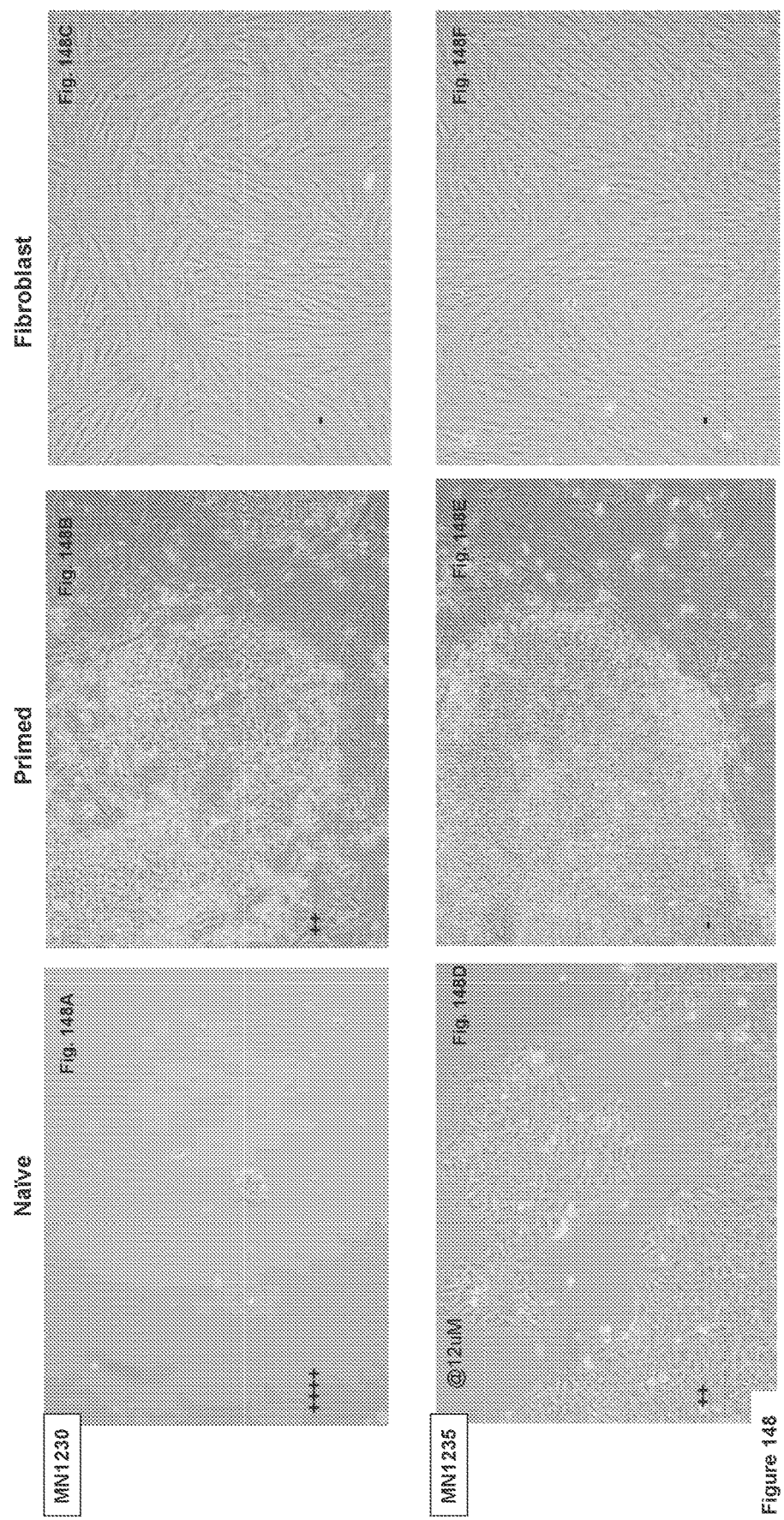
Figure 149:
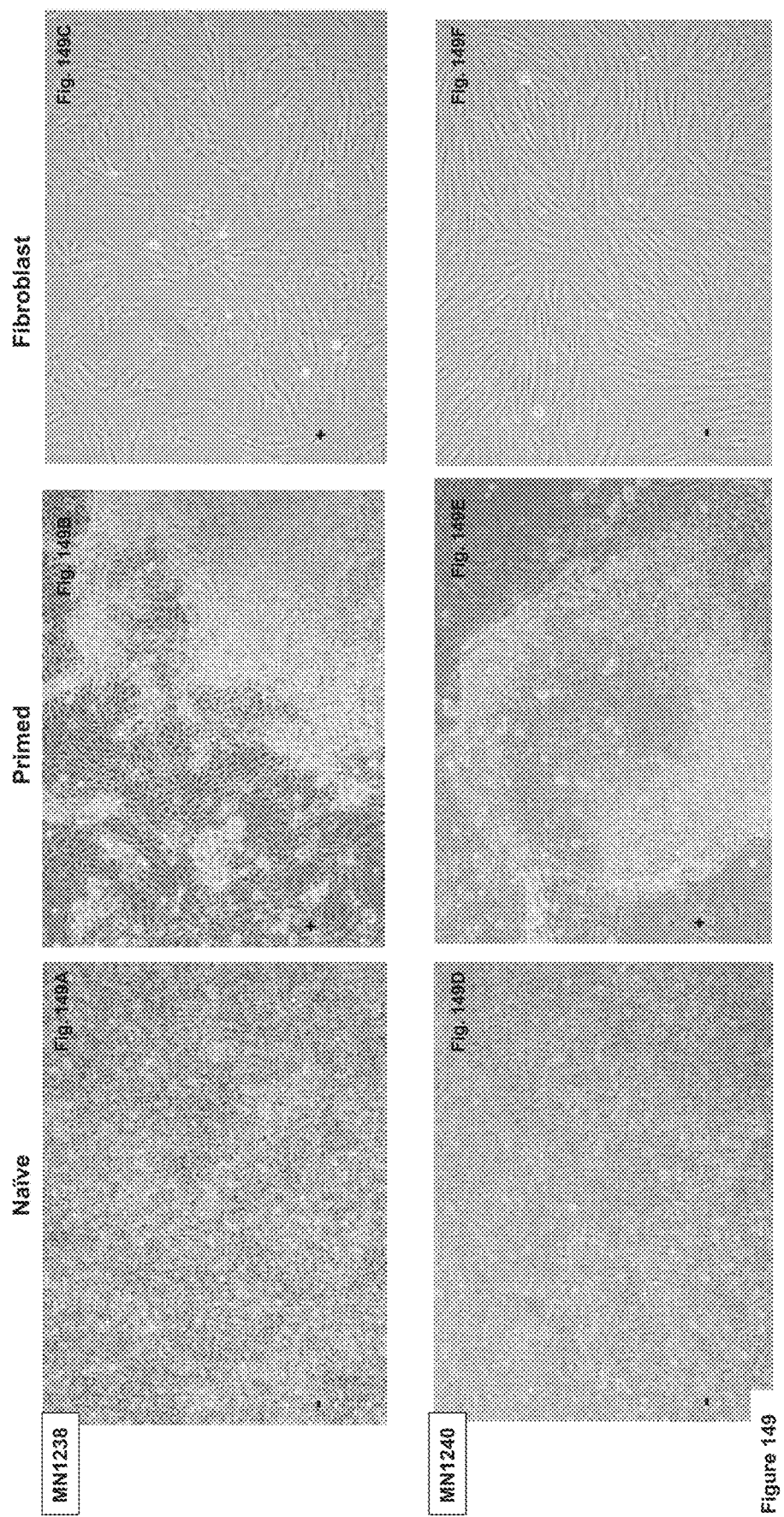
Figure 150:
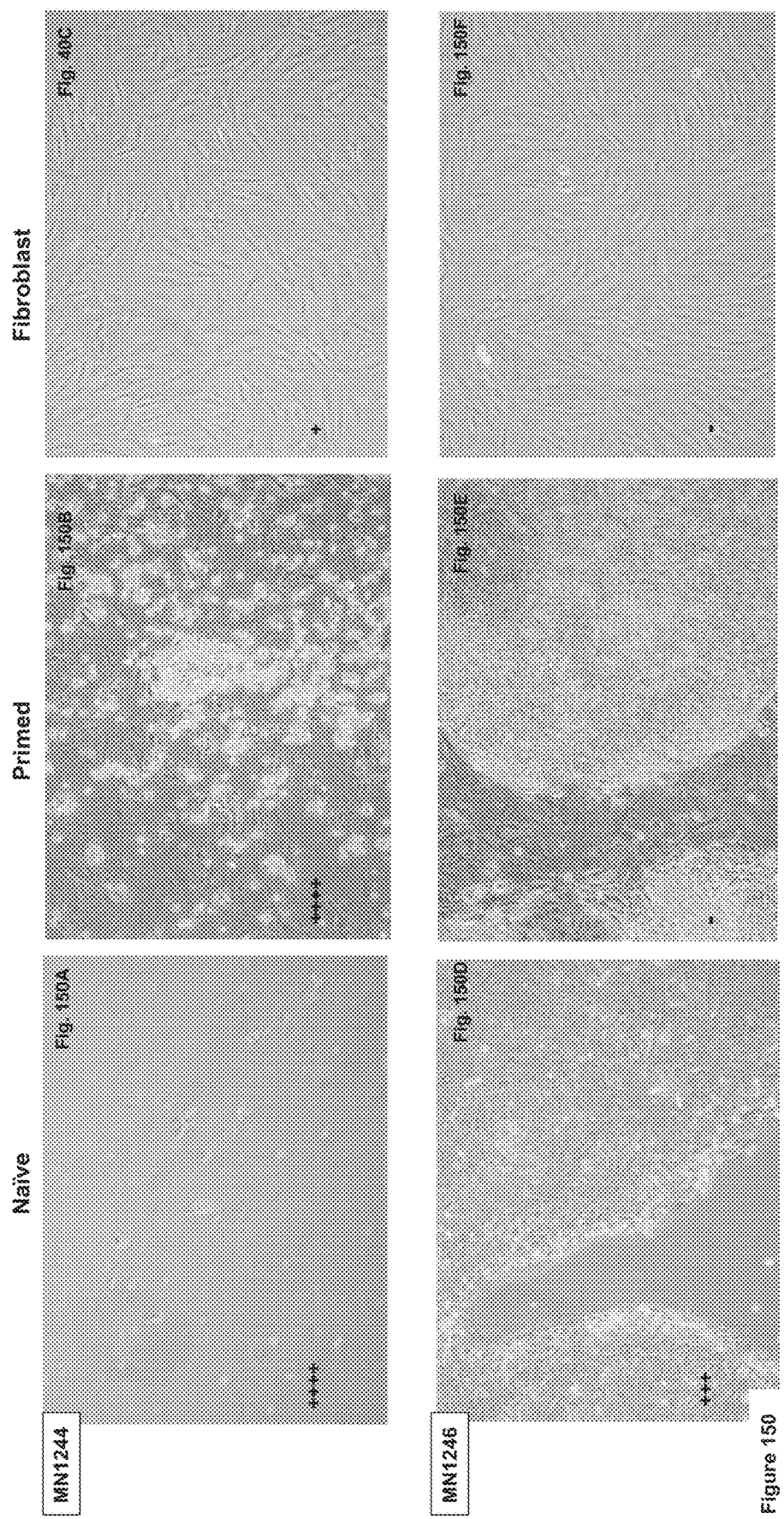
Figure 151:
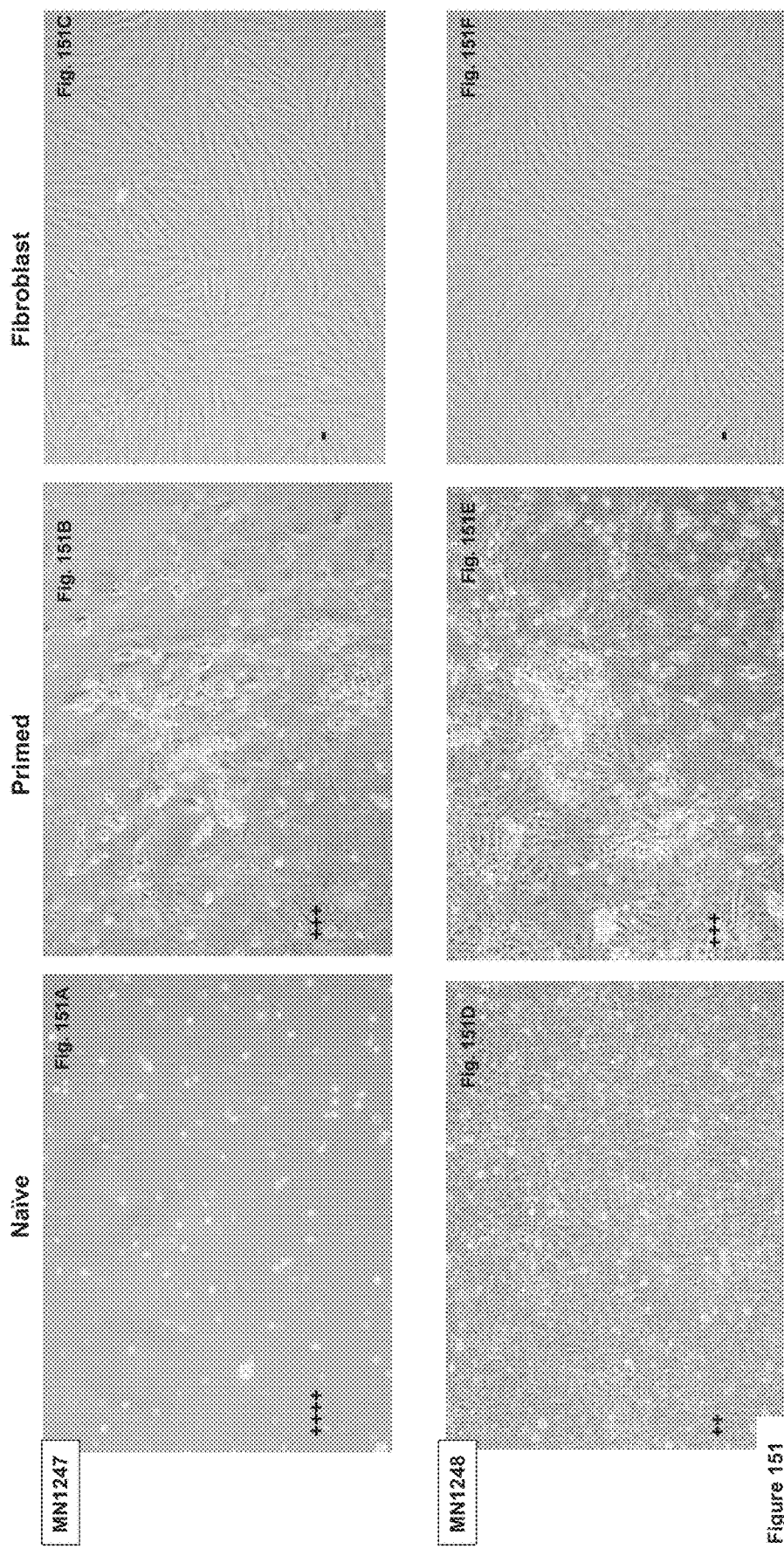
Figure 152:
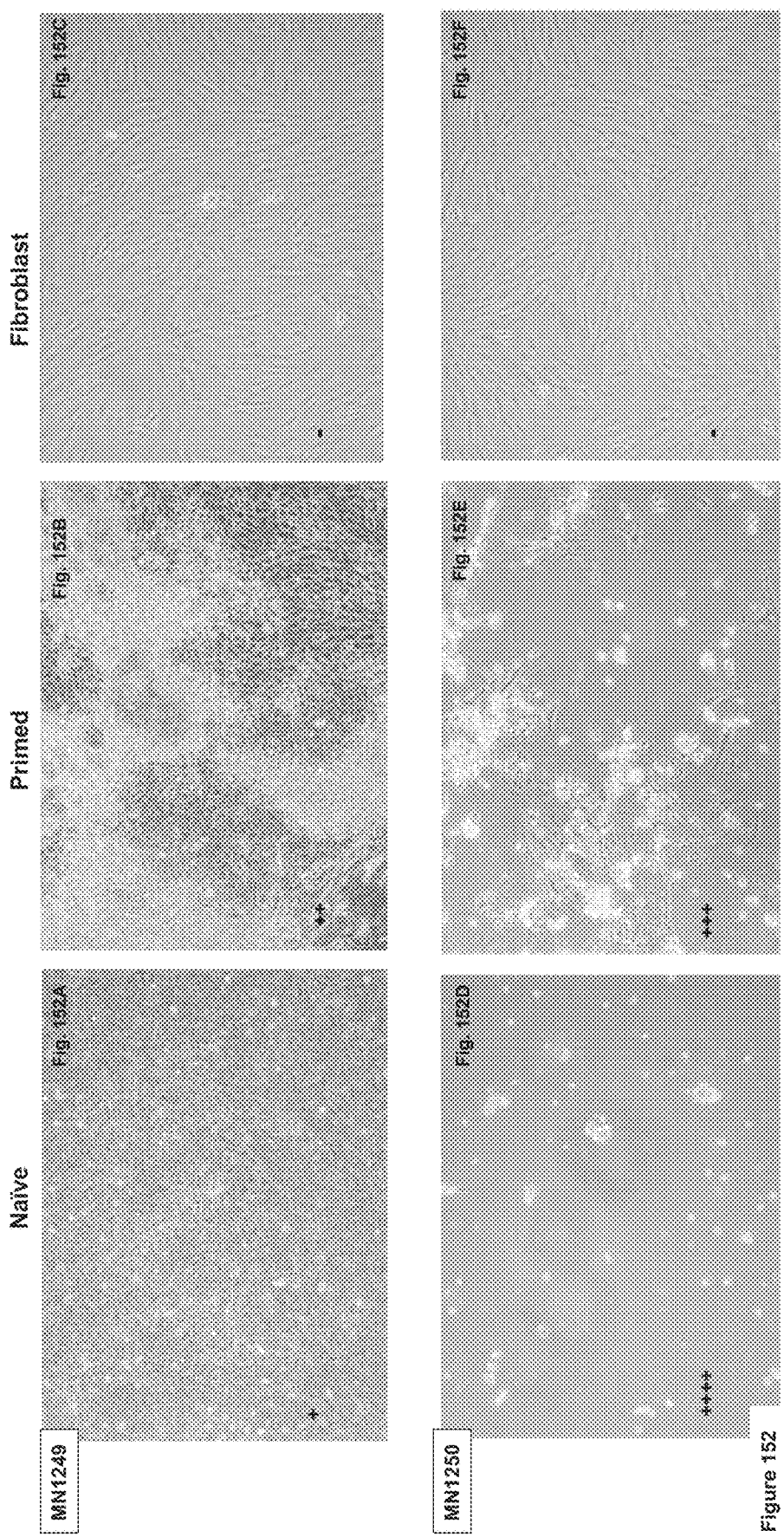
Figure 153:
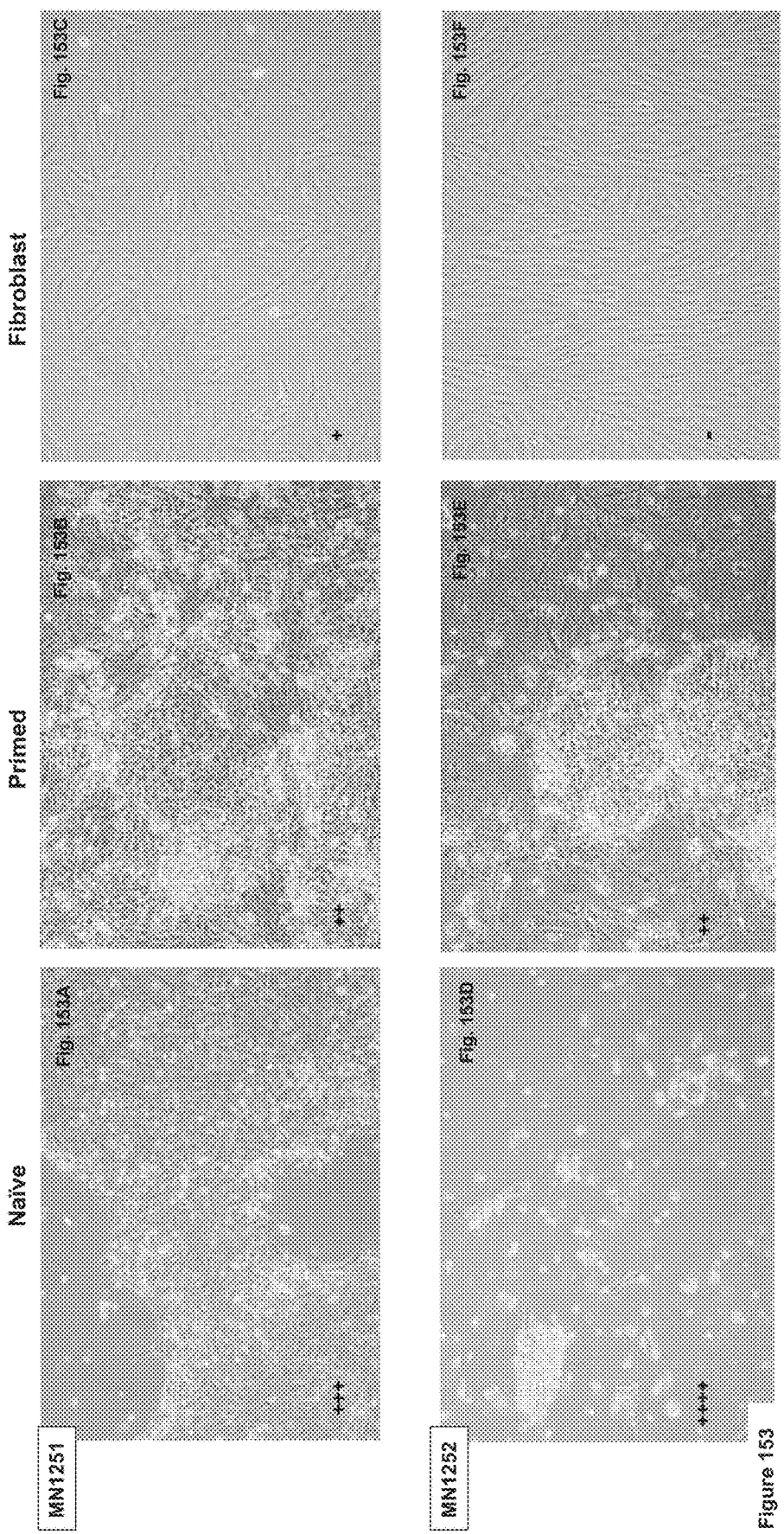
Figure 154:
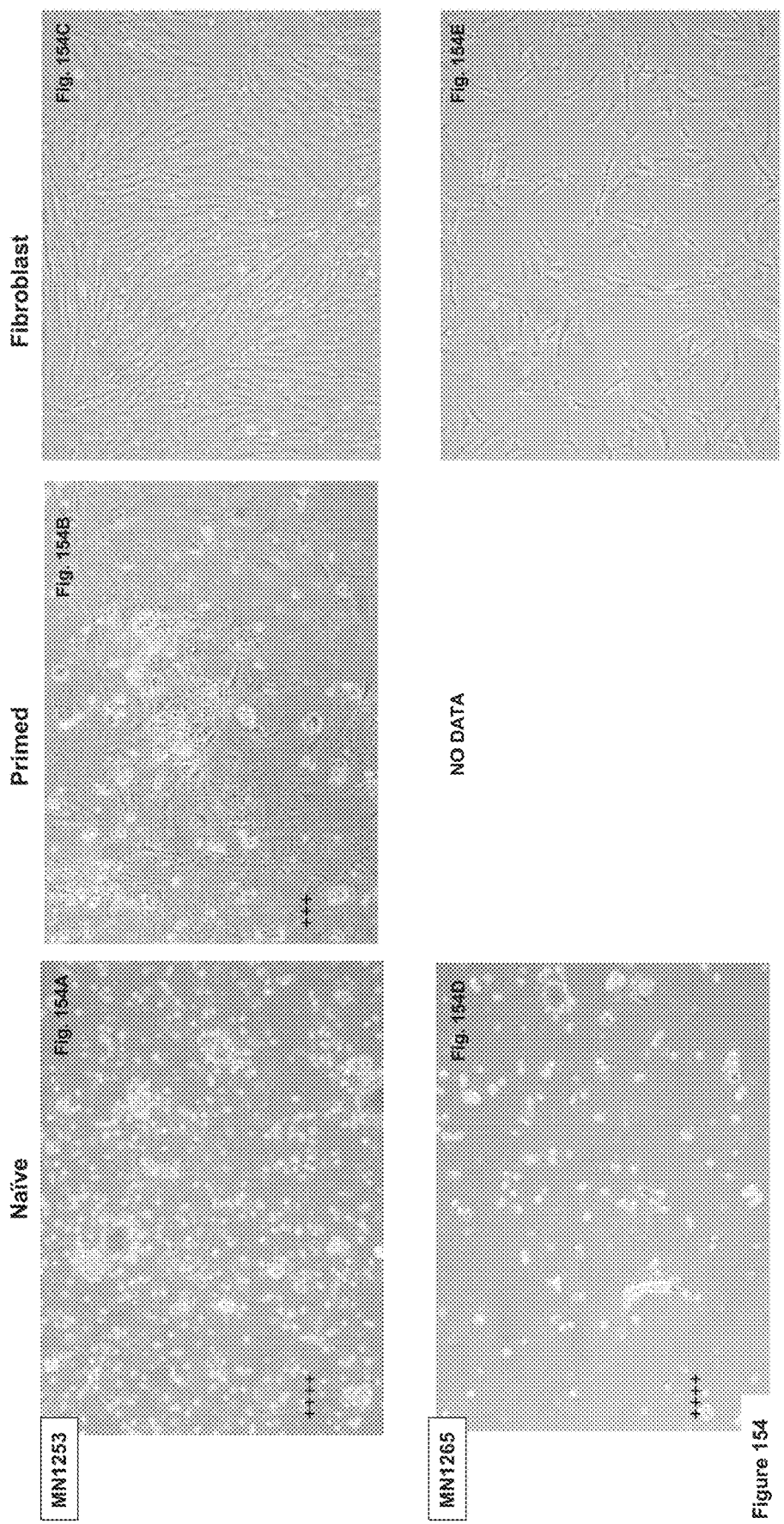
FIGS. 154A-154E show photographs of the effect of compounds of the invention on naïve stem cells (FIG. 154A,D), primed state stem cells (FIG. 154B) or fibroblast progenitor cells (FIG. 154C,E).
Figure 155:
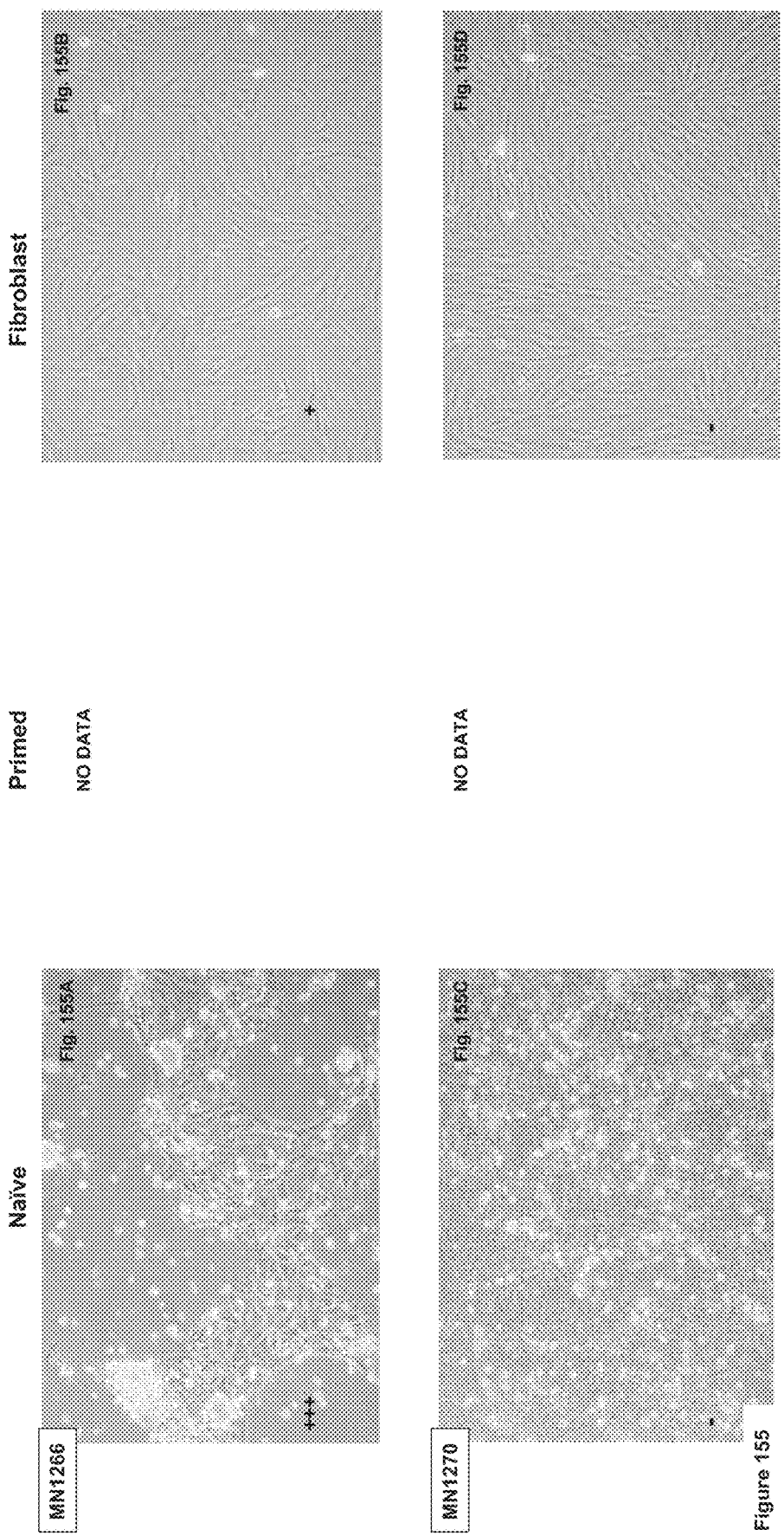
Figure 156:
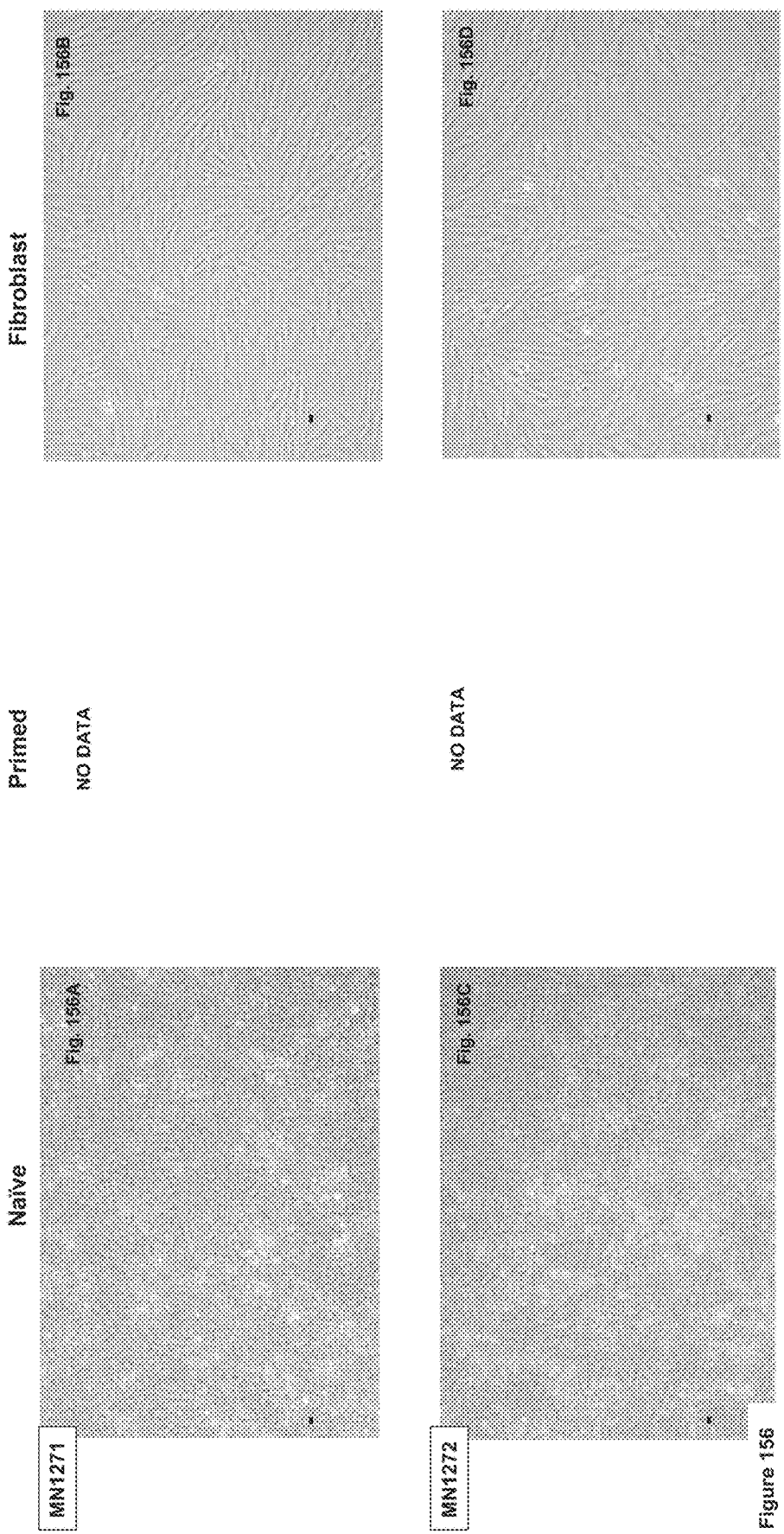
Figure 157:
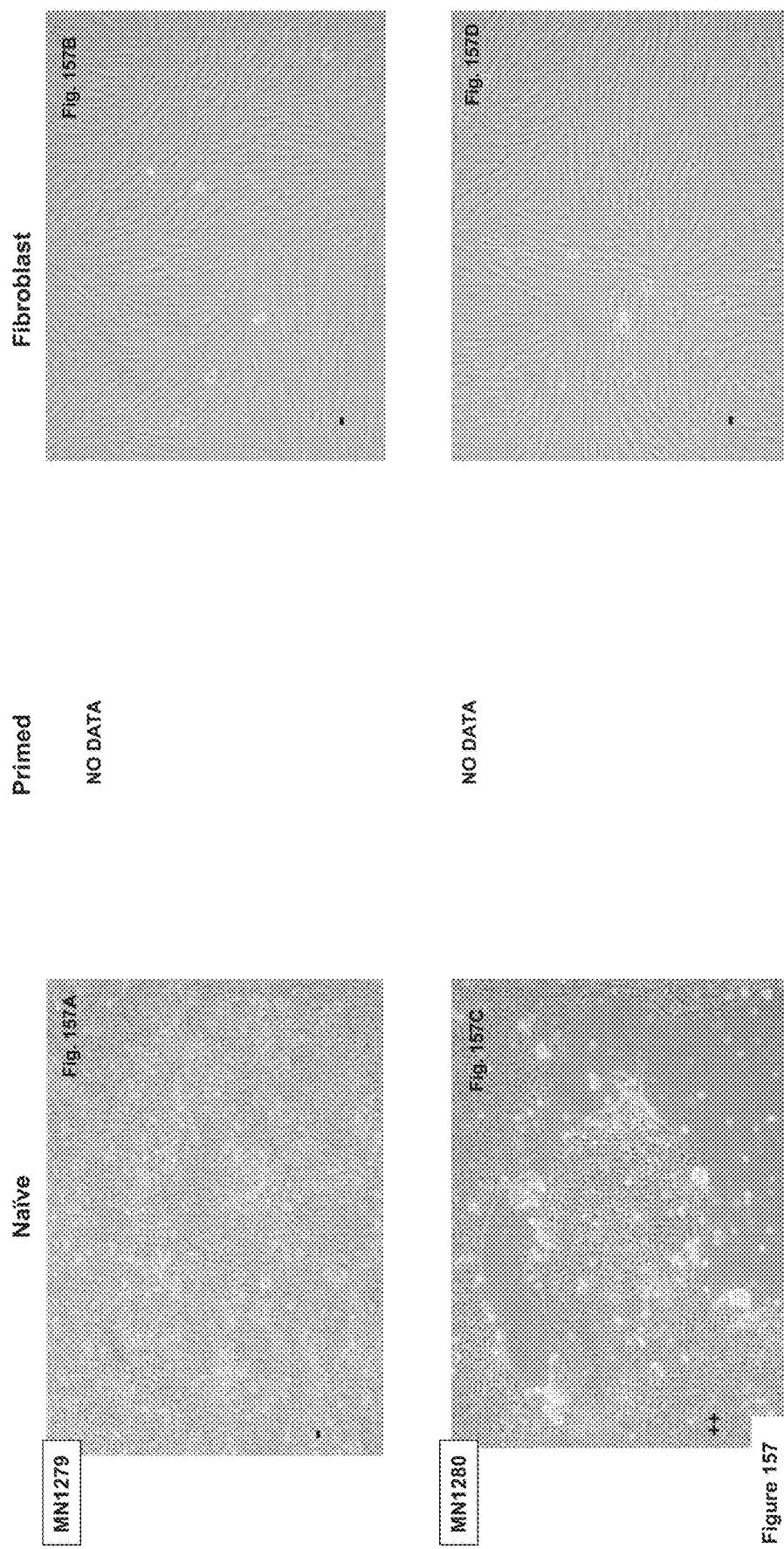
Figure 159:
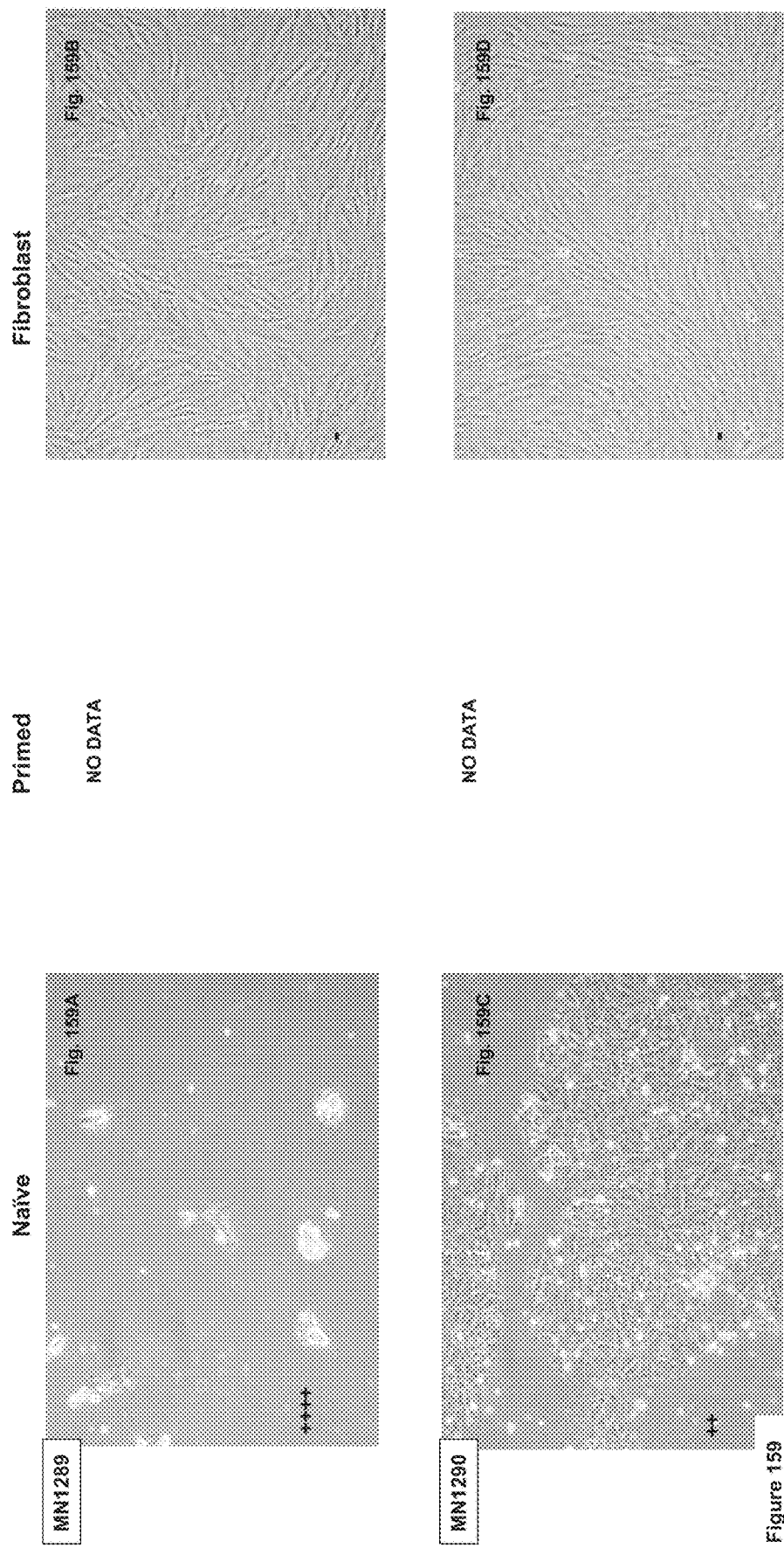
Figure 160:
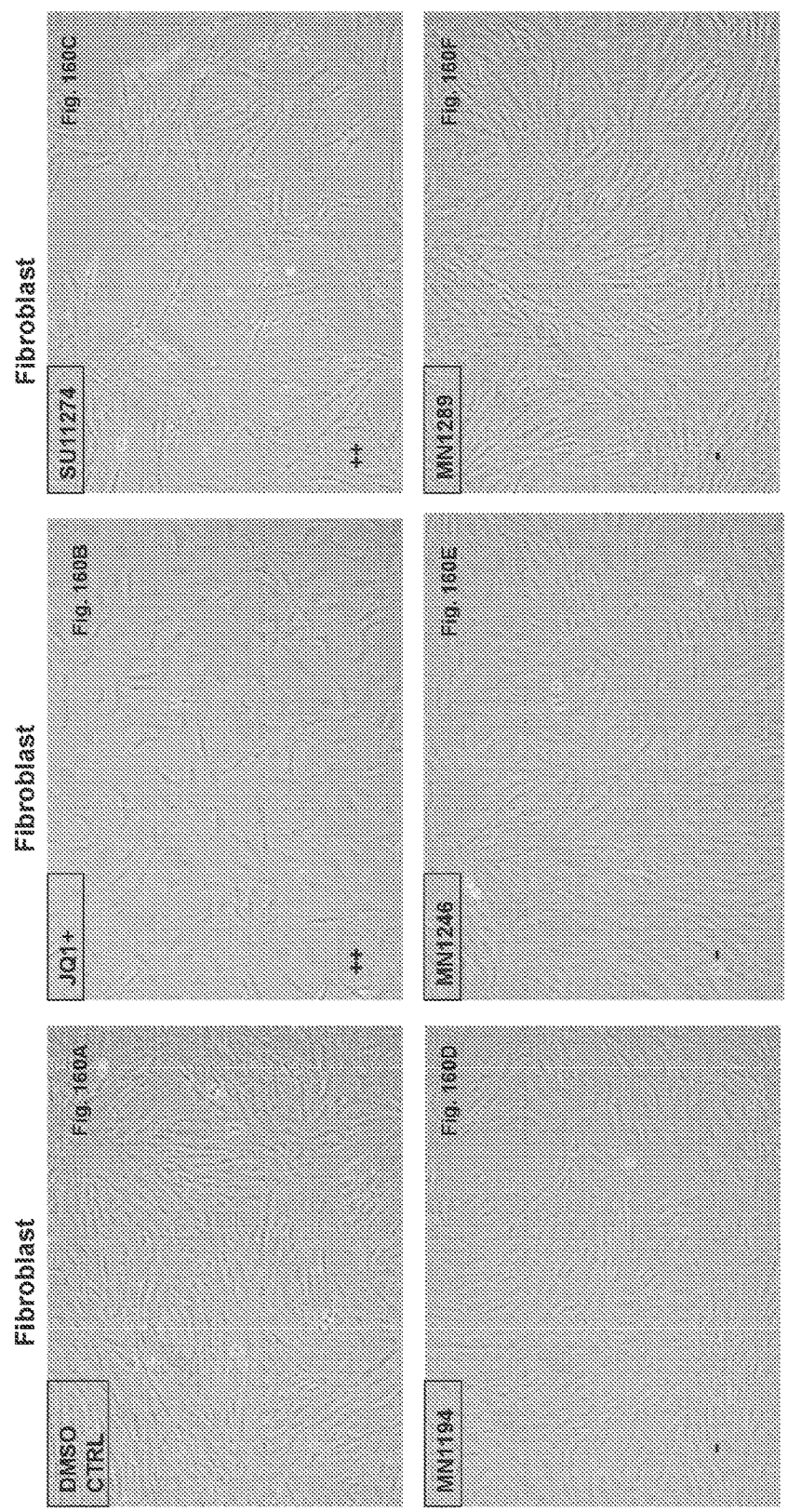
FIG. 160A-160F—show photographs of the effect of previously known cancer cell migration inhibitors, versus compounds of the invention, on the growth of human fibroblast progenitor cells.

As cancer treatments become more targeted, the goal is to develop therapeutics that preferentially inhibit the pluripotency or proliferation of cancer cells while having the smallest effect possible on normal, healthy cells. There are no "normal" cell lines because normal terminally differentiated cells do not keep dividing the way stem cell or cancer cells do. However, fibroblast are more differentiated than stem cells but are able to self-replicate for defined periods of time. We tested selected compounds of the invention to determine if these compounds were just cytotoxic or if they selectively affected stem cells and, importantly, cancer cells. Since fibroblasts do not change morphology, the readout of this assay was only what effect the compounds had on proliferation. Photographs were taken 48 hours after the test compounds at 6 uM were separately added to growing human fibroblasts. Each compound was scored for its effect on fibroblast proliferation where "+" indicates 25% inhibition of fibroblast growth, "++" 50% inhibition and "+++" 75% inhibition of growth. FIG. 142A-142D shows photographs of human fibroblasts in culture, treated only with 0.2% DMSO as a control. FIG. 143A-143F shows photographs of the effect of JQ1+(FIG. 143A-143C) versus the effect of the inactive enantiomer JQ1-, both at 500 nM final concentration, (FIG. 143D-143F) on human naïve state stem cells (FIG. 143A, 143D), human primed state stem cells (FIG. 143B, 143E), or human fibroblasts (FIG. 143C, 143F). As can be seen, JQ1+ has the same effect on fibroblasts as it does on primed state stem cells, which indicates it would have more side effects than a compound that did not affect the later fibroblast progenitor cells. FIGS. 144A-153F— show photographs of the effect of compounds of the invention on naïve stem cells (FIG. 144A,D-153A,D), primed state stem cells (FIG. 144B,E-153B,E) or fibroblast progenitor cells (FIG. 144C,F-153C,F). FIGS. 154A-154E show photographs of the effect of compounds of the invention on naïve stem cells (FIG. 154A,D), primed state stem cells (FIG. 154B) or fibroblast progenitor cells (FIG. 154C,E). FIGS. 155A-159D show photographs of the effect of compounds of the invention on naïve stem cells (FIG. 155A,C-

159A,C), or fibroblast progenitor cells (FIG. 155B,D-159B, D). FIG. 160A-160F show photographs of the effect of previously known cancer cell migration inhibitors, versus compounds of the invention, on the growth of human fibroblast progenitor cells. As can be seen in the figures, most of the novel compounds of the invention have little or no effect on the growth of fibroblast cells. The fact that the compounds of the invention robustly inhibit stem cell and cancer cell pluripotency and proliferation, but have little or usually no effect on fibroblast progenitor cells shows that the compounds are not cytotoxic agents. In contrast, other previously reported cancer cell migration inhibitors had the same effect on fibroblast progenitor cells as they had on stem and cancer cells, which indicates that they would likely have toxic side effects for the patient.

Figure 161:
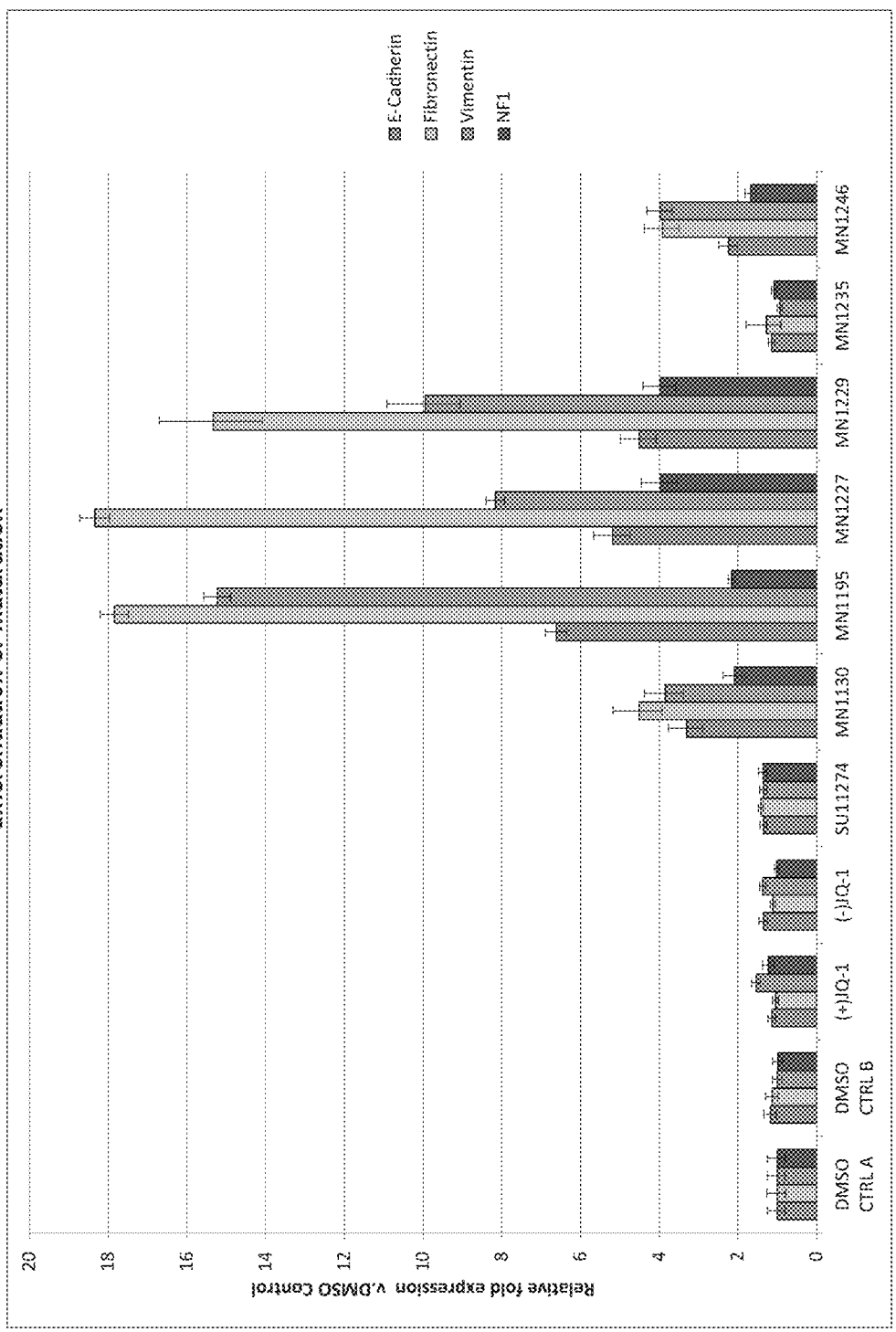
FIG. 161 is a graph of RT-PCR measurement of naïve stem cells that have been treated with compounds of the invention. The genes whose expression is measured are E-cadherin, which goes up as cells undergo epithelial to mesenchymal transition, fibronectin and vimentin, which both increase as stem cells initiate differentiation and NF1 which is one of the first genes to increase when stem cells begin to differentiate down the neural lineage.
Figure 162:
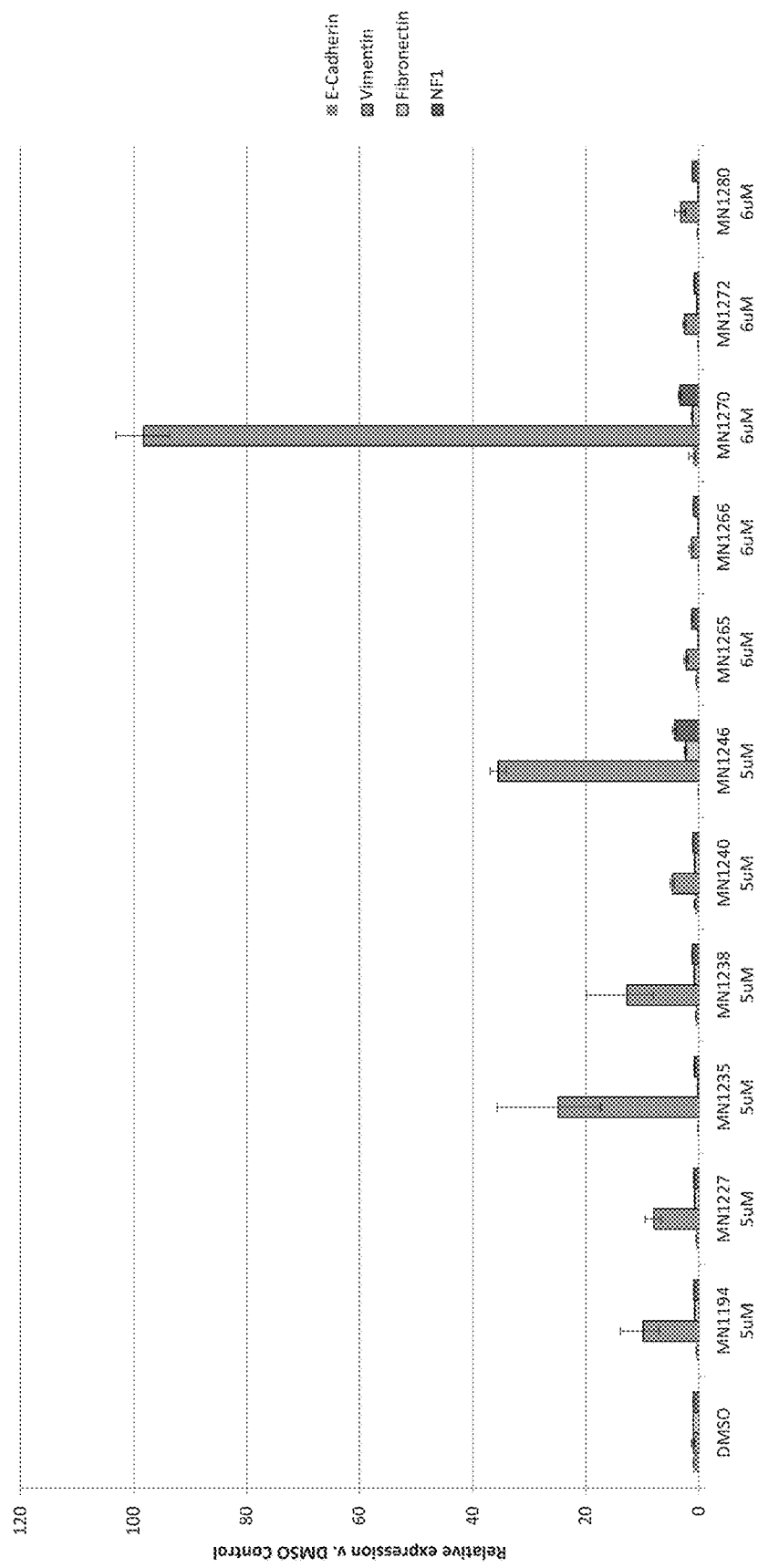
FIG. 162 is a graph of RT-PCR measurement of T47D cancer cells that have been treated with compounds of the invention. Metastatic marker E-cadherin is reduced in response to compounds, while markers of differentiation go up.
Figure 163:
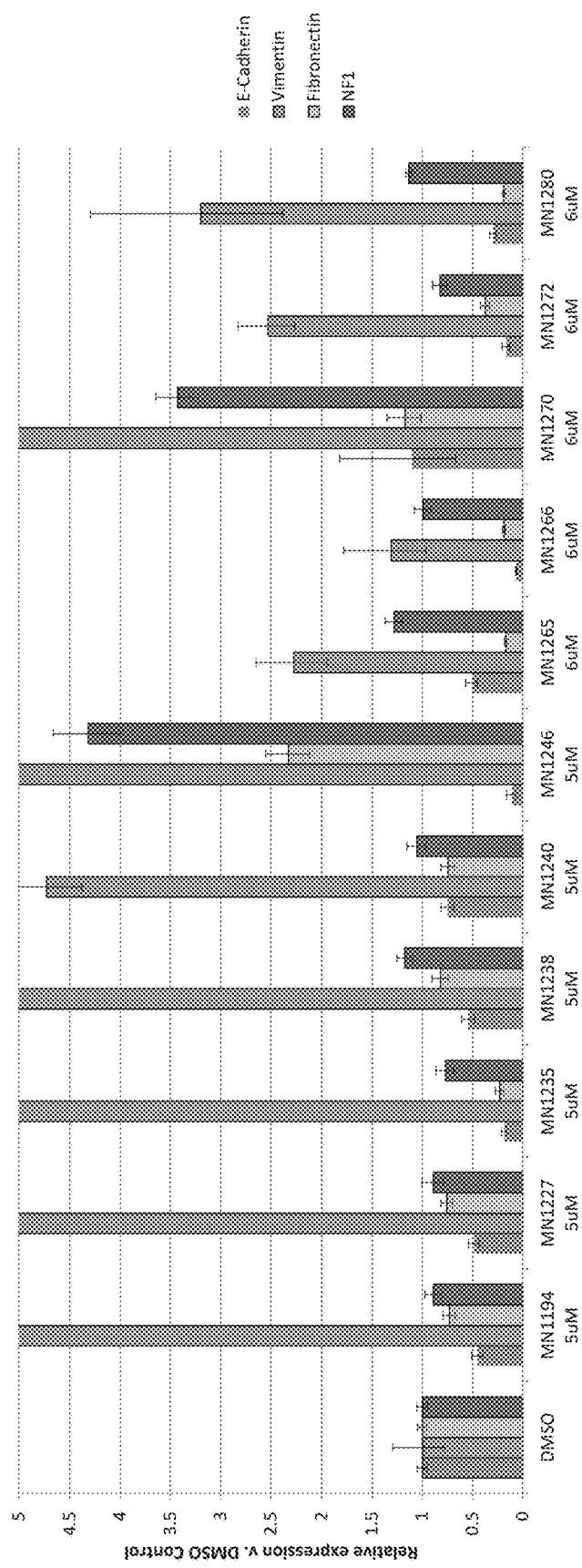
FIG. 163 the graph of RT-PCR measurement shown in FIG. 162 but with the Y-axis expanded to show differences in expression of genes.

Experiments indicate that the novel compounds of the invention inhibit pluripotency and/or proliferation of stem cells and cancer cells by inducing maturation, also known as differentiation. FIG. 161 is a graph of RT-PCR measurement of naïve stem cells that have been treated with compounds of the invention. The genes whose expression is measured are E-cadherin, which goes up as cells undergo epithelial to mesenchymal transition, fibronectin and vimentin, which both increase as stem cells initiate differentiation and NF1, which is one of the first genes to increase when stem cells begin to differentiate down the neural lineage. The fact that fibronectin, vimentin or NF1 expression increases in response to treatment with a compound shows that the compound induces differentiation and terminally differentiates cells do not self-replicate. E-cadherin is the opposite; it increases as cells become cancerous. Note that the previously known inhibitors of cancer cell migration and proliferation, JQ1+ and SU11274 did not cause up-regulation of markers of differentiation, i.e. induce differentiation of the stem cells. Compound MN1235 that had reduced activity compared to some of the other compounds also failed to induce differentiation. Similarly, novel compounds of the invention induced differentiation of cancer cells. Expression of metastatic marker E-cadherin was reduced and expression of differentiation markers fibronectin, vimentin and NF1 were increased (FIG. 162-FIG. 163). Novel compounds of the invention are highly specific. They specifically inhibit pluripotency and/or proliferation of stem cells and cancer cells. Novel compounds of the invention are most effective against cancers that are MUC1* positive and/or NME7$_{AB}$ or NME7-X1 positive. Although we discovered that NME1 dimers, NME7$_{AB}$ and NME7-X1 are all activating ligands of the MUC1* growth factor receptor and they bind to its extracellular domain, we have developed ample evidence that both NME7$_{AB}$ and NME7-X1 have other binding partners and can exert oncogenic effects, independent of MUC1*.

Figure 165:
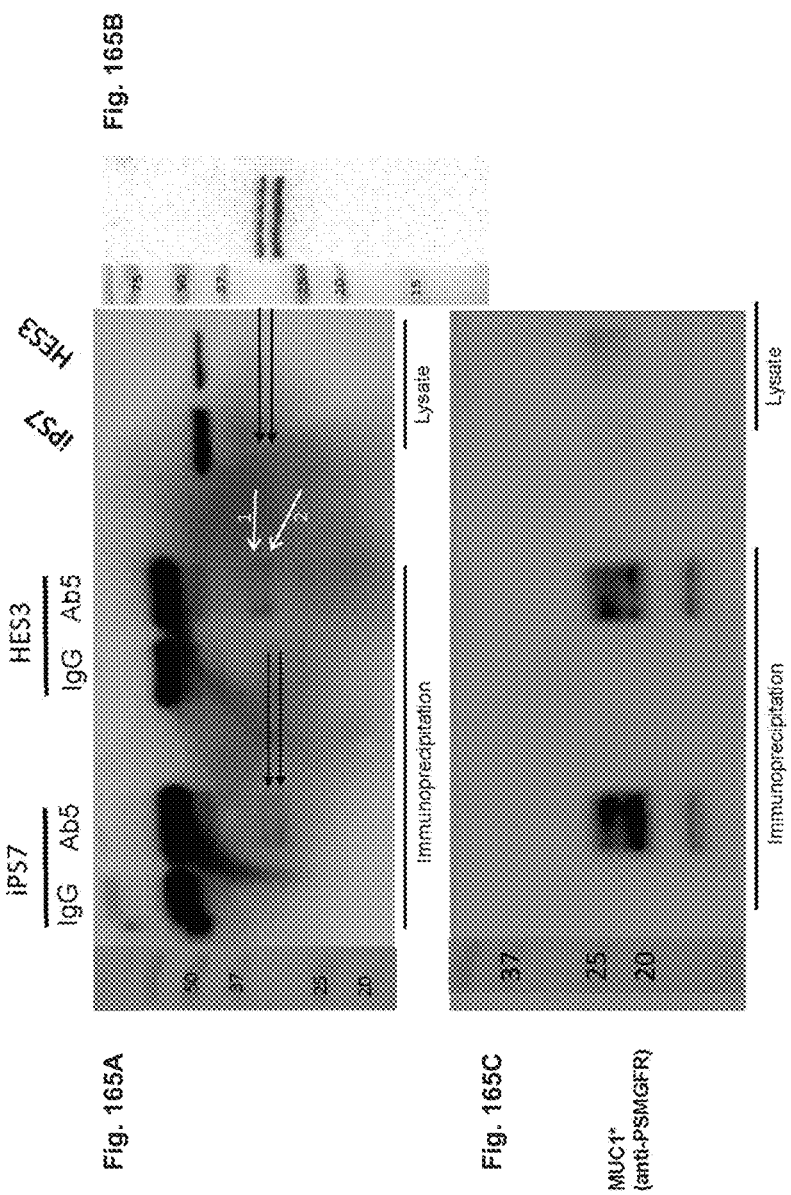
FIG. 165A-165C shows photographs of Western blots of a co-immunoprecipitation experiment. Human induced pluripotent stem (iPS clone 7) cells or human embryonic stem cells (HES clone 3) were lysed and immunoprecipitation experiments were performed with either a control IgG antibody or Ab5 which is an antibody that binds to the cytoplasmic tail of MUC1. The gel was then blotted with an antibody that binds to NME7 (FIG. 165A). The arrows point to two NME7-reactive species, 30 kDa and 33 kDa, that are pulled down by Ab5, the MUC1 antibody but not by the control antibody IgG. The lysate alone was loaded into the two right-most lanes and show that full-length NME7, 42 kDa, is in the lysate but does not bind to MUC1.
Figure 166:
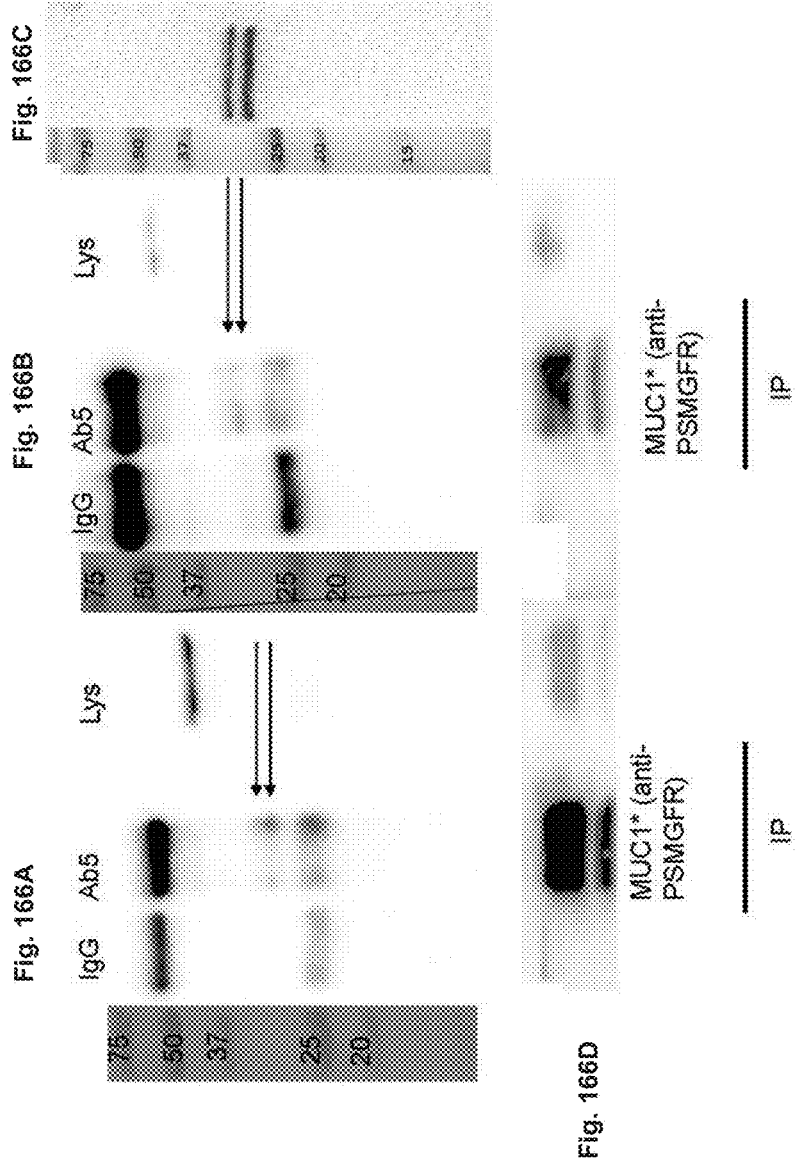
FIG. 166A-166D shows photographs of Western blots of a co-immunoprecipitation experiment. It is the same experiment described above in FIG. 165, but it was performed on T47D cancer cells. The experiment shows that NME7$_{AB}$ and NME7-X1 bind to MUC1* in cancer cells.

NME7$_{AB}$ is the natural growth factor that makes the earliest naïve stem cells grow. NME7$_{AB}$ alone is sufficient for the growth and pluripotency of naïve human stem cells. FIG. 164A-164B shows photographs of human embryos at Day 3 (FIG. 164A) or Day 5 (FIG. 164B) that were stained with anti-NME7$_{AB}$ antibody #61 that binds to the B3 peptide of the B domain of NME7$_{AB}$ or NME7-X1. As can be seen, all the cells at Day 3 are positive for NME7$_{AB}$ but by Day 5, when the morula begins to differentiate, the NME7$_{AB}$ positive cells are restricted to the naïve cells of the inner cell mass. Although NME7$_{AB}$ is expressed in all naïve stem cells, it reportedly is not expressed in adult tissues except in testis. However, we have found it in every metastatic cancer we have examined. We have shown that both naïve stem cells and cancer cells secrete NME7$_{AB}$ and NME7-X1. We show that in both stem cells and cancer cells, both NME7$_{AB}$ and NME7-X1 bind to the extracellular domain of MUC1* and activate pluripotency and growth via ligand-induced dimerization of the MUC1* extracellular domain. FIG. 165A-165C shows photographs of Western blots of a co-immunoprecipitation experiment. Human induced pluripotent stem (iPS clone 7) cells or human embryonic stem cells (HES clone 3) were lysed and immunoprecipitation experiments were performed with either a control IgG antibody or Ab5 which is an antibody that binds to the cytoplasmic tail of MUC1. The gel was then blotted with an antibody that binds to NME7 (FIG. 165A). The arrows point to two NME7-reactive species, 30 kDa and 33 kDa, that are pulled down by Ab5, the MUC1 antibody but not by the control antibody IgG. The lysate alone was loaded into the two right-most lanes and show that full-length NME7, 42 kDa, is in the lysate but does not bind to MUC1. FIG. 165B shows a Western blot of recombinant NME7$_{AB}$ and NME7-X1. To show that NME7$_{AB}$ and NME7-X1 bind to MUC1* and not to full-length MUC1, the gel of FIG. 165A was stripped and re-probed with an anti-MUC1* antibody that binds to the PSMGFR sequence. FIG. 166A-166D shows photographs of Western blots of a co-immunoprecipitation experiment. It is the same experiment described above in FIG. 165, but it was performed on T47D cancer cells. The experiment shows that NME7AB and NME7-X1 bind to MUC1* in cancer cells.

Figure 167:
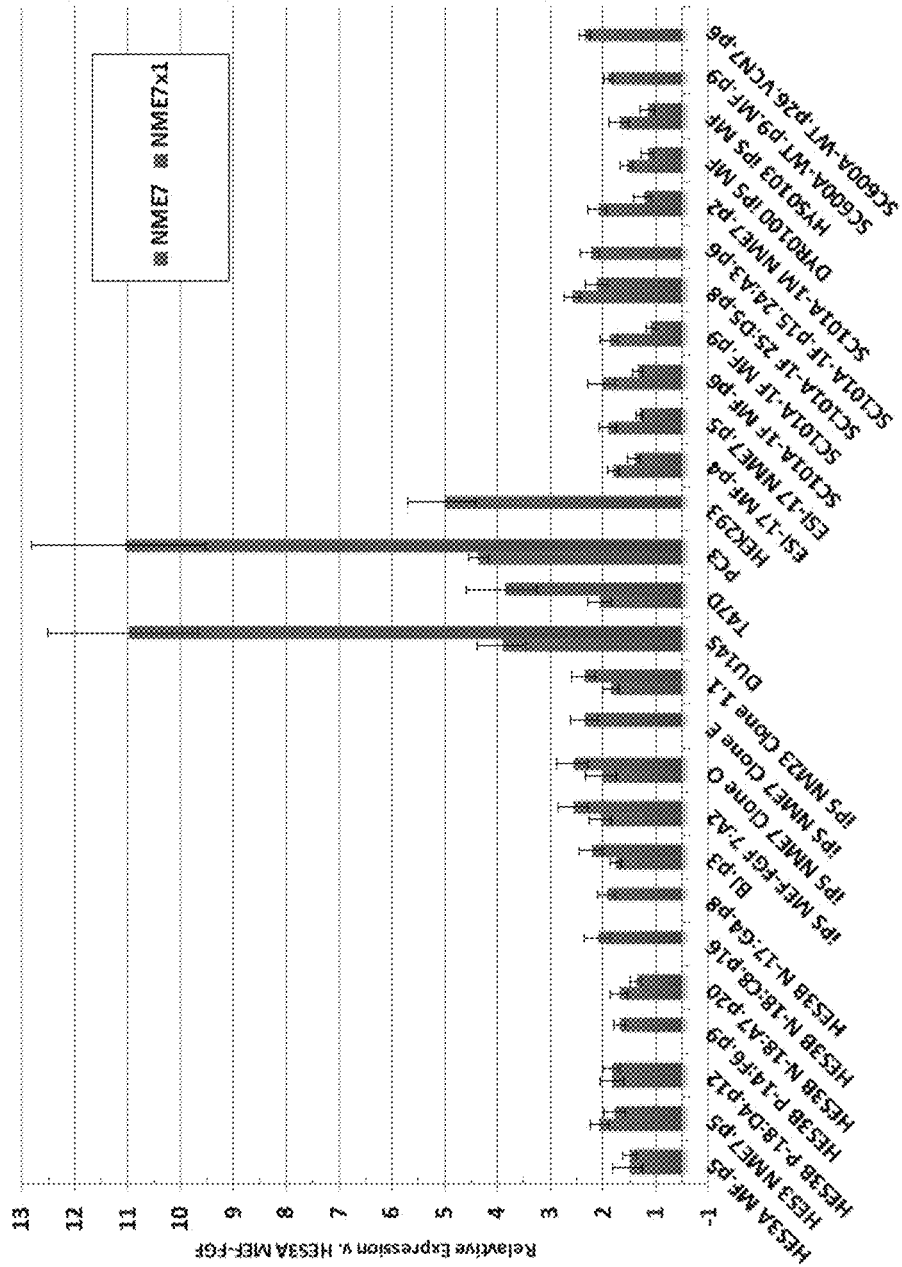
FIG. 167 is a graph of RT-PCR measurement of NME7$_{AB}$ and NME7-X1 in numerous primed state and naïve human stem cell lines and in cancer cell lines DU145, T47D and PC3. The measurements were normalized to primed state human stem cells grown in FGF over MEFs.
Figure 168:
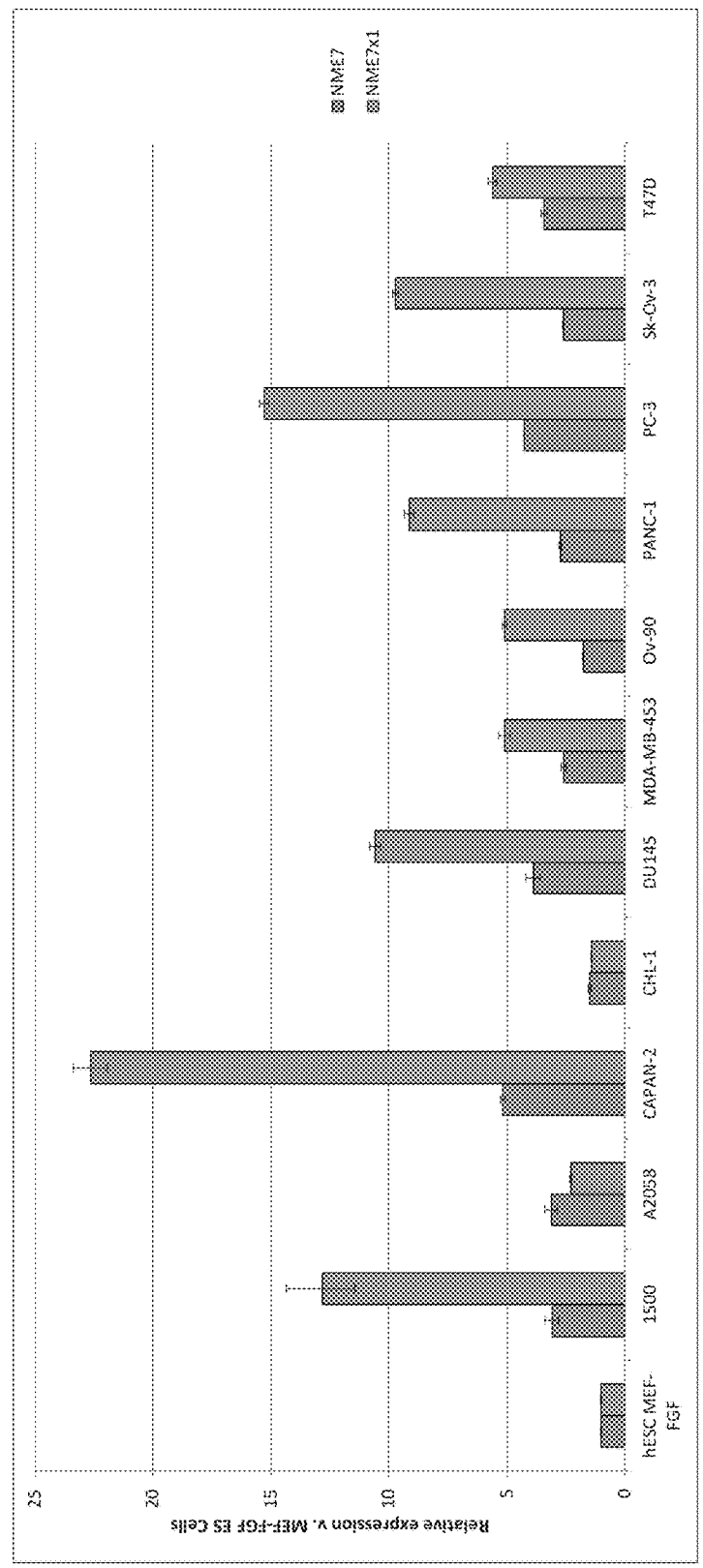
FIG. 168 is a graph of RT-PCR measurement of NME7AB and NME7-X1 in numerous cancer cell lines. The measurements were normalized to primed state human stem cells grown in FGF over MEFs.
Figure 169:
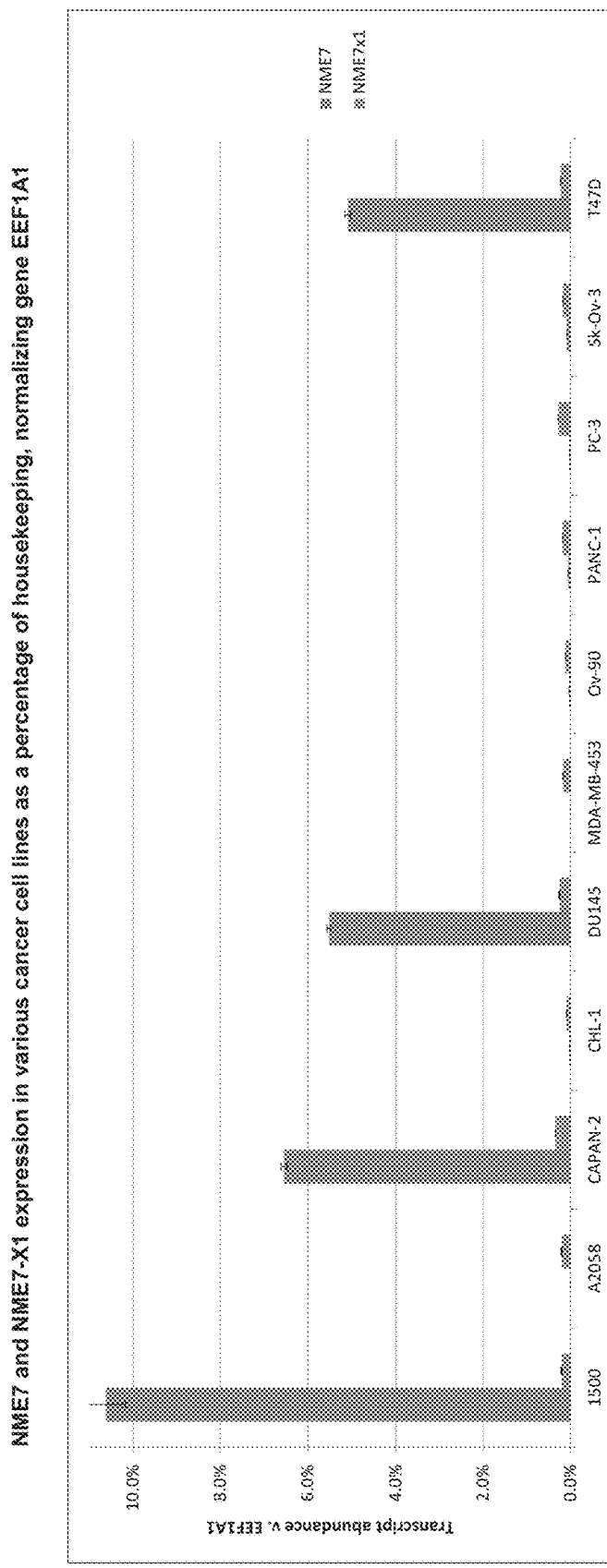
FIG. 169 is a graph of RT-PCR measurement of NME7$_{AB}$ and NME7-X1 in numerous cancer cell lines. Because stem cell lines express high levels of NME7$_{AB}$, in this graph, we show expression of each gene relative to EEF1A1, a housekeeping gene frequently used for comparison of expression across multiple cell lines.

We measured expression of NME7$_{AB}$ and NME7-X1 in numerous naïve and primed human stem cell lines and also in two MUC1* positive cancer cell lines and one MUC1* negative cancer cell line. FIG. 167 is a graph of RT-PCR measurement of NME7$_{AB}$ and NME7-X1 in numerous primed state and naïve human stem cell lines and in cancer cell lines DU145, T47D and PC3. The measurements were normalized to primed state human stem cells grown in FGF over MEFs. The graph shows that compared to stem cells, cancer cells express 2-4-times more NME7$_{AB}$ and 5-10-times more NME7-X1. We also performed RT-PCR on a panel of cancer cell lines to measure NME7$_{AB}$ and NME7-X1 normalized to primed state stem cells (FIG. 168). However, stem cells already express a huge amount of NME7$_{AB}$ as it is the only required growth factor. Therefore we also analyzed the PCR data so that in FIG. 168, expression of NME7$_{AB}$ and NME7-X1 is given as a percentage of EEF1A1, which is a housekeeping gene frequently used for comparison of gene expression across multiple cell lines.

Figure 171:
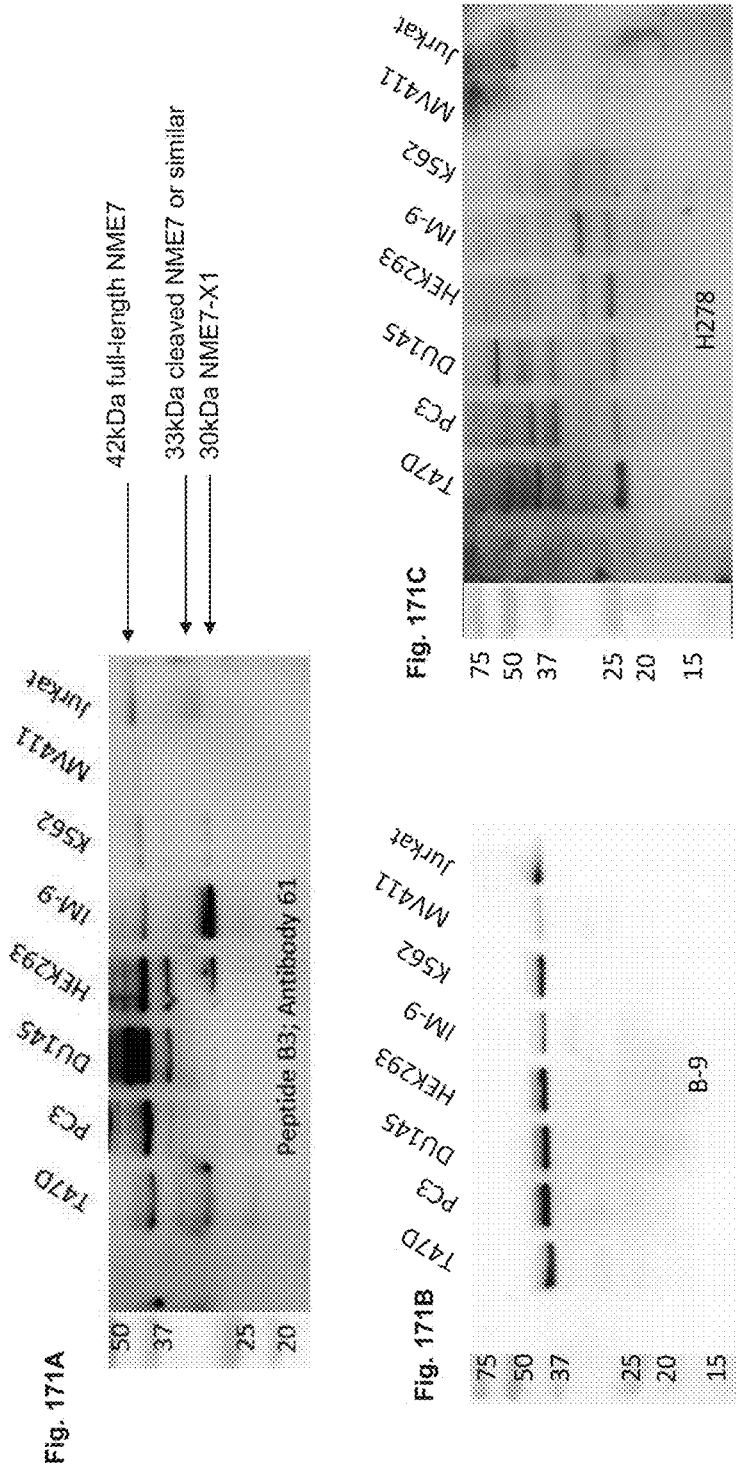
FIG. 171A-171C shows Western blots of various cancer cell lines probed with our antibody 61 or with commercially available antibodies.

Another way to assess expression of MUC1*, NME7$_{AB}$ and NME7-X1 is by Western blot. FIG. 170A-170C shows Western blots of various cancer cell lines. FIG. 170A shows a Western blot of cancer cell lines probed for expression of full-length MUC1, where the probing antibody was anti-tandem repeat antibody VU4H5. FIG. 170B shows a Western blot of cancer cell lines probed for expression of cleaved MUC1, MUC1*, where the probing antibody was an antibody that binds to the PSMGFR sequence of the MUC1* extracellular domain. MUC1* positive cell lines include breast cancer cell line T47D, prostate cancer cell line DU145, breast cancer cell line BT-474, melanoma line CHL-1, melanoma line A2058, and pancreatic cell line CAPAN-2. However, expression of MUC1* in BT-474, CHL-1, A2058 are MUC1 positive by PCR and according to literature but expression is very low and is not visible in this blot. Prostate cancer cell line PC-3 and pancreatic cancer cell line PANC-1 are both MUC1 negative by PCR and according to literature. FIG. 170C shows a Western blot of cancer cell lines probed for expression of NME7, where the probing antibody was a polyclonal antibody that binds to the sequence of NME7$_{AB}$ or NME7-X1. FIG. 171A-171C shows Western blots of various cancer cell lines probed with our antibody #61 or with commercially available antibodies. FIG. 171A shows a Western blot of cancer cell lines probed with our anti-NME7 antibody that binds to the B3 peptide. FIG. 171B-171C shows Western blots of cancer cell lines probed with commercially available anti-NME7 antibodies B9 and H278 respectively. As can be seen, antibody #61 binds to NME7AB and NME7-X1 (33 kDa and 30 kDa) but does not bind to related proteins NME1 and NME2 at 17 kDa and 21 kDa. NME1 and NME2 are expressed in all cells. In contrast, B9 only recognizes full-length NME7 42 kDa and H278 recognizes lower molecular weight NME1 and NME2.

Figure 172:
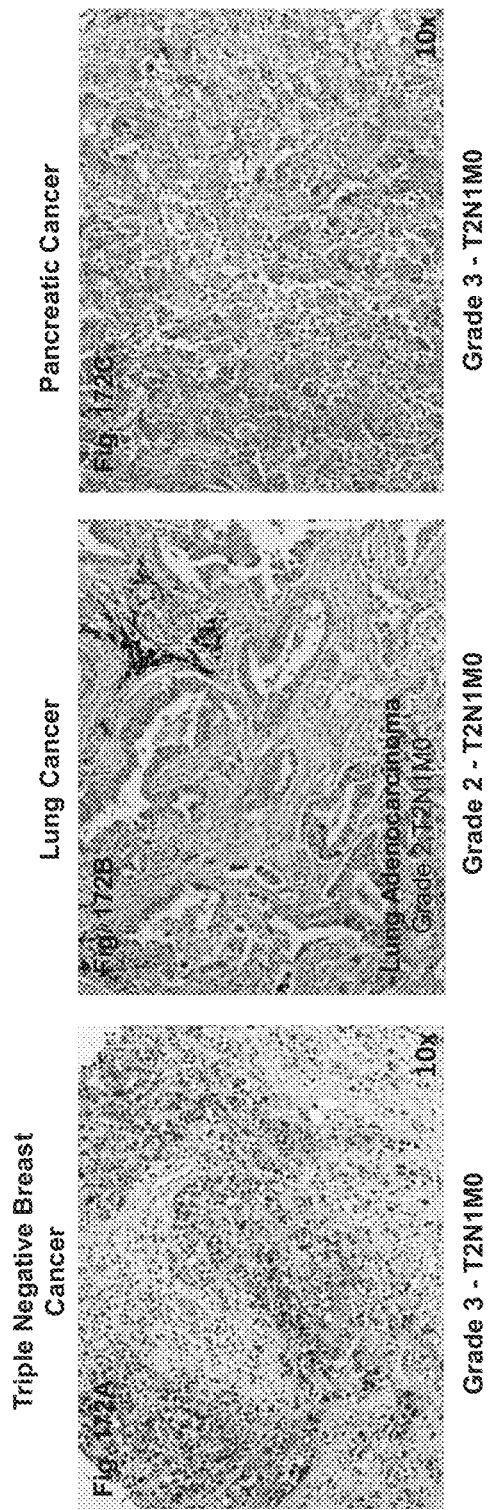
FIG. 172A-172C shows photographs of human cancerous tissue specimens stained with MNC2 anti-MUC1* monoclonal antibody that binds to the N-10 peptide of the MUC1* extracellular domain. Shown are breast cancer (FIG. 172A), lung cancer (FIG. 172B) and pancreatic cancer (FIG. 172C).
Figure 173:
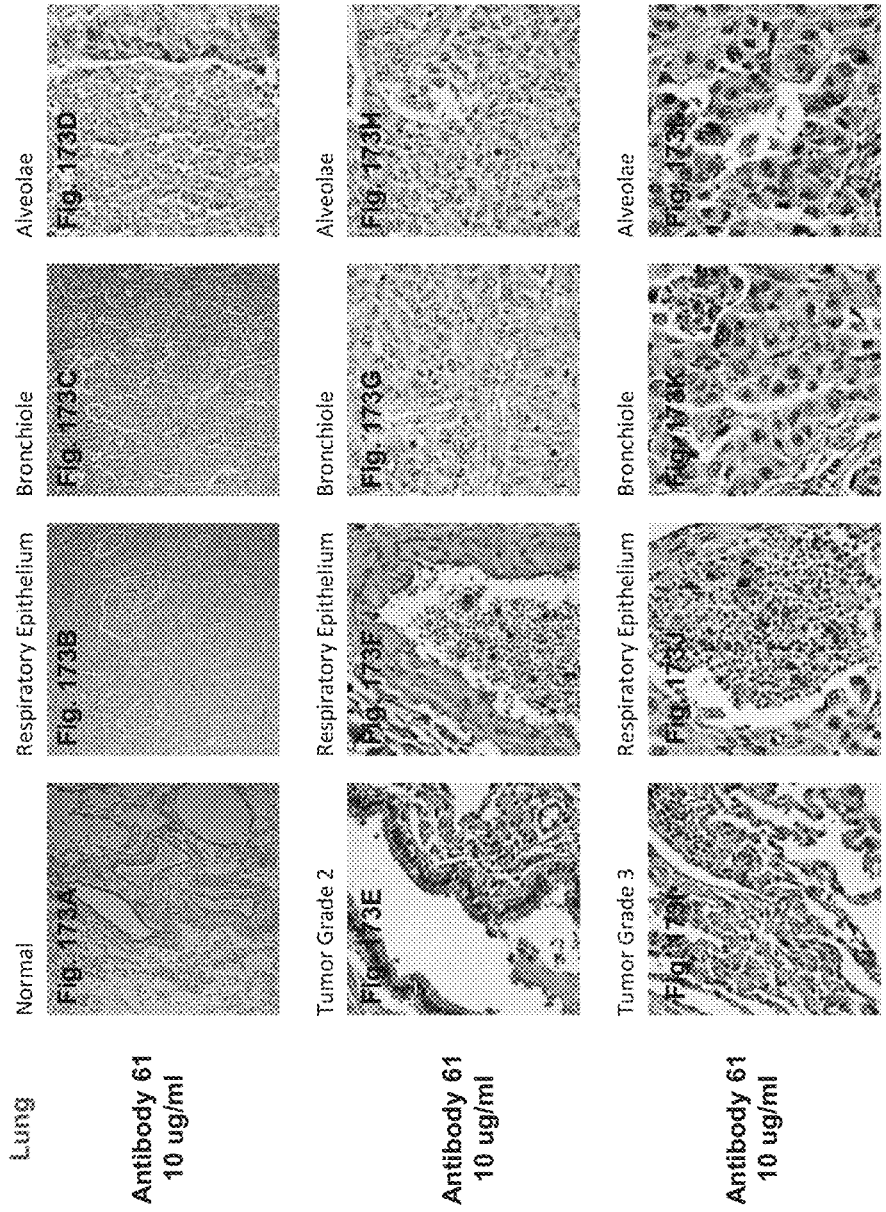
FIG. 173A-173L shows photographs of human lung tissue specimens stained with antibody #61 anti-NME7$_{AB}$ polyclonal antibody that binds to the B3 peptide of the B domain of NME7. Shown are normal lung (FIG. 173A-173D), Grade 2 lung cancer (FIGS. 173E-173H) and Grade 3 metastatic lung cancer (FIG. 1731-173L). As can be seen, antibody 61 does not bind to normal tissue but only binds to cancerous tissue and staining increases as metastatic status increases.

Human tissue specimens were also probed to determine the extent of MUC1* and NME7AB or NME7-X1 expression in tumors from multiple patients. Cancer arrays, containing roughly 300-400 tumors from different patients in one array were stained with either a polyclonal anti-MUC1* antibody that binds to the PSMGFR peptide or monoclonal antibody C2 that binds to the N-10 peptide. About 90% of the breast cancers were stained by the polyclonal antibody and the C2 monoclonal antibody stained 85% of triple negative breast cancers, 83% ovarian cancers, 78% pancreatic cancers and 71% lung cancers. FIG. 172A-172C shows photographs of human cancerous tissue specimens stained with MNC2 anti-MUC1* monoclonal antibody that binds to the N-10 peptide of the MUC1* extracellular domain. Shown are breast cancer (FIG. 172A), lung cancer (FIG. 172B) and pancreatic cancer (FIG. 172C). C2 antibody did not bind to normal tissues. Anti-NME7$_{AB}$ antibody that binds to the B3 peptide of the B domain of NME7$_{AB}$ and NME7-X1 selectively bound to cancerous tissues, where its expression dramatically increased with metastatic state. FIG. 173A-173L shows photographs of human lung tissue specimens stained with antibody #61 anti-NME7$_{AB}$ polyclonal antibody that binds to the B3 peptide of the B domain of NME7. Shown are normal lung (FIG. 173A-173D), Grade 2 lung cancer (FIGS. 173E-173H) and Grade 3 metastatic lung cancer (FIG. 173I-173L). As can be seen, antibody 61 does not bind to normal tissue but only binds to cancerous tissue and staining increases as metastatic status increases.

Novel compounds of the invention are powerful agents for the treatment or prevention of cancers and metastatic cancers. The novel compounds of the invention will be most effective for the treatment of cancers that are MUC1* positive and/or NME7AB or NME7-X1 positive. In one aspect of the invention, a biological sample from a patient is tested for the presence of MUC1*, NME7$_{AB}$ or NME7-X1, and upon finding that the patient's cancer is positive for MUC1*, NME7AB or NME7-X1, a compound of the invention is administered to the patient in an amount suitable to prevent or treat the cancer. In one instance, the patient sample is subjected to a test, such as PCR, to determine the amount of nucleic acid that encodes MUC1, NME7 or NME7-X1. In one aspect of the invention, the patient's cancer is considered to be MUC1* positive, NME7$_{AB}$ positive or NME7-X1 positive if expression of those genes is comparable to, or higher than, their expression in human pluripotent stem cells. In another aspect of the invention, the patient's cancer is considered to be MUC1* positive, NME7$_{AB}$ positive or NME7-X1 positive if expression of those genes is equal to or greater than 0.5% of EEF1A1 expression in those cells. In yet another aspect of the invention, the patient's cancer is considered to be MUC1* positive if the patient's tissue specimen is contacted with an antibody that binds to the PSMGFR peptide or the N-10 peptide and stains the tissue with a pathologist's standard score 1-4 ("+–++++"). In another aspect of the invention, the patient's cancer is considered to be NME7$_{AB}$ positive or NME7-X1 positive if the patient's tissue specimen is contacted with an antibody that binds to the B3 peptide of NME7 and stains the tissue with a pathologist's standard score 1-4 ("+–++++").

Compounds

Set forth below are exemplified compounds for use in the treatment or prevention of cancer. The below exemplified compounds are set forth also in FIGS. 18 to 27.

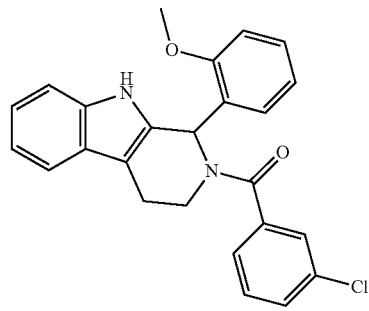

MN0477

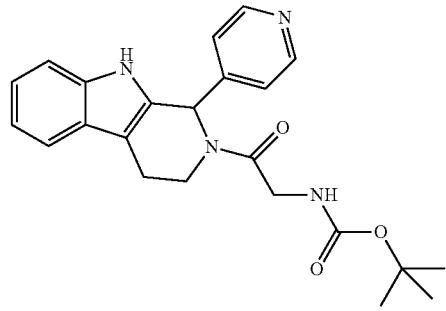

MN0580

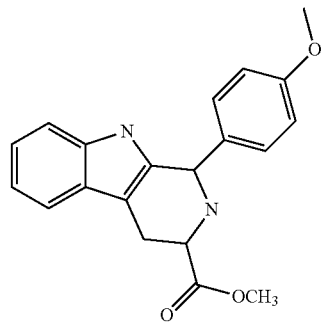

MN0618

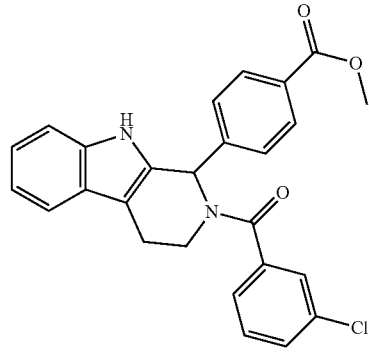

MN0642

MN0716
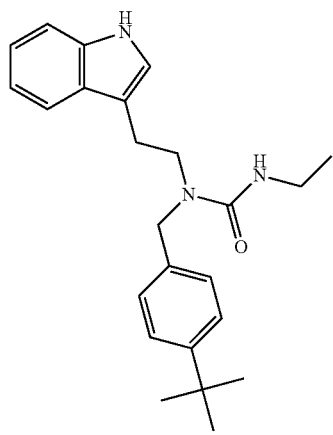
MN0733
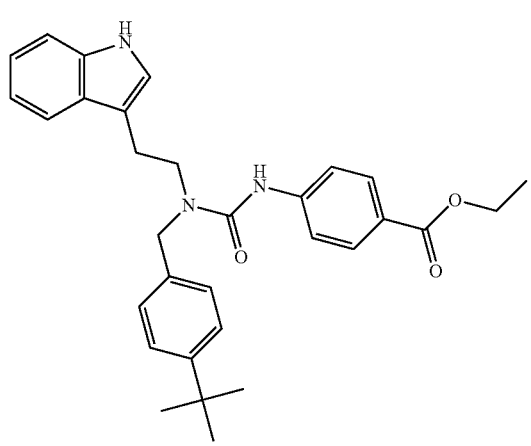
MN0908
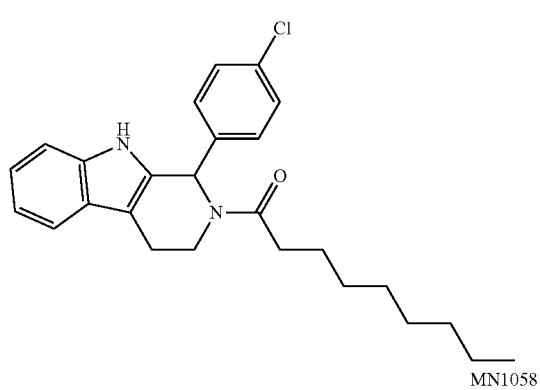
MN1058
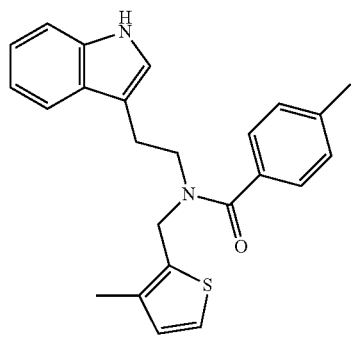
MN1130
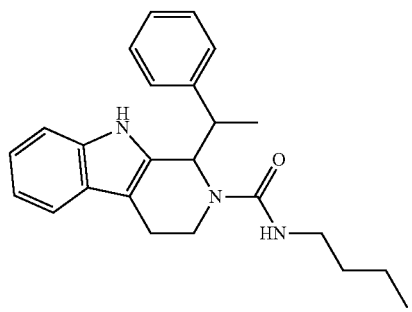
MN1131
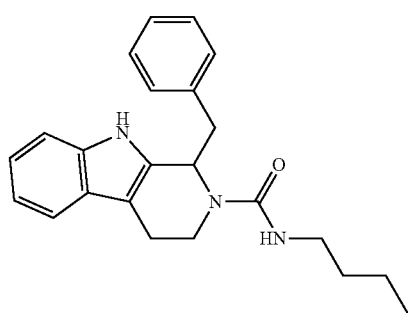
MN1132
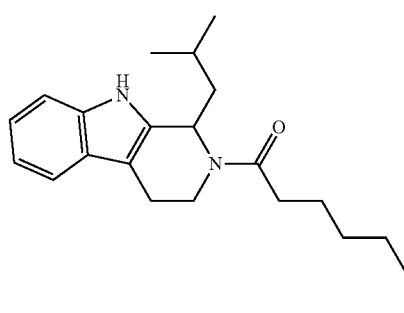
MN1133
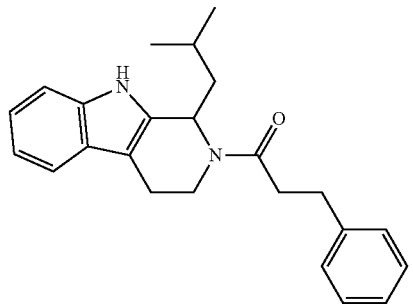
MN1135
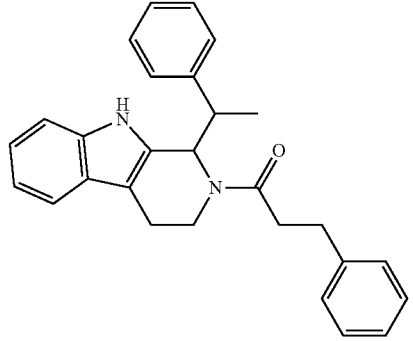

MN1137
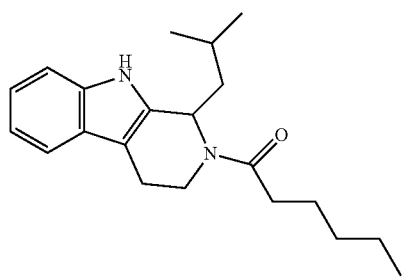
MN1157
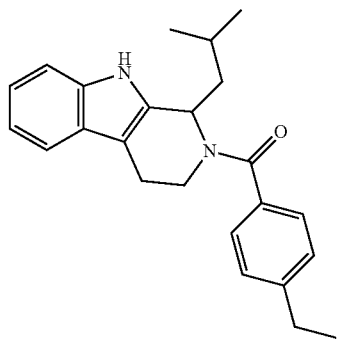
MN1138
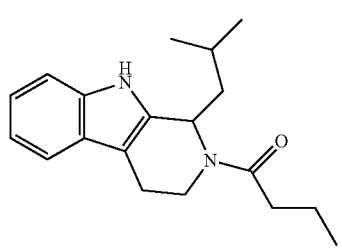
MN1158
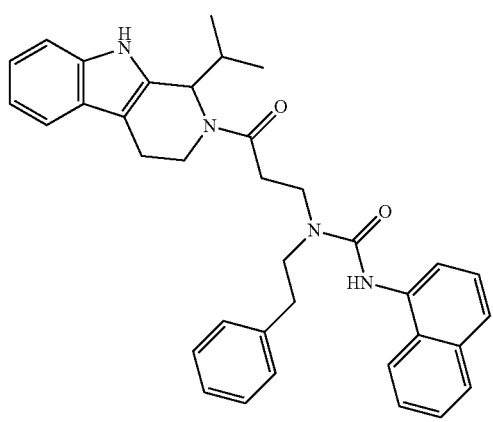
MN1151
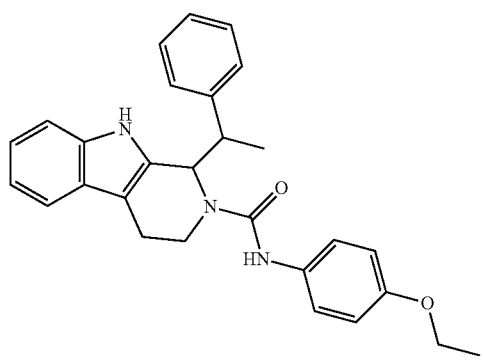
MN1160
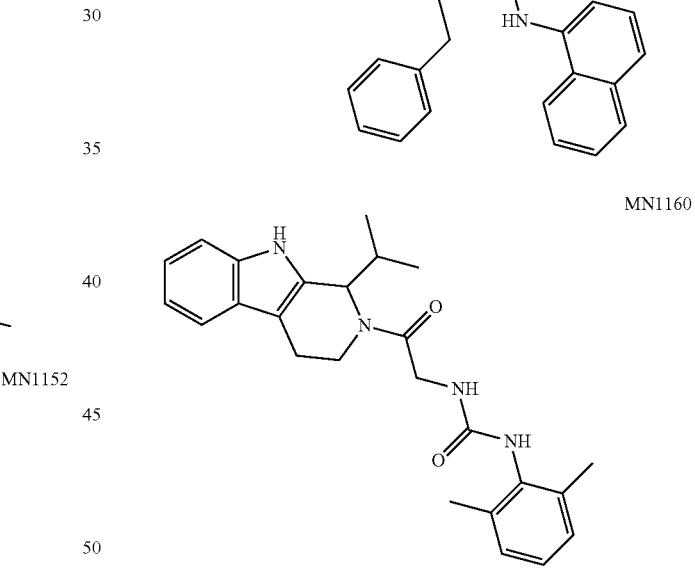
MN1152
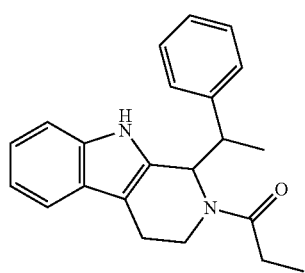
MN1156
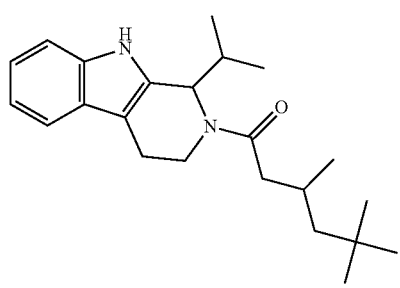
MN1169
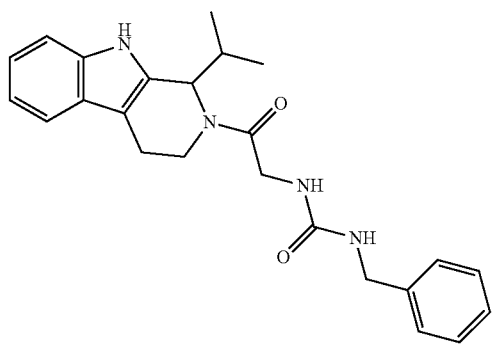

MN1171
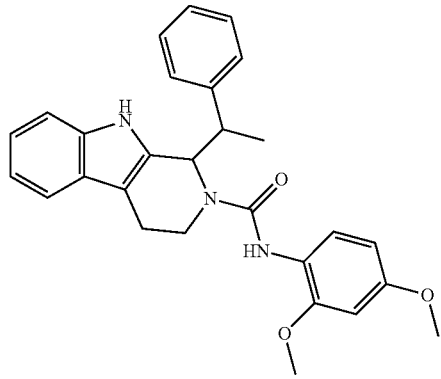
MN1172
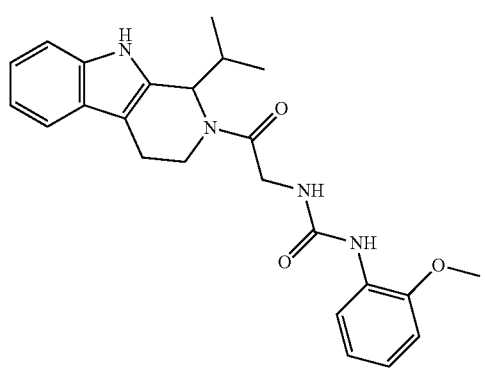
MN1184
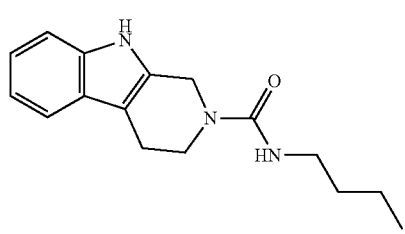
MN1186
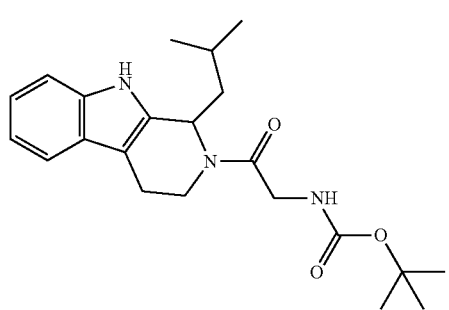
MN1188
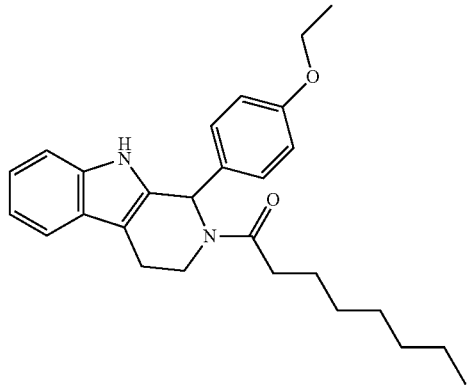
MN1189
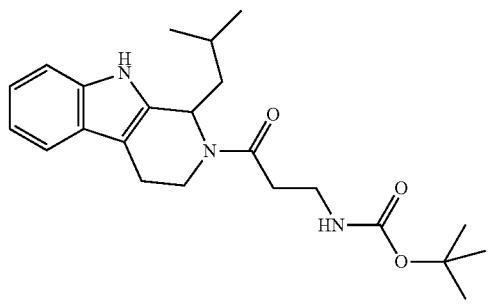
MN1190
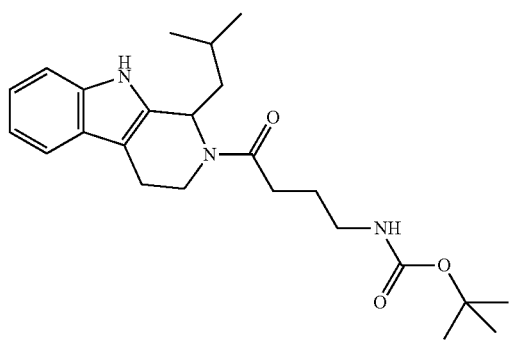
MN1193
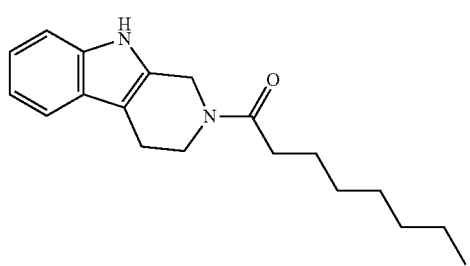

MN1194
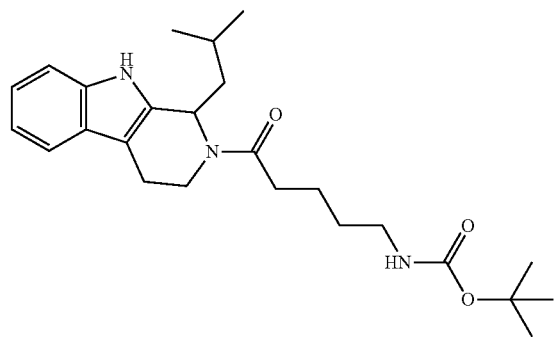
MN1207
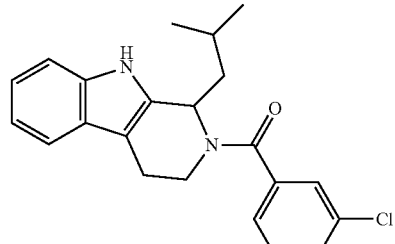
MN1195
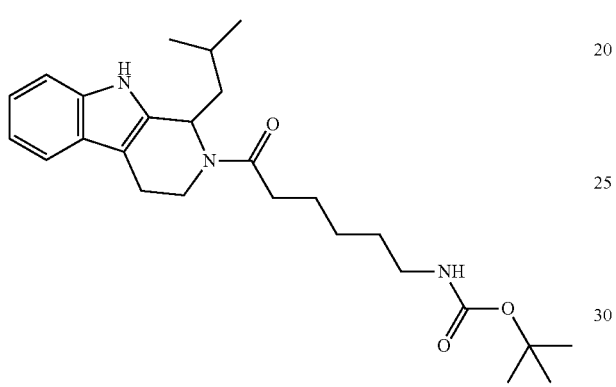
MN1208
MN1209
MN1197
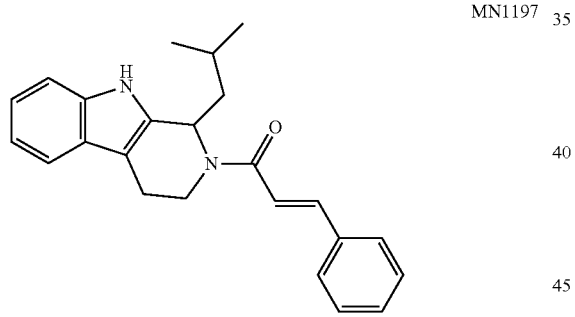
MN1203
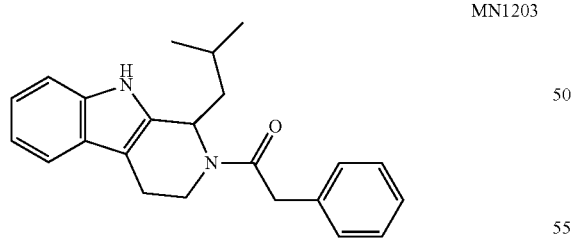
MN1210
MN1206
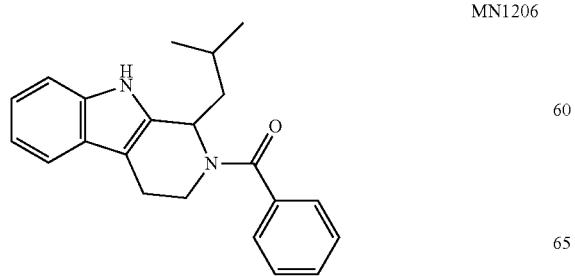
MN1211
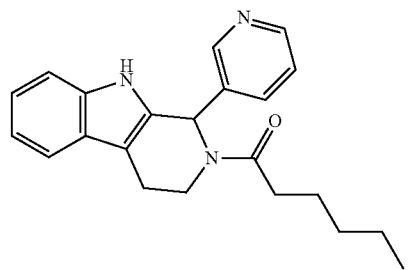

MN1212
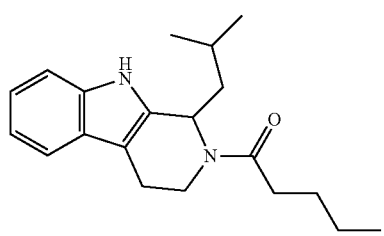
MN1213
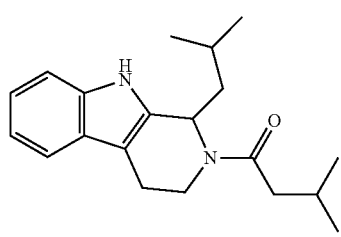
MN1214
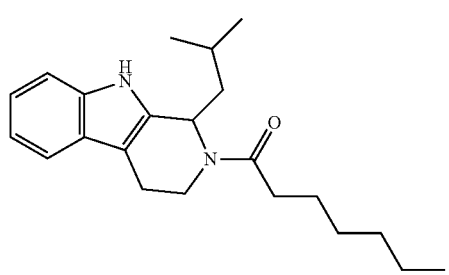
MN1216
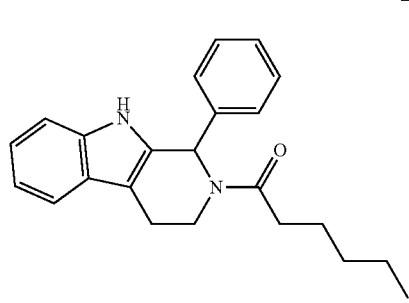
MN1217
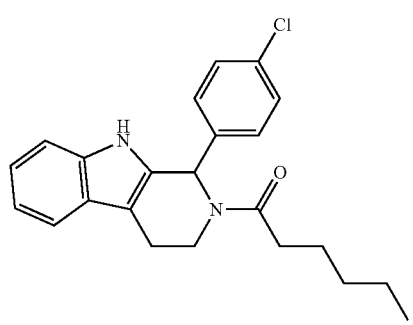
MN1218
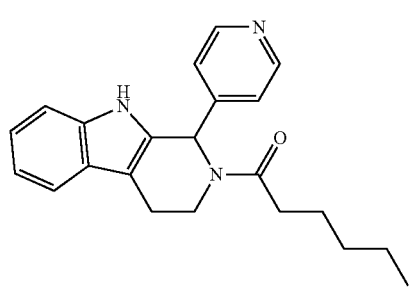
MN1219
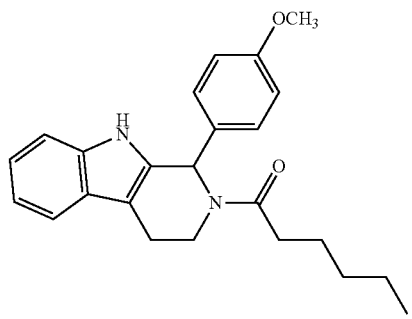
MN1220
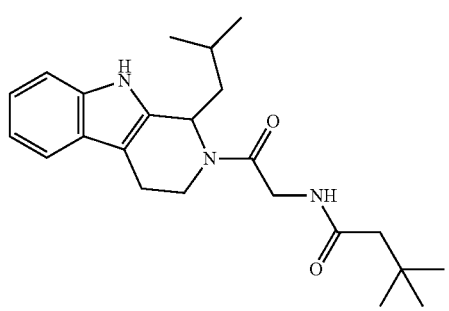
MN1221
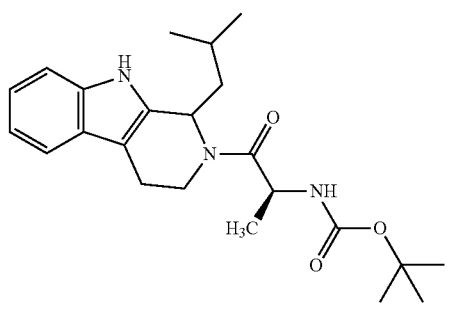
MN1222
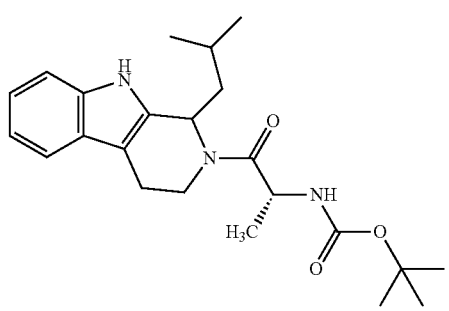
MN1223
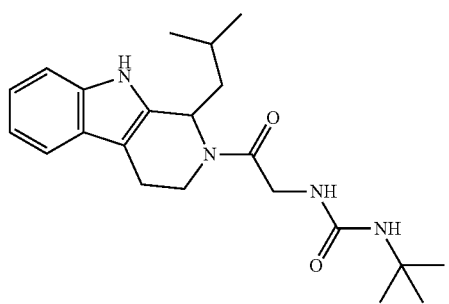

MN1224
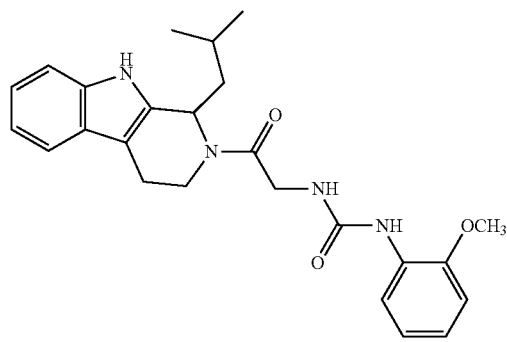
MN1228
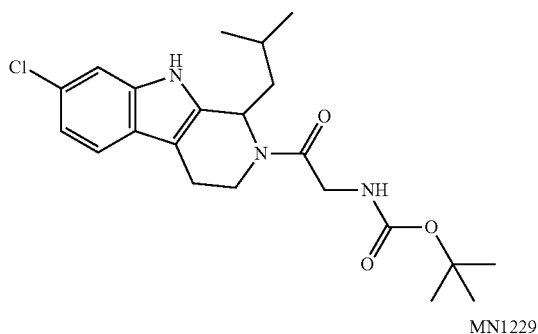
MN1225
MN1229
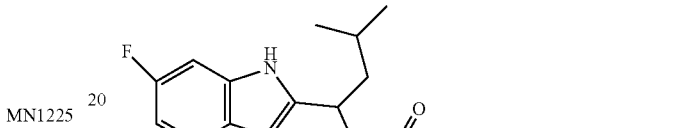
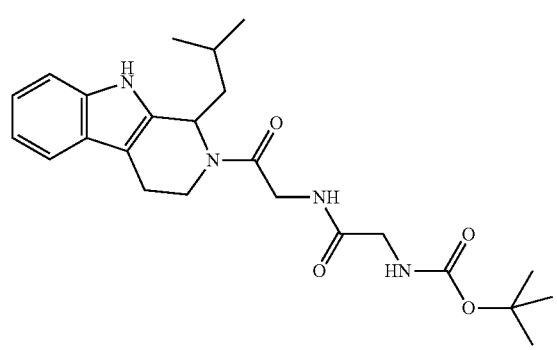
MN1230
MN1226
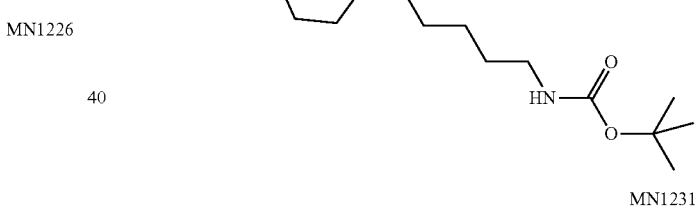
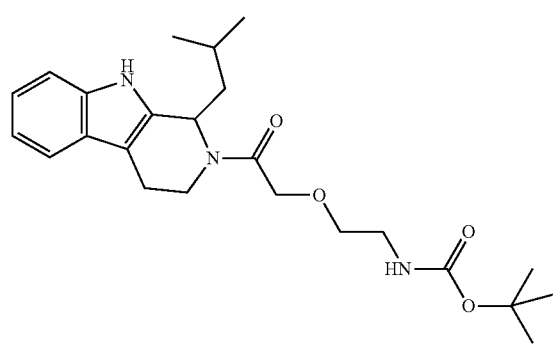
MN1231
MN1227
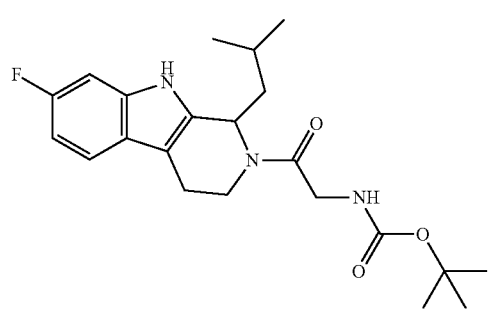
MN1232
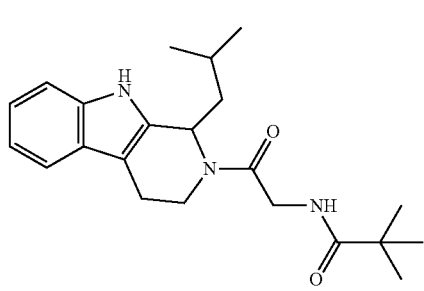

MN1233
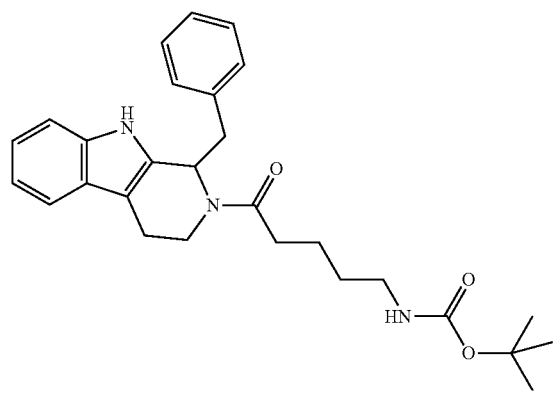
MN1234
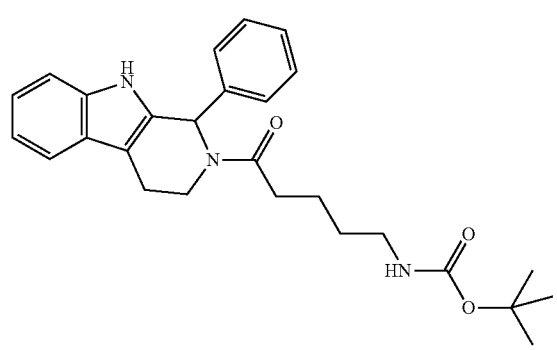
MN1235
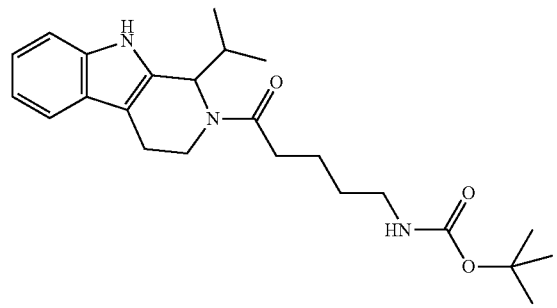
MN1236
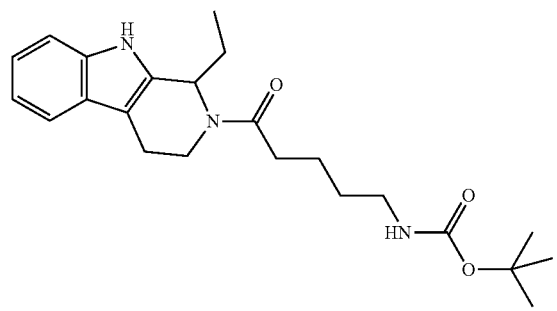
MN1237
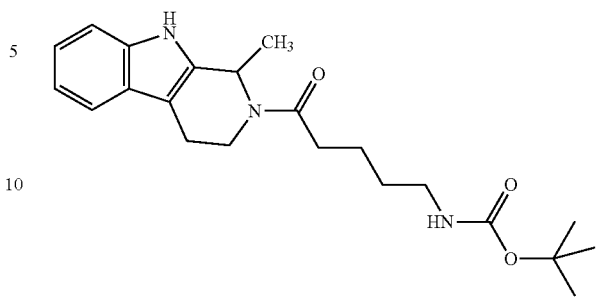
MN1238
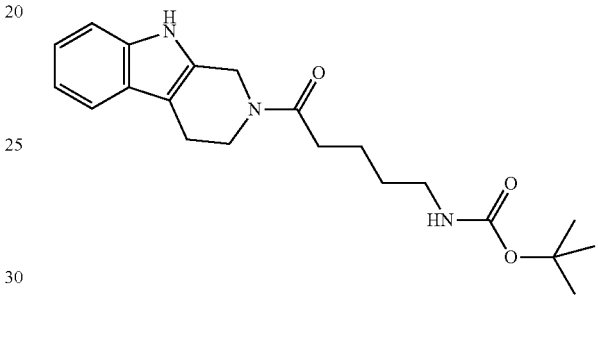
MN1239
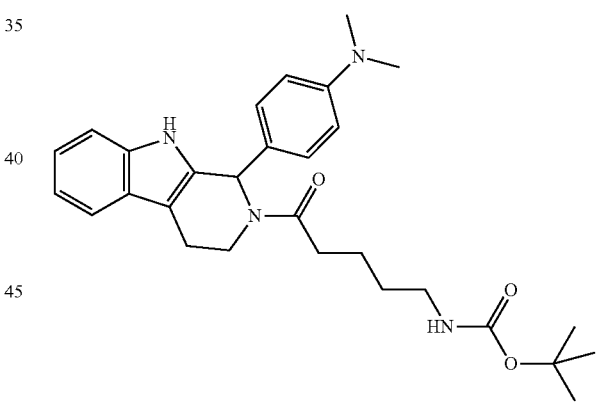
MN1240
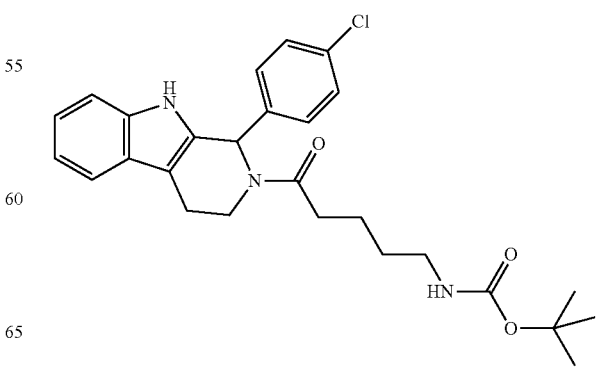

MN1241
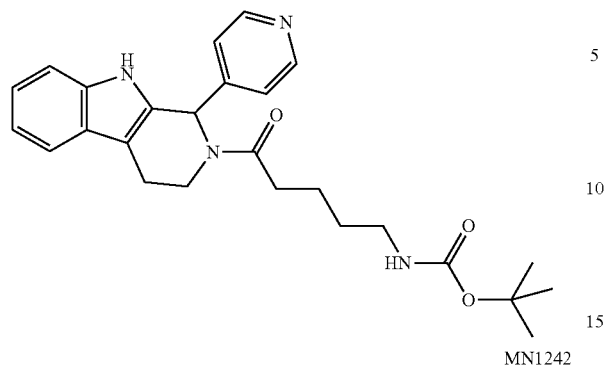
MN1245
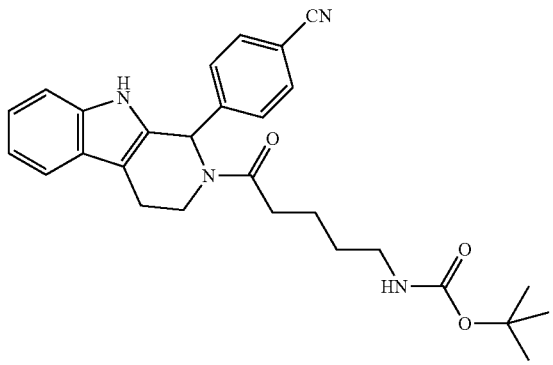
MN1242
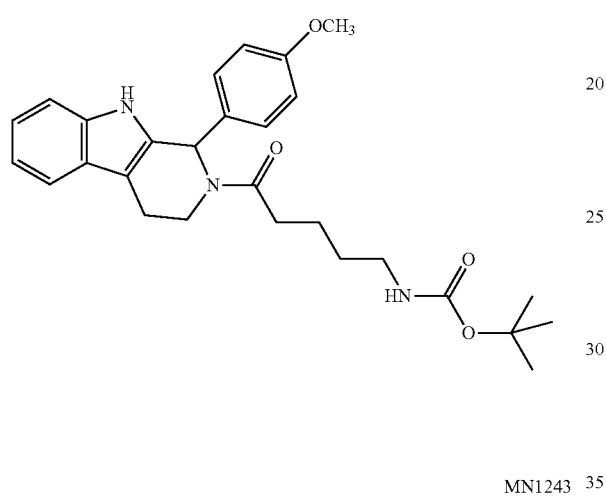
MN1246
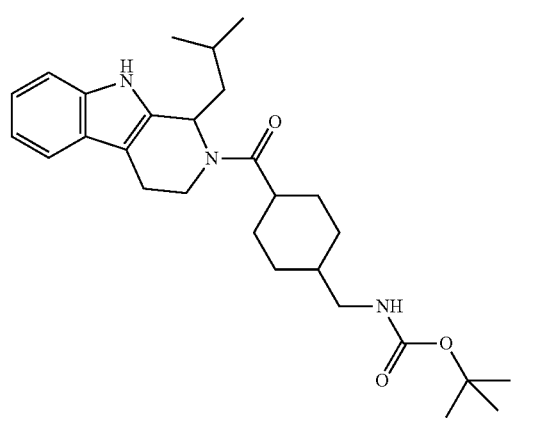
MN1243
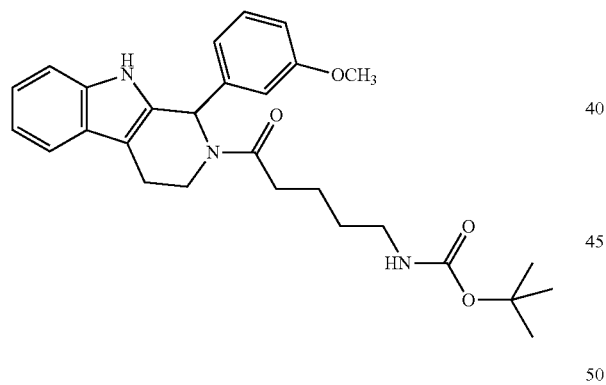
MN1247
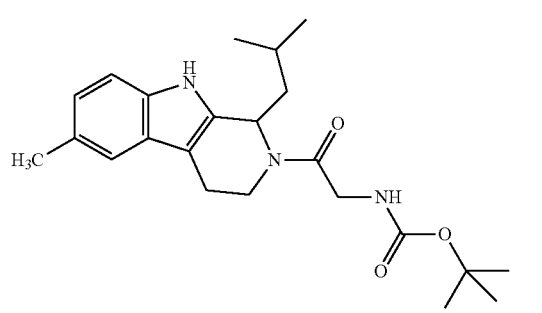
MN1244
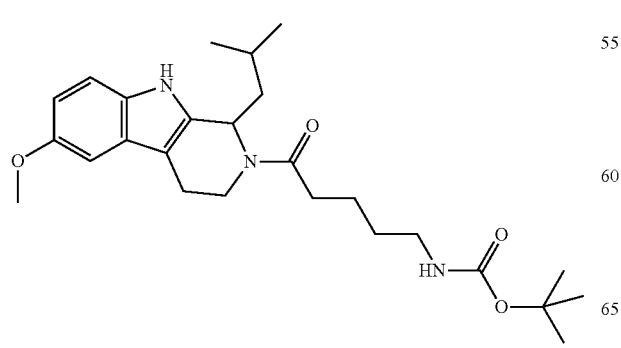
MN1248
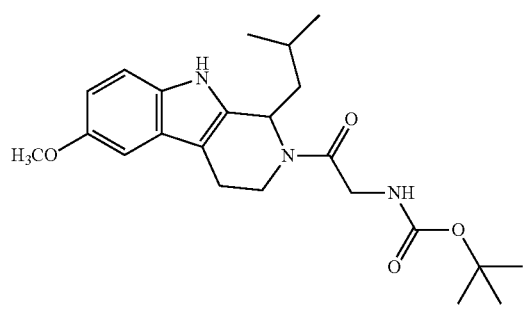

MN1249
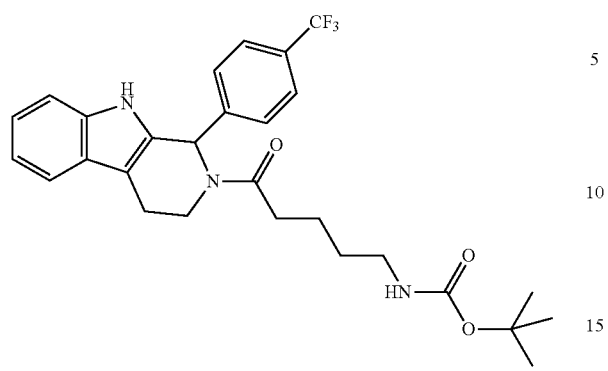
MN1250
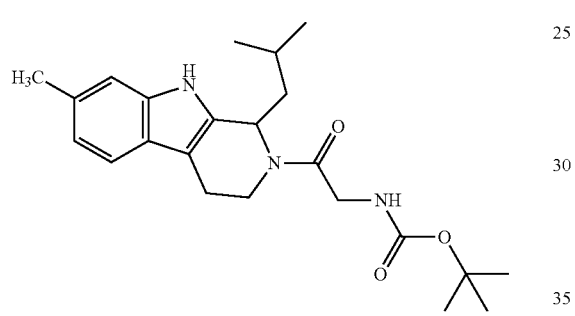
MN1251
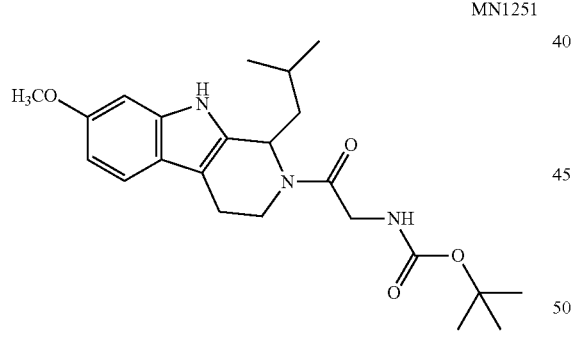
MN1252
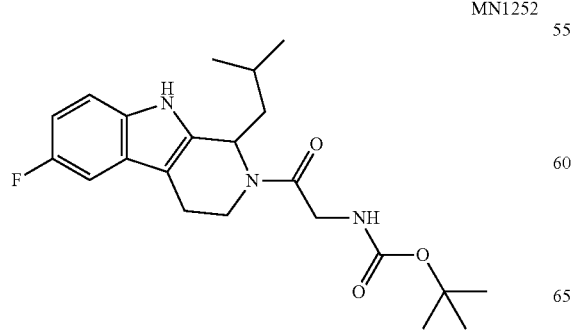
MN1253
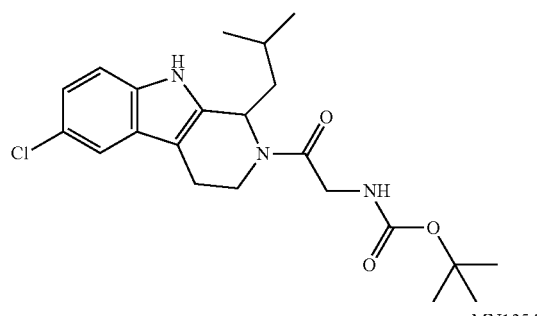
MN1254
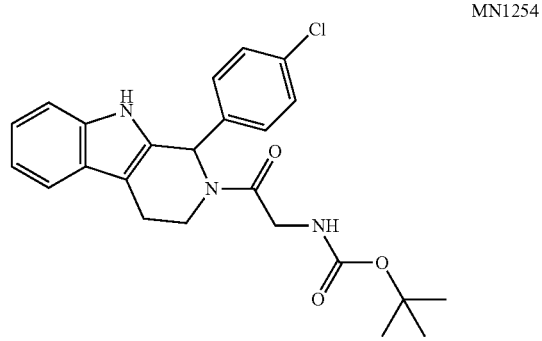
MN1255
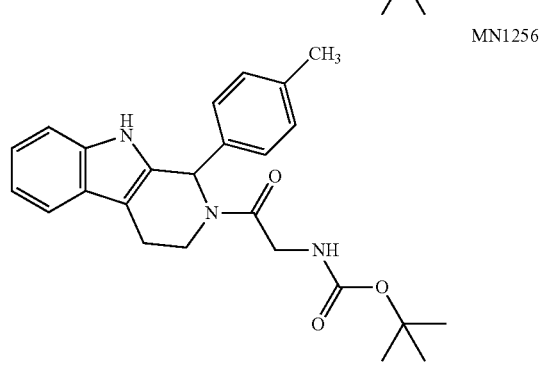
MN1256
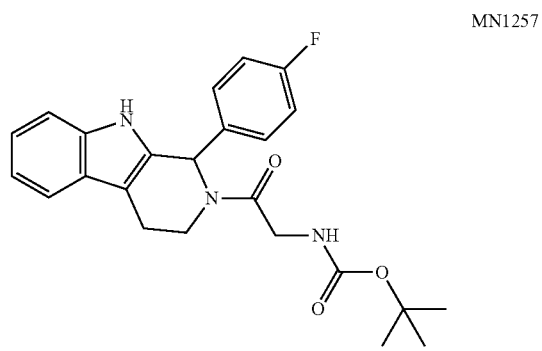
MN1257

MN1258
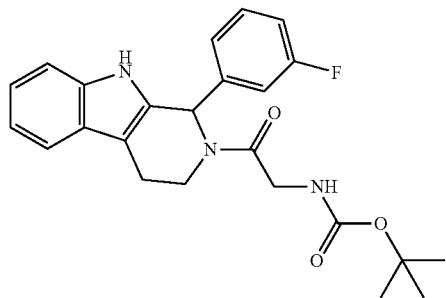
MN1259
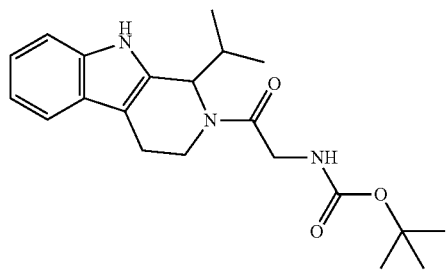
MN1260
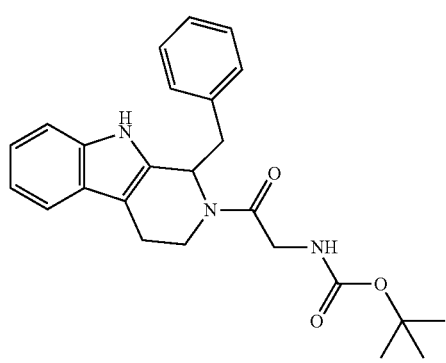
M1261
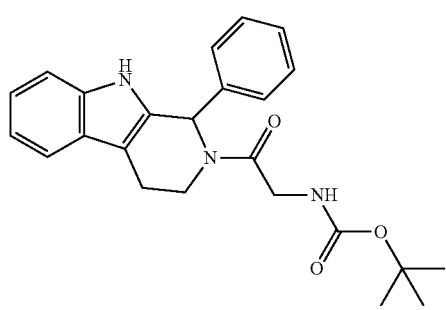
MN1262
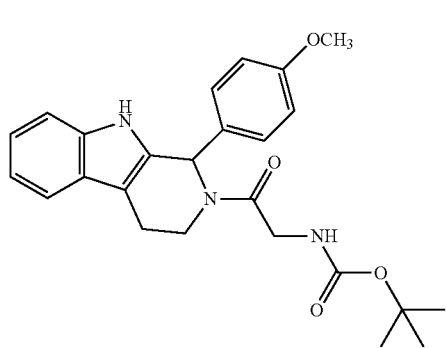
MN1263
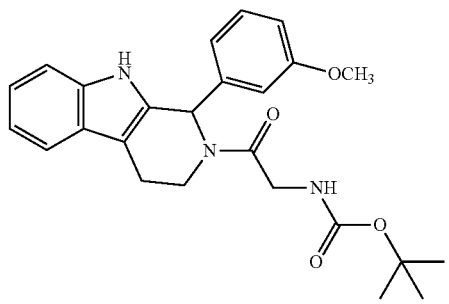
MN1264
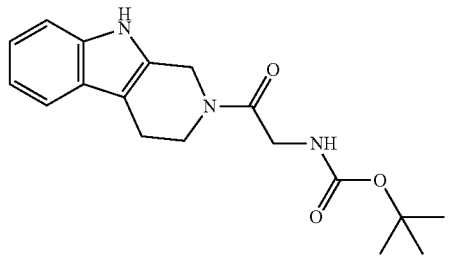
MN1265
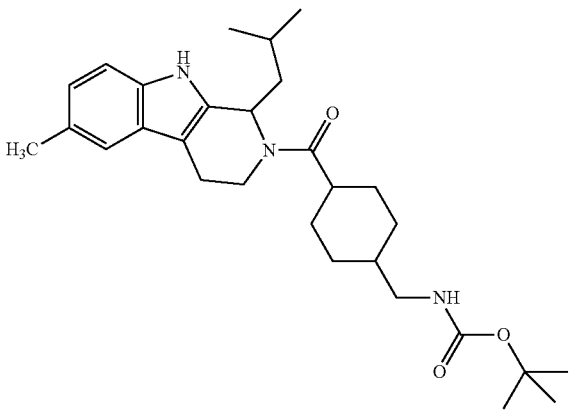
MN1266
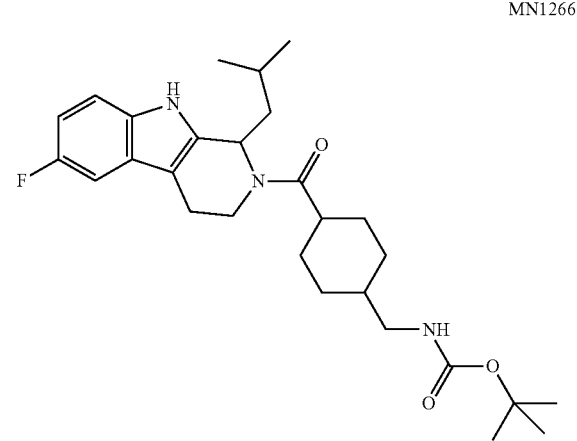

MN1270
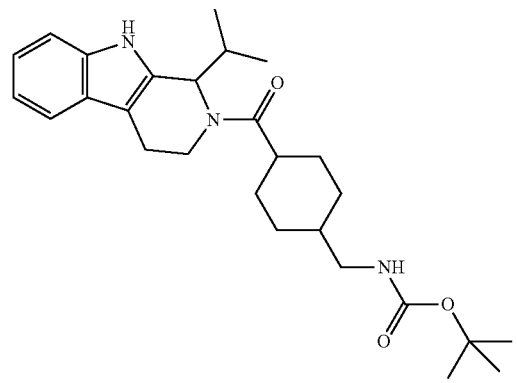
MN1271
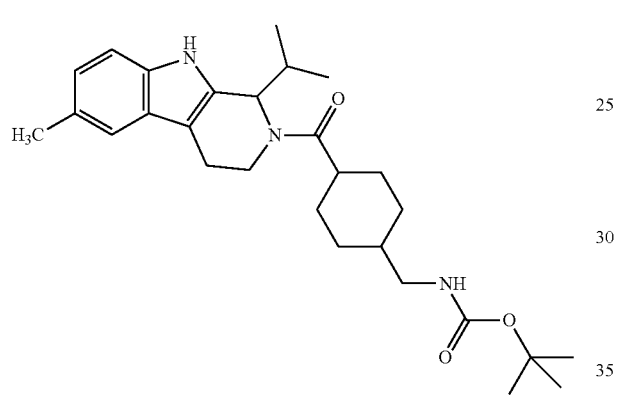
MN1272
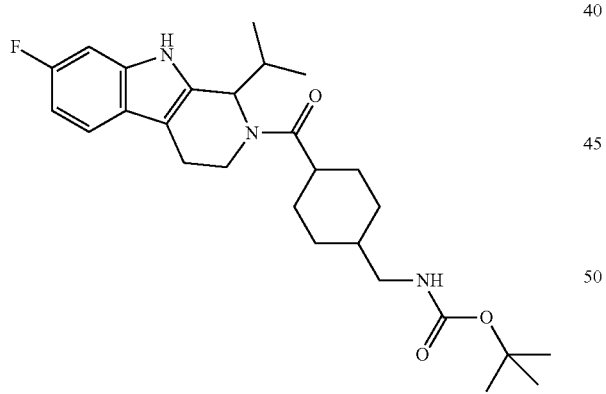
MN1279
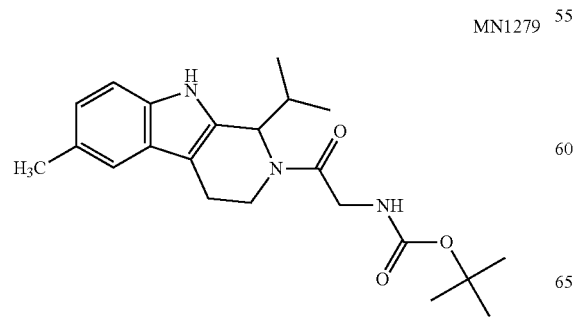
MN1280
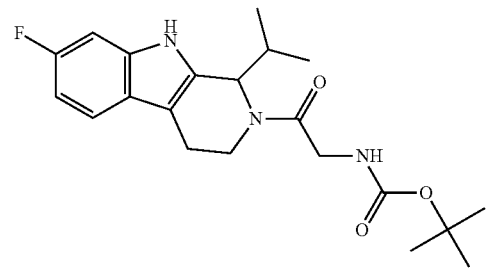
MN1285
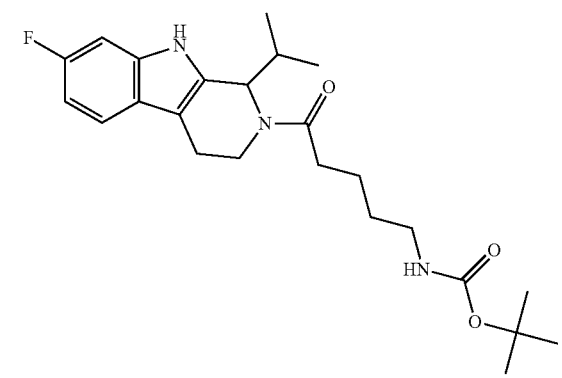
MN1286
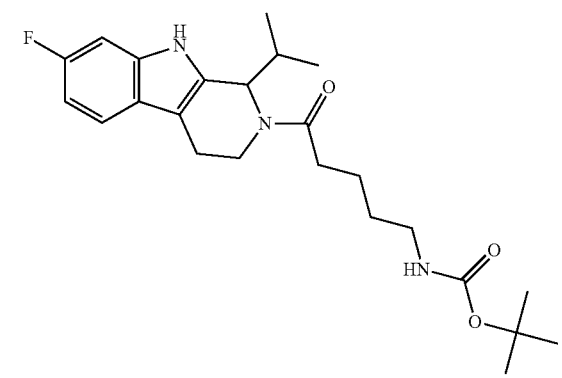
MN1289
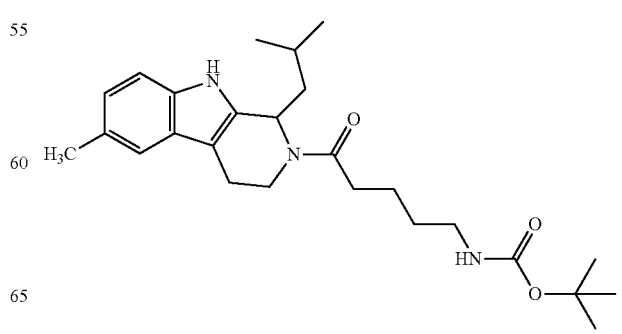

-continued

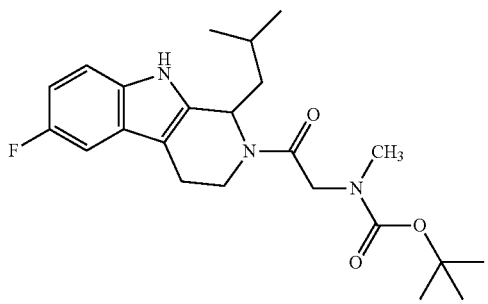
MN1290

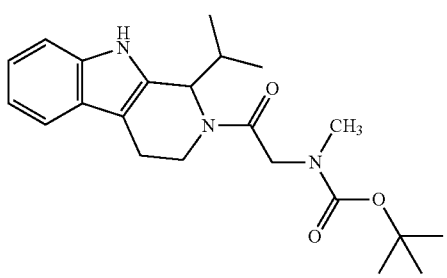
MN1291

Described herein are compounds for use in the treatment or prevention of cancer. In the context of the compounds described herein, the following definitions apply:

In the context of the present specification, unless otherwise stated, an "alkyl" substituent group or an alkyl moiety in a substituent group may be linear or branched, or be or include one or more cycloalkyl groups. Suitable alkyl groups include but are not limited to C1-C9 alkyl groups, C1-C6 alkyl groups, C1-C4 alkyl groups, and C1-C3 alkyl groups. Examples of alkyl groups/moieties include methyl, ethyl, n-propyl, i-propyl, n-butyl, i-butyl, t-butyl, n-pentyl, 2,4,4-trimethylpentyl, 2-methylcyclopentyl, cyclopentylmethyl and cycloalkyl groups/moieties as exemplified below. All alkyl groups, unless otherwise stated, may be substituted or unsubstituted.

"Alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —H(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$), —CH(CH$_3$)(CH$_2$CH$_3$), —CH$_2$CH$_2$CH(CH$_3$)$_2$, CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, CH$_2$CH$_2$C(CH$_2$CH$_3$)$_3$, —CH(CH$_3$)CH$_2$—CH(CH$_3$)$_2$, —CH(CH$_3$)CH(CH$_3$)CH(CH$_3$)$_2$, CH(CH$_2$CH$_3$)CH(CH$_3$)CH(CH$_3$)(CH$_2$CH$_3$), and others.

"Halogen" or "halo" refers to chloro, bromo, fluoro, and iodo groups. The term "haloalkyl" refers to an alkyl radical substituted with one or more halogen atoms. The term "haloalkoxy" refers to an alkoxy radical substituted with one or more halogen atoms.

A "haloalkyl" substituent group or a haloalkyl moiety in a substituent group refers to an alkyl group or moiety in which one or more, e.g. one, two, three, four or five, hydrogen atoms are replaced independently by halogen atoms, i.e. by fluorine, chlorine, bromine or iodine atoms. Suitable haloalkyl groups include but are not limited to halo (C1-C3)alkyl, and halo(C1-C)alkyl. Examples of haloalkyl groups/moieties include fluoromethyl, difluoromethyl, trifluoromethyl and 2,2,2-trifluoroethyl.

A "cycloalkyl" substituent group or a cycloalkyl moiety in a substituent group refers to a saturated hydrocarbyl ring containing, for example, from 3 to 8 carbon atoms, examples of which include cyclopropyl, cyclobutyl, cyclopentyl and cyclohexyl. Unless stated otherwise, a cycloalkyl substituent group or moiety may include monocyclic, bicyclic (e.g. fused or spiro) and polycyclic hydrocarbyl rings. A "cycloalkyl" substituent group or a cycloalkyl moiety in a substituent group includes cyclopropyl, cyclobutyl, cyclopentyl and cyclohexyl.

A "heteroalkyl" substituent group or a heteroalkyl moiety in a substituent group refers to an alkyl group or moiety in which from 1 to 4 secondary or tertiary carbon atoms, including any secondary or tertiary carbon atoms through which the group or moiety is attached to the rest of the molecule, are replaced independently by heteroatoms selected from nitrogen, oxygen and sulphur in the case of secondary carbon atoms, or by nitrogen in the case of tertiary carbon atoms. Examples of heteroalkyl groups/moieties include methoxy, methylamino, methylsulphanyl, ethoxy, ethylamino, dimethylamino, ethylsulphanyl, propyloxy, methoxyethyl, propylamino, methylethylamino, propylsulphanyl, methylsulphanylethyl, tetrahydropyranyloxy, N-methylpyrrolidinyl, and heterocycloalkyl groups/moieties as exemplified below.

A "heterocycloalkyl" substituent group or a heterocycloalkyl moiety in a substituent group refers to a cycloalkyl group or moiety in which from 1 to 4 secondary or tertiary carbon atoms, including any secondary or tertiary carbon atoms through which the group or moiety is attached to the rest of the molecule, are replaced independently by heteroatoms selected from nitrogen, oxygen and sulphur in the case of secondary carbon atoms, or by nitrogen in the case of tertiary carbon atoms. Examples of heterocycloalkyl groups/moieties include tetrahydrofuranyl, pyrrolidinyl, tetrahydrothiophenyl, tetrahydropyranyl, piperidinyl, piperazinyl, morpholinyl and thiomorpholinyl.

An "alkenyl" substituent group or an alkenyl moiety in a substituent group refers to an unsaturated alkyl group or moiety having one or more carbon-carbon double bonds. Suitable "alkenyl" group include but are not limited to C1-C9 alkenyl, C1-C6 alkenyl, C1-C4 alkenyl, and C1-C3 alkenyl. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl, 1,4-hexadienyl and cycloalkenyl groups/moieties as exemplified below.

A "cycloalkenyl" substituent group or a cycloalkenyl moiety in a substituent group refers to an unsaturated hydrocarbyl ring having one or more carbon-carbon double bonds and containing, for example, from 3 to 8 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic (e.g. fused or spiro) and polycyclic hydrocarbyl rings.

A "heteroalkenyl" substituent group or a heteroalkenyl moiety in a substituent group refers to an alkenyl group or moiety in which from 1 to 4 secondary or tertiary carbon atoms, including any secondary or tertiary carbon atoms through which the group or moiety is attached to the rest of the molecule, are replaced independently by heteroatoms selected from nitrogen, oxygen and sulphur in the case of secondary carbon atoms, or by nitrogen in the case of tertiary carbon atoms. Examples of heteroalkenyl groups/moieties include ethenyloxy, ethenylamino, ethenylsulphanyl, ethenyloxyethyl and heterocycloalkenyl groups/moieties as exemplified below.

A "heterocycloalkenyl" substituent group or a heterocycloalkenyl moiety in a substituent group refers to a cycloalkenyl group or moiety in which from 1 to 4 secondary or tertiary carbon atoms, including any secondary or tertiary carbon atoms through which the group or moiety is attached to the rest of the molecule, are replaced independently by heteroatoms selected from nitrogen, oxygen and sulphur in the case of secondary carbon atoms, or by nitrogen in the case of tertiary carbon atoms. Examples of heterocycloalkenyl groups/moieties include dihydropyranyl and dihydrofuranyl.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl.

A "heteroalkynyl" substituent group or a heteroalkynyl moiety in a substituent group refers to an alkynyl group or moiety in which from 1 to 4 secondary or tertiary carbon atoms, including any secondary or tertiary carbon atoms through which the group or moiety is attached to the rest of the molecule, are replaced independently by heteroatoms selected from nitrogen, oxygen and sulphur in the case of secondary carbon atoms, or by nitrogen in the case of tertiary carbon atoms. Examples of heteroalkynyl groups/moieties include ethynyloxy and propargylamino.

An "aryl" substituent group or an aryl moiety in a substituent group includes monocyclic aromatic hydrocarbons and polycyclic fused ring aromatic hydrocarbons. Examples of aryl groups/moieties include phenyl, naphthyl, anthracenyl and phenanthrenyl.

A "heteroaryl" substituent group or a heteroaryl moiety in a substituent group includes monocyclic aromatic and polycyclic fused ring aromatic groups in which from 1 to 4 ring atoms are independently selected from nitrogen, oxygen and sulphur, with the remainder of the ring atoms being carbon. Examples of heteroaryl groups/moieties include the following:

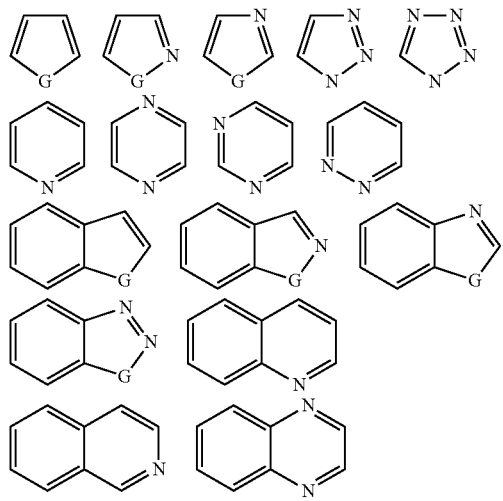

For the purposes of the present invention, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl. An example of cycloalkylalkyl is cyclopropylmethyl.

Where the prefix "hetero" is used in relation to a combination of moieties referred to as one group, for example "hetero(arylalkyl)", any or all of the moieties within the combination may be a hetero moiety. Thus, the term "hetero (arylalkyl)" encompasses heteroaryl-alkyl, aryl-heteroalkyl and heteroaryl-heteroalkyl. Examples of hetero(arylalkyl) groups/moieties include pyridinylmethyl, phenoxy, N-anilinyl and pyridinyloxyethyl.

Where it is stated that a group may be substituted, the group may be substituted by, for example, one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H In one aspect, the invention discloses compounds of Formula 1:

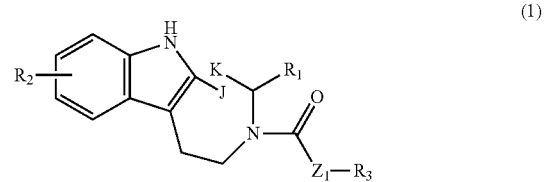

(1)

In Formula 1, J and K are both hydrogen, or J and K taken together form a bond resulting in a six-membered ring, or J and K taken together represent —CH2- resulting in a seven-membered ring.

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl.

R2 is H, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

Z1 is a bond, —NH—, —O—, —S—, —CH(CH$_3$)—, —(CH$_2$)$_n$—, —C3-C7 cycloalkyl-CH2-, —CH=CH—, —CO—, —SO—, —SO$_2$—, —C(=NH)—, —CH$_2$NH (CO)—, —CH$_2$NH(CO)O—, —CH$_2$NH(CO)NH—; —(CH$_2$)$_n$NH(CO)—, —(CH$_2$)$_n$NH(CO)O—, —(CH$_2$)$_m$NH (CO)NH—; —C3-C7 cycloalkyl-CH$_2$NH(CO)—, —C3-C7 cycloalkyl-CH$_2$NH(CO)O—, —C3-C7 cycloalkyl- CH$_2$NH (CO)NH—, —(CH$_2$)$_n$N(CH$_2$CH$_2$C$_6$H$_5$); or optionally substituted aryl.

R3 is H, optionally substituted C1-C9 alkyl; optionally substituted C2-C6 alkenyl; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C3-C7 cycloalkyl; —(CH2)$_p$—NH(CO)O—(C1-C6 alkyl); —CH$_2$O(CH$_2$)$_p$—NH(CO)O—(C1-C6) alkyl; —(CH$_2$)$_p$—NHCO—(CH$_2$)$_p$—NH(CO)O-C1-C6 alkyl); —NH(CO)O-tert-butyl; —O-tert-butyl; or -tert-butyl; CONH-aryl.

m=1-5; n=1-8; p=1-9;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, J and K may be both hydrogen; or J and K taken together may form a bond resulting in a six-membered ring.

In one embodiment, R1 can be H, methyl, ethyl, isopropyl, isobutyl, phenyl, phenyl substituted with halogen, methylcarboxy, methoxy, methyl, tert-butyl; heteroaryl, pyridyl, substituted heterocycle (such as thiofuranyl); benzyl or alpha-methylbenzyl.

In one embodiment, R2 can be H, halogen, methyl or methoxy.

In one embodiment, Z1 can be a bond, —NH—, —CH2-, —(CH2)2-, —(CH2)3-, —CH=CH—, substituted phenyl, —CH2NH(CO)O—, —(CH2)2NH(CO)O—, —(CH2)3NH(CO)O—, —(CH2)4NH(CO)O—, —(CH2)5NH(CO)O—, —CH2NH(CO)—, —CH(CH3)NH(CO)O—, CH2NH(CO)NH—, —CH2NH(CO)CH2NH(CO)O—, —CH2O(CH2)$_2$NH(CO)O— or -cyclohexyl-CH2NH(CO)O—.

In one embodiment, R3 can be ethyl, butyl, isobutyl, pentyl, 2,4,4-trimethylpentyl, heptyl, octyl, phenyl or phenyl substituted with methyl, ethyl, halogen, ethoxy or methoxy.

In one embodiment, J and K are taken together to form a bond resulting in a six-membered ring, R1 is isobutyl, and R3 is —NH(CO)O-tert-butyl, R2 can be hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment J and K taken together may form a bond resulting in a six-membered ring, R1 is isobutyl, Z1 is cyclohexylmethyl, R3 is —NH(CO)O-tert-butyl, R2 can be hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, J and K are taken together to form a bond resulting in a six-membered ring, R1 is isobutyl, Z1 is an alkyl chain composed of 1-5 methylene units, R3 is —NH(CO)O-tert-butyl or —NH(CO)CH2-isopropyl, R2 can be hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, J and K are taken together to form a bond resulting in a six-membered ring, R1 is isobutyl, Z1 is a linker of 4-9 bond lengths composed of a combination of —CH2-, —NHCO—, or —O—, R3 is —NH(CO)O-tert-butyl, and R2 can be hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, J and K are taken together to form a bond resulting in a six-membered ring, R1 is ethyl, isobutyl, isopropyl, benzyl, Z1 is a linker of 4-9 bond lengths composed of —CH2-, R3 is —NH(CO)O-tert-butyl, R2 can be hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, J and K are taken together to form a bond resulting in a six-membered ring, Z1 is —(CH2)$_{4-9}$, R3 is —NH(CO)O-tert-butyl, R2 can be hydrogen, R1 can be a phenyl ring substituted with hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, J and K are taken together to form a bond resulting in a six-membered ring, Z1 is cyclohexylmethyl or C3-C7 cycloalkyl-CH2-, R3 is —NH(CO)O-tert-butyl, R1 is isobutyl, R2 is halogen, methyl, or methoxy.

In one embodiment, J and K are both hydrogen, R1 is tert-butylphenyl, R2 is hydrogen, Z1 is —CONH— or —CO—, and R3 is ethyl, ethylcarboxyphenyl, or methylphenyl.

In one embodiment, J and K are both hydrogen, R1 is methylthiofuranyl, R2 is hydrogen, Z1 is —NH— or a bond, and R3 is ethyl, ethylcarboxyphenyl, or methylphenyl.

In one embodiment, J and K are both hydrogen, R1 is methylthiofuranyl or tert-butylphenyl, Z1 is —NH— or a bond, and R3 is ethyl, ethylcarboxyphenyl, or methylphenyl, and R2 can be hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, J and K are both hydrogen, R1 is methylthiofuranyl or tert-butylphenyl, Z1 is —NH— or a bond, R2 can be hydrogen or halogen, and R3 is substituted phenyl, where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one aspect, the invention discloses compounds of Formula 2:

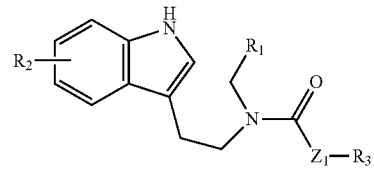

R1 can be H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; an optionally substituted unsubstituted C3-C8 cycloalkyl; or optionally substituted C4-C8 cycloalkylalkyl;

R2 can be H, C1-C6 alkoxy such as but not limited to methoxy or ethoxy; trifluoromethyl, halogen, methylcarboxy, ethylcarboxy, optionally substituted C1-C6 alkyl, —OH, —SH, —NH₂, —N₃, —CN, —NO₂, —CHO, —COOH, —CONH₂, —C(=NH)NH₂, or —SO3H;

Z1 can be a bond, —NH—, —O—, —S—, —CH(CH₃)—, —(CH₂)ₙ—, —CH=CH—, —CO—, —SO—, —SO₂—, —C(=NH)—, —CH₂NH(CO)—, —CH₂NH(CO)O—, —CH₂NH(CO)NH—; —(CH2)ₙNH(CO)—, —(CH₂)ₙNH(CO)O—, —(CH₂)ₘNH(CO)NH—; —C3-C7 cycloalkyl-CH₂NH(CO)—, —C3-C7 cycloalkyl-CH₂NH(CO)O—, —C3-C7 cycloalkyl-CH₂NH(CO)NH—, —(CH₂)ₙN(CH₂CH₂C₆H₅)—, optionally substituted C6-C12 aryl;

R3 can be H, optionally substituted C1-C9 alkyl; C2-C6 alkenyl; optionally substituted C6-C12 aryl; optionally substituted naphthyl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C3-C7 cycloalkyl; —(CH₂)ₚ—NH(CO)O—(C1-C6 alkyl); —CH₂O(CH₂)ₚ—NH(CO)O—(C1-C6) alkyl; —(CH₂)ₚ—NHCO—(CH₂)ₚ—NH(CO)O-C1-C6 alkyl); —NH(CO)O-tert-butyl; —O-tert-butyl; -tert-butyl; —CONH-aryl;

m=1-5; n=1-8; p=1-9;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH2, —N3, —CN, —NO2, —CHO, —COOH, —CONH2, —C(=NH)NH2, or —SO3H.

In one embodiment, R1 can be substituted phenyl or substituted heterocycle (such as thiofuranyl).

In one embodiment, R2 can be H.

In one embodiment, Z1 is a bond, —NH— or substituted phenyl.

In one embodiment, R3 can be ethyl, phenyl, substituted phenyl or substituted heteroaryl.

In one embodiment, R1 is tert-butylphenyl, R2 is hydrogen, Z1 is —NH— or a bond, and R3 is ethyl, ethylcarboxyphenyl, or methylphenyl.

In another embodiment, R1 is methylthiofuranyl, R2 is hydrogen, Z1 is —NH— or a bond, and R3 is ethyl, ethylcarboxyphenyl, or methylphenyl.

In another embodiment, R1 is methylthiofuranyl or tert-butylphenyl, Z1 is —NH— or a bond, and R3 is ethyl, ethylcarboxyphenyl, or methylphenyl, and R2 can be hydrogen, halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In another embodiment R1, is methylthiofuranyl or tert-butylphenyl, Z1 is —NH— or a bond, R2 can be hydrogen or halogen, and R3 is substituted phenyl, where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In one aspect, the invention discloses compounds of Formula 3:

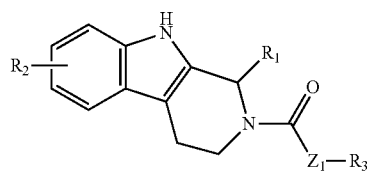

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is H, C1-C6 alkoxy such as but not limited to methoxy or ethoxy, trifluoromethyl, halogen, methylcarboxy, ethylcarboxy, optionally substituted C1-C6 alkyl, —OH, —SH, —NH₂, —N₃, —CN, —NO₂, —CHO, —COOH, —CONH₂, —C(=NH)NH₂, or —SO₃H;

Z1 is a bond, —NH—, —O—, —S—, —CH(CH₃)ₙ, —(CH₂)ₙ—, —C3-C7 cycloalkyl-CH2-, —CH=CH—, —CO—, —SO—, —SO₂— or —C(=NH)—, —CH₂NH(CO)—, —CH₂NH(CO)O—, CH₂NH(CO)NH—; —(CH₂)ₙNH(CO)—, —(CH₂)ₙNH(CO)O—, —(CH₂)ₘNH(CO)NH—; —C3-C7 cycloalkyl- CH₂NH(CO)—, —C3-C7 cycloalkyl-CH2NH(CO)O—, —C3-C7 cycloalkyl-CH₂NH(CO)NH—, —(CH₂)ₙN(CH₂CH₂C₆H₅)—, or optionally substituted C6-C12 aryl;

R3 is H, optionally substituted C1-C9 alkyl, C2-C6 alkenyl; optionally substituted C6-C12 aryl, optionally substituted C1-C9 heteroaryl with 1 to 4 ring atoms independently selected from N, S, and O; optionally substituted C7-C15 arylalkyl such as but not limited to benzyl or alpha-methylbenzyl; or an optionally substituted C3-C7 cycloalkyl; —(CH₂)ₙ—NH(CO)O—(C1-C6 alkyl); —CH₂O(CH₂)ₚ—NH(CO)O—(C1-C6) alkyl; —(CH₂)ₚ—NHCO—(CH₂)ₘ—NH(CO)O-C1-C6 alkyl); —NH(CO)O-tert-butyl; —O-tert-butyl; or -tert-butyl; CONH-aryl;

m=1-5; n=1-8; p=1-9;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In one embodiment, R1 can be H, methyl, ethyl, isopropyl, isobutyl, phenyl, phenyl substituted with halogen, methylcarboxy, methoxy, ethoxy, methyl; heteroaryl, pyridyl, benzyl or alpha-methylbenzyl.

In one embodiment, R2 can be H, halogen, methyl or methoxy.

In one embodiment, Z1 can be a bond, —NH—, —CH2-, —(CH2)2-, —(CH2)3-, —CH=CH—, substituted phenyl, —CH2NH(CO)O—, —(CH2)2NH(CO)O—, —(CH2)3NH(CO)O—, —(CH2)4NH(CO)O—, —(CH2)5NH(CO)O—, —CH2NH(CO)—, —CH(CH3)NH(CO)O—, CH2NH(CO)NH—, —CH2NH(CO)CH2NH(CO)O—, —CH2O(CH2)2NH(CO)O— or -cyclohexyl-CH2NH(CO)O—.

In one embodiment, R3 can be ethyl, butyl, isobutyl, pentyl, 2,4,4-trimethylpentyl, heptyl, octyl, phenyl, phenyl substituted with methyl, ethyl, halogen, ethoxy or methoxy.

In one embodiment, R1 is isobutyl, and R3 is —NH(CO)O-tert-butyl, R2 can be hydrogen, halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In another embodiment, R1 is isobutyl, Z1 is cyclohexylmethyl, R3 is —NH(CO)O-tert-butyl, R2 can be hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 is isobutyl, Z1 is C1-C5 alkyl, R3 is —NH(CO)O-tert-butyl or —NH(CO)CH2-isopropyl, R2 can be hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 is isobutyl, R3 is —NH(CO)O-tert-butyl, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 is ethyl, isobutyl, isopropyl, benzyl, Z1 is (CH2)$_{4-9}$-, R3 is —NH(CO)O-tert-butyl, R2 is hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, Z1 is (CH2)$_{4-9}$-, R3 is —NH(CO)O-tert-butyl, R2 can be hydrogen, R1 is a phenyl ring substituted with hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, Z1 cyclohexylmethyl or a C3-C7 cycloalkyl-CH2- group, R3 is —NH(CO)O-tert-butyl, R1 is isobutyl, R2 is halogen, methyl, or methoxy.

In one aspect, the invention discloses compounds of Formula 4:

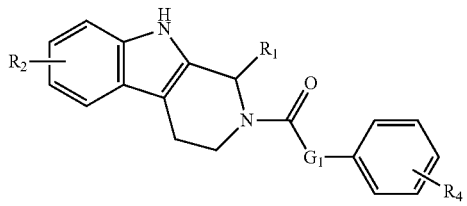

R1 is optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 can be H, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

G1 is a bond, —NH—, —O—, —S—, —CH(CH$_3$)—, —(CH$_2$)$_n$—, —CH=CH—, —CO—, —SO—, —SO$_2$— or —C(=NH)—, —CH$_2$NH(CO)—, —CH2NH(CO)O—, —CH$_2$NH(CO)NH—; —(CH$_2$)$_n$NH(CO)—, —(CH$_2$)$_n$NH(CO)O—, —(CH$_2$)$_m$NH(CO)NH—; —C3-C7 cycloalkyl-NH(CO)—, —C3-C7 cycloalkyl-CH$_2$NH(CO)O—, —C3-C7 cycloalkyl-NH(CO)NH—, —N(CH$_2$CH$_2$C$_6$H$_5$)—;

R4 is H, optionally substituted with halogen, ethylcarboxy, methylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

m=1-5; n=1-8;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 can be isopropyl, isobutyl, phenyl substituted with methylcarboxy, methoxy or alpha-methylbenzyl.

In one embodiment, R2 can be H.

In one embodiment, G1 can be a bond, —NH—, —CH2-, —(CH2)2-, —(CH2)3, —CH=CH— or —CH2NH(CO)NH—.

In one embodiment, R4 can be a hydrogen, halogen, methyl, ethyl, methoxy or ethoxy.

In one embodiment, R1 is isobutyl, R2 is hydrogen or halogen, G1 is a bond, —CH2-, or -CH2CH2-, R4 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is alpha-methylbenzyl, R2 is hydrogen or halogen, G1 is NH, a bond, —CH2-, or -CH2CH2-, R4 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl or isopropyl, R2 is hydrogen or halogen, G1 is —CH2NH(CO)NH— or is —CH2NH(CO)NHCH2-, R4 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, isopropyl or alpha-methylbenzyl, R2 is hydrogen or halogen, G1 is a bond, —CH2-, —CH2CH2-, or a C2-alkene, R4 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one aspect, the invention discloses compounds of Formula 5:

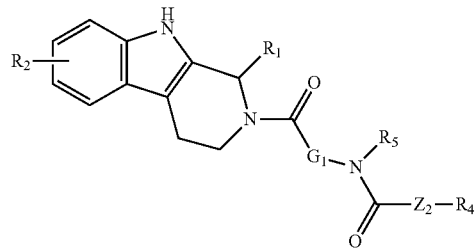

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; an optionally substituted unsubstituted C3-C8 cycloalkyl; or optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

G1 is a bond, —NH—, —O—, —S—, —CH(CH$_3$)—, —(CH$_2$)$_n$—, —CH=CH—, —CO—, —SO—, —SO$_2$— or —C(=NH)—, —CH$_2$NH(CO)—, —CH$_2$NH(CO)O—, —CH$_2$NH(CO)NH—; —(CH2)$_n$NH(CO)—, —(CH$_2$)NH(CO)O—, —(CH$_2$)$_m$NH(CO)NH—; —C3-C7 cycloalkyl-NH(CO)—, —C3-C7 cycloalkyl-CH$_2$NH(CO)O—, —C3-C7 cycloalkyl-NH(CO)NH—, —N(CH$_2$CH$_2$C$_6$H$_5$)—, —C3-C7 cycloalkyl-CH$_2$— such as but not limited to -cyclohexyl-CH$_2$—;

Z2 is a bond, —NH—, —O—, —S—, —CH(CH$_3$)—, —(CH$_2$)—, —CH=CH—, —CO—, —SO—, —SO$_2$— or —C(=NH)—, —CH$_2$NH(CO)—, —CH$_2$NH(CO)O—, —CH$_2$NH(CO)NH—; —(CH$_2$)$_p$NH(CO)—, —(CH$_2$)$_p$NH(CO)O—, —(CH$_2$)$_p$NH(CO)NH—; —C3-C7 cycloalkyl-NH(CO)—, —C3-C7 cycloalkyl-CH$_2$NH(CO)O—, —C3-C7 cycloalkyl-NH(CO)NH—, —N(CH$_2$CH$_2$C$_6$H$_5$)—; or optionally substituted C6-C12 aryl;

R5 is H, methyl, C1-C6 alkyl, C1-C3 arylalkyl, or 2-phenylethyl;

R4 is H, optionally substituted C1-C9 alkyl such as but not limited to tert-butyl; optionally substituted C2-C6 alkenyl; optionally substituted C6-C12 aryl such as but not limited to optionally substituted naphthyl; optionally substituted C1-C9 heteroaryl with 1 to 4 ring atoms independently selected from N, S, and O; optionally substituted C7-C15 arylalkyl such as but not limited to benzyl or alpha-methylbenzyl; an optionally substituted C3-C7 cycloalkyl; —(CH$_2$)$_p$—NH(CO)O—(C1-C6 alkyl); —CH$_2$O(CH$_2$)$_p$—NH(CO)O—(C1-C6) alkyl; —(CH$_2$)$_p$—NHCO—(CH$_2$)$_n$—NH(CO)O-C1-C6 alkyl); —NH(CO)O-tert-butyl; or —O-tert-butyl;

m=1-5; n=1-8; p=1-9;

where "substituted" means substituted with one or more independently selected from halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 can be hydrogen, methyl, ethyl, isopropyl, isobutyl, benzyl, heteroaryl such as pyridyl, phenyl, and phenyl substituted with halogen, trifluoromethyl, methoxy, cyano or dialkylamino.

In one embodiment, where R2 can be hydrogen, halogen, methyl or methoxy.

In one embodiment, Z2 can be O, NH, —CH2-, —(CH2)2-, —(CH2)3-, —(CH2)4-, —(CH2)5-, —CH(CH3)-, —CH2NH(CO)CH2-, —CH2O(CH2)2-, -cyclohexyl-CH2- or a bond.

In one embodiment, G1 is —(CH2)-, —(CH2)2-, —(CH2)3-, —(CH2)4-, —(CH2)5-, —CH2OCH2CH2-, —CH(CH3)-, —CH2NHCOCH2- or -cyclohexyl-CH2-.

In one embodiment, R5 can be hydrogen, methyl or 2-phenylethyl.

In one embodiment, R4 can be optionally substituted phenyl, naphthyl, benzyl, substituted isopropyl or t-butyl.

In one embodiment, R1 is isobutyl, R5 is hydrogen, Z2 is oxygen and R4 is tert-butyl, G1 has no oxygens, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, R5 is hydrogen, Z2 is oxygen, R4 is tert-butyl, G1 is cyclohexylmethyl, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, R5 is hydrogen, Z2 is oxygen or CH2, R4 is tert-butyl or isopropyl, G1 is C1-C5 alkylene, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment R1, is isobutyl, R5 is hydrogen, Z2 is oxygen, R4 is tert-butyl, and R2 can be hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 is ethyl, isobutyl, isopropyl, or benzyl, R5 is hydrogen, Z2 is oxygen, R4 is tert-butyl, G1 is (CH2)$_{4-9}$-, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R5 is hydrogen, Z2 is oxygen, R4 is tert-butyl, G1 is (CH2)$_{4-9}$-, R2 is hydrogen, R1 is a phenyl ring substituted with hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R5 is hydrogen, Z2 is oxygen, R4 is tert-butyl, R1 is isobutyl, R2 is halogen, methyl, or methoxy, G1 is cyclohexylmethyl or C3-C7 cycloalkyl-CH2- group.

In one aspect, the invention discloses compounds of Formula 6:

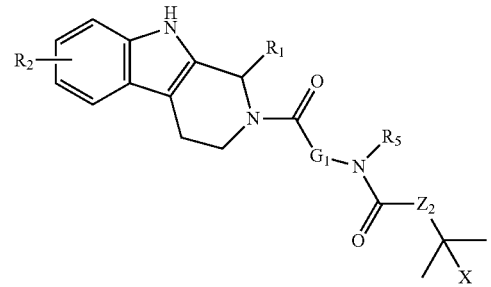

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N3, —CN, —NO2, —CHO, —COOH, —CONH$_2$, —C(=NH)NH$_2$, or —SO$_3$H;

G1 is a bond, —NH—, —O—, —S—, —CH(CH$_3$)—, —(CH$_2$)$_n$—, —CH=CH—, —CO—, —SO—, —SO2— or —C(=NH)—, —CH$_2$NH(CO)—, —CH$_2$NH(CO)O—, —CH$_2$NH(CO)NH—; —(CH$_2$)$_n$NH(CO)—, —(CH$_2$)$_n$NH(CO)O—, —(CH$_2$)$_m$NH(CO)NH—; —C3-C7 cycloalkyl-NH(CO)—, —C3-C7 cycloalkyl-CH$_2$NH(CO)O—, —C3-C7 cycloalkyl-NH(CO)NH—, —N(CH$_2$CH$_2$C$_6$H$_5$)—, —C3-C7 cycloalkyl-CH$_2$— such as but not limited to -cyclohexyl-CH$_2$—;

Z2 is a bond, —NH—, —O—, —S—, —CH(CH$_3$)—, —(CH$_2$)$_n$—; —CH=CH—, —CO—, —SO—, —SO$_2$— or —C(=NH)—, —CH$_2$NH(CO)—, —CH$_2$NH(CO)O—, —CH$_2$NH(CO)NH—; —(CH$_2$)$_p$NH(CO)—, —(CH$_2$)$_p$NH(CO)O—, —(CH$_2$)$_p$NH(CO)NH—; —C3-C7 cycloalkyl-NH(CO)—, —C3-C7 cycloalkyl-CH$_2$NH(CO)O—, —C3-C7 cycloalkyl-NH(CO)NH—, or —N(CH$_2$CH$_2$C$_6$H$_5$)—;

R5 is H, methyl, C1-C6 alkyl, C1-C3 arylalkyl, or 2-phenylethyl;

X is H, C1-C3 alkyl, or C1-C3 arylalkyl;

m=1-5; n=1-8; p=1-9;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 can be hydrogen, methyl, ethyl, isopropyl, isobutyl, benzyl, heteroaryl such as pyridyl, phenyl and phenyl substituted with halogen, methyl, trifluoromethyl, methoxy, cyano, or dialkylamino.

In one embodiment, R2 can be hydrogen, halogen, methyl or methoxy.

In one embodiment, G1 can be —(CH2)-, —(CH2)2-, —(CH2)3-, —(CH2)4-, —(CH2)5-, —CH2OCH2CH2-, —CH(CH3)-, —CH2NHCOCH2-, —CH2O(CH2)2-, -cyclohexyl-CH2- or a bond.

In one embodiment, Z2 can be O, NH, —CH2- or a bond.

In one embodiment, R5 can be hydrogen or methyl.

In one embodiment, X can be hydrogen or methyl.

In one embodiment, R1 is isobutyl, R5 is hydrogen, X is methyl, Z2 is oxygen, G1 is a chain spanning 4-9 bond lengths and has no oxygen atoms, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, R5 is hydrogen, X is methyl, Z2 is oxygen, G1 is cyclohexylmethyl, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, R5 is hydrogen, X is methyl or hydrogen, Z2 is oxygen or CH2, G1 is C1-5 methylene group, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, R5 is hydrogen, X is methyl, Z2 is oxygen, G1 is a linker of 4-9 bond lengths, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is ethyl, isobutyl, isopropyl, benzyl, R5 is hydrogen, X is methyl, Z2 is oxygen, G1 is (CH2)$_{4-9}$-, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R5 is hydrogen, X is methyl, Z2 is oxygen, G1 is (CH2)$_{4-9}$—, R2 is hydrogen, R1 is a phenyl ring substituted with hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R5 is hydrogen, X is methyl, Z2 is oxygen, R1 is isobutyl, R2 is halogen, methyl, or methoxy, G1 is cyclohexylmethyl or C3-C7 cycloalkyl-CH2- group.

In one aspect, the invention discloses compounds of Formula 7:

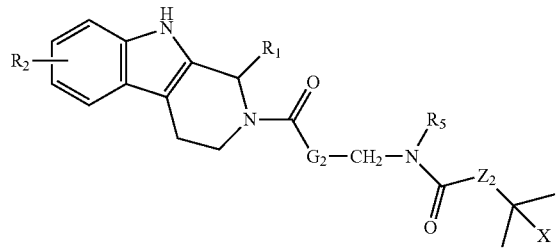

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted arylalkenyl; an optionally substituted C3-C8 cycloalkyl; or optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

G2 is a bond, —NH—, —O—, —S—, —CH(CH$_3$)—, —(CH$_2$)$_n$—, —CH=CH—, —CO—, —SO—, —SO$_2$— or —C(=NH)—, —CH₂NH(CO)—, —CH₂NH(CO)O—, —CH₂NH(CO)NH—; —(CH₂)ₙNH(CO)—, —(CH₂)ₙNH(CO)O—, —(CH₂)ₘNH(CO)NH—; —C3-C7 cycloalkyl- such as but not limited to -cyclohexyl-, or —N(CH₂CH₂C₆H₅)—;

Z2 is a bond, —NH—, —O—, —S—, —CH(CH₃)—, —(CH₂)ₙ—, —CH=CH—, —CO—, —SO—, —SO₂— or —C(=NH)—, —CH₂NH(CO)—, —CH₂NH(CO)O—, —CH₂NH(CO)NH—; —(CH₂)ₚNH(CO)—, —(CH₂)ₚNH(CO)O—, —(CH₂)ₚNH(CO)NH—; —C3-C7 cycloalkyl-NH(CO)—, —C3-C7 cycloalkyl-CH₂NH(CO)O—, —C3-C7 cycloalkyl-NH(CO)NH—, or —N(CH₂CH2C₆H₅)—;

R5 is H, methyl, C1-C6 alkyl, C1-C3 arylalkyl, or 2-phenylethyl;

X is H, C1-C3 alkyl, or C1-C3 arylalkyl;

m=1-5; n=1-8; p=1-9;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In one embodiment, R1 can be hydrogen, methyl, ethyl, isopropyl, isobutyl, benzyl, heteroaryl such as pyridyl, phenyl, phenyl substituted with halogen, trifluoromethyl, methyl, methoxy, cyano, or dialkylamino.

In one embodiment, R2 can be hydrogen, halogen, methyl or methoxy.

In one embodiment, G2 can be a bond, —CH2-, —(CH2)2-, —(CH2)3-, —(CH2)4-, —CH2OCH2-, —CH(CH3)-, —CH2NHCO— or -cyclohexyl-.

In one embodiment, Z2 is O, CH2 or NH.

In one embodiment, R5 can be hydrogen or methyl.

In one embodiment, X can be hydrogen or methyl.

In one embodiment, R1 is isobutyl, R5 is hydrogen, Z2 is oxygen, R5 is hydrogen, X is methyl, G2 has no oxygens, R2 is hydrogen, halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In another embodiment, R1 is isobutyl, R5 is hydrogen, X is methyl, Z2 is oxygen, G2 is cyclohexyl, R2 is hydrogen, halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In another embodiment, R1 is isobutyl, Z2 is oxygen or CH2, R5 is hydrogen or methyl, X is methyl, G2 is a bond or —(CH2)₁₋₄—, R2 is hydrogen, halogen, trifluoromethyl, methylcarboxy, ethylcarboxy, C1-C6 alkoxy such as methoxy or ethoxy, C1-C6 alkyl, —OH, —SH, —NH₂, —N₃, —CN, —NO₂, —CHO, —COOH, —CONH₂, —C(=NH)NH₂, or —SO₃H.

In one embodiment, R1 is isobutyl, Z2 is oxygen, R5 is hydrogen, X is methyl, and R2 is hydrogen, halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In another embodiment, R1 is ethyl, isobutyl, isopropyl, benzyl, Z2 is oxygen, R5 is hydrogen, X is methyl, G2 is —(CH2)₂₋₅, R2 can be hydrogen, halogen, trifluoromethyl, methylcarboxy, ethylcarboxy, C1-C6 alkoxy such as but not limited to methoxy and ethoxy, C1-C6 alkyl, —OH, —SH, —NH₂, —N₃, —CN, —NO₂, —CHO, —COOH, —CONH₂, —C(=NH)NH₂, or —SO₃H.

In another embodiment, R5 is hydrogen, X is methyl, Z2 is oxygen, G2 is —(CH2)₂₋₅, R2 is hydrogen, R1 is a phenyl ring substituted with hydrogen, halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In another embodiment, R5 is hydrogen, X is methyl, Z2 is oxygen, R1 is isobutyl, R2 is halogen, methyl, or methoxy, G2 is cyclohexyl or C3-C7 cycloalkyl-CH2- group.

In one aspect, the invention discloses compounds of Formula 8:

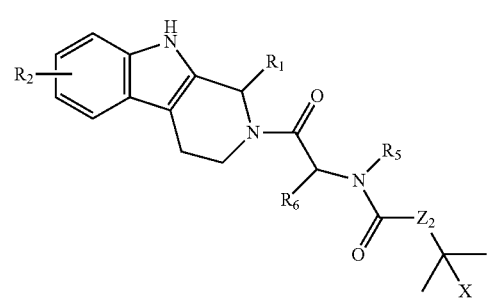

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted arylalkenyl; an optionally substituted C3-C8 cycloalkyl; or optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH₂, —N₃, —CN, —NO₂, —CHO, —COOH, —CONH₂, —C(=NH)NH₂, or —SO₃H;

Z2 is a bond, —NH—, —O—, —S—, —CH(CH₃)—, —(CH₂)ₙ—; —CH=CH—, —CO—, —SO—, —SO₂—, —C(=NH)—, —CH₂NH(CO)—, —CH₂NH(CO)O—, —CH₂NH(CO)NH—; —(CH₂)ₙNH(CO)—, (CH₂)ₙNH(CO)O—, —(CH₂)ₘNH(CO)NH—; —C3-C7 cycloalkyl-NH(CO)—, —C3-C7 cycloalkyl-CH₂NH(CO)O—, —C3-C7 cycloalkyl-NH(CO)NH—, or —N(CH₂CH₂C₆H₅)—;

R5 is H, methyl, C1-C6 alkyl, C1-C3 arylalkyl, or 2-phenylethyl;

X is H, C1-C3 alkyl, or C1-C3 arylalkyl;

R6 is H, or C1-C3 alkyl;

m=1-5; n=1-8;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In one embodiment, R1 can be hydrogen, methyl, ethyl isopropyl, isobutyl, benzyl, heteroaryl such as pyridyl, phenylor phenyl substituted with halogen, trifluoromethyl, methyl, methoxy, cyano, or dialkylamino.

In one embodiment, R2 can be hydrogen, halogen, methyl or methoxy.

In one embodiment, Z2 can be O, CH2, NH or a bond.

In one embodiment, R5 can be hydrogen or methyl.

In one embodiment, X can be hydrogen or methyl.

In one embodiment, R6 can be H or methyl.

In one embodiment, R1 is isobutyl, R5 is hydrogen, Z2 is oxygen and R5 is hydrogen, X is methyl, R6 is hydrogen or methyl, R2 is hydrogen, halogen, trifluoromethyl, methylcarboxy, ethylcarboxy, C1-C6 alkoxy such as but not limited to ethoxy and methoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, R5 is hydrogen, Z2 is oxygen or CH2, R5 is hydrogen or methyl, X is methyl, R6 is hydrogen or methyl, R2 is hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, R5 is hydrogen, Z2 is oxygen, X is methyl, R6 is hydrogen or methyl, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is ethyl, isobutyl, isopropyl, benzyl, R5 is hydrogen, Z2 is oxygen, X is methyl, R6 can be hydrogen or methyl, R2 is hydrogen, halogen, trifluoromethyl, methylcarboxy, ethylcarboxy, C1-C6 alkoxy such as but not limited to ethoxy and methoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R5 is hydrogen, X is methyl, Z2 is oxygen, R6 is hydrogen or methyl, R2 is hydrogen, R1 is a phenyl ring substituted with hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment R5 is hydrogen, X is methyl, Z2 is oxygen, R1 is isobutyl, R6 is hydrogen or methyl, R2 is halogen, methyl, or methoxy.

In one aspect, the invention discloses compounds of Formula 9:

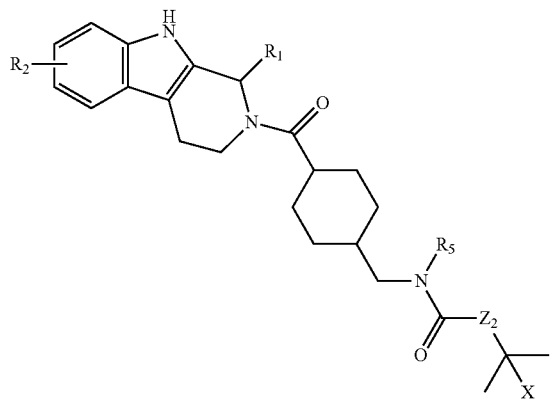

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

R5 is H, methyl, C1-C6 alkyl, C1-C3 arylalkyl, or 2-phenylethyl;

X is H, C1-C3 alkyl, or C1-C3 arylalkyl;

Z2 is a bond, —NH—, —O—, —S—, —CH(CH$_3$)—, —(CH$_2$)$_n$—; —CH=CH—, —CO—, —SO—, —SO$_2$—, —C(=NH)—, —CH$_2$NH(CO)—, —CH$_2$NH(CO)O—, —CH2NH(CO)NH—; —(CH$_2$)$_n$NH(CO)—, (CH$_2$)$_n$NH(CO)O—, —(CH$_2$)$_m$NH(CO)NH—; —C3-C7 cycloalkyl-NH(CO)—, —C3-C7 cycloalkyl-CH$_2$NH(CO)O—, —C3-C7 cycloalkyl-NH(CO)NH—, or —N(CH$_2$CH$_2$C$_6$H$_5$)—;

m=1-5; n=1-8;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 can be isopropyl or isobutyl.

In one embodiment, R2 can be H, halogen or methyl.

In one embodiment, R5 can be H.

In one embodiment, X can be methyl.

In one embodiment, Z2 can be O.

In one embodiment, R1 is isobutyl, R5 is hydrogen, Z2 is oxygen, X is hydrogen, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment R1 is isopropyl, R5 is hydrogen, Z2 is oxygen, X is hydrogen, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl or isopropyl, R5 is hydrogen or methyl, Z2 is oxygen, X is hydrogen, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl or isopropyl, R5 is hydrogen, Z2 is —CH2— or oxygen, X is hydrogen or CH3, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one aspect, the invention discloses compounds of Formula 10:

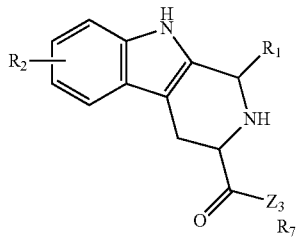

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

Z3 is a bond, —NH—, —O—, —S—, —CH(CH$_3$)—, —(CH$_2$)$_n$—; —CH=CH—, —CO—, —SO—, —SO$_2$— or —C(=NH)—, —CH$_2$NH(CO)—, —CH$_2$NH(CO)O—, —CH$_2$NH(CO)NH—; —(CH$_2$)$_n$NH(CO)—, —(CH$_2$)$_n$NH(CO)O—, —(CH$_2$)$_m$NH(CO)NH—; —C3-C7 cycloalkyl-NH(CO)—, —C3-C7 cycloalkyl-CH$_2$NH(CO)O—, —C3-C7 cycloalkyl-NH(CO)NH—, —N(CH$_2$CH$_2$C$_6$H$_5$)—;

R7 is H, methyl, C1-C6 alkyl, C1-C3 arylalkyl, or 2-phenylethyl;

m=1-5; n=1-8;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 can be methoxyphenyl.
In one embodiment, R2 can be H.
In one embodiment, Z3 can be O, CH2 or NH.
In one embodiment, R7 can be methyl.
In one embodiment, R2 is hydrogen, Z3 is oxygen, R7 is methyl, and R1 is ethyl, isopropyl, isobutyl, benzyl, phenyl, or substituted phenyl where "substituted" means substituted with one or more independently selected from halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R2 is hydrogen, Z3 is oxygen, R7 is methyl or ethyl, and R1 is ethyl, isopropyl, isobutyl, benzyl, phenyl, methoxyphenyl.

In another embodiment, Z3 is oxygen, R7 is methyl or ethyl, and R1 is ethyl, isopropyl, isobutyl, benzyl, phenyl, or methoxyphenyl, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 is isobutyl.

In one embodiment in the context of formulae 1-3, the —Z1-R3 moiety has a pathway starting from the atom binding Z1 to the carbonyl group of formula 1-3 and ending at a terminal atom of R3; said pathway being the pathway consisting of the greatest number of atoms; and said pathway having from 4 to 9 atoms. The pathway described above consists of carbon atoms and/or heteroatoms. Hydrogen atoms are not counted as part of the pathway.

In one embodiment, the —Z1-R3 moiety contains at least one oxygen atom.

In one embodiment, the —Z1-R3 moiety contains a hydrophobic terminal group, such as a terminal group selected from 3-methylbutyryl (isobutylcarbonyl), 2,2-dimethylpropionyl (tert-butylcarbonyl), 2-methylpropionyl (isopropylcarbonyl), phenyl, and benzyl.

In one embodiment, the —Z1-R3 moiety contains a terminal tert-butyloxycarbonyl (BOC) group.

In one embodiment, the —Z1-R3 moiety contains at least one oxygen atom.

In one embodiment, the —Z1-R3 moiety contains a hydrophobic terminal group, such as a terminal group selected from 3-methylbutyryl (isobutylcarbonyl), 2,2-dimethylpropionyl (tert-butylcarbonyl), 2-methylpropionyl (isopropylcarbonyl), phenyl, and benzyl.

In one embodiment, the —Z1-R3 moiety contains a terminal tert-butyloxycarbonyl (BOC) group.

In one embodiment in the context of formulae 4, the -G$_1$-phenyl-R$_4$ moiety has a pathway starting from the atom binding G1 to the carbonyl group of formula 4 and ending at a terminal atom of R4; said pathway being the pathway consisting of the greatest number of atoms; and said pathway having from 4 to 9 atoms. The pathway described above consists of carbon atoms and/or heteroatoms. Hydrogen atoms are not counted as part of the pathway.

In one embodiment, the -G$_1$-phenyl-R$_4$ moiety contains at least one oxygen atom.

In one embodiment, the -G$_1$-phenyl-R$_4$ moiety contains a hydrophobic terminal group, such as a terminal group selected from halogen or trifluoromethyl.

In one embodiment, the -G$_1$-phenyl-R$_4$ moiety contains a terminal tert-butyloxycarbonyl (BOC) group.

In one embodiment in the context of formulae 5, the -G1-N(R5)-C(O)—Z2-R4 moiety has a pathway starting from the atom binding G1 to the carbonyl group of formula 5 and ending at a terminal atom of R4; said pathway being the pathway consisting of the greatest number of atoms; and said pathway having from 4 to 9 atoms. The pathway described above consists of carbon atoms and/or heteroatoms. Hydrogen atoms are not counted as part of the pathway.

In one embodiment, the -G1-N(R5)-C(O)—Z2-R4 moiety contains at least one oxygen atom.

In one embodiment, the -G1-N(R5)-C(O)—Z2-R4 moiety contains a hydrophobic terminal group, such as a terminal group selected from 2-methylpropoxy, tert-butoxy, 1-methylethoxy, 3-methylbutyryl (isobutylcarbonyl), 2,2-dimethylpropionyl (tert-butylcarbonyl), 2-methylpropionyl (isopropylcarbonyl).

In one embodiment, the -G1-N(R5)-C(O)—Z2-R4 moiety contains a terminal tert-butyloxycarbonyl (BOC) group.

In one embodiment in the context of formulae 6, the -G1-N(R5)-C(O)—Z2-CH2(CH3)$_2$—X moiety has a pathway starting from the atom binding G1 to the carbonyl group of formula 6 and ending at a terminal atom of X; said pathway being the pathway consisting of the greatest number of atoms; and said pathway having from 4 to 9 atoms. The pathway described above consists of carbon atoms and/or heteroatoms. Hydrogen atoms are not counted as part of the pathway.

In one embodiment, G1 contains no oxygen atoms.

In one embodiment, the -G1-N(R5)-C(O)—Z2-CH2(CH3)$_2$—X moiety contains a hydrophobic terminal group, such as a terminal group selected from hydrogen, methyl, and ethyl.

In one embodiment, the -G1-N(R5)-C(O)—Z2-CH2(CH3)$_2$—X moiety contains a terminal tert-butyloxycarbonyl (BOC) group.

In one embodiment, G1 is -cyclohexylmethyl-.

In one embodiment in the context of formulae 7, the -G2-CH2-N(R5)-C(O)—Z2-CH2(CH3)$_2$—X moiety has a pathway starting from the atom binding G2 to the carbonyl group of formula 7 and ending at a terminal atom of X; said pathway being the pathway consisting of the greatest number of atoms; and said pathway having from 4 to 9 atoms. The pathway described above consists of carbon atoms and/or heteroatoms. Hydrogen atoms are not counted as part of the pathway.

In one embodiment, G2 contains no oxygen atoms. In one embodiment, Z2 contains no oxygen atoms.

In one embodiment, the -G2-CH2-N(R5)-C(O)—Z2-CH2(CH3)$_2$—X moiety contains a hydrophobic terminal group, such as a terminal group selected from hydrogen, methyl, and ethyl.

In one embodiment, the -G2-CH2-N(R5)-C(O)—Z2-CH2(CH3)$_2$—X moiety contains a terminal tert-butyloxycarbonyl (BOC) group.

In one embodiment in the context of formulae 8, the —CH(R6)-N(R5)-C(O)—Z2-CH2(CH3)$_2$—X moiety has a pathway starting from the carbon atom binding to the carbonyl group of formula 8 and ending at a terminal atom of X; said pathway being the pathway consisting of the greatest number of atoms; and said pathway having from 4 to 9 atoms. The pathway described above consists of carbon atoms and/or heteroatoms. Hydrogen atoms are not counted as part of the pathway.

In one embodiment, G2 contains no oxygen atoms. In one embodiment, Z2 contains no oxygen atoms.

In one embodiment, the —CH(R6)-N(R5)-C(O)—Z2-CH2(CH3)$_2$—X moiety contains a hydrophobic terminal group, such as a terminal group selected from hydrogen, methyl, and ethyl.

In one embodiment, the —CH(R6)-N(R5)-C(O)—Z2-CH2(CH3)$_2$—X moiety contains a terminal tert-butyloxycarbonyl (BOC) group.

In one embodiment in the context of formulae 10, the —Z3-R7 moiety has a pathway starting from the atom binding Z3 to the carbonyl group of formula 10 and ending at a terminal atom of R7; said pathway being the pathway consisting of the greatest number of atoms; and said pathway having from 4 to 9 atoms. The pathway described above consists of carbon atoms and/or heteroatoms. Hydrogen atoms are not counted as part of the pathway.

In one embodiment, the —Z3-R7 moiety contains at least one oxygen atom.

In one embodiment, the —Z3-R7 moiety contains a hydrophobic terminal group, such as a terminal group selected from 3-methylbutyryl (isobutylcarbonyl), 2,2-dimethylpropionyl (tert-butylcarbonyl), 2-methylpropionyl (isopropylcarbonyl), phenyl, and benzyl.

In one embodiment, the —Z3-R7 moiety contains a terminal tert-butyloxycarbonyl (BOC) group.

In relation to all of formulae 1-10, the following alternative embodiments are disclosed:

The option that R1 is H can be excluded from the definitions of Formulae 1-10.

The option that Z1 or G1 is "optionally substituted phenyl" can be excluded from the definitions of Formulae 1-10.

R1 can be benzyl or $C_{2-4}$ alkyl such as but not limited to, isobutyl, isopropyl, and ethyl.

R1 can be aryl, substituted or unsubstituted phenyl, optionally substituted with halogen, methoxy, dimethylamino, or cyano, unsubstituted benzyl, or heteroaryl such as but not limited to pyridyl.

R1 can be substituted or unsubstituted phenyl, e.g. substituted with halogen or methoxy, or an unsubstituted benzyl.

R2 can be methoxy.

R2 can be a halogen such as F or Cl.

R2 can be methyl.

In general as applicable to Formulae 1 to 10:

In general:

In one embodiment, R1 is isobutyl, isopropyl, ethyl, hydrogen, phenyl, chlorophenyl, trifluoromethyl-phenyl, fluorophenyl, or benzyl.

In one embodiment, R2 is fluoro, chloro, or methyl.

In one embodiment, the Z1-R3 moiety has a terminal group selected from BOC-tranexamic acid, BOC-valine, BOC-5-aminovaleric, BOC-6-aminocaproic, BOC-glycine, and BOC-gamma-aminobutyric. In Formula 1, these correspond to Z1 being a bond, and R3 being —(CH2)$_n$-NH(CO)O—(C1-C6 alkyl), where n=1 to 5 methylene units, i.e. —(CH2)$_{1-5}$—.

Synthetic Routes to Chemical Analogs

The compounds described in this application were synthesized using well known organic chemistry techniques previously described in the literature (see Reaction Scheme).

Cyclization Methods A-E: Unsubstituted tryptamine and substituted tryptamines were reacted with aliphatic and aromatic aldehydes in a Pictet-Spangler-type heterocyclization reaction to provide tetrahydro-beta-carbolines with substitutions at R1 and R2, using either 1,1,1,3,3,3-hexafluoroisopropanol (Lewis acid) or trifluoroacetic acid (Bronsted acid) in various solvents and temperatures.

Coupling Methods F-H: The basic secondary nitrogen of the tetrahydro-beta-carboline was then acylated with a carboxylic acid (in the presence of coupling agents), an acid chloride in the presence of a base, or with an isocyanate to generate ureas.

See Physical Data and Synthetic Methods Table for the specific synthetic methods used for each analog described herein.

Reaction Scheme

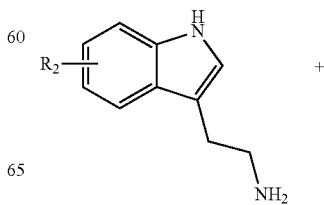

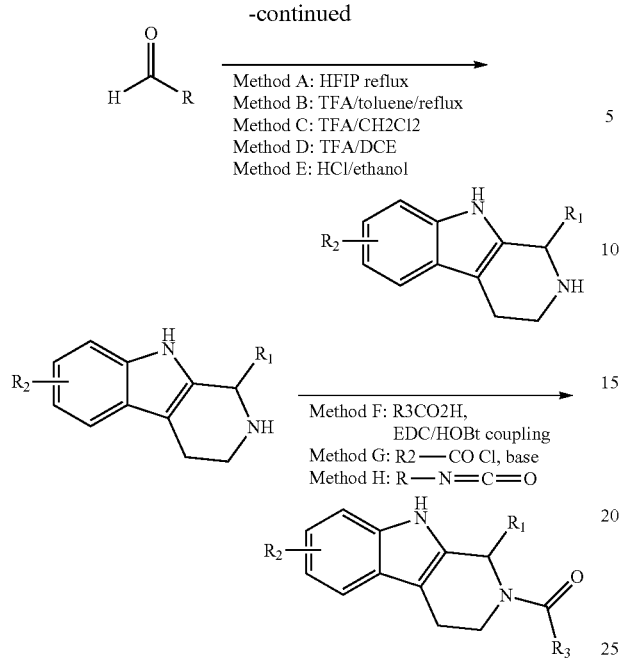

EXPERIMENTAL METHODS

All solvents and reagents were purchased from Sigma-Aldrich, Fisher Scientific, or other commercial vendors and were used without further purification. All deuterated solvents for use in NMR experiments were purchased from Sigma-Aldrich and used without further purification. All $^1$H NMR experiments were performed using a Varian 400 MHz Unity Inova NMR spectrometer. $^1$H NMR spectra were acquired with 16 scans, using a delay time (dl)=1 sec. Spectral width was =20 ppm (from −3 ppm to 20 ppm). NMR experiments were performed by Custom NMR Services (Ayer, Mass.). Mass spectroscopy experiments were performed using LC/MS. Samples were typically prepared in methylene chloride, at a concentration of 1 mg/mL, injecting 1 uL for each acquisition. Mass spectroscopy experiments were performed by Dr. Tun-Li Shen of Brown University (Providence, R.I.). pH measurements were determined either by using either Hydracid Papers 1-6 (Micro Essential Laboratory-Brookly, N.Y.) or with a Fisher Scientific pH meter, model number AB15. Controlled additions of reagents were performed using a Hamilton 10 mL gas tight syringe attached to a KD Scientific, model 100 syringe pump. All inert atmospheres were achieved using compressed argon (ultra high purity-Igo's Welding Supply-Watertown, Mass.) either as a balloon, using a perfectum needle tubing connector attached to a needle or in a Sigma-Aldrich Atmos glove bag. Laboratory glassware was manufactured either by Sigma-Aldrich, Ace glass, Chemglass or VWR scientific. Silica gel purifications were performed using Sigma-Aldrich Silica Gel (230-400 mesh, grade 60, cat. #717185). TLC's were performed using EMD TLC Silica Gel 60 F254 plates (2.5×7.5 cm, cat. #1153410001). TLC's were visualized by either I2-silica gel or UV-light. High performance liquid chromatograph (HPLC) analyses were obtained on an Agilent HP1090 HPLC using a Luna 5u C18 (2) 100A column (50×2.00 mm, Phenomenex) with UV detection at 254 nm and 220 nm using a standard solvent gradient program; Solvent A is 0.4% TFA in water; Solvent B is 0.4% TFA in Acetonitrile; HPLC gradient: 5% B (0-0.5 min), 100% B (ramp 0.5-5 min), 100% B (5-7 min), 5% B (7-7.01 min), 5% B (7.01-9 min).

Synthesis Example 1 (Cyclization by Method D)

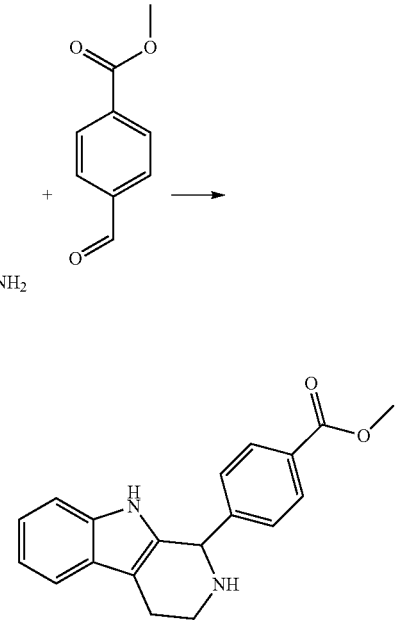

Tryptamine (1.00 g, 6.26 mmol), methyl 4-formylbenzoate (1.03 g, 6.24 mmol), and 4A molecular sieves (0.76 g) were suspended in 1,2-dichloroethene (DCE) (30 mL). Trifluoroacetic acid (TFA) (285 mg, 2.50 mmol) was added to the mixture and the reaction was brought to reflux, yielding a bright brown precipitate. The mixture was cooled to 30° C. and the 4A molecular sieves were removed by glass wool plug. The solution was quenched with sat. NaHCO$_3$ (15 mL) and diluted with EtOAc (50 mL). The organic layer was was with sat. NaCl and dried (anhyd. MgSO$_4$). The solvent was removed by vacuum, yielding a light brown solid. This material was further purified by flash column chromatography: eluting with of MeOH, EtOAc, and Hexane (1:3:6) were used. Fractions containing product were combined yielding a light brown solid (0.80 g, 42% yield; TLC R$_f$=0.129 (10% MeOH/30% EtOAc/Hexane); HPLC Rt=3.254 min). This intermediate was used in the synthesis of the following compounds: MN0642 and MN1210.

Synthesis Example 2 (Cyclization by Method D)

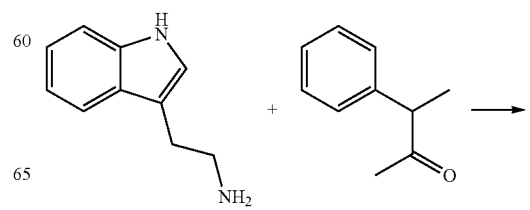

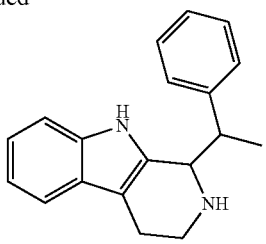

Tryptamine (4.25 g, 26.6 mmol) was added to 1,2-dichloroethane (85 mL). 2-phenylpropionaldehyde (3.6 mL, 27 mmol), trifluoroacetic acid(TFA) (0.80 mL, 10.6 mmol), 4A molecular sieves (2.5 g) were added to the mixture. The reaction was stirred and refluxed overnight. The reaction was cooled to room temperature, EtOAc (100 mL) was added, and the organic layer washed with sat. NaHCO$_3$ (3×25 mL) and then sat. NaCl (25 mL). The solvent was evaporated, yielding a brown solid. The crude solid was dissolved in CH$_2$Cl$_2$ and purified with vacuum flash chromatography: 5 fractions consisting of 0%, 1%, 2%, 3%, and 3% MeOH in CH$_2$Cl$_2$. Fractions containing product were combined, the solvent was removed under vacuum yielding a solid (3.58 g, 48.7% yield; TLC R$_f$=0.34 (3% MeOH/CH$_2$Cl$_2$); HPLC Rt=3.187 min). This intermediate was used in the synthesis of the following compounds: MN1130, MN1135, MN1151, MN1152, and MN1171.

Synthesis Example 3: MN1179 (Cyclization by Method B)

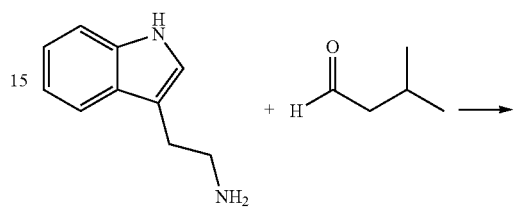

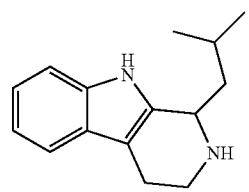

Tryptamine (5.00 g, 31.2 mmol) was added to toluene (100 mL). 2-phenylpropionaldehyde (4.2 mL, 31.2 mmol) and TFA (0.60 mL, 7.8 mmol) were added to the mixture. The reaction was stirred and refluxed overnight using a Dean-Stark trap to remove water. The reaction was cooled to room temperature, EtOAc (100 mL) was added, and the organic layer washed with sat. NaHCO$_3$ (3×25 mL) and then sat. NaCl (25 mL). The solvent was evaporated, yielding a brown solid. The solid was dissolved in EtOAc (50 mL), heptane (50 mL) was added, and the reaction was put on ice. The solution was filtered, and remaining mass was dried. The solid was dissolved in CH$_2$Cl$_2$ and further purified with vacuum flash chromatography: 5 fractions consisting of 0%, 1%, 3%, 5%, and 5% MeOH in CH$_2$Cl$_2$. Fractions containing product were combined, the solvent was removed under vacuum yielding a solid (5.10 g, 59.1% yield; TLC R$_f$=0.34 (3% MeOH/CH$_2$Cl$_2$); HPLC R$_t$=3.187 min). This intermediate was used in the synthesis of the following compounds: MN1130, MN1135, MN1151, MN1152, and MN1171.

Synthesis Example 4: MN1180 (Cyclization by Method A)

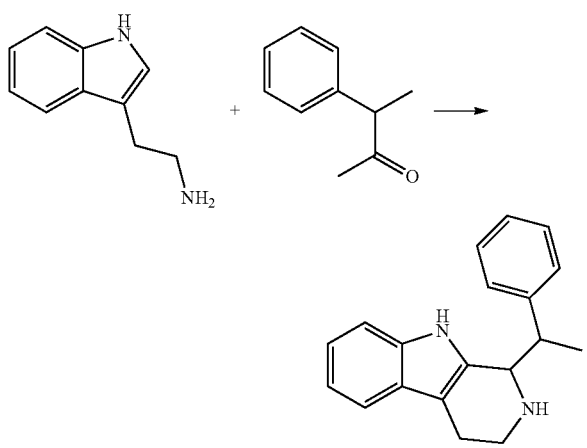

Tryptamine (1.6 g, 10 mmol) was dissolved in 1,1,1,3,3,3-hexafluoro-2-isopropanol (16 mL) and added to isovaleraldehyde (1.3 mL; 12 mmol) by syringe. The reaction was heated to reflux for 18.5 hrs and stirred under an inert atmosphere of nitrogen. The solvent was evaporated and azeotroped with CHCl$_3$ (3×50 mL) under vacuum. Hexane (16 mL) was added and the mixture was sonicated in a bath for 10 min and then stirred overnight. The mixture was filtered, yielding a solid (1.9 g). The material was further purified by trituration by stirring with 5N NH$_4$OH (10 mL) for 20 min. The result was filtered then washed with H2O (2×20 mL). The resulting solid was filtered and dried in a vacuum dissicator, yielding a solid (1.60 μg, 71.0% yield; TLC R$_f$=0.30 (10% MeOH/1% NH$_4$OH/CH$_2$Cl$_2$); HPLC R$_t$=3.081 min). This intermediate was used in the synthesis of the following compounds: MN1132, MN1133, MN1137, MN1138, MN1157, MN1186, MN1189, MN1190, MN1194, MN1195, MN1197, MN1203, MN1206, MN1207, MN1208, MN1209, MN1212, MN1213, MN1214, MN1220, MN1221, MN1222, MN1223, MN1224, MN1225, MN1226, MN1231, MN1232, MN1246.

Synthesis Example 5: MN1180 (Cyclization by Method C)

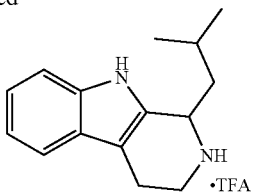

Tryptamine (8.0 g, 50 mmol) was dissolved in CH$_2$Cl$_2$ (400 mL) and placed under an inert atmosphere of argon for 20 min. Isovaleraldehyde (5.36 mL, 50.0 mmol) was added to the solution and the reaction was placed in a −80° C. ice bath for 20 minutes. TFA (38.3 mL) was added drop-wise over 15 minutes. The reaction was removed from the water bath, allowed to warm to room temperature, and stirred for 20 hrs. The solvent was evaporated, yielding a black oil. The oil was dissolved in CH$_2$Cl$_2$ (250 mL) and 1N NaOH was added and shaken. The precipitate was collected and dried under vacuum dissicator to provide 17.9 g of an olive-colored powder (TFA salt). The TFA salt was recrystallized from refluxing acetonitrile The collected solid was washed with cold ACN (~20 mL) and dried yielding a crystalline solid (9.3 g, 54% yield; TLC R$_f$=0.30 (10% MeOH/1% NH$_4$OH/CH$_2$Cl$_2$); HPLC R$_t$=3.099 min). This intermediate was used in the synthesis of the following compounds: MN1132, MN1133, MN1137, MN1138, MN1157, MN1186, MN1189, MN1190, MN1194, MN1195, MN1197, MN1203, MN1206, MN1207, MN1208, MN1209, MN1212, MN1213, MN1214, MN1220, MN1221, MN1222, MN1223, MN1224, MN1225, MN1226, MN1231, MN1232, MN1246.

Synthesis Example 6 (Cyclization by Method A)

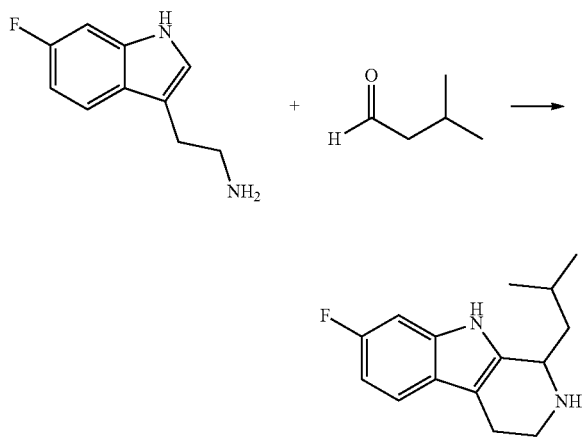

6-Fluorotryptamine (950 mg, 5.30 mmol) was dissolved in 1,1,1,3,3,3-hexafluoroisopropanol (8.5 mL). Isovaleraldehyde (690 uL, 6.40 mmol) was added by syringe. The reaction was placed in an oil bath at 60° C. under nitrogen gas and determined to be complete at 21 hr by HPLC. The solvent was removed under vacuum, azeotroped with CHCl$_3$ (3×10 mL), triturated with hexanes (2×5 mL), filtered, and dried under vacuum. The product was isolated as a yellow solid (1.36 g, 104% yield); TLC R$_f$=0.354 (5% MeOH/1% NH$_4$OH/CH$_2$Cl$_2$); HPLC Rt=3.240 min). This intermediate was used in the synthesis of the following compounds: MN1132, MN1133, MN1137, MN1138, MN1157, MN1186, MN1189, MN1190, MN1194, MN1195, MN1197, MN1203, MN1206, MN1207, MN1208, MN1209, MN1212, MN1213, MN1214, MN1220, MN1221, MN1222, MN1223, MN1224, MN1225, MN1226, MN1227, MN1228, MN1229, MN1230, MN1231, MN1232, MN1246, MN1247, MN1248, MN1250, MN1251, MN1252, MN1253, MN1254, MN1255, MN1256, MN1257, MN1258, MN1260, MN1261, MN1265, MN1266, MN1271, MN1272, MN1279, MN1280, MN1285, MN1286, MN1289.

Synthesis Example 7: MN1130 (Coupling by Method H)

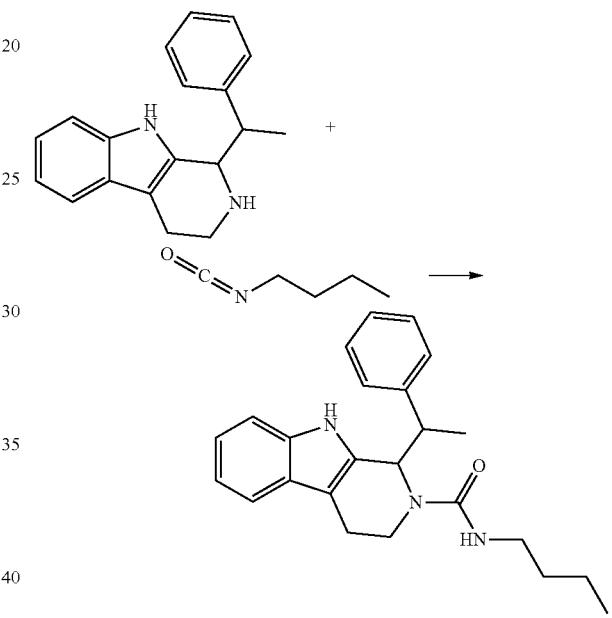

1-(1-Phenylethyl)-2,3,4,9-tetrahydro-1H-pyrido[3,4-b]indole (276 mg, 1.00 mmol) was dissolved in CHCl$_3$ (50 mL) and cooled in an ice bath under an inert atmosphere of nitrogen for 10 min. Butyl isocyanate (170 µL, 1.50 mmol) was added by syringe. The reaction was removed from the ice bath and allowed to warm to room temperature for 10 min. HPLC indicated the reaction was complete at 1 hr. The reaction was evaporated and dried under vacuum. The residue was dissolved in EtOAc (100 mL), washed with 1M citric acid (3×25 mL), sat. NaHCO$_3$ (3×25 mL), and sat. NaCl (25 mL). The organic layer was dried (anhyd. Na$_2$SO$_4$), filtered, and evaporated under vacuum to give of an off-white solid (339 mg). The material was further purified by trituration by stirring with 40% EtOAc/60% Hexane (3 mL) for 1 hr, followed by collecting the product by trituration. The trituration was repeated by stirring with 40% EtOAc/60% Hexane (3 mL) for 1 hr. The resulting solid was filtered and dried in a vacuum dissicator, yielding a white solid (138 mg, 36.7% yield; TLC R$_f$=0.46 (40% EtOAc in Hexane); HPLC R$_t$=4.598 min); MS m/z 375.2412 (100% rel. int.). This method was used in the synthesis of the following compounds: MN733, MN1130, MN1131, MN1158, MN1160, MN1169, MN1171, MN1172, MN1184.

Synthesis Example 8: MN1132 (Coupling by Method G)

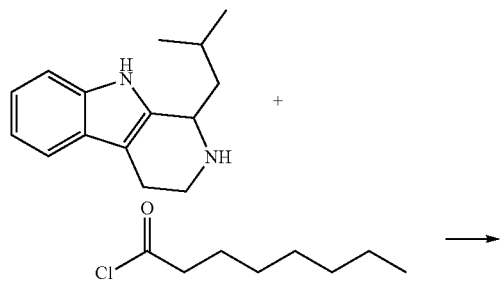

1-Isobutyl-2,3,4,9-tetrahydro-1H-pyrido[3,4-b]indole (228 mg, 1.00 mmol) was dissolved in $CH_2Cl_2$ (10 mL) and cooled in an ice bath under an inert atmosphere of nitrogen for 6 min. Octanoyl chloride (170 µL, 1.00 mmol) was added by syringe followed directly by triethylamine (TEA) (140 µL, 1.00 mmol). The reaction was removed from the ice bath and allowed to warm to room temperature for 10 min. HPLC indicated the reaction was complete at 10 min. The solution was diluted with EtOAc (100 mL), washed with 1N HCl (3×25 mL), sat. $NaHCO_3$ (3×50 mL), and sat. NaCl (25 mL). The organic layer was dried (anhyd. $Na_2SO_4$), filtered, and evaporated under vacuum. The resulting oil was dissolved in $CH_2Cl_2$ (5 mL), and the solvent was removed under vacuum. The oily residue was washed with hexanes (3 mL) top remove any hexane-soluable impurities. This material was further purified by silica gel chromatography: 5 fractions (200 mL each) consisting of 0%, 5%, 10%, 15%, and 20% EtOAc in hexane. Fractions containing product were combined, the solvent was removed under vacuum resulting in an oil. The oil was dissolved in $CH_2Cl_2$ (~1 mL) and was slowly evaporated in an ice bath, yielding a white solid. The solid was dried under high vacuum yielding a yellow oil (236 mg, 67.0% yield; TLC $R_f$=0.28 (10% EtOAc in Hexane); HPLC Rt=5.299 min); $^1$H NMR ($CDCl_3$, 0.003% v/v TMS, 400 MHz): δ 0.85-1.10 (9H, m), 1.20-1.40 (8H, m), 1.55-1.80 (5H, m), 2.30-2.55 (2H, dq), 2.65-2.90 (2H, m), 3.45-3.55 (1H, m), 4.00-4.10 (1H, dd), 5.87 (1H, t), 7.10 (1H, t), 7.15 (1H, t), 7.30 (1H, d), 7.47 (1H, d), 7.80 (1H, br s). This method was used in the synthesis of the following compounds: MN0477, MN0642, MN0908, MN1132, MN1133, MN1135, MN1137, MN1138, MN1152, MN1156, MN1157, MN1188, MN1193, MN1197, MN1203, MN1206, MN1207, MN1208, MN1209, MN1210, MN1211, MN1212, MN1213, MN1214, MN1216, MN1217, MN1218, MN1219.

Synthesis Example 9: MN1133 (Coupling by Method G)

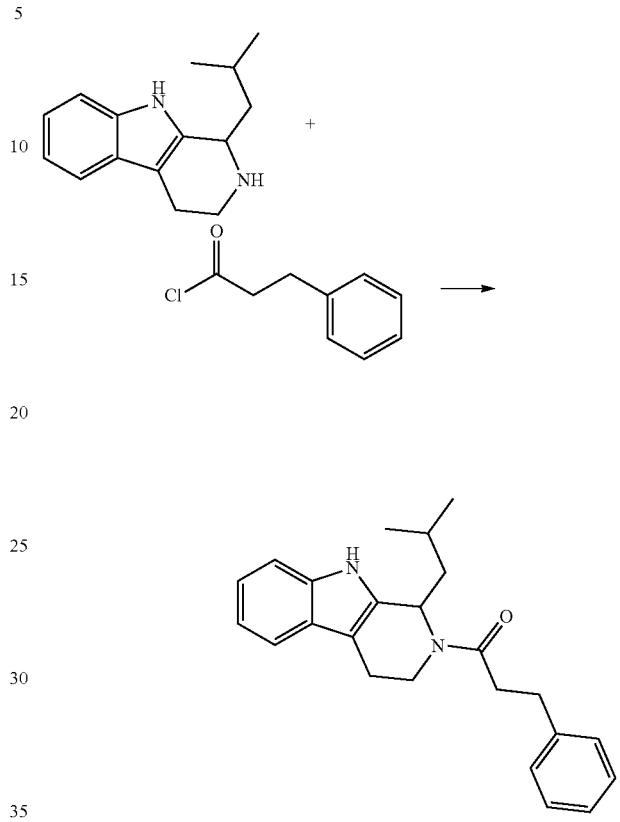

1-Isobutyl-2,3,4,9-tetrahydro-1H-pyrido[3,4-b]indole (220 mg, 0.963 mmol) was dissolved in $CH_2Cl_2$ (10 mL) and cooled in an ice bath under an inert atmosphere of nitrogen. Hydrocinnamoyl chloride (148 µL, 1.00 mmol) was added by syringe. After 45 min, H2O (10 mL) was added. The pH was then raised from 2 to ~8-9 with the addition of 1M NaOH (0.5 mL0. After stirring another 5 min, 1M naOH was added to a pH of 13-14. After 75 min, 1M NaOH (0.5 mL) was added. Then $CH_2Cl_2$ (80 mL) was added, the solution was evaporated and washed with 1N NaOH (2×75 mL), $H_2O$ (100 mL), 1N HCl (2×100 mL), and sat. NaCl (100 mL). The organic layer was dried (anhyd. $MgSO_4$) and filtered. This material was further purified by silica gel chromatography: 6 fractions (200 mL each) consisting of 0%, 0%, 1%, 2%, 3%, and 3% EtOAc in $CH_2Cl_2$. Fractions containing product were combined, the solvent was removed under vacuum yielding a white solid (244 mg, 70.3% yield; TLC $R_f$=0.41 (3% MeOH in $CH_2Cl_2$); HPLC $R_t$=4.803 min); $^1$H NMR ($CDCl_3$, 0.003% v/v TMS, 400 MHz): $δ_H$ 0.97 (3H, d), 1.18 (3H, d), 1.55-1.65 (1H, m), 1.66-1.71 (2H, m), 2.65-2.85 (4H, m), 2.95-3.1 (2H, m), 3.40-3.47 (1H, m), 3.92-4.05 (1H, m), 5.87-5.92 (1H, m), 7.05-7.30 (8H, m), 7.43 (1H, d), 7.77 (1H, br s). This method was used in the synthesis of the following compounds: MN0477, MN0642, MN0908, MN1132, MN1133, MN1135, MN1137, MN1138, MN1152, MN1156, MN1157, MN1188, MN1193, MN1197, MN1203, MN1206, MN1207, MN1208, MN1209, MN1210, MN1211, MN1212, MN1213, MN1214, MN1216, MN1217, MN1218, MN1219.

Synthesis Example 10: MN1137 (Coupling by Method G)

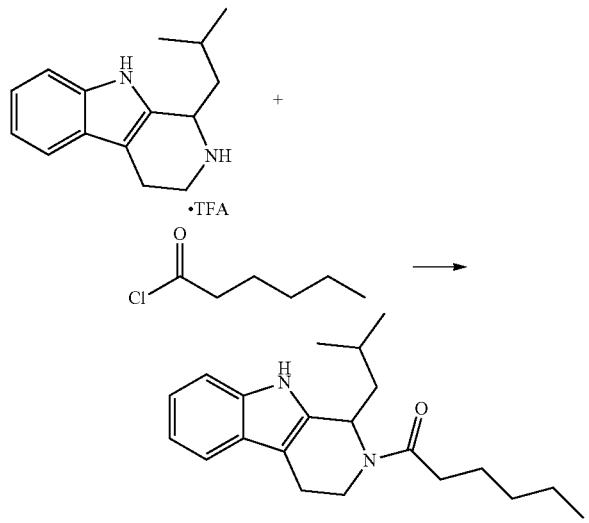

1-Isobutyl-2,3,4,9-tetrahydro-1H-pyrido[3,4-b]indole•TFA salt (410 mg, 1.20 mmol) was dissolved in CH$_2$Cl$_2$ (30 mL) and cooled in an ice bath under an inert atmosphere of nitrogen for 5 min. Hexanoyl chloride (168 µL, 1.20 mmol) was added by syringe followed directly by triethylamine (670 µL, 4.80 mmol). After 4 hours, the reaction was determined to be complete by HPLC. The solution was evaporated, yielding an off-white solid which was dissolved in EtOAc (200 mL), washed with 1N NaOH (3×50 mL), 1N HCl (3×50 mL), and sat. NaCl (3×50 mL). The organic layer was dried (anhyd. Na$_2$SO$_4$), filtered, and evaporated under vacuum. This material was further purified by silica gel chromatography: 6 fractions (200 mL each) consisting of 0%, 2%, 3%, 4%, 4%, and 7% EtOAc in CH$_2$Cl$_2$. Fractions containing product were combined, the solvent was removed under vacuum yielding a solid (167 mg, 42.6% yield; TLC R$_f$=0.50 (4% EtOAc in CH$_2$Cl$_2$); HPLC R$_t$=4.968 min). This method was used in the synthesis of the following compounds: MN0477, MN0642, MN0908, MN1132, MN1133, MN1135, MN1137, MN1138, MN1152, MN1156, MN1157, MN1188, MN1193, MN1197, MN1203, MN1206, MN1207, MN1208, MN1209, MN1210, MN1211, MN1212, MN1213, MN1214, MN1216, MN1217, MN1218, MN1219.

Synthesis Example 11: MN1186 (Coupling by Method F)

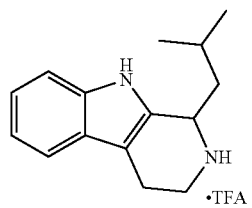

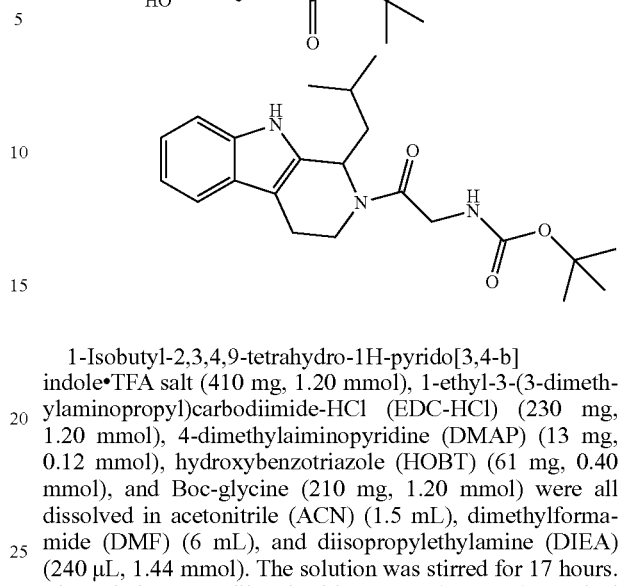

1-Isobutyl-2,3,4,9-tetrahydro-1H-pyrido[3,4-b]indole•TFA salt (410 mg, 1.20 mmol), 1-ethyl-3-(3-dimethylaminopropyl)carbodiimide-HCl (EDC-HCl) (230 mg, 1.20 mmol), 4-dimethylaiminopyridine (DMAP) (13 mg, 0.12 mmol), hydroxybenzotriazole (HOBT) (61 mg, 0.40 mmol), and Boc-glycine (210 mg, 1.20 mmol) were all dissolved in acetonitrile (ACN) (1.5 mL), dimethylformamide (DMF) (6 mL), and diisopropylethylamine (DIEA) (240 µL, 1.44 mmol). The solution was stirred for 17 hours. The solution was diluted with EtOAc (100 mL), washed with 1N HCl (3×25 mL), sat. NaHCO$_3$ (3×25 mL), and sat. NaCl (25 mL). The organic layer was dried (anhyd. Na$_2$SO$_4$), filtered, and evaporated under vacuum, yielding an oil. This material was further purified by silica gel chromatography using: 9 fractions (200 mL) consisting of 0%, 1%, 2%, 4%, 4%, 5%, 5%, 5% and 5% EtOAc in CH$_2$Cl$_2$. Fractions containing product were combined, and the solvent was evaporated under vacuum, yielding a white solid (331 mg, 71.6% yield; TLC R$_f$=0.59 (10% EtOAc in CH$_2$Cl$_2$); HPLC R$_t$=4.577 min); $^1$H NMR (CDCl$_3$, 0.003% v/v TMS, 400 MHz): δ$_H$ 0.95 (3H, d) 1.10 (3H, d), 1.45 (9H, s), 1.55-1.85 (3H, m), 2.70-2.93 (2H, m), 3.40-3.55 (1H, m), 3.87-4.20 (3H, m), 5.60 (1H, br s), 5.80 (1H, dt), 7.05-7.20 (2H, m), 7.30 (1H, d), 7.45 (1H, d), 7.80 (1H, br s).

This method was used in the synthesis of the following compounds: MN0580, MN1169, MN1172, MN1186, MN1189, MN1190, MN1194, MN1195, MN1220, MN1221, MN1222, MN1223, MN1224, MN1225, MN1226, MN1227, MN1228, MN1229, MN1230, MN1231, MN1232, MN1233, MN1234, MN1235, MN1236, MN1237, MN1238, MN1239, MN1240, MN1241, MN1242, MN1243, MN1244, MN1245, MN1246, MN1247, MN1248, MN1249, MN50, MN1251, MN1252, MN1253, MN1254, MN1255, MN1256, MN1257, MN1258, MN1259, MN1260, MN1261, MN1262, MN1263.

Synthesis Example 12: MN1189 (Coupling by Method F)

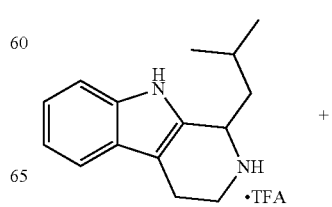

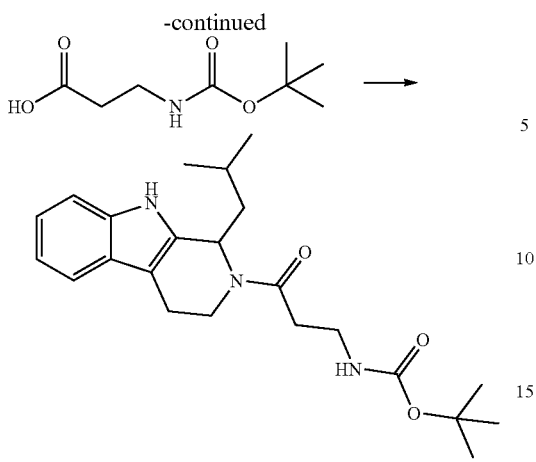

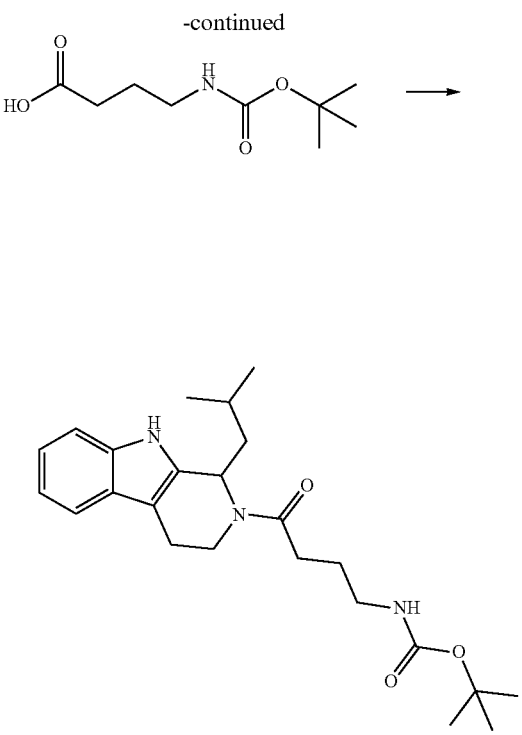

1-Isobutyl-2,3,4,9-tetrahydro-1H-pyrido[3,4-b]indole•TFA salt (410 mg, 1.20 mmol), 1-ethyl-3-(3-dimethylaminopropyl)carbodiimide-HCl (EDC-HCl) (230 mg, 1.20 mmol), 4-dimethylaminopyridine (DMAP) (13 mg, 0.12 mmol), hydroxybenzotriazole (HOBT) (61 mg, 0.40 mmol), and Boc-beta-alanine (227 mg, 1.20 mmol) were all dissolved in acetonitrile (1.5 mL), dimethylformamide (DMF) (6 mL), and diisopropylethylamine (DIEA) (240 μL, 1.44 mmol). The solution was stirred for 17 hours. The solution was diluted with EtOAc (100 mL), washed with 1M citric acid (3×25 mL), sat. NaHCO$_3$ (3×25 mL), and sat. NaCl (25 mL). The organic layer was dried (anhyd. Na$_2$SO$_4$), filtered, and evaporated under vacuum. This material was further purified by silica gel chromatography: 10 fractions (200 mL each) consisting of 0%, 2%, 4%, 5%, 5%, 6%, 6%, 8%, 10%, and 12% EtOAc in CH$_2$Cl$_2$. Fractions containing product were combined, and the solvent was evaporated under vacuum, yielding a solid (314 mg, 64.5% yield; TLC R$_f$=0.26 (10% EtOAc in CH$_2$Cl$_2$); HPLC R$_t$=4.573 min). $^1$H NMR (CDCl$_3$, 0.003% v/v TMS, 400 MHz): δ$_H$ 1.00 (3H, d), 1.07 (3H, d), 1.40 (9H, s), 1.55-1.85 (4H, m), 2.55-2.90 (4H, m), 3.40-3.55 (3H, m), 4.00 (1H, dd), 5.25 (1H, br s), 5.80-5.90 (1H, m), 7.10 (1H, dd), 7.15 (1H, dd), 7.30 (1H, d), 7.45 (1H, d), 7.77 (1H, br s). This method was used in the synthesis of the following compounds: MN0580, MN1169, MN1172, MN1186, MN1189, MN1190, MN1194, MN1195, MN1220, MN1221, MN1222, MN1223, MN1224, MN1225, MN1226, MN1227, MN1228, MN1229, MN1230, MN1231, MN1232, MN1233, MN1234, MN1235, MN1236, MN1237, MN1238, MN1239, MN1240, MN1241, MN1242, MN1243, MN1244, MN1245, MN1246, MN1247, MN1248, MN1249, MN50, MN1251, MN1252, MN1253, MN1254, MN1255, MN1256, MN1257, MN1258, MN1259, MN1260, MN1261, MN1262, MN1263.

Synthesis Example 13: MN1190 (Coupling by Method F)

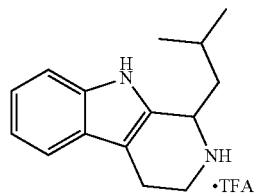

1-Isobutyl-2,3,4,9-tetrahydro-1H-pyrido[3,4-b]indole•TFA salt (410 mg, 1.20 mmol), 1-ethyl-3-(3-dimethylaminopropyl)carbodiimide-HCl (EDC-HCl) (230 mg, 1.2 mmol), 4-dimethylaminopyridine (DMAP) (13 mg, 0.12 mmol), hydroxybenzotriazole (HOBT) (61 mg, 0.40 mmol), and Boc-gamma-amino butyric acid (244 mg, 1.20 mmol) were all dissolved in acetonitrile (1.5 mL), dimethylformamide (DMF) (6 mL), and diisopropylethylamine (DIEA) (240 μL, 1.44 mmol). The solution was stirred for 17 hours. The solution was diluted with EtOAc (100 mL), washed with 1M citric acid (3×25 mL), sat. NaHCO$_3$ (3×25 mL), and sat. NaCl (25 mL). The organic layer was dried (anhyd. Na$_2$SO$_4$), filtered, and evaporated under vacuum. This material was further purified by silica gel chromatography: 9 fractions (200 mL each) consisting of 0%, 4%, 6%, 8%, 10%, 10%, 12%, 14%, and 14% EtOAc in CH$_2$Cl$_2$. Fractions containing product were combined, and the solvent was evaporated under vacuum, yielding a white powder (395 mg, 79.6%; TLC R$_f$=0.16 (10% EtOAc in CH$_2$Cl$_2$); HPLC Rt=4.580 min). $^1$H NMR (CDCl$_3$, 0.003% v/v TMS, 400 MHz): δ$_H$ 1.00 (3H, d), 1.07 (3H, d), 1.45 (9H, s), 1.65-1.95 (5H, m), 2.40-2.60 (2H, m), 2.67-2.90 (2H, m), 3.10-3.25 (2H, m), 3.45-3.55 (1H, m), 4.05 (1H, dd), 4.83 (1H, br s), 5.85 (1H, m), 7.10 (1H, dd), 7.15 (1H, dd), 7.30 (1H, d), 7.45 (1H, d), 7.80 (1H, br s). This method was used in the synthesis of the following compounds: MN0580, MN1169, MN1172, MN1186, MN1189, MN1190, MN1194, MN1195, MN1220, MN1221, MN1222, MN1223, MN1224, MN1225, MN1226, MN1227, MN1228, MN1229, MN1230, MN1231, MN1232, MN1233, MN1234, MN1235, MN1236, MN1237, MN1238, MN1239, MN1240, MN1241, MN1242, MN1243, MN1244, MN1245, MN1246, MN1247, MN1248, MN1249, MN50, MN1251, MN1252, MN1253, MN1254, MN1255, MN1256, MN1257, MN1258, MN1259, MN1260, MN1261, MN1262, MN1263.

Synthesis Example 14: MN1194 (Coupling by Method F)

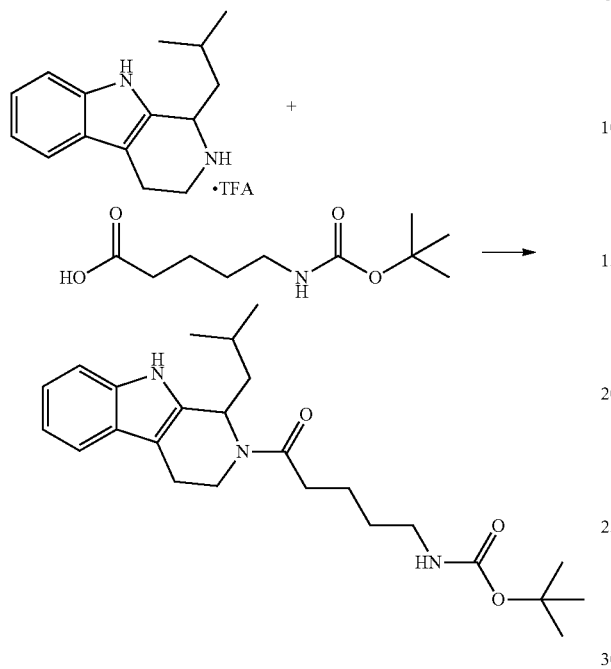

1-Isobutyl-2,3,4,9-tetrahydro-1H-pyrido[3,4-b]indole•TFA salt (410 mg, 1.20 mmol), 1-ethyl-3-(3-dimethylaminopropyl)carbodiimide-HCl (EDC-HCl) (230 mg, 1.20 mmol), 4-dimethylaminopyridine (DMAP) (13 mg, 0.12 mmol), hydroxybenzotriazole (HOBT) (61 mg, 0.40 mmol), and Boc-5-aminovaleric acid (261 mg, 1.20 mmol) were all dissolved in acetonitrile (1.5 mL), dimethylformamide (DMF) (6 mL), and diisopropylethylamine (DIEA) (240 µL, 1.44 mmol). The solution was stirred overnight. The solution was diluted with EtOAc (100 mL), washed with 1M citric acid (3×25 mL), sat. NaHCO3 (3×25 mL), and sat. NaCl (25 mL). The organic layer was dried (anhyd. Na2SO4), filtered, and evaporated under vacuum. This material was further purified by silica gel chromatography: 5 fractions (200 mL each) consisting of 0%, 1% MeOH, 1% MeOH/0.1% NH4OH, 2% MeOH/0.1% NH4OH, and 3% MeOH/0.1% NH4OH in CH2Cl2. Fractions containing product were combined, and the solvent was evaporated under vacuum, yielding a solid (412 mg, 80.3% yield; TLC Rf=0.14 (10% EtOAc in CH2Cl2); HPLC Rt=4.652 min). 1H NMR (CDCl3, 0.003% v/v TMS, 400 MHz): δH 0.97 (3H, d), 1.05 (3H, d), 1.45 (9H, s), 1.5-1.85 (7H, m), 2.30-2.60 (2H, m), 2.65-2.90 (2H, m), 3.05-3.20 (2H, m), 3.40-3.55 (1H, m), 4.05 (1H, dd), 4.65 (1H, br s), 5.85-5.90 (1H, m), 7.07 (1H, dd), 7.15 (1H, dd), 7.30 (1H, d), 7.45 (1H, d), 7.80 (1H, br s). This method was used in the synthesis of the following compounds: MN0580, MN1169, MN1172, MN1186, MN1189, MN1190, MN1194, MN1195, MN1220, MN1221, MN1222, MN1223, MN1224, MN1225, MN1226, MN1227, MN1228, MN1229, MN1230, MN1231, MN1232, MN1233, MN1234, MN1235, MN1236, MN1237, MN1238, MN1239, MN1240, MN1241, MN1242, MN1243, MN1244, MN1245, MN1246, MN1247, MN1248, MN1249, MN50, MN1251, MN1252, MN1253, MN1254, MN1255, MN1256, MN1257, MN1258, MN1259, MN1260, MN1261, MN1262, MN1263.

Synthesis Example 15: MN1197 (Coupling by Method G)

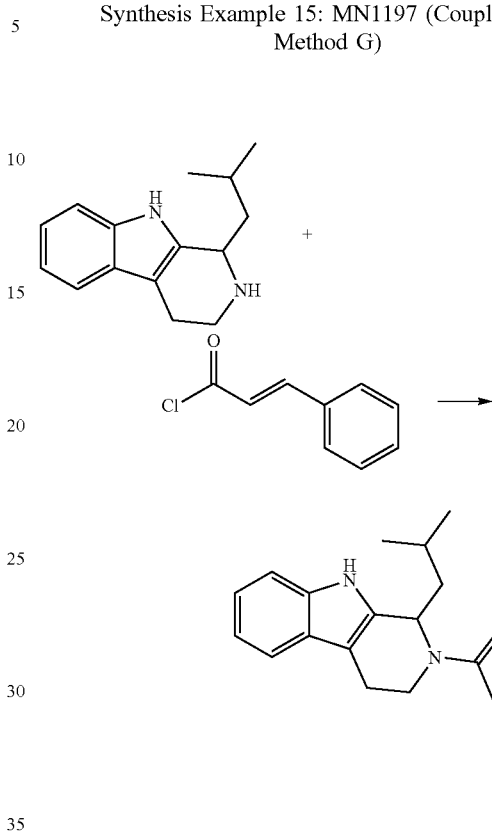

1-Isobutyl-2,3,4,9-tetrahydro-1H-pyrido[3,4-b]indole (228 mg, 1.00 mmol) was dissolved in CH2Cl2 (20 mL) and cooled in an ice bath under an inert atmosphere of nitrogen for 6 min. Cinnamoyl chloride (168 mg, 1.00 mmol) was added by syringe followed directly by triethylamine (210 µL, 1.50 mmol). The reaction was removed from the ice bath and allowed to warm to room temperature for 1 hr. HPLC indicated the reaction was complete at 1 hr. The solution was diluted with EtOAc (100 mL), washed with 1N HCl (3×25 mL), sat. NaHCO3 (3×50 mL), and sat. NaCl (25 mL). The organic layer was dried (anhyd. Na2SO4), filtered, and evaporated under vacuum yielding an off-white solid. This material was further purified by silica gel chromatography: fractions contained 0%-20% EtOAc in hexane. Fractions containing product were combined, the solvent was removed under vacuum yielding a solid (308 mg, 85.9% yield; TLC Rf=0.41 (3% MeOH in CH2Cl2); HPLC Rt=4.801 min). 1H NMR (CDCl3, 0.003% v/v TMS, 400 MHz): δHR 1.00 (3H, d), 1.10 (3H, d), 1.60-1.70 (1H, m), 1.75-1.95 (2H, m), 2.75-3.00 (2H, m), 3.55-3.65 (1H, m), 4.30 (1H, dd), 5.97-6.05 (1H, m), 7.03 (1H, d), 7.07 (1H, dd), 7.15 (1H, dd), 7.30-7.60 (7H, m), 7.70 (1H, d), 7.80 (1H, br s). This method was used in the synthesis of the following compounds: MN0477, MN0642, MN0908, MN1132, MN1133, MN1135, MN1137, MN1138, MN1152, MN1156, MN1157, MN1188, MN1193, MN1197, MN1203, MN1206, MN1207, MN1208, MN1209, MN1210, MN1211, MN1212, MN1213, MN1214, MN1216, MN1217, MN1218, MN1219.

Synthesis Example 16: MN1208 (Coupling by Method G)

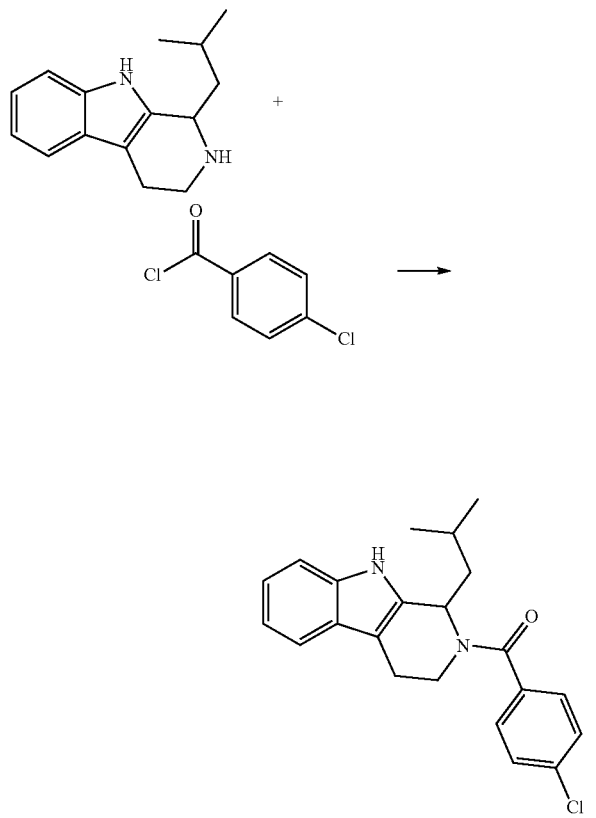

1-Isobutyl-2,3,4,9-tetrahydro-1H-pyrido[3,4-b]indole (228 mg, 1.00 mmol) was dissolved in CH$_2$Cl$_2$ (20 mL) and cooled in an ice bath under an inert atmosphere of nitrogen for 6 min. 4-Chlorobenzoyl chloride (130 µL, 1.00 mmol) was added by syringe followed directly by triethylamine (TEA) (210 µL, 1.50 mmol). The reaction was removed from the ice bath and allowed to warm to room temperature for 10 min. The reaction was stirred for 100 hrs at room temperature. The solution was diluted with EtOAc (100 mL), washed with 1N HCl (3×25 mL), sat. NaHCO$_3$ (3×50 mL), and sat. NaCl (50 mL). The organic layer was dried (anhyd. Na$_2$SO$_4$), filtered, and evaporated under vacuum. This material was further purified by silica gel chromatography: fractions contained 15%-20% EtOAc in hexane. Fractions containing product were combined, the solvent was removed under vacuum yielding a solid (268 mg, 75.9% yield; TLC R$_f$=0.36 (20% EtOAc in Hexane); HPLC R$_t$=4.876 min). $^1$H NMR (CDCl$_3$, 0.003% v/v TMS, 400 MHz): $\delta_H$ 1.05 (3H, d), 1.13 (3H, d), 1.60-1.95 (3H, m), 2.60-2.90 (2H, m), 3.45-3.57 (1H, m), 3.85 (1H, dd), 5.90-6.05 (1H, m), 7.10 (1H, dd), 7.17 (1H, dd), 7.27-7.50 (6H, m), 7.85 (1H, br s). This method was used in the synthesis of the following compounds: MN0477, MN0642, MN0908, MN1132, MN1133, MN1135, MN1137, MN1138, MN1152, MN1156, MN1157, MN1188, MN1193, MN1197, MN1203, MN1206, MN1207, MN1208, MN1209, MN1210, MN1211, MN1212, MN1213, MN1214, MN1216, MN1217, MN1218, MN1219.

Synthesis Example 17: MN1210 (Coupling by Method G)

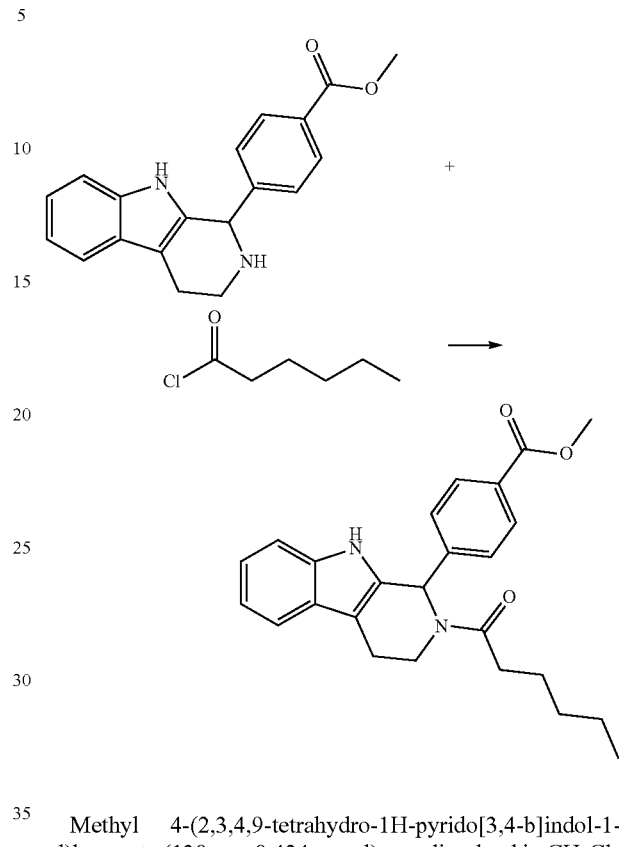

Methyl 4-(2,3,4,9-tetrahydro-1H-pyrido[3,4-b]indol-1-yl)benzoate (130 mg, 0.424 mmol) was dissolved in CH$_2$Cl$_2$ (20 mL) and cooled in an ice bath under an inert atmosphere of nitrogen for 6 min. Hexanoyl chloride (60 µL, 0.42 mmol) was added by syringe followed directly by triethylamine (TEA) (88 µL, 0.63 mmol). The reaction was removed from the ice bath and allowed to warm to room temperature overnight. The solvent was removed under vacuum and the residue was dissolved in EtOAc (100 mL), washed with 1N HCl (3×25 mL), sat. NaHCO$_3$ (3×50 mL), and sat. NaCl (50 mL). The organic layer was dried (anhyd. Na$_2$SO$_4$), filtered, and evaporated under vacuum. The solvent was removed under vacuum yielding a solid (178 mg). The crude product was purified by silica gel chromatography: 7 fractions (200 mL each) consisting of 0%, 1%, 1%, 2%, 2%, 2.5%, and 3% MeOH in CH$_2$Cl$_2$. Fractions containing product were combined, the solvent was removed under vacuum yielding a solid (131 mg, 76.4% yield; TLC R$_f$=0.27 (2% MeOH in CH$_2$Cl$_2$); HPLC R$_t$=4.834 min). $^1$H NMR (CDCl$_3$, 0.003% v/v TMS, 400 MHz): $\delta_H$ 0.90 (3H, t), 1.30-1.40 (4H, m), 1.63-1.73 (2H, m), 2.40-2.50 (2H, m), 2.85-3.00 (2H, m), 3.30-3.40 (1H, m), 3.90 (3H, s), 3.97 (1H, dd), 7.05 (1H, s), 7.15 (1H, dd), 7.20 (1H, dd), 7.33 (1H, d), 7.37 (2H, d), 7.55 (1H, d), 7.93 (2H, d), 8.05 (1H, br s). This method was used in the synthesis of the following compounds: MN0477, MN0642, MN0908, MN1132, MN1133, MN1135, MN1137, MN1138, MN1152, MN1156, MN1157, MN1188, MN1193, MN1197, MN1203, MN1206, MN1207, MN1208, MN1209, MN1210, MN1211, MN1212, MN1213, MN1214, MN1216, MN1217, MN1218, MN1219.

Synthesis Example 18: MN1212 (Coupling by Method G)

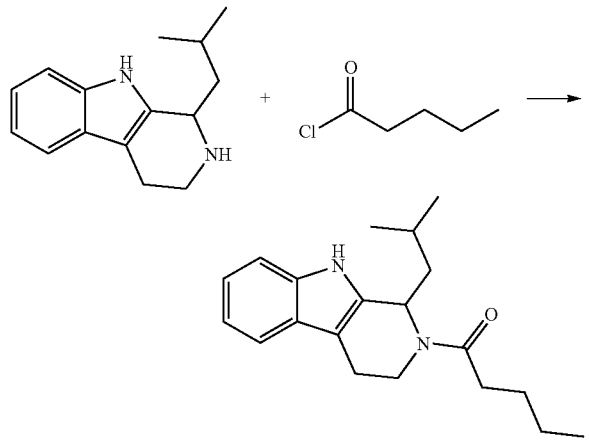

1-Isobutyl-2,3,4,9-tetrahydro-1H-pyrido[3,4-b]indole (228 mg, 1.00 mmol) was dissolved in $CH_2Cl_2$ (20 mL) and cooled in an ice bath under an inert atmosphere of nitrogen for 6 min. Valeroyl chloride (120 µL, 1.00 mmol) was added by syringe followed directly by trimethylamine (TEA) (210 µL, 1.5 mmol). The reaction was removed from the ice bath and allowed to warm to room temperature. HPLC indicated the reaction was complete at 3.5 hrs. The reaction was evaporated and dried under vacuum. The residue was dissolved in EtOAc (100 mL), washed with 1M citric acid (3×25 mL), sat. $NaHCO_3$ (3×50 mL), and sat. NaCl (50 mL). The organic layer was dried (anhyd. $Na_2SO_4$), filtered, and evaporated under vacuum yielding a solid. The crude product was purified by silica gel chromatography: 5 fractions (200 mL each) consisting of 0%, 0.5%, 0.75%, 1%, and 2% MeOH in $CH_2Cl_2$. Fractions containing product were combined, the solvent was removed under vacuum yielding a solid (219 mg, 70.0% yield; TLC $R_f$=0.29 (2% MeOH in $CH_2Cl_2$); HPLC $R_t$=4.747 min). $^1H$ NMR ($CDCl_3$, 0.003% v/v TMS, 400 MHz): $\delta_H$ 0.85-1.1$^5$ (9H, m), 1.30-1.45 (2H, m), 1.53-1.87 (5H, m), 2.35-2.55 (2H, m), 2.65-2.90 (2H, m), 3.43-3.55 (1H, m), 4.05 (1H, dd), 5.85-5.95 (1H, m), 7.07 (1H, dd), 7.15 (1H, dd), 7.30 (1H, d), 7.45 (1H, d), 7.80 (1H, br s). This method was used in the synthesis of the following compounds: MN0477, MN0642, MN0908, MN1132, MN1133, MN1135, MN1137, MN1138, MN1152, MN1156, MN1157, MN1188, MN1193, MN1197, MN1203, MN1206, MN1207, MN1208, MN1209, MN1210, MN1211, MN1212, MN1213, MN1214, MN1216, MN1217, MN1218, MN1219.

Synthesis Example 19: MN1213 (Coupling by Method F)

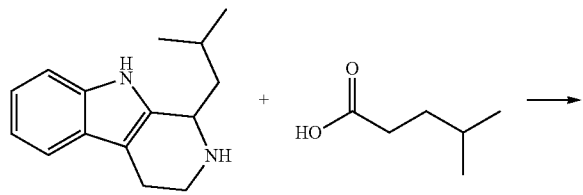

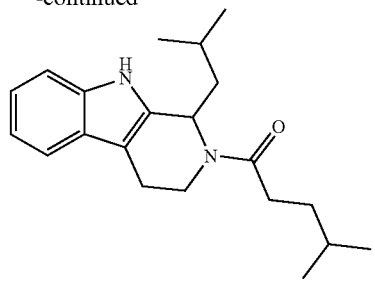

1-Isobutyl-2,3,4,9-tetrahydro-1H-pyrido[3,4-b]indole (228 mg, 1.00 mmol), 1-ethyl-3-(3-dimethylaminopropyl) carbodiimide-HCl (EDC-HCl) (191 mg, 1.00 mmol), 4-dimethylaminopyridine (DMAP) (12 mg, 0.10 mmol), and hydroxybenzotriazole (HOBT) (51 mg, 0.33 mmol) were all dissolved in acetonitrile (1.25 mL), dimethylformamide (DMF) (5 mL), and diisopropylethylamine (DIEA) (200 µL, 1.20 mmol). 4-Methylvaleric acid (126 µL, 1.00 mmol) was added by syringe. The solution was stirred for 18 hrs. The result was diluted with EtOAc (100 mL), washed with sat. NaCl (2×50 mL), 1M citric acid (3×25 mL), sat. $NaHCO_3$ (3×25 mL), and sat. NaCl (2×50 mL). The organic layer was dried (anhyd. $Na_2SO_4$), filtered, and evaporated under vacuum. The crude product was purified by silica gel chromatography: 5 fractions (200 mL each) consisting of 0%, 0.5%, 0.75%, 1%, and 2% MeOH in $CH_2Cl_2$. Fractions containing product were combined, the solvent was removed under vacuum yielding a solid (245 mg, 75.0% yield; TLC $R_f$=0.29 (2% MeOH in $CH_2Cl_2$); HPLC $R_t$=4.869 min). $^1H$ NMR ($CDCl_3$, 0.003% v/v TMS, 400 MHz): $\delta_H$ 0.87-1.15 (12H, m), 1.5-1.83 (4H, m), 2.35-2.55 (2H, m), 2.65-2.90 (2H, m), 3.45-3.55 (1H, m), 4.05 (1H, dd), 5.85-5.90 (1H, m), 7.10 (1H, dd), 7.15 (1H, dd), 7.33 (1H, d), 7.45 (1H, d), 7.83 (1H, br s). This method was used in the synthesis of the following compounds: MN0580, MN1169, MN1172, MN1186, MN1189, MN1190, MN1194, MN1195, MN1220, MN1221, MN1222, MN1223, MN1224, MN1225, MN1226, MN1227, MN1228, MN1229, MN1230, MN1231, MN1232, MN1233, MN1234, MN1235, MN1236, MN1237, MN1238, MN1239, MN1240, MN1241, MN1242, MN1243, MN1244, MN1245, MN1246, MN1247, MN1248, MN1249, MN50, MN1251, MN1252, MN1253, MN1254, MN1255, MN1256, MN1257, MN1258, MN1259, MN1260, MN1261, MN1262, MN1263.

Synthesis Example 20: MN1227 (Coupling by Method F)

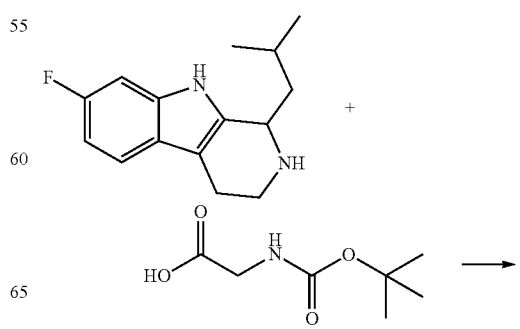

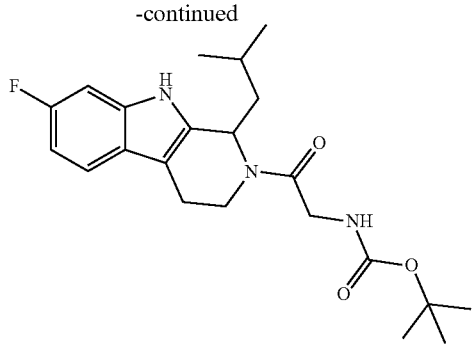

7-Fluoro-1-isobutyl-2,3,4,9-tetrahydro-1H-pyrido[3,4-b]indole (247 mg, 1.00 mmol), 1-ethyl-3-(3-dimethylaminopropyl)carbodiimide-HCl (EDC-HCl) (191 mg, 1.00 mmol), 4-dimethylaminopyridine (DMAP) (12 mg, 0.10 mmol), and hydroxybenzotriazole (HOBT) (51 mg, 0.33 mmol) were all dissolved in acetonitrile (1.25 mL), dimethylformamide (DMF) (5 mL), and diisopropylethylamine (DIEA) (200 uL, 1.20 mmol). N-Boc-glycine (175 mg, 1.00 mmol) was added to the mixture. The reaction was stirred at room temperature for 16.5 hr. The result was diluted with EtOAc (100 mL), washed with sat. NaCl (2×50 mL), 1M citric acid (3×25 mL), sat. NaHCO₃ (3×25 mL), and sat. NaCl (50 mL). The organic layer was dried (anhyd. Na₂SO₄), filtered, and evaporated under vacuum. The crude product was purified by silica gel chromatography: 8 fractions (200 mL each) consisting of 0%, 5%, 10%, 10%, 15%, 15%, 20% and 20% EtOAc in hexanes. Fractions containing product were combined and the solvent was removed under vacuum to yield a solid (219.4 mg, 54.37% yield; TLC $R_f$=0.250 (20% EtOAc in hexane); HPLC $R_t$=4.594 min). ¹H NMR (CDCl₃, 0.003% v/v TMS, 400 MHz): $\delta_H$ 0.95 (3H, d), 1.08 (3H, d), 1.45 (9H, s), 1.60-1.85 (3H, m), 2.65-2.90 (2H, m), 3.40-3.53 (1H, m), 3.85 (1H, dd), 3.95-4.20 (2H, m), 5.58 (1H, br s), 5.75-5.83 (1H, m), 6.80-6.90 (1H, m), 6.97-7.05 (1H, m), 7.30-7.37 (1H, m), 7.87 (1H, br s). This method was used in the synthesis of the following compounds: MN0580, MN1169, MN1172, MN1186, MN1189, MN1190, MN1194, MN1195, MN1220, MN1221, MN1222, MN1223, MN1224, MN1225, MN1226, MN1227, MN1228, MN1229, MN1230, MN1231, MN1232, MN1233, MN1234, MN1235, MN1236, MN1237, MN1238, MN1239, MN1240, MN1241, MN1242, MN1243, MN1244, MN1245, MN1246, MN1247, MN1248, MN1249, MN50, MN1251, MN1252, MN1253, MN1254, MN1255, MN1256, MN1257, MN1258, MN1259, MN1260, MN1261, MN1262, MN1263.

Synthesis Example 21: MN1246 (Coupling by Method F)

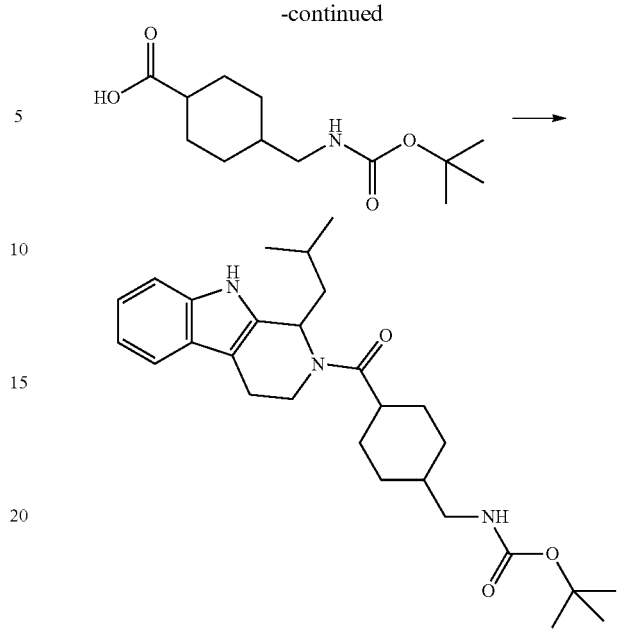

1-Isobutyl-2,3,4,9-tetrahydro-1H-pyrido[3,4-b]indole (228 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.10 mmol), and hydroxybenzotriazole (HOBT) (51 mg, 0.33 mmol) were all dissolved in acetonitrile (1.25 mL), dimethylformamide (DMF) (5 mL), and diisopropylethylamine (DIEA) (200 uL, 1.20 mmol). Boc-trans-4-(aminomethyl)cyclohexane-1-carboxylic acid (257 mg, 1.00 mmol) was added to the mixture. The reaction was stirred at room temperature for 16 hr. The result was diluted with EtOAc (100 mL), washed with sat. NaCl (2×50 mL), 1M citric acid (3×25 mL), sat. NaHCO₃ (3×25 mL), and sat. NaCl (50 mL). The organic layer was dried (anhyd. Na₂SO₄), filtered, and evaporated under vacuum. The crude product was purified by silica gel chromatography: 5 fractions (200 mL each) consisting of 0%, 1%, 1.5%, 2%, and 2.5%, MeOH in hexanes. Fractions containing product were combined and the solvent was removed under vacuum to yield a solid (401 mg, 86% yield; TLC $R_f$=0.16 (10% EtOAc in CH2Cl2); HPLC $R_t$=4.847 min). This method was used in the synthesis of the following compounds: MN0580, MN1169, MN1172, MN1186, MN1189, MN1190, MN1194, MN1195, MN1220, MN1221, MN1222, MN1223, MN1224, MN1225, MN1226, MN1227, MN1228, MN1229, MN1230, MN1231, MN1232, MN1233, MN1234, MN1235, MN1236, MN1237, MN1238, MN1239, MN1240, MN1241, MN1242, MN1243, MN1244, MN1245, MN1246, MN1247, MN1248, MN1249, MN50, MN1251, MN1252, MN1253, MN1254, MN1255, MN1256, MN1257, MN1258, MN1259, MN1260, MN1261, MN1262, MN1263.

Synthesis Example 22: MN1233 Intermediate Synthesis (Cyclization Via Azlactone)

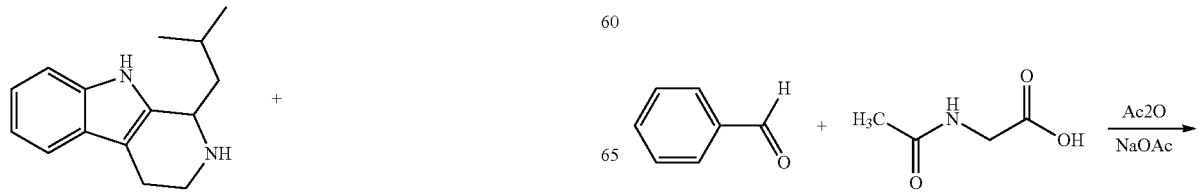

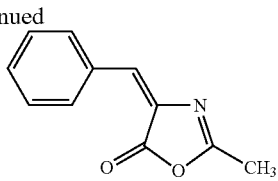

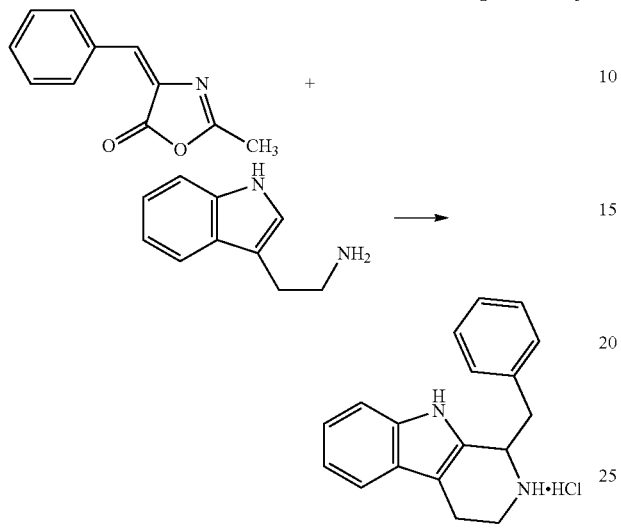

Reference: Herbst, R. M., and Shemin, D. α-Acetaminocinnamic acid. *Organic Syntheses, Coll.* Vol. 2, p.1 (1943); Vol. 19, p.1 (1939). Audia, J. E., Droste, J. J., Nissen, J. S., Murdoch, G. L., Evrard, D. A., "Pictet-Spengler-like" Synthesis of Tetrahydro-β-carbolines under Hydrolytic Conditions. Direct Use of Azalactones as Phenylacetaldehyde Equivalents, *J. Org. Chem.* 61, 22 7937-7939 (1996).

4-Benzylidene-2-methyloxazol-5(4H)-one synthesis: To a suspension of acetylglycine (5.86 g, 50 mmol), sodium acetate (4.10 g, 50 mmol), in acetic anhydride (47.3 mL, 500 mmol), was added benzaldehyde (5.11 mL, 50 mmol). The reaction mixture was heated in a 100 C oil bath for 10 min to dissolve. A reflux condenser was then added and the bath heated to 140 C for exactly 1 h. The reaction flask was then plunged into an ice-water bath with stirring and allowed to stir for 1 h. After 1 h, ice cold water (47 mL) was added to the suspension of yellow solid in a dark red solution. The product was collected on a fritted glass funnel, washed with ice cold water (3×50 mL) with stirring in the funnel. The crude product was dried in a desiccators over solid KOH overnight to provide 4.6 g of product as a yellow powder. This material was recrystallized from 85 mL of hot 2-propanol, cooling slowly to room temp, chilled in an ice bath, and then collected by filtration to provide 2.98 g, 32% yield of purified 4-benzylidene-2-methyloxazol-5(4H)-one: mp 148-151 C.

1-Benzyl-2,3,4,9-tetrahydro-1H-pyrido[3,4-b]indole hydrochloride synthesis: Tryptamine hydrochloride (2.4 g, 10.2 mmol) was suspended in 1N HCl. The azelactone (4-benzylidene-2-methyloxazol-5(4H)-one) (2.3 g, 12.2 mmol) was added and the mixture was then heated to reflux at 105 C in an oil bath with a reflux condenser under nitrogen. After 15 minutes the solution cleared, after 1 h a precipitate began to form along with mild effervescence. The reaction mixture was refluxed overnight, then cooled in an ice bath. The product was collected on fritted glass, washed with water (100 mL). The mud-like fine solid was dried in a vacuum desiccators over solid KOH for 3 days to provide 3.2 g of product as an off-white solid. This material was washed with ice-cold 2-propanol (2×10 mL), and then ice-cold diethyl ether (10 mL), then dried under vacuum overnight to give 3.0 g, 98% yield 1-benzyl-2,3,4,9-tetrahydro-1H-pyrido[3,4-b]indole hydrochloride as an off-white powder. This intermediate was used in the synthesis of the following compounds: MN1131, and MN1233.

Synthesis Example 23: MN1233 (Coupling by Method F)

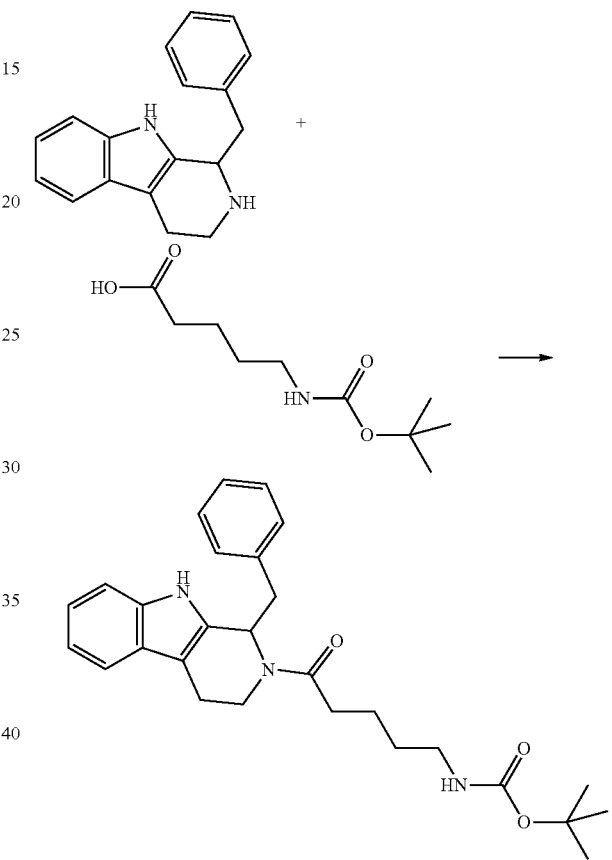

1-Benzyl-2,3,4,9-tetrahydro-1H-pyrido[3,4-b]indole hydrochloride (297 mg, 1.00 mmol), 1-ethyl-3-(3-dimethylaminopropyl)carbodiimide-HCl (EDC-HCl) (191 mg, 1.00 mmol), 4-dimethylaminopyridine (DMAP) (12 mg, 0.10 mmol), and hydroxybenzotriazole (HOBT) (51 mg, 0.33 mmol) were all dissolved in acetonitrile (1.25 mL), dimethylformamide (DMF) (5 mL), and diisopropylethylamine (DIEA) (400 uL, 2.40 mmol). Boc-5-aminovaleric acid (217 mg, 1.00 mmol) was added to the mixture. The reaction was stirred at room temperature for 16 hr. The result was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. The crude product was purified by silica gel chromatography: 5 fractions (200 mL each) consisting of 0%, 30%, 35%, 40%, and 45%, EtOAc in hexanes. Fractions containing product were combined and the solvent was removed under vacuum to yield a solid (293 mg, 63% yield): TLC R$_f$=0.25 (40% EtOAc in hexane); HPLC R$_t$=4.503 min). $^1$H NMR (CDCl$_3$, 0.003% v/v TMS, 400 MHz): δ$_H$ 1.45 (9H, s), 1.50-1.80 (6H, m), 2.40-2.55 (2H, m), 2.75-2.85 (2H, m), 3.10-3.25 (2H, m), 3.35-3.43 (1H, m), 4.05-4.10 (1H, m), 4.63 (1H, br s), 5.90-5.95 (1H, m), 6.97-7.25 (4H, m), 7.27-7.53 (6H, m). This method was used in the synthesis of the following compounds: MN0580, MN1169, MN1131, MN1172, MN1186, MN1189, MN1190, MN1194, MN1195, MN1220, MN1221, MN1222, MN1223, MN1224, MN1225, MN1226, MN1227, MN1228, MN1229, MN1230, MN1231, MN1232, MN1233, MN1234, MN1235, MN1236, MN1237, MN1238, MN1239, MN1240, MN1241, MN1242, MN1243, MN1244, MN1245, MN1246, MN1247, MN1248, MN1249, MN50, MN1251, MN1252, MN1253, MN1254, MN1255, MN1256, MN1257, MN1258, MN1259, MN1260, MN1261, MN1262, and MN1263.

Synthesis Example 24: MN1131 (Coupling by Method H)

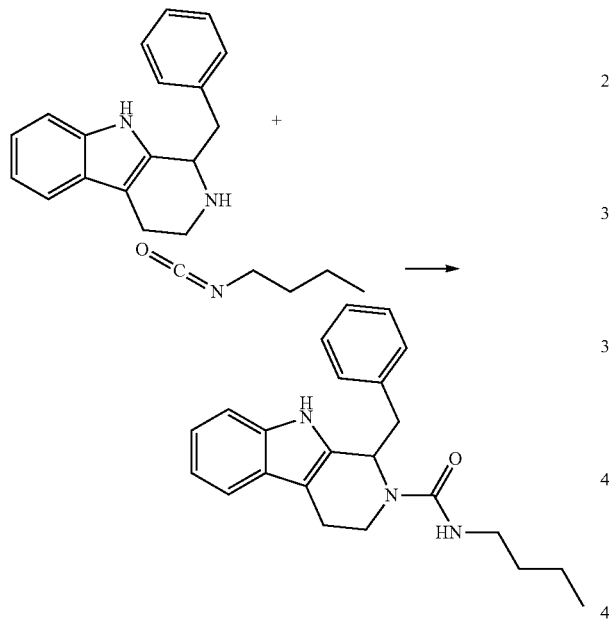

1-(1-1-Benzyl-2,3,4,9-tetrahydro-1H-pyrido[3,4-b]indole (781 mg, 2.98 mmol) was dissolved in CHCl₃ (40 mL) and cooled in an ice bath under an inert atmosphere of nitrogen for 10 min. Butyl isocyanate (504 μL, 4.47 mmol) was added by syringe. The reaction was removed from the ice bath and allowed to warm to room temperature for 10 min. HPLC indicated the reaction was complete at 1 hr. The reaction was evaporated and dried under vacuum. The residue was dissolved in EtOAc (100 mL), washed with sat. NaHCO₃ (3×30 mL), 1M citric acid (3×30 mL), and sat. NaCl (25 mL). The organic layer was dried (anhyd. Na₂SO₄), filtered, and evaporated under vacuum to give of an off-white solid (1.5 g). The material was further purified by chromatography through silica gel (70 g), elution with 8-200 mL fractions: 0%, 2%, 3%, 4%, 5% and 6% MeOH in CH2Cl2. Fractions containing the cleanest product were pooled and evaporated to yield 1.02 g of an off-white product: TLC $R_f$=0.1 (30% EtOAc in Hexane); HPLC $R_t$=4.191 min). This method was used in the synthesis of the following compounds: MN733, MN1130, MN1131, MN1158, MN1160, MN1169, MN1171, MN1172, MN1184.

Synthesis Example 25: MN1254 (Cyclization by Method E)

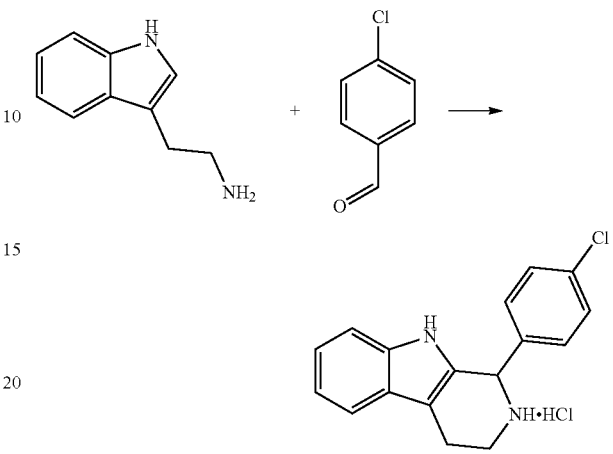

Tryptamine (1.60 g, 10 mmol) was dissolved in EtOAc (5 mL) by swirling and heating with a heat gun until dissolved. Then 4-chlorobenzaldehyde (1.48 g, 10.5 mmol) was added. The reaction vessel was swirled and heated with a heat gun to dissolve. The Schiff base intermediate precipitated within 2 min. The reaction mixture was cooled to room temperature and the intermediate Schiff base was collected on fritted glass and then dried under vacuum to yield 2.36 g of intermediate as a tan powder. The Schiff base was dissolved in acetonitrile/absolute ethanol (12.5 mL/12.5 mL). 4N HCl in dioxane (4 mL, 16 mmol) was added. The solution was heated to reflux at which point the HCl salt of the cyclized product began to precipitate. The reaction mixture was then cooled to −20 C and the solid was collected on fritted glass. The product, 1-(4-chlorophenyl)-2,3,4,9-tetrahydro-1H-pyrido[3,4-b]indole hydrochloride, was dried under vacuum to yield 2.16 g, 85% yield (68% overall) of an off-white powder: Mp: 163-165 C (free base).

Synthesis Example 26: MN1254 (Coupling by Method F)

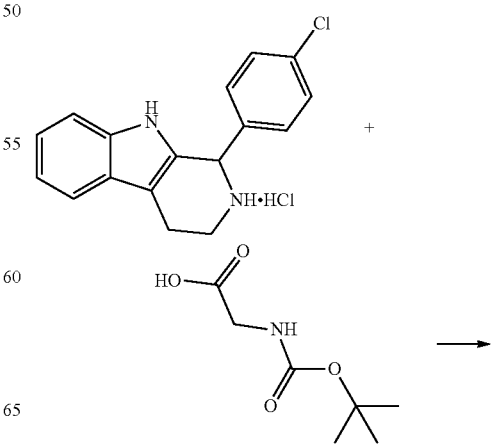

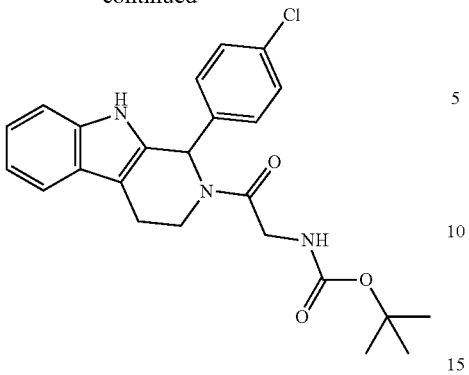

1-1-(4-Chlorophenyl)-2,3,4,9-tetrahydro-1H-pyrido[3,4-b]indole hydrochloride (319 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.10 mmol), and hydroxybenzotriazole (HOBT) (51 mg, 0.33 mmol) were all dissolved in acetonitrile (1.25 mL), dimethylformamide (DMF) (5 mL), and diisopropylethyl-amine (DIEA) (200 uL, 1.20 mmol). Boc-glycine (175 mg, 1.00 mmol) was added to the mixture. The reaction was stirred at room temperature for 16 hr. The result was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. The crude product was purified by silica gel chromatography: 3 fractions (200 mL each) consisting of 15%, 20%, and 25% EtOAc in hexanes. Fractions containing product were combined and the solvent was removed under vacuum to yield a solid (269 mg, 61% yield; TLC R$_f$=0.30 (25% EtOAc in Hexane); HPLC Rt=4.574 min). This method was used in the synthesis of the following compounds: MN0580, MN1169, MN1172, MN1186, MN1189, MN1190, MN1194, MN1195, MN1220, MN1221, MN1222, MN1223, MN1224, MN1225, MN1226, MN1227, MN1228, MN1229, MN1230, MN1231, MN1232, MN1233, MN1234, MN1235, MN1236, MN1237, MN1238, MN1239, MN1240, MN1241, MN1242, MN1243, MN1244, MN1245, MN1246, MN1247, MN1248, MN1249, MN50, MN1251, MN1252, MN1253, MN1254, MN1255, MN1256, MN1257, MN1258, MN1259, MN1260, MN1261, MN1262, MN1263.

Synthesis Example 27: MN0716 (Indole Analog Synthesis)

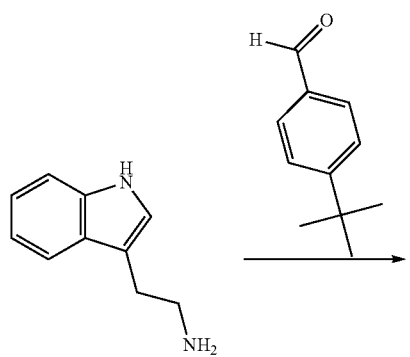

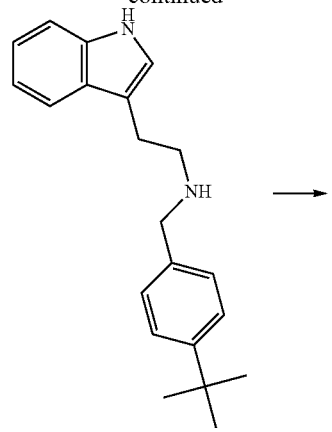

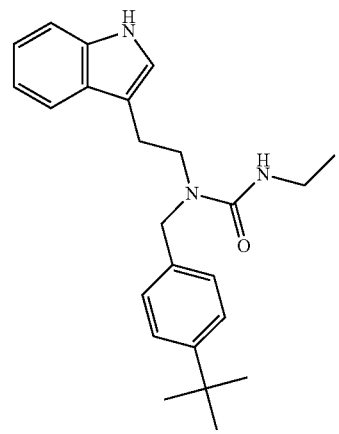

N-(4-tert-butylbenzyl)-2-(1H-indol-3-yl)ethanamine: To a solution of tryptamine (1.5 g, 9.4 mmol) was in abs. EtOH (15 mL) was added 4-t-butylbenzaldehyde (2.0 mL, 12 mmol). The reaction was stirred for 1 h before cooling to 0 C and then adding NaBH4 (750 mg, 19 mmol). The solution was stirred for 1 h at 0 C. The solution was concentrated in vacuo and then dried under high vacuum. The reaction was then quenched with 1N HCl (~20 mL), then EtOAc (100 mL) was added to form a precipitate. The mixture was made basic (pH 10) with solid K2CO3. The layers were separated, dried over Na2O4 and evaporated to yield 300 mg of oil. This material was purified by first adding 1N HCl (10 mL), then EtOAc (50 mL) was added to precipitate N-(4-tert-butylbenzyl)-2-(1H-indol-3-yl)ethanamine as a solid: 260 mg (9% yield); HPLC Rt (2.757 min).

To an ice-cold solution of N-(4-tert-butylbenzyl)-2-(1H-indol-3-yl)ethanamine (100 mg, 0.327 mmol) in CH2Cl2 was added ethyl isocyanate (26 uL, 0.327 mmol) (chilled to 0 C in 1.5 mL of CH2Cl2). The reaction was stirred at 0 C for 5 min. After 1 h, 0.2 equiv of ethyl isocyanate was then added and stirred for another 30 min. The solution was diluted with CH2Cl2 and washed with sat. NaHCO$_3$. The solution was chromatographed on silica gel eluting with hexane/ethyl acetate [2:1 to 1:1] to provide 129 mg, 100% yield of product; HPLC Rt 4.664 min; TLC Rf 0.16, 10% EtOAc in CH2Cl2. This method was used in the synthesis of the following compounds: MN0716, MN0733, and MN1058.

TABLE 1

Physical Data and Synthetic Methods Table

| Compound | HPLC Rt (min) | TLC Rf | TLC eluent | Cyclization Method | Amide Formation Method |
|---|---|---|---|---|---|
| MN0477 | 4.766 | 0.22 | 25% EtOAc in Hexane | B | G |
| MN0580 | 3.473 | 0.14 | 4% MeOH in CH2Cl2 | E | F |
| MN0618 | 3.364 | 0.14 | 2% MeOH in CH2Cl2 | C | F |
| MN0642 | 4.797 | 0.24 | 2% MeOH in CH2Cl2 | D | G |
| MN0716 | 4.664 | 0.16 | 10% EtOAc in CH2Cl2 | indole | H |
| MN0733 | 5.162 | 0.07 | 25% EtOAc in Hexane | indole | G |
| MN0908 | 5.106 | 0.47 | 25% EtOAc in Hexane | indole | G |
| MN1058 | 5.109 | 0.48 | 25% EtOAc in Hexane | indole | G |
| MN1130 | 4.598 | 0.46 | 40% EtOAc in Hexane | C | H |
| MN1131 | 4.462 | 0.22 | 2% MeOH in CH2Cl2 | azelactone | H |
| MN1132 | 5.299 | 0.28 | 10% EtOAc in Hexane | A | G |
| MN1133 | 4.803 | 0.41 | 3% MeOH in CH2Cl2 | A | G |
| MN1135 | 4.804 | 0.39 | 2% MeOH in CH2Cl2 | B | G |
| MN1137 | 4.968 | 0.5 | 4% EtOAc in CH2Cl2 | A | G |
| MN1138 | 4.548 | 0.22 | 2% MeOH in CH2Cl2 | A | G |
| MN1151 | 4.696 | 0.81 | 10% EtOAc in CH2Cl2 | B | H |
| MN1152 | 4.433 | 0.66 | 10% EtOAc in CH2Cl2 | B | G |
| MN1156 | 4.284 | 0.22 | 25% EtOAc in Hexane | B | G |
| MN1157 | 4.735 | 0.36 | 20% EtOAc in Hexane | B | G |
| MN1158 | 5.162 | 0.52 | 25% EtOAc in Hexane | B | H |
| MN1160 | 2.984 | 0.24 | 25% EtOAc in Hexane | B | H |
| MN1169 | 4.404 | 0.21 | 25% EtOAc in Hexane | B | H |
| MN1171 | 4.680 | 0.81 | 10% EtOAc in CH2Cl2 | B | H |
| MN1172 | 4.405 | 0.19 | 2% MeOH in CH2Cl2 | B | H |
| MN1184 | 3.957 | 0.1 | 2% MeOH in CH2Cl2 | Commercial | H |
| MN1186 | 4.577 | 0.59 | 10% EtOAc in CH2Cl2 | A | F |
| MN1188 | 5.299 | 0.41 | 25% EtOAc in Hexane | B | G |
| MN1189 | 4.533 | 0.26 | 10% EtOAc in CH2Cl2 | A | F |
| MN1190 | 4.58 | 0.16 | 10% EtOAc in CH2Cl2 | A | F |
| MN1193 | 4.703 | 0.18 | 2% MeOH in CH2Cl2 | Commercial | G |
| MN1194 | 4.652 | 0.14 | 10% EtOAc in CH2Cl2 | A | F |
| MN1195 | 4.777 | 0.1 | 25% EtOAc in Hexane | A | F |
| MN1197 | 4.801 | 0.41 | 3% MeOH in CH2Cl2 | A | G |
| MN1203 | 4.559 | 0.32 | 25% EtOAc in Hexane | A | G |
| MN1206 | 4.553 | 0.32 | 25% EtOAc in Hexane | A | G |
| MN1207 | 4.735 | 0.44 | 25% EtOAc in Hexane | A | G |
| MN1208 | 4.876 | 0.36 | 20% EtOAc in Hexane | A | G |
| MN1209 | 4.79 | 0.38 | 25% EtOAc in Hexane | A | G |
| MN1210 | 4.834 | 0.27 | 2% MeOH in CH2Cl2 | D | G |
| MN1211 | 3.734 | 0.14 | 4% MeOH in CH2Cl2 | B | G |
| MN1212 | 4.747 | 0.29 | 2% MeOH in CH2Cl2 | A | G |
| MN1213 | 4.869 | 0.29 | 2% MeOH in CH2Cl2 | A | G |
| MN1214 | 5.137 | 0.48 | 25% EtOAc in Hexane | A | G |
| MN1216 | 4.823 | 0.4 | 25% EtOAc in Hexane | B | G |
| MN1217 | 5.057 | 0.47 | 25% EtOAc in Hexane | E | G |
| MN1218 | 3.733 | 0.11 | 4% MeOH in CH2Cl2 | E | G |
| MN1219 | 4.808 | 0.27 | 25% EtOAc in Hexane | B | G |
| MN1220 | 4.412 | 0.1 | 25% EtOAc in Hexane | A | F |
| MN1221 | 4.639 | 0.32 | 25% EtOAc in Hexane | A | F |
| MN1222 | 4.637 | 0.34 | 25% EtOAc in Hexane | A | F |
| MN1223 | 4.256 | 0.08 | 25% EtOAc in Hexane | A | F |
| MN1224 | 4.404 | 0.19 | 2% MeOH in CH2Cl2 | A | F |
| MN1225 | 4.229 | 0.08 | 2% MeOH in CH2Cl2 | A | F |
| MN1226 | 4.517 | 0.1 | 2% MeOH in CH2Cl2 | A | F |
| MN1227 | 4.594 | 0.25 | 20% EtOAc in Hexane | A | F |
| MN1228 | 4.771 | 0.29 | 20% EtOAc in Hexane | A | F |
| MN1229 | 4.867 | 0.13 | 30% EtOAc in Hexane | A | F |
| MN1230 | 4.698 | 0.12 | 30% EtOAc in Hexane | A | F |
| MN1231 | 4.191 | 0.1 | 30% EtOAc in Hexane | A | F |
| MN1232 | 4.241 | 0.19 | 30% EtOAc in Hexane | A | F |
| MN1233 | 4.503 | 0.25 | 40% EtOAc in Hexane | A | F |
| MN1234 | 4.5 | 0.28 | 40% EtOAc in Hexane | A | F |
| MN1235 | 4.451 | 0.41 | 2% MeOH in CH2Cl2 | Commercial | F |
| MN1236 | 4.309 | 0.11 | 2% MeOH in CH2Cl2 | Commercial | F |
| MN1237 | 4.18 | 0.14 | 3% MeOH in CH2Cl2 | Commercial | F |
| MN1238 | 4.034 | 0.07 | 2% MeOH in CH2Cl2 | Commercial | F |
| MN1239 | 3.817 | 0.1 | 2% MeOH in CH2Cl2 | E | F |
| MN1240 | 4.771 | 0.14 | 2% MeOH in CH2Cl2 | D | F |
| MN1241 | 3.674 | 0.17 | 4% MeOH in CH2Cl2 | E | F |
| MN1242 | 4.511 | 0.09 | 10% EtOAc in CH2Cl2 | B | F |
| MN1243 | 4.507 | 0.1 | 10% EtOAc in CH2Cl2 | B | F |
| MN1244 | 4.465 | 0.08 | 10% EtOAc in CH2Cl2 | A | F |
| MN1245 | 4.435 | 0.1 | 10% EtOAc in CH2Cl2 | A | F |
| MN1246 | 4.847 | 0.16 | 10% EtOAc in CH2Cl2 | A | F |

TABLE 1-continued

Physical Data and Synthetic Methods Table

| Compound | HPLC Rt (min) | TLC Rf | TLC eluent | Cyclization Method | Amide Formation Method |
|---|---|---|---|---|---|
| MN1247 | 4.599 | 0.13 | 10% EtOAc in CH2Cl2 | A | F |
| MN1248 | 4.418 | 0.21 | 25% EtOAc in Hexane | A | F |
| MN1249 | 4.719 | 0.29 | 25% EtOAc in Hexane | A | F |
| MN1250 | 4.599 | 0.31 | 25% EtOAc in Hexane | A | F |
| MN1251 | 4.395 | 0.18 | 25% EtOAc in Hexane | A | F |
| MN1252 | 4.56 | 0.24 | 25% EtOAc in Hexane | A | F |
| MN1253 | 4.742 | 0.26 | 25% EtOAc in Hexane | A | F |
| MN1254 | 4.574 | 0.3 | 25% EtOAc in Hexane | E | F |
| MN1255 | 4.641 | 0.29 | 25% EtOAc in Hexane | A | F |
| MN1256 | 4.518 | 0.27 | 25% EtOAc in Hexane | E | F |
| MN1257 | 4.496 | 0.24 | 25% EtOAc in Hexane | B | F |
| MN1258 | 4.497 | 0.49 | 10% EtOAc in CH2Cl2 | B | F |
| MN1259 | 4.314 | 0.32 | 10% EtOAc in CH2Cl2 | Commercial | F |
| MN1260 | 4.467 | 0.44 | 10% EtOAc in CH2Cl2 | azelactone | F |
| MN1261 | 4.39 | 0.48 | 10% EtOAc in CH2Cl2 | B | F |
| MN1262 | 4.401 | 0.4 | 10% EtOAc in CH2Cl2 | B | F |
| MN1263 | 4.418 | 0.24 | 2% MeOH in CH2Cl2 | B | F |
| MN1264 | 3.893 | 0.14 | 2% MeOH in CH2Cl2 | Commercial | F |
| MN1265 | 4.714 | 0.11 | 2% MeOH in CH2Cl2 | A | F |
| MN1266 | 4.755 | 0.14 | 2% MeOH in CH2Cl2 | A | F |
| MN1270 | 4.596 | 0.11 | 2% MeOH in CH2Cl2 | A | F |
| MN1271 | 4.732 | 0.11 | 25% EtOAc in Hexane | A | F |
| MN1272 | 4.634 | 0.09 | 10% EtOAc in CH2Cl2 | A | F |
| MN1279 | 4.487 | 0.19 | 25% EtOAc in Hexane | A | F |
| MN1280 | 4.321 | 0.17 | 25% EtOAc in Hexane | A | F |
| MN1285 | 4.57 | 0.04 | 25% EtOAc in Hexane | A | F |
| MN1286 | 4.448 | 0.03 | 25% EtOAc in Hexane | A | F |
| MN1289 | 4.714 | 0.08 | 25% EtOAc in Hexane | A | F |
| MN1290 | 4.580 | 0.17 | 25% EtOAc in Hexane | A | F |
| MN1291 | 4.359 | 0.09 | 25% EtOAc in Hexane | A | F |

Summary of Biological Activity of the Compounds

FIG. 28 shows a structure activity relationship chart. Percent inhibition of cancer cell migration was performed in a wound healing assay. The Percent area that the invading cancer cells occupied, in the presence of a drug candidate compared to the controls, was quantified by Image J cell software which enables cell counting from photographs. IC50's were calculated by performing migration experiments at several compound concentrations and then applying Hill's equation. Inhibition of cancer cell proliferation was quantified by automated cell counting in the presence or absence of a drug candidate. The quantified data are presented in FIG. 28. Here, the potency of the drug candidate was simply scored 4 for the highest degree of inhibition and 0 for the lowest. The effect of the drug candidates on stem cell pluripotency or proliferation was scored by eye, based on cell morphology and cell density, with 0 being no change in morphology or cell number and 4 being the most profound effect, with the stem cells taking on the morphology of a differentiating cell, along with much fewer cells indicative of inhibition of proliferation. Photographs of the effect of each drug candidate is shown in FIGS. 29-72. Fibroblasts are a later stage progenitor cell, so they do not change morphology. The effect of each drug candidate was scored 0-4, with 4 being the highest in inhibiting cell proliferation (FIG. 28).

Pharmaceutical Composition

Certain of the compounds of the invention comprise asymmetrically substituted carbon atoms. Such asymmetrically substituted carbon atoms can result in the compounds of the invention comprising mixtures of stereoisomers at a particular asymmnetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13-30, 1976. The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the "Chemical Abstracts Index Guide," Appendix IV, paragraph 203, 1987.

As used herein, the term "pharmaceutically acceptable salts" refers to the nontoxic acid or alkaline earth metal salts of the compounds of the invention. These salts can be prepared in situ during the final isolation and purification of the compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, persulfate, 3-phenylproionate, picrate, pivalate, propionate, succinate, sulfate, tartrate, thiocyanate, p-toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the inventive compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, and the like.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in Higuchi, T., and V. Stella, "Pro-drugs as Novel Delivery Systems," A.C.S. Symposium Series 14, and in "Bioreversible Carriers in Drug Design," in Edward B. Roche (ed.), American Pharmaceutical Association, Pergamon Press, 1987, both of which are incorporated herein by reference.

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-3-cyclodextrin, polyvinyl-pyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey, 1991, incorporated herein by reference.

Effective amounts of the compounds of the invention generally include any amount sufficient to detectably inhibit MUC1* positive activity by any of the assays described herein, by other MUC1* positive activity assays known to those having ordinary skill in the art, or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

While the compounds of the invention can be administered as the sole active pharmaceutical agent, they can also be used in combination with one or more other agents used in the treatment of cancer. Representative agents useful in combination with the compounds of the invention for the treatment of cancer include, for example, irinotecan, topotecan, gemcitabine, gleevec, herceptin, 5-fluorouracil, leucovorin, carboplatin, cisplatin, taxanes, tezacitabine, cyclophosphamide, vinca alkaloids, imatinib, anthracyclines, rituximab, trastuzumab, topoisomerase I inhibitors, as well as other cancer chemotherapeutic agents.

The above compounds to be employed in combination with the compounds of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

In hematological cancers, such as chronic myelogenous leukemia (CML), chromosomal translocation is responsible for the constitutively activated BCR-ABL tyrosine kinase. The afflicted patients are responsive to GLEEVEC®, a small molecule tyrosine kinase inhibitor, as a result of inhibition of Abl kinase activity. However, many patients with advanced stage disease respond to GLEEVEC® initially, but then relapse later due to resistance-conferring mutations in the Abl kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, the inventive compounds are used in combination with at least one additional agent, such as GLEEVEC®, in the treatment of hematological cancers, such as chronic myelogenous leukemia (CML), to reverse or prevent resistance to the at least one additional agent.

In another aspect of the invention, kits that include one or more compounds of the invention are provided. Representative kits include a compound of the invention and a package insert or other labeling including directions for treating a cellular proliferative disease by administering MUC1* inhibitory amount of the compound.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1. Growth of Naïve State Stem Cells

Stem cells whether embryonic or induced pluripotent stem (iPS) cells were cultured in a minimal, serum-free media that contained human recombinant $NME7_{AB}$ at a concentration of 2-32 nM wherein 4-8 nM is preferred and 4 nM is more preferred. To facilitate surface attachment, cell culture plates were coated with an anti-MUC1* monoclonal antibody called MN-C3 or C3 or MN-C8 at a concentration of 2-100 ug/mL coating solution, wherein 3-50 ug/mL is preferred and 6-12.5 ug/mL is more preferred. In these experiments, 12.5 ug/mL of MN-C3 was used. Antibody coated plates were incubated at 4 degrees C. overnight prior to plating stem cells. A Rho kinase I inhibitor was added to enhance surface attachment. In some cases, $NME7_{AB}$ was substituted with human recombinant NME1 dimers which also induce stem cells to revert to a naïve-like state.

Example 2. Growth of Primed State Stem Cells

Stem cells whether embryonic or induced pluripotent stem (iPS) cells were cultured in a minimal, serum-free media that contained human recombinant bFGF at a concentration of 8 ng/mL. The stem cells were plated over a layer of inactivated mouse embryonic fibroblasts, aka MEFs, which secrete additional uncharacterized growth factors and cytokines.

Example 3. Drug Screen for Inhibitors of Metastatic Cancer

Human naïve state and primed stem cells were cultured in parallel for at least 5 passages to guarantee normal differentiation-free growth. The stem cells were plated in 12-well cell culture plates with 50,000 cells per well. Cells were cultured in their respective media, either bFGF media or $NME7_{AB}$ media for 24 hours. Media was then removed and replaced with media devoid of bFGF or $NME7_{AB}$, when indicated. Agents being tested for their ability to induce differentiation of naïve stem cells were added to the media at the concentrations indicated. After 72 hours, photographs were taken see FIGS. 1-10.

Example 4. Drug Screen for Inhibitors of Cancer or Metastatic Cancer

Human naïve state and primed stem cells were cultured in parallel for at least 5 passages to guarantee normal differentiation-free growth. The stem cells were plated in 12-well cell culture plates with 50,000 cells per well. Cells were cultured in their respective media, either bFGF media or NME7AB media for 24 hours. Media was then removed and replaced with media devoid of bFGF or NME7$_{AB}$. BRD4 inhibitor JQ1 or an inactive stereoisomer were added at 500 nM or 1 uM and tested for their ability to induce differentiation of naïve stem cells. Media was changed after 48 hours and replaced with fresh media containing the BRD4 inhibitors. After 4 days the experiment was stopped. Photographs were taken and cell pellets collected for further analysis, see FIGS. 11-16.

Example 5. Migration Assay

For the cancer cell migration experiment cancer cells were plated at varying densities into an Oris Cell Migration Assay Collagen-1 coated 96-well plate (Platypus Technologies LLC, Madison, Wis.). The Collagen-1 coated 96-well plate incorporates a specific vacuum plug which attaches to the bottom of each well, creating an area in which the cells cannot grow into. Once the cells have been plated at high densities into each well, they are allotted an 18-24 hour time period to attach to the bottom of the wells. Post-24 hour plugs are removed from the plate and then small molecule analogs are added to the wells. Images are taken of each well and represent time 0 (T=0) for each well. Images are taken of the wells at the 24, 48, 72, 96 and 120 hour time points. Data analysis is conducted using the images taken at these specific time point. Images are imported into ImageJ (Rasband, W. S., ImageJ, U. S. National Institutes of Health, Bethesda, Md., USA, http://imagej.nih.gov/ij/, 1997-2016.) and the area remaining free of cells is calculated. To determine the effectiveness of the small molecule analogs versus the DMSO control the areas collected at each time point are compared to the areas of the T=0 images resulting in a percent area remaining of each well. The data collected is then normalized to the DMSO controls in each experiment.

Example 6. Proliferation Assay

For the cancer cell proliferation experiment cancer cells were plated at constant densities (6000 cells/well) into a 96-well White-walled/Clear-bottom Tissue Culture Treated plate (Corning Incorporated, Big Flats, N.Y.). Small molecule analogs are added at T=24 hours in media with 2% FBS. Following the addition of the small molecules, the cells remain untouched for 120 hours with visual confirmations/inspections at 24, 48, 72 and 96 hours post plating. At the 120 hour mark a calcein fluorescence assay (Thermo Fisher Scientific, Waltham, Mass.) is performed on the plate. Calcein fluorescence (final concentration 0.5 uM) is used to assess cell viability. Cancer cell fluorescence is measured in a TECAN SAFIRE$^2$ spectrophotometer plate reader. The plate is then imaged using an Olympus IX71 fluorescence imaging microscope and montage of the resulting images are assembled using ImageJ.

REFERENCES

Nichols J, Smith A. Naïve and primed pluripotent states. Cell Stem Cell. 2009; 4:487-492.

Silva J, Barrandon O, Nichols J, Kawaguchi J, Theunissen T W, A Smith. Promotion of reprogramming to ground state pluripotency by signal inhibition. PLoS Biol. 2008; 6:e253.

Gafni O, Weinberger L, Mansour A A, Manor Y S, Chomsky E, Ben-Yosef D, Kalma Y, Viukov S, Maza I, Zviran A, Rais Y, Shipony Z, Mukamel Z, Krupalnik V, Zerbib M, Geula S, Caspi I, Schneir D, Shwartz T, Gilad S, Amann-Zalcenstein D, Benjamin S, Amit I, Tanay A, Massarwa R, Novershtern N, Hanna J H. Derivation of novel human ground state naïve pluripotent stem cells. Nature. 2013; 504:282-286.

Theunissen T W, Powell B E, Wang H, Mitalipova M, Faddah D A, Reddy J, Fan Z P, Maetzel D, Ganz K, Shi L, Lungjangwa T, Imsoonthornruksa S, Stelzer Y, Rangarajan S, D'Alessio A, Zhang J, Gao Q, Dawlaty M M, Young R A, Gray N S, Jaenisch R. Systematic identification of culture conditions for induction and maintenance of naïve human pluripotency. Cell Stem Cell. 2014; 15:471-487.

Smagghe B J, Stewart A K, Carter M G et al. MUC1* ligand, NM23-H1, is a novel growth factor that maintains human stem cells in a more naïve state. PLoS One. 2013; 8:e58601.

Hikita S T, Kosik K S, Clegg D O et al. MUC1* mediates the growth of human pluripotent stem cells. PLoS One. 2008; 3:e3312.

Hanna J, Cheng A W, Saha K, Kim J, Lengner C J, Soldner F, Cassady J P, Muffat J, Carey B W, Jaenisch R. Human embryonic stem cells with biological and epigenetic characteristics similar to those of mouse ESCs. Proc Natl Acad Sci USA. 2010; 107:9222-9227.

Ware C B, Nelson A M, Mecham B, Hesson J, Zhou W, Jonlin E C, Jimenez-Caliani A J, Deng X, Cavanaugh C, Cook S, Tesar P J, Okada J, Margaretha L, Sperber H, Choi M, Blau C A, Treuting P M, Hawkins R D, Cirulli V, Ruohola-Baker H. Derivation of naïve human embryonic stem cells. Proc Natl Acad Sci USA. 2014; 111:4484-4489.

Belkina A C, Nikolajczyk B S, Denis G V. BET protein function is required for inflammation: Brd2 genetic disruption and BET inhibitor JQ1 impair mouse macrophage inflammatory responses. J Immunol. 2013; 190(7):3670-8.

Tang X, Peng R, Phillips J E, Deguzman J, Ren Y, Apparsundaram S, Luo Q, Bauer C M, Fuentes M E, DeMartino J A, Tyagi G, Garrido R, Hogaboam C M, Denton C P, Holmes A M, Kitson C, Stevenson C S, Budd D C. Assessment of Brd4 inhibition in idiopathic pulmonary fibrosis lung fibroblasts and in vivo models of lung fibrosis. Am J Pathol. 2013 183(2):470-9

Filippakopoulos P, Qi J, Picaud S, Shen Y, Smith W B, Fedorov O, Morse E M, Keates T, Hickman T T, Felletar I, Philpott M, Munro S, McKeown M R, Wang Y, Christie A L, West N, Cameron M J, Schwartz B, Heightman T D, La Thangue N, French C A, Wiest O, Kung A L, Knapp S, Bradner J E. Selective inhibition of BET bromodomains. Nature. 2010; 468(7327):1067-73

Tang X, Peng R, Phillips J E, Deguzman J, Ren Y, Apparsundaram S, Luo Q, Bauer C M, Fuentes M E, DeMartino J A, Tyagi G, Garrido R, Hogaboam C M, Denton C P, Holmes A M, Kitson C, Stevenson C S, Budd D C. Assessment of Brd4 inhibition in idiopathic pulmonary fibrosis lung fibroblasts and in vivo models of lung fibrosis. Am J Pathol. 2013; 183(2):470-9

Horm T M, Bitler B G, Broka D M, Louderbough J M, Schroeder J A. MUC1 drives c-Met-dependent migration and scattering. Mol Cancer Res. 2012 10(12):1544-54

Meng X G, Yue S W. Dexamethasone disrupts cytoskeleton organization and migration of T47D Human breast cancer cells by modulating the AKT/mTOR/RhoA pathway. Asian Pac J Cancer Prev. 2014; 15(23):10245-50.

Zheng C$^1$, Fang Y, Tong W, Li G, Wu H, Zhou W, Lin Q, Yang F, Yang Z, Wang P, Peng Y, Pang X, Yi Z, Luo J, Liu M, Chen Y. Synthesis and biological evaluation of novel tetrahydro-1-carboline derivatives as antitumor growth and metastasis agents through inhibiting the transforming growth factor-β signaling pathway. J Med Chem. 2014; 57(3)

Carter M G, Smagghe B J, Stewart A K, Rapley J A, Lynch E, Bernier K J, Keating K W, Hatziioannou V M, Hartman E J, Bamdad C C. A Primitive Growth Factor, NME7AB, Is Sufficient to Induce Stable Naïve State Human Pluripotency; Reprogramming in This Novel Growth Factor Confers Superior Differentiation. Stem Cells. 2016; 34(4): 847-59.

Mani S A, Guo W, Liao M J, Eaton E N, Ayyanan A, Zhou A Y, Brooks M, Reinhard F, Zhang C C, Shipitsin M, Campbell L L, Polyak K, Brisken C, Yang J, Weinberg R A. The epithelial-mesenchymal transition generates cells with properties of stem cells. Cell. 2008; 133(4)

S. Meng, L. Zhang, Y. Tang, Q. Tu, L. Zheng, L. Yu, D. Murray, J. Cheng, S. H. Kim, X. Zhou and J. Chen, BET Inhibitor JQ1 Blocks Inflammation and Bone Destruction. J Dent Res. 2014; 93(7): 657-662.

All of the references cited herein are incorporated by reference in their entirety.

Those skilled in the art will recognize, or be able to ascertain using no more than routine experimentation, many equivalents to the specific embodiments of the invention specifically described herein.

What is claimed is:

1. A method of treating cancer in a subject, wherein the cancer is a MUC1 positive or MUC1* positive cancer, the method comprising administering to the subject a compound of Formula 5, Formula 6, Formula 7, or Formula 9;

Formula 5

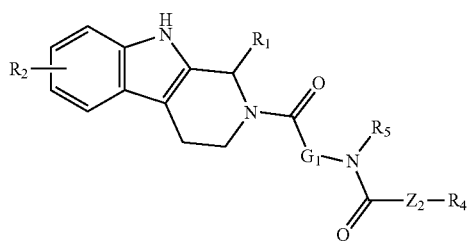

wherein,

R1 is H, optionally substituted C1-C6 alkyl; or optionally substituted unsubstituted C3-C8 cycloalkyl;

R2 is hydrogen, C1-C6 alkoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

G1 is —(CH$_2$)$_n$—, —CH=CH—, or —C3-C7 cycloalkylene-CH$_2$—;

Z2 is a bond, —NH—, —O—, —S—, —CH(CH$_3$)—, —(CH$_2$)$_n$—, —CH=CH—, —CO—, —SO—, —SO$_2$—, —C(=NH)—, —CH$_2$NH(CO)—, —CH$_2$NH(CO)O—, —CH$_2$NH(CO)NH—; —(CH$_2$)$_p$NH(CO)—, —(CH$_2$)$_p$NH(CO)O—, —(CH$_2$)$_p$NH(CO)NH—, —C3-C7 cycloalkylene-NH(CO)—, —C3-C7 cycloalkylene-CH$_2$NH(CO)O—, —C3-C7 cycloalkylene-NH(CO)NH—, —N(CH$_2$CH$_2$C$_6$H$_5$)—, or optionally substituted C6-C12 arylene;

R5 is H, C1-C6 alkyl, or 2-phenylethyl;

R4 is H, optionally substituted C1-C9 alkyl, optionally substituted C2-C6 alkenyl, optionally substituted C6-C12 aryl, optionally substituted C1-C9 heteroaryl with 1 to 4 ring atoms independently selected from N, S, and O, optionally substituted C7-C15 arylalkyl, optionally substituted C3-C7 cycloalkyl, —(CH$_2$)$_p$—NH(CO)O—(C1-C6 alkyl), —CH$_2$O (CH₂)ₚ—NH(CO)O—(C1-C6) alkyl; —(CH₂)ₚ—NHCO—(CH₂)ₙ—NH(CO)O—C1-C6 alkyl), —NH(CO)O-tert-butyl, —O-tert-butyl, or -tert-butyl;
each n is indpendentl selected from 1-8; each p is independently selected from 1-9;
where "substituted" means substituted with one or more substituents independently selected from halogen, trifluoromethyl, methylcarboxy, ethylcarboxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H;

Formula 6

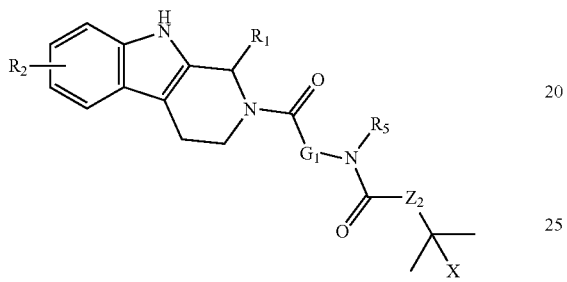

wherein,
R1 is H, optionally substituted C1-C6 alkyl, or optionally substituted C3-C8 cycloalkyl;
R2 is hydrogen, C1-C6 alkoxy, trifluoromethyl, halogen, methylcarboxy, ethylcarboxy, optionally substituted C1-C6 alkyl, —OH, —SH, —NH₂, —N₃, —CN, —NO₂, —CHO, —COOH, —CONH₂, —C(=NH)NH₂, or —SO₃H;
G1 is —(CH₂)ₙ—, —CH=CH—, or —C3-C7 cycloalkylene-CH₂—;
Z2 is a bond, —NH—, —O—, —S—, —CH(CH₃)—, —(CH₂)ₙ—, —CH=CH—, —CO—, —SO—, —SO₂—, —C(=NH)—, —CH₂NH(CO)—, —CH₂NH(CO)O—, —CH₂NH(CO)NH—; —(CH₂)ₚNH(CO)—, —(CH₂)ₚNH(CO)O—, —(CH₂)ₚNH(CO)NH—, —C3-C7 cycloalkylene-NH(CO)—, —C3-C7 cycloalkylene-CH₂NH(CO)O—, —C3-C7 cycloalkylene-NH(CO)NH—, or —N(CH₂CH₂C₆H₄)—;
R5 is H, C1-C6 alkyl, or 2-phenylethyl;
X is H, or C1-C3 alkyl;
each n is independently selected from 1-8; each p is independently selected from 1-9;
where "substituted" means substituted with one or more substituents independently selected from halogen, trifluoromethyl, methylcarboxy, ethylcarboxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H;

Formula 7

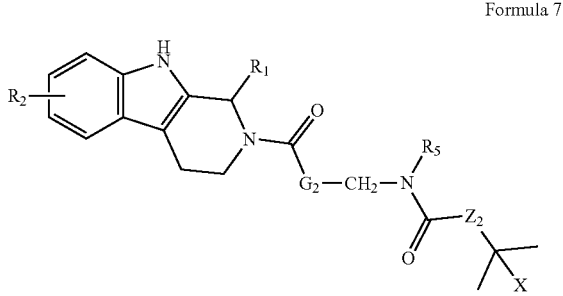

wherein,
R1 is H, optionally substituted C1-C6 alkyl; optionally substituted C2-C6 alkenyl; optionally substituted C1-C6 alkoxy; optionally substituted C1-C9 heteroaryl with 1 to 4 ring atoms independently selected from N, S, and O, optionally substituted C7-C15 arylalkyl, optionally substituted C2-C15 heteroarylalkyl with 1 to 4 ring atoms independently selected from N, S, and O, optionally substituted arylalkenyl, optionally substituted C3-C8 cycloalkyl, or optionally substituted C4-C8 cycloalkylalkyl;
R2 is hydrogen, C1-C6 alkoxy, trifluoromethyl, halogen, methylcarboxy, ethylcarboxy, optionally substitiued C1-C6 alkyl, —OH, —SH, —NH₂, —N₃, —CN, —NO₂, —CHO, —COOH, —CONH₂, —C(=NH)NH₂, or —SO₃H;
G2 is a bond, —(CH₂)ₙ—, —CH=CH—, CH₂NH(CO)—, —CH₂NH(CO)O—, —CH₂NH(CO)NH—; —(CH₂)ₙNH(CO)—, —(CH₂)ₙNH(CO)O—, —(CH₂)ₘNH(CO)NH—, or —C3-C7 cycloalkylene-,
Z2 is a bond, —NH—, —O—, —S—, —CH(CH₃)—, —(CH₂)ₙ—, —CH=CH—, —CO—, —SO—, —SO₂— or —C(=NH)—, —CH₂NH(CO)—, —CH₂NH(CO)O—, —CH₂NH(CO)NH—, —(CH₂)ₚ NH(CO)—, —(CH₂)ₚNH(CO)O—, —(CH₂)ₚNH(CO)NH—, —C3-C7 cycloalkylene-NH(CO)—, —C3-C7 cycloalkylene-CH₂NH(CO)O—, —C3-C7 cycloalkylene-NH(CO)NH—, or —N(CH₂CH₂C₆H₅)—;
R5 is H, C1-C6 alkyl, or 2-phenylethyl;
X is H, or C1-C3 alkyl;
each n is independenty selected from 1-8; each p is independently selected from 1-8; p=1-9;
where "substituted" means substituted with one or more substituents independently selected from halogen, trifluoromethyl, methylcarboxy, ethylcarboxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H;

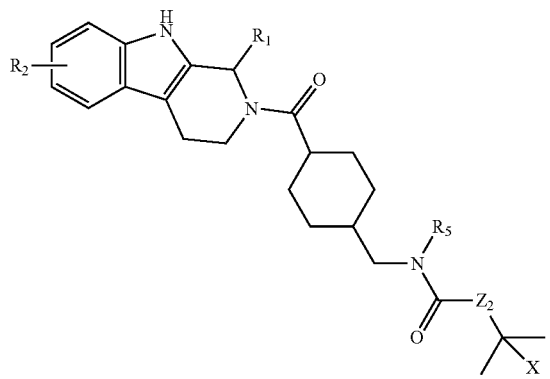

Formula 9 wherein,

R1 is H, optionally substituted C1-C6 alkyl, optionally substituted C2-C6 alkenyl, optionally substituted C1-C6 alkoxy, optionally substituted C6-C12 aryl, optionally substituted C1-C9 heteroaryl with 1 to 4 ring atoms independently selected from N, S, and O, optionally substituted C7-C15 arylalkyl, optionally substituted C2-C15 heteroarylalkyl with 1 to 4 ring atoms independently selected from N, S, and O, optionally substituted C7-C15 arylalkenyl, optionally substituted C3-C8 cycloalkyl, or optionally substituted C4-C8 cycloalkylalkyl;

R2 is hydrogen, C1-C6 alkoxy, trifluoromethyl, halogen, methylcarboxy, ethylcarboxy, optionally substituted C1-C6 alkyl, —OH, —SH, —$NH_2$, —$N_3$, —CN, —$NO_2$, —CHO, —COOH, —$CONH_2$, —C(=NH)$NH_2$, or —$SO_3$H;

R5 is H, C1-C6 alkyl, or 2-phenylethyl;

X is H, or C1-C3 alkyl;

Z2 is a bond, —NH—, —O—, —S—, —CH($CH_3$)—, —$(CH_2)_n$—, —CH=CH—, —CO—, —SO—, —$SO_2$—, —C(=NH)—, —$CH_2$NH(CO)—, —$CH_2$NH(CO)O—, —$CH_2$NH(CO)NH—, —$(CH_2)_n$NH(CO)—, —$(CH_2)_n$NH(CO)O—, —$(CH_2)_m$NH(CO)NH—, —C3-C7 cycloalkylene-NH(CO)—, —C3-C7 cycloalkylene-$CH_2$NH(CO)O—, —C3-C7 cycloalkylene-NH(CO)NH—, or —N($CH_2CH_2C_6H_4$)—;

each p is independently selected from 1-5; each n is independently selected from 1-8;

where "substituted" means substituted with one or more substituents independently selected from halogen, trifluoromethyl, methylcarboxy, ethylcarboxy, C1-C6 alkoxy, C1-C6 alkyl, —OH, —SH, —$NH_2$, —$N_3$, —CN, —$NO_2$, —CHO, —COOH, —$CONH_2$, —C(=NH)$NH_2$, or —$SO_3$H.

2. The method according to claim 1, wherein the cancer is an $NME7_{AB}$ or NME7-X1 positive cancer.

3. The method according to claim 1, further comprising analyzing a cancerous sample from the subject and determining that it is MUC1* positive, $NME7_{AB}$ positive or NME7-X1 positive.

4. The method according to claim 3, wherein the analyzing step is carried out by PCR.

5. The method according to claim 3, wherein when the cancerous sample expresses mRNA level of MUC1 gene, NME7 gene or NME7-X1 gene that is at least 0.5% of the mRNA expression level of EEF1A1 gene, it is determined to be MUC1* positive, $NME7_{AB}$ positive or NME7-X1 positive.

6. The method according to claim 3, wherein the analyzing step is carried out by immunohistochemistry.

7. The method according to claim 6, wherein when the cancerous sample is contacted with an antibody that binds to the PSMGFR peptide or the N-10 peptide and stains the tissue with a pathologist's standard score 1-4 ("+-++++"), it is determined to be MUC1* positive.

8. The method according to claim 6, wherein when the cancerous sample is contacted with an antibody that binds to the B3 peptide of NME7 and stains the tissue with a pathologist's standard score 1-4 ("+-++++"), it is determined to be $NME7_{AB}$ positive or NME7-X1 positive.

9. The method of claim 1, comprising administering to the subject the compound of Formula 5:

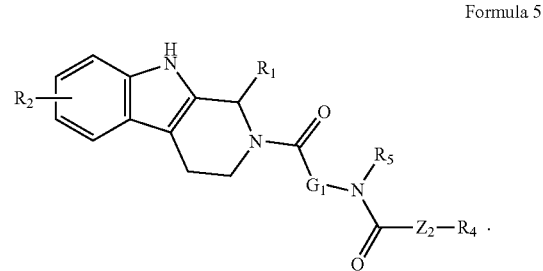

Formula 5

10. The method of claim 9, wherein in Formula 5, R1 an optionally substituted C1-C6 alkyl or an optionally substituted C3-C8 cycloalkyl.

11. The method of claim 1, comprising administering to the subject the compound of Formula 6:

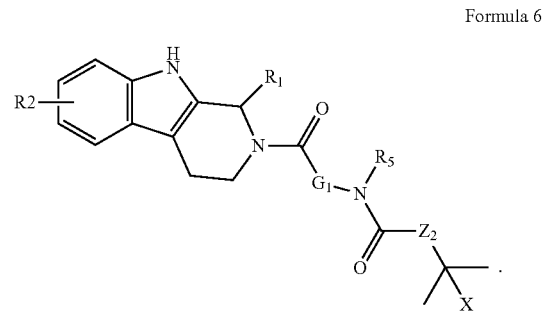

Formula 6

12. The method of claim 11, wherein in Formula 6, R1 is optionally substituted C1-C6 alkyl or optionally substituted C3-C8 cycloalkyl.

13. The method of claim 1, comprising administering to the subject the compound of Formula 7:

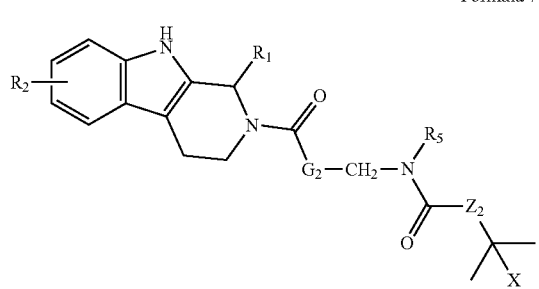

Formula 7 wherein,
R1 is H, optionally substituted C1-C6 alkyl, optionally substituted C2-C6 alkenyl, optionally substituted C1-C9 heteroaryl with 1 to 4 ring atoms independently selected from N, S, and O, optionally substituted C7-C15 arylalkyl, optionally substituted C2-C15 heteroarylalkyl with 1 to 4 ring atoms independently selected from N, S, and O, optionally substituted C7-C15 arylalkenyl, an optionally substituted C3-C8 cycloalkyl, or optionally substituted C4-C8 cycloalkylalkyl.

14. The method of claim 13, wherein in Formula 7, R1 is H, an optionally substituted C1-C6 alkyl, or an optionally substituted C3-C8 cycloalkyl.

15. The method of claim 13, wherein in Formula 7,
R1 is hydrogen, methyl, ethyl, isopropyl, isobutyl, benzyl, or pyridyl;
R2 is hydrogen, halogen, methyl or methoxy;
Z2 is O, NH, or —CH2—;
G2 is —CH2—, —(CH2)2—, —(CH2)3—, —(CH2)4—, —CH2NHCO— or —cyclohexylene—;
R5 is hydrogen, or methyl; and
X is hydrogen or methyl.

16. The method of claim 1, comprising administering to the subject the compound of Formula 9:

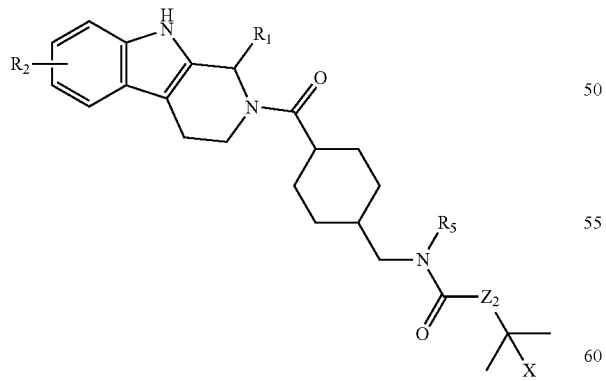

Formula 9 wherein,
R1 is H, optionally substituted C1-C6 alkyl, optionally substituted C2-C6 alkenyl, optionally C1-C9 heteroaryl with 1 to 4 ring atoms independently selected from N, S, and O, optionally substituted C7-C15 arylalkyl, optionally substituted C2-C15 heteroarylalkyl with 1 to 4 ring atoms independently selected from N, S, and O, optionally substituted C7-C15 arylalkenyl, optionally substituted C3-C8 cycloalkyl, or optionally substituted C4-C8 cycloalkylalkyl.

17. The method of claim 16, wherein in Formula 9, R1 is H, optionally substituted C1-C6 alkyl, or optionally substituted C3-C8 cycloalkyl.

18. The method of claim 16, wherein in Formula 9,
R1 is isopropyl or isobutyl;
R2 is hydrogen, halogen, or methyl;
Z2 is O or NH;
R5 is hydrogen; and
X is methyl.

19. A compound of Formula 5, Formula 6, Formula 7, or Formula 9,

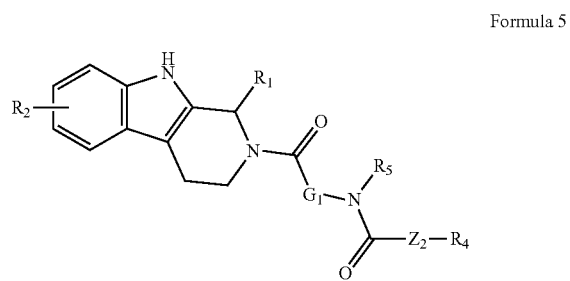

Formula 5 wherein,
R1 is H, optionally substituted C1-C6 alkyl or an optionally substituted C3-C8 cycloalkyl;
R2 is hydrogen, C1-C6 alkoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;
G1 is —(CH$_2$)$_n$—, —CH=CH—, or —C3-C7 cycloalkylene-CH$_2$—;
Z2 is a bond, —NH—, —O—, —S—, —CH(CH$_3$)—, —(CH$_2$)$_n$—, —CH=CH—, —CO—, —SO—, —SO$_2$—, —C(=NH)—, —CH$_2$NH(CO)—, —CH$_2$NH(CO)O—, —CH$_2$NH(CO)NH—, —(CH$_2$)$_p$NH(CO)—, —(CH$_2$)$_p$NH(CO)O—, —(CH$_2$)$_p$NH(CO)NH—, —C3-C7 cycloalkylene-NH(CO)—, —C3-C7 cycloalkylene-CH$_2$NH(CO)O—, —C3-C7 cycloalkylene-NH(CO)NH—, —N(CH$_2$CH$_2$C$_6$H$_4$)—, or optionally substituted C6-C12 arylene;
R5 is H, C1-C6 alkyl, or 2-phenylethyl;
R4 is H, optionally substituted C1-C9 alkyl, optionally substituted C2-C6 alkenyl; optionally substituted C6-C12 aryl, optionally substituted C1-C9 heteroaryl with 1 to 4 ring atoms independently selected from N, S, and O, optionally substituted C7-C15 arylalkyl, optionally substituted C3-C7 cycloalkyl, —(CH$_2$)$_p$—NH(CO)O—(C1-C6 alkyl), —CH$_2$O(CH$_2$)$_p$—NH(CO)O—(C1-C6) alkyl, —(CH$_2$)$_p$—NHCO—(CH$_2$)$_n$—NH(CO)O—C1-C6 alkyl), —NH(CO)O-tert-butyl, —O-tert-butyl, or -tert-butyl;
each n is independently selected from 1-8; each p is independently elected from 1-9;
where "substituted" means substituted with one or more substituents independently selected from halogen, trifluoromethyl, methylcarboxy, ethylcarboxy, C1-C6 alkoxy, C1-C6 alkyl, —OH, —SH, —NH$_2$, —$N_3$, —CN, —$NO_2$, —CHO, —COOH, —$CONH_2$, —C(=NH)$NH_2$, or —$SO_3H$;

Formula 6

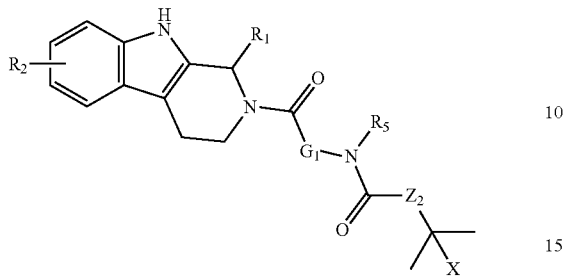

wherein,
- R1 is H, C1-C6 alkyl, or optionally substituted C3-C8 cycloalkyl,
- R2 is hydrogen, C1-C6 alkoxy, trifluoromethyl, halogen, methylcarboxy, ethylcarboxy, optionally substituted C1-C6 alkyl, —OH, —SH, —$NH_2$, —$N_3$, —CN, —$NO_2$, —CHO, —COOH, —$CONH_2$, —C(=NH)$NH_2$, or —$SO_3H$;
- G1 is —$(CH_2)_n$—, —CH=CH—, or —C3-C7 cycloalkylene-$CH_2$—;
- Z2 is a bond, —NH—, —O—, —S—, —CH(CH$_3$)—, —$(CH_2)_n$—, —CH=CH—, —CO—, —SO—, —$SO_2$—, —C(=NH)—, —$CH_2$NH(CO)—, —$CH_2$NH(CO)O—, —$CH_2$NH(CO)NH—, —$(CH_2)_p$NH(CO)—, —$(CH_2)_p$NH(CO)O—, —$(CH_2)_p$NH(CO)NH—, —C3-C7 cycloalkylene-NH(CO)—, —C3-C7 cycloalkylene-$CH_2$NH(CO)O—, —C3-C7 cycloalkylene-NH(CO)NH—, or —N($CH_2CH_2C_6H_5$)—;
- R5 is H, C1-C6 alkyl, or 2-phenylethyl;
- X is H, or C1-C3 alkyl;
- each n is independently selected from 1-8; each p is independently selected from 1-9;
- where "substituted" means substituted with one or more substituents independently selected from halogen, trifluoromethyl, methylcarboxy, ethylcarboxy, C1-C6 alkoxy, C1-C6 alkyl, —OH, —SH, —$NH_2$, —$N_3$, —CN, —$NO_2$, —CHO, —COOH, —$CONH_2$, —C(=NH)$NH_2$, or —$SO_3H$;

Formula 7

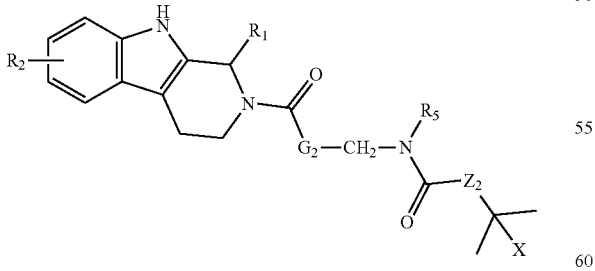

wherein,
- R1 is H, C1-C6 alkyl, optionally substituted C2-C6 alkenyl, optionally substituted C1-C6 alkoxy, optionally substituted C1-C9 heteroaryl with 1 to 4 ring atoms independently selected from N, S, and O, optionally substituted C7-C15 arylalkyl, optionally substituted C2-C15 heteroarylalkyl with 1 to 4 ring atoms independently selected from N, S, and O, optionally substituted arylalkenyl, an optionally substituted C3-C8 cycloalkyl, or optionally substituted C4-C8 cycloalkylalkyl;
- R2 is hydrogen, C1-C6 alkoxy, trifluoromethyl, halogen, methylcarboxy, ethylcarboxy, optionally substitituted C1-C6 alkyl, —OH, —SH, —$NH_2$, —$N_3$, —CN, —$NO_2$, —CHO, —COOH, —$CONH_2$, —C(=NH)$NH_2$, or —$SO_3H$;
- G2 is a bond, —$(CH_2)_n$—, —CH=CH—, —$CH_2$NH(CO)—, —$CH_2$NH(CO)O—, —$CH_2$NH(CO)NH—, —$(CH_2)_n$NH(CO)—, —$(CH_2)_n$NH(CO)O—, —$(CH_2)_m$NH(CO)NH—, or —C3-C7 cycloalkyl—,
- Z2 is a bond, —NH, —O—, —S—, —CH(CH$_3$)—, —$(CH_2)_n$—, —CH=CH—, —CO—, —SO—, —$SO_2$— or —C(=NH)—, —$CH_2$NH(CO)—, —$CH_2$NH(CO)O—, —$CH_2$NH(CO)NH—, —$(CH_2)_p$NH(CO)—, —$(CH_2)_p$NH(CO)O—, —$(CH_2)_p$NH(CO)NH—, —C3-C7 cycloalkylene-NH(CO)—, —C3-C7 cycloalkylene-$CH_2$NH(CO)O—, —C3-C7 cycloalkylene-NH(CO)NH—, or —N($CH_2CH_2C_6H_5$)—;
- R5 is H, C1-C6 alkyl, or 2-phenylethyl;
- X is H, or C1-C3 alkyl;
- each m is independently selected from 1-5; each n is independently selected from 1-8; each p is independently selected from 1-9;
- where "substituted" means substituted with one or more substituents independently selected from halogen, trifluoromethyl, methylcarboxy, ethylcarboxy, C1-C6 alkoxy, C1-C6 alkyl, —OH, —SH, —$NH_2$, —$N_3$, —CN, —$NO_2$, —CHO, —COOH, —$CONH_2$, —C(=NH)$NH_2$, or —$SO_3H$;

Formula 9

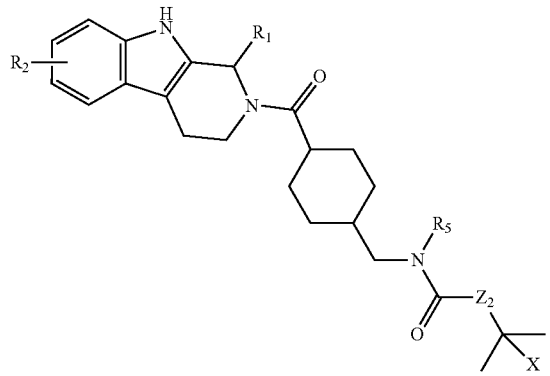

wherein,
- R1 is H, optionally substituted C1-C6 alkyl, optionally substituted C2-C6 alkenyl, optionally substituted C1-C6 alkoxy, optionally substituted C6-C12 aryl, optionally substituted C1-C9 heteroaryl with 1 to 4 ring atoms independently selected from N, S, and O, optionally substituted C7-C15 arylalkyl, optionally substituted C2-C15 heteroarylalkyl with 1 to 4 ring atoms independently selected from N, S, and O, optionally substituted C7-C15 arylalkenyl, optionally substituted C3-C8 cycloalkyl, or an optionally substituted C4-C8 cycloalkylalkyl;
- R2 is hydrogen, C1-C6 alkoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

R5 is H, C1-C6 alkyl, or 2-phenylethyl;

X is H, or C1-C3 alkyl;

Z2 is a bond, —NH—, —O—, —S—, —CH(CH$_3$)—, —(CH$_2$)$_n$—, —CH=CH—, —CO—, —SO—, —SO$_2$— or —C(=NH)—, —CH$_2$NH(CO)—, —CH$_2$NH(CO)O—, —CH$_2$NH(CO)NH—, —(CH$_2$)$_n$NH(CO)—, —(CH$_2$)$_n$NH(CO)O—, —(CH$_2$)$_m$NH(CO)NH—, —C3-C7 cycloalkylene-NH(CO)—, —C3-C7 cycloalkylene-CH$_2$NH(CO)O—, —C3-C7 cycloalkylene-NH(CO)NH—, or —N(CH$_2$CH$_2$C$_6$H$_4$)—, each p is independently selected from 1-5; each n is independently selected from 1-8;

where "substituted" means substituted with one or more substituents independently selected from halogen, trifluoromethyl, methylcarboxy, ethylcarboxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

20. The method according to claim 1, wherein the compound is selected from the group consisting of:

MN0580

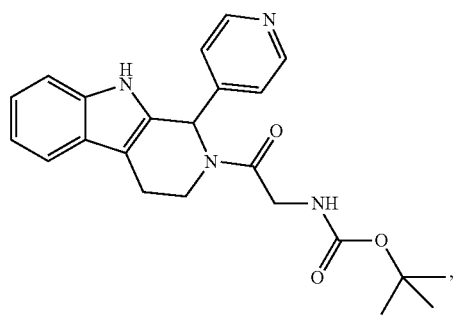

MN1158

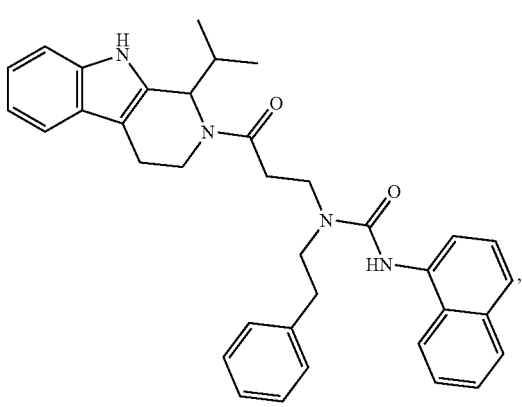

MN1160

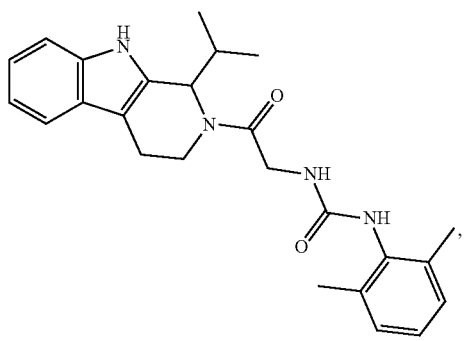

MN1169

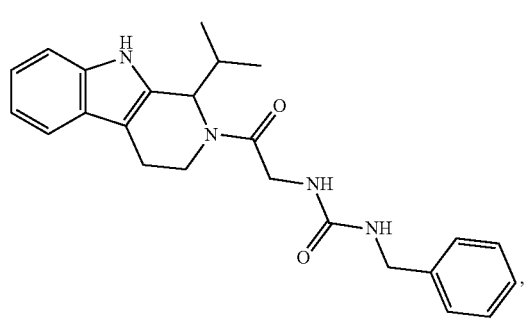

MN1172

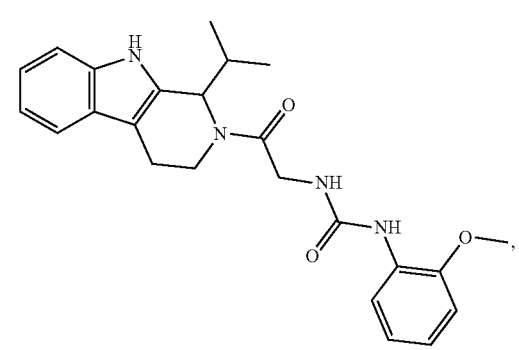

MN1186

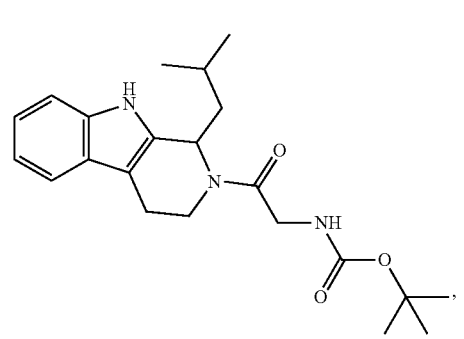

MN1189
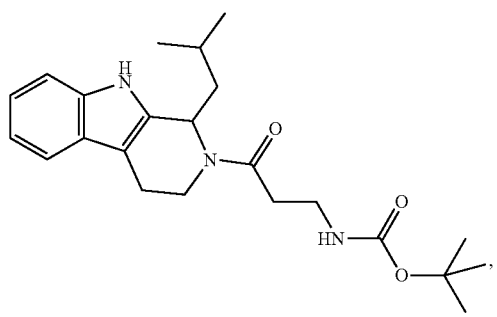
MN1220
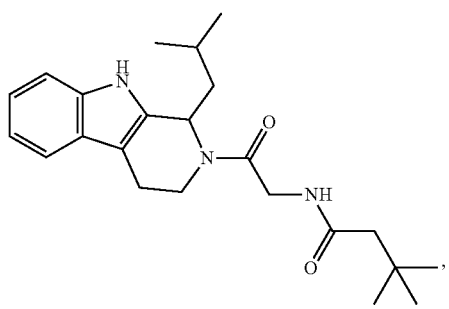
MN1190
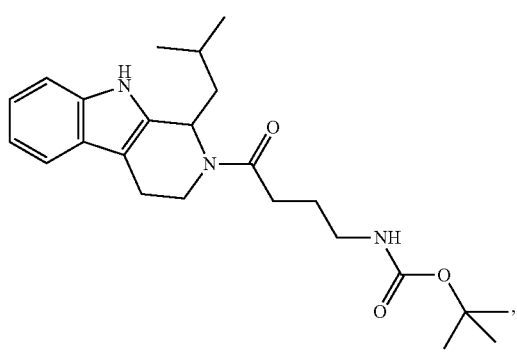
MN1223
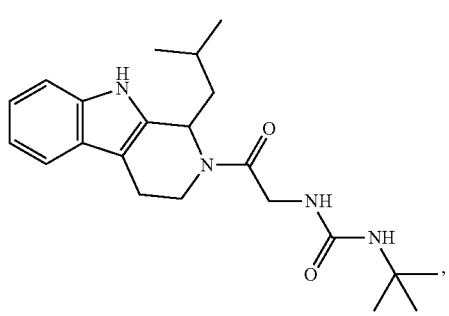
MN1194
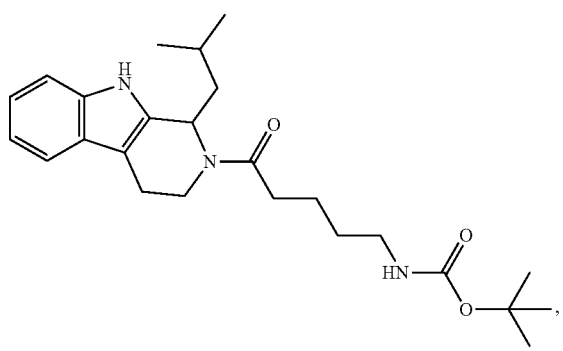
MN1224
MN1195
MN1225
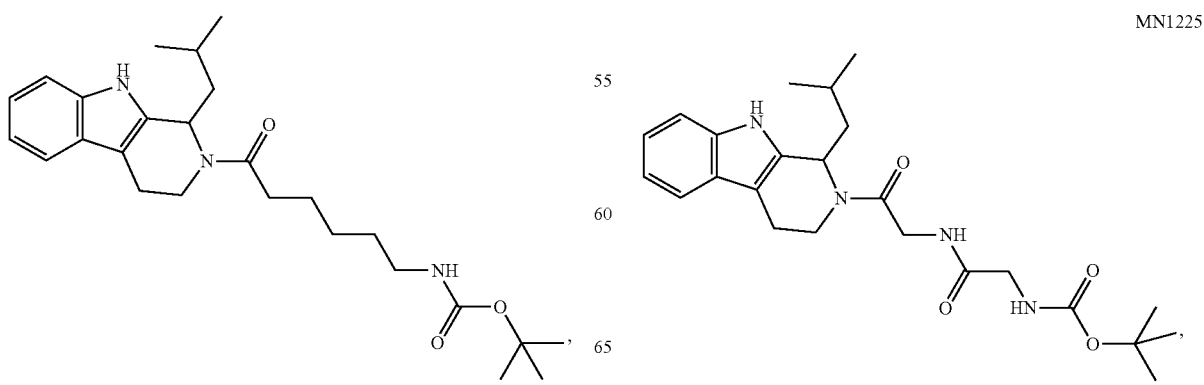

-continued
MN1227
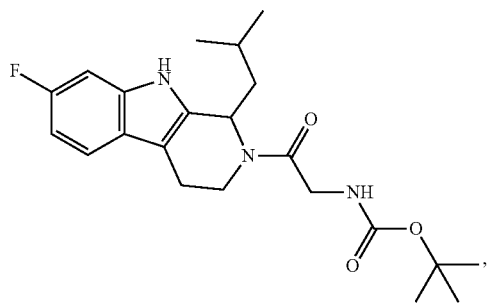
MN1228
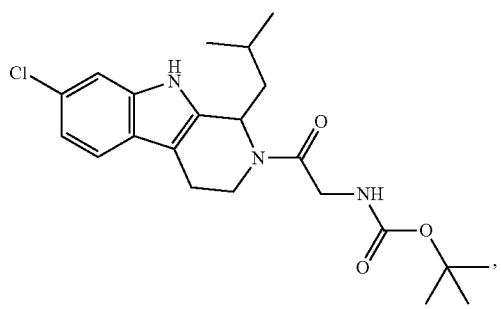
MN1229
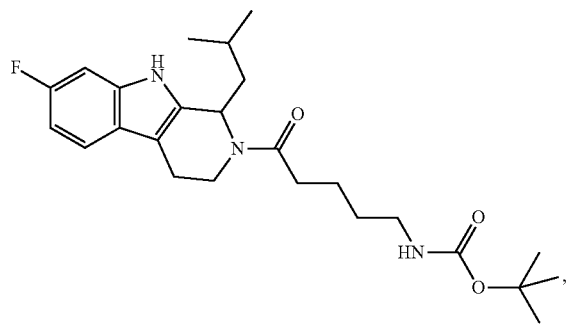
MN1230
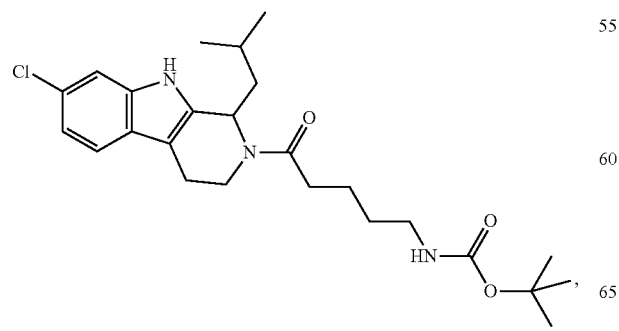
-continued
MN1231
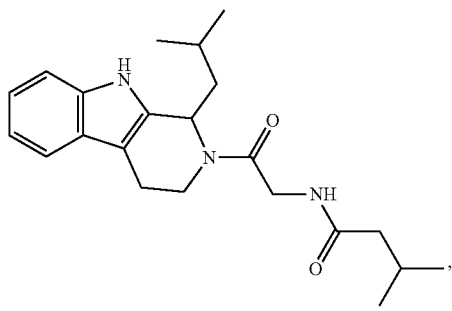
MN1232
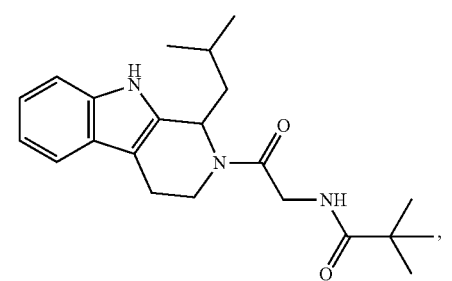
MN1233
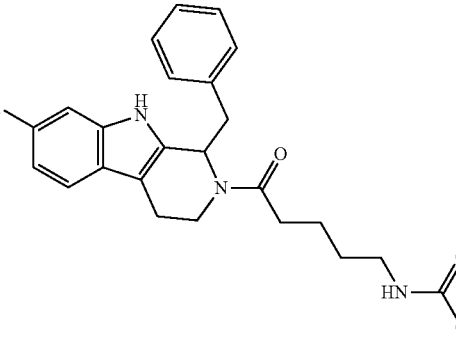
MN12235
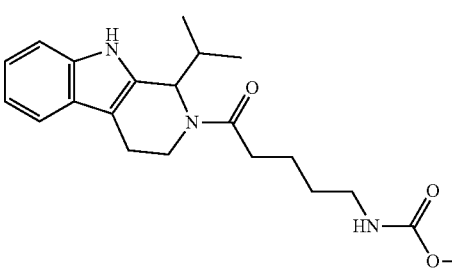
MN1236
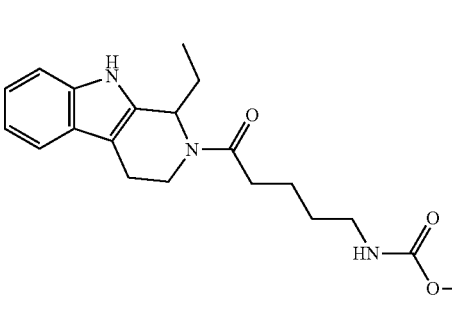

MN1237
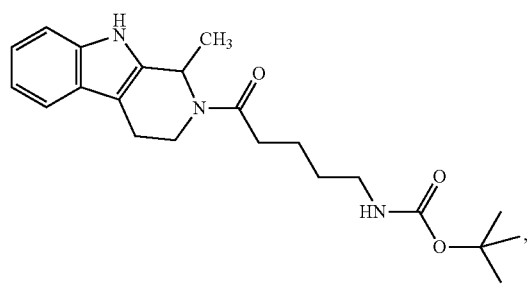
MN1238
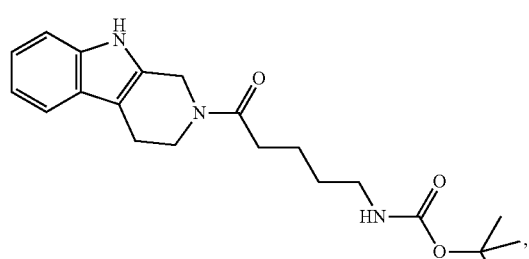
MN1241
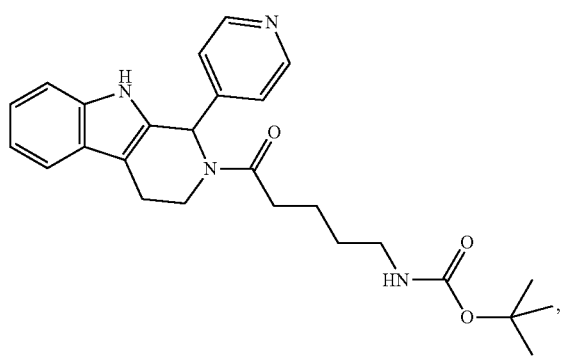
MN1244
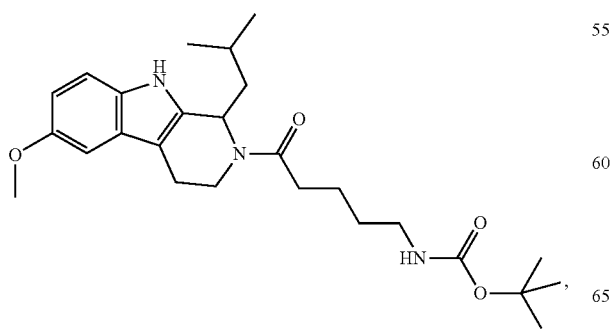
MN1246
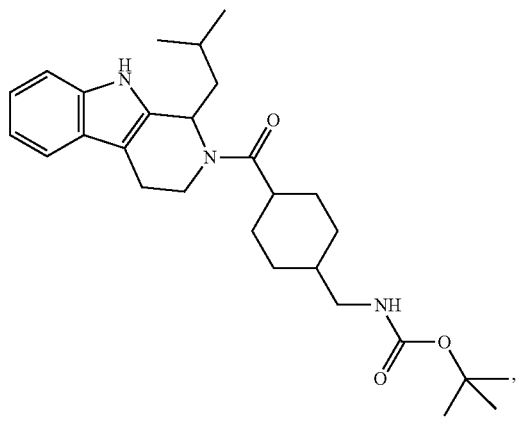
MN1247
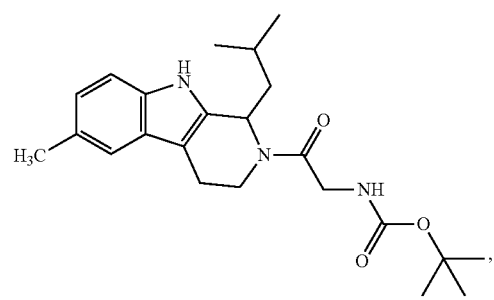
MN1248
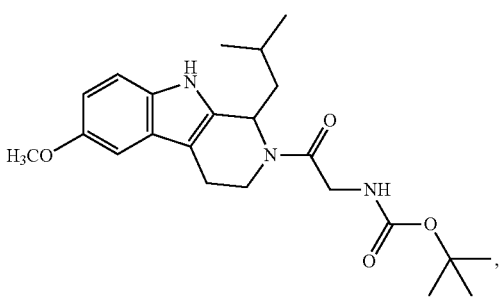
MN1250
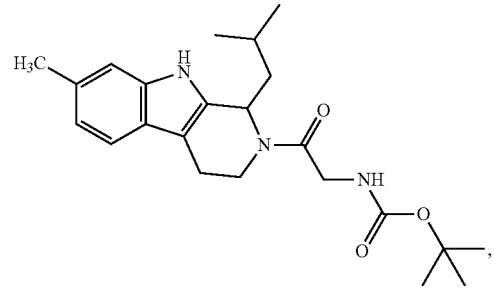

MN1251
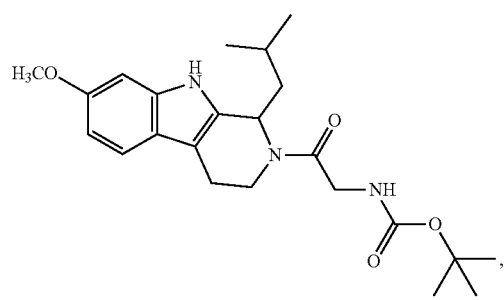
MN1252
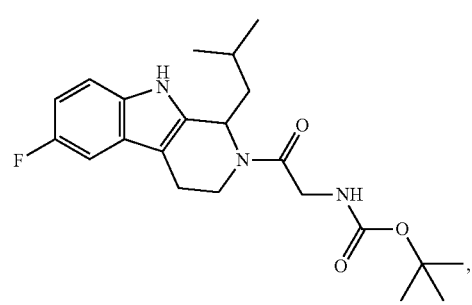
MN1253
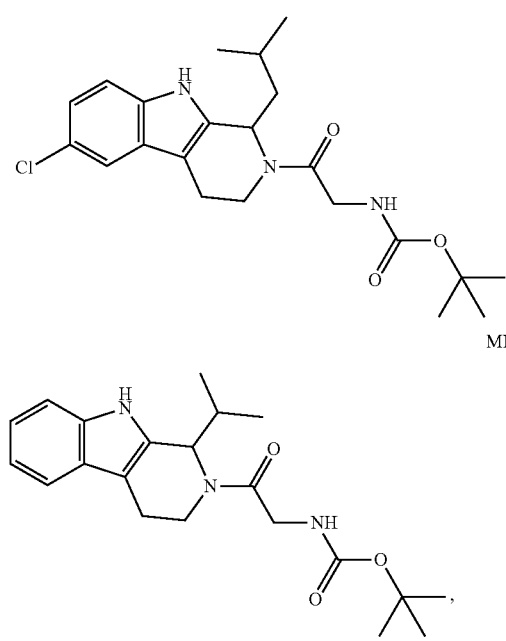
MN1259
MN1260
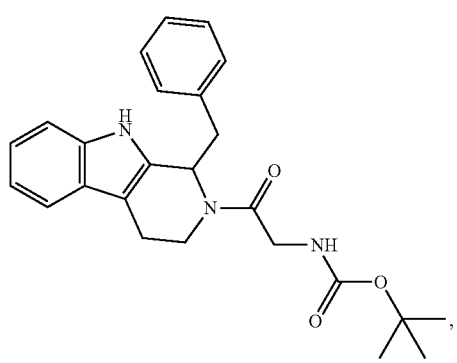
MN1264
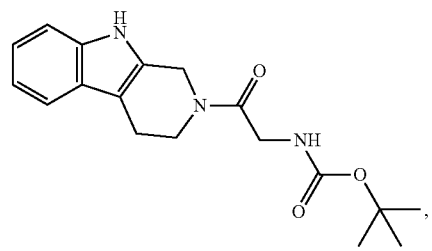
MN1265
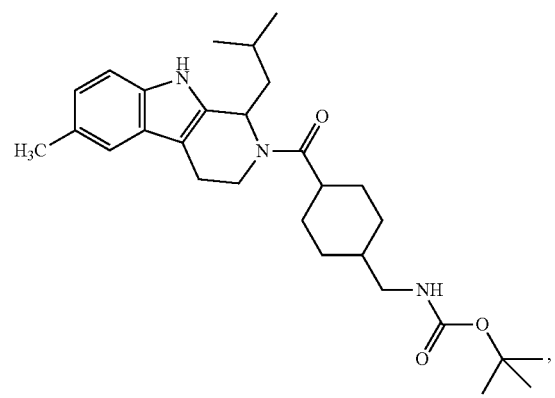
MN1266
MN1270
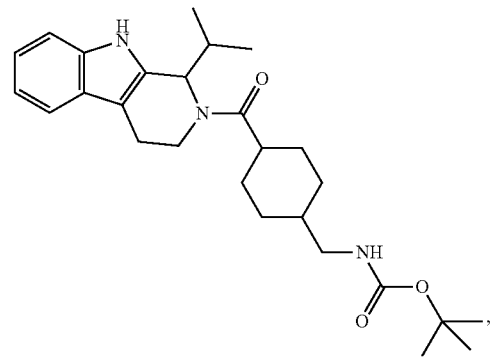

MN1271
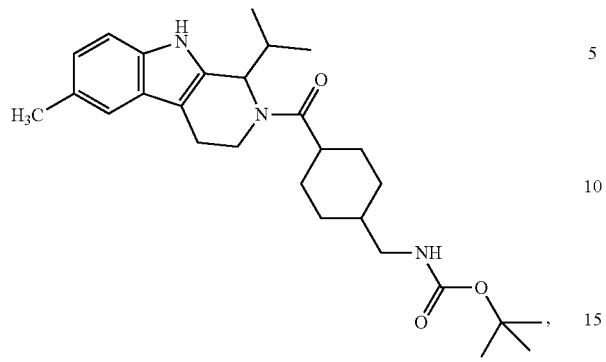
MN1272
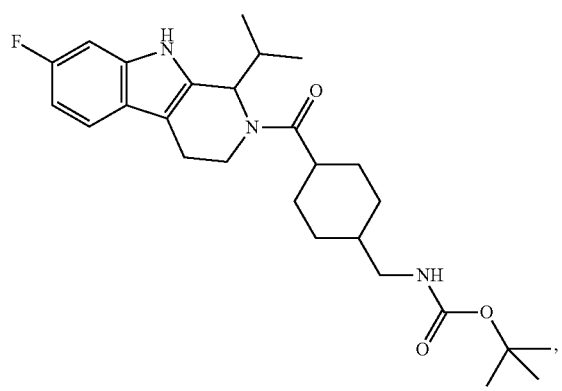
MN1279
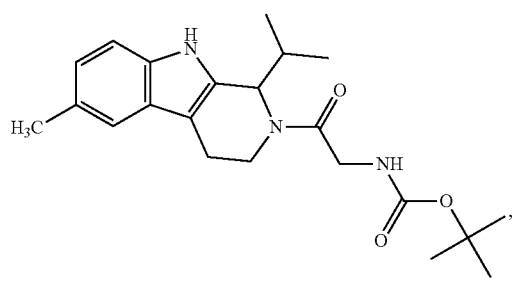
MN1280
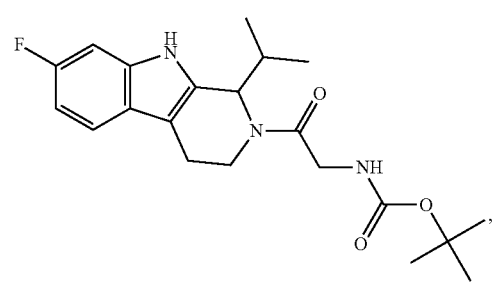
MN1285
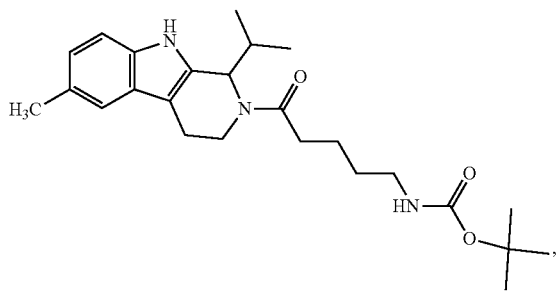
MN1286
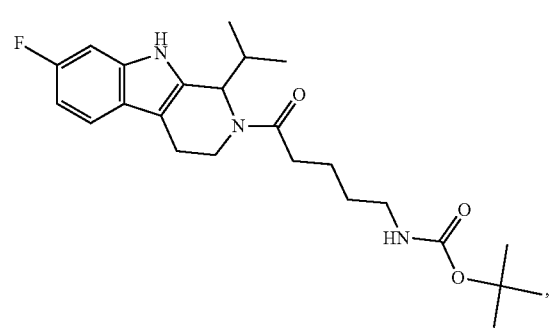
MN1289
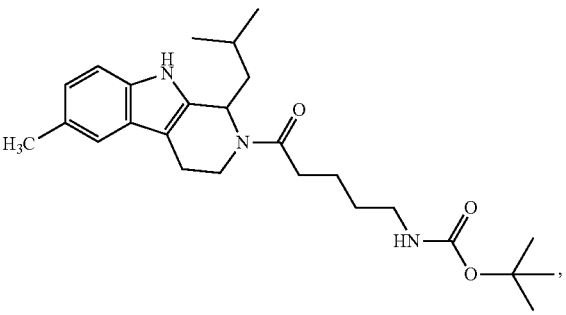
MN1290
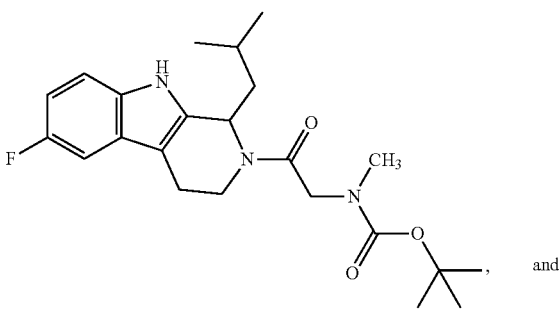
and
MN1291
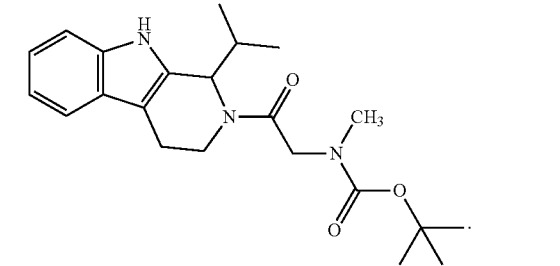

21. A compound selected from the group consisting of:
MN0580
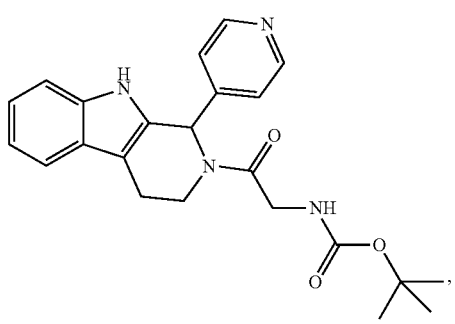
MN1172
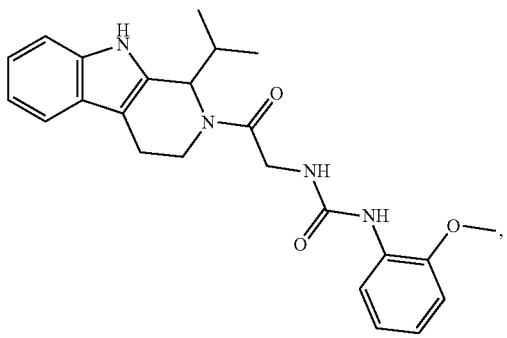
MN1158
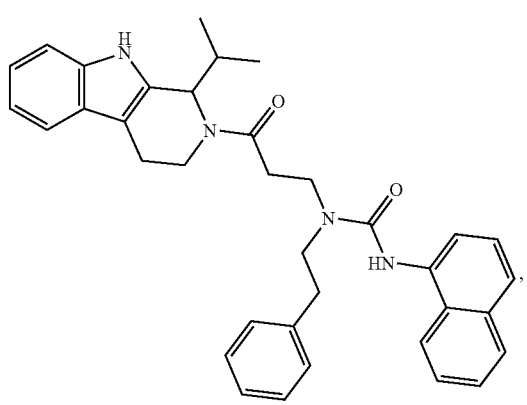
MN1186
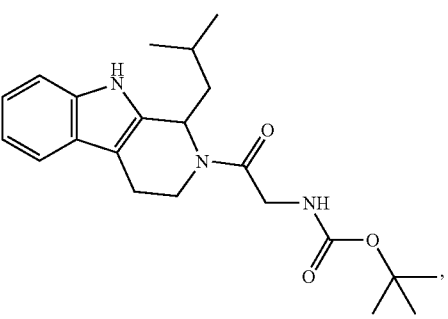
MN1160
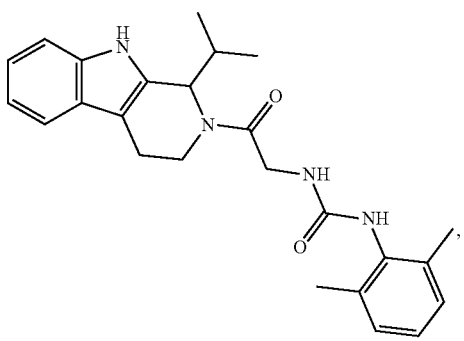
MN1189
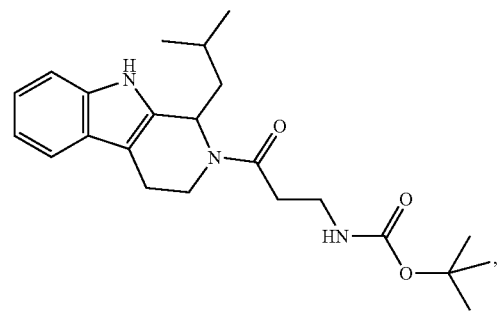
MN1169
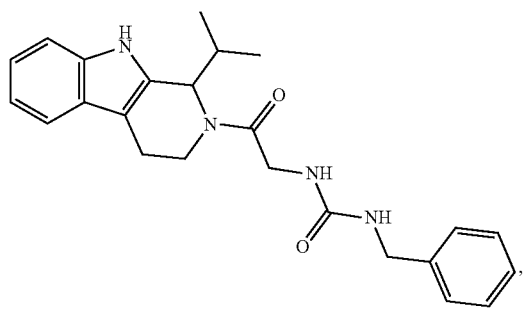
MN1190
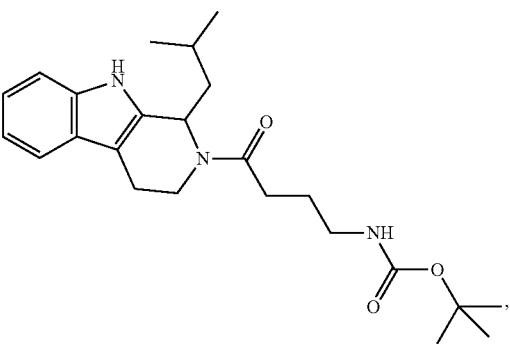

-continued
MN1194
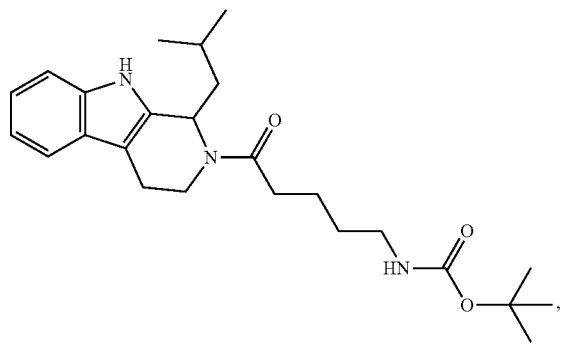
MN1224
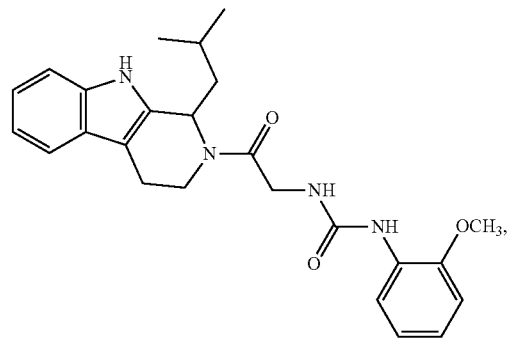
MN1195
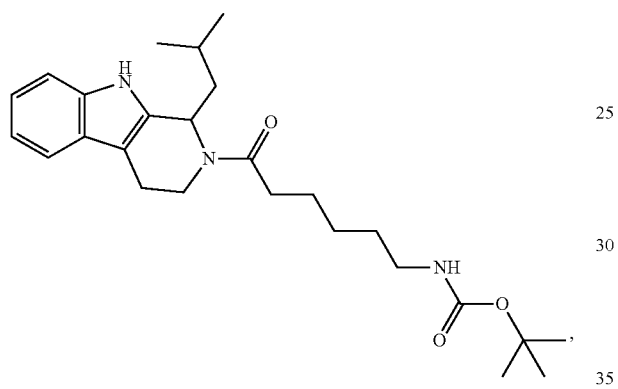
MN1225
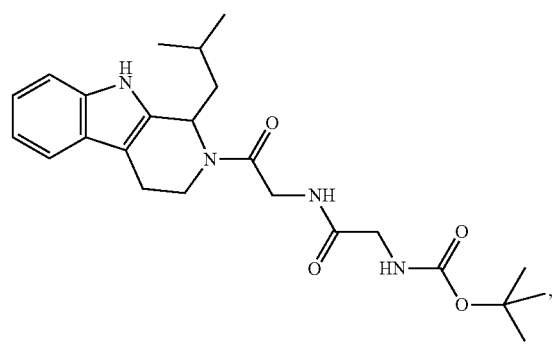
MN1220
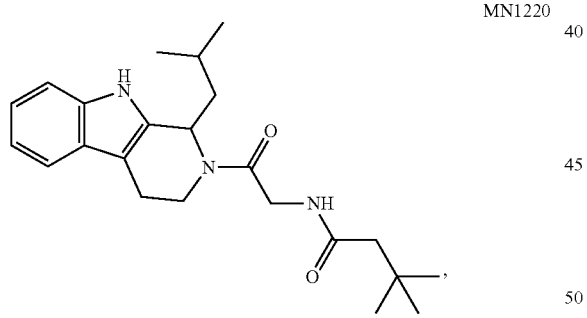
MN1227
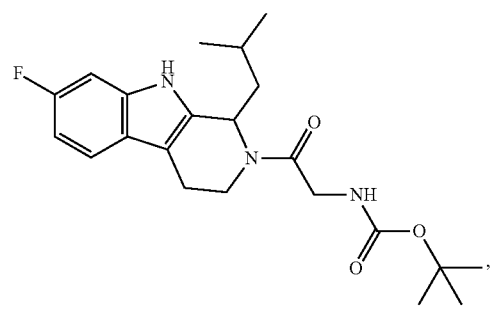
MN1223
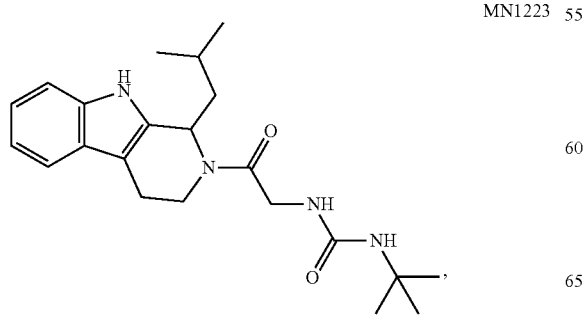
MN1228
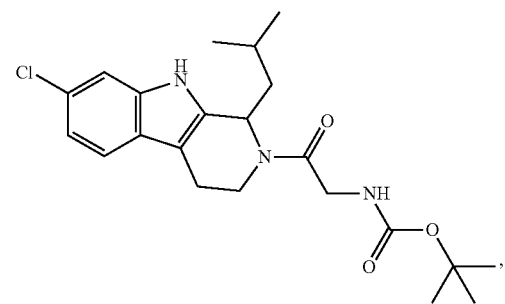

-continued
MN1229
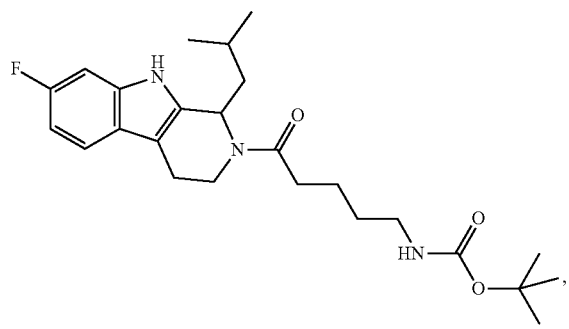
MN1230
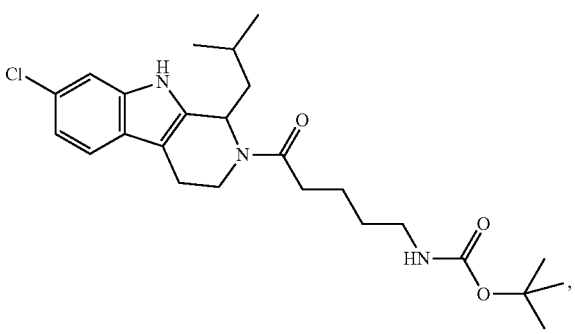
MN1231
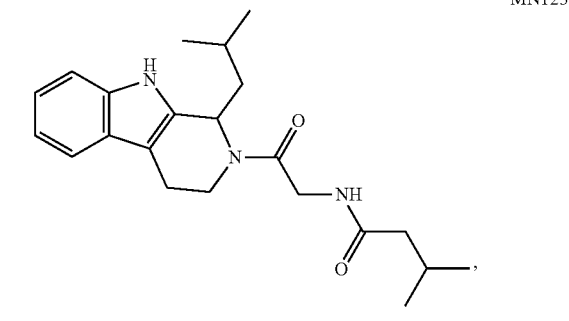
MN1232
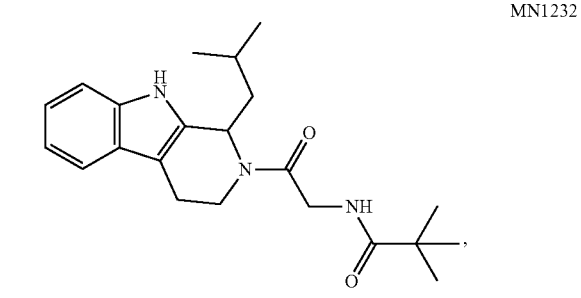
-continued
MN1233
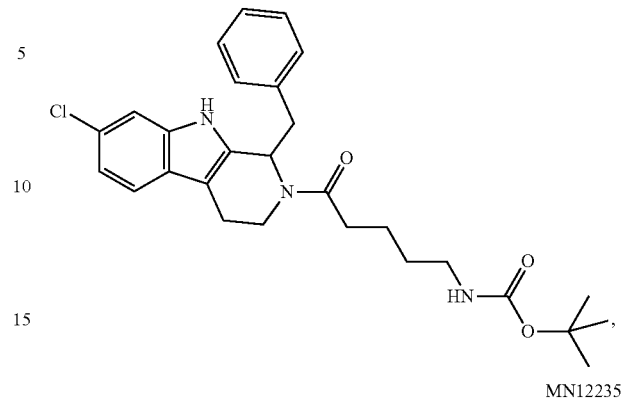
MN12235
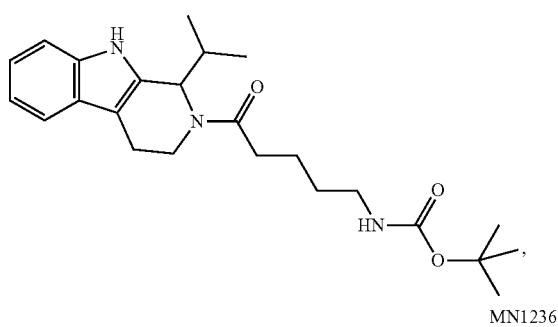
MN1236
MN1237
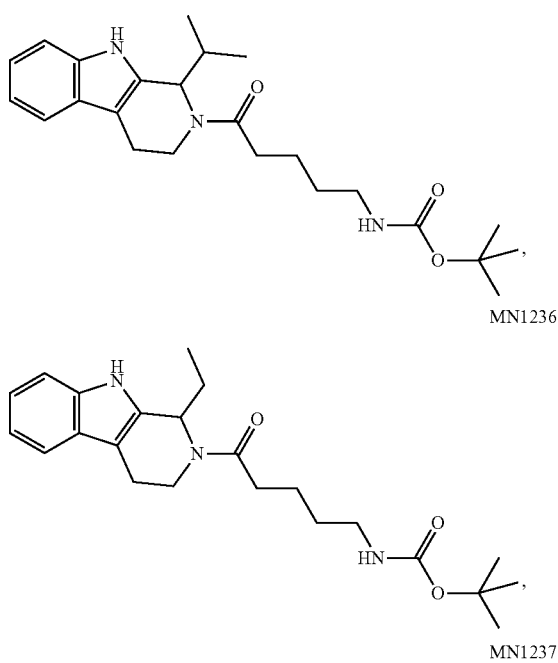
MN1238
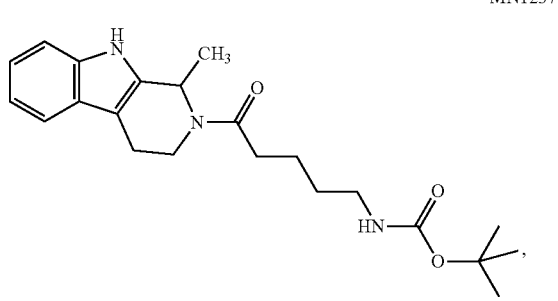

MN1241
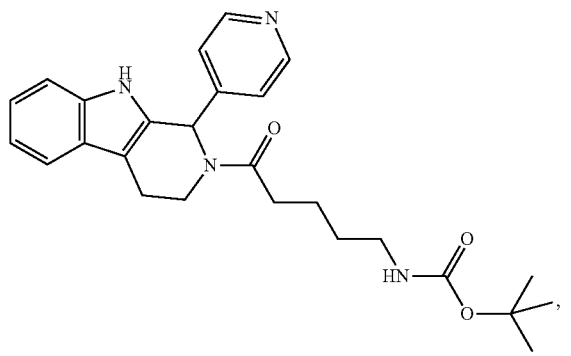
MN1244
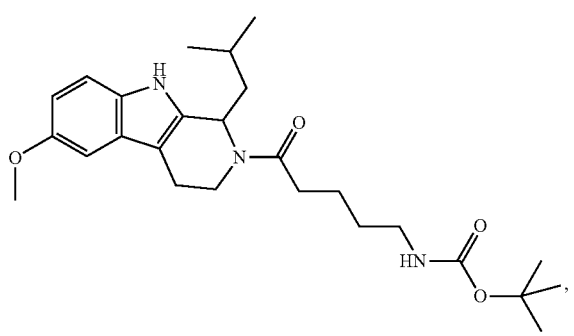
MN1246
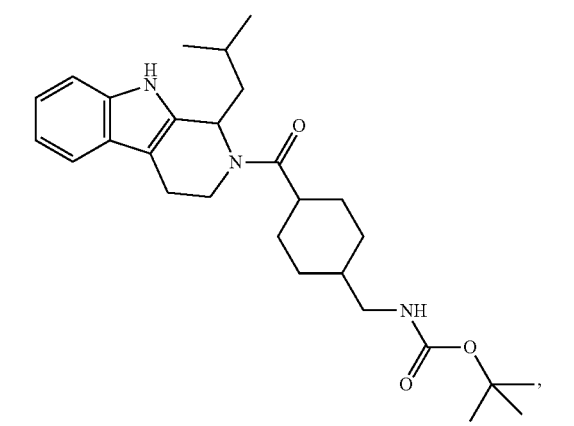
MN1247
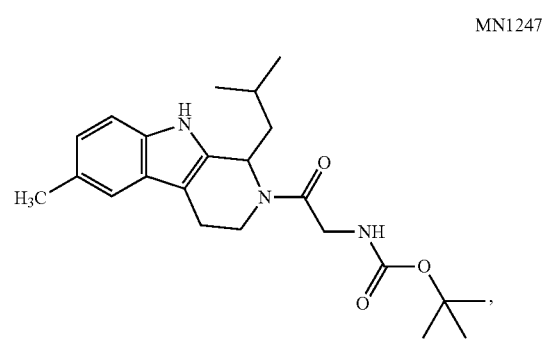
MN1248
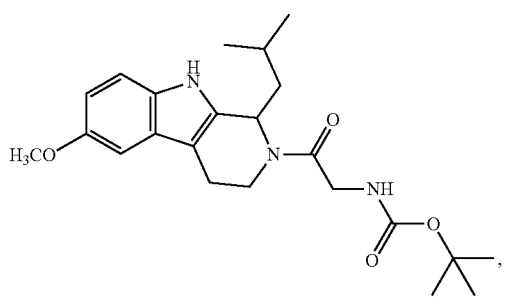
MN1250
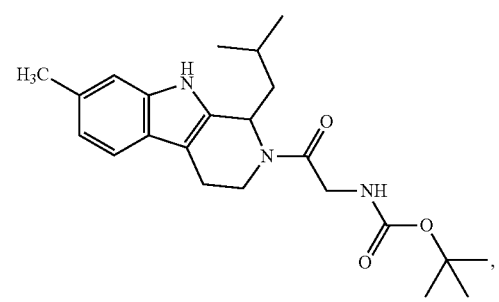
MN1251
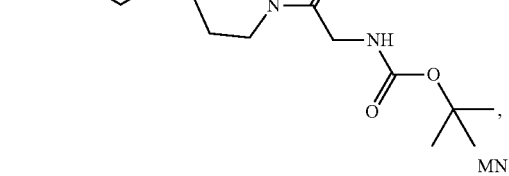
MN1252
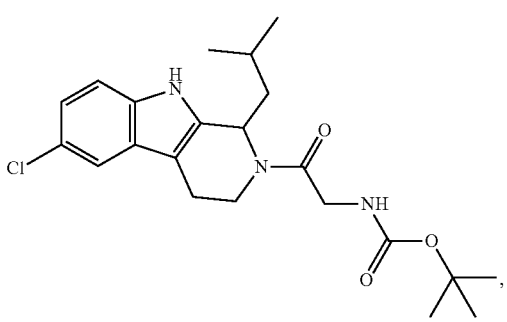
MN1253

167
-continued
MN1259
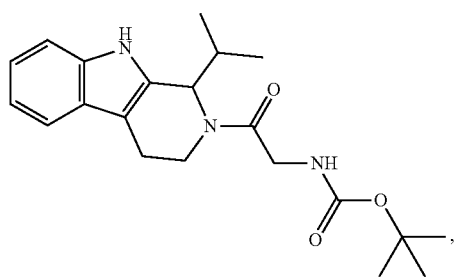
MN1260
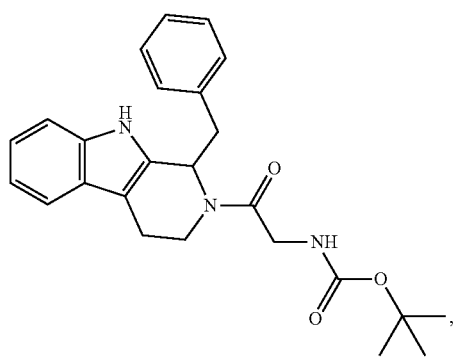
MN1264
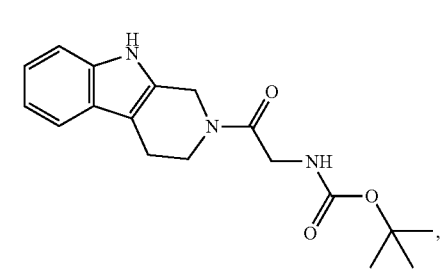
MN1265
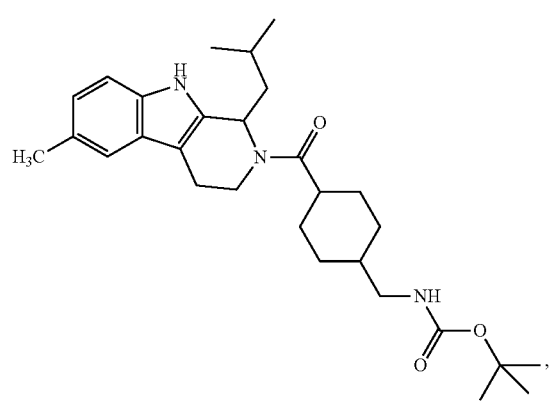
168
-continued
MN1266
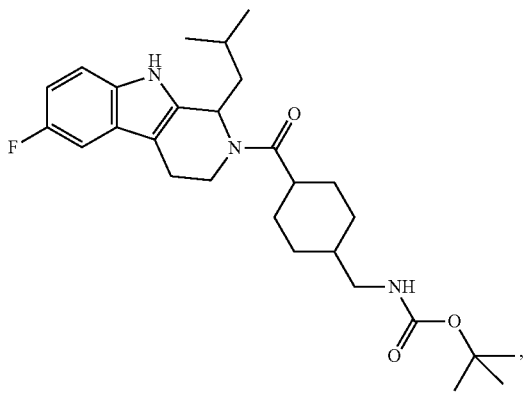
MN1270
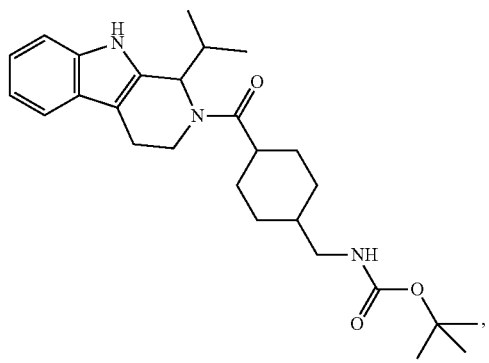
MN1271
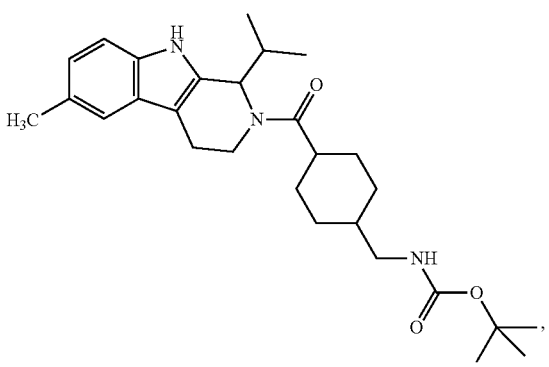
MN1272
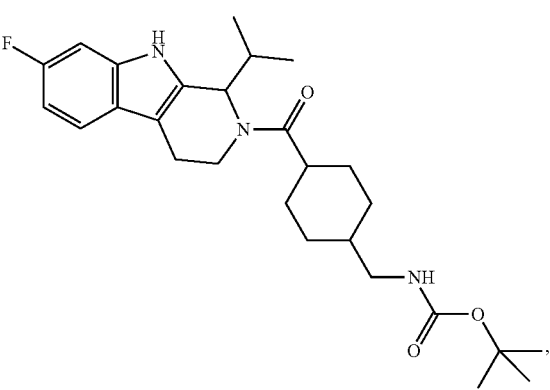

-continued
MN1279
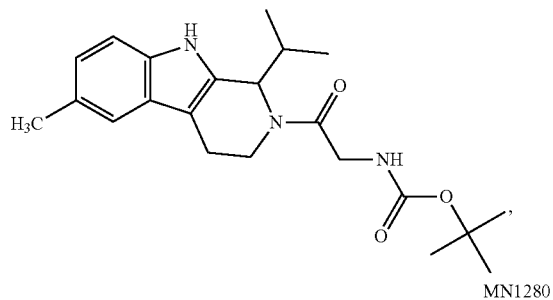
MN1280
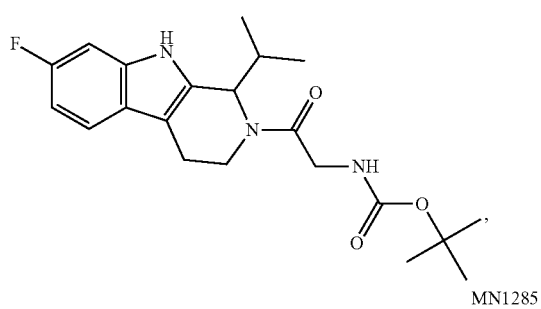
MN1285
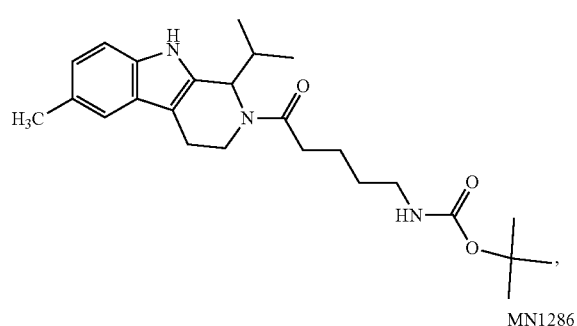
MN1286
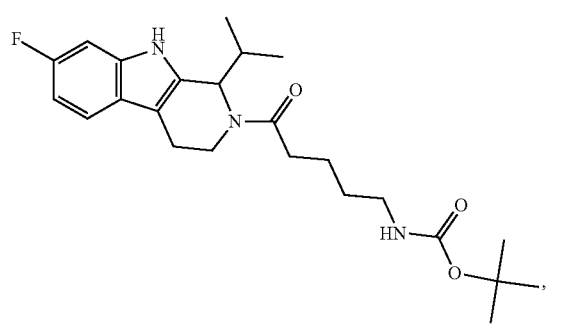
-continued
MN1289
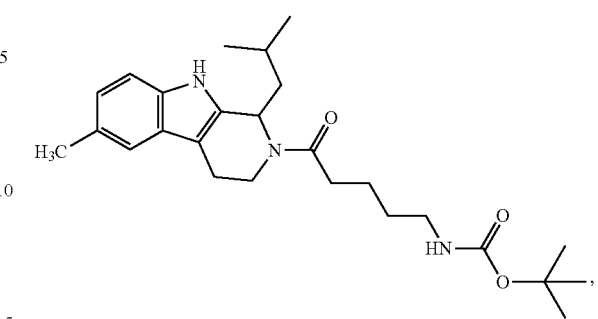
MN1290
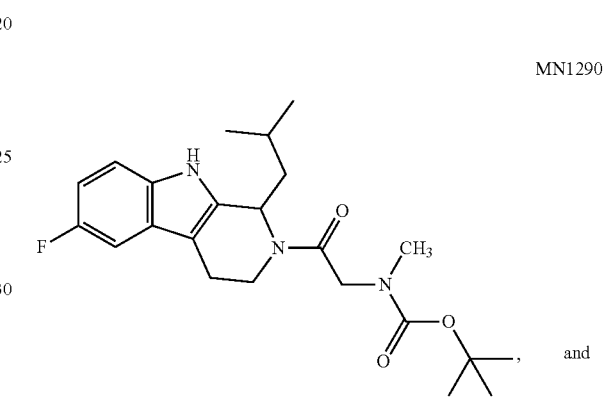
and
MN1291
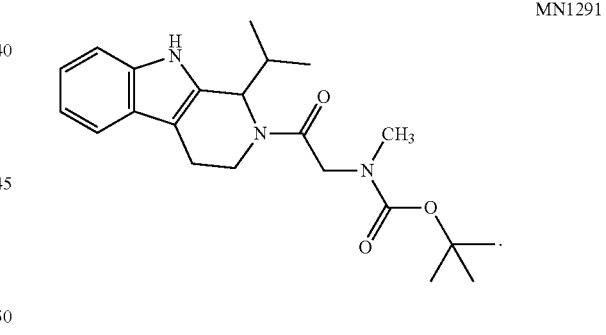
* * * * *

SEQUENCE LISTING

```
<160> NUMBER OF SEQ ID NOS: 12

<210> SEQ ID NO 1
<211> LENGTH: 1255
<212> TYPE: PRT
<213> ORGANISM: Artificial Sequence
<220> FEATURE:
<223> OTHER INFORMATION: full-length MUC1 Receptor (Mucin 1 precursor,
      Genbank Accession number: P15941)

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270
```

```
Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
        290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
                340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
        370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
                420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
        450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
                500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
        530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
                580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
        610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
                660                 665                 670

Pro Pro Ala His Gly Val Thr Ser Ala Pro Asp Thr Arg Pro Ala Pro
        675                 680                 685
```

```
Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
                740                 745                 750

Pro Pro Ala His Gly Val Thr Ser Ala Pro Asp Thr Arg Pro Ala Pro
            755                 760                 765

Gly Ser Thr Ala Pro Pro Ala His Gly Val Thr Ser Ala Pro Asp Thr
770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
                820                 825                 830

Pro Pro Ala His Gly Val Thr Ser Ala Pro Asp Thr Arg Pro Ala Pro
            835                 840                 845

Gly Ser Thr Ala Pro Pro Ala His Gly Val Thr Ser Ala Pro Asp Thr
850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
                900                 905                 910

Pro Pro Ala His Gly Val Thr Ser Ala Pro Asp Thr Arg Pro Ala Pro
            915                 920                 925

Gly Ser Thr Ala Pro Pro Ala His Gly Val Thr Ser Ala Pro Asp Asn
930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
                980                 985                 990

Ser Ile Pro Ser His His Ser Asp Thr Pro Thr Thr Leu Ala Ser His
                995                 1000                1005

Ser Thr Lys Thr Asp Ala Ser Ser Thr His His Ser Ser Val Pro
        1010                1015                1020

Pro Leu Thr Ser Ser Asn His Ser Thr Ser Pro Gln Leu Ser Thr
        1025                1030                1035

Gly Val Ser Phe Phe Phe Leu Ser Phe His Ile Ser Asn Leu Gln
        1040                1045                1050

Phe Asn Ser Ser Leu Glu Asp Pro Ser Thr Asp Tyr Tyr Gln Glu
        1055                1060                1065

Leu Gln Arg Asp Ile Ser Glu Met Phe Leu Gln Ile Tyr Lys Gln
        1070                1075                1080

Gly Gly Phe Leu Gly Leu Ser Asn Ile Lys Phe Arg Pro Gly Ser
        1085                1090                1095

Val Val Val Gln Leu Thr Leu Ala Phe Arg Glu Gly Thr Ile Asn
```

```
                     1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Ala Ser Ala Asn Leu
    1250                1255

<210> SEQ ID NO 2
<211> LENGTH: 146
<212> TYPE: PRT
<213> ORGANISM: Artificial Sequence
<220> FEATURE:
<223> OTHER INFORMATION: a truncated MUC1 receptor isoform having
      nat-PSMGFR at its N-terminus and including the transmembrane and
      cytoplasmic sequences of a full-length MUC1 receptor

<400> SEQUENCE: 2

Gly Thr Ile Asn Val His Asp Val Glu Thr Gln Phe Asn Gln Tyr Lys
1               5                  10                  15

Thr Glu Ala Ala Ser Arg Tyr Asn Leu Thr Ile Ser Asp Val Ser Val
                20                  25                  30

Ser Asp Val Pro Phe Pro Phe Ser Ala Gln Ser Gly Ala Gly Val Pro
            35                  40                  45

Gly Trp Gly Ile Ala Leu Leu Val Leu Val Cys Val Leu Val Ala Leu
        50                  55                  60

Ala Ile Val Tyr Leu Ile Ala Leu Ala Val Cys Gln Cys Arg Arg Lys
65                  70                  75                  80

Asn Tyr Gly Gln Leu Asp Ile Phe Pro Ala Arg Asp Thr Tyr His Pro
                85                  90                  95

Met Ser Glu Tyr Pro Thr Tyr His Thr His Gly Arg Tyr Val Pro Pro
            100                 105                 110

Ser Ser Thr Asp Arg Ser Pro Tyr Glu Lys Val Ser Ala Gly Asn Gly
        115                 120                 125

Gly Ser Ser Leu Ser Tyr Thr Asn Pro Ala Val Ala Ala Ala Ser Ala
    130                 135                 140

Asn Leu
145

<210> SEQ ID NO 3
<211> LENGTH: 45
<212> TYPE: PRT
<213> ORGANISM: Artificial Sequence
```

```
<220> FEATURE:
<223> OTHER INFORMATION: the extracellular domain of Native Primary
      Sequence of the MUC1 Growth Factor Receptor (nat-PSMGFR - an
      example of "PSMGFR")

<400> SEQUENCE: 3

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
            35                  40                  45

<210> SEQ ID NO 4
<211> LENGTH: 35
<212> TYPE: PRT
<213> ORGANISM: Artificial Sequence
<220> FEATURE:
<223> OTHER INFORMATION: N-10 peptide of PSMGFR in which ten amino acids
      at the N-terminus has been removed

<400> SEQUENCE: 4

Gln Phe Asn Gln Tyr Lys Thr Glu Ala Ala Ser Arg Tyr Asn Leu Thr
1               5                   10                  15

Ile Ser Asp Val Ser Val Ser Asp Val Pro Phe Pro Phe Ser Ala Gln
            20                  25                  30

Ser Gly Ala
        35

<210> SEQ ID NO 5
<211> LENGTH: 283
<212> TYPE: PRT
<213> ORGANISM: Artificial Sequence
<220> FEATURE:
<223> OTHER INFORMATION: NME7 amino acid sequence (NME7: GENBANK
      ACCESSION AB209049)

<400> SEQUENCE: 5

Asp Pro Glu Thr Met Asn His Ser Glu Arg Phe Val Phe Ile Ala Glu
1               5                   10                  15

Trp Tyr Asp Pro Asn Ala Ser Leu Leu Arg Arg Tyr Glu Leu Leu Phe
            20                  25                  30

Tyr Pro Gly Asp Gly Ser Val Glu Met His Asp Val Lys Asn His Arg
        35                  40                  45

Thr Phe Leu Lys Arg Thr Lys Tyr Asp Asn Leu His Leu Glu Asp Leu
    50                  55                  60

Phe Ile Gly Asn Lys Val Asn Val Phe Ser Arg Gln Leu Val Leu Ile
65                  70                  75                  80

Asp Tyr Gly Asp Gln Tyr Thr Ala Arg Gln Leu Gly Ser Arg Lys Glu
                85                  90                  95

Lys Thr Leu Ala Leu Ile Lys Pro Asp Ala Ile Ser Lys Ala Gly Glu
            100                 105                 110

Ile Ile Glu Ile Ile Asn Lys Ala Gly Phe Thr Ile Thr Lys Leu Lys
        115                 120                 125

Met Met Met Leu Ser Arg Lys Glu Ala Leu Asp Phe His Val Asp His
    130                 135                 140

Gln Ser Arg Pro Phe Phe Asn Glu Leu Ile Gln Phe Ile Thr Thr Gly
145                 150                 155                 160

Pro Ile Ile Ala Met Glu Ile Leu Arg Asp Asp Ala Ile Cys Glu Trp
                165                 170                 175
```

```
Lys Arg Leu Leu Gly Pro Ala Asn Ser Gly Val Ala Arg Thr Asp Ala
            180                 185                 190

Ser Glu Ser Ile Arg Ala Leu Phe Gly Thr Asp Gly Ile Arg Asn Ala
        195                 200                 205

Ala His Gly Pro Asp Ser Phe Ala Ser Ala Arg Glu Met Glu Leu
    210                 215                 220

Phe Phe Pro Ser Ser Gly Gly Cys Gly Pro Ala Asn Thr Ala Lys Phe
225                 230                 235                 240

Thr Asn Cys Thr Cys Cys Ile Val Lys Pro His Ala Val Ser Glu Gly
            245                 250                 255

Met Leu Asn Thr Leu Tyr Ser Val His Phe Val Asn Arg Arg Ala Met
            260                 265                 270

Phe Ile Phe Leu Met Tyr Phe Met Tyr Arg Lys
            275                 280
```

<210> SEQ ID NO 6
<211> LENGTH: 286
<212> TYPE: PRT
<213> ORGANISM: Artificial Sequence
<220> FEATURE:
<223> OTHER INFORMATION: human NME7-AB

<400> SEQUENCE: 6

```
Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255
```

```
Lys Thr Lys Ile Gln Asn Ala Val His Cys Thr Asp Leu Pro Glu Asp
            260                 265                 270

Gly Leu Leu Glu Val Gln Tyr Phe Phe Lys Ile Leu Asp Asn
        275                 280                 285

<210> SEQ ID NO 7
<211> LENGTH: 252
<212> TYPE: PRT
<213> ORGANISM: Artificial Sequence
<220> FEATURE:
<223> OTHER INFORMATION: human NME7-X1

<400> SEQUENCE: 7

Met Met Met Leu Ser Arg Lys Glu Ala Leu Asp Phe His Val Asp His
1               5                   10                  15

Gln Ser Arg Pro Phe Phe Asn Glu Leu Ile Gln Phe Ile Thr Thr Gly
            20                  25                  30

Pro Ile Ile Ala Met Glu Ile Leu Arg Asp Asp Ala Ile Cys Glu Trp
        35                  40                  45

Lys Arg Leu Leu Gly Pro Ala Asn Ser Gly Val Ala Arg Thr Asp Ala
    50                  55                  60

Ser Glu Ser Ile Arg Ala Leu Phe Gly Thr Asp Gly Ile Arg Asn Ala
65                  70                  75                  80

Ala His Gly Pro Asp Ser Phe Ala Ser Ala Arg Glu Met Glu Leu
                85                  90                  95

Phe Phe Pro Ser Ser Gly Gly Cys Gly Pro Ala Asn Thr Ala Lys Phe
            100                 105                 110

Thr Asn Cys Thr Cys Cys Ile Val Lys Pro His Ala Val Ser Glu Gly
        115                 120                 125

Leu Leu Gly Lys Ile Leu Met Ala Ile Arg Asp Ala Gly Phe Glu Ile
    130                 135                 140

Ser Ala Met Gln Met Phe Asn Met Asp Arg Val Asn Val Glu Glu Phe
145                 150                 155                 160

Tyr Glu Val Tyr Lys Gly Val Val Thr Glu Tyr His Asp Met Val Thr
                165                 170                 175

Glu Met Tyr Ser Gly Pro Cys Val Ala Met Glu Ile Gln Gln Asn Asn
            180                 185                 190

Ala Thr Lys Thr Phe Arg Glu Phe Cys Gly Pro Ala Asp Pro Glu Ile
        195                 200                 205

Ala Arg His Leu Arg Pro Gly Thr Leu Arg Ala Ile Phe Gly Lys Thr
    210                 215                 220

Lys Ile Gln Asn Ala Val His Cys Thr Asp Leu Pro Glu Asp Gly Leu
225                 230                 235                 240

Leu Glu Val Gln Tyr Phe Phe Lys Ile Leu Asp Asn
                245                 250

<210> SEQ ID NO 8
<211> LENGTH: 132
<212> TYPE: PRT
<213> ORGANISM: Artificial Sequence
<220> FEATURE:
<223> OTHER INFORMATION: Human NME7-A1

<400> SEQUENCE: 8

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
```

```
                    20                  25                  30
Leu Lys Met Met Met Leu Ser Arg Lys Glu Ala Leu Asp Phe His Val
             35                  40                  45

Asp His Gln Ser Arg Pro Phe Phe Asn Glu Leu Ile Gln Phe Ile Thr
         50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                 85                  90                  95

Asp Ala Ser Glu Ser Ile Arg Ala Leu Phe Gly Thr Asp Gly Ile Arg
             100                 105                 110

Asn Ala Ala His Gly Pro Asp Ser Phe Ala Ser Ala Ala Arg Glu Met
         115                 120                 125

Glu Leu Phe Phe
     130

<210> SEQ ID NO 9
<211> LENGTH: 155
<212> TYPE: PRT
<213> ORGANISM: Artificial Sequence
<220> FEATURE:
<223> OTHER INFORMATION: Human NME7-B3

<400> SEQUENCE: 9

Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
             20                  25                  30

Leu Gly Lys Ile Leu Met Ala Ile Arg Asp Ala Gly Phe Glu Ile Ser
         35                  40                  45

Ala Met Gln Met Phe Asn Met Asp Arg Val Asn Val Glu Glu Phe Tyr
     50                  55                  60

Glu Val Tyr Lys Gly Val Val Thr Glu Tyr His Asp Met Val Thr Glu
65                  70                  75                  80

Met Tyr Ser Gly Pro Cys Val Ala Met Glu Ile Gln Gln Asn Asn Ala
                 85                  90                  95

Thr Lys Thr Phe Arg Glu Phe Cys Gly Pro Ala Asp Pro Glu Ile Ala
             100                 105                 110

Arg His Leu Arg Pro Gly Thr Leu Arg Ala Ile Phe Gly Lys Thr Lys
         115                 120                 125

Ile Gln Asn Ala Val His Cys Thr Asp Leu Pro Glu Asp Gly Leu Leu
     130                 135                 140

Glu Val Gln Tyr Phe Phe Lys Ile Leu Asp Asn
145                 150                 155

<210> SEQ ID NO 10
<211> LENGTH: 29
<212> TYPE: PRT
<213> ORGANISM: Artificial Sequence
<220> FEATURE:
<223> OTHER INFORMATION: B3, which is NME7B peptide 3 (B domain)

<400> SEQUENCE: 10

Ala Ile Phe Gly Lys Thr Lys Ile Gln Asn Ala Val His Cys Thr Asp
1               5                   10                  15

Leu Pro Glu Asp Gly Leu Leu Glu Val Gln Tyr Phe Phe
             20                  25
```

```
<210> SEQ ID NO 11
<211> LENGTH: 45
<212> TYPE: PRT
<213> ORGANISM: Artificial Sequence
<220> FEATURE:
<223> OTHER INFORMATION: the extracellular domain of "SPY" functional
      variant of the native Primary Sequence of the MUC1 Growth Factor
      Receptor having enhanced stability (var-PSMGFR - An example of
      "PSMGFR")

<400> SEQUENCE: 11

Gly Thr Ile Asn Val His Asp Val Glu Thr Gln Phe Asn Gln Tyr Lys
1               5                  10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 12
<211> LENGTH: 91
<212> TYPE: PRT
<213> ORGANISM: Artificial Sequence
<220> FEATURE:
<223> OTHER INFORMATION: DM10 domain of NME7

<400> SEQUENCE: 12

Met Asn His Ser Glu Arg Phe Val Phe Ile Ala Glu Trp Tyr Asp Pro
1               5                  10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys
                85                  90
```